US012691186B2

(12) United States Patent
Goodman et al.

(10) Patent No.: US 12,691,186 B2
(45) Date of Patent: Jul. 28, 2026

(54) B7-H3 MINIPROTEINS, CONJUGATES, AND USES THEREOF

(71) Applicant: Aktis Oncology, Inc., Boston, MA (US)

(72) Inventors: Brian Scott Goodman, Boston, MA (US); Ved Srivastava, Cary, NC (US); Paul L. Feldman, Durham, NC (US); William C. Blackwell, III, Raleigh, NC (US); Matthew Roden, Princeton, NJ (US); Dasa Lipovsek, Pepperell, MA (US); Hyun Joo Kil, Cary, NC (US); Jeff Kovacs, Raleigh, NC (US); Michael Lawrence Doligalski, Chapel Hill, NC (US); Isaiah Nathaniel Gober, Durham, NC (US); Victoria Anne Haberman, Durham, NC (US); Stanley Richard Krystek, Jr., Ringoes, NJ (US); Marci Lynn Copeland, Cary, NC (US); Tatsiana Kosciuk, Durham, NC (US); Mehran Makvandi, Durham, NC (US); Andrew Clay, Durham, NC (US); Wai Leung Lau, Brighton, MA (US)

(73) Assignee: Aktis Oncology, Inc., Boston, MA (US)

( * ) Notice: Subject to any disclaimer, the term of this patent is extended or adjusted under 35 U.S.C. 154(b) by 0 days.

(21) Appl. No.: 19/375,848

(22) Filed: Oct. 31, 2025

(65) Prior Publication Data

US 2026/0048158 A1 Feb. 19, 2026

Related U.S. Application Data

(63) Continuation of application No. PCT/US2024/059036, filed on Dec. 6, 2024.

(60) Provisional application No. 63/721,990, filed on Nov. 18, 2024, provisional application No. 63/650,364, filed on May 21, 2024, provisional application No. 63/650,365, filed on May 21, 2024, provisional application No. 63/636,076, filed on Apr. 18, 2024, provisional application No. 63/607,988, filed on Dec. 8, 2023.

(51) Int. Cl.

| | |
|---|---|
| ***A61K 51/08*** | (2006.01) |
| ***A61K 38/00*** | (2006.01) |
| ***A61P 35/00*** | (2006.01) |
| ***C07K 14/00*** | (2006.01) |

(52) U.S. Cl.

CPC ............ *A61K 51/088* (2013.01); *A61P 35/00* (2018.01); *C07K 14/001* (2013.01); *A61K 38/00* (2013.01); *A61K 2121/00* (2013.01)

(58) Field of Classification Search

CPC ...... A61K 51/00; A61K 51/08; A61K 51/088; A61K 38/00; A61K 2121/00; A61P 35/00; C07K 14/001

See application file for complete search history.

(56) References Cited

U.S. PATENT DOCUMENTS

| | | | |
|---|---|---|---|
| 2021/0162058 | A1 | 6/2021 | Farias et al. |
| 2021/0340257 | A1 | 11/2021 | Abou-Elkacem et al. |
| 2022/0160908 | A1 | 5/2022 | Li et al. |

FOREIGN PATENT DOCUMENTS

| | | | | |
|---|---|---|---|---|
| WO | WO-2020041626 | A1 * | 2/2020 | ........... A61K 49/223 |
| WO | WO-2024010957 | A2 | 1/2024 | |
| WO | WO-2024249501 | A2 | 12/2024 | |

OTHER PUBLICATIONS

Burvenich, et al., Molecular imaging of T cell co-regulator factor B7-H3 with 89Zr-DS-5573a, Theranostics, 8(15): 4199-4209 (2018).
Carvajal-Hausdorf, et al., Expression and clinical significance of PDL1, B7-H3, B7-H4 and TILs in human small cell lung Cancer (SCLC), J. Immuno Ther. Cancer, 7(65): 1-9 (2019).
Chen, et al., B7-H3 expression associates with tumor invasion and patient's poor survival in human esophageal cancer, Am. J. Transl. Res., 7(12): 2646-2660 (2015).
Kang, et al., Hepatocellular carcinomas promote tumor-associated macrophage M2-polarization via increased B7-H3 expression, Oncol. Rep., 33: 274-282.
Loo, et al., Development of an Fc-Enhanced Anti-B7-H3 Monoclonal Antibody with Potent Antitumor Activity, Clin. Cancer Res., 18(14): 3834-45 (2012).
Loos, et al., Expression of the costimulatory molecule B7-H3 is associated with prolonged survival in human pancreatic cancer, BMC Cancer, 9(463): 1-10 (2009).
Majzner, et al., Car T Cells Targeting B7-H3, a Pan-Cancer Antigen, Demonstrate Potent Preclinical Activity Against Pediatric Solid Tumors and Brain Tumors, Clin. Cancer Res., 25(8): 2560-2574 (2019).
Mao, et al., B7-H1 and B7-H3 are independent predictors of poor prognosis in patients with non-small cell lung cancer, Oncotarget, 6(5): 3452-3461 (2014).

(Continued)

*Primary Examiner* — D. L. Jones
(74) *Attorney, Agent, or Firm* — Goodwin Procter LLP

(57) ABSTRACT

Provided herein are B7-H3-binding miniproteins, conjugates, and uses thereof. B7-H3 binding peptides and conjugates, including radionuclide conjugates, as well as one or more additional proteins such as a decoy peptide are disclosed herein. Such peptides, conjugates, and/or decoys can be used in compositions and methods of treating, diagnosing, monitoring, and/or imaging a disease, disorder, or condition associated with expression of one or more targets (e.g., B7-H3).

24 Claims, 28 Drawing Sheets

Specification includes a Sequence Listing.

(56) References Cited

OTHER PUBLICATIONS

PCT/US2024/059036 International Search Report and Written Opinion mailed Feb. 20, 2025, 16 pages.
Roth, et al., B7-H3 Ligand Expression by Prostate Cancer: A Novel Marker of Prognosis and Potential Target for Therapy, Cancer Res., 67(16): 7893-7900 (2007).
Roth, et al., Supplement of "B7-H3 Ligand Expression by Prostate Cancer: A Novel Marker of Prognosis and Potential Target for Therapy, Cancer Res., 67(16): 7893-7900 (2007)."
Seaman, et al., Eradication of Tumors through Simultaneous Ablation of CD276/B7-H3-Positive Tumor Cells and Tumor Vasculature, Cancer Cell, 31: 501-515 (2017).
Sun, et al., Characterization of Mouse and Human B7-H3 Genes, J. Immunol., 168: 6294-6297 (2002).
Wang, et al., B7-H3 is Overexpressed in Patients Suffering Osteosarcoma and Associated with Tumor Aggressiveness and Metastasis, Plos One, 8(8): e70689 (2013).
Xu, et al., MicroRNA miR-29 Modulates Expression of Immunoinhibitory Molecule B7-H3: Potential Implications for Immune Based Therapy of Human Solid Tumors, Cancer Res., 69(15): 6275-6281 (2009).
Yamato, et al., Clinical importance of B7-H3 expression in human pancreatic cancer, Br. J. Cancer, 101: 1709-1716 (2009).
Yamato, et al., DS-7300a, a DNA Topoisomerase I Inhibitor, DXd-based Antibody-Drug Conjugate Targeting B7-H3 Exerts Potent Antitumor Activities in Preclinical Models, Mol. Cancer Ther., 21(4): 635-646 (2022).
Yonesaka, et al., B7-H3 Negatively Modulates CTL-Mediated Cancer Immunity, Clin. Cancer Res., 24(11): 2653-2664 (2018).
PCT/US2024/031449 International Search Report and Written Opinion mailed Nov. 20, 2024.
Simecek, J., et al., Benefits of NOPO as chelator in gallium-68 peptides, exemplified by preclinical characterization of (68)Ga-NOPO-c(RGDfK), Mol. Pharm., 11(5): 1687-1695 (2014).

* cited by examiner

1. Compound C8
2. Compound C8 + 20X Compound C10

1. C8
2. C8 + 20X C118
3. C8 + 20X C119
4. C8 + 20X C120

12A

12B

1. C8
2. C8 + 20X C10

1. C117
2. C117 + 100X C10

FIG. 19A
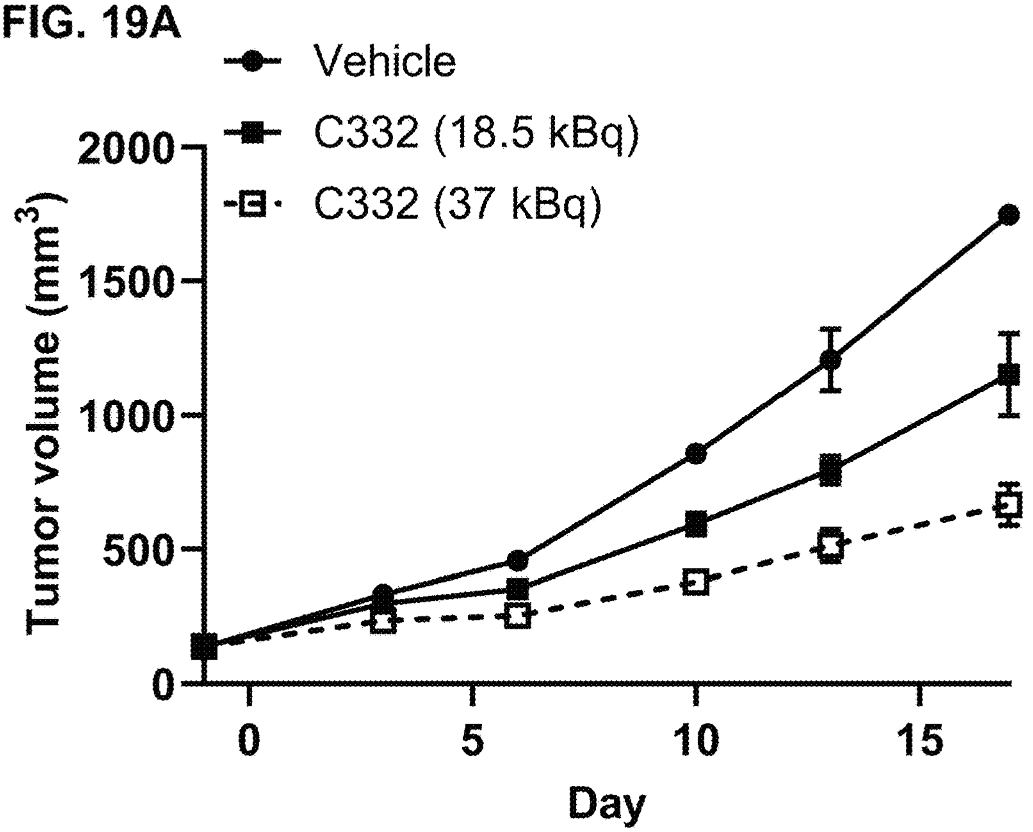
FIG. 19B
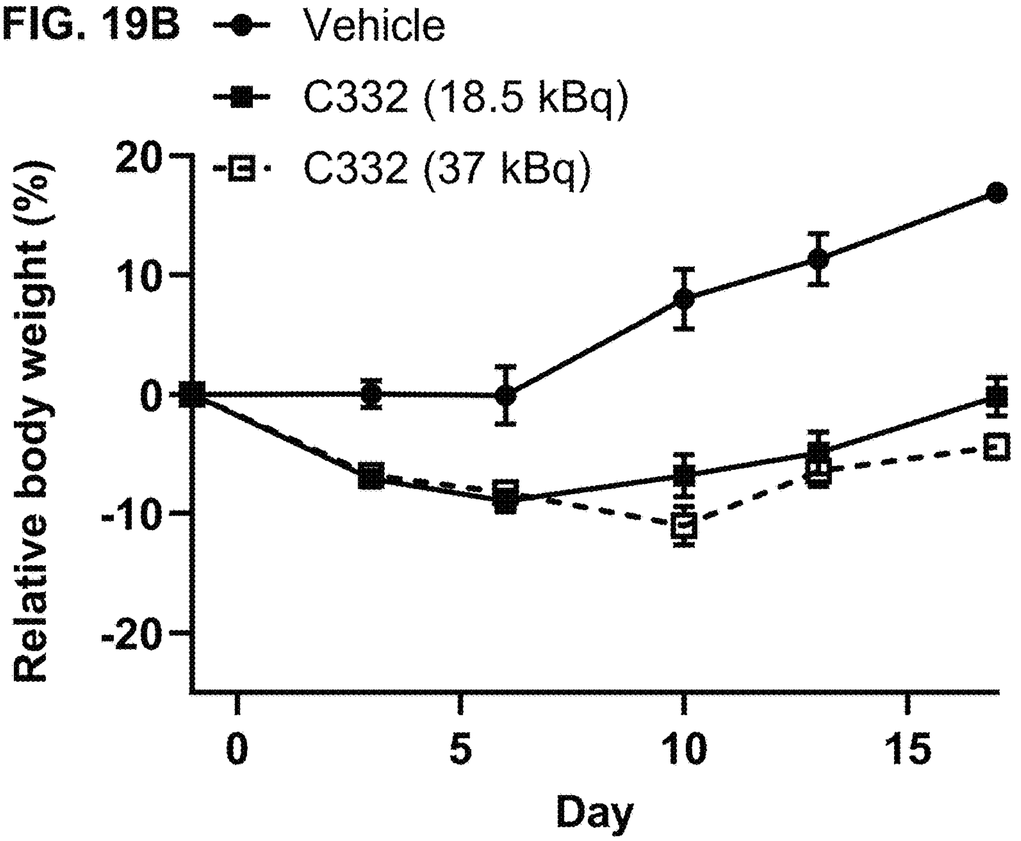
FIGS. 19A-19B

FIG. 19C
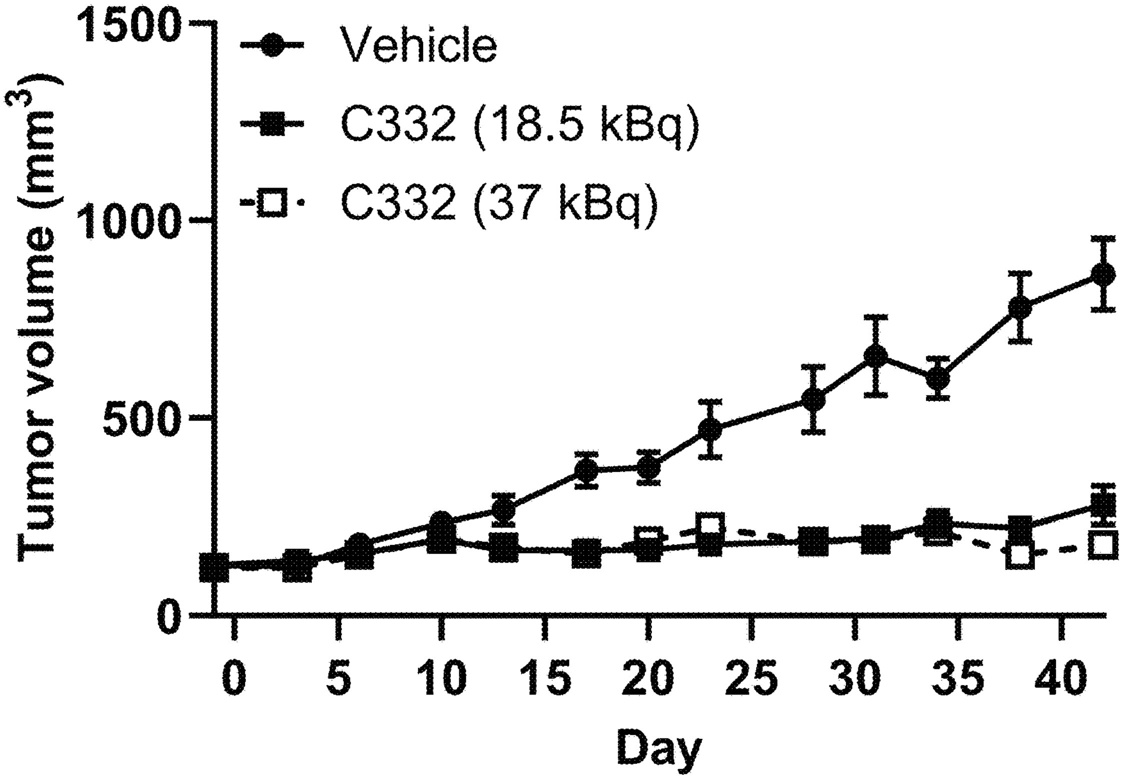
FIG. 19D
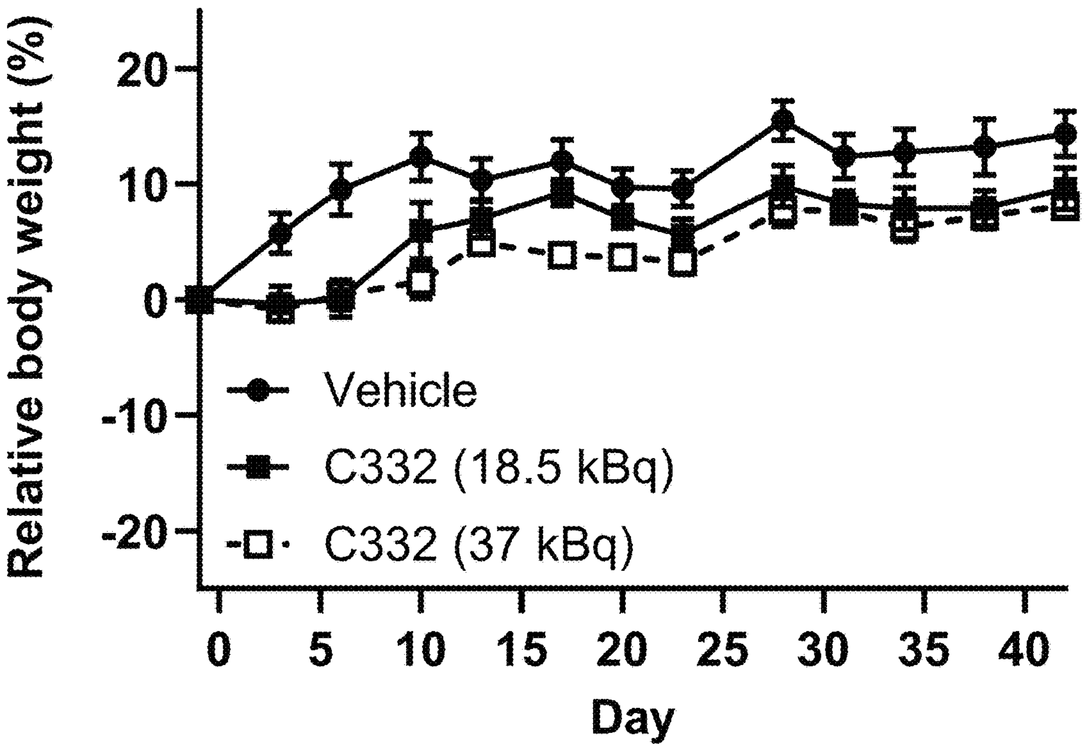
FIGS. 19C-19D

FIG. 20A
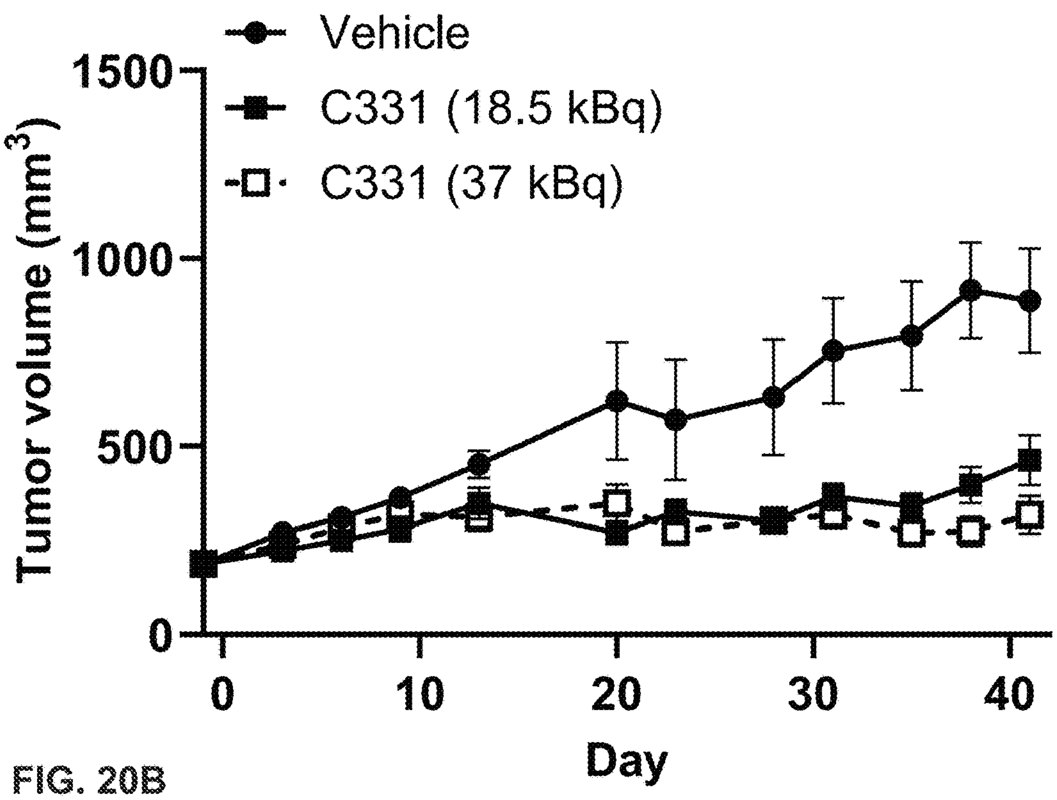
FIG. 20B
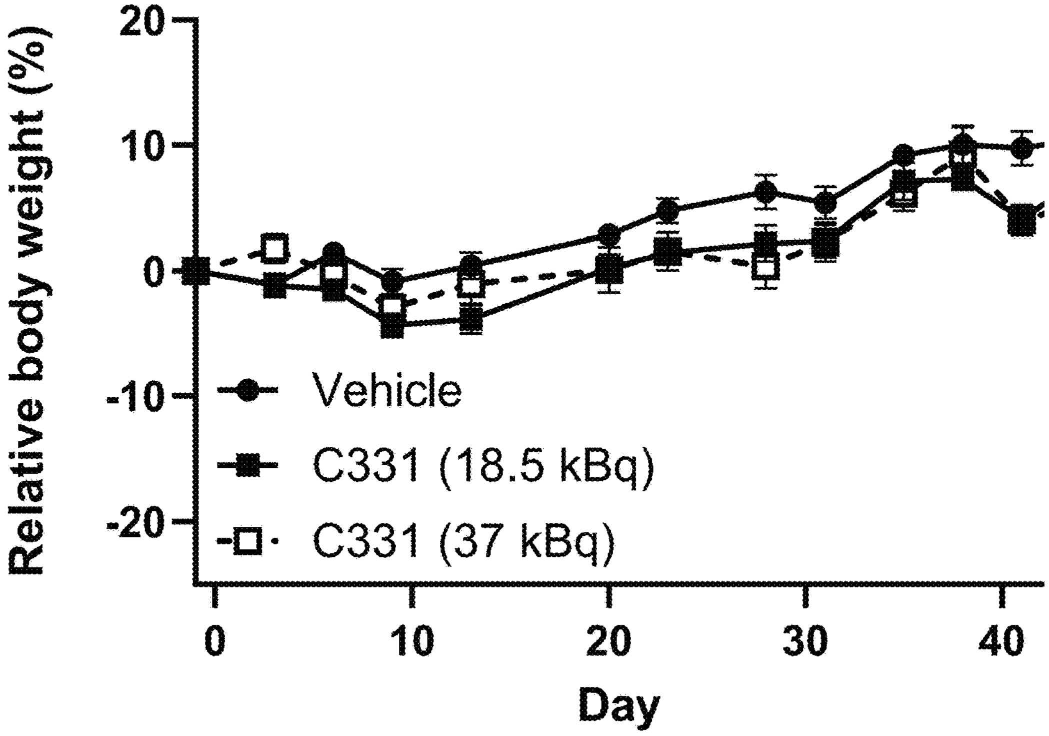
FIGS. 20A - 20B

B7-H3 MINIPROTEINS, CONJUGATES, AND USES THEREOF

CROSS-REFERENCE TO RELATED APPLICATIONS

This application is a continuation of International Application No. PCT/US2024/059036, filed on Dec. 6, 2024, which claims the benefit of and priority to U.S. Provisional Patent Application Nos. 63/607,988, filed on Dec. 8, 2023; 63/636,076, filed on Apr. 18, 2024; 63/650,364 and 63/650,365, each filed on May 21, 2024; and 63/721,990 filed on Nov. 18, 2024, the disclosures of each of which are incorporated by reference herein in their entireties for all purposes.

SEQUENCE LISTING

This application contains a Sequence Listing that has been submitted electronically in XML format and is hereby incorporated by reference in its entirety. The XML file, created on Dec. 6, 2024, is named AKT-035WO_SL.xml, and is 931,498 bytes in size.

BACKGROUND

Cancer is a leading cause of death worldwide. Classical cancer therapies such as radiotherapy, chemotherapy, and surgical procedures can be accompanied by severe side effects including due to killing of healthy non-cancerous cells. Newer therapeutics enhance the targeting of cytotoxic drugs to tumor cells, relative to earlier therapies, including those that use biologics conjugates.

SUMMARY

The present disclosure provides technologies such as compositions and methods of use and manufacture thereof to address needs in the field of cancer. For example, in contrast to classical cancer diagnostics or therapies, targeted molecules can be designed to increase specificity and decrease toxicity of, e.g., imaging or therapeutic modalities. For instance, delivery of a therapeutic such as a chelator and/or radionuclide (e.g., alpha emitter) using a polypeptide to specifically target the therapeutic to the tumor microenvironment provides focused treatment to tumor cells and avoids or reduces risk of toxicity to surrounding healthy tissues by the therapeutic targeted to, e.g., a tumor.

In contrast to classical cancer therapies, radionuclide therapies are more targeted and less toxic. For instance, delivery of a radionuclide specifically to a tumor microenvironment allows for selective direction of radiation towards tumor tissue, effectively killing malignant cells while preserving the surrounding healthy tissue. For example, a radionuclide can employ a targeting molecule that specifically binds to an antigen expressed at an increased level and/or density on the surface of tumor cells relative to non-tumor cells. Binding of the radionuclide to the antigen-positive tumor cells targets radiation to those cells without targeting healthy tissue. Full-length antibodies have previously been evaluated as targeting moieties; however, due to considerations such as their large size, full length antibodies can have several challenges such as having poor tumor tissue penetration and a long-circulating half-life. Accordingly, a need remains for new approaches to specifically target tumors, and particularly solid tumors. The present disclosure provides technologies that meet this and other needs.

Among other things, the present disclosure provides polypeptides, compositions comprising the polypeptides and conjugates comprising the polypeptides (e.g., miniproteins) that target tumor microenvironments and/or tumor cells conjugated to one or more additional components including, for example, a linker, chelator, and/or radionuclide (e.g., an alpha emitter). In some embodiments, the polypeptides specifically and strongly bind to B7-H3. In certain embodiments, a polypeptide or conjugate of the disclosure confers improved tumor penetration, decreased off-target toxicity and/or accumulation, improved stability (e.g., relative to a comparator polypeptide), as well as improved affinity for B7-H3 (e.g., relative to currently existing technologies (e.g., antibodies, e.g., antibody-drug conjugates, polypeptides, etc.) In some embodiments, such conjugates are used in treatment of cells expressing a target (e.g., B7-H3). In some such embodiments, the cells are cancer cells.

The disclosure also provides the insight that compositions and conjugates provided herein can be even further improved, such as by increasing stability (e.g., thermal stability), while maintaining or increasing strength of binding to B7-H3. For example, contemplated herein, in some embodiments, conjugates, such as radionuclide conjugates of the disclosure may be improved, such as by improvement on one or more measures including thermal stability, efficacy and/or reduction in toxicity grade and/or off-target effects (e.g., in a cell-based assay, e.g., when administered to a subject in need thereof), by modification of one or more amino acids in a polypeptide sequence of the conjugate (e.g., relative to a reference or starting sequence) and/or addition of one or more decoys.

These and other aspects and features of the disclosure are provided and described in the following detailed description and claims.

In one aspect, the disclosure provides a composition, comprising a polypeptide having an amino acid sequence, wherein the amino acid sequence comprises: at least two constraints; an arginine, modified arginine, or modified lysine at a position corresponding to amino acid 3, a lysine at a position corresponding to amino acid 5, an isoleucine at a position corresponding to amino acid 6, a tryptophan at a position corresponding to amino acid 14, at least one modified lysine residue at a position corresponding to amino acid 24, and an alanine, arginine, or modified lysine at a position corresponding to 29, where each position is linear, from N-to-C-terminus, beginning at position 1, relative to SEQ ID NO: 267, wherein the modification comprises at least one small alkyl group attached to the nitrogen of the lysine side chain or to the Guanidino group nitrogen of the arginine side chain, wherein the at least one small alkyl group optionally comprises a methyl, dimethyl, or trimethyl; at least 48 amino acids in length; and has a binding affinity for B7-H3 stronger than 100 nM as measured in a cell-based assay.

In some embodiments, the at least two constraints comprises at least two disulfide bridges. In some embodiments, the composition further comprises at least one additional constraint. In certain embodiments, the at least one additional constraint is a lactam bridge. In some embodiments, the at least one additional constraint is a disulfide bridge.

In certain embodiments, the polypeptide has an amino acid sequence comprising any one of SEQ ID NOs: 204 and 262-272. In some embodiments, the polypeptide is part of a compound selected from any one of C234-235 and C309-C332.

In one aspect, the disclosure provides a composition comprising a polypeptide of at least 48 amino acids in length and having an amino sequence according to Formula VI (SEQ ID NO: 541), comprising at least four cysteines and two disulfide bonds, wherein X24 is (Kme) or (Kme2); X29 is (Kme) or A or R; X32 is (Kme), D, or (Cit); and X45 is (Kme) or K.

In another aspect, the disclosure provides a composition comprising a polypeptide having an amino acid sequence comprising an amino acid sequence according to Formula III (SEQ ID NO: 538) as follows:

CAX3EKIAALSEIIWLPCLX19YAQIX24AFIX28X29LNX32DPCX36SX38X39ILSEAX4 5ELCS, wherein X3 is (Kme3) or R or (Rme); X19 is T or N; X24 is (Kme) or (Kme2); X28 is A or (Kme); X29 is (Kme) or A or R; X32 is (Kme) or D or (Cit); X36 is Q or N; X38 is S or A; X39 is E or N; and X45 is K or (Kme). In certain embodiments, the polypeptide has an amino acid sequence comprising any one of SEQ ID NOs: 204 and 262-272. In some embodiments, the polypeptide is part of a compound selected from any one of C234-235 and C309-C332.

In one aspect, the composition comprising a polypeptide having an amino acid sequence comprising an amino acid sequence according to Formula IV (SEQ ID NO: 539) as follows:

```
CAX3EKIAALSEIIWLPCLX19YAQIX24AFIAX29LNX32DPCQSSEIL

SEAX45ELCS,
```

wherein X3 is (Kme3) or R or (Rme); X19 is T or N; X24 is (Kme) or (Kme2); X29 is (Kme) or A; X32 is (Kme) or D; and X45 is (Kme) or K. In some embodiments, the polypeptide has an amino acid sequence comprising any one of SEQ ID NOs: 204, 262, 265, 267, and 268.

In certain embodiments, the polypeptide is part of a compound selected from any one of C234, C235, C298, C299, C304, C305, C308, C309, C310, C311, C320, C323, C325, C326, and C332.

In another aspect, the disclosure provides a composition comprising a polypeptide having an amino acid sequence comprising an amino sequence according to Formula V (SEQ ID NO: 540) as follows:

```
CAX3EKIAALSEIIWLPCLTYAQIX24AFIX28X29LNX32DPCQSSEIL

SEAX45ELCS,
```

wherein X3 is (Kme3) or (Rme) or R; X24 is (Kme) or (Kme2); X28 is A or (Kme); X29 is (Kme) or A or R; X32 is (Kme) or D or (Cit); and X45 is (Kme) or K. In some embodiments, the polypeptide has an amino acid sequence comprising any one of SEQ ID NOs: 265, 266, 267, 270, and 272. In certain embodiments, the polypeptide is part of a compound selected from any one of C304-C309, C314, C315, C318, C319, C323, C324, C325, C328, C330, and C332.

In one aspect, the disclosure provides a composition comprising a polypeptide having an amino acid sequence comprising an amino acid sequence according to Formula VI (SEQ ID NO: 541) as follows:

```
CA(Kme3)EKIAALSEIIWLPCLTYAQIX24AFIAX29LNX32DPCQSSE

ILSEAX45ELCS,
```

wherein X24 is (Kme) or (Kme2); X29 is (Kme) or A or R; X32 is (Kme) or D or (Cit); and X45 is (Kme) or K. In some embodiments, the polypeptide has an amino acid sequence comprising any one of SEQ ID NOs: 204, 262, 265, 266, 267, 270, and 272. In certain embodiments, the polypeptide is part of a compound selected from any one of C234, C235, C298, C299, C304-C309, C314, C315, C318-C320, C323, C324, C325, C328, C330, and C332.

In another aspect, the disclosure provides a composition, comprising a B7-H3 binding polypeptide having an amino acid sequence comprising at least 48 amino acids, wherein the amino acids include (i) a cysteine at each of four positions corresponding to 1, 17, 35, and 48 of SEQ ID NO: 267 and wherein X3 is (Kme3) or R or (Rme); X19 is T or N; X24 is (Kme) or (Kme2); X28 is (Kme) or A; X29 is (Kme) or A or R; X32 is (Kme) or D or (Cit); X36 is Q or N; X38 is S or A; X39 is E or N; X45 is (Kme) or K, and X49 is S or absent.

In one aspect, the disclosure provides a composition, comprising a B7-H3 binding polypeptide having an amino acid sequence, wherein the amino acid sequence comprises: at least four cysteines, which form two disulfide bonds; at least one modified lysine residue at a position corresponding to X24 of SEQ ID NO: 267, wherein the modification comprises at least one small alkyl group attached to the nitrogen of the lysine side chain, optionally comprising a methyl, dimethyl, or trimethyl; at least 48 amino acids in length; and has a binding affinity for B7-H3 stronger than 100 nM as measured in a cell-based assay. In some embodiments, the polypeptide is a miniprotein. In certain embodiments, the polypeptide is at least 48 amino acids in length, but no greater than 100 amino acids in length. In certain embodiments, the polypeptide binds to B7-H3 with an affinity of stronger than 100 nM as measured in a cell-based assay.

In some embodiments, the amino acid sequence of a polypeptide according to the present disclosure shares at least 90% identity to any one of SEQ ID NOs: 204 and 262-537, and includes at least one lysine or arginine with at least one modification comprising at least one small alkyl group bonded to the nitrogen of the lysine side chain or to the Guanidino group nitrogen of the arginine side chain, optionally selected from: trimethyl, dimethyl, and monomethyl. In some embodiments, the amino acid sequence of the polypeptide shares at least 90% identity to at least 44 amino acids of a reference polypeptide, which reference polypeptide is longer than 47 amino acids in length and binds to B7-H3 with a strength of at least 10 nM on a cell-based assay, and/or has an inhibition constant of no weaker than 10 nM. In some embodiments, the amino acid sequence of the polypeptide shares at least 90% identity to at least 44 amino acids of any one of SEQ ID NOs: 198-537, provided that the 44 amino acids include at least four cysteine residues that form at least two disulfide bridges. In some embodiments, the amino acid sequence of the polypeptide shares 100% identity to at least 44 amino acids of a reference polypeptide, which reference polypeptide is longer than 47 amino acids in length. In some embodiments, the amino acid sequence shares at least 90% identity to at least 44 amino acids as set forth in any one of SEQ ID NO: 199, 204, 241, or 262-272. In some embodiments, the amino acid sequence shares 100% identity to at least 44 amino acids as set forth in any one of SEQ ID NO: 199, 204, 241, or 262-272.

In some embodiments, the amino acid sequence comprises at least four cysteines with at least two disulfide bridges. In some embodiments, the polypeptide is at least 48 amino acids in length. In one aspect, the disclosure provides a composition comprising a polypeptide having an amino acid sequence comprising SEQ ID NO: 267. In certain embodiments, the composition comprises C234, C235, and C298-C333 as set forth in Table 2C.

In one aspect, the disclosure provides a composition comprising a polypeptide having an amino acid sequence comprising any one of SEQ ID NOs: 204 and 262-272.

In certain embodiments, a composition of the disclosure (e.g., a B7-H3 polypeptide, e.g., a B7-H3 binding miniprotein) further comprises a radionuclide. Depending on context, the radionuclide is selected from Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211. In certain embodiments, a polypeptide of the disclosure comprises a C-terminus comprising an —OH or an —NH2. In some embodiments, the binding affinity of a composition provided herein, for B7-H3, is stronger than 100 nM. In certain embodiments, the inhibition constant is no weaker than 100 nM.

In some embodiments, a composition of the disclosure (e.g., comprising a polypeptide), further comprises one or more of a linker, chelator, and radionuclide. In some embodiments, the linker comprises or consists of a polyethylene glycol (PEG) linker of PEG4, PEG2, PEG, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, or (Gly)n-(gGlu)n- or (PEG)n, wherein n is from 1 to 36, (Gly)1-10, or any fragment or combination via covalent bond thereof. In some embodiments, the chelator comprises or consists of DOTA, Crown, NOPO, Macropa, lead specific chelator (PSC), N-succinimidyl 3-(tri-n-butylstannyl)benzoate (BuSTB), or N-succinimidyl 3-trimethylstannylbenzoate (MeSTB). In some embodiments, the radionuclide is selected from Ac-225, Cu-64, Ga-68, Lu-177, Pb-212, In-111, Cu-67, La-132, La-135, Ce-134, F-18, 1-131, I-124, Pb-203, Th-232, Bi-123, Sm-153, Ra-225, Tb-165, or At-211.

In certain embodiments, if the polypeptide comprises any one of SEQ ID NOs: 198-537 the polypeptide further comprises a linker, wherein the linker is PEG4, and an optional chelator, wherein the chelator is DOTA. In some embodiments, when present, the linker is attached to the N-terminus of the polypeptide. In some embodiments, the C-terminal amino acid of the polypeptide is not a cysteine. In some embodiments, when present, the chelator is attached to either the polypeptide or the linker. In some embodiments, when present, the radionuclide is attached to the chelator.

In one aspect, the disclosure provides a composition comprising a formula selected from one or more of (M)x-L-C-R, (M)x-L-C, (M)x-C-R, (M)x-L-R, (M)x-C, (M)x-L, and (M)x-R, wherein M comprises a polypeptide (M), L comprises a linker (L), C comprises a chelator (C), R comprises a radionuclide (R), and x is 1, 2, 3, or 4, wherein M has an amino acid sequence comprising an amino acid sequence with at least 90% identity to at least 44 amino acids of any one of SEQ ID NOs: 198-537. In some embodiments, M has an amino acid sequence comprising an amino acid sequence with at least 90% identity to any one of SEQ ID NOs: 198-537. In certain embodiments, M has an amino acid sequence comprising an amino acid sequence with 100% identity to at least 44 amino acids of any one of SEQ ID NOs: 198-537. In some embodiments, M has an amino acid sequence comprising an amino acid sequence with 100% identity to any one of SEQ ID NOs: 198-537. In certain embodiments, the linker comprises or consists of a polyethylene glycol (PEG) linker of PEG4, PEG, PEG2, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, or (Gly)n-(gGlu)n- or (PEG)n, wherein n is from 1 to 36, (Gly)1-10, or any fragment or combination via covalent bond thereof. In certain embodiments, the chelator comprises or consists of DOTA, Crown, NOPO, Macropa, lead specific chelator (PSC), N-succinimidyl 3-(tri-n-butylstannyl)benzoate (BuSTB), or N-succinimidyl 3-trimethylstannylbenzoate (MeSTB). In some embodiments, the radionuclide Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211.

In one aspect, the disclosure provides a composition comprising a formula selected from one or more of (M)x-L-C-R, (M)x-L-C, (M)x-C-R, (M)x-L-R, (M)x-C, (M)x-L, and (M)x-R, wherein M comprises a polypeptide (M), L comprises a linker (L), C comprises a chelator (C), R comprises a radionuclide (R), and x is 1, 2, 3, or 4, wherein M has an amino acid sequence comprising an amino acid sequence with at least 90% identity to at least 44 amino acids of any one of SEQ ID NOs: 204 and 262-272. In certain embodiments, M has an amino acid sequence comprising an amino acid sequence with at least 90% identity to any one of SEQ ID NOs: 204 and 262-272. In some embodiments, M has an amino acid sequence comprising an amino acid sequence with 100% identity to at least 44 amino acids of any one of SEQ ID NOs: 204 and 262-272. In certain embodiments, M has an amino acid sequence comprising an amino acid sequence with 100% identity to any one of SEQ ID NOs: 204 and 262-272. In some embodiments, L is present, L comprises or consists of a polyethylene glycol (PEG) linker of PEG4, PEG, PEG2, PEG6, PEG8, PEG12, PEG24, lys(MPB)-PEG4, PEG36, an ester linker, an amide linker, a maleimide linker a valine-citrulline linker, a hydrazone linker, a N-succinimidyl-4-(2-pyridyldithio)butyrate (SPDB) linker, a succinimidyl-4-(N-maleimidomethyl)cyclohexane-1-carboxylate (SMCC) linker, a vinylsulfone-based linker, a propanoic acid linker, a dTyr-Gly-Phe (yGF) linker, a caproleic acid linker, or (Gly)n-(gGlu)n- or (PEG)n, wherein n is from 1 to 10, (Gly)1-10, or any fragment or combination via covalent bond thereof. In some embodiments, when C is present, C comprises or consists of DOTA, Crown, NOPO, Macropa, lead-specific chelator (PSC), N-succinimidyl 3-(tri-n-butylstannyl)benzoate (BuSTB), or N-succinimidyl 3-trimethylstannylbenzoate (MeSTB). In some embodiments, when R is present, R comprises or consists of Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211. In certain embodiments, when present, the linker is attached to the N-terminus of the polypeptide. In certain embodiments, the C-terminal amino acid of the polypeptide is not a cysteine. In some embodiments, when present, the chelator is attached to either the polypeptide or the linker. In some embodiments, when present, the radionuclide is attached to the chelator. In certain embodiments, the polypeptide comprises at least one disulfide bridge. In certain embodiments, the polypeptide comprises at least two disulfide bridges. In certain embodiments, the composition and/or polypeptide thereof selectively binds to B7-H3. In some embodiments, the polypeptide has a binding affinity for B7-H3 of 10 pM to 200 nM, 10 pM to 100 nM, or 10 nM to 100 nM, in vivo, ex vivo, or in vitro and/or as measured in a cell-based assay. In some embodiments, the polypeptide has a binding inhibition constant of no weaker than 100 nM.

In one aspect, the disclosure provides a composition comprising a polypeptide-drug conjugate, comprising a polypeptide and at least one drug moiety, wherein the polypeptide comprises an amino acid sequence having at least 90% identity to at least 48 amino acids a polypeptide having an amino acid sequence set forth in any one of SEQ ID NOs: 198-537. In certain embodiments, the polypeptide comprises at least four cysteines and two disulfide bridges. In some embodiments, the drug moiety is selected from a topoisomerase inhibitor, an auristatin (e.g., monomethyl auristatin E), a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, a dolastatin, a maytansinoid, a MetAP (methionine aminopeptidase), an inhibitor of nuclear export of proteins CRM1, a DPPIV inhibitor, proteasome inhibitors, inhibitors of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder, a DHFR inhibitor, and an immunotoxin.

In one aspect, the disclosure provides a composition comprising an isolated compound or pharmaceutically acceptable salt thereof, or a neutral molecule, comprising an optional linker (L), and one or more of a polypeptide (M), chelator (C) or radionuclide (R), wherein M has an amino acid sequence comprising an amino acid sequence with at least 90% identity to at least 44 amino acids any one of SEQ ID NOs: 198-537 and 538-543 and 546-550, including amino acid substitutions as set forth in Table 1E.

In another aspect, the disclosure provides a composition comprising, a compound designed to bind to B7-H3, which compound comprises or consists of a polypeptide having an amino acid sequence comprising an amino acid sequence with at least 90% identity to at least 44 amino acids any one of SEQ ID NOs: 198-537 or 538-543 and 546-550, including amino acid substitutions as set forth in Table 1E, and further comprises a modified N and/or C-terminus. In some embodiments, M has an amino acid sequence comprising an amino acid sequence with at least 90% identity to at least 44 amino acids of any one of SEQ ID NOs: 198-537 or 538-543 and 546-550, including amino acid substitutions as set forth in Table 1E. In some embodiments, M has an amino acid sequence comprising an amino acid sequence with at least 90% identity to any one of SEQ ID NOs: 198-537 or 538-543 and 546-550, including amino acid substitutions as set forth in Table 1E. In some embodiments, M has an amino acid sequence comprising an amino acid sequence with 100% identity to at least 44 amino acids of any one of SEQ ID NOs: 198-537 or 538-543 and 546-550, including amino acid substitutions as set forth in Table 1E. In some embodiments, M has an amino acid sequence comprising an amino acid sequence with 100% identity to any one of SEQ ID NOs: 198-537 or 538-543 and 546-550, including amino acid substitutions as set forth in Table 1E. In some embodiments, the modified N-terminus comprises one or more of an NH2-, Acetyl-, PEGn-, wherein n=0-36, DOTA-, or Biotin-. In certain embodiments, the C terminus comprises an —NH2 or an —OH. In certain embodiments, the polypeptide selectively binds to B7-H3. In some embodiments, the polypeptide has a binding affinity of stronger than about 100 nM to B7-H3, in vivo or in a cell-based assay.

In one aspect, the disclosure provides a compound comprising a miniprotein having an amino acid sequence comprising an amino acid sequence with at least 90% identity to at least 44 amino acids of SEQ ID NO: 267, and further comprising one or more additional components according to a formula M-L-C-R, wherein M is the miniprotein, L is a linker, C is a chelator, and R is a radionuclide. In some embodiments, M has an amino acid sequence comprising an amino acid sequence with 100% identity to at least 44 amino acids of SEQ ID NO: 267. In certain embodiments, M has an amino acid sequence comprising an amino acid sequence with at least 90% identity to SEQ ID NO: 267. In some embodiments, M has an amino acid sequence comprising an amino acid sequence with 100% identity to SEQ ID NO: 267. In some embodiments, L comprises or consists of a polyethylene glycol (PEG) linker of PEG4, PEG, PEG2, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, any linker set forth in Table 2A or Table 2C, or (Gly)n-(gGlu)n- or (PEG)n, wherein n is from 1 to 10, (Gly)1-10, or any fragment or combination via covalent bond thereof. In certain embodiments, C comprises or consists of DOTA, Crown, NOPO, Macropa, lead specific chelator (PSC), N-succinimidyl 3-(tri-n-butylstannyl)benzoate (BuSTB), or N-succinimidyl 3-trimethylstannylbenzoate (MeSTB). In some embodiments, R comprises or consists of Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211.

In one aspect, the disclosure provides a compound comprising a miniprotein with at least 90% identity to at least 48 amino acids of the amino acid sequence of SEQ ID NO: 267, wherein the N and/or C-terminus comprise between one and thirty additional amino acids, and/or wherein the C-terminus comprises one fewer amino acids or up to 30 additional amino acids, provided that the entire miniprotein is no greater than about 100 amino acids in length.

In one aspect, the disclosure provides a pharmaceutical composition comprising a polypeptide or compound as provided herein; and a pharmaceutically acceptable excipient.

In one aspect, the disclosure provides, in a method of improving binding affinity strength of a polypeptide to B7-H3, the improvement comprising modifying at least three amino acid residues of a polypeptide, which polypeptide has at least 48 amino acids in length and has cysteines at positions corresponding to 1, 17, 35, and 48 of SEQ ID NO: 267, wherein a position corresponding to X24 is (Kme) or (Kme2); X29 is A or (Kme); and X32 is D or (Kme) or (Cit), and wherein X49 is S or absent.

In one aspect, the disclosure provides a method of treating cancer, the method comprising administering to a subject in need thereof, a composition comprising a conjugate comprising a polypeptide having an amino acid sequence, which comprises an amino acid sequence with at least 90% identity to at least 44 amino acids of any one of SEQ ID NOs: 198-537 and a radionuclide. In some embodiments, the polypeptide has at least four cysteines and two disulfide bridges. In certain embodiments, the radionuclide is associated with the polypeptide with a linker and/or chelator according to a formula M-L-C-R, wherein M is the polypeptide, L is a linker, C is a chelator, and R is the radionuclide. In some embodiments, the polypeptide has an amino acid sequence comprising or consisting of any of SEQ ID NOs: 204, or 262-272. In certain embodiments, L comprises or consists of a polyethylene glycol (PEG) linker of PEG4, PEG, PEG2, PEG6, PEG8, PEG12, PEG24, PEG36, lys (MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, any linker set forth in Table 2A, or (Gly)n-(gGlu)n- or (PEG)n, wherein n is from 1 to 10, (Gly)1-10, or any fragment or combination via covalent bond thereof. In certain embodiments, C comprises or consists of DOTA, Crown, NOPO, Macropa, lead specific chelator (PSC), N-succinimidyl 3-(tri-n-butylstannyl)benzoate (BuSTB), or N-succinimidyl 3-trimethylstannylbenzoate (MeSTB). In certain embodiments, R is Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211. In some embodiments, R is a therapeutic agent and/or an imaging agent. In some embodiments, R is Cu-64, Ga-68, Lu-177, In-111, Cu-67, La-132, or F-18.

In certain embodiments, the polypeptide is no longer than 100 amino acids in length.

In one aspect, the disclosure provides a method of reducing kidney cell uptake and/or increasing tumor uptake of a composition comprising administering to a subject a B7-H3 binding protein having an amino acid sequence comprising at least one modified lysine residue at a position corresponding to X24 of SEQ ID NO: 241, wherein the modification comprises at least one small alkyl group attached to the nitrogen of the lysine side chain, optionally comprising a methyl, dimethyl, or trimethyl, and the reduction is as compared to administering to the subject or a control subject an otherwise identical composition but not comprising the modified lysine residue at the position corresponding to X24.

In one aspect, the disclosure provides, in a method of treating cancer, the improvement comprising administering a composition comprising a B7-H3 binding protein having an amino acid sequence comprising at least one modified lysine residue at a position corresponding to X24 of SEQ ID NO: 241, wherein the modification comprises at least one small alkyl group attached to the nitrogen of the lysine side chain, optionally comprising a methyl, dimethyl, or trimethyl, and the reduction is as compared to administering to the subject or a control subject an otherwise identical composition but not comprising the modified lysine residue at the position corresponding to X24.

In one aspect, the disclosure provides a method of treating a subject with refractory or recurrent cancer comprising administering a composition, compound, or pharmaceutical composition as provided herein, thereby treating the cancer.

In one aspect, the disclosure provides a method of improving biodistribution of a pharmaceutical composition for a B7-H3 positive population of cancer cells in a subject having a B7-H3-positive cancer, comprising contacting the population with a polypeptide that has a modified lysine at a position corresponding to X24 of SEQ ID NO: 241, wherein the lysine is modified by adding at least one small alkyl group to a lysine side chain and wherein the biodistribution is improved as compared to contacting the population without the modified lysine at a position corresponding to X24 of SEQ ID NO: 241.

In one aspect, the disclosure provides a method of diagnosing presence of a B7-H3 positive population of cancer cells comprising: contacting a population of cells with the composition, compound, or pharmaceutical composition as provided herein; detecting the presence of the composition, compound, or pharmaceutical composition of step (a) by measuring a signal; and comparing the detection in step (b) to a control signal; and diagnosing cancer if the composition, compound, or pharmaceutical composition of step (a) is detected above the control signal. In some embodiments, the contacting is performed by administering to a subject in need thereof. In certain embodiments, the administering is intravenous or subcutaneous. In some embodiments, the contacting is outside of the subject, optionally in vitro with a biopsy sample.

In one aspect, the disclosure provides a method of treating a cancer in a subject, the method comprising administering to the subject a composition comprising a composition, compound, or pharmaceutical composition as provided herein.

In one aspect, the disclosure provides use of a composition, compound, or pharmaceutical composition in accordance with the disclosure.

In one aspect, the disclosure provides a method of treating a subject in need thereof comprising administering to the subject in need thereof a composition, compound, or pharmaceutical composition in accordance with the disclosure In certain embodiments, the subject is diagnosed as having cancer. In certain embodiments, a cancer cell from the subject expresses B7-H3. In certain embodiments, the expression of B7-H3 is higher in the cancer cell than in a non-cancer cell, which expression can be measured by protein and/or nucleic acid levels. In certain embodiments, the non-cancer cell is obtained from the subject. In some embodiments, the composition, compound, or pharmaceutical composition is internalized in a cell expressing human B7-H3. In some embodiments, the cancer is selected from breast cancer, ovarian cancer, melanoma, pancreatic cancer, peripheral neuroma, glioblastoma, adrenocortical carcinoma, AIDS-related lymphoma, anal cancer, urothelial cancer, bladder cancer, meningioma, glioma, astrocytoma, cervical cancer, chronic myeloproliferative disorders, colon cancer, endometrial cancer, ependymoma, esophageal cancer, Ewing's sarcoma, extracranial germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma, Kaposi sarcoma, laryngeal cancer, leukemia, lip cancer, oral cavity cancer, liver cancer, male breast cancer, malignant mesothelioma, medulloblastoma, Merkel cell carcinoma, metastatic squamous neck cell carcinoma, multiple myeloma and other plasma cell neoplasms, mycosis fungoides and Sezary syndrome, myelodysplastic syndromes, nasopharyngeal cancer, neuroblastoma, non-small cell lung cancer, small cell lung cancer, head and neck cancer, skin cancer, oropharyngeal cancer, bone cancers, including osteosarcoma and malignant fibrous histiocytoma of bone, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilms tumor and other childhood kidney tumors. In some embodiments, the composition, compound, or pharmaceutical composition is administered intravenously or subcutaneously.

In one aspect, the disclosure provides a method of targeting cancer cells expressing B7-H3, the method comprising:

(i) determining or having determined a level of expression of B7-H3 in a population of cancer cells; and (ii) administering to a subject in need thereof a composition comprising a composition, compound, or pharmaceutical composition as provided herein, wherein the polypeptide of the composition, compound, or pharmaceutical composition is designed to specifically bind to human B7-H3, wherein the composition, compound, or pharmaceutical composition is attached to the surface and/or internalized into one or more B7-H3 expressing cancer cells.

In one aspect, the disclosure provides a method of targeting cancer cells expressing B7-H3, the method comprising administering to a subject in need thereof a composition comprising a composition, compound, or pharmaceutical composition as provided herein, wherein the polypeptide of the composition, compound, or pharmaceutical composition is designed to specifically bind to human B7-H3; wherein (i) the subject has cancer cells that express B7-H3; and (ii) the composition, compound, or pharmaceutical composition is attached to the surface and/or internalized into one or more B7-H3 expressing cancer cells. In some embodiments, the method further comprises determining or having determined that the cancer cells express B7-H3. In certain embodiments, the subject is treated after the administering as compared to prior to the administering.

In one aspect, the disclosure provides in a method of targeting a population of cancer cells expressing B7-H3, the improvement comprising contacting the population with the composition according to a composition, compound, or pharmaceutical composition as provided herein, wherein a position corresponding to X24 (relative to SEQ ID NO: 241) comprises a lysine with at least one additional small alkyl group attached to the nitrogen in the side chain, wherein the composition is taken up less by kidney cells than in a composition comprising a polypeptide that does not have a small alkyl group attached to a nitrogen on the side chain of a lysine at X24, wherein, optionally, the small alkyl group is part of a monomethyl, dimethyl, or trimethyl group.

In one aspect, the disclosure provides a conjugate comprising: (i) a polypeptide (M) that specifically binds to B7-H3; (ii) a chelator (C) conjugated to (M) through an optional linker (L), wherein (C) comprises DOTA, and (L), when present, comprises PEG, wherein the PEG is optionally PEG-4; and (iii) a radionuclide (R) chelated to (C), wherein (R) is Actinium-225.

In one aspect, the disclosure provides a conjugate comprising: (i) a polypeptide (M) that specifically binds to B7-H3; (ii) a chelator (C) conjugated to (M) through an optional linker (L), wherein (C) comprises DOTA, and (L), when present, comprises PEG, wherein the PEG is optionally PEG-4; and (iii) a radionuclide (R) chelated to (C), wherein (R) is Copper-64.

In one aspect, the disclosure provides a conjugate comprising: (i) a polypeptide (M) that specifically binds to B7-H3; (ii) a chelator (C) conjugated to (M) through an optional linker (L), wherein (C) comprises DOTA, and (L), when present, comprises PEG, wherein the PEG is optionally PEG-4; and (iii) a radionuclide (R) chelated to (C), wherein (R) is Gallium-68.

In one aspect, the disclosure provides a conjugate comprising: (i) a polypeptide (M) that specifically binds to B7-H3; (ii) a chelator (C) conjugated to (M) through an optional linker (L), wherein (C) comprises DOTA, and (L), when present, comprises PEG, wherein the PEG is optionally PEG-4; and (iii) a radionuclide (R) chelated to (C), wherein (R) is Indium-111.

In one aspect, the disclosure provides a conjugate comprising: (i) a polypeptide (M) that specifically binds to B7-H3; (ii) a chelator (C) conjugated to (M) through an optional linker (L), wherein (C) comprises DOTA, and (L), when present, comprises PEG, wherein the PEG is optionally PEG-4; and (iii) a radionuclide (R) chelated to (C), wherein (R) is Lead-212.

In one aspect, the disclosure provides a conjugate comprising: (i) a polypeptide (M) that specifically binds to B7-H3; (ii) a chelator (C) conjugated to (M) through an optional linker (L), wherein (C) comprises DOTA, and (L), when present, comprises PEG, wherein the PEG is optionally PEG-4; and (iii) a radionuclide (R) chelated to (C), wherein (R) is Lutetium-177.

A conjugate comprising: (i) a miniprotein (M) that specifically binds to B7-H3; (ii) an N-terminal modification, conjugated to (M) through an optional linker (L), wherein (L), when present, comprises PEG, wherein the PEG is optionally PEG-4; and (iii) the N-terminal modification comprises a biotin.

In certain embodiments, M has an amino acid sequence comprising an amino acid sequence with at least 90% identity to at least 44 amino acids of any one of SEQ ID NOs: 198-537. In some embodiments, M has an amino acid sequence comprising an amino acid sequence with at least 90% identity to any one of SEQ ID NOs: 198-537. In some embodiments, M has an amino acid sequence comprising an amino acid sequence with 100% identity to at least 44 amino acids of any one of SEQ ID NOs: 198-537. In certain embodiments, M has an amino acid sequence comprising an amino acid sequence with 100% identity to any one of SEQ ID NOs: 198-537. In certain embodiments, the amino acid sequence has an amino acid sequence comprising at least 90% identity to at least 44 amino acids of SEQ ID NO: 267, wherein the polypeptide has: at least four cysteines, which form two disulfide bonds; an arginine, modified arginine, or modified lysine at a position corresponding to amino acid 3, a lysine at a position corresponding to amino acid 5, an isoleucine at a position corresponding to amino acid 6, a tryptophan at a position corresponding to amino acid 14, at least one modified lysine residue at a position corresponding to amino acid 24, and an alanine, arginine, or modified lysine at a position corresponding to 29, where each position is linear, from N-to-C-terminus relative to SEQ ID NO: 267, wherein the modification comprises at least one small alkyl group attached to the nitrogen of the lysine side chain or to the Guanidino group of the arginine side chain, optionally comprising a methyl, dimethyl, or trimethyl; at least 48 amino acids in length; and has a binding affinity for B7-H3 stronger than 100 nM in a cell-based assay. In some embodiments, the amino acid sequence comprises an amino acid sequence with at least 90% identity to any one of SEQ ID NOs: 204 or 262-272. In some embodiments, the amino acid sequence comprises an amino acid sequence with 100% identity to at least 44 amino acids of any one of SEQ ID NOs: 204 or 262-272. In certain embodiments, the an amino acid sequence comprises an amino acid sequence with 100% identity to at least 44 amino acids of SEQ ID NO: 267. In certain embodiments, the amino acid sequence comprises an amino acid sequence with at least 90% identity to SEQ ID NO: 267. In certain embodiments, the amino acid sequence comprises an amino acid sequence with 100% identity to SEQ ID NO: 267. In some embodiments, the amino acid sequence comprises or consists of any one of SEQ ID NOs: 204 and 262-272. In some embodiments, the amino acid sequence comprises or consists of SEQ ID NO: 267.

In one aspect, the disclosure provides an isolated polynucleotide comprising one or more nucleic acid sequences encoding a polypeptide selected from any one of SEQ ID NOs: 198-537; or a nucleic acid sequence encoding a polypeptide comprising at least 90%, 95%, 96%, 97%, 98%, 99% or greater identity to any one of SEQ ID NOs: 198-573. In some embodiments, the disclosure provides a vector comprising an isolated polynucleotide as provided herein. In some embodiments the disclosure provides a host cell transformed with an isolated polynucleotide or vector as provided herein.

In one aspect, the disclosure provides a method of evaluating locations of one or more populations of cancerous cells in a subject, the method comprising administering to the subject a composition, compound, pharmaceutical composition, or conjugate as provided herein, and detecting to determine location of the composition in the subject, wherein the composition, compound, or pharmaceutical composition comprises a detectable label. In certain embodiments, the detectable label comprises a radionuclide.

In one aspect, the disclosure provides, in a method of decreasing kidney uptake of a composition administered to detect and/or treat one or more populations of cancer cells, the improvement comprising administering to a subject in need thereof, a composition, compound, pharmaceutical composition, or conjugate as provided herein, wherein a position corresponding to X24 of SEQ ID NO: 241 comprises a lysine with at least one additional small alkyl group attached to the nitrogen in the side chain, wherein the composition is taken up less by kidney cells than in a composition comprising a polypeptide that does not have a small alkyl group attached to a nitrogen on the side chain of a lysine at a position corresponding to X24 of SEQ ID NO: 241, wherein, optionally, the small alkyl group is part of a monomethyl, dimethyl, or trimethyl group. In certain embodiments, the detecting comprises an imaging procedure allows for selecting subjects, monitoring subjects, and/or treating subjects with a therapeutic comprising a miniprotein designed to bind to B7-H3 expressed on one or more cancer cells in the one or more populations of cancer cells. In some embodiments, the therapeutic comprises a composition, compound, conjugate, or pharmaceutical composition as provided herein.

In one aspect, the disclosure provides a method of improving delivery of a radionuclide to a population of cancer cells in a subject, the method comprising administering a composition, compound, conjugate, or pharmaceutical composition as provided herein, wherein the amino acid sequence of the polypeptide comprises an amino acid at a position corresponding to X24 of SEQ ID NO: 241 comprising a lysine with at least one additional small alkyl group attached to the nitrogen in the side chain, wherein uptake by kidney cells is less than with a polypeptide that does not have a small alkyl group attached to a nitrogen on the side chain of a lysine at a position corresponding to X24 of SEQ ID NO: 241. In some embodiments, the small alkyl group comprises a monomethyl, dimethyl, or trimethyl group.

In one aspect, the disclosure provides, in a method of treating an individual with cancer, the improvement comprising reducing one or more off-target effects or toxicity measures by administering a composition, compound, conjugate, or pharmaceutical composition as provided herein, wherein the amino acid sequences of the polypeptide comprises an amino acid at a position corresponding to X24 of SEQ ID NO: 241 comprising a lysine with at least one additional small alkyl group attached to the nitrogen in the side chain, wherein uptake by kidney cells is less than with a polypeptide that does not have a small alkyl group attached to a nitrogen on the side chain of a lysine at a position corresponding to X24 of SEQ ID NO: 241.

In one aspect, the disclosure provides, in a method of treating an individual with cancer, the improvement comprising achieving a reduction in concentration of R in a kidney tissue in the presence of a composition, compound, conjugate, or pharmaceutical composition as provided herein, wherein the amino acid sequence of the polypeptide comprises an amino acid corresponding to position X24 of SEQ ID NO: 241, and wherein X24 comprises a lysine with at least one additional small alkyl group attached to the nitrogen in the side chain, wherein uptake by kidney cells is less than with a polypeptide having an amino acid sequence that does not comprise a small alkyl group attached to a nitrogen on the side chain of a lysine at a position corresponding to X24 of SEQ ID NO: 241, as compared to the concentration of R in the kidney tissue in the absence the composition, compound, pharmaceutical composition, or conjugate. In some embodiments, the reduction in concentration of R in the kidney tissue is measured by urine output of R as measured by percent of administered radiation recovered or by detection as measured by a cell-based in vitro assay, or an in vivo detection assay. In some embodiments, the administering of the composition can be repeated at least 2, 3, 4, 5, 6, 7, 8, 9, or 10 times or more in the presence of the composition having 90% identity to at least 44 amino acids of SEQ ID NO: 241 including a modified lysine at positions corresponding to X24 of SEQ ID NO: 241 than in the presence of an Q, V, L, or K at positions corresponding to X24.

In one aspect, the disclosure provides, in a method of reducing uptake by a kidney tissue of a composition, the improvement comprising administering a composition comprising (a) a radionuclide therapeutic comprising at least a polypeptide and a radionuclide (R); wherein the polypeptide has at least 90% identity to at least 44 amino acids of SEQ ID NO: 241 and/or has a modified lysine at positions corresponding X24 of SEQ ID NO: 241, such that in the presence of the modified lysine, the radionuclide is less concentrated in the kidney tissue than in the absence of the polypeptide.

In another aspect, the disclosure provides a method comprising administering to a subject in need thereof a compound that binds to B7-H3 and includes at least one modified lysine at a position corresponding to X24 of SEQ ID NO: 241, wherein the administering of the compound having a miniprotein with the at least one modified lysine reduces one or more off target effects, toxicity grades, and/or uptake and/or retention in a kidney tissue as compared to a compound not having a modified lysine (e.g., an unmodified lysine, e.g., an L, V, or Q) at a position corresponding to X24. In some embodiments, the polypeptide has an amino acid sequence comprising an amino acid sequence with 100% identity to at least 44 amino acids of any one of SEQ ID NOs: 204 and 262-272. In some embodiments, the polypeptide has an amino acid sequence comprising an amino acid sequence with at least 90% identity to any one of SEQ ID NOs: 204 and 262-272. In some embodiments, the polypeptide has an amino acid sequence comprising an amino acid sequence with 100% identity to any one of SEQ ID NOs: 204 and 262-272.

In one aspect, the disclosure provides a method of treating an individual having or suspected of having a B7-H3-positive cancer, the method comprising administering to the individual: a means for blocking uptake and/or retention of a radiotherapeutic to kidney tissue, and a linker, a chelator, and a radionuclide. In some embodiments, the means for blocking uptake and/or retention of a radiotherapeutic to kidney tissue binds to B7-H3 and includes a modified lysine at a position corresponding to X24 of SEQ ID NO: 267 and/or have at least 90% identity to 40 amino acids of SEQ ID NO: 267 and/or have a modified lysine at a position corresponding to X24 of SEQ ID NO: 267. In some embodiments, the means further comprises a modified lysine at a position corresponding to X3 of SEQ ID NO: 267. In some embodiments, the means for blocking uptake and/or retention of a radiotherapeutic to the kidney tissue blocks uptake and/or retention to the kidney tissue greater than as compared to the blocking of uptake and/or retention to the kidney tissue by a means that does not include a modified lysine at a position corresponding to X24 of SEQ ID NO: 267 and/or have at least 90% identity to at least 44 amino acids of SEQ ID NO: 267 and/or have a modified lysine at a position corresponding to X24 of SEQ ID NO: 267. In some embodiments, the means for blocking uptake and/or retention of a radiotherapeutic to the kidney tissue blocks uptake and/or retention to the kidney tissue greater than as compared to the blocking of uptake and/or retention to the kidney tissue by a means that does not include a modified lysine at a position corresponding to X24 of SEQ ID NO: 267 and/or have at least 90% identity to at least 44 amino acids of SEQ ID NO: 267 and/or have a modified lysine at a position corresponding to X24 of SEQ ID NO: 267. In some embodiments, the means for blocking uptake and/or retention of a radiotherapeutic to the kidney tissue is a radiotherapeutic. In certain embodiments, the radiotherapeutic is targeted to a tumor or a population of cancer cells. In certain embodiments, the radiotherapeutic targeted to the tumor or the population of cancer cells is at a greater concentration than in the absence of the means for binding to kidney tissue. In some embodiments, the radiotherapeutic comprises a polypeptide that targets B7-H3. In some embodiments, the radiotherapeutic comprises or consists of a compound selected from C227-C608 and C611. In certain embodiments, the radionuclide of the radiotherapeutic is selected from Ac-225, Cu-64, Ga-68, In-111, Lu-177, or Pb-212.

In one aspect, the disclosure provides a kit comprising a polypeptide and instructions for use, wherein the polypeptide has an amino acid sequence as set forth in a polypeptide of a composition, compound, conjugate, or pharmaceutical composition as provided herein. In some embodiments, the polypeptide further comprises one or more of a linker, chelator, and radionuclide. In some embodiments, the linker comprises or consists of a polyethylene glycol (PEG) linker of PEG4, PEG, PEG2, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, or (Gly)n-(gGlu)n- or (PEG)n, wherein n is from 1 to 10, (Gly)1-10, or any fragment or combination via covalent bond thereof. In certain embodiments, the chelator comprises or consists of DOTA, NOPO, Crown, Macropa, lead specific chelator (PSC), N-succinimidyl 3-(tri-n-butylstannyl)benzoate (BuSTB), or N-succinimidyl 3-trimethylstannylbenzoate (MeSTB). In certain embodiments, prior to use, the compound is labeled with a radionuclide, wherein the radionuclide is chelated to the chelator to produce a composition with a formula M-L-C-R. In some embodiments, the radionuclide is selected from Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211. In some embodiments, the radionuclide is Ac-225, Cu-64, Ga-68, In-111, Lu-177, or Pb-212.

In certain embodiments, if the polypeptide has an amino acid comprising any of those set forth in any one of SEQ ID NOs: 199, 204, 241, or 262-272 and wherein the polypeptide further comprises a linker and/or a chelator, wherein the linker, when present, is PEG4, and the chelator, when present, is DOTA. In some embodiments, when present, the linker is attached to the N-terminus amino acid of the polypeptide. In some embodiments, the C-terminal amino acid of the polypeptide is not cysteine. In certain embodiments, when present, the chelator is attached to either the polypeptide or the linker. In certain embodiments, when present, the radionuclide is attached to the chelator. In certain embodiments, when present, the radionuclide is attached to the N-terminus amino acid of the polypeptide.

BRIEF DESCRIPTION OF FIGURES

FIG. 5A shows the median fluorescent intensity (MFI) plotted as a function of concentration of miniprotein administered to cancer cells. FIG. 5B shows the overlay of representative histograms of MFI for cancer cells treated with different concentrations of miniprotein relative to a vehicle control.

FIG. 10A is a bar graph showing percent uptake (on the y-axis) of an exemplary B7-H3-targeting scaffold B miniprotein conjugate (C4) alone/without a decoy (20 μM; column 1, x-axis) or in combination (column 2, x-axis) with a 20-fold molar excess of an exemplary scaffold A decoy (C120). FIG. 10B is a bar graph showing percent uptake (on the y-axis) of 20 μM of an exemplary B7-H3-targeting scaffold B miniprotein (C8) alone (20 μM; column 1, x-axis) or in combination (column 2; x-axis) with a 20-fold molar excess of an exemplary scaffold A decoy (C120). Error bars represent standard error of the mean (SEM).

FIG. 12A is a bar graph showing percent uptake (on the y-axis) of an exemplary B7-H3-targeting scaffold B miniprotein conjugate (C8) alone/without a decoy (20 μM; column 1, x-axis) or in combination (column 2, x-axis) with a 20-fold molar excess of an exemplary scaffold B decoy (C10). FIG. 12B is a bar graph showing percent uptake (on the y-axis) of an exemplary B7-H3-targeting scaffold B miniprotein conjugate (C117) alone/without a decoy (1 μM; column 1, x-axis) or in combination (column 2, x-axis) with a 100-fold molar excess of an exemplary scaffold B decoy (C10). Error bars represent standard error of the mean (SEM).

FIG. 16A shows % ID/g in kidney at 1, 4, 24, and 48 hours after administration. FIG. 16B shows % ID/g in tumor at 1, 4, 24, and 48 hours after administration.

FIG. 17A shows % ID/g in kidney at 1, 4, 24, and 48 hours after administration. FIG. 17B shows % ID/g in tumor at 1, 4, 24, and 48 hours after administration.

FIGS. 19A-19D show line graphs of efficacy data, as measured by tumor volume in a low (H1915) and high (H358) B7-H3 expressing cell line after 17 days (FIG. 19A, 1915 cells) and 42 days (FIG. 19C, H358 cells) respectively, each evaluated following administration of a single dose of vehicle or one of two concentrations (500 or 1000 nCi) of an exemplary 225-Ac labeled constrained B7-H3 miniprotein conjugate (C332). Corresponding bodyweights for FIG. 19A are shown in FIG. 19C and bodyweights for FIG. 19B are shown in FIG. 19D.

FIGS. 20A-20B show line graphs of efficacy data as measured by tumor volume (FIG. 20A) and bodyweight (FIG. 20B) between about 0-6 weeks after administration of a single dose of vehicle or one of two concentrations (500 or 1000 nCi) of an exemplary 225-Ac labeled constrained B7-H3 miniprotein conjugate (C331).

DETAILED DESCRIPTION

Figure 1A:
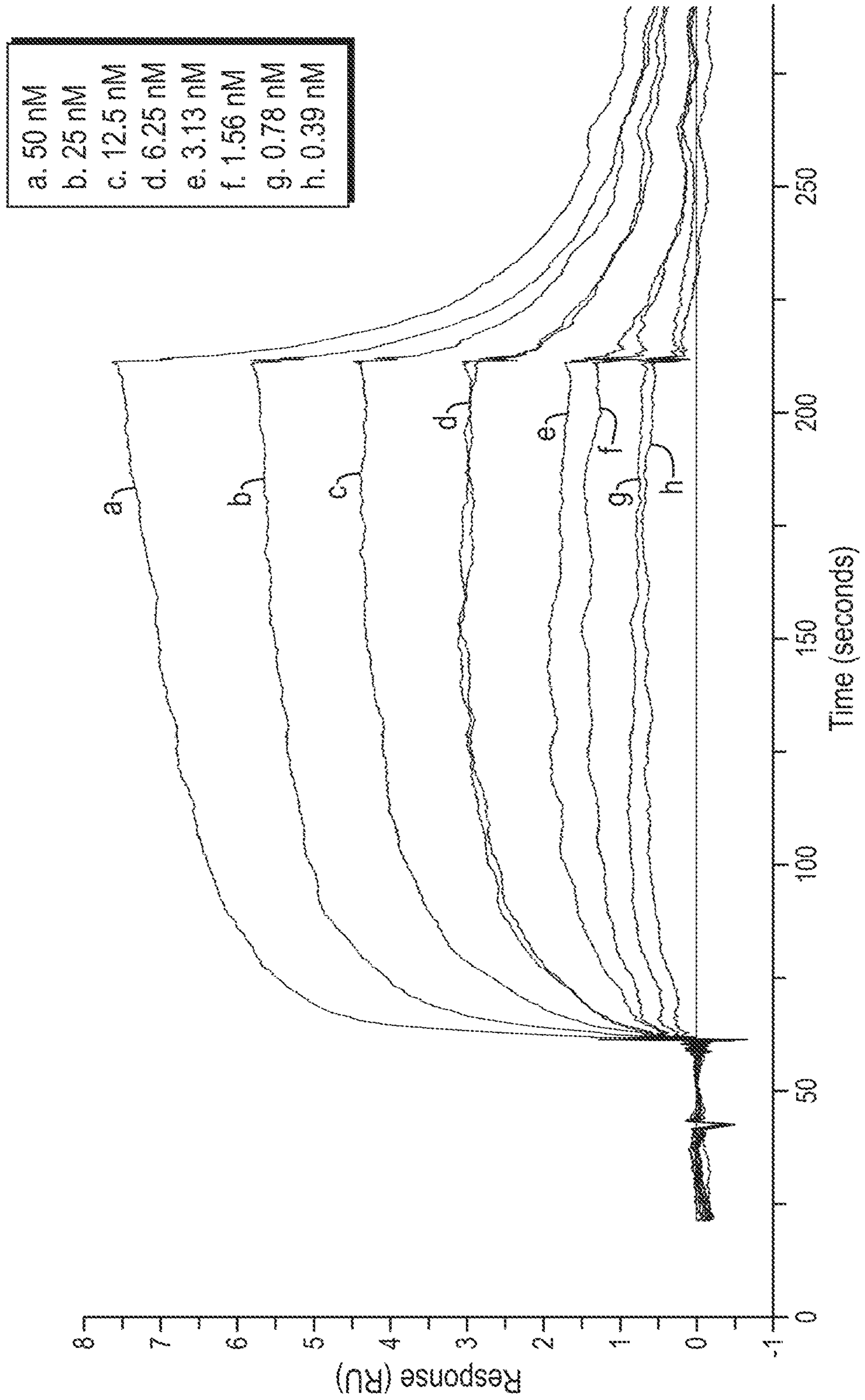
FIG. 1A shows binding affinity of an exemplary miniprotein (SEQ ID NO: 3) for B7-H3 at 50 nM (a), 25 nM (b), 12.5 nM (c), 6.25 nM (d), 3.13 nM (e), 1.56 nM (f), 0.78 nM (g), and 0.39 nM (h).
Figure 1B:
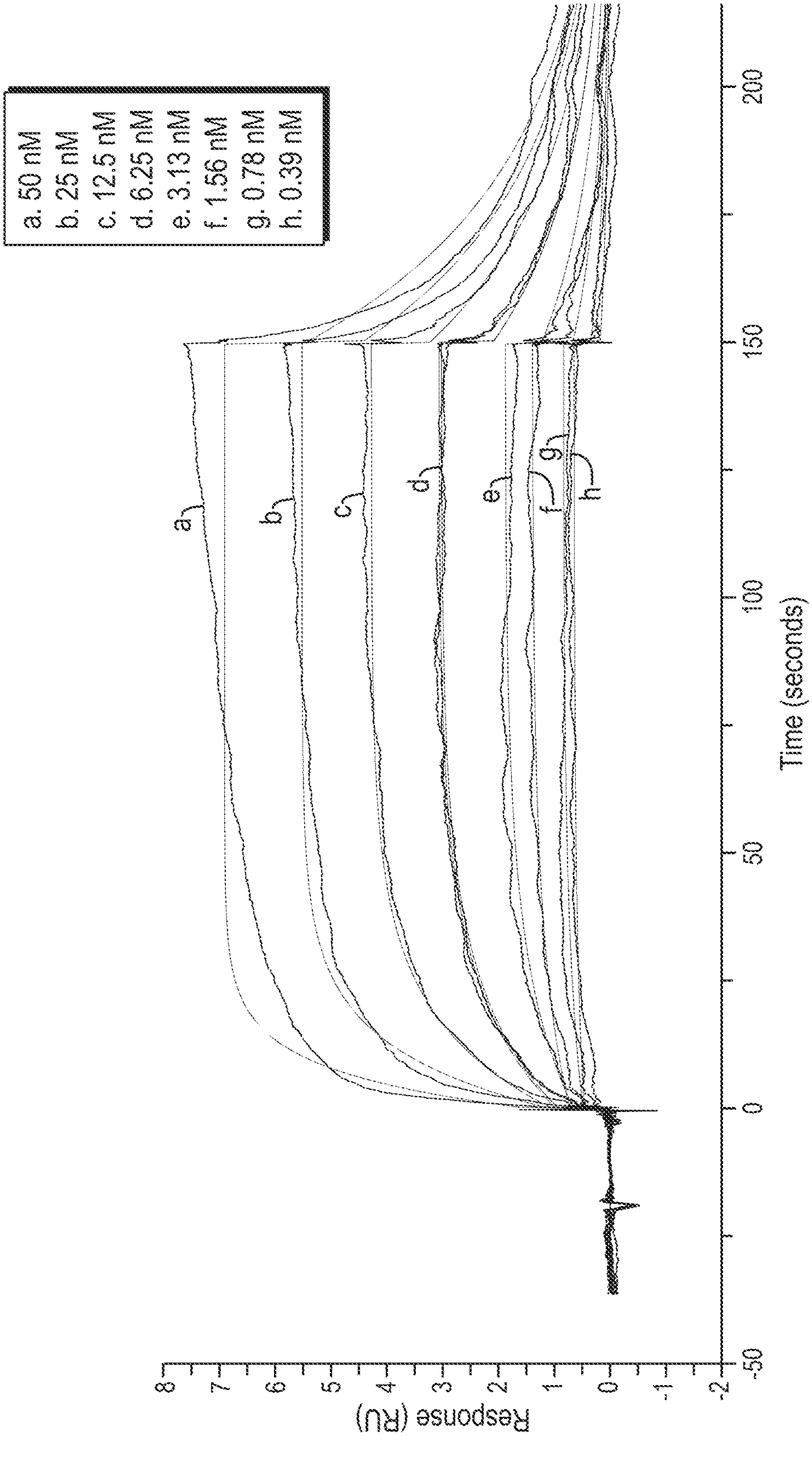
FIG. 1B shows the 1:1 binding model analysis for an exemplary miniprotein (SEQ ID NO: 3). Black lines are fitted by the model.
Figure 2A:
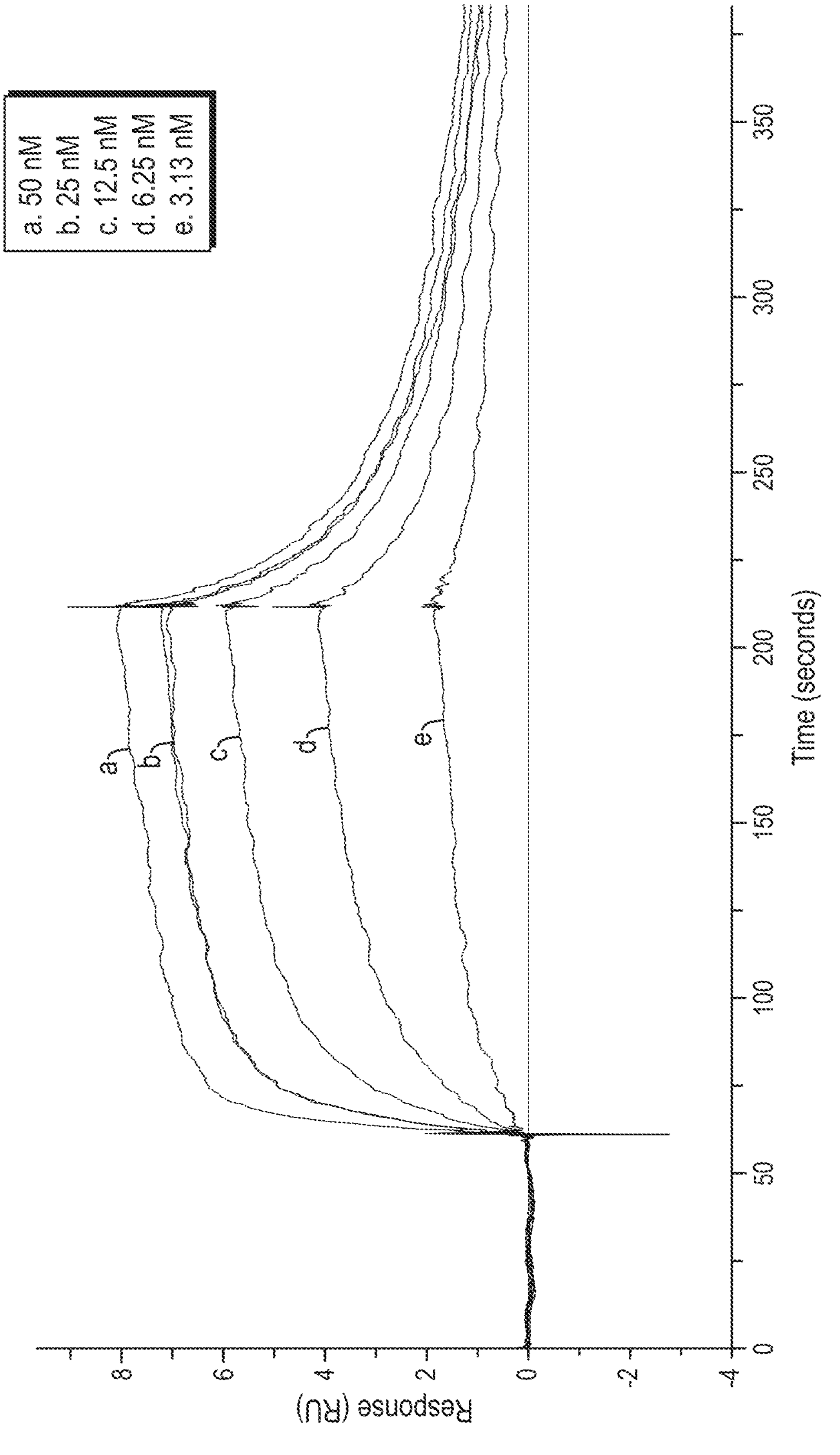
FIG. 2A shows binding affinity of an exemplary miniprotein (SEQ ID NO: 4, Run #1) for B7-H3 at 50 nM (a), 25 nM (b), 12.5 nM (c), 6.25 nM (d), and 3.13 nM (e).
Figure 2B:
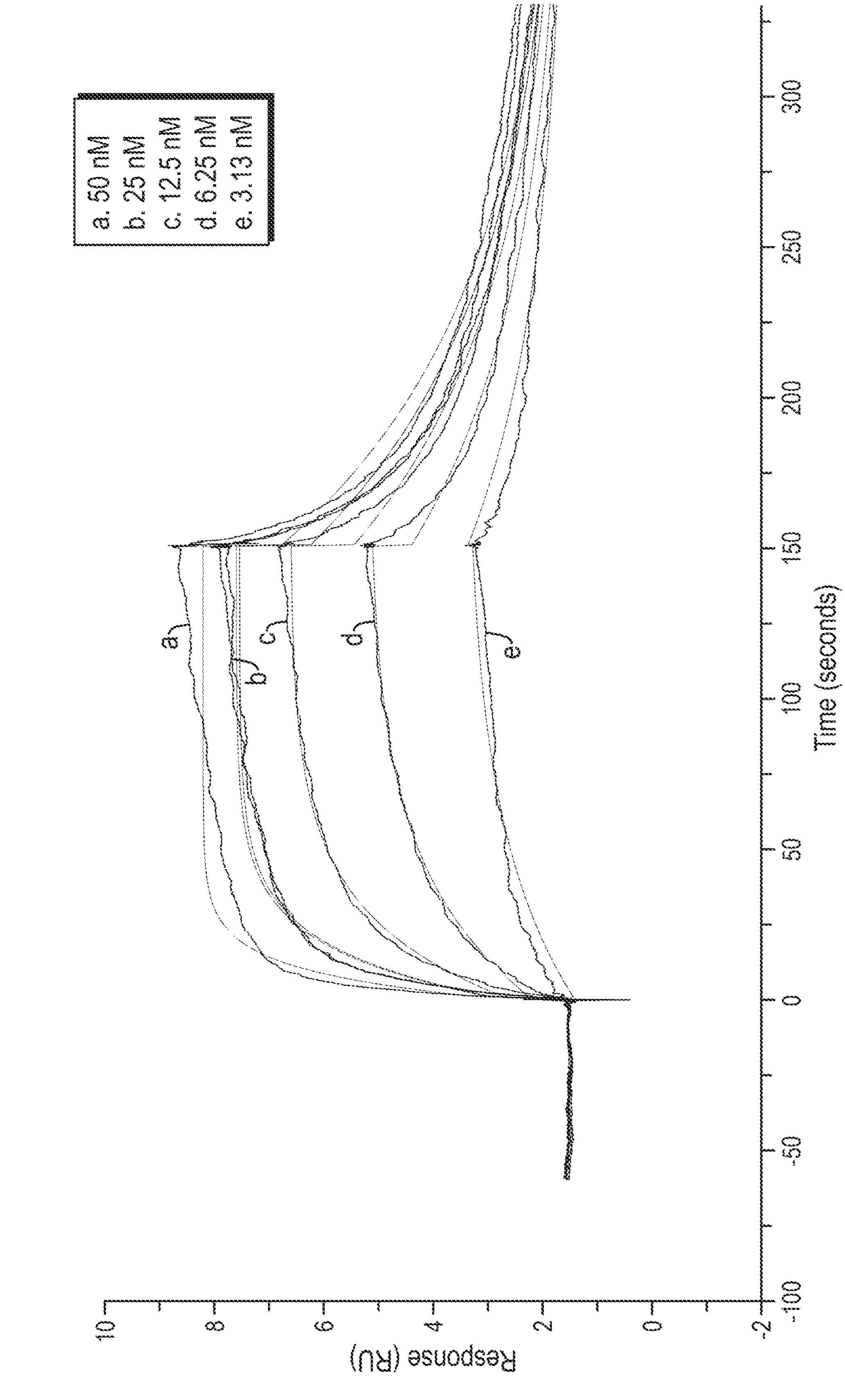
FIG. 2B shows the 1:1 binding model analysis for an exemplary miniprotein (SEQ ID NO: 4, Run #1). Black lines are fitted by the model.
Figure 3A:
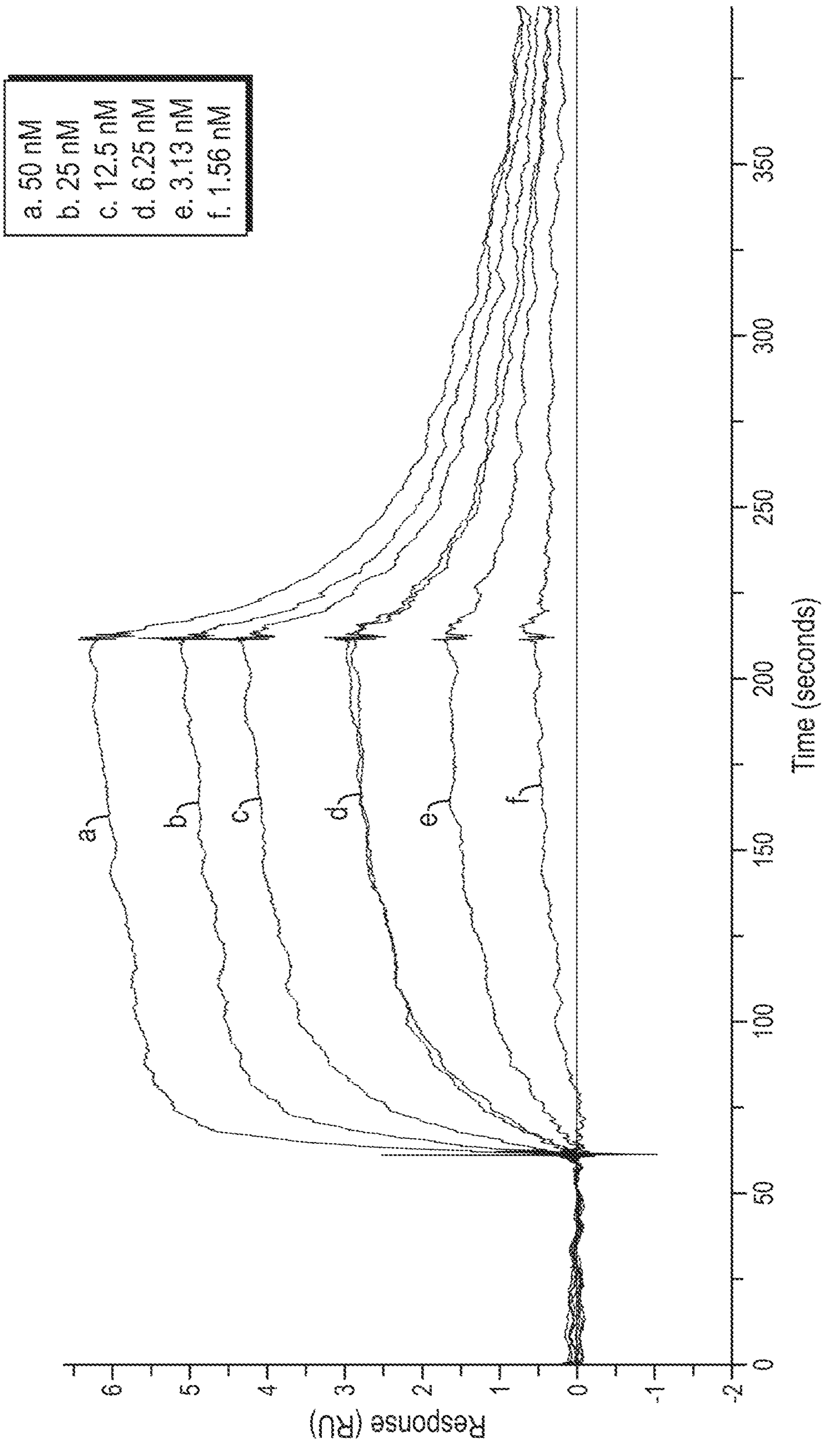
FIG. 3A shows binding affinity of an exemplary miniprotein (SEQ ID NO: 4, Run #2) for B7-H3 at 50 nM (a), 25 nM (b), 12.5 nM (c), 6.25 nM (d), 3.13 nM (e), and 1.56 nM (f).
Figure 3B:
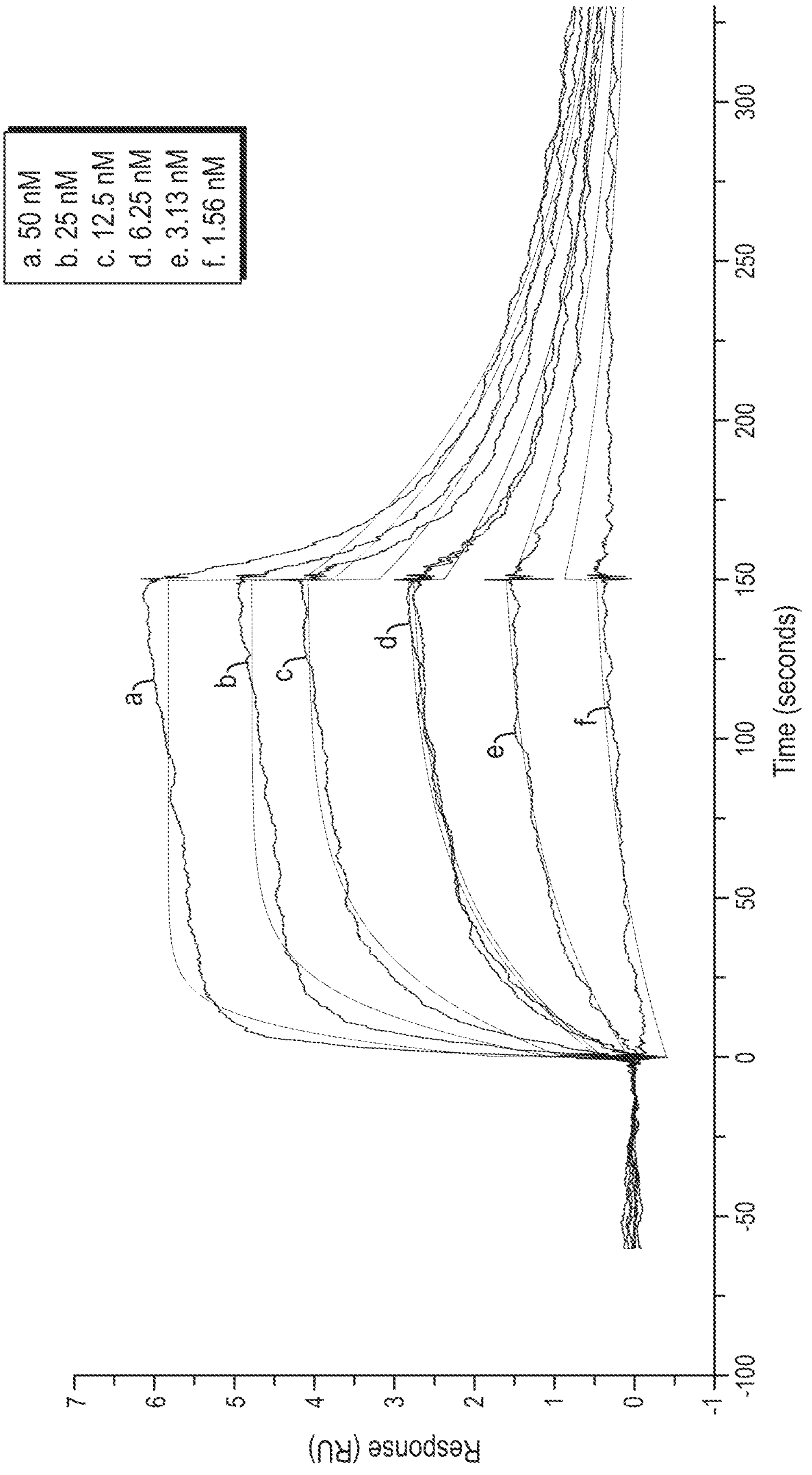
FIG. 3B shows the 1:1 binding model analysis for an exemplary miniprotein (SEQ ID NO: 4, Run #2). Black lines are fitted by the model.
Figure 4:
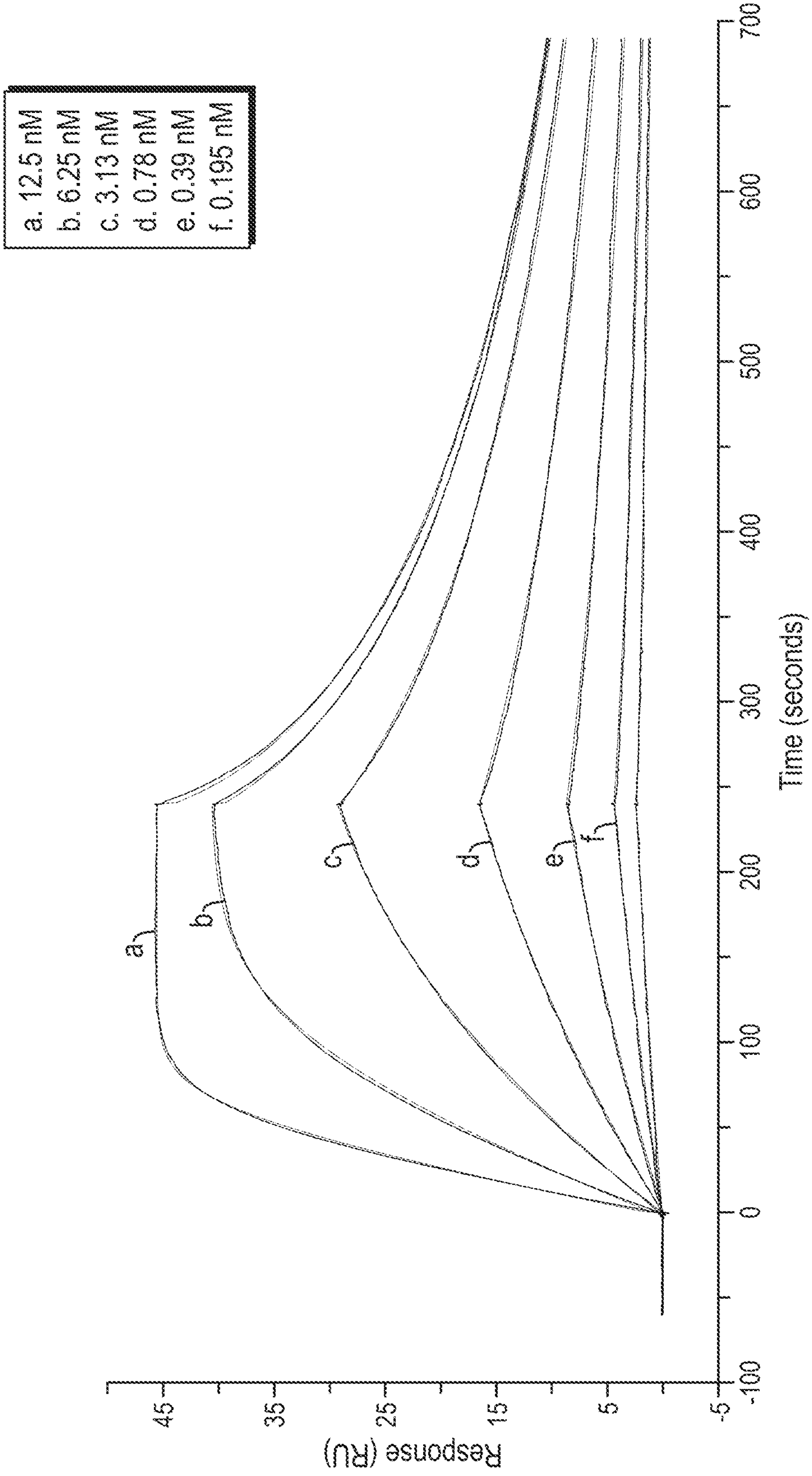
FIG. 4 shows the 1:1 binding model analysis for an exemplary miniprotein (SEQ ID NO: 6). Black lines are fitted by the model.

Among other things, the present disclosure provides compositions and methods of use thereof. In some embodiments, a composition selectively binds to a target (e.g., B7-H3). In some embodiments the composition comprises one or more therapeutic agents (e.g., a chelator, a radionuclide), wherein the therapeutic agent is selectively targeted to a cell expressing B7-H3 such that the B7-H3-expressing cell is treated and cells not expressing B7-H3 are not treated. The present disclosure recognizes that a source of a problem in treating cells expressing a target (e.g., cancer cells) is that traditional therapies are not selective enough to specifically target cells (e.g., cancer cells) and to deliver a therapeutic in a way that minimizes damage to surrounding cells (e.g., non-cancer cells) including, for example, cells around cancer cells and cells in non-target organs (e.g., kidney). Surrounding cells (e.g., as may be present in one or more non-tumor tissues) can also express the target at lower amounts or levels than the target cells. In some such embodiments, such expression may be undetectable. The present disclosure provides the insight that a combination of selective targeting (e.g., of B7-H3, e.g., by a polypeptide, e.g., a miniprotein, e.g., as provided herein) with a specific therapeutic such as a chelator and/or radionuclide (e.g., an alpha emitter) provides an advantage over previously and/or currently used therapeutics (e.g., antibodies, beta-emitters, etc.).

Furthermore, the present disclosure provides the insight that even with more specifically targeting therapeutics (e.g., such as those disclosed herein), certain challenges can still arise. Among other things, uptake to a tumor may be challenged by uptake, retention, and/or clearance by one or more non-target (e.g., non-tumor) tissues, for example, the kidney resulting in (1) faster clearance; (2) reduced tumor targeting (e.g., including due to uptake and/or retention by non-target tissue); and/or (3) non-target tissue (e.g., kidney) damage. The present disclosure recognizes that any or all of these challenges may be mitigated or prevented (i) with miniproteins as provided herein (e.g., such as disclosed in Table 2A and/or 2C), including, for example, miniproteins having particular features (e.g., constraints, e.g., as in Table 2C) and/or (ii) by combining administration of a therapeutic with administration of a decoy (e.g., as set forth in Table 2D). In some embodiments, the decoy reduces or prevents uptake by the kidney of a composition comprising a radionuclide. Without wishing to be bound by theory, the disclosure contemplates that improvement in treatment efficacy is at least maintained while reducing damage to the kidney and, in some embodiments, treatment efficacy is improved while simultaneously reducing risk of harm or actual harm to kidney tissue and/or renal system tissues (e.g., ureters, bladder, etc.).

Unless otherwise defined herein, scientific and technical terms used in connection with the present disclosure shall have the meanings that are commonly understood by those of ordinary skill in the art. Furthermore, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well-known and commonly used in the art.

The methods and techniques of the present disclosure are generally performed according to conventional methods well known in the art and as described in various general and more specific references that are cited and discussed throughout the present specification unless otherwise indicated. See, e.g., Sambrook et al., Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lane, Antibodies: A Laboratory Manual, Cold Spring Harbor Laboratory Press, Cold Spring Harbor, N.Y. (1990); Wittrup and VanAntwerp, Fine Affinity Discrimination by Yeast Surface Display and Flow Cytometry, Biotechnol. Prog. 2002, (16) 31-37; C. Queen et al., A humanized antibody that binds to the interleukin 2 receptor, Proc. Natl. Acad. Sci. USA 1989, 86 (24) 10029-10033; Scheinberg D A and McDevitt M R. Actinium-225 in targeted alpha-particle therapeutic applications. Curr Radiopharm. 2011; 4(4):306-320.

All publications, patents, and other references mentioned herein are hereby incorporated by reference in their entireties. In case of conflict, the present specification, including definitions, will control. Materials, methods, and examples as disclosed herein are illustrative only and not intended to be limiting.

Unless otherwise defined, all technical and scientific terms used herein have the same meaning as commonly understood by one of ordinary skill in the art to which this present disclosure pertains. Further, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well-known and commonly used in the art.

Throughout this specification and claims, the word "comprise" or variations such as "comprises" or "comprising," will be understood to imply the inclusion of a stated integer or group of integers but not the exclusion of any other integer or group of integers.

As used herein, ranges and amounts can be expressed as "about" a particular value or range, e.g., "about" one particular value, and/or to "about" another particular value. About also includes the exact amount. Hence "about 100 nucleotides" means "about 100 nucleotides" and also "100 nucleotides." Given context, the term "about" as used herein also includes an amount that would be expected to be within experimental error. If "about" appears before a quantitative value, the present disclosure also includes the specific quantitative value itself, unless specifically stated otherwise. In such instances "about" can also refer to a ±10% variation from the nominal value unless otherwise indicated or inferred. When values are expressed as approximations by use of the antecedent "about," it is understood that the disclosure also contemplates embodiments that specify the particular values and ranges of values without the approximations.

As used herein, the singular forms "a," "an" and "the" include plural referents unless context clearly dictates otherwise. Thus, for example, in some embodiments, reference to, e.g., decoys includes a plurality of decoys, a single decoy, etc.

As used herein, the expression "and/or" in connection with two or more recited objects includes individually each of the recited objects and the various combinations of two or more of the recited objects, unless otherwise understood from the context and use.

Unless otherwise indicated, and as an example for all sequences described herein under the general format "SEQ ID NO:", "nucleic acid comprising SEQ ID NO: 1" refers to a nucleic acid, at least a portion of which has either (i) the sequence of SEQ ID NO: 1, or (ii) a sequence complementary to SEQ ID NO: 1. The choice between the two is dictated by the context. For instance, if the nucleic acid is used as a probe, the choice between the two is dictated by the requirement that the probe be complementary to the desired target.

As used herein, the term "administration" refers providing a composition to a subject or system. Administration to a subject may be by any appropriate route, dose and/or dose schedule.

As used herein, the term "affibody" refers to a subgenus of miniproteins. An affibody is a molecule derived from the Z-domain of staphylococcal protein A that consists of three alpha helices with 58 amino acids and has a molar mass of about 6 kDa. See, for exemplary details of affibody structures and uses, Orlova, A; Magnusson, M; Eriksson, T L; Nilsson, M; Larsson, B; Höidén-Guthenberg, I; Widström, C; Carlsson, J et al. (2006). "Tumor imaging using a picomolar affinity HER2 binding affibody molecule," Cancer Res. 66 (8): 4339-48. Exemplary Affibody® Molecules are commercially available from Abcam Corp. Cambridge Mass. An affibody is stable at high temperatures and under acidic or alkaline conditions. Target specificity is obtained by randomization of 13 amino acids located in two alpha-helices involved in the binding activity of the parent protein domain (Feldwisch J, Tolmachev V.; (2012) Methods Mol Biol. 899:103-26).

As used herein, the term "affinity maturation" generally refers to a process whereby successive changes to a sequence (e.g., successive mutations) are made and selection of the polypeptide sequences are performed to choose one or more sequences with increased affinity relative to the "starting" sequence or another sequence with less affinity as compared to one with greater affinity.

As used herein, the terms "amino acid sequence" and "polypeptide" refer to a polymer of amino acids connected by one or more peptide bonds. A polypeptide of the present disclosure encompasses both naturally-occurring and non-naturally-occurring proteins, and any fragments, portions, peptides, mutants, derivatives, and analogs thereof. A polypeptide may be monomeric or polymeric. Further, a polypeptide may comprise a number of different domains each of which has one or more distinct activities. A polypeptide may be fully or partially synthetic or otherwise modified (i.e., comprising one or more synthetically-produced amino acids and/or modifications thereof). The term "peptide" may be used to refer to a short polypeptide, such as one comprising fewer than about 70 amino acids (e.g., between about 5, 10, 15, 20, 25, 30, 35, 40, 45, 50, 55, 60, 65, or 70 amino acids).

As used herein, a "compound" refers at least to a miniprotein with an amino acid sequence. Compounds may include miniproteins with different modifications, such as a N-terminal modification or a C-terminal modification. In various embodiments, a "compound" can include a miniprotein and one or more additional elements, examples of which include a linker, a chelator, and/or a radionuclide. For example, a compound may include a miniprotein conjugated to a chelator and/or a radionuclide e.g., via a linker. As denoted herein, compounds are identified with a specific compound number e.g., "C1," "C2," C3", etc. Different compounds may have different sequences. In various embodiments, different compounds may have the same sequence (e.g., assigned the same SEQ ID NO), but may have one or more of different modifications (e.g., different N-terminal or C-terminal modifications), different linkers, different chelators, and/or different radionuclides. N- and C-terminal modifications may include but not be limited to acetyl, acid, or amide (e.g., Acetyl, NH2, OH/COOH), such as provided in exemplary compounds and miniproteins of Table 2A or Table 2C. In some embodiments, a polypeptide according to the disclosure may have various modifications to its N-terminus (e.g., such as set forth in exemplary compounds in Table 2A or Table 2C), and can have an acid or amide group on its C-terminus (see, e.g., Table 2A or Table 2C). A given polypeptide having a particular amino acid sequence can have one or more N-terminal and/or C-terminal differences without materially changing the utility or function of the polypeptide, such as for binding to B7-H3 (e.g., for detection and/or treatment of cancer).

As used herein, the term "attenuate" as used herein generally refers to a functional deletion, including a mutation, partial or complete deletion, insertion, or other variation made to a gene sequence or a sequence controlling the transcription of a gene sequence, which reduces or inhibits production of the gene product, or renders the gene product non-functional. In some instances, a functional deletion is described as a knockout mutation. Attenuation also includes amino acid sequence changes by altering the nucleic acid sequence, placing the gene under the control of a less active promoter, down-regulation, expressing interfering RNA, ribozymes or antisense sequences that target the gene of interest, or through any other technique known in the art. In one example, the sensitivity of a particular enzyme to feedback inhibition or inhibition caused by a composition that is not a product or a reactant (non-pathway specific feedback) is lessened such that the enzyme activity is not impacted by the presence of a compound. In other instances, an enzyme that has been altered to be less active can be referred to as attenuated.

As used herein, the term "binder" refers to a subgenus of miniprotein. A binder is characterized in that it comprises or consists of a polypeptide (e.g., peptide) that is capable of binding or has known ability to engage and associate a target. Binders generally comprise a cysteine-containing peptide comprising one or more disulfide bonds, though some binders do not comprise cysteine-residues and/or disulfide bonds. Binders are preferably cleared rapidly from circulation when administered systemically to a mammalian subject. As will be understood, given context, reference to a binder may be or include its nucleic acid sequence or amino acid sequence encoding it. A binder may be provided, for instance, as a polynucleotide, polypeptide, using a vector, host cell, etc., and/or any combination of modalities. A binder may be derived or manufactured using any method known to those of skill in the art. For instance, in some embodiments, a binder can be recombinant (i.e., produced using recombinant nucleic acids encoding a polypeptide). In some embodiments, a binder can be synthetic (e.g., synthesized such as using standard solid phase synthesis methods, such as solid phase peptide synthesis, known to those of skill in the art (see, e.g., Palomo, J. *RSC Adv.,* 2014, 4, 32658-32672) and described herein.

As used herein, the term "block" refers to preventing, slowing, suppressing, or otherwise reducing or decreasing uptake and/or retention of a compound into a tissue (e.g., a non-tumor tissue, e.g., a kidney tissue, e.g., a liver tissue). In some embodiments, a decoy blocks uptake of a conjugate or compound of the disclosure into a non-tumor tissue, such as kidney tissue. In some embodiments, a decoy blocks by reducing retention of a compound (e.g., a radiotherapeutic compound, e.g., comprising a miniprotein) in a non-tumor tissue (e.g., kidney, e.g., liver).

As used herein, the term "chelator" refers to any molecule or moiety that is capable of forming a complex (i.e., "chelates") with a metal ion. Chelators generally have two or more unshared electron pairs that can be used to donate to a metal ion. Metal ions are usually coordinated to the chelator by two or more pairs of electrons.

As used herein, the term "conjugated" refers to the joining by covalent or noncovalent means of two compounds or agents.

As used herein, a "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, Methods Mol. Biol. 24:307-31 and 25:365-89 (herein incorporated by reference). The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

As used herein the terms "cysteine-dense peptide" and "CDP" are used interchangeably and refer to a subgenus of miniproteins that generally comprise at least two independent folding domains and a high density of cysteines. In some embodiments, the CDP comprises at least one, two, three, four, or more cysteine residues in a span of from about 10 to about 90 amino acid residues, preferably 13 to 80 amino acid residues, see, e.g., pubmed.ncbi.nlm.nih.gov/29483648/. In some embodiments, the CDP comprises a constrained distribution of cysteines, Cys-$X_{[0-15]}$-Cys-$X_{[0-15]}$-Cys-$X_{[0-15]}$-Cys-$X_{[0-15]}$-Cys-$X_{[0-15]}$-Cys (wherein X represents any amino acid) (SEQ ID NO: 553).

As used herein, the term "deletion" generally refers to the removal of one or more nucleotides from a nucleic acid molecule or one or more amino acids from a protein, the regions on either side being joined together.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

As used herein, the term "derived from," with reference to a nucleic acid sequence refers to a nucleic acid sequence that was developed using and has at least 85% sequence identity to a reference nucleic acid sequence. The term "derived from," with reference to an amino acid sequence refers to an amino acid sequence that has at least 85% sequence identity to a reference naturally occurring amino acid sequence from which it is derived. The term "derived from" as used herein does not denote any specific process or method for obtaining the derived nucleic acid or amino acid sequence. For example, the nucleic acid or amino acid sequence can be chemically synthesized.

As used herein, the term "having determined" refers to the process or the act of requesting from a third party (e.g., lab, hospital, nurse, physician) to carry out or provide results from a test, procedure, experiment, assay, analysis, etc., that defines the presence (or absence) of a given marker, e.g. a biomarker or a genetic mutation (e.g., the level of expression of B7-H3 in a biological sample, such as a sample from a tumor), from a patient.)

As used herein, the term "domain" as used herein refers to a structure of a biomolecule that contributes to a known or suspected function of the biomolecule. Domains may be co-extensive with regions or portions thereof; domains may also include distinct, non-contiguous regions of a biomolecule. Examples of protein domains include, but are not limited to, an Ig domain, an extracellular domain, a transmembrane domain, and a cytoplasmic domain.

As used herein, the term "expression control sequence" as used herein refers to polynucleotide sequences which are necessary to affect the expression of coding sequences to which they are operatively linked. Expression control sequences are sequences which control the transcription, post-transcriptional events, and translation of nucleic acid sequences. Expression control sequences include appropriate transcription initiation, termination, promoter, and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

As used herein, the term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusions that include the entirety of the proteins of the present disclosure have particular utility. The heterologous polypeptide included within the fusion protein of the present disclosure is at least 6 amino acids in length, often at least 8 amino acids in length, and usefully at least 15, 20, and 25 amino acids in length. Fusions that include larger polypeptides, such as an IgG Fc region, and even entire proteins, such as the green fluorescent protein ("GFP") chromophore-containing proteins, have particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

As used herein, when referring to a protein, "homology" to a second protein can exist if the nucleic acid sequence that encodes the protein has a similar sequence to the nucleic acid sequence that encodes the second protein. Alternatively, a protein has homology to a second protein if the two proteins "have similar" amino acid sequences. (Thus, the term "homologous proteins" is defined to mean that the two proteins have similar amino acid sequences.) Homology between two regions of amino acid sequences (especially with respect to predicted structural similarities) can be interpreted as implying similarity in function. Homologous proteins or peptides with residue positions that are not identical are often recognized to differ by conservative amino acid substitutions.

As used herein the term "identical" refers to a nucleic acid sequence or of least two nucleic acid or refers to an amino acid sequence of at least two amino acid sequences or subsequences that have a specified percentage of nucleotides or amino acids, respectively, that are the same, when compared and aligned for maximum correspondence, as measured using a sequence comparison algorithm or by visual inspection. For sequence comparison, typically one sequence acts as a reference sequence, to which test sequences are compared. A length of sequence identity comparison may be over a stretch of any number of nucleotides or amino acids. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. A number of algorithms are known in the art. Non-limiting examples of algorithms that are suitable for determining percent sequence identity and sequence similarity are the BLAST and BLAST 2.0 algorithms, which are described in, e.g., Altschul et al. (1990) J. Mol. Biol. 215: 403-410 and Altschul et al. (1977) Nucleic Acids Res. 25: 3389-3402, respectively. Software for performing BLAST analyses is publicly available through the National Center for Biotechnology Information. Additionally or alternatively sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, Methods Enzymol. 183:63-98 (1990) (hereby incorporated by reference in its entirety). For instance, percent sequence identity can be determined using FASTA with its default parameters (a word size of 6 and the NOPAM factor for the scoring matrix) or using Gap with its default parameters as provided in GCG Version 6.1, herein incorporated by reference.

As used herein, the term "isolated" polynucleotide or polypeptide is one which is substantially separated from other cellular components that naturally accompany the native polynucleotide in its natural host cell, e.g., ribosomes, polymerases and genomic sequences with which it is naturally associated. For instance, an isolated molecule is one that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polynucleotide or polypeptide found in nature or it includes amino acid analogs or derivatives not found in nature or linkages other than standard peptide bonds). Thus, a polynucleotide or polypeptide that is chemically synthesized or synthesized in a cellular system different from the cell from which it naturally originates will be "isolated" from its naturally associated components. A polynucleotide or polypeptide may also be rendered substantially free of naturally associated components by isolation, using protein purification techniques well known in the art. As thus defined, "isolated" does not necessarily require that any molecule so described has been physically removed from its native environment. In some embodiments, as used in reference to an isolated construct, isolated means in the absence of a pharmaceutically acceptable salt.

As used herein, the term "$K_D$" or "Kd" refers to the dissociation equilibrium constant for a particular entity and a target (e.g., antibody-antigen (or, e.g., targeting miniprotein-target protein), for example, a particular interaction between an entity and its target (e.g., a polypeptide-target interaction, e.g., a polypeptide as provided herein and B7-H3). Typically, the antibody (e.g., targeting miniprotein, e.g., B7-H3 binding miniprotein) of the present disclosure binds to B7-H3 with a dissociation equilibrium constant ($K_D$) of less than about $10^{-7}$ M, such as less than about $10^{-8}$ M, $10^{-9}$ M, or $10^{-10}$ M or less, for example, as determined using surface plasmon resonance (SPR) techniques in a BIACORE instrument. $K_D=k_d/k_a$.

As used herein, the term "Ki" (M) refers to the binding inhibition constant of a given entity and a target (e.g., a particular polypeptide-target interaction).

As used herein, the term "$k_d$" ($s^{-1}$) refers to the dissociation rate constant between a given entity and a target (e.g., of a particular polypeptide-target interaction). This value is also referred to as the $k_{off}$ value.

As used herein, the term "$k_a$" ($M^{-1}\times s^{-1}$) refers to the association rate constant of a given entity and a target (e.g., a particular polypeptide-target interaction). This value is also referred to as the $k_{on}$ value.

As used herein, the term "$K_A$" ($M^{-1}$) refers to the association equilibrium constant of a given entity and a target (e.g., a particular polypeptide-target interaction). $K_A=k_a/k_d$.

The affinity of a molecule X for its target Y can be represented by the dissociation equilibrium constant ($K_D$). The kinetic components that contribute to the dissociation equilibrium constant are as described above. For clarity, as known in the art, a smaller $K_D$ value indicates a higher affinity interaction, while a larger $K_D$ value indicates a lower affinity interaction. Affinity can be measured by common methods known in the art, including those described herein, such as surface plasmon resonance (SPR) technology (e.g., BIACORE®) or biolayer interferometry (e.g., FORTEBIO®).

As used herein, the term "knock out" generally refers to a gene whose level of expression or activity has been reduced to zero. In some examples, a gene is knocked out via deletion of some or all of its coding sequence. In other examples, a gene is knocked out via introduction of one or more nucleotides into its open reading frame, which results in translation of a nonsense or otherwise nonfunctional protein product.

The term "knottin" as used herein refers to a structural motif of a miniprotein containing three disulfide bridges.

The term "knottin peptide" as used herein refers to a subgenus of miniproteins that comprises at least one knottin.

The term "linker" as used herein refers to a moiety that is used to conjugate a miniprotein to a chelator.

As used herein, the term "miniprotein" refers to short proteins of less than or equal to 100 amino acids with well-defined folds comprising two or more secondary structure elements, a sequestered hydrophobic core, and/or cooperative folding. Affibodies, CDPs, knottins, and binders as disclosed herein are all examples of miniproteins.

As used herein, the term "modification," with reference to a nucleic acid sequence, refers to a nucleic acid sequence that comprises at least one substitution, alteration, inversion, addition, or deletion of nucleotide compared to a reference nucleic acid sequence. As used herein, the term "modification," with reference to an amino acid sequence refers to an amino acid sequence that comprises at least one substitution, alteration, inversion, addition, or deletion of an amino acid residue compared to a reference amino acid sequence.

As used herein, the term "modified derivative" refers to polypeptides or fragments thereof that are substantially homologous in primary structural sequence but which include, e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g., with radionuclides, and various enzymatic modifications, as will be readily appreciated by those skilled in the art. A variety of methods for labeling polypeptides and of substituents or labels useful for such purposes are well known in the art, and include radioactive isotopes such as 125I, 32P, 35S, and 3H, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well known in the art. See, e.g., Ausubel et al., Current Protocols in Molecular Biology, Greene Publishing Associates (1992, and Supplements to 2002) (hereby incorporated by reference).

As used herein, the term “molecule” means any compound, including, but not limited to, a miniprotein, a small molecule, peptide, protein, sugar, nucleotide, nucleic acid, lipid, etc., and such a molecule (e.g., miniprotein, compound, etc.) can be natural or synthetic or a combination of natural and synthetic.

As used herein, the term “monobody” or “adnectin” are used interchangeably and refer to a subgenus of miniproteins. A monobody is a molecule, preferably based on the 10th extracellular domain of human fibronectin III (10Fn3), which adopts an Ig-like b-sandwich fold of preferably 94 residues with 2 to 3 exposed loops but lacks the central disulfide bridge (Gebauer and Skerra (2009) Curr Opinion in Chemical Biology 13:245-255). Adnectins with the desired target specificity can be genetically engineered by introducing modifications in specific loops of the protein.

As used herein, the term “mutein” or “mutant protein” or “variant” means a protein comprising an amino acid sequence with at least one variation (e.g., an insertion, a deletion, or a substitution, which can be a conservative or non-conservative substitution) compared to a reference sequence. When applied to sequences (e.g., nucleic acid sequences, amino acid sequences) “mutated” means that nucleotides in a nucleic acid sequence or amino acids in an amino acid sequences may be inserted, deleted, or changed compared to a reference sequence. A single alteration may be made at a locus (a point mutation) or multiple nucleotides or amino acids may be inserted, deleted, or changed at a single locus. In addition, one or more alterations may be made at any number of loci within a nucleic acid or amino acid sequence. A nucleic acid or amino acid sequence may be mutated by any method known in the art including but not limited to mutagenesis techniques such as “error-prone PCR” (a process for performing PCR under conditions where the copying fidelity of the DNA polymerase is low, such that a high rate of point mutations is obtained along the entire length of the PCR product; see, e.g., Leung et al., Technique, 1:11-15 (1989) and Caldwell and Joyce, PCR Methods Applic. 2:28-33 (1992)); “oligonucleotide-directed mutagenesis” (a process which enables the generation of site-specific mutations in any cloned DNA segment of interest; see, e.g., Reidhaar-Olson and Sauer, Science 241: 53-57 (1988)); directed evolution (e.g., exposing a polypeptide to differing sets of conditions resulting in production of different polypeptides with one or more amino acid changes that may or may not confer greater fitness upon the polypeptide); and site-directed mutagenesis (e.g., specifically directed changes in a sequence).

As used herein, the terms “polypeptide mutant” or “mutein” refer to a polypeptide whose sequence contains an insertion, duplication, deletion, rearrangement, or substitution of one or more amino acids compared to the amino acid sequence of a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. A mutein may have the same but preferably has a different biological activity compared to the naturally-occurring protein. A mutein has at least 85% overall sequence homology to its wild-type counterpart. Even more preferred are muteins having at least 90% overall sequence homology to the wild-type protein. In an even more preferred embodiment, a mutein exhibits at least 95% sequence identity, even more preferably 98%, even more preferably 99% and even more preferably 99.9% overall sequence identity. Sequence homology may be measured by any common sequence analysis algorithm, such as Gap or Bestfit. Amino acid substitutions can include those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs.

As used herein, the term “non-disulfide sequence” refers to an amino acid sequence encoding a polypeptide that does not comprise more than one cysteine residue and/or disulfide bonds in its folded and active form. For example, in some embodiments, a miniprotein may comprise or consist of a non-disulfide sequence.

As used herein, the term “non-peptide analog” refers to a compound with properties that are analogous to those of a reference polypeptide. A non-peptide compound may also be termed a “peptide mimetic” or a “peptidomimetic.” See, e.g., Jones, Amino Acid and Peptide Synthesis, Oxford University Press (1992); Jung, Combinatorial Peptide and Nonpeptide Libraries: A Handbook, John Wiley (1997); Bodanszky et al., Peptide Chemistry—A Practical Textbook, Springer Verlag (1993); Synthetic Peptides: A Users Guide, (Grant, ed., W. H. Freeman and Co., 1992); Evans et al., J. Med. Chem. 30:1229 (1987); Fauchere, J. Adv. Drug Res. 15:29 (1986); Veber and Freidinger, Trends Neurosci., 8:392-396 (1985); and references sited in each of the above, which are incorporated herein by reference. Such compounds are often developed with the aid of computerized molecular modeling. Peptide mimetics that are structurally similar to useful peptides of the present disclosure may be used to produce an equivalent effect and are therefore envisioned to be part of the present disclosure.

As used herein, the terms “nucleic acid sequence” and “polynucleotide” are used interchangeably to refer to a polymer of nucleotides. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation. The nucleic acid sequence can contain natural, non-natural, or altered nucleotides; and contain a natural, non-natural, or altered internucleotide linkage, such as a phosphoramidate linkage or a phosphorothioate linkage, instead of the phosphodiester found between the nucleotides of an unmodified nucleic acid sequence. Nucleic acid sequences include, but are not limited to, all nucleic acid sequences which are obtained by any means available in the art, including, without limitation, recombinant means, e.g., the cloning of nucleic acid sequences from a recombinant library or a cell genome, using ordinary cloning technology and polymerase chain reaction, and the like, and by synthetic means. Polynucleotides of the present disclosure may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

As used herein, the terms "operatively linked" or "operably linked" expression control sequences refers to a linkage in which the expression control sequence is contiguous with the gene of interest to control the gene of interest, as well as expression control sequences that act in trans or at a distance to control the gene of interest.

As used herein, the term "polypeptide fragment" as used herein refers to a polypeptide that has a deletion, e.g., an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring or parent sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

As used herein, the term "radionuclide" refers to an atom capable of undergoing radioactive decay.

As used herein, the term "radiotherapeutic" refers to a radionuclide-labeled miniprotein or compound as provided herein, comprising a radionuclide. A radiotherapeutic may be administered to a subject, such as a test subject (e.g., a mouse or rat, e.g., a non-human primate, e.g., a healthy volunteer), and/or a subject in need of radiotherapy, e.g., a subject with a cancer.

As used herein, the term "recombinant" refers to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, and/or (4) does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids. As used herein, an endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "recombinant" because it is separated from at least some of the sequences that naturally flank it. A nucleic acid is also considered "recombinant" if it contains any modifications that do not naturally occur to the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, the term "recombinant host cell" (or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

As used herein, the term "region" as used herein refers to a physically contiguous portion of the primary structure of a biomolecule. In the case of proteins, a region is defined by a contiguous portion of the amino acid sequence of that protein.

As used herein the phrase "secondary structure elements" refers to local folded structures that form within a polypeptide due to interactions between atoms of its backbone. Examples of secondary structure elements can include an alpha helix, a beta sheet, a 310 helix, a pi helix, and a random coil. A miniprotein of the present disclosure may comprise one or more of any of such secondary structures (e.g., one or more alpha helix, one or more alpha helices and one or more beta sheets). It will be understood by those of skill in the art that secondary structure elements may be joined by loop regions, which may or may not be modified to change the interactions of secondary structure elements of the polypeptide. As will be understood to those of skill in the art, in some embodiments, loops may be secondary structural elements. In some embodiments, loops may be interstructural elements that are not necessarily considered secondary structural elements.

As used herein, "sequence homology" for polypeptides, also referred to as "percent sequence identity," is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions, and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1. A preferred algorithm when comparing a particular polypeptide sequence to a database containing a large number of sequences from different organisms is the computer program BLAST (Altschul et al., J. Mol. Biol. 215:403-410 (1990); Gish and States, Nature Genet. 3:266-272 (1993); Madden et al., Meth. Enzymol. 266:131-141 (1996); Altschul et al., Nucleic Acids Res. 25:3389-3402 (1997); Zhang and Madden, Genome Res. 7:649-656 (1997)), especially blastp or tblastn (Altschul et al., Nucleic Acids Res. 25:3389-3402 (1997)). Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOSUM62. The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson, Methods Enzymol. 183:63-98 (1990) (incorporated by reference herein). For example, percent sequence identity between amino acid sequences can be determined using FASTA with its default parameters (a word size of 2 and the PAM250 scoring matrix), as provided in GCG Version 6.1, herein incorporated by reference.

As used herein, the term "specific activity" generally refers to the activity per unit (e.g., mass, e.g., moles) of a radionuclide. Units of specific activity may include units of megabecquerel per microgram (MBq/μg), microcurie per microgram (μCi/μg), microcurie per nanomole (μCi/nmole), etc.

As used herein, the term "specificity" generally refers to a sequence (e.g., of a protein, e.g., of a miniprotein, .e.g., a miniprotein having certain amino acids) that, when in a conformation that can bind, selectively or "specifically" binds to a specific target (e.g., an antigen, such as expressed on a tumor, e.g., B7-H3, e.g., certain cell types, e.g., kidney cells, e.g., kidney proximal tubule cells, etc.).

As used herein, "specifically binds" means that the binding of a polynucleotide, polypeptide, or protein is selective for a specified antigen (e.g., target) and can be discriminated from unwanted or non-specific interactions. Hallmarks of "specific binding" include saturability of binding to the target as well as a demonstrable ability of that binding to be competed by the introduction of additional specifically binding molecules against that same target. For example, the ability of a protein (e.g., cysteine-dense peptides) to bind to a specific antigenic determinant can be measured techniques familiar to one of skill in the art, for example through an enzyme-linked immunosorbent assay (ELISA) or surface plasmon resonance. Between two molecules (e.g., entities such as miniproteins), "specific binding" refers to the ability of two molecules to bind to each other in preference to binding to other molecules in the environment. Typically, "specific binding" discriminates over adventitious binding in a reaction by at least two-fold, more typically by at least 10-fold, often at least 100-fold, or even 1,000-fold. Typically, the affinity or avidity of a specific binding reaction, as quantified by a dissociation constant, is about 10-7 M or stronger (e.g., about 10-8 M, 10-9 M or even stronger). Specific binding requires specificity of a particular first entity (e.g., a polypeptide) for a particular second entity (e.g., an antigen binding sequence).

As used herein "stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization. In general, "stringent hybridization" is performed at about 25° C. below the thermal melting point (Tm) for the specific DNA hybrid under a particular set of conditions. "Stringent washing" is performed at temperatures about 5° C. lower than the Tm for the specific DNA hybrid under a particular set of conditions. The Tm is the temperature at which 50% of the target sequence hybridizes to a perfectly matched probe. See Sambrook et al., Molecular Cloning: A Laboratory Manual, 2d ed., Cold Spring Harbor Laboratory Press, Cold Spring Harbor, N.Y. (1989), page 9.51, hereby incorporated by reference. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

As used herein, the term "synthetic" is used to refer to an entity that is made is lab-created and not naturally produced or isolated, without modification, from a naturally occurring source. A recombinant polymer, such as a recombinant polynucleotide or polypeptide, may be synthetic. Synthetic polymers such as polynucleotides or polypeptides may be produced by any method known to those of skill in the art, including but not limited to solid phase synthesis, solution phase synthesis, biological synthesis by, e.g., host cells, etc.

As used herein, the term "subject" is a mammal. A subject may be a human or non-human mammal. Given context, a subject may be used interchangeably with patient, individual, donor, etc. In some embodiments, a subject is a healthy subject without a disease that is contemplated for treatment by a composition of the disclosure (e.g., a healthy volunteer being administered one or more compositions provided herein). In some embodiments, a subject is one suspected or diagnosed as having a disease, disorder, or condition, such as a cancer and/or tumor, as provided herein. In some such embodiments, such a subject is considered for treatment by a composition of the disclosure. In some embodiments, analyses of results achieved with technologies disclosed herein are evaluated in a population comprising a plurality of subjects.

As used herein, the terms "substantial homology" or "substantial similarity," when referring to a polynucleotide or polypeptide, indicate that, when optimally aligned with appropriate nucleotide or amino acid insertions or deletions with another reference molecule (or its complementary strand when appropriate), there is sequence identity in at least about 70%, 75%, 80%, 85%, preferably at least about 90%, and more preferably at least about 95%, 96%, 97%, 98% or 99% or more of the nucleic acid or amino acid residues, as measured by any well-known algorithm of sequence identity, such as, e.g., FASTA, BLAST, Gap, etc. Alternatively or additionally, substantial homology or similarity exists when, for example, a nucleic acid or fragment thereof hybridizes to another nucleic acid, to a strand of another nucleic acid, or to the complementary strand thereof, under stringent hybridization conditions.

As used herein, the term "target" refers to a protein or functional portion or variant thereof. A target is a protein to which another protein (e.g., a miniprotein) is designed to bind. A target may be or comprise a binding region, such as an epitope, to which a miniprotein (e.g., affibody, CDP, knottin, binder, engineered Kunitz domain, monobody, anticalin, designed ankyrin repeat domain (DARPin), avimer) of the present disclosure binds. Further, the term "antigen" refers to a protein or functional portion or variant thereof to which a polypeptide (e.g., a miniprotein, etc.) or variant thereof binds to. A target may be or comprise an antigen. A target may be expressed on the surface of a particular cell (a "target cell") or expressed within (e.g., on the surfaces of) cells in a population of cells. A target may have a certain percent identity to a reference protein and still be referred to as a target by a particular name (e.g., B7-H3). In certain embodiments that will be clear from context, a target may also refer to a protein in a pathway related to another protein. For example, if a target is B7-H3, a target may also be a protein in a pathway that is necessary for B7-H3 activity. A target may be or comprise a binding region, such as an epitope, to which a miniprotein (e.g., affibody, CDP, knottin, binder, engineered Kunitz domain, monobody, anticalin, designed ankyrin repeat domain (DARPin), avimer) of the present disclosure binds. In certain embodiments that will be clear given context, a target may also be a particular cell type (or be localized to a particular cell type) characterized by expression of particular surface entities such as receptors (e.g., a cell in a tissue, e.g., a proximal tubule cell in a kidney). Such targets may be different or the same as a target to which a miniprotein (M) is designed to bind; in some embodiments, a target (e.g., a non-tumor cell, e.g., a kidney cell, a liver cell, etc.) is bound by a decoy rather than a polypeptide (e.g., a miniprotein) of a composition (e.g., a radiotherapeutic composition) provided herein.

As used herein, the term "treatment" (as well as "treat" or "treating") refers to partial or complete alleviation, amelioration, mitigation, prevention, reduction in risk of onset, relief, inhibition, delay in onset of, reduction in severity of, reduction in frequency or incidence of one or more causes, features, and/or symptoms of or associated with a particular disease, disorder, and/or condition.

As used herein, the term "vector" as used herein is intended to refer to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply "expression vectors").

As used herein, the term "decharged molecules" refers to molecules that have been modified to contain fewer positively charged or polar features, greater negatively charged features, and/or both as compared to a parent molecule.

As used herein, the term "surface charge" refers to the electrostatic charge present at the surface of a protein (e.g., such as a miniprotein). In various embodiments, the surface charge of a miniprotein can influence the kidney uptake of the miniprotein (e.g., increase the kidney uptake of the miniprotein or reduce the kidney uptake of the miniprotein).

As used herein, the term "surface patch" refers to regions on the surface of a protein (e.g., a miniprotein) with surface characterizations. For example, a surface patch can be defined according to surface charges and/or surface hydrophobicities, that may influence the kidney uptake of the protein (e.g., miniprotein).

As used herein, the term "cleavable linker" refers to a linker that can be cleaved. A cleavable linker contains a cleavable bond that is cleaved in vivo, for example: by an acidic pH (pH less than 7, typically about 4 to 6), by glutathione, or where there is up-regulation of enzymes such as matrix proteases or peptidases from the proximal tubule. Examples of cleavable linkers are linkers that contain hydrazine, or disulfide bonds, or enzymatically cleavable peptide sequences.

As used herein, the term "scaffold" refers to a particular set of structural characteristics of a given protein (e.g., a miniprotein, e.g., a binder, e.g., a decoy peptide). Scaffold is also used to describe miniproteins that share a general set of structural characteristics (e.g., certain constraints, secondary structures, tertiary structures, etc.). Any individual scaffold may include varying amounts of alpha helix, turn, and/or beta sheet, e.g., all alpha helix proteins ("a"), all beta sheet proteins ("b"), blended alpha helix/beta sheet proteins ("a/b"), blended alpha and beta proteins ("a+b"), and small proteins. Examples and features of certain scaffolds are provided herein. To give but one example, a scaffold may be an "affibody" scaffold as provided herein, and the affibody may be a target-binding affibody (e.g., B7-H3 binding) or an affibody decoy, where each entity has an affibody scaffold comprising, e.g., certain secondary structural features (e.g., alpha helices and/or beta sheets, disulfide bridges at particular, consistent cysteine residues, etc.). Scaffolds of the disclosure may be characterized as "Scaffold A" and "Scaffold B" types. Exemplary Scaffold A decoys include compounds C118-C120. Exemplary Scaffold B decoys have affibody scaffolds and include compounds C10; B7-H3-targeting polypeptides of the disclosure are also Scaffold B affibodies, such as C1-C9, C11-C117.

As used herein, the term "decoy peptides" or "decoys" refers to molecules specifically designed to mimic the role of a certain receptor protein and interact with certain target entities. One such type of decoy peptides or decoys is a subgenus of miniproteins specifically designed to (i)

decrease accumulation of a compound (e.g., a miniprotein, e.g., a radiolabeled miniprotein, e.g., a radiotherapeutic as provided herein) in a non-tumor tissue (e.g., kidney tissue or liver tissue when the tumor is elsewhere); and/or (ii) have substantially no impact to minimal impact on compound uptake by a tumor (e.g., a tumor expressing a target, e.g., B7-H3); and/or (iii) decrease adverse (e.g., toxic) accumulation in a, non-tumor containing organ (e.g., liver, e.g., kidney, etc.) of a subject. To give but one example, an exemplary decoy may be combined with a composition of the disclosure (e.g., comprising a miniprotein and a radionuclide such as a radiotherapeutic) to block the composition from kidney tissue, as compared to uptake and/or retention in kidney tissue in the absence of the decoy peptide. Without wishing to be bound by theory, the disclosure describes, in some embodiments, a decoy peptide (or decoy) that decoys a composition such as a radiotherapeutic, which means that presence of the decoy in a non-tumor tissue blocks uptake and/or retention of the radiotherapeutic into the non-tumor tissue (e.g., kidney, e.g., liver). For clarity, when a decoy peptide is referred to as "decoying," e.g., a composition, e.g., a compound, e.g., a miniprotein that binds to a target (e.g., B7-H3), the decoy is not acting on the composition (or compound or miniprotein), rather, it is acting on its own and, for example, even in the absence of a composition that it is decoying, if administered alone, would still be present in the non-tumor tissue (e.g., kidney, e.g., liver).

Compositions

Provided herein are novel compositions comprising one or more of a polypeptide, linker, chelator, and/or radionuclide. In some embodiments, a composition comprises a linker and a chelator. In some such embodiments, the composition is metalated (e.g., with a cold-metal form of an elemental label, such as provided herein). In some embodiments, the composition is radiolabeled (e.g., with a radionuclide such as provided herein). In some embodiments, a composition comprises a linker, chelator, and radionuclide. In some embodiments, a composition comprises or consists of a polypeptide (i.e., a miniprotein), an optional linker, and a chelator and/or radionuclide. In some embodiments, a chelator and/or radionuclide are conjugated to a miniprotein via a linker. In some embodiments, a miniprotein of the present disclosure comprises or consists of an affibody, a CDP, a knottin and/or a binder. In some embodiments, the miniprotein comprises or consists of an affibody. In some embodiments, the miniprotein comprises or consists of a CDP. In some such embodiments, the miniprotein comprises or consists of a knottin. In some such embodiments, the miniprotein comprises or consists of a binder. In some embodiments the miniprotein (e.g., affibody, CDP, knottin, binder, engineered Kunitz domain, monobody, anticalin, designed ankyrin repeat domain (DARPin), avimer) is designed to be linked to one or more other components. For example, in some embodiments, a miniprotein (e.g., affibody, CDP, knottin, binder, engineered Kunitz domain, monobody, anticalin, designed ankyrin repeat domain (DARPin), avimer) may be linked (conjugated) to another component such as a chelator and/or a radionuclide. In some embodiments, a radionuclide of the present disclosure is an alpha emitter. In some such embodiments, a chelator and/or radionuclide are conjugated to a miniprotein via a linker.

Without wishing to be bound by any particular theory, the present disclosure contemplates that compositions of the present disclosure are more effective than previously described compositions (e.g., such as those comprising antibodies and/or beta-emitter radionuclides). For example, while miniproteins (e.g., to be used in compositions as provided herein) have several key features of antibody-based therapeutics (e.g., affinity, potency, specificity, and ability to disrupt protein:protein interactions), they can avoid undesirable limitations such as, e.g., large size, expensive manufacturing, and the necessity of chimerization or humanization. For instance, in some embodiments, a miniprotein (e.g., affibody, CDP, knottin, binder, engineered Kunitz domain, monobody, anticalin, designed ankyrin repeat domain (DARPin), avimer) of the present disclosure is no more than about 100 amino acids in length. In some embodiments, such a miniprotein (e.g., affibody, CDP, knottin, binder, engineered Kunitz domain, monobody, anticalin, designed ankyrin repeat domain (DARPin), avimer) may be or comprise a cysteine dense peptide. In some embodiments, a miniprotein (e.g., affibody, CDP, knottin, binder, engineered Kunitz domain, monobody, anticalin, designed ankyrin repeat domain (DARPin), avimer) comprises one or more disulfide bridges. In some embodiments, a miniprotein (e.g., affibody, CDP, knottin, binder, engineered Kunitz domain, monobody, anticalin, designed ankyrin repeat domain (DARPin), avimer) comprises multiple cysteine residues that crosslink to maintain a very stable, folded state for a peptide of its length (e.g., relative to a peptide of the same length without as many cysteine residues).

Among other things, the present disclosure contemplates that in some embodiments, a miniprotein does not comprise multiple cysteine residues such as, for example, a miniprotein comprising a single cysteine residue. In some such embodiments, the miniprotein may form a dimer, such as with another miniprotein (e.g., self-dimerization). In certain embodiments, a miniprotein (e.g., that binds to B7-H3) comprises at least two cysteine residues. In some embodiments, a miniprotein comprises at least four cysteine residues. In certain embodiments, where a miniprotein comprises at least two or at least four cysteine residues, the miniprotein also comprises a disulfide bridge between pairs of the cysteine residues. In certain embodiments, a miniprotein must have at least one or two disulfide bridges. In some embodiments, the miniprotein comprises three disulfide bridges (and at least six cysteine residues). In certain embodiments, constraints include more than one type of constraint (e.g., a disulfide bridge, a lactam bridge, an alkyl stapled bridge, and any combinations thereof). For example, in some embodiments, the disclosure provides a polypeptide comprising at least one or two disulfide bridges and a lactam bridge. Without wishing to be bound by theory, the present disclosure contemplates that stability conferred by cross-linked cysteines contributes to reduced immunogenicity of miniproteins or comprising such miniproteins. In some embodiments, such stability may also confer resistance to harsher conditions provided for efficient chelation (e.g., high temperature, low pH incubations, etc.), while continuing to retain biological activity (e.g., capability of binding a target) and drug-like physicochemical properties (e.g., stability, solubility, monomeric).

In some embodiments, miniproteins as provided herein function as targeting moieties, e.g., specifically binding to a target expressed on the surface of a tumor cell. In some such embodiments, a miniprotein is designed such that it may be joined to one or more additional components. For example, miniproteins of the present disclosure may be formulated such that they are combined with other components such as a therapeutic molecule (e.g., chelator compositions and/or radionuclide) and/or a detectable agent (e.g., a visualizable agent, e.g., a metabolizable and visualizable agent, etc.). In some such embodiments, such miniproteins conjugated to one or more additional components may be used, for example, in diagnosis, prognosis, monitoring and/or treatment of one or more diseases, disorders or conditions such as those with expression of particular targets on particular populations of cells.

In some embodiments a miniprotein (e.g., affibody, CDP, knottin, binder, engineered Kunitz domain, monobody, anticalin, designed ankyrin repeat domain (DARPin), avimer) has low immunogenicity relative to a larger protein. In some such embodiments, the lower immunogenicity increases amenability to harsher environmental conditions (e.g., high temperature and low pH incubations) while retaining biological activity. Thus, in some embodiments, a conjugate comprising a miniprotein has lower immunogenicity than a composition comprising a larger protein or different targeting moiety (i.e., other than a miniprotein).

In some embodiments, a composition comprising a linker, chelator, and/or radionuclide can efficiently penetrate a tumor.

In some embodiments, miniproteins (e.g., affibody, CDP, knottin, binder, engineered Kunitz domain, monobody, anticalin, designed ankyrin repeat domain (DARPin), avimer) have superior penetration efficiency relative to larger proteins. That is, in some embodiments, a miniprotein or composition comprising a miniprotein can penetrate a solid tumor better than a larger protein or composition comprising a protein larger than a miniprotein. For example, in some embodiments, a binder has superior tumor penetration efficiency with a hydrodynamic radius on the order of about 1 nm-25 nm. In some embodiments, the hydrodynamic radius is between about 1 nm-5 nm. In some embodiments, the hydrodynamic radius is between about 1 nm-3 nm. In some embodiments, the hydrodynamic radius is about 1, 2, 3, 4, 5, 6, 7, 8, 9, 10, 11, 12, 13, 14, 15, 16, 17, 18, 19, 20, 21, 22, 23, 24, or 25 nm.

As described herein, miniproteins (e.g., affibody, CDP, knottin, binder), are conjugated to a chelator. In some embodiments, the chelator binds a radionuclide (e.g., an alpha-emitter radionuclide, e.g., actinium). In some such embodiments, such radionuclide conjugates combine specific-binding capabilities and properties of a miniprotein (e.g., affibody, CDP, knotting, binder) with a radionuclide. That is, without being bound by any particular theory, the present disclosure provides a conjugate wherein, in some embodiments, a miniprotein (e.g., affibody, CDP, knottin, binder, engineered Kunitz domain, monobody, anticalin, designed ankyrin repeat domain (DARPin), avimer) targets a radioisotope to which it's conjugated to a cell expressing a target. In some embodiments, the target is expressed on the surface of a cell. In some embodiments, the target is B7-H3. In some embodiments, the cell is a tumor cell. In some embodiments, the conjugate binds to the B7-H3 on the surface of the tumor cell. In some such embodiments, the radionuclide is targeted to the tumor cell. In some embodiments, the radionuclide is an alpha-emitter radionuclide and when internalized, serves to specifically target (e.g., without damaging surrounding tissue/cells) the tumor cell.

Targets

Any cell expressing a target may be targeted by a miniprotein (e.g., affibody, CDP, knottin, binder, engineered Kunitz domain, monobody, anticalin, designed ankyrin repeat domain (DARPin), avimer) as provided herein.

In some embodiments, a cell is a mammalian cell. In some embodiments, a cell is a human cell. In some embodiments, a cell is from a cell line. In some embodiments, a cell is a primary cell. In some embodiments, a primary cell is from a sample from a subject such as from a tumor or from corresponding tissue without a tumor (e.g., from another area of an organ or from a healthy donor). In some embodiments, a cell is in vitro (e.g., a primary cell, a cell line, etc.). In some embodiments, a cell is in vivo (e.g., in a subject, e.g., in a human subject, e.g., in a tumor of a human subject.) In some embodiments, a cell expresses or has been induced to express (e.g., via recombinant technology) a target. In some embodiments, the target is expressed on the surface of a cell. In some embodiments, a cell is contacted by a composition binding to a target expressed on its surface. In some embodiments, upon binding (e.g., upon binding of a miniprotein provided by the present disclosure), a target and any bound proteins and/or payloads is/are internalized into the cell. In some embodiments, a cell is killed by a payload (e.g., a radionuclide and/or chelator, etc.) after internalization.

In some embodiments, a target is a protein or portion thereof that is upregulated or overexpressed on cancer cells as compared to non-cancer cells. That is, in some embodiments, a target is expressed or overexpressed in a tumor or in a tumor microenvironment relative to a level of the target in non-diseased tissue (e.g., tissue without a tumor or tumor microenvironment). In some such embodiments, the target is absent or non-detectable in non-diseased (e.g., healthy) tissue. In some embodiments, a target is a biomarker for cancer (e.g., for cancer cells, for a tumor).

In some embodiments, a target may be related to a protein such as, for example, a protein in a pathway activated or acted upon by another protein. For instance, in some embodiments, a protein may be expressed on the surface of a cancer cell and a target may be a pathway that the surface-cell protein acts upon. In some embodiments, a protein may be expressed on a cancer cell and a target may be a protein on a different cell that causing a cancer cell to proliferate or otherwise be refractory to a treatment. In some embodiments, a tumor-associated cell surface molecule or tumor-specific cell surface molecule may be targeted by a miniprotein or composition comprising a miniprotein as provided herein.

In some embodiments, the miniprotein or composition comprising a miniprotein specifically binds a target (e.g., B7-H3) expressed on the surface of a cell. In some embodiments, a target is cleaved from a cell surface. In some such embodiments, if the target is in an organism, cleavage of the target results in circulation of the target throughout the system of the organism. In some such embodiments, a target is found at a particular level in, e.g., blood, serum, plasma, etc. In some embodiments, however, a substantial portion of expressed target is localized to cell surfaces; thus, in some embodiments, measurements of a level of a target may not accurately reflect the amount of target in a population of cells (e.g., a tumor). In some embodiments, a target is a secreted protein. In some such embodiments, a target is found at a particular level in, e.g., blood, serum, plasma, etc. In some such embodiments, the miniprotein binds to a region of a target such as, for example, an epitope. In some embodiments, a miniprotein or composition comprising a miniprotein specifically binds a target expressed on the surface of a cancer cell. In some embodiments, the cancer cell is in, on, or near a solid tumor. In some embodiments, the cancer cell is a circulating cancer cell. In some embodiments, a miniprotein or composition comprising a miniprotein specifically binds a target or expressed at a higher level on a cancer cell than a reference cell. In some embodiments, the cell is a mammalian cell. In some embodiments, the cell is a human cell.

In some embodiments, the miniprotein or composition comprising a miniprotein specifically binds to B7-H3. In some embodiments, the target comprises or consists of B7-H3. In some embodiments, the miniprotein specifically binds to a target comprising an amino acid sequence or portion thereof as set forth in Table 1A.

B7-H3

B7-H3 is also known as CD276. B7-H3 is considered an immune checkpoint protein and is expressed by immune cells (e.g., APCs, macrophages) and tumor cells. B7-H3 has also been shown to play an inhibitory role on T cells and has been found to contribute to tumor cell immune evasion. (Dong et al., Front Oncol. 2018 Jul. 6; 8:264).

B7-H3 overexpression has been documented in many cancers including, for example, bladder, breast, cervical, colorectal, esophageal, glioma, kidney, liver, lung, ovarian, pancreatic, prostate, intrahepatic cholangiocarcinoma, liver, oral squamous cell carcinoma, endometrial cancer, and squamous cell carcinoma and gastric cancer, glioma, and melanoma. (Dong et al., Front Oncol. 2018 Jul. 6; 8:264). Studies of B7-H3 overexpression have also shown association of B7-H3 levels with advanced tumor stage, high tumor grade, and poor clinical prognosis. Without being bound by any particular theory, such overexpression of B7-H3 is thought to contribute to metastasis in a number of different cancer types and by a number of possible mechanisms. For example, in some embodiments, B7-H3 may play a role in cancer cell proliferation and invasiveness. (Id.). In studies documenting B7-H3 knockdown, significant suppression of cell migration and invasion was observed in cells from prostate, breast, gastric, liver, pancreatic, colorectal and melanoma cancers. (Id.).

In some embodiments, overexpressed B7-H3 on tumor cells has been shown to be successfully targeted including with T-cell-mediated immunotherapy. For example, one study showed that specific cytotoxic activity of activated T cell (ATC) also having a novel anti-CD3× anti-B7-H3 bispecific antibody showed increase in cytotoxicity relative to ATC alone, resulting in inhibition of tumor growth and increased survival in xenograft models. (Ma J., et al, Oncotarget (2016) 7(20):29480-91). In some embodiments, a binder of the present disclosure binds to B7-H3 expressed on one or more cells (e.g., cancer cells). In some such embodiments, the present disclosure contemplates targeting of B7-H3 with one or more binders of the present disclosure, wherein the B7-H3 is expressed at higher levels on cancer cells relative to non-cancer cells, and wherein the binding of the miniprotein is specific for cancer cells.

In some embodiments, compositions provided by the present disclosure more specifically and effectively target a cell overexpressing B7-H3 while minimizing or eliminating damage to surrounding cells not expressing or lowly expressing B7-H3 by providing a targeted composition including, in some embodiments, a chelator and/or alpha-emitter, which when combined with a miniprotein as provided herein provide specific, efficient and effective approaches to target cells overexpressing B7-H3. As used herein, cells that "lowly express B7-H3" refer to cells that do not express B7-H3 and/or cells that express B7-H3 at a level less than 50% of the level of expression of B7-H3 of cells that overexpress B7-H3. In particular embodiments, cells that "lowly express B7-H3" refer to cells that express B7-H3 at a level less than 40%, less than 30%, less than 20%, less than 10%, or less than 5% of the level of expression of B7-H3 of cells that overexpress B7-H3.

In some embodiments, there is a relationship between B7-H3 levels and metastasis. For example, some studies have documented a relationship between B7-H3 and metastasis such as increased expression levels of metastasis-associated proteins such as MMP2, STAT3, and IL-8 (Tekle et al., Int J Cancer (2012) 130(10):2282-90) and increased levels of CXCR4 and activation of AKT, ERK, and JAK2/STAT3 pathways. (Wang et al., Tumour Biol (2016) 37(3):2961-71). In some embodiments, changes in B7-H3 can impact cancer treatment. For example, studies have shown that changes in B7-H3 can impact efficacy of some cancer treatments. In breast cancer, specifically, B7-H3 has been shown to reduce efficacy of paclitaxel through activation of JAK2/STAT3 and silencing of B7-H3 both abrogates JAK2/STAT3 phosphorylation and improves paclitaxel sensitivity. (Liu et al., Mol Cancer Ther (2011) 10(6):960-71). Similarly, in colorectal cancer, overexpression of B7-H3 has been shown to reduce efficacy of 5-fluorouracil through JAK2/STAT3 activation. (Zhang et al., World J Gastroenterol (2015) 21(6):1804-13). In some embodiments, immunoglobulin-like-transcript 4 (ILT4), an inhibitory receptor of certain immune cells, may upregulate B7-H3 expression through the PI3K/AKT/mTOR pathway in lung cancer cells (see, e.g., Zhang P et al., FEBS Lett (2015) 589(17):2248-56). In some embodiments, co-expression of ILT4 and B7-H3 may be positively associated with lymph node metastasis, advanced tumor stage and poor clinical prognosis in NSCLC (see, e.g., Zhang P et al., FEBS Lett (2015) 589(17):2248-56).

Without wishing to be bound by theory, B7-H3 may play a role in cell transitions and potential. For instance, in some embodiments, B7-H3 may increase cell transitions and stemness. For example, B7-H3 has been shown to increase epithelial-mesenchymal transition and cancer "stemness" through increased expression of several proteins including vimentin, CD133, CD44 and OCT4 and decreased expression of E-cadherin. (Jiang et al., Oncotarget (2016) 7(22):31755-71). In some embodiments, B7-H3 overexpression may occur due to genomic DNA amplification. In some embodiments, B7-H3 overexpression may occur due to increased transcription. In some embodiments, B7-H3 overexpression may occur due to decreased degradation.

By way of non-limiting example, though it is not presently known whether B7-H3 overexpression is due to, e.g., genomic DNA amplification or increased transcription, chromatin immunoprecipitation has demonstrated an androgen receptor-binding site upstream of B7-H3, as well as B7-H3 expression reduction in presence of androgens (Benzon B. et al., Prostate Cancer Prostatic Dis (2017) 20(1):28-35). Along similar lines, in some embodiments, B7-H3 may increase expression of genes (e.g., thymidylate synthase) via PI3K/AKT pathway. (see, e.g., Jiang et al., Tumour Biol (2016) 37(7):9465-72). Furthermore, data have shown that oxaliplatin treatment in colorectal cancer can be made more efficacious through inhibition. In some embodiments, B7-H3 is contemplated as contributing to chemoresistance by increasing expression of XRCC1 via PI3K/AKT pathway (see, e.g., Zhang et al., Biochem Biophys Res Commun (2017) 490(3):1132-8), which may, in some embodiments, increase expression of BRCC3, which also opposes DNA damaging effects of 5-FU (see, e.g., Sun et al., Oncol Rep (2016) 36(1):231-8).

Without limitation, in some embodiments, B7-H3 may play a role in cancer metabolism. Specifically, it has been contemplated that B7-H3 promotes the "Warburg Effect" of preferential metabolism of glucose to lactate when abundance oxygen is present. This Warburg Effect phenomenon has been observed through HIF1α in breast cancer cells and in a mouse model of breast cancer. (Lim et al., Cancer Res (2016) 76(8):2231-42). Similarly, in some embodiments, B7-H3-mediated decrease may impact proliferation and Warburg effect. Specifically, data have shown that in metastatic melanoma, B7-H3-mediated decrease during treatment of metastatic melanoma has been shown to be overcome through use of a monoclonal B7-H3 antibody, which decreased proliferation and the Warburg effect in melanoma. (Flem-Karlsen K, et al., Pigment Cell Melanoma Res (2017) 30(5):467-76). Treatment with monoclonal anti-B7-H3 has also demonstrated efficacy in the rare stage IV pediatric neuroblastoma, DIPG. (Zhou Z, J Neurooncol (2013) 111 (3):257-64).

In some embodiments, B7-H3 interacts with other cellular components or units, such as miRNA. For example, B7-H3 has also been found to interact with many miRNAs that are thought to be involved in cancer. (Dong et al., Front Oncol. 2018 Jul. 6; 8:264). For example, the 3' UTR of B7-H3 transcripts has been observed to interact with miR-214, miR-363*, miR-326, miR-940, miR-29c, miR-665, miR-34b*, miR-708, miR-601, miR-124a, miR-380-5p, miR-885-3p, and miR-593 in breast cancer, resulting in reduced B7-H3 expression (Nygren M K, et al., Br J Cancer (2014) 110(8):2072-80). In osteosarcoma, the 3' UTRs of B7-H3 transcripts have been shown to interact with miR-124 and a study in colorectal cancer cells showed that iASPP-mediated p53 repression led to downregulation of miR-124, which was accompanied by increased expression of B7-H3. (Dong et al., Front Oncol. 2018 Jul. 6; 8:264). Furthermore, in a colorectal cancer study, oncogenesis was promoted via miR-155/miR-143 axis (Zhou et al., Oncotarget (2016) 7(41): 67196-211). Specifically, in colorectal cancer cells, TGFβ elevated miR-155 expression (via SMAD3 and SMAD4) resulted in reduced CEPBP expression, which led to reduced miR-143 expression in colorectal cancer cells. B7-H3 is a target of miR-143, thus reduced miR-143 expression resulted in increased B7-H3 expression supporting the possibility that in some contexts, TGFB may contribute to cancer immune escape by upregulating B7-H3. (Zhou et al., Oncotarget (2016) 7(41):67196-211; Dong et al., Front Oncol. 2018 Jul. 6; 8:264).

Importantly, novel compositions provided by the present disclosure are capable of specifically, efficiently, and effectively targeting B7-H3 overexpressing cells with reduced toxicity as compared to presently available treatments. That is, in some embodiments, a composition targeting B7-H3 as provided by the present disclosure provides improved treatment as compared to presently available treatments.

In some embodiments, a target of compositions of the present disclosure comprises or consists of B7-H3 (e.g., human B7-H3).

In certain embodiments, a miniprotein is selected from any of Tables 1B-1E, 2A and 2C, or portions or fragments thereof. In certain embodiments, a miniprotein binds to B7-H3 and is selected from any of Tables 1B-1E, 2A, and 2C. In some embodiments, the miniprotein that binds to B7-H3 is not selected from any of Tables 1B, 1C, or 2A.

In some embodiments, a B7-H3 binding miniprotein has an amino acid sequence comprising or consisting of an amino acid sequence according to any one of SEQ ID NOs: 4-6, 8-94 and 100-537 and can have different N- and/or C-terminal ends, such as, for example, an Acetyl, NH2, Biotin-PEG4, DOTA-PEG4, radiolabel, etc. on its N-terminus and an —OH/COOH or —NH2 on its C-terminus. N- and/or C-termini of B7-H3 binding miniproteins of the disclosure can include but are not limited to acetyl, acid, or amide (e.g., Acetyl, NH2, OH/COOH), such as provided in exemplary compounds and miniproteins of Table 2A or Table 2C.

In some embodiments, a B7-H3 binding miniprotein does not have an amino acid sequence comprising or consisting of an amino acid sequence according to any one of SEQ ID NOs: 4-6, 8-94 and 100-197.

In some embodiments, a polypeptide according to the disclosure may have various modifications to its N-terminus (e.g., a linker, chelator, and/or radionuclide, e.g., such as set forth in exemplary compounds in Table 2A or Table 2C) or its C-terminus (e.g., a linker, chelator, and/or radionuclide). In some embodiments, the C-terminus of a given polypeptide can have an acid or amide group on its C-terminus (see, e.g., Table 2A, e.g., Table 2C). A given polypeptide having a particular amino acid sequence can have one or more N-terminal and/or C-terminal differences without materially changing the utility or function of the polypeptide, such as for binding to B7-H3 (e.g., for detection and/or treatment of cancer).

In some embodiments, a target of compositions of the present disclosure comprises or consists of B7-H3. In some embodiments, a material change in a basic and novel characteristic of a polypeptide (e.g., miniprotein) provided herein is the ability to strongly and specifically bind to its intended target (e.g., B7-H3, e.g., B7-H3 on a cancer cell) with minimal or no off-target effects and minimal kidney uptake (e.g., as compared to kidney uptake of previously developed B7-H3 binding molecules). In some embodiments, B7-H3 is expressed on the surface of a cell. Alternatively, in some embodiments, B7-H3 is released from tumor associated cells and present in the tumor microenvironment. (see, e.g., Zhang et al., Immunology. 2008 April; 123(4): 538-546). In some embodiments, the cell is a cancer cell. In some such embodiments, the cancer cell is a tumor cell and the tumor is a solid tumor. In some embodiments, a level of B7-H3 expressed in a tumor cell or population of tumor cells is higher than that expressed in non-tumor cells. In some embodiments, targeting of B7-H3 by a miniprotein or composition comprising a miniprotein as provided by the present disclosure specifically targets a composition or one or more components thereof (e.g., a chelator and/or radionuclide) to a cancer cell or a tumor microenvironment (e.g., a location comprising a population of cancer cells or cells at risk of becoming cancer cells).

In some embodiments, compositions in accordance with the present disclosure specifically bind to B7-H3 (e.g., through a polypeptide that binds to B7-H3, e.g., through a miniprotein that specifically binds to B7-H3). In some embodiments, a compound targeting B7-H3 is disclosed in Table 2A or Table 2C.

In some embodiments, a composition comprising a miniprotein comprises or consists of a protein comprising a specific an amino acid sequence that binds to B7-H3 or a portion thereof. In some embodiments, certain exemplary B7-H3 binding miniproteins are engineered to have an amino acid sequence comprising one or more non-natural amino acids (e.g., such as set forth herein, e.g., such as set forth in Tables 2A and/or 2C, e.g., an amino acid with a small alkyl group on its side chain, etc.). In some such embodiments, such a B7-H3 miniprotein comprises or consists of an amino acid sequence selected from any of SEQ ID NOs: 4-6, 8-94 and 100-537 or a functional variant or portion thereof (e.g., a functional fragment, e.g., a miniprotein that folds and binds to B7-H3 or a portion thereof). In some embodiments, such a B7-H3 miniprotein is a binding protein or part of a conjugate comprising such a binding protein as set forth in Table 2A or Table 2C. In certain embodiments, a B7-H3 miniprotein has an amino acid sequence comprising that set forth according to any of Tables 1B-1E.

In some embodiments, a composition comprising a miniprotein comprises or consists of a protein comprising a specific an amino acid sequence that binds to B7-H3 or a portion thereof.

In some embodiments, the present disclosure provides a polynucleotide encoding a polypeptide that comprises or consists of one or more portions of a composition as provided herein. In some embodiments, the present disclosure provides a vector and/or host cell comprising a sequence encoding one or more components of a composition as provided herein.

In some embodiments, the present disclosure provides methods of detecting a target. In some embodiments, a method as provided herein comprises detecting presence of a target for, e.g., imaging, e.g., diagnostic, prognostic, and/or monitoring purposes, e.g., treatment. In some embodiments, the present disclosure provides methods of treatment and/or methods of manufacturing using composition as provided herein (e.g., a miniprotein, e.g., a linker-chelator, e.g., a miniprotein comprising one or more of a linker, chelator, and radionuclide, etc.). In some embodiments, a method of treatment comprises administering a composition as provided herein to a subject in need thereof.

In some embodiments, when present, the linker is attached to the N-terminus of the polypeptide (e.g., the B7-H3 binding miniprotein). In some embodiments, when present, the linker is attached to the C-terminus of the polypeptide (e.g., the B7-H3 binding miniprotein).

In some embodiments, the C-terminal amino acid of the polypeptide is not a cysteine.

In some embodiments, when present, the chelator is attached to either the polypeptide or the linker. In some embodiments, when the chelator is present without a linker, the chelator is attached to the N-terminus of the polypeptide. In some embodiments, when the chelator is present without a linker, the chelator is attached to the C-terminus of the polypeptide.

In some embodiments, when present, the radionuclide is attached to the chelator. In some embodiments, when the radionuclide is present without a linker or chelator, the radionuclide is attached to the N-terminus of the polypeptide. In some embodiments, when the radionuclide is present without a linker or chelator, the radionuclide is attached to the C-terminus of the polypeptide.

In some embodiments, the disclosure provides a composition comprising a formula selected from one or more of (M)x-L-C-R, (M)x-L-C, (M)x-C-R, (M)x-L-R, (M)x-C, (M)x-L, and (M)x-R, wherein M comprises a polypeptide (M), L comprises a linker (L), C comprises a chelator (C), R comprises a radionuclide (R), and x is 1, 2, 3, or 4, wherein M comprises an amino acid sequence of any one of SEQ ID NO: 4-6, 8-94 and 100-537.

In some embodiments, the linker comprises or consists of a polyethylene glycol (PEG) linker of PEG4, PEG, PEG2, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, or (Gly)n-(gGlu)n-(SEQ ID NO: 551) or (PEG)n, wherein n is from 1 to 36, (Gly)1-10 (SEQ ID NO: 552), or any fragment or combination via covalent bond thereof.

In some embodiments, the chelator comprises or consists of DOTA, Crown, NOPO, Macropa, lead specific chelator (PSC), N-succinimidyl 3-(tri-n-butylstannyl)benzoate (BuSTB), or N-succinimidyl 3-trimethylstannylbenzoate (MeSTB).

In some embodiments, the radionuclide Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211.

In some embodiments, the disclosure provides a composition comprising a formula selected from one or more of (M)x-L-C-R, (M)x-L-C, (M)x-C-R, (M)x-L-R, (M)x-C, (M)x-L, and (M)x-R, wherein M comprises a polypeptide (M), L comprises a linker (L), C comprises a chelator (C), R comprises a radionuclide (R), and x is 1, 2, 3, or 4, wherein M has an amino acid sequence comprising any one of those set forth in SEQ ID NOs: 198-537.

In some embodiments, when L is present, L comprises or consists of a polyethylene glycol (PEG) linker of PEG4, PEG, PEG2, PEG6, PEG8, PEG12, PEG24, lys(MPB)-PEG4, PEG36, an ester linker, an amide linker, a maleimide linker a valine-citrulline linker, a hydrazone linker, a N-succinimidyl-4-(2-pyridyldithio)butyrate (SPDB) linker, a succinimidyl-4-(N-maleimidomethyl)cyclohexane-1-carboxylate (SMCC) linker, a vinylsulfone-based linker, a propanoic acid linker, a dTyr-Gly-Phe (yGF) linker, a caproleic acid linker, or (Gly)n-(gGlu)n (SEQ ID NO: 551)— or (PEG)n, wherein n is from 1 to 36, (Gly)1-10 (SEQ ID NO: 552), or any fragment or combination via covalent bond thereof.

In some embodiments, when C is present, C comprises or consists of DOTA, Crown, NOPO, Macropa, lead-specific chelator (PSC), N-succinimidyl 3-(tri-n-butylstannyl)benzoate (BuSTB), or N-succinimidyl 3-trimethylstannylbenzoate (MeSTB).

In some embodiments, when R is present, R comprises or consists of Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211.

In some embodiments, when present, the linker is attached to the N-terminus of the polypeptide (e.g., the B7-H3 binding miniprotein). In some embodiments, when present, the linker is attached to the C-terminus of the polypeptide (e.g., the B7-H3 binding miniprotein).

In some embodiments, the C-terminal amino acid of the polypeptide is not a cysteine.

In some embodiments, when present, the chelator is attached to either the polypeptide or the linker. In some embodiments, when the chelator is present without a linker, the chelator is attached to the N-terminus of the polypeptide. In some embodiments, when the chelator is present without a linker, the chelator is attached to the C-terminus of the polypeptide.

In some embodiments, when present, the radionuclide is attached to the chelator. In some embodiments, when the radionuclide is present without a linker or chelator, the radionuclide is attached to the N-terminus of the polypeptide. In some embodiments, when the radionuclide is present without a linker or chelator, the radionuclide is attached to the C-terminus of the polypeptide.

In some embodiments, a polypeptide provided herein (e.g., a miniprotein that binds to B7-H3) comprises at least one disulfide bridge.

In some embodiments, a polypeptide provided herein (e.g., a miniprotein that binds to B7-H3) comprises at least two disulfide bridges.

In some embodiments, the composition and/or polypeptide thereof selectively binds to B7-H3 or a portion thereof.

In some embodiments, the polypeptide has a binding affinity for B7-H3 or a portion thereof of 10 pM to 200 nM, 10 pM to 100 nM, or 10 nM to 100 nM, in vivo, ex vivo, or in vitro and/or as measured in a cell-based assay.

In some embodiments, the polypeptide has a binding inhibition constant of no greater than 100 nM.

A composition comprising a polypeptide-drug conjugate, comprising a polypeptide and at least one drug moiety, wherein the polypeptide comprises an amino acid sequence having at least 90% identity to at least 44 amino acids a polypeptide having an amino acid sequence set forth in any one of SEQ ID NOs: 198-537. In some embodiments, the polypeptide comprises at least one disulfide bridge. In some embodiments, the polypeptide comprises at least two disulfide bridges. In some embodiments, the polypeptide comprises one or two disulfide bridges. In some embodiments, the polypeptide comprises at least one non-natural amino acid (e.g., methylated lysine, citrulline, etc.). In some embodiments, the polypeptide comprises at least one modified amino acid. In some such embodiments, a modified amino acid is an amino acid that comprises a small alkyl group on the side chain of the amino acid (e.g., methylated lysine, e.g., mono, di, tri-methyllysine, etc.). For example, in some embodiments, a lysine can have a small alkyl group (e.g., a methyl group, e.g., mono, di, tri-methyl, etc.) on the nitrogen on its side chain. In some embodiments, an arginine can have a small alkyl group on the Guanidino group of its side chain.

In some embodiments, a B7-H3 binding miniprotein comprises or consists of an amino acid sequence according to any one of SEQ ID NOs: 4-6, 8-94 and 100-537 and can have different N- and/or C-terminal ends, such as, for example, an Acetyl, NH2, Biotin-PEG4, DOTA-PEG4, radiolabel, etc. on its N-terminus and an —OH or —NH2 on its C-terminus. N- and/or C-termini of B7-H3 binding miniproteins of the disclosure can include but are not limited to acetyl, acid, or amide (e.g., Acetyl, NH2, OH), such as provided in exemplary compounds and miniproteins of Table 2A or Table 2C. In some embodiments, a polypeptide according to the disclosure may have various modifications to its N-terminus (e.g., a linker, chelator, and/or radionuclide, e.g., such as set forth in exemplary compounds in Table 2A and/or Table 2C) or its C-terminus (e.g., a linker, chelator, and/or radionuclide). In some embodiments, the C-terminus of a given polypeptide can have an acid or amide group on its C-terminus (see, e.g., Table 2A and/or Table 2C). A given polypeptide having a particular amino acid sequence can have one or more N-terminal and/or C-terminal differences without materially changing the utility or function of the polypeptide, such as for binding to B7-H3 (e.g., for detection and/or treatment of cancer).

In some embodiments, a B7-H3 binding miniprotein comprises or consists of an amino acid sequence according to any one of SEQ ID NOs: 198-537 and can have different N- and/or C-terminal ends, such as, for example, an Acetyl, NH2, Biotin-PEG4, DOTA-PEG4, radiolabel, etc. on its N-terminus and an —OH or —NH2 on its C-terminus. N- and/or C-termini of B7-H3 binding miniproteins of the disclosure can include but are not limited to acetyl, acid, or amide (e.g., Acetyl, NH2, OH), such as provided in exemplary compounds and miniproteins of Table 2A or Table 2C. In some embodiments, a polypeptide according to the disclosure may have various modifications to its N-terminus (e.g., a linker, chelator, and/or radionuclide, e.g., such as set forth in exemplary compounds in Table 2C) or its C-terminus (e.g., a linker, chelator, and/or radionuclide). In some embodiments, the C-terminus of a given polypeptide can have an acid or amide group on its C-terminus (see, e.g., Table 2C). A given polypeptide having a particular amino acid sequence can have one or more N-terminal and/or C-terminal differences without materially changing the utility or function of the polypeptide, such as for binding to B7-H3 (e.g., for detection and/or treatment of cancer).

In certain embodiments, the disclosure provides a composition comprising a polypeptide that binds to B7-H3, has at least 48 amino acids, two disulfide bonds, and a modified amino acid at positions corresponding to 3, 24, and 29 relative to SEQ ID NO: 267, wherein the modification is a small alkyl group on the side chain of the amino acid (e.g., on the nitrogen of a lysine side chain, e.g., on the Guanidino group of an arginine side chain, etc.).

In one aspect, the disclosure provides a composition with one or more modified amino acids. In some such embodiments, the one or more modifications comprises a small alkyl group. In one aspect, the disclosure provides a composition comprising a B7-H3 binding polypeptide having an amino acid sequence comprising at least 48 amino acids, wherein the amino acids include (i) a cysteine at each of four positions corresponding to 1, 17, 35, and 48 of SEQ ID NO: 267 and wherein X3 is (Kme3) or R or (Rme); X19 is T or N; X24 is (Kme2) or (Kme); X28 is A or (Kme); X29 is A or (Kme) or R; X32 is D or (Kme) or (Cit); X36 is Q or N; X38 is S or A; X39 is E or N; X45 is K or (Kme), and X49 is S or absent.

In one aspect, the disclosure provides a composition, comprising a B7-H3 binding polypeptide having an amino acid sequence, wherein the amino acid sequence comprises: at least four cysteines, which form two disulfide bonds; an arginine, modified arginine, or modified lysine at a position corresponding to amino acid 3, a lysine at a position corresponding to amino acid 5, an isoleucine at a position corresponding to amino acid 6, a tryptophan at a position corresponding to amino acid 14, at least one modified lysine residue at a position corresponding to amino acid 24, and an alanine, arginine, or modified lysine at a position corresponding to 29, where each position is linear, from N-to-C-terminus relative to SEQ ID NO: 267, wherein the modification comprises at least one small alkyl group attached to the nitrogen of the lysine side chain or to the Guanidino group of the arginine side chain, optionally comprising a methyl, dimethyl, or trimethyl group; at least 48 amino acids in length; and has a binding affinity for B7-H3 stronger than 100 nM as measured in a cell-based assay.

In one aspect, the disclosure provides a composition, comprising a B7-H3 binding polypeptide having an amino acid sequence, wherein the amino acid sequence comprises: at least four cysteines, which form two disulfide bonds; at least one modified lysine residue at a position corresponding to X24 of SEQ ID NO: 267, wherein the modification comprises at least one small alkyl group attached to the nitrogen of the lysine side chain, optionally comprising a methyl, dimethyl, or trimethyl group; at least 48 amino acids in length; and has a binding affinity for B7-H3 stronger than 100 nM as measured in a cell-based assay.

In some embodiments, the polypeptide is at least 48 amino acids in length, but no greater than 100 amino acids in length. In some embodiments, the polypeptide binds to B7-H3 with an affinity of stronger than 10 nM in a cell-based assay.

In some embodiments, overexpressed B7-H3 on tumor cells has been shown to be successfully targeted including with T-cell-mediated immunotherapy. For example, one study showed that specific cytotoxic activity of activated T cell (ATC) also having a novel anti-CD3× anti-B7-H3 bispecific antibody showed increase in cytotoxicity relative to ATC alone, resulting in inhibition of tumor growth and increased survival in xenograft models. (Ma J., et al., Oncotarget (2016) 7(20):29480-91). In some embodiments, a binder of the present disclosure binds to B7-H3 expressed on one or more cells (e.g., cancer cells). In some such embodiments, the present disclosure contemplates targeting of B7-H3 with one or more binders of the present disclosure, wherein the B7-H3 is expressed at higher levels on cancer cells relative to non-cancer cells, and wherein the binding of the miniprotein is specific for cancer cells. the amino acid sequence of the polypeptide shares at least 90% identity to any one of SEQ ID NOs: 198-537, but includes at least one lysine and/or arginine with at least one modification comprising at least one small alkyl group bonded to the nitrogen of the lysine side chain or the Guanidino group of the arginine side chain, optionally selected from: trimethyl, dimethyl, and monomethyl. In some embodiments, the amino acid sequence of the polypeptide shares at least 90% identity to at least 44 amino acids of a reference polypeptide, which reference polypeptide is longer than 48 amino acids in length and binds to B7-H3 with a strength of at least 10 nM on a cell-based assay, and/or has an inhibition constant of no greater than 10 nM.

In some embodiments, the amino acid sequence of the polypeptide shares at least 90% identity to at least 44 amino acids of any one of SEQ ID NOs: 198-537, provided that the 44 amino acids include at least two cysteine residues that form one disulfide bridge.

In some embodiments, the amino acid sequence shares 90% identity to at least 44 amino acids as set forth in any one of SEQ ID NO: 199, 204, 241, or 262-272.

In some embodiments, the amino acid sequence shares 100% identity to at least 44 amino acids as set forth in any one of SEQ ID NO: 199, 204, 241, or 262-272.

In some embodiments, the disclosure provides composition comprising a polypeptide having an amino acid sequence comprising SEQ ID NO: 267.

In some embodiments, the disclosure provides a composition comprising a compound as set forth in C234, C235, C309, C325, or C332 of Table 2C and/or a compound having an amino acid sequence comprising SEQ ID NO: 204 or 267.

In some embodiments, the composition further comprises a radionuclide. In some embodiments, the radionuclide is Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211.

In some embodiments, the disclosure provides a composition comprising a polypeptide having an amino acid sequence of at least 48 amino acids in length, but with four cysteines positions corresponding to 1, 17, 35, and 48 of SEQ ID NO: 267, wherein the following amino acids are present; an arginine, modified arginine, or modified lysine at a position corresponding to amino acid 3, a lysine at a position corresponding to amino acid 5, an isoleucine at a position corresponding to amino acid 6, a tryptophan at a position corresponding to amino acid 14, at least one modified lysine residue at a position corresponding to amino acid 24, and an alanine, arginine, or modified lysine at a position corresponding to 29, where each position is linear, from N-to-C-terminus relative to SEQ ID NO: 267, wherein the modification comprises at least one small alkyl group attached to the nitrogen of the lysine side chain or to the Guanidino group of the arginine side chain, optionally comprising a methyl, dimethyl, or trimethyl.

In some embodiments, the C-terminus has an —OH or an —NH2.

In some embodiments, the binding affinity of the composition (e.g., the polypeptide) for B7-H3 is stronger than 100 nM.

In some embodiments, the inhibition constant is no greater than 100 nM.

In some embodiments, the composition further comprises one or more of a linker, chelator, and radionuclide.

In some embodiments, the linker comprises or consists of a polyethylene glycol (PEG) linker of PEG4, PEG, PEG2, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, or (Gly)n-(gGlu)n-(SEQ ID NO: 551) or (PEG)n, wherein n is from 1 to 36, (Gly)1-10 (SEQ ID NO: 552), or any fragment or combination via covalent bond thereof.

In some embodiments, the chelator comprises or consists of DOTA, Crown, NOPO, Macropa, lead specific chelator (PSC), N-succinimidyl 3-(tri-n-butylstannyl)benzoate (BuSTB), or N-succinimidyl 3-trimethylstannylbenzoate (MeSTB).

In some embodiments, the radionuclide is selected from Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211.

In some embodiments, if the polypeptide has an amino acid sequence comprising any one of SEQ ID NOs: 198-537. In some embodiments, the polypeptide sequence comprises any one of SEQ ID NOs: 199, 204, 241, or 262-272 and further comprises a linker, wherein the linker is PEG4, and an optional chelator, wherein the chelator is DOTA.

In some embodiments, when present, the linker is attached to the N-terminus of the polypeptide. In some embodiments, when present, the linker is attached to the C-terminus of the polypeptide.

In some embodiments, the C-terminal amino acid of the polypeptide is not a cysteine.

In some embodiments, when present, the chelator is attached to either the polypeptide or the linker.

In some embodiments, when present, the radionuclide is attached to the chelator.

In some embodiments, the disclosure provides a composition comprising a formula selected from one or more of (M)x-L-C-R, (M)x-L-C, (M)x-C-R, (M)x-L-R, (M)x-C, (M)x-L, and (M)x-R, wherein M comprises a polypeptide (M), L comprises a linker (L), C comprises a chelator (C), R comprises a radionuclide (R), and x is 1, 2, 3, or 4, wherein M comprises an amino acid sequence of any one of SEQ ID NO: 4-6, 8-94 and 100-537 or according to any of SEQ ID NOs: 538-543 and 546-550 and Table 1E. In some embodiments, the amino acid sequence comprises any one of SEQ ID NOs: 204 and 262-272.

In some embodiments, the linker comprises or consists of a polyethylene glycol (PEG) linker of PEG4, PEG, PEG2, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, or (Gly)n-(gGlu)n-(SEQ ID NO: 551) or (PEG)n, wherein n is from 1 to 36, (Gly)1-10 (SEQ ID NO: 552), or any fragment or combination via covalent bond thereof.

In some embodiments, the chelator comprises or consists of DOTA, Crown, NOPO, Macropa, lead specific chelator (PSC), N-succinimidyl 3-(tri-n-butylstannyl)benzoate (BuSTB), or N-succinimidyl 3-trimethylstannylbenzoate (MeSTB).

In some embodiments, the radionuclide Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211.

In some embodiments, the disclosure provides a composition comprising a formula selected from one or more of (M)x-L-C-R, (M)x-L-C, (M)x-C-R, (M)x-L-R, (M)x-C, (M)x-L, and (M)x-R, wherein M comprises a polypeptide (M), L comprises a linker (L), C comprises a chelator (C), R comprises a radionuclide (R), and x is 1, 2, 3, or 4, wherein M has an amino acid sequence comprising any one of those set forth in SEQ ID NOs: 4-6 and 8-94 and 100-537 or according to any of SEQ ID NOs: 95 and 96 and Tables 1B and 1C, and SEQ ID NOs: 538-543 and 546-550 (Table 1D) and Table 1E. In some embodiments, the amino acid sequence comprises any one of SEQ ID NOs: 204 and 262-272.

In some embodiments, when L is present, L comprises or consists of a polyethylene glycol (PEG) linker of PEG4, PEG, PEG2, PEG6, PEG8, PEG12, PEG24, lys(MPB)-PEG4, PEG36, an ester linker, an amide linker, a maleimide linker a valine-citrulline linker, a hydrazone linker, a N-succinimidyl-4-(2-pyridyldithio)butyrate (SPDB) linker, a succinimidyl-4-(N-maleimidomethyl)cyclohexane-1-carboxylate (SMCC) linker, a vinylsulfone-based linker, a propanoic acid linker, a dTyr-Gly-Phe (yGF) linker, a caproleic acid linker, or (Gly)n-(gGlu)n- (SEQ ID NO: 551) or (PEG)n, wherein n is from 1 to 36, (Gly)1-10 (SEQ ID NO: 552), or any fragment or combination via covalent bond thereof.

In some embodiments, when C is present, C comprises or consists of DOTA, Crown, NOPO, Macropa, lead-specific chelator (PSC), N-succinimidyl 3-(tri-n-butylstannyl)benzoate (BuSTB), or N-succinimidyl 3-trimethylstannylbenzoate (MeSTB).

In some embodiments, when R is present, R comprises or consists of Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211.

In some embodiments, when present, the linker is attached to the N-terminus of the polypeptide. In some embodiments, when present, the linker is attached to the C-terminus of the polypeptide.

In some embodiments, the C-terminal amino acid of the polypeptide is not a cysteine.

In some embodiments, when present, the chelator is attached to either the polypeptide or the linker.

In some embodiments, when present, the radionuclide is attached to the chelator.

In some embodiments, the polypeptide comprises at least one disulfide bridge.

In some embodiments, the polypeptide comprises at least two disulfide bridges.

In some embodiments, the composition and/or polypeptide thereof selectively binds to B7-H3 or a portion thereof.

In some embodiments, the polypeptide has a binding affinity for B7-H3 or a portion thereof of 10 pM to 200 nM, 10 pM to 100 nM, or 10 nM to 100 nM, in vivo, ex vivo, or in vitro and/or as measured in a cell-based assay.

In some embodiments, the polypeptide has a binding inhibition constant of no greater than 100 nM.

In one aspect, the disclosure provides a composition comprising a polypeptide-drug conjugate, comprising a polypeptide and at least one drug moiety, wherein the polypeptide comprises an amino acid sequence having at least 90% identity to at least 44 amino acids a polypeptide having an amino acid sequence set forth in any one of SEQ ID NOs: 4-6, 8-94 and 100-197 or according to SEQ ID NOs: 95 or 96 and Tables 1B and 1C.

A composition comprising a polypeptide-drug conjugate, comprising a polypeptide and at least one drug moiety, wherein the polypeptide comprises an amino acid sequence having at least 90% identity to at least 44 amino acids a polypeptide having an amino acid sequence set forth in any one of SEQ ID NOs: 198-537, Table 2C, or according to any of SEQ ID NOs: 538-543 and 546-550 (Table 1D) and Table 1E.

In some embodiments, the drug moiety is selected from a topoisomerase inhibitor, an auristatin (e.g., monomethyl auristatin E), a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, a dolastatin, a maytansinoid, a MetAP (methionine aminopeptidase), an inhibitor of nuclear export of proteins CRM1, a DPPIV inhibitor, proteasome inhibitors, inhibitors of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder, a DHFR inhibitor, and an immunotoxin.

In some embodiments, the disclosure provides a composition comprising an isolated compound, or a pharmaceutically acceptable salt thereof or a neutral molecule comprising an optional linker (L), and one or more of a polypeptide (M), chelator (C) or radionuclide (R), wherein M has an amino acid sequence comprising any one of SEQ ID NOs: 4-6, 8-94 and 100-197 or SEQ ID NOs: 95 and 96 and Tables 1B and 1C, and/or wherein M has an amino acid sequence comprising any one of SEQ ID NOs: 198-537, Table 2C, or according to any of SEQ ID NOs: 538-543 and 546-550 (Table 1D) and Table 1E.

In some embodiments, the disclosure provides a composition comprising, a compound designed to bind to B7-H3, which compound comprises or consists of a polypeptide having an amino acid sequence comprising any one of SEQ ID NOs: 4-6, 8-94 and 100-197 or SEQ ID NOs: 95 and 96 and Tables 1B and 1C, or an amino acid sequence comprising any one of SEQ ID NOs: 198-537, Table 2C, or according to any of SEQ ID NOs: 538-543 and 546-550 (Table 1D) and Table 1E.

In some embodiments, the modified N-terminus comprises one or more of an NH2, Acetyl, PEGn, wherein n=1-36, DOTA, or Biotin.

In some embodiments, the C terminus comprises an —NH2 or an —OH.

In some embodiments, the polypeptide selectively binds to B7-H3 or a portion thereof.

In some embodiments, the polypeptide has a binding affinity of stronger than about 100 nM to B7-H3, or a portion thereof, in vivo or in a cell-based assay.

Polypeptides

Among other things, the present disclosure provides polypeptides. In some embodiments a polypeptide is assembled using solid phase synthesis methods. In some embodiments, a polypeptide is recombinant. In some embodiments, a polypeptide comprises or consists of a miniprotein. In some such embodiments, a miniprotein comprises or consists of a binder. In some embodiments, polypeptides of the present disclosure (including muteins, allelic variants, fragments, derivatives, and analogs) are encoded by polynucleotides as described and provided herein.

In some embodiments, a miniprotein of the present disclosure comprises or consists of a polypeptide capable of binding to target as shown in Table 1A.

In some embodiments, the present disclosure provides binders comprising or consisting of a fragment of a polypeptide as provided herein. In some such embodiments, fragments include at least 20 contiguous amino acids, more preferably at least 25, 30, 35, 40, 45, 50, 55, 60, 65, 70, 75, 80, 85, 90, 95 or more contiguous amino acids.

In some embodiments, miniproteins of the present disclosure can also include fusions or conjugates with one or more other components, such as heterologous polypeptides. For example, in some embodiments, heterologous sequences can comprise or consist of sequences designed to facilitate purification, e.g., histidine tags, and/or visualization of recombinantly-expressed proteins. Other non-limiting examples of such fusions or conjugates include those that permit display of the encoded protein on the surface of a phage or a cell, including any detectable or visualizable component such as, e.g., green fluorescent protein (GFP), and fusions to the IgG Fc region.

In some embodiments, a miniprotein comprises or consists of a specific amino acid sequence. In some embodiments, a miniprotein has an amino acid sequence that is 70%, 75%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in any of SEQ ID NOs: 4-6, SEQ ID NOs: 12-94, or SEQ ID NOs: 100-537, and/or according to any of 1B, 1C, 1D, 1E, 2A, 2C, or 2D.

In some embodiments, a miniprotein has an amino acid sequence that is 70%, 75%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in any amino acid sequences set forth in Table 2A.

In some embodiments, a miniprotein does not have an amino acid sequence selected from any one of those according to Tables 1B, 1C, and/or 2A.

In some embodiments, a miniprotein has an amino acid sequence that is 75%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 contiguous amino acids of a given polypeptide such as those set forth in Table 2A or Table 2C. In some embodiments, the miniprotein does not have an amino acid sequence as set forth in Table 2A.

In some embodiments, a miniprotein has an amino acid sequence that is 70%, 75%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in any amino acid sequences set forth in Table 2A or Table 2C.

In some embodiments, a miniprotein has an amino acid sequence that is 75%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to a portion or all of an amino acid sequence set forth in Table 2A. For example, in some embodiments, a miniprotein has an amino acid sequence that is 75%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to 20, 21, 22, 23, 24, 25, 26, 27, 28. 29, 30, 31, 32, 33, 34, 35, 36, 37, 38, 39, 40, 41, 42, 43, or 44 amino acids of a given polypeptide such as those set forth in Table 2A.

In some embodiments, a miniprotein has an amino acid sequence that is 75%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to a portion or all of an amino acid sequence set forth in Table 2C. For example, in some embodiments, a miniprotein has an amino acid sequence that is 75%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to 20, 21, 22, 23, 24, 25, 26, 27, 28. 29, 30, 31, 32, 33, 34, 35, 36, 37, 38, 39, 40, 41, 42, 43, or 44 amino acids of a given polypeptide such as those set forth in Table 2C.

In some embodiments, a miniprotein has an amino acid sequence that is 75%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 contiguous amino acids of a given polypeptide such as those set forth in Table 2C.

In some embodiments, a polypeptide (e.g., a miniprotein) has an amino acid sequence with a certain percent identity over a certain percent coverage (e.g., of a reference sequence). Unless otherwise stated, percent identity refers to a maximum percent identity measured according to any one of the approaches set forth herein. That is, a B7-H3 binding polypeptide (e.g., a reference molecule) as provided herein can have 70, 75, 80, 85, 90, 95, 99, or 100 percent identity to a given query but over a percent coverage of that molecule (e.g., 10, 20, 30, 40, 50, 60, 70, 80, 90, 100%), where if the query molecule is shorter it may have a percent identity and a percent coverage that are different (e.g., 100% identity and 90% coverage). If the query molecule is longer, than the percent identity and coverage could each be 100% with respect to the reference molecule, and the reference molecule would have a percent identity over a length (e.g., at least 20, 25, 30, amino acids) of the query molecule. For example, in some embodiments, if a reference sequence (e.g., a miniprotein as provided herein) is shorter than a query sequence, such a query sequence is within the scope of the present disclosure if it has a length of reference sequence that aligns with the query sequence, wherein the percent identity is determined over at least a minimum length of the alignment between the two sequences (query and reference). That is, if a polypeptide disclosed herein is longer than a query sequence, a percent identity is determined by aligning the reference and query and determining the percent identity as between the query and the portion of the reference sequence over which it aligns. Conversely, where a query sequence is longer than a reference sequence, percent identity equals an identity over an aligned portion with the reference sequence. That is, if the reference sequence is shorter, the query sequence can fall within the scope of a reference sequence if it aligns at a claimed percent identity over the aligned portion between the two polypeptides (reference and query).

As used herein and known to those of skill in the art, the twenty conventional amino acids and their abbreviations follow conventional usage. See Immunology-A Synthesis (Golub and Gren eds., Sinauer Associates, Sunderland, Mass., 2nd ed. 1991), which is incorporated herein by reference. In some embodiments, an amino acid of the present disclosure may be a stereoisomer (e.g., D-amino acids) of the twenty conventional amino acids. In some embodiments, an amino acid in a polypeptide of the present disclosure may be a non-natural amino acid. For example, amino acids such as α-, α-disubstituted amino acids, N-alkyl amino acids, and other unconventional amino acids may also be suitable components for polypeptides of the present disclosure. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, N-methylarginine, and other similar amino acids and imino acids (e.g., 4-hydroxyproline). Arrangements of polypeptide sequence notations used herein have a left-side end corresponding to the amino terminal and a right-side end corresponding to the carboxy-terminal end, in accordance with standard usage and convention.

In some embodiments, miniproteins of the present disclosure comprising two or more cysteine residues, such as those set forth in Table 2C, have cysteine residues connected via disulfide bridges (e.g., via natural folding). In some embodiments a miniprotein (e.g., that binds to B7-H3) comprises one disulfide bridge. In some embodiments, a miniprotein comprises two disulfide bridges.

In some embodiments, the one disulfide bridge can be between cysteine residues corresponding to, for example, Cys4 and Cys37; Cys5 and Cys34; Cys5 and Cys37; Cys12 and Cys26; Cys12 and Cys44; Cys17 and Cys48, with positions relative to linear position from N-to-C-terminus with reference to SEQ ID NO: 267.

In some embodiments, cysteine connections can be between two different pairs of cysteine residues. For example, in some embodiments, two disulfide bridges can be between positions corresponding to pairs of cysteines such as Cys1 and Cys35 and Cys17 and Cys52, with reference to the miniprotein of SEQ ID NO: 213. For example, in some embodiments, disulfide bridges can be between positions corresponding to Cys1 and Cys35; and Cys17 and Cys48 of a reference sequence such as set forth in Table 2C (e.g., SEQ ID NO: 267). In some embodiments, cysteine connections are between Cys1 and Cys17; and Cys35 and Cys48. In some embodiments, cysteine connections are between Cys1 and Cys48; and Cys17 and Cys35.

In some embodiments, In some embodiments, the disulfide bridge or bridges comprise two or four cysteines at positions corresponding to 1, 17, 35, and 48 of SEQ ID NO: 267, wherein the cysteine corresponding to position 1 can form a disulfide bridge with the cysteine corresponding to position 17, 35, or 48. In some embodiments, the cysteine corresponding to position 17 can form a disulfide bridge with the cysteine corresponding to position 1, 35, or 48. In some embodiments, the cysteine corresponding to position 35 can form a disulfide bridge with the cysteine corresponding to position 1, 17, or 48. In some embodiments, the cysteine corresponding to position 48 can form a disulfide bridge with the cysteine corresponding to position 1, 17, or 35. In some embodiments, where four cysteines are present and correspond to positions 1, 17, 35, and 48 of SEQ ID NO: 267, pairings can comprise 1 paired with 35 and 17 paired with 48, 1 paired with 17 and 35 paired with 48, or 1 paired with 48 and 17 paired with 35 (e.g., disulfide bridges between the two cysteines of the pair).

In some embodiments, the present disclosure provides a miniprotein as set forth in Tables 1B, 1C, 1D, 1E, 2A, 2C and/or 2D or a portion or functional variant thereof and/or comprising or consisting of an amino acid sequence set forth in any of SEQ ID NOs: 4-6, 8-94 and 100-537.

In some embodiments, a miniprotein comprises or consists of an amino acid sequence having at least 70%, 75%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or greater sequence identity to as set forth in any of SEQ ID NOs: 4-6, 8-94 and 100-537 and/or Tables 1B, 1C, 1D, 1E, 2A, 2C or 2D or a portion or functional variant thereof.

In some embodiments, the miniprotein comprises or consists of an amino acid sequence having at least 1, at least 2, at least 3, at least 4, at least 5, at least 6, at least 7, at least 8, at least 9, at least 10, at least 15, at least 20 or more amino acid residue differences from SEQ ID NOs: 4-6, 8-94 and 100-537 and/or as set forth in Tables 1B, 1C, 1D, 1E, 2A, 2C, 2D, or a portion or functional variant thereof.

In some embodiments, the miniprotein comprises or consists of an amino acid sequence having no more than 1, no more than 2, no more than 3, no more than 4, no more than 5, no more than 6, no more than 7, no more than 8, no more than 9, no more than 10, no more than 15, no more than 20, no more than 25, no more than 30, or no more than 35 amino acid residue differences from SEQ ID NOs: 4-6, 8-94 and 100-537 and/or as set forth in Tables 1B, 1C, 1D, 1E, 2A, 2C, 2D, or a portion or functional variant thereof.

In some embodiments, the miniprotein has an amino acid sequence comprising or consisting of any of SEQ ID NOs: 4-6, SEQ ID NOs: 12-94, or SEQ ID NOs: 100-537, and/or as set forth in Tables 1B, 1C, 1D, 1E, 2A, 2C, 2D, or a portion or functional variant thereof selectively binds to the target B7-H3.

Polypeptides of the disclosure may have one or more modifications. A modification can refer to an amino acid sequence that comprises at least one substitution, alteration, inversion, addition, or deletion of an amino acid residue compared to a reference amino acid sequence. An alteration can include but is not limited to a change to or of one or more atoms of a side chain, such as, for example addition of a methyl-group (e.g., methylated versions of lysine). In some embodiments, a natural amino acid is modified such as set forth herein. In some embodiments, a modification includes addition of at least one small alkyl group attached to the nitrogen of an amino acid side chain, such as, for example, a lysine side chain. As used herein, a "small alkyl group" refers to an alkyl group with a short carbon chain, typically having one to four carbon atoms, such as methyl, ethyl, propyl, or butyl, and also including, for example, dimethyl, trimethyl, isopropyl, etc. In some embodiments, for example one or more small alkyl groups can be added to the nitrogen of a lysine side chain to produce monomethyl, dimethyl, or trimethyllysine. In some embodiments, one, two, three, four or more small alkyl groups may be added to a given amino acid (e.g., through attachment to the nitrogen of the side chain). In some embodiments no more than five, four, three, two, or one small alkyl groups are added.

Miniproteins

The present disclosure provides a polypeptide, comprising: an amino acid sequence, wherein the amino acid sequences comprises Formula I:

X1X2X3X4YX6X7EX9IX11ALX14EIIWLPNX22X23 X24X25QIX28AFIAALNX36DPSQ SSELLSEAX49X50LX52DSX55X56X57X58 (SEQ ID NO: 95), wherein X1 is A, N, or absent; X2 is A, E, or absent; X3 is A, Q, or absent; X4 is K, (KAc), L, or absent; X6 is A, D, E, I, L, N, Q, S, T, or Y; X7 is A, E, K, (KAc), (Kme3), L, Q, or S; X9 is K, (KAc), or (Kme3); X11 is A, Q, S, T, or Y; X14 is E, Q, S, or Y; X22 is A, D, F, (homo-leucine), I, L, N, (Nle), T, or Y; X23 is T or V; X24 is H or Y; X25 is A or G; X28 is A, (homo-leucine), M, M(O2), (Nle), S, T, or V; X36 is A, (Cit), D, E, L, N, Q, S, or T; X49 is A, E, G, K, (KAc), L, Q, S, or Y; X50 is A, (Cit), D, E, G, (hSer), K, (KAc), L, Q, S, or Y; X52 is A, D, G, N, Q, T, or Y; X55 is D, E, L, Q, S, Y, or absent; X56 is A or absent; X57 is P or absent; and X58 is G, K, (KAc), or absent; wherein if X28 is A, (homo-leucine), M(O2), S, T, or V, then X24 is Y; or wherein if X28 is M, then X7 is A, E, (Kme3), L, Q, or S.

In some embodiments, if X4 is K or (KAc), then X24 is Y.

In some embodiments, the amino acid sequence comprises Formula II:

X1X2X3X4YAX7EKIAALSEIIWLPNX22TX24X25QI X28AFIAALNX36DPSQSSELLSE AX49X50LNDSQAP (SEQ ID NO: 96), wherein X1 is A or absent; X2 is E or absent; X3 is A or absent; X4 is L or absent; X7 is K or Q; X22 is D or L; X24 is H or Y; X25 is A or G; X28 is ((homo-leucine)) or M; X36 is D or N; X49 is E or K; and X50 is E.

In some embodiments, the amino acid sequence comprises Formula III (SEQ ID NO: 538) as set forth in Tables 1D and 1E.

In some embodiments, the amino acid sequence comprises Formula IV (SEQ ID NO: 539) as set forth in Tables 1D and 1E.

In some embodiments, the amino acid sequence comprises Formula V (SEQ ID NO: 540) as set forth in Tables 1D and 1E:

In some embodiments, the amino acid sequence comprises Formula VI (SEQ ID NO: 541) as set forth in Tables 1D and 1E.

In some embodiments, the amino acid sequence comprises Formula VII (SEQ ID NO: 542) as set forth in Tables 1D and 1E.

In some embodiments, the amino acid sequence comprises Formula VIII (SEQ ID NO: 543) as set forth in Tables 1D and 1E.

In some embodiments, the amino acid sequence comprises Formula IX (SEQ ID NO: 546) as set forth in Tables 1D and 1E.

In some embodiments, the amino acid sequence comprises Formula X (SEQ ID NO: 547) as set forth in Tables 1D and 1E.

In some embodiments, the amino acid sequence comprises Formula XI (SEQ ID NO: 548) as set forth in Tables 1D and 1E.

In some embodiments, the amino acid sequence comprises Formula XII (SEQ ID NO: 549) as set forth in Tables 1D and 1E.

In some embodiments, the amino acid sequence comprises Formula XIII (SEQ ID NO: 550) as set forth in Tables 1D and 1E.

In some embodiments, the amino acid sequence shares at least 90% (e.g., 91, 92, 93, 94, 95, 96, 97, 98, 99 or more percent) identity to any one of the SEQ ID NOs: 4-6 or SEQ ID NOs: 12-94.

In some embodiments, the amino acid sequence shares 90% (e.g., 91, 92, 93, 94, 95, 96, 97, 98, 99 or more percent) identity to any one of SEQ ID NOs: 6, 21, or 30.

In some embodiments, the amino acid sequence shares 100% identity to any one of the SEQ ID NOs: 4-6 or SEQ ID NOs: 12-94.

In some embodiments, the amino acid sequence shares 100% identity to any one of SEQ ID NOs: 6, 21, or 30.

In some embodiments, the amino acid sequence shares 90% (e.g., 91, 92, 93, 94, 95, 96, 97, 98, 99 or more percent) identity to SEQ ID NO: 6.

In some embodiments, the amino acid sequence shares 100% identity to SEQ ID NO: 6.

The present disclosure also provides a polypeptide that has an amino acid sequence comprising or consisting of any of SEQ ID NOs: 4-6, 8-94, or 100-537.

The present disclosure also provides a polypeptide that has an amino acid sequence comprising or consisting of any of SEQ ID NOs: 4-6, 8-94, or 100-197.

The present disclosure also provides a polypeptide that has an amino acid sequence comprising or consisting of any of SEQ ID NOs: 198-537. In some embodiments, the miniprotein comprises at least one constraint, wherein the constraint is a disulfide bridge.

In some embodiments, the polypeptide further comprises one or more of a linker, chelator, and radionuclide.

In some embodiments, when present, the linker comprises or consists of a polyethylene glycol (PEG) linker of PEG4, PEG, PEG2, PEG6, PEG8, PEG12, PEG24, PEG36, lys (MPB)-PEG4, an ester linker, an amide linker, a maleimide linker, a succinimidyl-4-(N-maleimidomethyl) cyclohexane-1-carboxylate (SMCC) linker, a propanoic acid linker, a caproleic acid linker, an aminocaproic acid (Ahx) linker, or (Gly)n-(γGlu)n- or (PEG)n, wherein n is from 1 to 36, $(Gly)_{1-10}$, or any fragment or combination via covalent bond thereof.

In some embodiments, when present, the chelator comprises or consists of:

i) NOPO

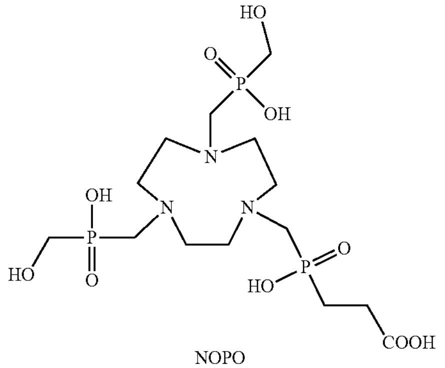

NOPO

-continued ii) Crown

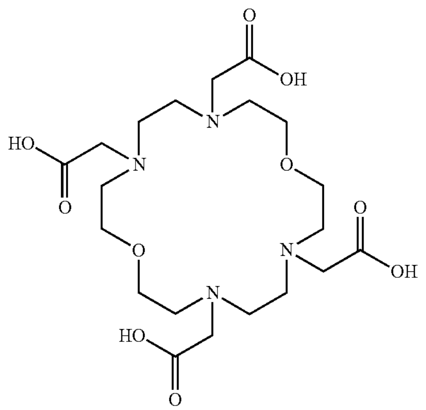

Crown iii) DOTA

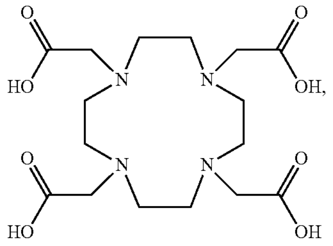

or iv) Macropa

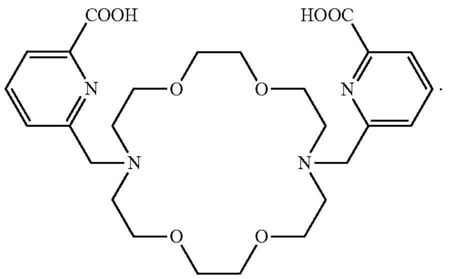

Macropa

In some embodiments, the chelator comprises or consists of derivative of NOPO, Crown, Macropa, or tetrazacyclododecane-1,4,7,10-tetraacetic acid (DOTA).

In some embodiments, the radionuclide comprises or consists of Ac-225, Ga-68, In-111, Pb-212, Lu-177, Cu-67, Cu-64, La-132, La-135, Ce-134, F-18, or At-211.

In some embodiments, the linker, when present, is attached to the N-terminal or C-terminal end of the polypeptide.

In some embodiments, the chelator, when present is attached to either the polypeptide or the linker.

In some embodiments, the radionuclide, when present, is attached to the chelator.

In some embodiments, the polypeptide comprises or consists of a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer.

In some embodiments, the polypeptide comprises at least one disulfide bridge.

In some embodiments, the polypeptide selectively binds to B7-H3 or a portion thereof.

In some embodiments, the polypeptide exhibits a binding affinity of 10 pM to 200 nM, 10 pM to 100 nM, or 10 nM to 100 nM to B7-H3, or a portion thereof, in vivo or in a cell-based assay.

In some embodiments, the polypeptide exhibits a binding affinity of 10 pM to 50 nM (e.g., 10 pM to 10 nM, e.g., 20 pM to 40 pM, e.g., 25 pM to 50 to B7-H3 in a cell-based assay.

Miniproteins

Provided herein are novel polypeptides (e.g., miniproteins) and methods of use thereof. In some embodiments, a polypeptide comprises or consists of a miniprotein. The present disclosure recognizes that a source of a problem in therapeutics (e.g., miniprotein therapeutics) is binding to B7-H3 with sufficient specificity and affinity. Thus, provided herein are miniproteins that bind strongly, efficiently, and specifically to B7-H3 (e.g., on a cell, e.g., on a cancer cell).

Another source of a problem includes toxicity (e.g., renal toxicity). In some embodiments, specificity and strength of binding for B7-H3 in cancer cells reduces uptake into kidney.

In some such embodiments, the miniprotein comprises or consists of an affibody, a CDP, a knottin, a binder, a monobody, an anticalin, a designed ankyrin repeat, an engineered Kunitz domain, and/or an avimer. In some embodiments the miniprotein is designed to be linked to one or more other components. For example, in some embodiments, a miniprotein may be linked (conjugated) to another component such as a chelator and/or a radionuclide. In some embodiments, conjugation is via a lysine or cysteine residue. For example, in some embodiments, a miniprotein is engineered to remove all lysine residues except for one, which is, in some embodiments, used for conjugation. In some embodiments, conjugation occurs via an optional linker. In some embodiments, conjugation between a miniprotein and a chelator and/or radionuclide is direct.

Without wishing to be bound by any particular theory, the present disclosure contemplates that therapeutics comprising compositions provided by the present disclosure are characterized by several features relative to other (e.g., antibody-based) therapeutics. For example, in some embodiments, miniproteins display several key features of antibody-based therapeutics (e.g., affinity, potency, specificity, and ability to disrupt protein:protein interactions) but also have several advantages as compared to antibody-based therapeutics such as smaller size, cheaper manufacturing, and elimination of need to chimerize or humanize the proteins. In addition, the size and specificity of binding increases tumor penetrance and uptake into cells expressing the target of the miniprotein or composition (e.g., conjugate) comprising a miniprotein.

In some embodiments, a miniprotein of the present disclosure is no more than about 100 amino acids in length. In some embodiments, a miniprotein is about 10, 15, 20, 25, 30, 35, 40, 45, 50, 55, 60, 65, 70, 75, 80, 85, 90, 95 or more amino acids in length, up to about 100 amino acids in length. In some such embodiments, however, a miniprotein of the present disclosure does not exceed about 100 amino acids in length. In some embodiments a miniprotein is between about 10 to about 30, about 20 to about 40, about 30 to about 50, about 40 to about 60, about 45 to about 65, about 50 to about 70, about 55 to about 75, about 65 to about 85 or more amino acids in length, but not exceeding about 100 amino acids in length. In some preferred embodiments, a miniprotein is about 65 amino acids or less. In some preferred embodiments, a miniprotein is about 50 amino acids or less.

In some embodiments, a miniprotein of the present disclosure is not larger than about 12 kDa. In some embodiments, a miniprotein of the present disclosure is about 2, 2.5, 3, 3.5, 4, 4.5, 5, 5.5, 6, 6.5, 7, 7.5, 8, 8.5, 9, 9.5, 10, 10.5, 11, 11.5 or more kDa. In some such embodiments, however, a miniprotein of the present disclosure does not exceed about 12 kDa.

In some embodiments, a miniprotein of the present disclosure comprises or consists of a cysteine-dense peptide, knottin, and/or binder.

In some embodiments, a miniprotein comprises one or more disulfide bridges. In some embodiments, a miniprotein comprises multiple cysteine residues. In some such embodiments, cysteine residues crosslink to maintain a very stable, folded state for a peptide of its length (e.g., relative to a peptide of the same length without as many cysteine residues). The present disclosure contemplates that such crosslinking confers improved stability with reduced (i.e., very low to no) immunogenicity and/or sustains or improves ability to maintain biological activity in harsh but efficient chelation conditions (e.g., high temperature and low pH).

In some embodiments a miniprotein or composition comprising a miniprotein (e.g., a radionuclide conjugate) has low immunogenicity relative to a larger protein or composition comprising or consisting of a larger protein (e.g., an antibody).

In some embodiments, miniproteins (e.g., affibody, CDP, knottin, binder, engineered Kunitz domain, monobody, anticalin, designed ankyrin repeat domain (DARPin), avimer) have superior penetration efficiency relative to larger proteins. That is, in some embodiments, a miniprotein or composition comprising a miniprotein can penetrate a solid tumor better than a larger protein or composition comprising a protein larger than a miniprotein. For example, in some such embodiments, a miniprotein or composition comprising a miniprotein has a hydrodynamic radius of about 1 to about 25 nm. In some embodiments, a hydrodynamic radius is in a range of about 1-25 nm, 10-20 nm, 5-15 nm, 1-5 nm, 2-4 nm, or 1-3 nm. In some embodiments, hydrodynamic radius is measured using light scatter methods known to those of skill in the art.

In some embodiments, a miniprotein of the present disclosure is characterized in that it has one or more properties relative to a protein larger than 100 amino acids like an antibody, antibody fragment, VHH domain, single chain antibody or other protein or binder greater than 12 kDa. In some embodiments a property is selected from increased protein expression, increased thermoactivity, increased thermostability, increased pH activity, increased stability, increased activity, increased receptor binding specificity and/or affinity, increased specific activity, increased resistance to substrate and/or end-product inhibition, increased chemical stability, improved chemoselectivity, improved solvent stability, increased tolerance to acidic pH, increased tolerance to proteolytic activity (i.e., reduced sensitivity to proteolysis), reduced aggregation, increased solubility, reduced immunogenicity, and altered temperature profile, increased resistance to liver uptake, kidney uptake or healthy tissue binding, increased tumor penetration, and/or increased volume of distribution.

In some embodiments, a miniprotein or composition comprising a miniprotein (e.g., conjugate, e.g., radionuclide conjugate) provided by the present disclosure exhibits binding affinity to B7-H3. In some embodiments, the B7-H3 is human B7-H3. In some embodiments, the human B7-H3 is on a cell. In some embodiments, the cell is a cell line, a primary cell, or a cell in a human (e.g., in a tumor).

In some embodiments, the binding affinity of a miniprotein or conjugate thereof to human B7-H3 is about 500 nM, 400 nM, 300 nM, 200 nM, 100 nM, or stronger (e.g., 90 nM, 75 nM, 50 nM, 25 nM, 10 nM, 5 nM, etc.). In some embodiments, the miniprotein comprises picomolar binding affinity. In some embodiments, the miniprotein or conjugate thereof comprises a binding affinity characterized by a dissociation constant ranging from about 900 nM to about 1 nM, e.g., 900, 800, 700, 600, 500, 400, 300, 200, 100, 90, 80, 70, 60, 50, 40, 30, 20, 10, 9, 8, 7, 6, 5, 4, 3, 2, 1, 0.9, 0.8, 0.7, 0.6, 0.5, 0.4 nM or stronger (e.g., 0.3, 0.2, 0.1, 0.09 nM, etc.) binding affinity to human B7-H3. In some embodiments, the binding is selective to human B7-H3 and, not, e.g., non-human B7-H3.

In some embodiments, a miniprotein or conjugate thereof displays a binding inhibition constant. In some embodiments, the binding inhibition constant (Ki) to human B7-H3 is about 300 nM, 200 nM, 100 nM, 50 nM, 25 nM, 10 nM, 5 nM, or less (e.g., 1 nM, etc.). In some embodiments, the miniprotein comprises picomolar binding affinity. In some embodiments, the miniprotein or conjugate thereof comprises a binding affinity characterized by a dissociation constant ranging from about 900 nM to about 1 nM, e.g., 900, 800, 700, 600, 500, 400, 300, 200, 100, 90, 80, 70, 60, 50, 40, 30, 20, 10, 9, 8, 7, 6, 5, 4, 3, 2, 1, 0.9, 0.8, 0.7, 0.6, 0.5, 0.4 nM or stronger (e.g., 0.3, 0.2, 0.1, 0.09 nM, etc.) binding affinity to human B7-H3. In certain embodiments, the binding inhibition constant of a B7-H3 binding polypeptide of the disclosure is between about 100 pM to about 50 nM (e.g., in a cell-based assay, e.g., DELFIA). In some embodiments, the binding is selective to human B7-H3 and, not, e.g., non-human B7-H3.

In some embodiments, a miniprotein or conjugate thereof provided by the present disclosure has high affinity for B7-H3 (e.g., as measured by binding affinity and/or inhibition constant, etc.). In some such embodiments, the B7-H3 is human B7-H3. In some embodiments, a miniprotein of the present disclosure is stable, including in the presence of one or more additional molecules (e.g., a cytotoxic molecule, e.g., radionuclide).

In some embodiments, a miniprotein or composition comprising a miniprotein (e.g., conjugate, e.g., radionuclide conjugate) displays nm or sub-nm binding affinity to B7-H3. In some embodiments, the affinity is measured in an in vitro assay. In some embodiments, the in vitro assay is a cell-based assay. In some embodiments, affinity is measured in an in vivo assay (e.g., a PET scan) or using a sample from a subject (e.g., an in vitro assay using a biological specimen such as blood or a cell biopsy from a subject).

In some embodiments, a miniprotein or conjugate thereof displays a binding affinity to B7-H3. In some embodiments, the binding affinity of a miniprotein or conjugate thereof to human B7-H3 is about 500 nM. In some embodiments, the miniprotein comprises picomolar binding affinity. In some embodiments, the miniprotein or conjugate thereof comprises a binding affinity characterized by a dissociation constant ranging from about 900 nM to about 1 nM, e.g., 900, 800, 700, 600, 500, 400, 300. 200, 100, 90, 80, 70, 60, 50, 40, 30, 20, 10, 9, 8, 7, 6, 5, 4, 3, 2, 1, 0.9, 0.8, 0.7, 0.6, 0.5, 0.4 nM or less binding affinity to human B7-H3. In some embodiments, the binding is selective to human B7-H3 and, not, e.g., non-human B7-H3.

In some embodiments, a miniprotein or conjugate thereof provided by the present disclosure has high affinity for B7-H3. In some such embodiments, the B7-H3 is human B7-H3. In some embodiments, a miniprotein of the present disclosure is stable, including in the presence of one or more additional molecules (e.g., a cytotoxic molecule, e.g., radiation).

In some embodiments, binding ability of a miniprotein or conjugate thereof to a target is improved by one or more modifications. For example, in some embodiments, binding ability of a miniprotein or conjugate thereof as provided herein to B7-H3, is improved using chemical crosslinking. In some embodiments, binding may be enhanced by using one or more of lysine residues, fusion proteins, non-natural amino acids, or other chemical moieties to enhance binding and/or functional activity.

In some embodiments, to ensure proper folding and connectivity, selected cysteine pairs can be replaced with selenocysteines. It is contemplated that, in some embodiments, diselenide crosslinks form more readily than disulfide crosslinks due to their lower redox potential and such a replacement may cross-couple remaining cysteine residues.

In some embodiments, a miniproteins or conjugates thereof provided by the present disclosure comprises or consists of monomers that make up a dimer, polymer or a multimer. In some such embodiments, the monomers all bind to the same target. For example, in some embodiments, where more than one miniprotein is present, each miniprotein is no greater than about 30-40 amino acids in length or a total of about 8 kDa in size (with both miniproteins). In some embodiments, the monomers each bind to a different target. In some embodiments, some monomers bind to one target and others bind to one or more additional targets.

In some embodiments, a miniprotein of the present disclosure comprises or consists of an antigen for use in generating an antibody that specifically binds to at least one epitope on B7-H3. In some embodiments, such an antibody may be used for, e.g., diagnostic purposes, blocking (e.g., antagonism), etc.

In some embodiments, the miniprotein comprises one or more disulfide bridges.

In some embodiments, a miniprotein or conjugate thereof as provided herein does not comprises one or more cysteine residues. In some embodiments, the miniprotein does not comprise one or more disulfide bridges.

In some embodiments, a miniprotein or conjugate thereof as provided herein is specific for a target. In some embodiments, a binder is specific for B7-H3 or a fragment thereof.

In some embodiments, a miniprotein or conjugate thereof as provided herein comprises or consists of a specific amino acid sequence.

In some embodiments, miniproteins or compositions comprising miniproteins (e.g., radionuclide conjugates) are conjugated to a chelator that optionally binds a radionuclide (e.g., actinium). In some embodiments, the conjugation is via a linker. In some embodiments, conjugation is direct conjugation. In some embodiments, such radionuclide conjugates combine and synergize to provide target specificity (e.g., via the miniprotein) and superior treatment (e.g., via directed radioisotope delivery to the cell expressing the target).

In some embodiments, miniproteins or compositions comprising miniproteins are conjugated to a chelator that optionally binds a cold-metal surrogate. In some embodiments, a cold-metal surrogate is a natural isotope of an element that is not radioactive. In some embodiments, an element may have more than one natural isotope that is not radioactive. In some embodiments, "cold" is used to refer to an isotype of an element that is not radioactive. In some embodiments, "hot" refers to an isotope of an element that is radioactive.

As used herein and known to those of skill in the art, the twenty conventional amino acids and their abbreviations follow conventional usage. See Immunology—A Synthesis (Golub and Gren eds., Sinauer Associates, Sunderland, Mass., 2nd ed. 1991), which is incorporated herein by reference. In some embodiments, an amino acid of the present disclosure may be a stereoisomer (e.g., D-amino acids) of the twenty conventional amino acids. In some embodiments, an amino acid in a polypeptide of the present disclosure may be a non-natural amino acid. For example, amino acids such as α-, α-disubstituted amino acids, N-alkyl amino acids, and other unconventional amino acids may also be suitable components for polypeptides of the present disclosure. Examples of unconventional amino acids include: 4-hydroxyproline, γ-carboxyglutamate, trimethyllysine, ε-N,N,N-trimethyllysine, ε-N-acetyllysine (Lys(Ac)), O-phosphoserine, N-acetylserine, N-formylmethionine, 3-methylhistidine, 5-hydroxylysine, N-methylarginine, norleucine, citrulline, L-citrulline, methylated arginine (Rme, Rme2), symmetrically dimethylated arginine (sRme2, Rme2s, or SDMA), nitroarginine (Arg(NO2)), Leu-13C6, 15N (an enriched stable isotope version of Leucine), and other similar amino acids and imino acids (e.g., 4-hydroxyproline). Arrangements of polypeptide sequence notations used herein have a left-side end corresponding to the amino terminal and a right-side end corresponding to the carboxy-terminal end, in accordance with standard usage and convention.

In some embodiments, a miniprotein disclosed herein has one or more of the following unconventional amino acids: trimethyllysine, dimethyllysine, monomethyllysine, isopropyl-lysine, Lys(Ac), norleucine, citrulline, L-citrulline, methylated arginine (Rme, Rme2), symmetrically dimethylated arginine (sRme2, Rme2s, or SDMA), nitroarginine (Arg(NO2)), or Leu-13C6,15N. ε-N,N,N-trimethyllysine, ε-N-acetyllysine, O-phosphoserine, N-acetylserine, N-formylmethionine, 3-methylhistidine, 5-hydroxylysine, N-methylarginine, and other similar amino acids and imino acids (e.g., 4-hydroxyproline). Arrangements of polypeptide sequence notations used herein have a left-side end corresponding to the amino terminal and a right-side end corresponding to the carboxy-terminal end, in accordance with standard usage and convention.

In some embodiments, a miniprotein comprises or consists of a specific amino acid sequence. In some embodiments, a miniprotein has an amino acid sequence that is 70%, 75%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in any of SEQ ID NOs: 4-6, 8-94 and 100-537. In various embodiments, a miniprotein has an amino acid sequence that is 90% identical to the amino acid sequence set forth in any of SEQ ID NOs: 4-6, 8-94 and 100-537. In various embodiments, a miniprotein has an amino acid sequence that is 100% identical to the amino acid sequence set forth in any of SEQ ID NOs: 4-6, 8-94 and 100-537.

In some embodiments, a miniprotein comprises or consists of a specific amino acid sequence. In some embodiments, a miniprotein has an amino acid sequence that is 70%, 75%, 80%, 85%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in any of SEQ ID NOs: 4-6, 8-94 or 100-537. In various embodiments, a miniprotein has an amino acid sequence that is 90% identical to the amino acid sequence set forth in any of SEQ ID NOs: 4-6, 8-94 or 100-537. In various embodiments, a miniprotein has an amino acid sequence that is 100% identical to the amino acid sequence set forth in any of SEQ ID NOs: 4-6, 8-94 or 100-537.

A polypeptide (e.g., a miniprotein) in accordance with the present disclosure can have an amino acid sequence with a certain percent identity over a certain percent coverage (e.g., of a reference sequence). That is, for example, a B7-H3 binding polypeptide (e.g., a reference molecule) as provided herein can have 70, 75, 80, 85, 90, 95, 99, or 100 percent identity to a given query but over a percent coverage of that molecule (e.g., 10, 20, 30, 40, 50, 60, 70, 80, 90, 100%), where if the query molecule is shorter it may have a percent identity and a percent coverage that are different (e.g., 100% identity and 90% coverage). If the query molecule is longer, than the percent identity and coverage could each be 100% with respect to the reference molecule, and the reference molecule would have a percent identity over a length (e.g., at least 20, 25, 30, amino acids) of the query molecule. For example, in some embodiments, if a reference sequence (e.g., a miniprotein as provided herein) is shorter than a query sequence, such a query sequence is within the scope of the present disclosure if it has a length of reference sequence that aligns with the query sequence, wherein the percent identity is determined over at least a minimum length of the alignment between the two sequences (query and reference). That is, if a polypeptide disclosed herein is longer than a query sequence, a percent identity is determined by aligning the reference and query and determining the percent identity as between the query and the portion of the reference sequence over which it aligns. Conversely, where a query sequence is longer than a reference sequence, percent identity equals an identity over an aligned portion with the reference sequence. That is, if the reference sequence is shorter, the query sequence can fall within the scope of a reference sequence if it aligns at a claimed percent identity over the aligned portion between the two polypeptides (reference and query).

In some embodiments, a miniprotein has an amino acid sequence that is 70%, 75%, 80%, 85%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in any of SEQ ID NOs: 4-6, SEQ ID NOs: 12-94, or SEQ ID NOs: 100-537. In various embodiments, a miniprotein has an amino acid sequence that is 90% identical to the amino acid sequence set forth in any of SEQ ID NOs: 4-6, SEQ ID NOs: 12-94, or SEQ ID NOs: 100-537. In various embodiments, a miniprotein has an amino acid sequence that is 100% identical to the amino acid sequence set forth in any of SEQ ID NOs: 4-6, SEQ ID NOs: 12-94, or SEQ ID NOs: 100-537.

In some embodiments, a miniprotein has an amino acid sequence that is at least 90% (91, 92, 93, 94, 95, 96, 97, 98, 99% or greater) identical to at least 40, 41, 42, 43, 44, 45, 46, 47, or 48 amino acids as set forth in any one of SEQ ID NOs: 4-6, SEQ ID NOs: 12-94, or SEQ ID NOs: 100-537. In some embodiments, a miniprotein has an amino acid sequence that is 100% identical to at least 40, 41, 42, 43, 44, 45, 46, 47, or 48 amino acids as set forth in any one of SEQ ID NOs: 4-6, SEQ ID NOs: 12-94, or SEQ ID NOs: 100-537.

In some embodiments, a miniprotein has an amino acid sequence that is at least 90% (91, 92, 93, 94, 95, 96, 97, 98, 99% or greater) identical to at least 40, 41, 42, 43, 44, 45, 46, 47, or 48 amino acids as set forth in any one of SEQ ID NOs: 198-537. In some embodiments, a miniprotein has an amino acid sequence that is 100% identical to at least 40, 41, 42, 43, 44, 45, 46, 47, or 48 amino acids as set forth in any one of SEQ ID NOs: 198-537.

In some embodiments, a miniprotein has an amino acid sequence that is at least 90% (91, 92, 93, 94, 95, 96, 97, 98, 99% or greater) identical to at least 40, 41, 42, 43, 44, 45, 46, 47, or 48 amino acids as set forth in any one of SEQ ID NOs: 204 and 262-272. In some embodiments, a miniprotein has an amino acid sequence that is 100% identical to at least 40, 41, 42, 43, 44, 45, 46, 47, or 48 amino acids as set forth in any one of SEQ ID NOs: 204 and 262-272.

In some embodiments, a miniprotein has an amino acid sequence that is 70%, 75%, 80%, 85%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in any of SEQ ID NOs: 6, 21, 30, 130-131, 183, 199, 204, 241 or 267. In various embodiments, a miniprotein has an amino acid sequence that is 90% identical to the amino acid sequence set forth in any of SEQ ID NOs: 6, 21, or 30. In various embodiments, a miniprotein has an amino acid sequence that is 100% identical to the amino acid sequence set forth in any of SEQ ID NOs: 6, 21, 30, 130-131, 183, 199, 204, 241, or 267.

In some embodiments, a miniprotein has an amino acid sequence that is 70%, 75%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in SEQ ID NO: 6. In various embodiments, a miniprotein has an amino acid sequence that is 90% identical to the amino acid sequence set forth in SEQ ID NO: 6. In various embodiments, a miniprotein has an amino acid sequence that is 100% identical to the amino acid sequence set forth in SEQ ID NO: 6.

In some embodiments, a miniprotein has an amino acid sequence that is 70%, 75%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in SEQ ID NO: 21. In various embodiments, a miniprotein has an amino acid sequence that is 90% identical to the amino acid sequence set forth in SEQ ID NO: 21. In various embodiments, a miniprotein has an amino acid sequence that is 100% identical to the amino acid sequence set forth in SEQ ID NO: 21.

In some embodiments, a miniprotein has an amino acid sequence that is 70%, 75%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in SEQ ID NO: 30. In various embodiments, a miniprotein has an amino acid sequence that is 90% identical to the amino acid sequence set forth in SEQ ID NO: 30. In various embodiments, a miniprotein has an amino acid sequence that is 100% identical to the amino acid sequence set forth in SEQ ID NO: 30.

In some embodiments, a miniprotein has an amino acid sequence that is 70%, 75%, 80%, 85%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in SEQ ID NO: 130. In various embodiments, a miniprotein has an amino acid sequence that is 90% identical to the amino acid sequence set forth in SEQ ID NO: 130. In various embodiments, a miniprotein has an amino acid sequence that is 100% identical to the amino acid sequence set forth in SEQ ID NO: 130.

In some embodiments, a miniprotein has an amino acid sequence that is 70%, 75%, 80%, 85%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in SEQ ID NO: 131. In various embodiments, a miniprotein has an amino acid sequence that is 90% identical to the amino acid sequence set forth in SEQ ID NO: 131. In various embodiments, a miniprotein has an amino acid sequence that is 100% identical to the amino acid sequence set forth in SEQ ID NO: 131.

In some embodiments, a miniprotein has an amino acid sequence that is 70%, 75%, 80%, 85%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in SEQ ID NO: 183. In various embodiments, a miniprotein has an amino acid sequence that is 90% identical to the amino acid sequence set forth in SEQ ID NO: 183. In various embodiments, a miniprotein has an amino acid sequence that is 100% identical to the amino acid sequence set forth in SEQ ID NO: 183.

In some embodiments, a miniprotein has an amino acid sequence that is 70%, 75%, 80%, 85%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in SEQ ID NO: 199. In various embodiments, a miniprotein has an amino acid sequence that is 90% identical to the amino acid sequence set forth in SEQ ID NO: 199. In various embodiments, a miniprotein has an amino acid sequence that is 100% identical to the amino acid sequence set forth in SEQ ID NO: 199. In some embodiments, a miniprotein has an amino acid sequence that is at least 90% (91, 92, 93, 94, 95, 96, 97, 98, 99% or greater) identical to at least 40, 41, 42, 43, 44, 45, 46, 47, or 48 amino acids as set forth in SEQ ID NO: 199. In some embodiments, a miniprotein has an amino acid sequence that is 100% identical to at least 40, 41, 42, 43, 44, 45, 46, 47, or 48 amino acids as set forth in SEQ ID NO: 199.

In some embodiments, a miniprotein has an amino acid sequence that is 70%, 75%, 80%, 85%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in SEQ ID NO: 204. In various embodiments, a miniprotein has an amino acid sequence that is 90% identical to the amino acid sequence set forth in SEQ ID NO: 204. In various embodiments, a miniprotein has an amino acid sequence that is 100% identical to the amino acid sequence set forth in SEQ ID NO: 204. In some embodiments, a miniprotein has an amino acid sequence that is at least 90% (91, 92, 93, 94, 95, 96, 97, 98, 99% or greater) identical to at least 40, 41, 42, 43, 44, 45, 46, 47, or 48 amino acids as set forth in SEQ ID NO: 204. In some embodiments, a miniprotein has an amino acid sequence that is 100% identical to at least 40, 41, 42, 43, 44, 45, 46, 47, or 48 amino acids as set forth in SEQ ID NO: 204.

In some embodiments, a miniprotein has an amino acid sequence that is 70%, 75%, 80%, 85%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in SEQ ID NO: 241. In various embodiments, a miniprotein has an amino acid sequence that is 90% identical to the amino acid sequence set forth in SEQ ID NO: 241. In various embodiments, a miniprotein has an amino acid sequence that is 100% identical to the amino acid sequence set forth in SEQ ID NO: 241. In some embodiments, a miniprotein has an amino acid sequence that is at least 90% (91, 92, 93, 94, 95, 96, 97, 98, 99% or greater) identical to at least 40, 41, 42, 43, 44, 45, 46, 47, or 48 amino acids as set forth in SEQ ID NO: 241. In some embodiments, a miniprotein has an amino acid sequence that is 100% identical to at least 40, 41, 42, 43, 44, 45, 46, 47, or 48 amino acids as set forth in SEQ ID NO: 241.

In some embodiments, a miniprotein has an amino acid sequence that is 70%, 75%, 80%, 85%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in SEQ ID NO: 267. In various embodiments, a miniprotein has an amino acid sequence that is 90% identical to the amino acid sequence set forth in SEQ ID NO: 267. In various embodiments, a miniprotein has an amino acid sequence that is 100% identical to the amino acid sequence set forth in SEQ ID NO: 267. In some embodiments, a miniprotein has an amino acid sequence that is at least 90% (91, 92, 93, 94, 95, 96, 97, 98, 99% or greater) identical to at least 40, 41, 42, 43, 44, 45, 46, 47, or 48 amino acids as set forth in SEQ ID NO: 267. In some embodiments, a miniprotein has an amino acid sequence that is 100% identical to at least 40, 41, 42, 43, 44, 45, 46, 47, or 48 amino acids as set forth in SEQ ID NO: 267.

In some embodiments, the miniprotein can further comprise additions on its N- and/or C-terminus, for example, one or more additional amino acids.

In some embodiments, a B7-H3 binding miniprotein in accordance with the disclosure can have different N- and/or C-terminal ends, such as, for example, an Acetyl, NH2, Biotin-PEG4, DOTA-PEG4, radiolabel, etc. on its N-terminus and an —OH or —NH2 on its C-terminus. N- and/or C-termini of B7-H3 binding miniproteins of the disclosure can include but are not limited to acetyl, acid, or amide (e.g., Acetyl, NH2, OH), such as provided in exemplary compounds and miniproteins of Table 2A or Table 2C.

In some embodiments, a polypeptide according to the disclosure may have various modifications to its N-terminus (e.g., a linker, chelator, and/or radionuclide, e.g., such as set forth in exemplary compounds in Table 2A or Table 2C) or its C-terminus (e.g., a linker, chelator, and/or radionuclide). In some embodiments, the C-terminus of a given polypeptide can have an acid or amide group on its C-terminus (see, e.g., Table 2A, e.g., Table 2C). A given polypeptide having a particular amino acid sequence can have one or more N-terminal and/or C-terminal differences without materially changing the utility or function of the polypeptide, such as for binding to B7-H3 (e.g., for detection and/or treatment of cancer).

In some embodiments, an addition on the N and/or C-terminus can include one or more of a linker and/or chelator, etc., such as, for example, an N-terminal DOTA-PEG4. In some embodiments, the C-terminus of a miniprotein comprises and NH2, OH, and/or COOH.

In some embodiments, the miniprotein further comprising additions on its N- and/or C-terminus has an amino acid sequence that is 70%, 75%, 80%, 85%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in SEQ ID NOs: 4-6, 8-94 and 100-537. In some such embodiments, the miniprotein is included in a compound. In some embodiments, the compound is selected from any of Compound Nos: C1-C608 and C611.

In some embodiments, the miniprotein further comprising additions on its N- and/or C-terminus has an amino acid sequence that is 70%, 75%, 80%, 85%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in SEQ ID NOs: 4-6, 8-94, or 100-537. In some such embodiments, the miniprotein is included in a compound. In some embodiments, the compound is selected from any of Compound Nos: C1-C9, C11-C117, or C121-C608 and C611.

In some embodiments, the miniprotein does not comprise one or more constraints (e.g., a disulfide bridge). In some embodiments, the miniprotein has an amino acid sequence that is 70%, 75%, 80%, 85%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in SEQ ID NOs: 4-6, 8-94 or 100-197. In some embodiments, the miniprotein is part of a compound. In some embodiments, the compound is selected from any of Compound Nos: C1-C226.

In some embodiments, the miniprotein does not comprise one or more constraints (e.g., a disulfide bridge). In some embodiments, the miniprotein has an amino acid sequence that is 70%, 75%, 80%, 85%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in SEQ ID NOs: 198-537. In some embodiments, the miniprotein is part of a compound. In some embodiments, the compound is selected from any of Compound Nos: C227-C608 and C611.

In some embodiments, the miniprotein comprises further changes such as, for example, one or more constraints (e.g., as disclosed herein). In some embodiments, a constraint is a disulfide bridge. In some embodiments, the miniprotein has at least one, two, or three disulfide bridges. In some embodiments, the miniprotein has one disulfide bridge. In some embodiments, the miniprotein has two disulfide bridges. In some such embodiments, such a miniprotein can be referred to as a constrained miniprotein. In some embodiments, the constrained miniprotein is more stable than, for example, a miniprotein without one or more constraints as characterized by having a higher melting temperature, e.g., such as one having the same or a similar amino acid sequence without one or more constraints (e.g., such as a disulfide bridge). In some embodiments, the constrained miniprotein has an amino acid sequence that is 70%, 75%, 80%, 85%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in SEQ ID NOs: 198-537. In some embodiments, the miniprotein is part of a compound. In some embodiments, the compound is selected from any of Compound Nos: C227-C608 and C611.

In some embodiments, a miniprotein as provided herein is specific for or binds to a polypeptide or portion thereof having an amino acid sequence or portion thereof as set forth in Table 1A.

TABLE 1A

Exemplary Target Protein Amino Acid Sequences

| Target Protein (Uniprot Acc. No.) | Amino Acid Sequence | SEQ ID NO. |
|---|---|---|
| Human B7-H3 (Q5ZPR3) | MLRRRGSPGMGVHVGAALGALWFCLTGALEVQVPEDPVVALVGTDA<br>TLCCSFSPEPGFSLAQLNLIWOLTDTKOLVHSFAEGQDQGSAYANR<br>TALFPDLLAQGNASLRLQRVRVADEGSFTCFVSIRDFGSAAVSLQV<br>AAPYSKPSMTLEPNKDLRPGDTVTITCSSYQGYPEAEVFWQDGQGV<br>PLTGNVTTSQMANEQGLFDVHSILRVVLGANGTYSCLVRNPVLQQD<br>AHSSVTITPQRSPTGAVEVqVPEDPVVALVGTDATLRCSFSPEPGF<br>SLAQLNLIWQLTDTKQLVHSFTEGRDQGSAYANRTALFPDLLAQGN<br>ASLRLQRVRVADEGSFTCFVSIRDFGSAAVSLOVAAPYSKPSMTLE<br>PNKDLRPGDTVTITCSSYRGYPEAEVFWQDGQGVPLTGNVTTSQMA<br>NEQGLFDVHSVLRVVLGANGTYSCLVRNPVLQQDAHGSVTITGQPM<br>TFPPEALWVTVGLSVCLIALLVALAFVCWRKIKQSCEEENAGAEDQ<br>DGEGEGSKTALQPLKHSDSKEDDGQEIA | 1 |
| Murine B7-H3 (Q8VE98) | MLRGWGGPSVGVCVRTALGVLCLCLTGAVEVQVSEDPVVALVDTDA<br>TLRCSFSPEPGFSLAQLNLIWQLTDTKOLVHSFTEGRDQGSAYSNR<br>TALFPDLLVQGNASLRLQRVRVTDEGSYTCFVSIQDFDSAAVSLQV<br>AAPYSKPSMTLEPNKDLRPGNMVTITCSSYQGYPEAEVFWKDGQGV<br>PLTGNVTTSQMANERGLFDVHSVLRVVLGANGTYSCLVRNPVLQQD<br>AHGSVTITGQPLTFPPEALWVTVGLSVCLVVLLVALAFVCWRKIKQ<br>SCEEENAGAEDQDGDGEGSKTALRPLKPSENKEDDGQEIA | 2 |

Consensus Sequences and Substitutions

In some embodiments, a miniprotein provided by the present disclosure is set forth in one or more consensus sequences provided in Table 1B. In some embodiments, a miniprotein with a sequence set forth in Table 1B has amino acid substitutions as provided in Table 1C.

TABLE 1B

Consensus Sequences of Exemplary B7-H3 Miniproteins

| SEQ ID NO: | Formula | Consensus Sequence[1] |
|---|---|---|
| 95 | I | X1X2X3X4YX6X7EX9IX11ALX14EIIWLPNX22 X23X24X25QIX28AFIAALNX36DPSQSSELLSEA X49X50LX52DSX55X56X57X58 |
| 96 | II | X1X2X3X4YAX7EKIAALSEIIWLPNX22TX24X25 QIX28AFIAALNX36DPSQSSELLSEAX49X50LND SQAP |

[1]In consensus sequences throughout the application, each X is followed by a number indicating its linear position along a miniprotein, where amino acid position 1 is the N-terminal amino acid of a particular sequence and 58 is the C-terminal amino acid of a particular amino acid sequence.
For example, X1 is a substitutable position at the first amino acid, X28 is a substitutable amino acid at the 28th amino acid, and so on.
Amino acid positions can be determined relative to, for example, SEQ ID NO: 3.

TABLE 1C

Consensus Sequences Substitutions

| SEQ ID NO | Position | Amino Acids |
|---|---|---|
| 95, 96 | X1 | A or N when present |
| 95, 96 | X2 | A or E when present |
| 95, 96 | X3 | A or Q when present |
| 95, 96 | X4 | K, (KAc), or L when present |
| 95, 96 | X6 | A, D, E, I, L, N, Q, S, T, or Y |
| 95, 96 | X7 | A, E, K, (KAc), (Kme3), L, Q, or S |
| 95, 96 | X9 | K, (KAc), or (Kme3) |
| 95, 96 | X11 | A, Q, S, T, or Y |
| 95, 96 | X14 | E, Q, S, or Y |
| 95, 96 | X22 | A, D, F, (homo-leucine), I, L, N, (Nle), T, or Y |
| 95, 96 | X23 | T or V |
| 95, 96 | X24 | H or Y |
| 95, 96 | X25 | A or G |
| 95, 96 | X28 | A, (homo-leucine), M, (MO2), (Nle), S, T, or V |
| 95, 96 | X36 | A, (Cit), D, E, L, N, Q, S, or T |
| 95, 96 | X49 | A, E, G, K, (KAc), L, Q, S, or Y |
| 95, 96 | X50 | A, (Cit), D, E, G, (hSer), K, (KAc), L, Q, S, or Y |
| 95 | X52 | A, D, G, N, Q, T, or Y |
| 95 | X55 | D, E, L, Q, S, or Y when present |
| 95 | X56 | A when present |

TABLE 1C-continued

Consensus Sequences Substitutions

| SEQ ID NO | Position | Amino Acids |
|---|---|---|
| 95 | X57 | P when present |
| 95 | X58 | G, K, or (KAc) when present |

"(KAc)" refers to acetylated lysine, "((Kme3)" refers to trimethyllysine, "(MO2)" refers to methionine sulfone, "Cit" refers to citrulline, and "hSer" refers to homo-serine.

In some embodiments, a miniprotein provided by the present disclosure has an amino acid sequence comprising that set forth according to Formula I:

(SEQ ID NO: 95)
X1X2X3X4YX6X7EX9IX11ALX14EIIWLPNX22X23X24X25QIX28
AFIAALNX36DPSQSSELLSEAX49X50LX52DSX55X56X57X58, wherein X1 is A, N, or absent; X2 is A, E, or absent; X3 is A, Q, or absent; X4 is K, (KAc), L, or absent; X6 is A, D, E, I, L, N, Q, S, T, or Y; X7 is A, E, K, (KAc), (Kme3), L, Q, or S;

X9 is K, (KAc), or (Kme3); X11 is A, Q, S, T, or Y; X14 is E, Q, S, or Y; X22 is A, D, F, (homo-leucine), I, L, N, (Nle), T, or Y; X23 is T or V; X24 is H or Y; X25 is A or G; X28 is A, (homo-leucine), M, M(O2), (Nle), S, T, or V; X36 is A, (Cit), D, E, L, N, Q, S, or T; X49 is A, E, G, K, (KAc), L, Q, S, or Y; X50 is A, (Cit), D, E, G, (hSer), K, (KAc), L, Q, S, or Y; X52 is A, D, G, N, Q, T, or Y; X55 is D, E, L, Q, S, Y, or absent; X56 is A or absent; X57 is P or absent; and X58 is G, K, (KAc), or absent;

wherein if X28 is A, (homo-leucine), (MO2), S, T, or V, then X24 is Y; or wherein if X28 is M, then X7 is A, E, (Kme3), L, Q, or S.

In various embodiments, if X4 is K or (KAc), then X24 is Y.

In various embodiments, a miniprotein provided by the present disclosure has an amino acid sequence comprising that set forth according to Formula II:

(SEQ ID NO: 96)
X1X2X3X4YAX7EKIAALSEIIWLPNX22TX24X25QIX28AFIAALN
X36DPSQSSELLSEAX49X50LNDSQAP, wherein X1 is A or absent; X2 is E or absent; X3 is A or absent; X4 is L or absent; X7 is K or Q; X22 is D or L; X24 is H or Y; X25 is A or G; X28 is (homo-leucine) or M; X36 is D or N; X49 is E or K; and X50 is E.

In some embodiments, a miniprotein provided by the present disclosure is set forth in one or more consensus sequences provided in Table 1D. In some embodiments, a miniprotein with a sequence set forth in Table 1D has amino acid substitutions as provided in Table 1E.

TABLE 1D

Consensus Sequences of Exemplary Constrained B7-H3 Miniproteins

| SEQ ID NO: | Formula | Consensus Sequence[2] |
|---|---|---|
| 538 | III | CAX3EKIAALSEIIWLPCLX19YAQIX24AFIX28X29LNX32DPCX36 SX38X39ILSEAX45ELCS |
| 539 | IV | CAX3EKIAALSEIIWLPCLX19YAQIX24AFIAX29LNX32DPCQSSEI LSEAX45ELCS |

TABLE 1D-continued

| Consensus Sequences of Exemplary Constrained B7-H3 Miniproteins | | |
|---|---|---|
| SEQ ID NO: | Formula | Consensus Sequence[2] |
| 540 | V | CAX3EKIAALSEIIWLPCLTYAQIX24AFIX28X29LNX32DPCQSSEILSEAX45ELCS |
| 541 | VI | CA(Kme3)EKIAALSEIIWLPCLTYAQIX24AFIAX29LNX32DPCQSSEILSEAX45ELCS |
| 542 | VII | CAX3EKIX7ALX10EIIWLPX17LTYX21QIX24AFIX28X29LNX32DPCQSX38X39X40LX42EAX45ELCS |
| 543 | VIII | CAX3EKIX7ALX10EIIWLPCLTYX21QIX24AFIX28X29LNX32DPCQSX38X39X40LX42EAX45ELCS |
| 546 | IX | CAX3EKIX7ALX10EIIWLPX17LTYX21QIX24X25FIX28X29LNX32DPCQSX38X39X40LX42EAX45X46LX48S |
| 547 | X | CAX3EKIX7ALX10EIIWLPX17LTYX21QIX24AFIX28X29LNX32DPCQSX38X39X40LX42EAX45ELX48S |
| 548 | XI | CAX3EKIX7ALX10EIIWLPCLTYX21QIX24AFIX28X29LNDDPCOSX38X39X40LX42EAX45ELX48S |
| 549 | XII | CAX3EKIX7ALX10EIIWLPCLTYX21QIX24AFIX28X29LNDDPCQSX38X39X40LX42EAX45ELX48S |
| 550 | XIII | CAX3EKIX7ALX10EIIWLPCLTYX21QIX24AFIAX29LNDDPCQSX38EILSEAX45ELCS |

[2]In consensus sequences throughout the application, each X is followed by a number indicating its linear position along a miniprotein, where amino acid position 1 is the N-terminal amino acid of a particular sequence and 49 is the C-terminal amino acid of a particular amino acid sequence. For example, X3 is a substitutable position at the third amino acid(counting length from N-to-C terminus), X28 is a substitutable amino acid at the 28$^{th}$ amino acid, and so on.
Amino acid positions can be determined relative to, for example, SEQ ID NO: 267.

TABLE 1E

| Constrained Consensus Sequences Substitutions | | |
|---|---|---|
| SEQ ID NO:/ Formula | Position | Amino Acids |
| 538/III | X3 | (Kme3), R, (Rme) |
| 538/III | X19 | T, N |
| 538/III | X24 | (Kme2), (Kme) |
| 538/III | X28 | A, (Kme) |
| 538/III | X29 | A, (Kme), R |
| 538/III | X32 | D, (Kme), (Cit) |
| 538/III | X36 | Q, N |
| 538/III | X38 | S, A |
| 538/III | X39 | E, N |
| 538/III | X45 | K, (Kme) |
| 539/IV | X3 | (Kme3), R, (Rme) |
| 539/IV | X19 | T, N |
| 539/IV | X24 | (Kme2), (Kme) |
| 539/IV | X29 | A, (Kme) |
| 539/IV | X32 | D, (Kme) |
| 539/IV | X45 | K, (Kme) |
| 540/V | X3 | (Kme3), (Rme), R |
| 540/V | X24 | (Kme2), (Kme) |
| 540/V | X28 | A, (Kme) |
| 540/V | X29 | A, (Kme), R |
| 540/V | X32 | D, (Kme), (Cit) |
| 540/V | X45 | (Kme), K |
| 541/VI | X24 | (Kme), (Kme2) |
| 541/VI | X29 | (Kme), A, R |
| 541/VI | X32 | D, (Kme), (Cit) |
| 541/VI | X45 | (Kme), K |
| 542/VII | X3 | (Kme3), R, K |
| 542/VII | X7 | A, N |
| 542/VII | X10 | S, G |
| 542/VII | X17 | C, N |
| 542/VII | X21 | A, D |

TABLE 1E-continued

| Constrained Consensus Sequences Substitutions | | |
|---|---|---|
| SEQ ID NO:/ Formula | Position | Amino Acids |
| 542/VII | X24 | (Kme3), (Kme2), (Kme) |
| 542/VII | X28 | A, (Kme) |
| 542/VII | X29 | A, (Kme), R |
| 542/VII | X32 | D, (Kme) |
| 542/VII | X38 | S, A |
| 542/VII | X39 | E, N |
| 542/VII | X40 | I, L |
| 542/VII | X42 | S, A |
| 542/VII | X45 | K, (Kme), (Kme3), Q |
| 543/VIII | X3 | (Kme3), R |
| 543/VIII | X7 | A, N |
| 543/VIII | X10 | S, G |
| 543/VIII | X21 | A, D |
| 543/VIII | X24 | (Kme3), (Kme2), (Kme) |
| 543/VIII | X28 | A, (Kme) |
| 543/VIII | X29 | A, (Kme), R |
| 543/VIII | X32 | D, (Kme) |
| 543/VIII | X38 | S, A |
| 543/VIII | X39 | E, N |
| 543/VIII | X40 | I, L |
| 543/VIII | X42 | S, A |
| 543/VIII | X45 | K, (Kme), (Kme3), Q |
| 546/IX | X3 | (Kme3), K, Q, R |
| 546/IX | X7 | A, N |
| 546/IX | X10 | S, G |
| 546/IX | X17 | C, N |
| 546/IX | X21 | A, D |
| 546/IX | X24 | (Kme2), (Kme), (homo-leucine) |
| 546/IX | X25 | A, E |
| 546/IX | X28 | A, (Kme) |
| 546/IX | X29 | A, (Kme), R |

TABLE 1E-continued

Constrained Consensus Sequences Substitutions

| SEQ ID NO:/ Formula | Position | Amino Acids |
|---|---|---|
| 546/IX | X32 | D, (Kme), (Cit), A |
| 546/IX | X38 | S, A |
| 546/IX | X39 | E, N |
| 546/IX | X40 | I, L |
| 546/IX | X42 | S, A |
| 546/IX | X45 | K, (Kme), (Kme3), Q, R |
| 546/IX | X46 | E, A |
| 546/IX | X48 | C, N |
| 547/X | X3 | (Kme3), K, R |
| 547/X | X7 | A, N |
| 547/X | X10 | S, G |
| 547/X | X17 | C, N |
| 547/X | X21 | A, D |
| 547/X | X24 | (Kme2), (Kme), (homo-leucine) |
| 547/X | X28 | A, (Kme) |
| 547/X | X29 | A, (Kme), R |
| 547/X | X32 | D, (Kme) |
| 547/X | X38 | S, A |
| 547/X | X39 | E, N |
| 547/X | X40 | I, L |
| 547/X | X42 | S, A |
| 547/X | X45 | K, (Kme), (Kme3), Q |
| 547/X | X48 | C, N, a |
| 548/XI | X3 | (Kme3), K, R |
| 548/XI | X7 | A, N |
| 548/XI | X10 | S, G |
| 548/XI | X21 | A, D |
| 548/XI | X24 | (Kme2), (Kme) |
| 548/XI | X28 | A, (Kme) |
| 548/XI | X29 | A, (Kme), R |
| 548/XI | X38 | S, A |
| 548/XI | X39 | E, N |
| 548/XI | X40 | I, L |
| 548/XI | X42 | S, A |
| 548/XI | X45 | K, (Kme), Q |
| 548/XI | X48 | C, N |
| 549/XII | X3 | (Kme3), K, R |
| 549/XII | X7 | A, N |
| 549/XII | X10 | S, G |
| 549/XII | X21 | A, D |
| 549/XII | X24 | (Kme2), (Kme) |
| 549/XII | X28 | A, (Kme) |
| 549/XII | X29 | A, (Kme) |
| 549/XII | X38 | S, A |
| 549/XII | X39 | E, N |
| 549/XII | X40 | I, L |
| 549/XII | X42 | S, A |
| 549/XII | X45 | K, (Kme) |
| 549/XII | X48 | C, N |
| 550/XIII | X3 | (Kme3), R |
| 550/XIII | X7 | A, N |
| 550/XIII | X10 | S, G |
| 550/XIII | X21 | A, D |
| 550/XIII | X24 | (Kme2), (Kme) |
| 550/XIII | X29 | A, (Kme) |
| 550/XIII | X38 | S, A |
| 550/XIII | X45 | K, (Kme) |

"(Kme)" refers to monomethyllysine; "(Kme2)" refers to dimethyllysine; "(Kme3)" refers to trimethyllysine; (Cit) refers to citrulline; and (Rme) refers to methylated arginine In one aspect, the disclosure provides a polypeptide (e.g., a B7-H3-binding miniprotein) with an amino acid sequence comprising an amino acid sequence according to Formula III (SEQ ID NO: 538) as follows:

CAX3EKIAALSEIIWLPCLX19YAQIX24AFIX28X29 LNX32DPCX36SX38X39ILSEAX4 5ELCS, wherein X3 is (Kme3) or R or (Rme); X19 is T or N; X24 is (Kme2) or (Kme); X28 is A or (Kme); X29 is A or (Kme) or R; X32 is D or (Kme) or (Cit); X36 is Q or N; X38 is S or A; X39 is E or N; and X45 is K or (Kme). In some embodiments, X49 is absent.

In certain embodiments, the polypeptide (e.g., a B7-H3-binding miniprotein) has an amino acid sequence comprising an amino acid sequence of any one of SEQ ID NOs: 204, 238, 239, 241, 247, 262-273, 292, 295, 297, 298, 307, 309, 310, 314-317, 335, 336, 338, 352, 374, 389, 392, 396, 401, 460-462, 466-468, 470, 471, 497, and 528.

In one aspect, the disclosure provides a polypeptide (e.g., a B7-H3-binding miniprotein) with an amino acid sequence comprising an amino acid sequence according to Formula IV (SEQ ID NO: 539) as follows:

```
CAX3EKIAALSEIIWLPCLX19YAQIX24AFIAX29LNX32DPCQSSEIL

SEAX45ELCS,
```

wherein X3 is (Kme3) or R or (Rme); X19 is T or N; X24 is (Kme2) or (Kme); X29 is A or (Kme); X32 is D or (Kme); and X45 is K or (Kme). In some embodiments, X49 is absent.

In certain embodiments, the polypeptide (e.g., a B7-H3-binding miniprotein) has an amino acid sequence comprising an amino acid sequence of any one of SEQ ID NOs: 204, 241, 262, 265, 267, 268, 292, 307, 314-317, 338, 352, 392, 396, and 401.

In one aspect, the disclosure provides a polypeptide (e.g., a B7-H3-binding miniprotein) with an amino acid sequence comprising an amino acid sequence according to Formula V (SEQ ID NO: 540) as follows:

```
CAX3EKIAALSEIIWLPCLTYAQIX24AFIX28X29LNX32DPCQSSEIL

SEAX45ELCS,
```

wherein X3 is (Kme3) or R or (Rme); X24 is (Kme2) or (Kme); X28 is A or (Kme); X29 is A or (Kme) or R; X32 is D or (Kme) or (Cit); and X45 is K or (Kme). In some embodiments, X49 is absent.

In certain embodiments, the polypeptide (e.g., a B7-H3-binding miniprotein) has an amino acid sequence comprising an amino acid sequence of any one of SEQ ID NOs: 204, 241, 262, 265-267, 270, 272, 292, 307, 314-317, 338, 352, 374, 389, 392, 396, 401, 460-462, 466, 467, 468, 470, 471, and 497.

In one aspect, the disclosure provides a polypeptide (e.g., a B7-H3-binding miniprotein) with an amino acid sequence comprising an amino acid sequence according to Formula VI (SEQ ID NO: 541) as follows:

```
CA(Kme3)EKIAALSEIIWLPCLTYAQIX24AFIAX29LNX32DPCQSSE

ILSEAX45ELCS,
```

wherein X24 is (Kme2) or (Kme); X29 is (Kme) or A or R; X32 is D or (Kme) or (Cit); and X45 is K or (Kme). In some embodiments, X49 is absent.

In certain embodiments, the polypeptide (e.g., a B7-H3-binding miniprotein) has an amino acid sequence comprising an amino acid sequence of any one of SEQ ID NOs: 204, 262, 265, 267, 270, 272, 314-317, 338, 352, 389, 392, 396, 401, 462, and 471.

In one aspect, the disclosure provides a polypeptide (e.g., a B7-H3-binding miniprotein) with an amino acid sequence comprising an amino acid sequence according to Formula VII (SEQ ID NO: 542) as follows:

CAX3EKIX7ALX10EIIWLPX17LTYX21QIX24AFIX2 8X29LNX32DPCQSX38X39X40L X42EAX45ELCS, wherein X3 is (Kme3) or R or K; X7 is A or N; X10 is S or G; X17 is C or N; X21 is A or D; X24 is (Kme3) or (Kme2) or (Kme); X28 is A or (Kme); X29 is A or (Kme) or R; X32 is D or (Kme); X38 is S or A; X39 is E or N; X40 is I or L; X42 is S or A; and X45 is K or (Kme) or (Kme3) or Q. In some embodiments, X49 is absent.

In certain embodiments, the polypeptide (e.g., a B7-H3-binding miniprotein) has an amino acid sequence comprising an amino acid sequence of any one of SEQ ID NOs: 204, 206, 217, 219, 221, 238, 239, 241, 247, 250, 262-267, 273, 278-280, 287, 288, 292, 295, 297-302, 304, 305, 307, 309-319, 321-326, 328-331, 335-338, 352, 356, 366, 367, 374-377, 383-385, 389, 392, 394-396, 401, 402, 404-409, 414-418, 426, 437-439, 449-451, 460-462, 465-468, 470, 471, 489, 497, 502-508, 518-521, 523, and 527.

In one aspect, the disclosure provides a polypeptide (e.g., a B7-H3-binding miniprotein) with an amino acid sequence comprising an amino acid sequence according to Formula VIII (SEQ ID NO: 543) as follows:

CAX3EKIX7ALX10EIIWLPCLTYX21QIX24AFIX28X29LNX32DPCQSX38X39X40LX4 2EAX45ELCS, wherein X3 is (Kme3) or R; X7 is A or N; X10 is S or G; X21 is A or D; X24 is (Kme3) or (Kme2) or (Kme); X28 is A or (Kme); X29 is A or (Kme) or R; X32 is D or (Kme); X38 is S or A; X39 is E or N; X40 is I or L; X42 is S or A; and X45 is K or (Kme) or (Kme3) or Q. In some embodiments, X49 is absent.

In certain embodiments, the polypeptide (e.g., a B7-H3-binding miniprotein) has an amino acid sequence comprising an amino acid sequence of any one of SEQ ID NOs: 204, 206, 238, 239, 241, 247, 250, 262-267, 273, 278-280, 287, 288, 292, 295, 297-302, 304, 305, 307, 309-319, 321-326, 328, 329, 330, 331, 335-338, 352, 356, 366, 367, 374, 375-377, 383-385, 389, 392, 394-396, 401, 402, 404-409, 414-418, 426, 437-439, 449-451, 460-462, 465-468, 470, 471, 489, 497, 502-508, 518-521, 523, and 527.

In one aspect, the disclosure provides a polypeptide (e.g., a B7-H3-binding miniprotein) with an amino acid sequence comprising an amino acid sequence according to Formula IX (SEQ ID NO: 546) as follows:

CAX3EKIX7ALX10EIIWLPX17LTYX21QIX24X25FIX28X29LNX32DPCQSX38X39X40 LX42EAX45X46LX48S, wherein X3 is (Kme3) or K or Q or R; X7 is A or N; X10 is S or G; X17 is C or N; X21 is A or D; X24 is (Kme2) or (Kme) or (homo-leucine); X25 is A or E; X28 is A or (Kme); X29 is A or (Kme) or R; X32 is D or (Kme) or (Cit) or A; X38 is S or A; X39 is E or N; X40 is I or L; X42 is S or A; X45 is K or (Kme) or (Kme3) or Q or R; X46 is E or A; and X48 is C or N. In some embodiments, X49 is absent.

In certain embodiments, the polypeptide (e.g., a B7-H3-binding miniprotein) has an amino acid sequence comprising an amino acid sequence of any one of SEQ ID NOs: 203-205, 209-213, 216-220, 225, 226, 230-233, 235, 238, 239, 241, 242, 247, 248, 250, 262-267, 270, 272, 273, 278-280, 287, 288, 292, 294-302, 304, 305, 307, 309-319, 321-326, 328, 329, 330, 331, 335-338, 352, 356, 358, 366, 367, 374-377, 380, 383-385, 389, 392, 394-396, 399, 401, 402, 404-409, 414-418, 426, 434, 437-439, 447, 449, 450, 451, 460-462, 465-468, 470, 471, 474, 475, 489, 497, 499, 502-508, 515, 518-521, 523, 524, 527, 532, 533, 535, and 537.

In one aspect, the disclosure provides a polypeptide (e.g., a B7-H3-binding miniprotein) with an amino acid sequence comprising an amino acid sequence according to Formula X (SEQ ID NO: 547) as follows:

CAX3EKIX7ALX10EIIWLPX17LTYX21QIX24AFIX2 8X29LNX32DPCQSX38X39X40L X42EAX45ELX48S, wherein X3 is (Kme3) or K or R; X7 is A or N; X10 is S or G; X17 is C or N; X21 is A or D; X24 is (Kme2) or (Kme) or (homo-leucine); X28 is A or (Kme); X29 is A or (Kme) or R; X32 is D or (Kme); X38 is S or A; X39 is E or N; X40 is I or L; X42 is S or A; X45 is K or (Kme) or (Kme3) or Q; and X48 is C or N. In some embodiments, X49 is absent.

In certain embodiments, the polypeptide (e.g., a B7-H3-binding miniprotein) has an amino acid sequence comprising an amino acid sequence of any one of SEQ ID NOs: 204, 209-213, 217-220, 225, 226, 238, 239, 241, 242, 247, 250, 262-267, 273, 278-280, 287, 288, 292, 295, 297-302, 304, 305, 307, 309-319, 321-326, 328, 329, 330, 331, 335-338, 352, 356, 366, 367, 374-377, 383-385, 389, 392, 394-396, 401, 402, 404-409, 414-418, 426, 437-439, 449-451, 460-462, 465-468, 470, 471, 489, 497, 502-508, 518-521, 523, and 527.

In one aspect, the disclosure provides a polypeptide (e.g., a B7-H3-binding miniprotein) with an amino acid sequence comprising an amino acid sequence according to Formula XI (SEQ ID NO: 548) as follows:

CAX3EKIX7ALX10EIIWLPCLTYX21QIX24AFIX28 X29LNDDPCQSX38X39X40LX42E AX45ELX48S, wherein X3 is (Kme3) or K or R; X7 is A or N; X10 is S or G; X21 is A or D; X24 is (Kme2) or (Kme); X28 is A or (Kme); X29 is A or (Kme) or R; X38 is S or A; X39 is E or N; X40 is I or L; X42 is S or A; X45 is K or (Kme) or Q; and X48 is C or N. In some embodiments, X49 is absent.

In certain embodiments, the polypeptide (e.g., a B7-H3-binding miniprotein) has an amino acid sequence comprising an amino acid sequence of any one of SEQ ID NOs: 204, 217-220, 238, 239, 241, 242, 247, 250, 262-266, 273, 278, 279, 280, 287, 288, 292, 295, 297-302, 304, 305, 307, 309-319, 321-326, 328, 329, 330, 331, 335-338, 352, 356, 366, 367, 374-377, 383-385, 389, 392, 394-396, 402, 404-409, 414-418, 426, 437-439, 449, 460, 466-468, 471, 489, 497, and 502-508.

In one aspect, the disclosure provides a polypeptide (e.g., a B7-H3-binding miniprotein) with an amino acid sequence comprising an amino acid sequence according to Formula XII (SEQ ID NO: 549) as follows:

CAX3EKIX7ALX10EIIWLPCLTYX21QIX24AFIX28 X29LNDDPCQSX38X39X40LX42E AX45ELX48S, wherein X3 is (Kme3) or K or R; X7 is A or N; X10 is S or G; X21 is A or D; X24 is (Kme2) or (Kme); X28 is A or (Kme); X29 is A or (Kme); X38 is S or A; X39 is E or N; X40 is I or L; X42 is S or A; X45 is K or (Kme); and X48 is C or N. In some embodiments, X49 is absent.

In certain embodiments, the polypeptide (e.g., a B7-H3-binding miniprotein) has an amino acid sequence comprising an amino acid sequence of any one of SEQ ID NOs: 204, 217-220, 238, 239, 241, 242, 247, 262-266, 273, 278, 279, 280, 287, 292, 295, 297-302, 304, 305, 307, 309-319, 321-326, 328-330, 335-338, 352, 356, 366, 367, 374, 383, 384, 392, 395, 396, 402, 404-406, 414, 415, 417, 426, 437, 439, 460, 466, 468, 502, 503, 505, and 506.

In one aspect, the disclosure provides a polypeptide (e.g., a B7-H3-binding miniprotein) with an amino acid sequence comprising an amino acid sequence according to Formula XIII (SEQ ID NO: 550) as follows:

CAX3EKIX7ALX10EIIWLPCLTYX21QIX24AFIAX2 9LNDDPCQSX38EILSEAX45ELC S, wherein X3 is (Kme3) or R; X7 is A or N; X10 is S or G; X21 is A or D; X24 is (Kme2) or (Kme); X29 is A or (Kme); X38 is S or A; and X45 is K or (Kme). In some embodiments, X49 is absent.

In certain embodiments, the polypeptide (e.g., a B7-H3-binding miniprotein) has an amino acid sequence comprising an amino acid sequence of any one of SEQ ID NOs: 204, 238, 241, 262, 263, 265, 292, 295, 297, 302, 304, 305, 307, 309, 313-319, 321-323, 326, 328, 335, 337, 338, 352, 367, 384, 392, 396, 402, 404, 414, 415, 417, 426, 437, 439, 502, 503, 505, and 506.

In one aspect, the disclosure provides a composition, comprising a polypeptide of at least 48 amino acids in length and having an amino sequence comprising that set forth in SEQ ID NO: 541, comprising at least four cysteines and two disulfide bonds, wherein X24 is (Kme) or (Kme2); X29 is (Kme) or A or R; X32 is D or (Kme) or (Cit), and X45 is (Kme) or K. In some embodiments, X49 is absent.

In certain embodiments, the disclosure provides a composition comprising a polypeptide that binds to B7-H3, has at least 48 amino acids, two disulfide bonds, and a modified amino acid at positions corresponding to 3, 24, and 29 relative to SEQ ID NO: 267, wherein the modification is a small alkyl group on the side chain of the amino acid.

In one aspect, the disclosure provides a composition with one or more modified amino acids. In some such embodiments, the one or more modifications comprises a small alkyl group. In one aspect, the disclosure provides a composition comprising a B7-H3 binding polypeptide having an amino acid sequence comprising at least 48 amino acids, wherein the amino acids include (i) a cysteine at each of four positions corresponding to 1, 17, 35, and 48 of SEQ ID NO: 267 and wherein X3 is (Kme3) or R or (Rme); X19 is T or N; X24 is (Kme2) or (Kme); X28 is A or (Kme); X29 is A or (Kme) or R; X32 is D or (Kme) or (Cit); X36 is Q or N; X38 is S or A; X39 is E or N; X45 is K or (Kme), and X49 is S or absent.

In one aspect, the disclosure provides a composition, comprising a B7-H3 binding polypeptide having an amino acid sequence, wherein the amino acid sequence comprises: at least four cysteines, which form two disulfide bonds; an arginine, modified arginine, or modified lysine at a position corresponding to amino acid 3, a lysine at a position corresponding to amino acid 5, an isoleucine at a position corresponding to amino acid 6, a tryptophan at a position corresponding to amino acid 14, at least one modified lysine residue at a position corresponding to amino acid 24, and an alanine, arginine, or modified lysine at a position corresponding to 29, where each position is linear, from N-to-C-terminus relative to SEQ ID NO: 267, wherein the modification comprises at least one small alkyl group attached to the nitrogen of the lysine side chain or to the Guanidino group of the arginine side chain, optionally comprising a methyl, dimethyl, or trimethyl group; at least 48 amino acids in length; and the miniprotein has a binding affinity for B7-H3 stronger than 100 nM as measured in a cell-based assay.

In one aspect, the disclosure provides a composition, comprising a B7-H3 binding polypeptide having an amino acid sequence, wherein the amino acid sequence comprises: at least four cysteines, which form two disulfide bonds; at least one modified lysine residue at a position corresponding to X24 of SEQ ID NO: 267, wherein the modification comprises at least one small alkyl group attached to the nitrogen of the lysine side chain, optionally comprising a methyl, dimethyl, or trimethyl group; at least 48 amino acids in length; and has a binding affinity for B7-H3 stronger than 100 nM as measured in a cell-based assay.

CDPs

In some embodiments, miniproteins of the present disclosure comprise or consist of a cysteine-dense peptides (CDPs). In some embodiments, conjugates provided herein comprise a CDP. In some embodiments, a CDP functions as a targeting moiety, e.g., specifically binding to a protein target or antigen expressed on the surface of a target tumor cell. In some embodiments, a CDP comprises or consists of at least two independent folding domains and a high density of cysteines. In some embodiments, the CDP comprises at least one, two, three, four, five, six, or more than six cysteine residues in a span of from about 10 to about 90 amino acid residues, preferably 13 to 80 amino acid residues. (See, e.g., Correnti et al., Nat Struct Mol Biol. 2018 March; 25(3):270-278, for exemplary CDPs and characteristics thereof). In some embodiments, the CDP comprises a constrained distribution of cysteines, Cys-X[0-15]-Cys-X[0-15]-Cys-X[0-15]-Cys-X[0-15]-Cys-X[0-15]-Cys (wherein X represents any amino acid) (SEQ ID NO: 553). In some embodiments, a CDP comprises one or more cysteine dense regions comprising at least one cysteine residue, preferably at least two, three, four, or more cysteine residues in a span of from about 10 to 80 amino acid residues. In some embodiments, a CDP can be further engineered to modify binding, folding, and/or related properties.

In some embodiments, a CDP specifically binds to a target. In some embodiments, the target is located in, on, or near a cell. In some embodiments, the CDP specifically binds to B7-H3 or a fragment thereof. In some embodiments, a CDP is conjugated to a chelator and/or radionuclide. In some embodiments, conjugation is via a linker. It will be understood by those of skill in the art, that in some embodiments, the particular CDP employed in a conjugate of the present disclosure may vary depending on the target protein or antigen of interest.

In some embodiments, in miniproteins having cysteine residues, to ensure proper folding and connectivity, selected cysteine pairs can be replaced with selenocysteines. In some embodiments, diselenide crosslinks may form more readily than disulfide crosslinks due to their lower redox potential. In some such embodiments, such replacement can lead to cross-coupling of remaining cysteines.

Knottins

In some embodiments, miniproteins of the present disclosure comprise or consist of knottin peptides. In some embodiments, conjugates provided herein comprise a knottin peptide. In some embodiments, a knottin peptide functions as a targeting moiety, e.g., specifically binding to an antigen expressed on the surface of a target tumor cell. In some embodiments, a knottin comprises at least three disulfide bonds connected in an arrangement that generates the so-called "cysteine-knot" for which knottins are named. (See, e.g., Kintzing & Cochran et al., Curr Opin Chem Biol. 2016 October; 34:143-150.). In some embodiments, knottins have high stability (e.g., thermal, proteolytic, chemical, etc.). In some embodiments, a knottin can be further engineered to modify binding, folding, and/or related properties.

In some embodiments, a given knottin is highly specific for a given target. In some embodiments, a knottin specifically binds to a target. In some embodiments, the target is located in, on, or near a cell. In some embodiments, the knottin specifically binds to B7-H3 or a fragment thereof. In some embodiments, a knottin is conjugated to a chelator and/or radionuclide. In some embodiments, conjugation is via a linker. It will be understood by those of skill in the art, that in some embodiments, the particular knottin employed in a conjugate of the present disclosure may vary depending on the target protein or antigen of interest.

In some embodiments, folded structures of miniproteins (e.g., affibodies, CDPs, knottins, binders) make them rigid, providing for very tight and potent binding to the target protein or antigen (relative to less structured peptides). In some such embodiments, a miniprotein (e.g., affibody, CDP, knottin, binder, engineered Kunitz domain, monobody, anticalin, designed ankyrin repeat domain (DARPin), avimer) exhibits extraordinary stability with resistance to heat, peptidase cleavage, and pH.

Binders

In some embodiments, a miniprotein of the present disclosure comprises or consists of a binder. In some embodiments, the binder functions as a targeting moiety, e.g., specifically binding to a target expressed on the surface of a tumor cell. In some embodiments a binder that binds to B7-H3 is provided herein.

In some embodiments, a binder has certain structural features; for example, in some embodiments, a binder may be rich in alpha-helices, such as a helix-helix-helix structure (see, e.g., Crook et al., Nat Commun. (2017) 8, 2244; Berger et al, Elife (2016) 5, e20352; and Procko et al., Cell (2014), 157, 1644-1656). In some embodiments, a binder may comprise an alpha helix, a beta sheet, or a combination of one or more of each. In some embodiments, a binder comprises sufficient surface to functionalize the molecule on a disparate surface to a binding surface. In some embodiments, a binder comprises a sequestered hydrophobic core. In some embodiments, a binder displays cooperative folding. In some embodiments, a binder has two or more of the following features: (i) represented by an amino acid sequence of 100 amino acids or fewer; (ii) at least two secondary structure elements; (iii) a sequestered hydrophobic core; and/or (iv) cooperative folding.

In some embodiments, a given binder is highly specific for a given target. In some embodiments, a binder specifically binds to a target. In some embodiments, the target is located in, on, or near a cell. In some embodiments, the miniprotein specifically binds to B7—H3 or a fragment thereof. In some embodiments, a binder is conjugated to a chelator and/or radionuclide. In some embodiments, conjugation is via a linker. It will be understood by those of skill in the art, that in some embodiments, the particular binder employed in a conjugate of the present disclosure may vary depending on the target protein or antigen of interest.

Affibodies

In some embodiments, miniproteins of the present disclosure comprise or consist of affibodies. In some embodiments, the affibody functions as a targeting moiety, e.g., specifically binding to a target expressed on the surface of a tumor cell. In some embodiments an affibody that binds to B7-H3 is provided herein. In some embodiments, a miniprotein (e.g., an affibody) comprises part or all of any of the compounds (e.g., comprising or consisting of miniproteins) set forth in Table 2A and/or Table 2C. In some embodiments, the miniprotein (e.g., affibody) comprises, consists essentially of, or consists of an amino acid sequence of any of SEQ ID NOs: 4-6, 8-94 and 100-537 or portions thereof. Table 2B shows certain characteristics of selected exemplary compounds/miniproteins of Table 2A. In some embodiments, conjugates provided herein comprise an affibody. In some embodiments, an affibody functions as a targeting moiety, e.g., specifically binding to a protein target or antigen expressed on the surface of a target tumor cell. In some embodiments, an affibody comprises or consists of no more than 100 amino acids, 90 amino acids, 80 amino acids, 70 amino acids, 60 amino acids, 50 amino acids, 40 amino acids, 30 amino acids, 20 amino acids, or 10 amino acids. In some embodiments, an affibody comprises or consists of at least three alpha helices with 58 amino acids. In some embodiments, the affibody comprises target specificity that is obtained by randomization of 13 amino acids located in two alpha-helices involved in the binding activity of the parent protein domain (Feldwisch J, Tolmachev V.; (2012) Methods Mol Biol. 899:103-26). In some embodiments, an affibody can be further engineered to modify binding, folding, and/or related properties.

The present disclosure also provides the surprising finding that by truncating (e.g., removing residues from N- and/or C-termini of an affibody with three alpha helices spanning 58 amino acids) an affibody, such as by removing some or all of, for example, amino acids corresponding to positions 1-6 beginning at the N-terminus and positions 54-58 at the C-terminus with reference to N-to-C terminal positions along the length of SEQ ID NO: 3, and/or removing and replacing such amino acids with for example, a cysteine, the binding affinity and/or specificity to B7-H3 improves. The disclosure further contemplates that in addition to truncations, one or more constraints may be introduced. In some embodiments, the constraints comprise at least one, two, or three disulfide bridges and/or at least one additional constraint such as disclosed herein (e.g., a lactam bridge, e.g., a staple). In some embodiments, an affibody of a particular scaffold comprises three alpha helices with at least four cysteines (between which disulfides can be introduced), spanning 49 amino acids. Thus, in some such embodiments, the scaffold, relative to affibodies of 58 amino acids, differs in its length (e.g., is truncated) and constraint pattern. In some such embodiments, such truncated and constrained affibodies may have one or more desirable characteristics, such as, for example, improved affinity and/or specificity for B7-H3. In certain embodiments, such affibodies may be further modified to introduce one or more non-natural amino acids which can, in certain embodiments, impact toxicity by decreasing kidney cell uptake (e.g., in vitro, e.g., in vivo).

In some embodiments, an affibody specifically binds to a target. In some embodiments, the target is located in, on, or near a cell. In some embodiments, the affibody specifically binds to B7-H3 or a fragment thereof. In some embodiments, an affibody is conjugated to a chelator and/or radionuclide. In some embodiments, conjugation is via a linker. It will be understood by those of skill in the art, that in some embodiments, the particular affibody employed in a conjugate of the present disclosure may vary depending on the target protein or antigen of interest.

Engineered Kunitz Domains

In some embodiments, miniproteins of the present disclosure comprise or consist of engineered Kunitz domains. In some embodiments, conjugates provided herein comprise an engineered Kunitz domain. In some embodiments, an engineered Kunitz domain functions as a targeting moiety, e.g., specifically binding to a protein target or antigen expressed on the surface of a target tumor cell. In some embodiments, an engineered Kunitz domain comprises or consists of at least one peptide derived from the Kunitz domain of a Kunitz-type protease inhibitor such as bovine pancreatic trypsin inhibitor (BPTI), amyloid precursor protein (APP) or tissue factor pathway inhibitor (TFPI). In some embodiments, an engineered Kunitz domain can be further engineered to modify binding, folding, and/or related properties.

In some embodiments, an engineered Kunitz domain specifically binds to a target. In some embodiments, the target is located in, on, or near a cell. In some embodiments, the engineered Kunitz domain specifically binds to B7-H3 or a fragment thereof. In some embodiments, an engineered Kunitz domain is conjugated to a chelator and/or radionuclide. In some embodiments, conjugation is via a linker. It will be understood by those of skill in the art, that in some embodiments, the particular engineered Kunitz domain employed in a conjugate of the present disclosure may vary depending on the target protein or antigen of interest.

Monobodies

In some embodiments, miniproteins of the present disclosure comprise or consist of monobodies. In some embodiments, conjugates provided herein comprise a monobody. In some embodiments, a monobody functions as a targeting moiety, e.g., specifically binding to a protein target or antigen expressed on the surface of a target tumor cell. In some embodiments, a monobody comprises or consists of a molecule based on the 10th extracellular domain of human fibronectin III (10Fn3), which adopts an Ig-like b-sandwich fold of about 94 residues with 2 to 3 exposed loops but lacks the central disulfide bridge. In some embodiments, a monobody can be further engineered to modify binding, folding, and/or related properties.

In some embodiments, a monobody specifically binds to a target. In some embodiments, the target is located in, on, or near a cell. In some embodiments, the monobody specifically binds to B7-H3 or a fragment thereof. In some embodiments, a monobody is conjugated to a chelator and/or radionuclide. In some embodiments, conjugation is via a linker. It will be understood by those of skill in the art, that in some embodiments, the particular monobody employed in a conjugate of the present disclosure may vary depending on the target protein or antigen of interest.

Anticalins

In some embodiments, miniproteins of the present disclosure comprise or consist of anticalins. In some embodiments, conjugates provided herein comprise an anticalin. In some embodiments, an anticalin functions as a targeting moiety, e.g., specifically binding to a protein target or antigen expressed on the surface of a target tumor cell. In some embodiments, an anticalin comprises or consists of an eight-stranded b-barrel which forms a highly conserved core unit among the lipocalins and naturally forms binding sites for ligands by means of four structurally variable loops at the open end. In some embodiments, an anticalin can be further engineered to modify binding, folding, and/or related properties.

In some embodiments, an anticalin specifically binds to a target. In some embodiments, the target is located in, on, or near a cell. In some embodiments, the anticalin specifically binds to B7-H3 or a fragment thereof. In some embodiments, an anticalin is conjugated to a chelator and/or radionuclide. In some embodiments, conjugation is via a linker. It will be understood by those of skill in the art, that in some embodiments, the particular anticalin employed in a conjugate of the present disclosure may vary depending on the target protein or antigen of interest.

Designed Ankyrin Repeat Domains

In some embodiments, miniproteins of the present disclosure comprise or consist of designed Ankyrin repeat domains. In some embodiments, conjugates provided herein comprise a designed Ankyrin repeat domain. In some embodiments, a designed Ankyrin repeat domain functions as a targeting moiety, e.g., specifically binding to a protein target or antigen expressed on the surface of a target tumor cell. In some embodiments, a designed Ankyrin repeat domain comprises a peptide derived from Ankyrin. In some embodiments, a designed Ankyrin repeat domain comprises a single ankyrin repeat, preferably comprising a 33-residue motif comprising two alpha-helices and a beta-turn. In some embodiments a designed Ankyrin repeat domain provides a rigid interface and lacks structural flexibility. In some embodiments, a designed Ankyrin repeat domain can be further engineered to modify binding, folding, and/or related properties.

In some embodiments, a designed Ankyrin repeat domain specifically binds to a target. In some embodiments, the target is located in, on, or near a cell. In some embodiments, the designed Ankyrin repeat domain specifically binds to B7-H3 or a fragment thereof. In some embodiments, a designed Ankyrin repeat domain is conjugated to a chelator and/or radionuclide. In some embodiments, conjugation is via a linker. It will be understood by those of skill in the art, that in some embodiments, the particular designed Ankyrin repeat domain employed in a conjugate of the present disclosure may vary depending on the target protein or antigen of interest.

Avimers

In some embodiments, miniproteins of the present disclosure comprise or consist of avimers. In some embodiments, conjugates provided herein comprise an avimer. In some embodiments, an avimer functions as a targeting moiety, e.g., specifically binding to a protein target or antigen expressed on the surface of a target tumor cell. In some embodiments, an avimer comprises a peptide of about 10 amino acids, 20 amino acids, 30 amino acids, 40 amino acids, 50 amino acids, 60 amino acids, 70 amino acids, 80 amino acids, 90 amino acids, or 100 amino acids. In some embodiments, an avimer comprises at least one peptide sequence of about 30 to 35 amino acids. In some embodiments, an avimer comprises two or more of two peptide sequences of about 30 to 35 amino acids. In some embodiments, an avimer comprises one or more peptide sequences derived from A-domains of various membrane receptors. (Weidle U H, et al., (2013), Cancer Genomics Proteomics; 10(4): 155-68). For further details see Nature Biotechnology 23(-2), 1556-1561 (2005) and Expert Opinion on Investigational Drugs 16(6), 909-917 (June 2007). In some embodiments, an avimer can be further engineered to modify binding, folding, and/or related properties.

In some embodiments, an avimer specifically binds to a target. In some embodiments, the target is located in, on, or near a cell. In some embodiments, the avimer specifically binds to B7-H3 or a fragment thereof. In some embodiments, an avimer is conjugated to a chelator and/or radionuclide. In some embodiments, conjugation is via a linker. It will be understood by those of skill in the art, that in some embodiments, the particular avimer employed in a conjugate of the present disclosure may vary depending on the target protein or antigen of interest.

Constraints

Constraints can be designed (e.g., from an initial polypeptide sequence) or introduced (e.g., engineered, e.g., into an existing miniprotein) into proteins, such as any miniprotein provided herein. Constraints may be introduced by modifications to an existing miniprotein sequence such as, for example, by substituting and/or adding two or more cysteine residues to form at least one disulfide bond.

A constraint can alter function (e.g., binding, e.g., binding affinity, etc.) and/or structure (e.g., folding) of a protein. In certain embodiments, constraints can assist in maintaining secondary structure of a given protein (e.g., a miniprotein as provided herein, e.g., a conjugate as provided herein). For example, a common protein secondary structure is an α-helix. Alpha helices can play key roles in both structure and function of a protein, such as impacting how a particular protein can interact with a binding partner. Alpha helices can mediate protein-protein interactions (PPIs) by serving as recognition motifs. In proteins comprising alpha helical structures, introducing a constraint can change one or more features of a protein such as affinity of a protein for a target (e.g., increase affinity), cell penetration (e.g., increased cell penetration), resistance to proteolysis (e.g., increased resistance to proteolytic degradation).

Examples of constraints (e.g., α-helix constraints) can include, but are not limited to disulfide bridges/bonds, staples (e.g., hydrocarbon staples), salt bridges between charged amino acid side chain residues, lactam bridges, hydrogen bond surrogates, hydrophobic interactions, metal ligation, triazole staples synthesized from alkenyl and azido side chain residues, photocontrollable macrocycles, and introduction amino acids, such as, e.g., α,α-disubstituted amino acids. As will be known to those of skill in the art, a staple can refer to a synthetic constraint (e.g., a brace) between two previously independent entities. For example, a staple can be formed via covalent linkage between two previously independent entities such as, for example, amino acid side-chains (e.g., forming, for example, a peptide macrocycle).

The present disclosure provides the insight that engineering a B7-H3 binding protein to have constraints (e.g., one, two, three). In some embodiments, the constraints are the same (e.g., the same type, e.g., disulfide bonds). In certain embodiments, constraints are combinations of different types of constraints (e.g., disulfide bridge and lactam bridge, a disulfide bridge and a stapled alkyl bridge, two disulfide bridges and a lactam bridge, etc.). In certain embodiments, constraints can be added. For example, in certain embodiments, a miniprotein can have one, two, or three disulfide bridges; one or two disulfide bridges and another constraint such as a lactam bridge; one or two constraints such as a lactam bridge or a stapled alkyl bridge and one disulfide bridge, etc. In certain embodiments, a miniprotein of the disclosure has one, two, or three disulfide bridges and/or one or more additional constraints (e.g., one disulfide bridge and one additional constraint, e.g., two disulfide bridges and one additional constraint, wherein, for example, the one additional constraint is a lactam bridge), creates a miniprotein that not only binds with strong affinity to B7-H3, but is also taken up by cancerous cells (e.g., in a tumor), in higher concentrations than as compared to an unconstrained B7-H3 miniprotein (e.g., such as disclosed in Table 2A). The disclosure contemplates that features such as size (e.g., folded size, e.g., linear size) and stability (e.g., thermal stability) are important to efficacy of a B7-H3-binding conjugate and also important to limiting or preventing toxicity (e.g., renal toxicity) due to off-target effects. Without wishing to be bound by theory, the disclosure provides the insight that engineering B7-H3 binding proteins to add constraints, and, in some embodiments, adding such constraints after truncation (e.g., such as set forth in Table 2C relative to Table 2A) provides miniproteins with stronger affinity (e.g., for B7-H3), better efficacy (e.g., of accessing cancer cells), greater stability (e.g., thermal stability), and less toxicity (e.g., renal toxicity) as compared to molecules that are neither truncated nor constrained (e.g., as set forth in Table 2A). In some embodiments, miniproteins provided herein comprise one or more constraints such as, for example, a disulfide bridge or a staple. Exemplary constrained miniproteins are provided in Table 2C. In certain embodiments, a constraint confers an increase in thermal stability of a miniprotein (e.g., such as compared to a miniprotein having an amino acid sequence comprising or consisting of that of SEQ ID NO: 6, or as compared to compound C8; e.g., such as compared to a miniprotein with the same or similar primary sequence, but no constraints). In some embodiments, a miniprotein of the present disclosure comprises one or more disulfide bridges. In some embodiments, a miniprotein provided by the present disclosure comprises two or more disulfide bridges. In some embodiments, a miniprotein of the disclosure comprises one disulfide bridge. In some embodiments, a miniprotein of the disclosure comprises two disulfide bridges. For example, miniproteins of the present disclosure herein may contain a set of amino acids that together support formation of or are part of a constraint (e.g., a disulfide bridge, e.g., a staple). In some embodiments, a structural feature of a miniprotein is having at least two cysteine residues, positioned relative to one another so that disulfide bridge can be formed (e.g., as provided herein, see, e.g., Table 2C). In some embodiments, a miniprotein provided by the present disclosure has at least three, or at least four cysteine residues, which form one or two disulfide bridges. In certain embodiments, a miniprotein has three disulfide bridges (from three pairs of cysteines).

In some embodiments, miniproteins of the present disclosure comprising two or more cysteine residues, such as those set forth in Table 2C, have cysteine residues connected via disulfide bridges (e.g., via natural folding).

In some embodiments, a miniprotein has an amino acid sequence comprising two cysteines and a single disulfide bridge. In some embodiments, a miniprotein has an amino acid sequence comprising four cysteines and two disulfide bridges. In some embodiments, a miniprotein has an amino acid sequence comprising six cysteines and three disulfide bridges.

In some embodiments, miniproteins of the present disclosure comprising two or more cysteine residues, such as those set forth in Table 2C, have cysteine residues connected via disulfide bridges (e.g., via natural folding). In some embodiments a miniprotein (e.g., that binds to B7-H3) comprises one disulfide bridge. In some embodiments, a miniprotein comprises two disulfide bridges. In some embodiments, a miniprotein comprises three disulfide bridges.

In some embodiments, the one disulfide bridge can be between cysteine residues corresponding to, for example, Cys4 and Cys37; Cys5 and Cys34; Cys5 and Cys37; Cys12 and Cys26; Cys12 and Cys44; Cys17 and Cys48, with positions relative to linear position from N-to-C-terminus with reference to SEQ ID NO: 267.

In some embodiments, cysteine connections can be between two different pairs of cysteine residues. For example, in some embodiments, two disulfide bridges can be between positions corresponding to pairs of cysteines such as Cys1 and Cys35 and Cys17 and Cys52, with reference to the miniprotein of SEQ ID NO: 213. For example, in some embodiments, disulfide bridges can be between positions corresponding to Cys1 and Cys35; and Cys17 and Cys48 of a reference sequence such as set forth in Table 2C (e.g., SEQ ID NO: 267). In some embodiments, cysteine connections are between Cys1 and Cys17; and Cys35 and Cys48. In some embodiments, cysteine connections are between Cys1 and Cys48; and Cys17 and Cys35.

In some embodiments, the disulfide bridge or bridges comprise two or four cysteines at positions corresponding to 1, 17, 35, and 48 of SEQ ID NO: 267, wherein the cysteine corresponding to position 1 can form a disulfide bridge with the cysteine corresponding to position 17, 35, or 48. In some embodiments, the cysteine corresponding to position 17 can form a disulfide bridge with the cysteine corresponding to position 1, 35, or 48. In some embodiments, the cysteine corresponding to position 35 can form a disulfide bridge with the cysteine corresponding to position 1, 17, or 48. In some embodiments, the cysteine corresponding to position 48 can form a disulfide bridge with the cysteine corresponding to position 1, 17, or 35. In some embodiments, where four cysteines are present and correspond to positions 1, 17, 35, and 48 of SEQ ID NO: 267, pairings can comprise 1 paired with 35 and 17 paired with 48, 1 paired with 17 and 35 paired with 48, or 1 paired with 48 and 17 paired with 35 (e.g., disulfide bridges between the two cysteines of the pair).

In certain embodiments, cysteine connections (disulfide bridges) are between positions corresponding to Cys1 and Cys35; and Cys17 and Cys48 of a reference sequence such as set forth in Table 2C, for example, SEQ ID NO: 267. In some embodiments, cysteine connections are between Cys1 and Cys17; and Cys35 and Cys48 (with reference to a reference sequence, e.g., SEQ ID NO: 267). In some embodiments, cysteine connections are between Cys1 and Cys48; and Cys17 and Cys35.

In some embodiments, the disulfide bridge or bridges comprise two or four cysteines at positions corresponding to 1, 17, 35, and 48 of SEQ ID NO: 267, wherein the cysteine corresponding to position 1 can form a disulfide bridge with the cysteine corresponding to position 17, 35, or 48. In some embodiments, the cysteine corresponding to position 17 can form a disulfide bridge with the cysteine corresponding to position 1, 35, or 48. In some embodiments, the cysteine corresponding to position 35 can form a disulfide bridge with the cysteine corresponding to position 1, 17, or 48. In some embodiments, the cysteine corresponding to position 48 can form a disulfide bridge with the cysteine corresponding to position 1, 17, or 34. In some embodiments, where four cysteines are present and correspond to positions 1, 17, 35, and 48 of SEQ ID NO: 267, pairings can comprise 1 paired with 35 and 17 paired with 48, 1 paired with 17 and 35 paired with 48, or 1 paired with 48 and 17 paired with 35 (e.g., disulfide bridges between the two cysteines of the pair).

In some embodiments, a miniprotein with two disulfide bridges (e.g., from cysteines at positions corresponding to Cys1, Cys17, Cys35, and Cys48, e.g., of SEQ ID NO: 267) further comprises a third disulfide bridge, introduced between a third pair of cysteines. In some embodiments, cysteines can also be introduced at positions corresponding to Cys11 and Cys45.

In some embodiments, such a miniprotein further comprises one or more additional constraints (e.g., staples, e.g., lactam bridges). For example, in certain embodiments, a combination of constraint types (e.g., disulfide bond and lactam bridges) can be used in a single miniprotein. For example, in some embodiments, a miniprotein can comprise one, two, or three disulfide bridges and, further comprise at least one additional constraint (e.g., a staple, e.g., a lactam bridge). In some embodiments, a lactam bridge can be between positions corresponding to 11 and 45 of SEQ ID NO: 544.

In some embodiments, a miniprotein of the present disclosure comprising changes such as, for example, one or more constraints (e.g., as disclosed herein) further comprises an amino acid sequence that is 80%, 85%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in any of SEQ ID NOs: 198-537. In various embodiments, the amino acid sequence is 90% (e.g., 91%, 92%, 93%, 94%, 95, 96, 97, 98, 99 or more percent) identical to the amino acid sequence set forth in any of SEQ ID NOs: 198-537. In various embodiments, the amino acid sequence that is 100% identical to the amino acid sequence set forth in any of SEQ ID NOs: 198-537.

In some embodiments, a miniprotein of the present disclosure comprising changes such as, for example, one or more constraints (e.g., as disclosed herein), is part of a compound. In some embodiments, the compound is selected from any of C227-C608 and C611, and/or has an amino acid sequence selected from any of SEQ ID NOs: 198-537.

In some embodiments, a miniprotein of the present disclosure comprising changes such as, for example, one or more constraints (e.g., as disclosed herein) further comprises an amino acid sequence that is 80%, 85%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in any of SEQ ID NOs: 204 and 262-272. In various embodiments, the amino acid sequence is 90% (e.g., 91%, 92%, 93%, 94%, 95, 96, 97, 98, 99 or more percent) identical to the amino acid sequence set forth in any of SEQ ID NOs: 204 and 262-272. In various embodiments, the amino acid sequence that is 100% identical to the amino acid sequence set forth in any of SEQ ID NOs: 204 and 262-272.

In some embodiments, a miniprotein of the present disclosure comprising changes such as, for example, one or more constraints (e.g., as disclosed herein), is part of a compound. In some embodiments, the compound is selected from any of C234, C235, and C298-C332, and/or has an amino acid sequence selected from any of SEQ ID NOs: 204 or 262-272.

In some embodiments, a miniprotein of the present disclosure comprising changes such as, for example, one or more constraints (e.g., as disclosed herein), comprises an amino acid sequence that is 80%, 85%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in any of SEQ ID NOs: 199, 204, 241, or 267. In various embodiments, the amino acid sequence is 90% (e.g., 95, 96, 97, 98, 99 or more percent) identical to the amino acid sequence set forth in any of SEQ ID NOs: 199, 204, 241, or 267. In various embodiments, the amino acid sequence is 100% identical to the amino acid sequence set forth in any of SEQ ID NOs: 199, 204, 241, or 267.

In some embodiments, a miniprotein of the present disclosure comprising changes such as, for example, one or more constraints (e.g., as disclosed herein), is part of a compound. In some embodiments, the compound is selected from any of C228, C234, C235, C275, C309, C325, C332 or any other disclosed compound in Table 2C having an amino acid sequence comprising any of SEQ ID NOs; 199, 204, 241, or 267, and/or has an amino acid sequence selected from any of SEQ ID NOs: 199, 204, 241 or 267.

In some embodiments, a miniprotein of the present disclosure comprising changes such as, for example, one or more constraints (e.g., as disclosed herein), comprises an amino acid sequence that is 80%, 85%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in SEQ ID NO: 199. In various embodiments, the amino acid sequence is 90% (e.g., 95, 96, 97, 98, 99 or more percent) identical to the amino acid sequence set forth in SEQ ID NO: 199. In various embodiments, the amino acid sequence is 100% identical to the amino acid sequence set forth in SEQ ID NO: 199.

In some embodiments, a miniprotein of the present disclosure comprising changes such as, for example, one or more constraints (e.g., as disclosed herein) is part of a compound. In some embodiments, the compound is C228 and/or has an amino acid sequence of SEQ ID NO: 199.

In some embodiments, a miniprotein of the present disclosure comprising changes such as, for example, one or more constraints (e.g., as disclosed herein), comprises an amino acid sequence that is 80%, 85%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in SEQ ID NO: 204. In various embodiments, the amino acid sequence is 90% (e.g., 95, 96, 97, 98, 99 or more percent) identical to the amino acid sequence set forth in SEQ ID NO: 204. In various embodiments, the amino acid sequence is 100% identical to the amino acid sequence set forth in SEQ ID NO: 204.

In some embodiments, a miniprotein of the present disclosure comprising changes such as, for example, one or more constraints (e.g., as disclosed herein) is part of a compound. In some embodiments, the compound is C234 or C235 and/or has an amino acid sequence of SEQ ID NO: 204.

In some embodiments, a miniprotein of the present disclosure comprising changes such as, for example, one or more constraints (e.g., as disclosed herein), comprises an amino acid sequence that is 80%, 85%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in SEQ ID NO: 241. In various embodiments, the amino acid sequence is 90% (e.g., 95, 96, 97, 98, 99 or more percent) identical to the amino acid sequence set forth in SEQ ID NO: 241. In various embodiments, the amino acid sequence is 100% identical to the amino acid sequence set forth in SEQ ID NO: 241.

In some embodiments, a miniprotein of the present disclosure comprising changes such as, for example, one or more constraints (e.g., as disclosed herein) is part of a compound. In some embodiments, the compound is C275 and/or has an amino acid sequence of SEQ ID NO: 241.

In some embodiments, a miniprotein of the present disclosure comprising changes such as, for example, one or more constraints (e.g., as disclosed herein), comprises an amino acid sequence that is 80%, 85%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in SEQ ID NO: 267. In various embodiments, the amino acid sequence is 90% (e.g., 95, 96, 97, 98, 99 or more percent) identical to the amino acid sequence set forth in SEQ ID NO: 267. In various embodiments, the amino acid sequence is 100% identical to the amino acid sequence set forth in SEQ ID NO: 267.

In some embodiments, a miniprotein of the present disclosure comprising changes such as, for example, one or more constraints (e.g., as disclosed herein) is part of a compound. In some embodiments, the compound is or comprises that set forth in C234, C235, C309, C325, C332, and/or has a miniprotein with an amino acid sequence comprising SEQ ID NO: 267.

In some embodiments, a miniprotein of the present disclosure comprises a staple. In some embodiments, the present disclosure provides stapled miniproteins that bind to B7-H3, wherein presence of the staple changes at least one binding characteristic relative to the miniprotein without the staple (e.g., increased binding affinity for B7-H3, e.g., a change in avidity for B7-H3). Those skilled in the art, reading the present disclosure, will appreciate that, a stapled miniprotein may be prepared using any desired stapling technology.

As will be understood by one of ordinary skill in the art, certain amino acid sequences disclosed herein may be duplicated (i.e., have the same amino acid sequence and the same or different N-termini) but be identified by different SEQ ID NOs and Compound ID Nos. For example, SEQ ID NO: 204 and SEQ ID NO: 262 each have the same amino acid sequence. In addition, they are each used in multiple compounds. For example, in certain embodiments, various compounds may comprise an amino acid sequence having the same amino acid sequence and identified by different SEQ ID NOs, e.g., C234 and C235 having an amino acid comprising SEQ ID NO: 204 have an amino acid sequence identical to that of C298 and C299 having an amino acid sequence of SEQ ID NO: 262, wherein SEQ ID NOs: 204 and 262 have the same amino acid sequence. In such situations, such compounds and SEQ ID NOs should be considered interchangeable.

TABLE 2A

Exemplary B7-H3 Miniproteins

| Compound ID NO[3] | SEQ ID NO[4] | N-Term | Sequence5 | C-Term |
|---|---|---|---|---|
| C1 | 3 | Ac | AEAKYAKEKIAALSEIIWLPNLTHGQIMAFIAALNDD PSQSSELLSEAKKLNDSQAPK | COOH |
| C2 | 4 | Ac | AEAKYAKEKIAALSEIIWLPNLTHGQI(Nle)AFIAA LNDDPSQSSELLSEAKKLNDSQAPK | COOH |
| C3 | 5* | Ac | AEAKYDKEKIAALSEIIWLPNLTHGQIMAFIAALNND PSQSSELLSEAKKLNDSQAPK | COOH |
| C4 | 4 | Biotin-PEG4 | AEAKYAKEKIAALSEIIWLPNLTHGQI(Nle)AFIAA LNDDPSQSSELLSEAKKLNDSQAPK | COOH |
| C5 | 4 | DOTA-PEG4 | AEAKYAKEKIAALSEIIWLPNLTHGQI(Nle)AFIAA LNDDPSQSSELLSEAKKLNDSQAPK | COOH |

TABLE 2A-continued

Exemplary B7-H3 Miniproteins

| Compound ID NO[3] | SEQ ID NO[4] | N-Term | Sequence5 | C-Term |
|---|---|---|---|---|
| C6 | 6 | Ac | YAKEKIAALSEIIWLPNLTYAQI(homo-leucine)AFIAALNDDPSQSSELLSEAKELNDSQAP | NH2 |
| C7 | 6 | In: DOTA-PEG4 | YAKEKIAALSEIIWLPNLTYAQI(homo-leucine)AFIAALNDDPSQSSELLSEAKELNDSQAP | NH2 |
| C8 | 6 | Biotin-PEG4 | YAKEKIAALSEIIWLPNLTYAQI(homo-leucine)AFIAALNDDPSQSSELLSEAKELNDSQAP | NH2 |
| C9 | 6 | DOTA-PEG4 | YAKEKIAALSEIIWLPNLTYAQI(homo-leucine)AFIAALNDDPSQSSELLSEAKELNDSQAP | NH2 |
| C10 | 7 | Ac | AEAKYAKEKIAALSEII(3-(1-naphthyl)-L-alanine)LPNLTHGQIMAFIAALNDDPSQSSELLSEAKKLNDSQAPK | OH |
| C11 | 8 | DOTA-PEG4 | YAKEKIAALSEIIWLPNLTHGQI(homo-leucine)AFIAALNDDPSQSSELLSEAKKLNDSQAP | NH2 |
| C12 | 9 | DOTA-PEG4 | AEA(KAc)YA(KAc)E(KAc)IAALSEIIWLPNLTHGQI(homo-leucine)AFIAALNDDPSQSSELLSEA(KAc)(KAC)LNDSQAP(KAc) | NH2 |
| C13 | 10 | DOTA-PEG4 | AEA(KAC)YAKEKIAALSEIIWLPNLTHGQI(homo-leucine)AFIAALNDDPSQSSELLSEAKKLNDSQAP(KAc) | NH2 |
| C14 | 11 | DOTA-PEG4 | AEA(KAc)YA(KAc)E(KAc)IAALSEIIWLPNLTHGQI(homo-leucine)AFIAALNDDPSQSSELLSEAKKLNDSQAP(KAc) | NH2 |
| C15 | 8 | In: DOTA-PEG4 | YAKEKIAALSEIIWLPNLTHGQI(homo-leucine)AFIAALNDDPSQSSELLSEAKKLNDSQAP | NH2 |
| C16 | 9 | In: DOTA-PEG4 | AEA(KAC)YA(KAc)E(KAc)IAALSEIIWLPNLTHGQI(homo-leucine)AFIAALNDDPSQSSELLSEA(KAC)(KAC)LNDSQAP(KAc) | NH2 |
| C17 | 10 | In: DOTA-PEG4 | AEA(KAC)YAKEKIAALSEIIWLPNLTHGQI(homo-leucine)AFIAALNDDPSQSSELLSEAKKLNDSQAP(KAc) | NH2 |
| C18 | 11 | In: DOTA-PEG4 | AEA(KAc)YA(KAc)E(KAc)IAALSEIIWLPNLTHGQI(homo-leucine)AFIAALNDDPSQSSELLSEAKKLNDSQAP(KAc) | NH2 |
| C19 | 12 | Ac | AEAKYAKEKIAALSEIIWLPNDTYAQI(homo-leucine)(homo-leucine)AFIAALNDDPSQSSELLSEAKKLNDSQAPK | NH2 |
| C20 | 13 | Ac | AEAKYAKEKIAALSEIIWLPNATYAQI(homo-leucine)AFIAALNDDPSOSSELLSEAKKLNDSQAPK | NH2 |
| C21 | 14 | Ac | AEAKYAKEKIAALSEIIWLPNFTYAQI(homo-leucine)AFIAALNDDPSQSSELLSEAKKLNDSQAPK | NH2 |
| C22 | 15 | Ac | AEAKYAKEKIAALSEIIWLPNNTYAQI(homo-leucine)AFIAALNDDPSQSSELLSEAKKLNDSQAPK | NH2 |
| C23 | 16 | Ac | AEAKYAKEKIAALSEIIWLPNYTYAQI(homo-leucine)AFIAALNDDPSQSSELLSEAKKLNDSQAPK | NH2 |
| C24 | 17 | Ac | AEAKYAKEKIAALSEIIWLPNITYAQI(homo-leucine)AFIAALNDDPSQSSELLSEAKKLNDSQAPK | NH2 |

TABLE 2A-continued

Exemplary B7-H3 Miniproteins

| Compound ID NO[3] | SEQ ID NO[4] | N-Term | Sequence5 | C-Term |
|---|---|---|---|---|
| C25 | 18 | Ac | AEAKYAKEKIAALSEIIWLPNTTYAQI(homo-leucine) AFIAALNDDPSQSSELLSEAKKLNDSQAPK | NH2 |
| C26 | 19 | Ac | AEAKYAKEKIAALSEIIWLPNDVYAQI(homo-leucine) AFIAALNDDPSQSSELLSEAKKLNDSQAPK | NH2 |
| C27 | 20 | Ac | YAKEKIAALSEIIWLPNDTYAQI(homo-leucine) AFIAALNDDPSQSSELLSEAKKLNDSQAPK | NH2 |
| C28 | 21 | Ac | YAKEKIAALSEIIWLPNDTYAQI(homo-leucine) AFIAALNDDPSQSSELLSEAKKLNDSQAP | NH2 |
| C29 | 21 | DOTA-PEG4 | YAKEKIAALSEIIWLPNDTYAQI(homo-leucine) AFIAALNDDPSOSSELLSEAKKLNDSQAP | NH2 |
| C30 | 21 | In: DOTA-PEG4 | YAKEKIAALSEIIWLPNDTYAQI(homo-leucine) AFIAALNDDPSQSSELLSEAKKLNDSQAP | NH2 |
| C31 | 21 | Biotin-PEG4 | YAKEKIAALSEIIWLPNDTYAQI(homo-leucine) AFIAALNDDPSQSSELLSEAKKLNDSQAP | NH2 |
| C32 | 22 | Ac | AEAKYAKEKIAALSEIIWLPN(Nle)TYAQI(homo-leucine)AFIAALNDDPSQSSELLSEAKKLNDSQAPK | NH2 |
| C33 | 23 | Ac | AEAKYAKEKIAALSEIIWLPN(homo-leucine)TYAQI(homo-leucine)AFIAALNDDPSQSSELLSEAKKLNDSQAPK | NH2 |
| C34 | 24 | Ac | YAKEKIAALSEIIWLPNLTYAQI(homo-leucine)AFIAALNDDPSQSSELLSEAKGLNDSQAP | NH2 |
| C35 | 25 | Ac | YAKEKIAALSEIIWLPNLTYAQI(homo-leucine)AFIAALNDDPSQSSELLSEAKALNDSQAP | NH2 |
| C36 | 26 | Ac | YAKEKIAALSEIIWLPNLTYAQI(homo-leucine)AFIAALNDDPSOSSELLSEAKOLNDSQAP | NH2 |
| C37 | 27 | Ac | YAKEKIAALSEIIWLPNLTYAQI(homo-leucine)AFIAALNDDPSQSSELLSEAKLLNDSQAP | NH2 |
| C38 | 28 | Ac | YAKEKIAALSEIIWLPNLTYAQI(homo-leucine)AFIAALNDDPSQSSELLSEAKSINDSQAP | NH2 |
| C39 | 29 | Ac | YAKEKIAALSEIIWLPNLTYAQI(homo-leucine)AFIAALNDDPSQSSELLSEAKYLNDSQAP | NH2 |
| C40 | 30 | DOTA-PEG4 | AEALYAQEKIAALSEIIWLPNLTHGQIMAFIAALNNDPSQSSELLSEAEQLNDSQAPG | COOH |
| C41 | 30 | In: DOTA-PEG4 | AEALYAQEKIAALSEIIWLPNLTHGQIMAFIAALNNDPSQSSELLSEAEQLNDSQAPG | COOH |
| C42 | 30 | Biotin-PEG4 | AEALYAQEKIAALSEIIWLPNLTHGQIMAFIAALNNDPSQSSELLSEAEQLNDSQAPG | COOH |
| C43 | 31 | In: DOTA-PEG4 | YALEKIAALSEIIWLPNLTHGQIMAFIAALNDDPSQSSELLSEAQALNDSQAPG | COOH |
| C44 | 32 | In: DOTA-PEG4 | YAQEKIAALSEIIWLPNLTHGQIMAFIAALNNDPSQSSELLSEALALNDSQAPG | COOH |
| C45 | 33 | Biotin-PEG4 | YAQEKIAALSEIIWLPNLTHGQIMAFIAALNNDPSQSSELLSEALALNDSQAPG | COOH |
| C46 | 34 | In: DOTA-PEG4 | AEALYAEEKIAALSEIIWLPNLTHGQIMAFIAALNDDPSQSSELLSEALQLNDSQAPG | COOH |
| C47 | 35 | Ac | YAKEKIAALSEIIWLPNLTYAQI(homo-leucine)AFIAALNDDPSQSSELLSEAGELNDSQAP | NH2 |

TABLE 2A-continued

| Exemplary B7-H3 Miniproteins | | | | |
|---|---|---|---|---|
| Compound ID NO[3] | SEQ ID NO[4] | N-Term | Sequence5 | C-Term |
| C48 | 36 | Ac | YAKEKIAALSEIIWLPNLTYAQI(homo-leucine)AFIAALNDDPSQSSELLSEAAELNDSQAP | NH2 |
| C49 | 37 | Ac | YAKEKIAALSEIIWLPNLTYAQI(homo-leucine)AFIAALNDDPSQSSELLSEAQELNDSQAP | NH2 |
| C50 | 38 | Ac | YAKEKIAALSEIIWLPNLTYAQI(homo-leucine)AFIAALNDDPSQSSELLSEAEELNDSQAP | NH2 |
| C51 | 39 | Ac | YAKEKIAALSEIIWLPNLTYAQI(homo-leucine)AFIAALNDDPSQSSELLSEALELNDSQAP | NH2 |
| C52 | 40 | Ac | YAKEKIAALSEIIWLPNLTYAQI(homo-leucine)AFIAALNDDPSQSSELLSEASELNDSQAP | NH2 |
| C53 | 41 | Ac | YAKEKIAALSEIIWLPNLTYAQI(homo-leucine)AFIAALNDDPSQSSELLSEAYELNDSQAP | NH2 |
| C54 | 42 | Ac | YAKEKIAALSEIIWLPNLTYAQI(homo-leucine)AFIAALNDDPSQSSELLSEAKDLNDSQAP | NH2 |
| C55 | 43 | In: DOTA-PEG4 | YAQEKIAALSEIIWLPNLTHGQIMAFIAALNDDPSQSSELLSEALELNDSQAPG | OH |
| C56 | 44 | Biotin-PEG4 | YAKEKIAALSEIIWLPNLTYAQI(homo-leucine)AFIAALNADPSQSSELLSEAKELNDSQAP | NH2 |
| C57 | 45 | Biotin-PEG4 | YAKEKIAALSEIIWLPNLTYAQI(homo-leucine)AFIAALNEDPSQSSELLSEAKELNDSQAP | NH2 |
| C58 | 46 | Biotin-PEG4 | YAKEKIAALSEIIWLPNLTYAQI(homo-leucine)AFIAALNLDPSQSSELLSEAKELNDSQAP | NH2 |
| C59 | 47 | Biotin-PEG4 | YAKEKIAALSEIIWLPNLTYAQI(homo-leucine)AFIAALNSDPSQSSELLSEAKELNDSQAP | NH2 |
| C60 | 48 | Biotin-PEG4 | YAKEKIAALSEIIWLPNLTYAQI(homo-leucine)AFIAALNNDPSQSSELLSEAKELNDSQAP | NH2 |
| C61 | 49 | Biotin-PEG4 | YAKEKIAALSEIIWLPNLTYAQI(homo-leucine)AFIAALNTDPSQSSELLSEAKELNDSQAP | NH2 |
| C62 | 50 | Biotin-PEG4 | YAKEKIAALSEIIWLPNLTYAQI(homo-leucine)AFIAALNCitDPSQSSELLSEAKELNDSQAP | NH2 |
| C63 | 51 | Biotin-PEG4 | YAKEKIAALSEIIWLPNLTYAQI(homo-leucine)AFIAALNDDPSQSSELLSEALDLNDSQAP | NH2 |
| C64 | 52 | Biotin-PEG4 | YAKEKIAALSEIIWLPNLTYAQI(homo-leucine)AFIAALNODPSQSSELLSEAKELNDSQAP | NH2 |
| C65 | 53 | Biotin-PEG4 | YAKEKIAALSEIIWLPNLTYAQI(homo-leucine)AFIAALNDDPSQSSELLSEAKCit LNDSQAP | NH2 |
| C66 | 54 | Biotin-PEG4 | YDKEKIAALSEIIWLPNLTYAQI(homo-leucine)AFIAALNDDPSQSSELLSEAKELNDSQAP | NH2 |
| C67 | 55 | Biotin-PEG4 | YIKEKIAALSEIIWLPNLTYAQI(homo-leucine)AFIAALNDDPSQSSELLSEAKELNDSQAP | NH2 |
| C68 | 56 | Biotin-PEG4 | YYKEKIAALSEIIWLPNLTYAQI(homo-leucine)AFIAALNDDPSQSSELLSEAKELNDSQAP | NH2 |
| C69 | 57 | Biotin-PEG4 | YSKEKIAALSEIIWLPNLTYAQI(homo-leucine)AFIAALNDDPSQSSELLSEAKELNDSQAP | NH2 |
| C70 | 58 | Biotin-PEG4 | YTKEKIAALSEIIWLPNLTYAQI(homo-leucine)AFIAALNDDPSQSSELLSEAKELNDSQAP | NH2 |
| C71 | 59 | Biotin-PEG4 | YNKEKIAALSEIIWLPNLTYAQI(homo-leucine)AFIAALNDDPSQSSELLSEAKELNDSQAP | NH2 |

TABLE 2A-continued

| Exemplary B7-H3 Miniproteins | | | | |
|---|---|---|---|---|
| Compound ID NO[3] | SEQ ID NO[4] | N-Term | Sequence5 | C-Term |
| C72 | 60 | Biotin-PEG4 | YEKEKIAALSEIIWLPNLTYAQI(homo-leucine)AFIAALNDDPSQSSELLSEAKELNDSQAP | NH2 |
| C73 | 61 | Biotin-PEG4 | YLKEKIAALSEIIWLPNLTYAQI(homo-leucine)AFIAALNDDPSQSSELLSEAKELNDSQAP | NH2 |
| C74 | 62 | Biotin-PEG4 | YOKEKIAALSEIIWLPNLTYAQI(homo-leucine)AFIAALNDDPSQSSELLSEAKELNDSQAP | NH2 |
| C75 | 63 | Biotin-PEG4 | YAEEKIAALSEIIWLPNLTHGQIMAFIAALNDDPSQSSELLSEALQLNDSQAPG | COOH |
| C76 | 64 | Biotin-PEG4 | YALEKIAALSEIIWLPNLTYAQI(homo-leucine) AFIAALNDDPSQSSELLSEAKELNDSQAP | NH2 |
| C77 | 65 | Biotin-PEG4 | YAAEKIAALSEIIWLPNLTYAQI(homo-leucine) AFIAALNDDPSQSSELLSEAKELNDSQAP | NH2 |
| C78 | 66 | Biotin-PEG4 | YASEKIAALSEIIWLPNLTYAQI(homo-leucine) AFIAALNDDPSQSSELLSEAKELNDSQAP | NH2 |
| C79 | 67 | Biotin-HE | YAKEKIAALSEIIWLPNLTYAQI(homo-leucine) AFIAALNDDPSQSSELLSEAKELNDSQAP | NH2 |
| C80 | 67 | Biotin-HEHE | YAKEKIAALSEIIWLPNLTYAQI(homo-leucine) AFIAALNDDPSQSSELLSEAKELNDSQAP | NH2 |
| C81 | 67 | Biotin-HEHEHE | YAKEKIAALSEIIWLPNLTYAQI(homo-leucine) AFIAALNDDPSQSSELLSEAKELNDSQAP | NH2 |
| C82 | 67 | Biotin-SE | YAKEKIAALSEIIWLPNLTYAQI(homo-leucine) AFIAALNDDPSQSSELLSEAKELNDSQAP | NH2 |
| C83 | 67 | Biotin-SESE | YAKEKIAALSEIIWLPNLTYAQI(homo-leucine) AFIAALNDDPSQSSELLSEAKELNDSQAP | NH2 |
| C84 | 67 | Biotin-SESESE | YAKEKIAALSEIIWLPNLTYAQI(homo-leucine) AFIAALNDDPSQSSELLSEAKELNDSQAP | NH2 |
| C85 | 67 | Biotin-E | YAKEKIAALSEIIWLPNLTYAQI(homo-leucine) AFIAALNDDPSQSSELLSEAKELNDSQAP | NH2 |
| C86 | 67 | Biotin-EE | YAKEKIAALSEIIWLPNLTYAQI(homo-leucine) AFIAALNDDPSQSSELLSEAKELNDSQAP | NH2 |
| C87 | 67 | Biotin-EEE | YAKEKIAALSEIIWLPNLTYAQI(homo-leucine) AFIAALNDDPSQSSELLSEAKELNDSQAP | NH2 |
| C88 | 68 | Biotin-PEG4 | YAKEKIAALSEIIWLPNLTYAQI(homo-leucine)AFIAALNDDPSQSSELLSEAK(hSer) LNDSQAP | NH2 |
| C89 | 69 | Biotin-PEG4 | AEAKYAKEKIQALSEIIWLPNITYAQI(homo-leucine)AFIAALNDDPSQSSELLSEAKKLNDSQAP K | NH2 |
| C90 | 70 | Biotin-PEG4 | AEAKYAKEKIYALSEIIWLPNITYAQI(homo-leucine)AFIAALNDDPSQSSELLSEAKKLNDSQAP K | NH2 |
| C91 | 71 | Biotin-PEG4 | AEAKYAKEKIAALQEIIWLPNITYAQI(homo-leucine)AFIAALNDDPSQSSELLSEAKKLNDSQAP K | NH2 |
| C92 | 72 | Biotin-PEG4 | AEAKYAKEKIAALYEIIWLPNITYAQI(homo-leucine)AFIAALNDDPSQSSELLSEAKKLNDSQAP K | NH2 |
| C93 | 73 | Biotin-PEG4 | AEAKYAKEKIAALEEIIWLPNITYAQI(homo-leucine)AFIAALNDDPSQSSELLSEAKKLNDSQAP K | NH2 |

TABLE 2A-continued

| Exemplary B7-H3 Miniproteins | | | | |
|---|---|---|---|---|
| Compound ID NO[3] | SEQ ID NO[4] | N-Term | Sequence5 | C-Term |
| C94 | 74 | Biotin-PEG4 | AEAKYAKEKISALSEIIWLPNITYAQI(homo-leucine)AFIAALNDDPSQSSELLSEAKKLNDSQAPK | NH2 |
| C95 | 75 | Biotin-PEG4 | AEAKYAKEKITALSEIIWLPNITYAQI(homo-leucine)AFIAALNDDPSQSSELLSEAKKLNDSQAPK | NH2 |
| C96 | 76 | Biotin-PEG4 | NAQLYAKEKIAALSEIIWLPNLTYAQI(homo-leucine)AFIAALNDDPSQSSELLSEAKELNDSQAP | NH2 |
| C97 | 77 | Biotin-PEG4 | YAKE(Kme3)IAALSEIIWLPNLTYAQI(homo-leucine)AFIAALNDDPSQSSELLSEAKELNDSQAP | NH2 |
| C98 | 78 | Biotin-PEG4 | YAKEKIAALSEIIWLPNITYAQI(homo-leucine)AFIAALNDDPSQSSELLSEAKGLADSQAP | NH2 |
| C99 | 79 | Biotin-PEG4 | YAKEKIAALSEIIWLPNITYAQI(homo-leucine)AFIAALNDDPSQSSELLSEAKGLODSQAP | NH2 |
| C100 | 80 | Biotin-PEG4 | YAKEKIAALSEIIWLPNITYAQI(homo-leucine)AFIAALNDDPSQSSELLSEAKGLTDSQAP | NH2 |
| C101 | 81 | Biotin-PEG4 | YAKEKIAALSEIIWLPNITYAQI(homo-leucine)AFIAALNDDPSQSSELLSEAKGLNDSSAP | NH2 |
| C102 | 82 | Biotin-PEG4 | YAKEKIAALSEIIWLPNITYAQI(homo-leucine)AFIAALNDDPSQSSELLSEAKGLNDSDAP | NH2 |
| C103 | 83 | Biotin-PEG4 | YAKEKIAALSEIIWLPNITYAQI(homo-leucine)AFIAALNDDPSQSSELLSEAKGLNDSYAP | NH2 |
| C104 | 84 | Biotin-PEG4 | YAKEKIAALSEIIWLPNLTYAQI(MO2) AFIAALNDDPSQSSELLSEAKELNDSQAP | NH2 |
| C105 | 67 | Biotin-Ahx | YAKEKIAALSEIIWLPNLTYAQI(homo-leucine) AFIAALNDDPSQSSELLSEAKELNDSQAP | NH2 |
| C106 | 67 | Biotin | YAKEKIAALSEIIWLPNLTYAQI(homo-leucine) AFIAALNDDPSQSSELLSEAKELNDSQAP | NH2 |
| C107 | 85 | Biotin-PEG4 | YAKEKIAALSEIIWLPNLTYAQITAFIAALNDDPSQSSELLSEAKELNDSQAP | NH2 |
| C108 | 86 | Biotin-PEG4 | YAKEKIAALSEIIWLPNLTYAQIVAFIAALNDDPSQSSELLSEAKELNDSQAP | NH2 |
| C109 | 87 | Biotin-PEG4 | YAKEKIAALSEIIWLPNITYAQI(homo-leucine)AFIAALNDDPSQSSELLSEAKGLNDSLAP | NH2 |
| C110 | 88 | Biotin-PEG4 | YA(Kme3)EKIAALSEIIWLPNLTYAQI(homo-leucine) AFIAALNDDPSQSSELLSEAKELNDSQAP | NH2 |
| C111 | 89 | Biotin-PEG4 | YAKEKIAALSEIIWLPNITYAQI(homo-leucine)AFIAALNDDPSQSSELLSEAKGLYDSQAP | NH2 |
| C112 | 90 | Biotin-PEG4 | YAKEKIAALSEIIWLPNITYAQI(homo-leucine)AFIAALNDDPSQSSELLSEAKGLGDSQAP | NH2 |
| C113 | 91 | Biotin-PEG4 | YAKEKIAALSEIIWLPNITYAQI(homo-leucine)AFIAALNDDPSQSSELLSEAKGLDDSQAP | NH2 |
| C114 | 92 | Biotin-PEG4 | YAKEKIAALSEIIWLPNITYAQI(homo-leucine)AFIAALNDDPSQSSELLSEAKGLNDSEAP | NH2 |
| C115 | 93 | Biotin-PEG4 | YAKEKIAALSEIIWLPNLTYAQIAAFIAALNDDPSQSSELLSEAKELNDSQAP | NH2 |
| C116 | 94 | Biotin-PEG4 | YAKEKIAALSEIIWLPNLTYAQISAFIAALNDDPSQSSELLSEAKELNDSQAP | NH2 |
| C117 | 4 | AZ647-PEG4 | AEAKYAKEKIAALSEIIWLPNLTHGQI(Nle)AFIAALNDDPSQSSELLSEAKKLNDSQAPK | OH |

TABLE 2A-continued

| Compound ID NO[3] | SEQ ID NO[4] | N-Term | Sequence5 | C-Term |
|---|---|---|---|---|
| Exemplary B7-H3 Miniproteins | | | | |
| C121 | 100 | Biotin-PEG4 | AAKEKIAALSEIIWLPNLTYAQI(homo-leucine)AFIAALNDDPSQSSELLSEAKELNDSQAP | NH2 |
| C122 | 101 | Biotin-PEG4 | EAKEKIAALSEIIWLPNLTYAQI(homo-leucine)AFIAALNDDPSQSSELLSEAKELNDSQAP | NH2 |
| C123 | 102 | Biotin-PEG4 | LAKEKIAALSEIIWLPNLTYAQI(homo-leucine)AFIAALNDDPSQSSELLSEAKELNDSQAP | NH2 |
| C124 | 103 | Biotin-PEG4 | QAKEKIAALSEIIWLPNLTYAQI(homo-leucine)AFIAALNDDPSQSSELLSEAKELNDSQAP | NH2 |
| C125 | 104 | Biotin-PEG4 | SAKEKIAALSEIIWLPNLTYAQI(homo-leucine)AFIAALNDDPSQSSELLSEAKELNDSQAP | NH2 |
| C126 | 105 | Biotin-PEG4 | TAKEKIAALSEIIWLPNLTYAQI(homo-leucine)AFIAALNDDPSQSSELLSEAKELNDSQAP | NH2 |
| C127 | 106 | Biotin-PEG4 | YAAEKIAALSEIIWLPNLTYAQI(Kme2)AFIAALNDDPSQSSELLSEAKELNDSQAP | NH2 |
| C128 | 107 | Biotin-PEG4 | YA(Kme2)EKIAALSEIIWLPNLTYAQI(Kme2)AFIAALNDDPSQSSEILSEAKELNDSQAP | NH2 |
| C129 | 108 | Biotin-PEG4 | YA(Kme2)EKIAALSEIIWLPNLTYAQI(Kme2)EFIAALNDDPSQSSELLSEAKELNDSQAP | NH2 |
| C130 | 109 | Biotin-PEG4 | YA(Kme3)EKIAALSEIIWLPNLTYAQI(Kme2)AFIAALNDDPSQSSEILSEAKELNDSQAP | NH2 |
| C131 | 109 | DOTA-PEG4 | YA(Kme3)EKIAALSEIIWLPNLTYAQI(Kme2)AFIAALNDDPSQSSEILSEAKELNDSQAP | NH2 |
| C132 | 110 | Biotin-PEG4 | YA(Kme3)EKIAALSEIIWLPNLTYAQI(Kme2)EFIAALNDDPSQSSELLSEAKELNDSQAP | NH2 |
| C133 | 111 | Biotin-PEG4 | YA(Kme3)EKIAALSEIIWLPNLTYAQIMAFIAALNDDPSQSSELLSEAKELNDSQAP | NH2 |
| C134 | 112 | Biotin-PEG4 | YA(Kme3)EKIAALSEIIWLPNLTYAQINvaAFIAALNDDPSQSSELLSEAKELNDSQAP | NH2 |
| C135 | 113 | Biotin-PEG4 | YA(Kme3)EKIAALSEIIWLPNLTYAQIVAFIAALNDDPSQSSELLSEAKELNDSQAP | NH2 |
| C136 | 114 | Biotin-PEG4 | YAKAKIAALSEIIWLPNLTYAQI(Kme2)AFIAALNDDPSQSSELLSEAKELNDSQAP | NH2 |
| C137 | 115 | Biotin-PEG4 | YAKCKIAALSEIIWLPNLTYAQI(homo-leucine)AFIAALNDDPSQCSELLSEAKELNDSQAP | NH2 |
| C138 | 116 | Biotin-PEG4 | YAKE(k)IAALSEIIWLPNLTYAQIVAFIAALNDDPSQSSELLSEAKELNDSQAP | NH2 |
| C139 | 117 | Biotin-PEG4 | YAKECIAALSEIIWLPNLTYAQI(homo-leucine)AFIAALNDDCSQSSELLSEAKELNDSQAP | NH2 |
| C140 | 118 | Biotin-PEG4 | YAKECIAALSEIIWLPNLTYAQI(homo-leucine)AFIAALNDDPSQCSELLSEAKELNDSQAP | NH2 |
| C141 | 119 | Biotin-PEG4 | YAKEEIAALSEIIWLPNLTYAQ IVAFIAALNDDPSQSSELLSEAKELNDSQAP | NH2 |
| C142 | 120 | Biotin-PEG4 | YAKE(HO-(Nle))IAALSEIIWLPNLTYAQIVAFIAALNDDPSQSSELLSEAKELNDSQAP | NH2 |
| C143 | 121 | Biotin-PEG4 | YAKE(Kme2)IAALSEIIWLPNLTYAQI(homo-leucine)AFIAALNDDPSQSSELLSEAKELNDSQAP | NH2 |
| C144 | 122 | Biotin-PEG4 | YAKE(Kme)IAALSEIIWLPNLTYAQI(homo-leucine)AFIAALNDDPSQSSELLSEAKELNDSQAP | NH2 |

TABLE 2A-continued

| Exemplary B7-H3 Miniproteins | | | | |
|---|---|---|---|---|
| Compound ID NO[3] | SEQ ID NO[4] | N-Term | Sequence5 | C-Term |
| C145 | 123 | Biotin-PEG4 | YAKEKIAALSECIWLPNLTYAQI(homo-leucine)ACIAALNDDPSQSSELLSEAKELNDSQAP | NH2 |
| C146 | 124 | Biotin-PEG4 | YAKEKIAALSECIWLPNLTYAQI(homo-leucine)AFIAALNDDPSQSSELLSECKELNDSQAP | NH2 |
| C147 | 125 | Biotin-PEG4 | YAKEKIAALSEIIWCPNCTYAQI(homo-leucine)AFIAALNDDPSQSSELLSEAKELNDSQAP | NH2 |
| C148 | 126 | Biotin-PEG4 | YAKEKIAALSEIIWLPCLTYAQI(homo-leucine)AFIAALNDDPSQSSELLSEAKELCDSQAP | NH2 |
| C149 | 127 | Biotin-PEG4 | YAKEKIAALSEIIWLPNCTYAQC(homo-leucine)AFIAALNDDPSQSSELLSEAKELNDSQAP | NH2 |
| C150 | 128 | Biotin-PEG4 | YAKEKIAALSEIIWLPNLCYACI(homo-leucine)AFIAALNDDPCOSSELLSEAKELNDSQAP | NH2 |
| C151 | 129 | Biotin-PEG4 | YAKEKIAALSEIIWLPNLCYCQI(homo-leucine)AFIAALNDDPSQSSELLSEAKELNDSQAP | NH2 |
| C152 | 130 | Biotin-PEG4 | YAKEKIAALSEIIWLPNLTYAQI(Kme2)AFIAALNDDPSQSSEILSEAKELNDSQAP | NH2 |
| C153 | 131 | Biotin-PEG4 | YAKEKIAALSEIIWLPNLTYAQI(Kme2)EFIAALNDDPSQSSEILSEAKELNDSQAP | NH2 |
| C154 | 132 | Biotin-PEG4 | YAKEKIAALSEIIWLPNLTYAQI(homo-leucine)ACIAALNDDPSQSSELLSECKELNDSQAP | NH2 |
| C155 | 133 | Biotin-PEG4 | YAKEKIAALSEIIWLPNLTYAQI(homo-leucine)AFIAALNDCPSCSSELLSEAKELNDSQAP | NH2 |
| C156 | 134 | Biotin-PEG4 | YAKEKIAALSEIIWLPNLTYAQI(Abu)AFIAALNDDPSQSSELLSEAKELNDSQAP | NH2 |
| C157 | 135 | Biotin-PEG4 | YAKEKIAALSEIIWLPNLTYAQI(C(t-butyl))AFIAALNDDPSQSSELLSEAKELNDSQAP | NH2 |
| C158 | 136 | Biotin-PEG4 | YAKEKIAALSEIIWLPNLTYAQIEthionineAFIAALNDDPSQSSELLSEAKELNDSQAP | NH2 |
| C159 | 137 | Biotin-PEG4 | YAKEKIAALSEIIWLPNLTYAQIGAFIAALNDDPSQSSELLSEAKELNDSQAP | NH2 |
| C160 | 138 | Biotin-PEG4 | YAKEKIAALSEIIWLPNLTYAQI(Kme2)AFAAALNDDPSQSSEILSEAKELNDSQAP | NH2 |
| C161 | 139 | Biotin-PEG4 | YAKEKIAALSEIIWLPNLTYAQI(Kme2)AFAbuAALNDDPSQSSEILSEAKELNDSQAP | NH2 |
| C162 | 140 | Biotin-PEG4 | YAKEKIAALSEIIWLPNLTYAQI(Kme2)AFFAALNDDPSQSSEILSEAKELNDSQAP | NH2 |
| C163 | 141 | DOTA-PEG4 | YAKEKIAALSEIIWLPNLTYAQI(Kme2)AFIAALNDDPSQSSEILSEAKELNDSQAP | NH2 |
| C176 | 142 | Biotin-PEG4 | YAKEKIAALSEIIWLPNLTYAQI(Kme2)AFIAALNDDPSQSSELLSEAKELNDSQAP | NH2 |
| C165 | 142 | DOTA-PEG4 | YAKEKIAALSEIIWLPNLTYAQI(Kme2)AFIAALNDDPSQSSELLSEAKELNDSQAP | NH2 |
| CD16 | 143 | Biotin-PEG4 | YAKEKIAALSEIIWLPNLTYAQI(Kme2)AFIAALNEDPSQSSELLSEAKELNDSQAP | NH2 |
| C167 | 144 | Biotin-PEG4 | YAKEKIAALSEIIWLPNLTYAQI(Kme2)AFIAALNSDPSQSSELLSEAKELNDSQAP | NH2 |
| C168 | 145 | Biotin-PEG4 | YAKEKIAALSEIIWLPNLTYAQI(Kme2)AFIA(Cit)LNDDPSQSSELLSEAKELNDSQAP | NH2 |
| C169 | 146 | Biotin-PEG4 | YAKEKIAALSEIIWLPNLTYAQI(Kme2)AFIAELNDDPSQSSELLSEAKELNDSQAP | NH2 |

TABLE 2A-continued

Exemplary B7-H3 Miniproteins

| Compound ID NO[3] | SEQ ID NO[4] | N-Term | Sequence5 | C-Term |
|---|---|---|---|---|
| C170 | 147 | Biotin-PEG4 | YAKEKIAALSEIIWLPNLTYAQI(Kme2)AFIALLNDDPSQSSELLSEAKELNDSQAP | NH2 |
| C171 | 148 | Biotin-PEG4 | YAKEKIAALSEIIWLPNLTYAQI(Kme2)AFIAQLNDDPSQSSELLSEAKELNDSQAP | NH2 |
| C172 | 149 | Biotin-PEG4 | YAKEKIAALSEIIWLPNLTYAQI(Kme2)AFIASLNDDPSQSSELLSEAKELNDSQAP | NH2 |
| C173 | 150 | Biotin-PEG4 | YAKEKIAALSEIIWLPNLTYAQI(Kme2)AFIAYLNDDPSQSSELLSEAKELNDSQAP | NH2 |
| C174 | 151 | Biotin-PEG4 | YAKEKIAALSEIIWLPNLTYAQI(Kme2)AFI(Cit)ALNDDPSQSSEILSEAKELNDSQAP | NH2 |
| C175 | 152 | Biotin-PEG4 | YAKEKIAALSEIIWLPNLTYAQI(Kme2)AFIEALNDDPSQSSELLSEAKELNDSQAP | NH2 |
| C176 | 153 | Biotin-PEG4 | YAKEKIAALSEIIWLPNLTYAQI(Kme2)AFIHALNDDPSQSSELLSEAKELNDSQAP | NH2 |
| C177 | 154 | Biotin-PEG4 | YAKEKIAALSEIIWLPNLTYAQI(Kme2)AFIIALNDDPSQSSEILSEAKELNDSQAP | NH2 |
| C178 | 155 | Biotin-PEG4 | YAKEKIAALSEIIWLPNLTYAQI(Kme2)AFILALNDDPSQSSELLSEAKELNDSQAP | NH2 |
| C179 | 156 | Biotin-PEG4 | YAKEKIAALSEIIWLPNLTYAQI(Kme2)AFIQALNDDPSQSSELLSEAKELNDSQAP | NH2 |
| C180 | 157 | Biotin-PEG4 | YAKEKIAALSEIIWLPNLTYAQI(Kme2)AFISALNDDPSQSSEILSEAKELNDSQAP | NH2 |
| C181 | 158 | Biotin-PEG4 | YAKEKIAALSEIIWLPNLTYAQI(Kme2)AFITALNDDPSQSSEILSEAKELNDSQAP | NH2 |
| C182 | 159 | Biotin-PEG4 | YAKEKIAALSEIIWLPNLTYAQI(Kme2)AFIYALNDDPSQSSELLSEAKELNDSQAP | NH2 |
| C183 | 160 | Biotin-PEG4 | YAKEKIAALSEIIWLPNLTYAQI(Kme2)AFLAALNDDPSQSSEILSEAKELNDSQAP | NH2 |
| C184 | 161 | Biotin-PEG4 | YAKEKIAALSEIIWLPNLTYAQI(Kme2)AF(Nle)AALNDDPSQSSEILSEAKELNDSQAP | NH2 |
| C185 | 162 | Biotin-PEG4 | YAKEKIAALSEIIWLPNLTYAQI(Kme2)AF(Nva)AALNDDPSQSSEILSEAKELNDSQAP | NH2 |
| C186 | 163 | Biotin-PEG4 | YAKEKIAALSEIIWLPNLTYAQI(Kme2)AFVAALNDDPSQSSEILSEAKELNDSQAP | NH2 |
| C187 | 164 | Biotin-PEG4 | YAKEKIAALSEIIWLPNLTYAQI(Kme2)DFIAALNDDPSQSSELLSEAKELNDSQAP | NH2 |
| C188 | 165 | Biotin-PEG4 | YAKEKIAALSEIIWLPNLTYAQI(Kme2)EFIAALNDDPSQSSEILSEAKELNDSQAP | NH2 |
| C189 | 165 | DOTA-PEG4 | YAKEKIAALSEIIWLPNLTYAQI(Kme2)EFIAALNDDPSQSSEILSEAKELNDSQAP | NH2 |
| C190 | 166 | Biotin-PEG4 | YAKEKIAALSEIIWLPNLTYAQI(Kme2)EFIAALNDDPSQSSELLSEAKELNDSQAP | NH2 |
| C191 | 167 | Biotin-PEG4 | YAKEKIAALSEIIWLPNLTYAQI(Kme)AFIAALNDDPSQSSELLSEAKELNDSQAP | NH2 |
| C192 | 168 | Biotin-PEG4 | YAKEKIAALSEIIWLPNLTYAQI(MO2)AFIAALNDDPSQSSELLSEAKELNDSQAP | NH2 |
| C193 | 168 | DOTA-PEG4 | YAKEKIAALSEIIWLPNLTYAQI(MO2)AFIAALNDDPSQSSELLSEAKELNDSQAP | NH2 |
| C194 | 169 | Biotin-PEG4 | YAKEKIAALSEIIWLPNLTYAQIMAFIAALNDDPSOSSEILSEAKELNDSQAP | NH2 |

TABLE 2A-continued

Exemplary B7-H3 Miniproteins

| Compound ID NO[3] | SEQ ID NO[4] | N-Term | Sequence5 | C-Term |
|---|---|---|---|---|
| C195 | 170 | Biotin-PEG4 | YAKEKIAALSEIIWLPNLTYAQIMAFIAALNDDPSQSSELLSEAKELNDSQAP | NH2 |
| C196 | 170 | DOTA-PEG4 | YAKEKIAALSEIIWLPNLTYAQIMAFIAALNDDPSQSSELLSEAKELNDSQAP | NH2 |
| C197 | 171 | Biotin-PEG4 | YAKEKIAALSEIIWLPNLTYAQI(Nle)AFIAALNDDPSQSSELLSEAKELNDSQAP | NH2 |
| C198 | 172 | Biotin-PEG4 | YAKEKIAALSEIIWLPNLTYAQINvaAFIAALNDDPSQSSEILSEAKELNDSQAP | NH2 |
| C199 | 173 | Biotin-PEG4 | YAKEKIAALSEIIWLPNLTYAQINvaAFIAALNDDPSQSSELLSEAKELNDSQAP | NH2 |
| C200 | 174 | Biotin-PEG4 | YAKEKIAALSEIIWLPNLTYAQIVAFIAALNDDPSQSSEILSEAKELNDSQAP | NH2 |
| C201 | 86 | Acetyl | YAKEKIAALSEIIWLPNLTYAQIVAFIAALNDDPSQSSELLSEAKELNDSQAP | NH2 |
| C202 | 86 | DOTA-PEG4 | YAKEKIAALSEIIWLPNLTYAQIVAFIAALNDDPSQSSELLSEAKELNDSQAP | NH2 |
| C203 | 175 | Biotin-PEG4 | YAKEKIAALSELIWLPNLTYAQI(Kme2)AFIAALNDDPSQSSELLSEAKELNDSQAP | NH2 |
| C204 | 176 | Biotin-PEG4 | YAKEKIEALSEIIWLPNLTYAQI(Kme2)AFIAALNDDPSQSSELLSEAKELNDSQAP | NH2 |
| C205 | 177 | Biotin-PEG4 | YAKELIAALSEIIWLPNLTYAQIVAFIAALNDDPSQSSELLSEAKELNDSQAP | NH2 |
| C206 | 178 | Biotin-PEG4 | YAKEQIAALSEIIWLPNLTYAQIVAFIAALNDDPSQSSELLSEAKELNDSQAP | NH2 |
| C207 | 179 | Biotin-PEG4 | YAKERIAALSEIIWLPNLTYAQIVAFIAALNDDPSOSSELLSEAKELNDSQAP | NH2 |
| C208 | 180 | Biotin-PEG4 | YAKESIAALSEIIWLPNLTYAQIVAFIAALNDDPSQSSELLSEAKELNDSQAP | NH2 |
| C209 | 181 | Biotin-PEG4 | YAKEYIAALSEIIWLPNLTYAQIVAFIAALNDDPSQSSELLSEAKELNDSQAP | NH2 |
| C210 | 182 | Biotin-PEG4 | YAQEKIAALSEIIWLPNLTYAQI(Kme2)AFIAALNDDPSQSSELLSEAKELNDSQAP | NH2 |
| C211 | 183 | Biotin-PEG4 | YAREKIAALSEIIWLPNLTYAQI(Kme2)AFIAALNDDPSQSSEILSEAKELNDSQAP | NH2 |
| C212 | 184 | Biotin-PEG4 | YAREKIAALSEIIWLPNLTYAQI(Kme2)AFIAALNDDPSQSSEALSEAKELNDSQAP | NH2 |
| C213 | 185 | DOTA-PEG4 | YAREKIAALSEIIWLPNLTYAQI(Kme2)AFIAALNDDPSQSSEILSEAKELNDSQAP | NH2 |
| C214 | 186 | Biotin-PEG4 | YAREKIAALSEIIWLPNLTYAQI(Kme2)AFIAALNDDPSQSSEILSEAKELNS | NH2 |
| C215 | 187 | Biotin-PEG4 | YAREKIAALSEIIWLPNLTYAQI(Kme2)AFIAALNDDPSQSSE(Nle)LSEAKELNDSQAP | NH2 |
| C216 | 188 | Biotin-PEG4 | YAREKIAALSEIIWLPNLTYAQI(Kme2)AFIAALNDDPSQSSEQLSEAKELNDSQAP | NH2 |
| C217 | 189 | Biotin-PEG4 | YAREKIAALSEIIWLPNLTYAQI(Kme2)AFIAALNDDPSQSSESLSEAKELNDSQAP | NH2 |
| C218 | 190 | Biotin-PEG4 | YAREKIAALSEIIWLPNLTYAQI(Kme2)AFIAALNDDPSQSSEVLSEAKELNDSQAP | NH2 |
| C219 | 191 | Biotin-PEG4 | YAREKIAALSEIIWLPNLTYAQI(Kme2)AFIAALNDDPSQSSEYLSEAKELNDSQAP | NH2 |

TABLE 2A-continued

| Exemplary B7-H3 Miniproteins | | | | |
|---|---|---|---|---|
| Compound ID NO[3] | SEQ ID NO[4] | N-Term | Sequence5 | C-Term |
| C220 | 192 | DOTA-PEG4 | YAREKIAALSEIIWLPNLTYAQI(Kme2)EFIAALND DPSQSSEILSEAKELNDSQAP | NH2 |
| C221 | 192 | Biotin-PEG4 | YAREKIAALSEIIWLPNLTYAQI(Kme2)EFIAALND DPSQSSEILSEAKELNDSQAP | NH2 |
| C222 | 193 | Biotin-PEG4 | YAREKIAALSEIIWLPNLTYAQI(Kme2)EFIAALND DPSQSSELLSEAKELNDSQAP | NH2 |
| C223 | 194 | Biotin-PEG4 | YARNKIAALSEIIWLPNLTYAQI(Kme2)AFIAALND DPSQSSEILSEAKELNDSQAP | NH2 |
| C224 | 195 | Biotin-PEG4 | YARQKIAALSEIIWLPNLTYAQI(Kme2)AFIAALND DPSQSSEILSEAKELNDSQAP | NH2 |
| C225 | 196 | Biotin-PEG4 | YARSKIAALSEIIWLPNLTYAQI(Kme2)AFIAALND DPSQSSEILSEAKELNDSQAP | NH2 |
| C226 | 197 | Biotin-PEG4 | YASEKIAALSEIIWLPNLTYAQI(Kme2)AFIAALND DPSQSSELLSEAKELNDSQAP | NH2 |

[3]Each compound is identified via a compound # (e.g., "C1", "C2", C3", etc.) and refers to the combination of the N-terminal, Linker (if present), Sequence, and C-terminal components.

[4]Refers to sequences in the "Sequence" column.

[5]"Cit" refers to citrulline; "(Kme)" refers to monomethyllysine; "(Kme)2" refers to dimethyllysine; "(Kme3)" refers to trimethyllysine; "K(Ac)" refers to acetylated lysine; "N4-methyl-A" refers to N4-methyl-L-asparagine; "Nva" refers to norvaline; "(Nle)" refers to (Nle); "OH-(Nle)" refers to hydroxy(Nle); "(k)" refers to D-lysine; "(MO2)" refers to methionine sulfone; "Abu" refers to alpha-aminobutyric acid; C(t-butyl) can also be written as Cys-(t-butyl) or tert-butylcysteine; "dD" refers to D-aspartic acid; "hR" refers to homo-arginine; "hyP" refers to hydroxyproline; "1Nal" refers to 1-naphthylamine; "sRme2" refers to symmetric dimethyl arginine; "Rme" and "Rme2" refer to mono and di-methylated arginine, respectively; "Kipr" refers to Ne-isopropyl-L-Lysine; "Dap" refers to diaminopimelic acid; "K(Ac)" refers to acetylated lysine; "RNO2" or "Arg(NO2)" refer to nitroarginine; "LCN" refers to Leu-13C6,15N; "NI" refers to hydroxynorleucine, "Nle" refers to Norleucine.

*expected m/z, M+4H/4 for the miniprotein of SEQ ID NO: 5 is 1.0073.

TABLE 2B

| Data for Exemplary Miniproteins of Table 2A | | | | | |
|---|---|---|---|---|---|
| Compound ID NO | Molecular Weight | Exact Mass | Expected m/z, M + 4H+/4 | Measured m/z, M + 4H+/4 | error (ppm) |
| C1 | 6352.241 | 6348.299 | 1589.068 | 1590.3 | −775.581 |
| C2 | 6334.201 | 6330.343 | 1584.558 | 1585.7 | −720.99 |
| C6 | 5860.622 | 5857.035 | 1466.163 | 1465.69 | 322.4744 |

TABLE 2C

| Additional Exemplary B7-H3 Miniproteins[6] | | | | |
|---|---|---|---|---|
| Compound ID NO[7] | SEQ ID NO[8] | N-Term | Sequence[9] | C-Term |
| C227 | 198 | Biotin-PEG4 | CAEEKIAALSEIIWLPCLTYAQI(Kme2)AFIAAL NDDPCQSSEILSEAKELCS | NH2 |
| C228 | 199 | Biotin-PEG4 | CA(Kme2)EKIAALSEIIWLPCLTYAQI(Kme2)A FIAALNDDPCQSSEILSEAKELCS | NH2 |
| C229 | 199 | DOTA-PEG4 | CA(Kme2)EKIAALSEIIWLPCLTYAQI(Kme2)A FIAALNDDPCQSSEILSEAKELCS | NH2 |
| C230 | 200 | Biotin-PEG4 | CA(Kme3)EKIAADSEIIWLPCLTYAQI(Kme2)A FIAALNDDPCQSSEILSEAKELCS | NH2 |
| C231 | 201 | Biotin-PEG4 | CA(Kme3)EKIAALSEIIWLPCLTYAQI(Kme2)A FIAALNDDPCESSEILSEAKALCS | NH2 |

TABLE 2C-continued

Additional Exemplary B7-H3 Miniproteins[6]

| Compound ID NO[7] | SEQ ID NO[8] | N-Term | Sequence[9] | C-Term |
|---|---|---|---|---|
| C232 | 202 | Biotin-PEG4 | CA(Kme3)EKIAALSEIIWLPCLTYAQI(Kme2)AFIAALNDDPCESSEILSEAKELCS | NH2 |
| C233 | 203 | Biotin-PEG4 | CA(Kme3)EKIAALSEIIWLPCLTYAQI(Kme2)AFIAALNDDPCQSSEILSEAKALCS | NH2 |
| C234 | 204 | Biotin-PEG4 | CA(Kme3)EKIAALSEIIWLPCLTYAQI(Kme2)AFIAALNDDPCQSSEILSEAKELCS | NH2 |
| C235 | 204 | DOTA-PEG4 | CA(Kme3)EKIAALSEIIWLPCLTYAQI(Kme2)AFIAALNDDPCQSSEILSEAKELCS | NH2 |
| C236 | 205 | Biotin-PEG4 | CA(Kme3)EKIAALSEIIWLPCLTYAQI(Kme2)EFIAALNDDPCQSSEILSEAKELCS | NH2 |
| C237 | 206 | Biotin-PEG4 | CA(Kme3)EKIAALSEIIWLPCLTYAQI(Kme3)AFIAALNDDPCQSSEILSEAKELCS | NH2 |
| C238 | 207 | Biotin-PEG4 | CA(Kme3)EKSAALSEIIWLPCLTYAQI(Kme2)AFIAALNDDPCQSSEILSEAKELCS | NH2 |
| C239 | 208 | Biotin-PEG4 | CAKEKIAALSCIIWLPNLTYAQI(homo-leucine)AFIAALNDDPCQSSELCSEAKELNDSQAP | NH2 |
| C240 | 209 | Biotin-PEG4 | CAKEKIAALSEIIWLPCLTYAQI(homo-leucine)AFIAALNDDPCQSSELLSEAKELCDS | NH2 |
| C241 | 210 | Biotin-PEG4 | CAKEKIAALSEIIWLPCLTYAQI(homo-leucine)AFIAALNDDPCQSSELLSEAKELCDSQAP | NH2 |
| C242 | 210 | DOTA-PEG4 | CAKEKIAALSEIIWLPCLTYAQI(homo-leucine)AFIAALNDDPCQSSELLSEAKELCDSQAP | NH2 |
| C243 | 211 | Biotin-PEG4 | CAKEKIAALSEIIWLPCLTYAQI(homo-leucine)AFIAALNDDPCQSSELLSEAKELCS | NH2 |
| C244 | 212 | Biotin-PEG4 | CAKEKIAALSEIIWLPCLTYAQI(homo-leucine)AFIAALNDDPCQSSELLSEAKELNDSCAP | NH2 |
| C245 | 213 | Biotin-PEG4 | CAKEKIAALSEIIWLPCLTYAQI(homo-leucine)AFIAALNDDPCQSSELLSEAKELNDSQCP | NH2 |
| C246 | 214 | Biotin-PEG4 | CAKEKIAALSEIIWLPCLTYAQI(Kme2)AFIAALDDDPCQSSEILSEAKELCS | NH2 |
| C247 | 215 | Biotin-PEG4 | CAKEKIAALSEIIWLPCLTYAQI(Kme2)AFIAALNDDPCESSEILSEAKELCS | NH2 |
| C248 | 216 | Biotin-PEG4 | CAKEKIAALSEIIWLPCLTYAQI(Kme2)AFIAALNDDPCQSSEILSEAKALNDSQCP | NH2 |
| C249 | 217 | Biotin-PEG4 | CAKEKIAALSEIIWLPCLTYAQI(Kme2)AFIAALNDDPCQSSEILSEAKELCS | NH2 |
| C250 | 218 | Biotin-PEG4 | CAKEKIAALSEIIWLPCLTYAQI(Kme2)AFIAALNDDPCQSSEILSEAKELNDSQCP | NH2 |
| C251 | 218 | DOTA-PEG4 | CAKEKIAALSEIIWLPCLTYAQI(Kme2)AFIAALNDDPCQSSEILSEAKELNDSQCP | NH2 |
| C252 | 219 | Biotin-PEG4 | CAKEKIAALSEIIWLPCLTYAQI(Kme2)AFIAALNDDPCQSSELLSEAKELCS | OH |
| C253 | 220 | Biotin-PEG4 | CAKEKIAALSEIIWLPCLTYAQI(Kme2)AFIAALNDDPCQSSELLSEAKELNDSQCP | NH2 |
| C254 | 221 | Biotin-PEG4 | CAKEKIAALSEIIWLPCLTYAQI(Kme3)AFIAALNDDPCQSSEILSEAKELCS | NH2 |

TABLE 2C-continued

| Additional Exemplary B7-H3 Miniproteins[6] | | | | |
|---|---|---|---|---|
| Compound ID NO[7] | SEQ ID NO[8] | N-Term | Sequence[9] | C-Term |
| C255 | 222 | Biotin-PEG4 | CAKEKIAALSEIIWLPCLTYAQI(Kme3)AFIAAL NDDPCQSSELLSEAKELNDSQCP | NH2 |
| C256 | 223 | Biotin-PEG4 | CAKEKIAALSEIIWLPCLTYAQIMAFIAALNDDPC QSSELLSEAKELNDSCAP | NH2 |
| C257 | 224 | Biotin-PEG4 | CAKEKIAALSEIIWLPCLTYAQINVAAFIAALNDD PCQSSELLSEAKELNDSCAP | NH2 |
| C258 | 225 | Biotin-PEG4 | CAKEKIAALSEIIWLPNLTYAQI(homo-leucine)AFIAALNDDPCQSSELLSEAKELNDSQ AP | NH2 |
| C259 | 226 | Biotin-PEG4 | CAKEKIAALSEIIWLPNLTYAQI(Kme2)AFIAAL NDDPCQSSELLSEAKELNDSQAP | NH2 |
| C260 | 226 | DOTA-PEG4 | CAKEKIAALSEIIWLPNLTYAQI(Kme2)AFIAAL NDDPCQSSELLSEAKELNDSQAP | NH2 |
| C261 | 227 | Biotin-PEG4 | CAKERIAALSEIIWLPCLTYAQI(homo-leucine)AFIAALNDDPCQSSELLSEAKELCDSQ AP | NH2 |
| C262 | 228 | Biotin-PEG4 | CA(OH-Nle)EKIAALSEIIWLPCLTYAQI(Kme2)AFIAAL NDDPCQSSEILSEAKELCS | NH2 |
| C263 | 229 | Biotin-PEG4 | CAQEKIAALSEIIWLPCLTHAQI(Kme2)AFIYAL NDDPCQSSELLSEAKSLNDSQCP | NH2 |
| C264 | 230 | Biotin-PEG4 | CAQEKIAALSEIIWLPCLTYAQI(Kme2)AFIAAL NDDPCQSSEILSEAKALCS | NH2 |
| C265 | 231 | Biotin-PEG4 | CAQEKIAALSEIIWLPCLTYAQI(Kme2)AFIAAL NDDPCQSSEILSEAKALNDSQCP | NH2 |
| C266 | 232 | Biotin-PEG4 | CAQEKIAALSEIIWLPCLTYAQI(Kme2)AFIAAL NDDPCQSSEILSEAKELCS | NH2 |
| C267 | 233 | Biotin-PEG4 | CAQEKIAALSEIIWLPCLTYAQI(Kme2)AFIAAL NDDPCQSSEILSEAKELNDSQCP | NH2 |
| C268 | 234 | Biotin-PEG4 | CAQEKIAALSEIIWLPCLTYAQI(Kme2)AFIYAL NDDPCQSSELLSEAKSLNDSQCP | NH2 |
| C269 | 235 | Biotin-PEG4 | CAQEKIAALSEIIWLPCLTYAQI(Kme2)EFIAAL NDDPCQSSEILSEAKELCS | NH2 |
| C270 | 236 | Biotin-PEG4 | CAREKIAALSEIIWLPCLTYAQI(Cit)AFIAALN DDPCQSSEILSEAKELCS | NH2 |
| C271 | 237 | Biotin-PEG4 | CAREKIAALSEIIWLPCLTYAQIIAFIAALNDDPC QSSEILSEAKELCS | NH2 |
| C272 | 238 | Biotin-PEG4 | CAREKIAALSEIIWLPCLTYAQI(Kme2)AFIAAL NDDPCQSAEILSEAKELCS | NH2 |
| C273 | 239 | Biotin-PEG4 | CAREKIAALSEIIWLPCLTYAQI(Kme2)AFIAAL NDDPCQSANILSEAKELCS | NH2 |
| C274 | 240 | Biotin-PEG4 | CAREKIAALSEIIWLPCLTYAQI(Kme2)AFIAAL NDDPCQSSEILSEA(Cit)(Cit)LCS | NH2 |
| C275 | 241 | Biotin-PEG4 | CAREKIAALSEIIWLPCLTYAQI(Kme2)AFIAAL NDDPCQSSEILSEAKELCS | NH2 |
| C276 | 241 | DOTA-PEG4 | CAREKIAALSEIIWLPCLTYAQI(Kme2)AFIAAL NDDPCQSSEILSEAKELCS | NH2 |
| C277 | 242 | Biotin-PEG4 | CAREKIAALSEIIWLPCLTYAQI(Kme2)AFIAAL NDDPCQSSEILSEAKELNDSQCP | NH2 |
| C278 | 243 | Biotin-PEG4 | CAREKIAALSEIIWLPCLTYAQI(Kme2)AFIAAL NDDPCQSSEILSEAKLLCS | NH2 |

TABLE 2C-continued

Additional Exemplary B7-H3 Miniproteins[6]

| Compound ID NO[7] | SEQ ID NO[8] | N-Term | Sequence[9] | C-Term |
|---|---|---|---|---|
| C279 | 244 | Biotin-PEG4 | CAREKIAALSEIIWLPCLTYAQI(Kme2)AFIAAL NDDPCQSSEILSEALDLCS | NH2 |
| C280 | 245 | Biotin-PEG4 | CAREKIAALSEIIWLPCLTYAQI(Kme2)AFIAAL NDDPCQSSEILSEALELCS | NH2 |
| C281 | 246 | Biotin-PEG4 | CAREKIAALSEIIWLPCLTYAQI(Kme2)AFIAAL NDDPCQSSEILSEAQDLCS | NH2 |
| C282 | 247 | Biotin-PEG4 | CAREKIAALSEIIWLPCLTYAQI(Kme2)AFIAAL NDDPCQSSNILSEAKELCS | NH2 |
| C283 | 248 | Biotin-PEG4 | CAREKIAALSEIIWLPCLTYAQI(Kme2)EFIAAL NDDPCQSSEILSEAKELCS | NH2 |
| C284 | 249 | Biotin-PEG4 | CAREKIAALSEIIWLPCLTYAQIKAFIAALNDDPC QSSEILSEAKELCS | NH2 |
| C285 | 250 | Biotin-PEG4 | CAREKIAALSEIIWLPCLTYAQI(Kme2)AFIAAL NDDPCQSSEILSEAQELCS | NH2 |
| C286 | 251 | Biotin-PEG4 | CAREKIAALSEIIWLPCLTYAQILAFIAALNDDPC QSSEILSEAKELCS | NH2 |
| C287 | 252 | Biotin-PEG4 | CAREKIAALSEIIWLPCLTYAQIMAFIAALNDDPC QSSEILSEAKELCS | NH2 |
| C288 | 253 | Biotin-PEG4 | CAREKIAALSEIIWLPCLTYAQIN(4-methyl-Asn)AFIAALNDDPCQSSEILSEAKELCS | NH2 |
| C289 | 254 | Biotin-PEG4 | CAREKIAALSEIIWLPCLTYAQINAFIAALNDDPC QSSEILSEAKELCS | NH2 |
| C290 | 255 | Biotin-PEG4 | CAREKIAALSEIIWLPCLTYAQIQAFIAALNDDPC QSSEILSEAKELCS | NH2 |
| C291 | 256 | Biotin-PEG4 | CAREKIAALSEIIWLPCLTYAQIVAFIAALNDDPC QSSEILSEAKELCS | NH2 |
| C292 | 257 | Biotin-PEG4 | CYAKEKIAALSEIIWLPCLTYAQI(homo-leucine)AFIAALNDDPCQSSELLSEAKELNDSQ CP | NH2 |
| C293 | 258 | Biotin-PEG4 | TAKEKIAALSCIIWLPNLTYAQI(homo-leucine)AFIAALNDDPSQSSELCSEAKELNDSQ AP | NH2 |
| C294 | 259 | Biotin-PEG4 | YAKEKIAALSCIIWLPNLTYAQI(homo-leucine)AFIAALNDDPSQSSELCSEAKELNDSQ AP | NH2 |
| C295 | 259 | DOTA-PEG4 | YAKEKIAALSCIIWLPNLTYAQI(homo-leucine)AFIAALNDDPSQSSELCSEAKELNDSQ AP | NH2 |
| C296 | 260 | Biotin-PEG4 | YAKEKIAALSCIIWLPNLTYAQI(Kme2)AFIAAL NDDPSQSSELCSEAKELNDSQAP | NH2 |
| C297 | 261 | Biotin-PEG4 | YAKERIAALSCIIWLPNLTYAQI(homo-leucine)AFIAALNDDPSQSSELCSEAKELNDSQ AP | NH2 |
| C298 | 262 | Biotin-PEG4 | CA(Kme3)EKIAALSEIIWLPCLTYAQI(Kme2)A FIAALNDDPCQSSEILSEAKELCS | NH2 |
| C299 | 262 | DOTA-PEG4 | CA(Kme3)EKIAALSEIIWLPCLTYAQI(Kme2)A FIAALNDDPCQSSEILSEAKELCS | NH2 |
| C300 | 263 | Biotin-PEG4 | CAREKIAALSEIIWLPCLTYAQI(Kme2)AFIAAL NDDPCQSAEILSEAKELCS | NH2 |
| C301 | 263 | DOTA-PEG4 | CAREKIAALSEIIWLPCLTYAQI(Kme2)AFIAAL NDDPCQSAEILSEAKELCS | NH2 |

TABLE 2C-continued

| Additional Exemplary B7-H3 Miniproteins[6] | | | | |
|---|---|---|---|---|
| Compound ID NO[7] | SEQ ID NO[8] | N-Term | Sequence[9] | C-Term |
| C302 | 264 | Biotin-PEG4 | CAREKIAALSEIIWLPCLTYAQI(Kme)AFIAALNDDPCQSANILSEA(Kme)ELCS | NH2 |
| C303 | 264 | DOTA-PEG4 | CAREKIAALSEIIWLPCLTYAQI(Kme)AFIAALNDDPCQSANILSEA(Kme)ELCS | NH2 |
| C304 | 265 | Biotin-PEG4 | CA(Kme3)EKIAALSEIIWLPCLTYAQI(Kme)AFIAALNDDPCQSSEILSEA(Kme)ELCS | NH2 |
| C305 | 265 | DOTA-PEG4 | CA(Kme3)EKIAALSEIIWLPCLTYAQI(Kme)AFIAALNDDPCQSSEILSEA(Kme)ELCS | NH2 |
| C306 | 266 | Biotin-PEG4 | CA(Kme3)EKIAALSEIIWLPCLTYAQI(Kme)AFI(Kme)ALNDDPCQSSEILSEA(Kme)ELCS | NH2 |
| C307 | 266 | DOTA-PEG4 | CA(Kme3)EKIAALSEIIWLPCLTYAQI(Kme)AFI(Kme)ALNDDPCQSSEILSEA(Kme)ELCS | NH2 |
| C308 | 267 | Biotin-PEG4 | CA(Kme3)EKIAALSEIIWLPCLTYAQI(Kme)AFIA(Kme)LN(Kme)DPCQSSEILSEA(Kme)ELCS | NH2 |
| C309 | 267 | DOTA-PEG4 | CA(Kme3)EKIAALSEIIWLPCLTYAQI(Kme)AFIA(Kme)LN(Kme)DPCQSSEILSEA(Kme)ELCS | NH2 |
| C310 | 268 | Biotin-PEG4 | CA(Kme3)EKIAALSEIIWLPCLNYAQI(Kme)AFIAALNDDPCQSSEILSEA(Kme)ELCS | NH2 |
| C311 | 268 | DOTA-PEG4 | CA(Kme3)EKIAALSEIIWLPCLNYAQI(Kme)AFIAALNDDPCQSSEILSEA(Kme)ELCS | NH2 |
| C312 | 269 | Biotin-PEG4 | CA(Kme3)EKIAALSEIIWLPCLTYAQI(Kme)AFIAALNDDPCNSSEILSEA(Kme)ELCS | NH2 |
| C313 | 269 | DOTA-PEG4 | CA(Kme3)EKIAALSEIIWLPCLTYAQI(Kme)AFIAALNDDPCNSSEILSEA(Kme)ELCS | NH2 |
| C314 | 270 | Biotin-PEG4 | CA(Kme3)EKIAALSEIIWLPCLTYAQI(Kme2)AFIAALN(Cit)DPCQSSEILSEA(Kme)ELCS | NH2 |
| C315 | 270 | DOTA-PEG4 | CA(Kme3)EKIAALSEIIWLPCLTYAQI(Kme2)AFIAALN(Cit)DPCQSSEILSEA(Kme)ELCS | NH2 |
| C316 | 271 | Biotin-PEG4 | CA(Rme)EKIAALSEIIWLPCLTYAQI(Kme)AFIARLNDDPCQSAEILSEA(Kme)ELCS | NH2 |
| C317 | 271 | DOTA-PEG4 | CA(Rme)EKIAALSEIIWLPCLTYAQI(Kme)AFIARLNDDPCQSAEILSEAKmeELCS | NH2 |
| C318 | 272 | Biotin-PEG4 | CA(Kme3)EKIAALSEIIWLPCLTYAQI(Kme2)AFIA(Kme)LN(Cit)DPCQSSEILSEA(Kme)ELCS | NH2 |
| C319 | 272 | DOTA-PEG4 | CA(Kme3)EKIAALSEIIWLPCLTYAQI(Kme2)AFIA(Kme)LN(Cit)DPCQSSEILSEA(Kme)ELCS | NH2 |
| C320 | 262 | In:DOTA-PEG4 | CA(Kme3)EKIAALSEIIWLPCLTYAQI(Kme2)AFIAALNDDPCQSSEILSEAKELCS | NH2 |
| C321 | 263 | In:DOTA-PEG4 | CAREKIAALSEIIWLPCLTYAQI(Kme2)AFIAALNDDPCQSAEILSEAKELCS | NH2 |
| C322 | 264 | In:DOTA-PEG4 | CAREKIAALSEIIWLPCLTYAQI(Kme)AFIAALNDDPCQSANILSEA(Kme)ELCS | NH2 |
| C323 | 265 | In:DOTA-PEG4 | CA(Kme3)EKIAALSEIIWLPCLTYAQI(Kme)AFIAALNDDPCQSSEILSEA(Kme)ELCS | NH2 |
| C324 | 266 | In:DOTA-PEG4 | CA(Kme3)EKIAALSEIIWLPCLTYAQI(Kme)AFI(Kme)ALNDDPCQSSEILSEA(Kme)ELCS | NH2 |
| C325 | 267 | In:DOTA-PEG4 | CA(Kme3)EKIAALSEIIWLPCLTYAQI(Kme)AFIA(Kme)LN(Kme)DPCQSSEILSEA(Kme)ELCS | NH2 |

TABLE 2C-continued

Additional Exemplary B7-H3 Miniproteins[6]

| Compound ID NO[7] | SEQ ID NO[8] | N-Term | Sequence[9] | C-Term |
|---|---|---|---|---|
| C326 | 268 | In:DOTA-PEG4 | CA(Kme3)EKIAALSEIIWLPCLNYAQI(Kme)AFIAALNDDPCQSSEILSEA(Kme)ELCS | NH2 |
| C327 | 269 | In:DOTA-PEG4 | CA(Kme3)EKIAALSEIIWLPCLTYAQI(Kme)AFIAALNDDPCNSSEILSEA(Kme)ELCS | NH2 |
| C328 | 270 | In:DOTA-PEG4 | CA(Kme3)EKIAALSEIIWLPCLTYAQI(Kme2)AFIAALN(Cit)DPCQSSEILSEA(Kme)ELCS | NH2 |
| C329 | 271 | In:DOTA-PEG4 | CA(Rme)EKIAALSEIIWLPCLTYAQI(Kme)AFIARLNDDPCQSAEILSEA(Kme)ELCS | NH2 |
| C330 | 272 | In:DOTA-PEG4 | CA(Kme3)EKIAALSEIIWLPCLTYAQI(Kme2)AFIA(Kme)LN(Cit)DPCQSSEILSEA(Kme)ELCS | NH2 |
| C331 | 263 | Ac[10]:DOTA-PEG4 | CAREKIAALSEIIWLPCLTYAQI(Kme2)AFIAALNDDPCQSAEILSEAKELCS | NH2 |
| C332 | 267 | Ac:DOTA-PEG4 | CA(Kme3)EKIAALSEIIWLPCLTYAQI(Kme)AFIA(Kme)LN(Kme)DPCQSSEILSEA(Kme)ELCS | NH2 |
| C333 | 273 | DOTA-PEG4 | CAREKIAALSEIIWLPCLTYAQI(Kme2)AFIAALNDDPCQSANILSEAKELCS | NH2 |
| C334 | 274 | Biotin-PEG4 | CAREKIAALSEIIWLPCLTYAQI(Kme2)AFIAALNDDPCQSSEILSEA(Cit)ELCS | NH2 |
| C335 | 275 | Biotin-PEG4 | CAREKIAALSEIIWLPCLTYAQI(Kme2)AFIAALNDDPCQSSEILSEAK(Cit)LCS | NH2 |
| C336 | 276 | Biotin-PEG4 | CAREKIAALSEIIWLPCLTYAQI(hArg)AFIAALNDDPCQSSEILSEAKELCS | NH2 |
| C337 | 277 | Biotin-PEG4 | CAREKIAALSEIIWLPCLTYAQI(Orn)AFIAALNDDPCQSSEILSEAKELCS | NH2 |
| C338 | 278 | Biotin-PEG4 | CAREKIAALSEIIWLPCLTYAQI(Kme2)AFIAALNDDPCQSSEILAEAKELCS | NH2 |
| C339 | 279 | Biotin-PEG4 | CAREKIAALSEIIWLPCLTYAQI(Kme2)AFIAALNDDPCQSSNILAEAKELCS | NH2 |
| C340 | 280 | Biotin-PEG4 | CAREKIAALSEIIWLPCLTYAQI(Kme2)AFIAALNDDPCQSANILAEAKELCS | NH2 |
| C341 | 281 | Biotin-PEG4 | CA(Kme3)EKIAANSEIIWLPCLTYAQI(Kme2)AFIAALNDDPCQSSEILSEAKELCS | NH2 |
| C342 | 282 | Biotin-PEG4 | CA(Kme3)EKNAALSEIIWLPCLTYAQI(Kme2)AFIAALNDDPCQSSEILSEAKELCS | NH2 |
| C343 | 283 | Biotin-PEG4 | CA(Kme3)EKQAALSEIIWLPCLTYAQI(Kme2)AFIAALNDDPCQSSEILSEAKELCS | NH2 |
| C344 | 284 | Biotin-PEG4 | CAREKIAALSEIIWLPNLTYAQI(Kme3)AFIAALNDDPCQSSEILSEAKELNDSQAP | NH2 |
| C345 | 285 | Biotin-PEG4 | CAREKIAALSEIIWLPCLTYAQI(K(Ac))AFIAALNDDPCQSSEILSEAKELCS | NH2 |
| C346 | 286 | Biotin-PEG4 | CAREKIAALSEIIWLPCLTYAQI(K(Ac))AFIAALNDDPCQSAEILSEAKELCS | NH2 |
| C347 | 287 | Biotin-PEG4 | CAREKIAALSEIIWLPCLTYAQI(Kme)AFIAALNDDPCQSAEILAEAKELCS | NH2 |
| C348 | 288 | Biotin-PEG4 | CAREKIAALSEIIWLPCLTYAQI(Kme)AFIAALNDDPCQSAEILSEAQELCS | NH2 |
| C349 | 288 | DOTA-PEG4 | CAREKIAALSEIIWLPCLTYAQI(Kme)AFIAALNDDPCQSAEILSEAQELCS | NH2 |
| C350 | 289 | Biotin-PEG4 | CAREKIAALSEIIWLPCLTYAQI(hGln)AFIAALNDDPCQSSEILSEAKELCS | NH2 |

TABLE 2C-continued

| Additional Exemplary B7-H3 Miniproteins[6] | | | | |
|---|---|---|---|---|
| Compound ID NO[7] | SEQ ID NO[8] | N-Term | Sequence[9] | C-Term |
| C351 | 290 | Biotin-PEG4 | CARE(hGln)IAALSEIIWLPCLTYAQI(Kme)AFIAALNDDPCQSSEILSEAKELCS | NH2 |
| C352 | 291 | Biotin-PEG4 | CAREKIAALSEIIWLPCLTYAQI(Kme)AFIAALNDDPCQSSEILSEA(hGln)ELCS | NH2 |
| C353 | 292 | Biotin-PEG4 | CAREKIAALSEIIWLPCLTYAQI(Kme)AFIAALNDDPCQSSEILSEA(Kme)ELCS | NH2 |
| C354 | 292 | DOTA-PEG4 | CAREKIAALSEIIWLPCLTYAQI(Kme)AFIAALNDDPCQSSEILSEA(Kme)ELCS | NH2 |
| C355 | 293 | Biotin-PEG4 | CAREKIAALSEIIWLPCLTYAQI(Kme)AFIAALNDDPCQSAEILSEA(Kme)(Kme)LCS | NH2 |
| C356 | 294 | Biotin-PEG4 | CAREKIAALSEIIWLPCLTYAQI(Kme)EFIAALNDDPCQSAEILSEAKELCS | NH2 |
| C357 | 295 | Biotin-PEG4 | CAREKIAALSEIIWLPCLTYAQI(Kme)AFIAALNDDPCQSAEILSEA(Kme)ELCS | NH2 |
| C358 | 296 | Biotin-PEG4 | CAREKIAALSEIIWLPCLTYAQI(Kme)EFIAALNDDPCQSANILAEAKELCS | NH2 |
| C359 | 297 | Biotin-PEG4 | CA(Kme3)EKIAALSEIIWLPCLTYAQI(Kme2)AFIAALNDDPCQSAEILSEAKELCS | NH2 |
| C360 | 298 | Biotin-PEG4 | CA(Kme3)EKIAALSEIIWLPCLTYAQI(Kme2)AFIAALNDDPCQSANILSEAKELCS | NH2 |
| C361 | 299 | Biotin-PEG4 | CA(Kme3)EKIAALSEIIWLPCLTYAQI(Kme2)AFIAALNDDPCQSANILAEAKELCS | NH2 |
| C362 | 300 | Biotin-PEG4 | CAREKIAALSEIIWLPCLTYAQI(Kme)AFIAALNDDPCQSANILAEA(Kme)ELCS | NH2 |
| C363 | 301 | Biotin-PEG4 | CAREKIAALSEIIWLPCLTYAQI(Kme)AFIAALNDDPCQSSNILAEA(Kme)ELCS | NH2 |
| C364 | 302 | Biotin-PEG4 | CAREKIAALSEIIWLPCLTYDQI(Kme)AFIAALNDDPCQSSEILSEAKELCS | NH2 |
| C365 | 303 | Biotin-PEG4 | CAREKIAALAEIIWLPCLTYAQI(Kme)AFIAALNDDPCQSSEILSEAKELCS | NH2 |
| C366 | 304 | Biotin-PEG4 | CAREKIAALGEIIWLPCLTYDQI(Kme)AFIAALNDDPCQSSEILSEAKELCS | NH2 |
| C367 | 305 | Biotin-PEG4 | CAREKINALGEIIWLPCLTYDQI(Kme)AFIAALNDDPCQSSEILSEAKELCS | NH2 |
| C368 | 305 | DOTA-PEG4 | CAREKINALGEIIWLPCLTYDQI(Kme)AFIAALNDDPCQSSEILSEAKELCS | NH2 |
| C369 | 305 | In:DOTA-PEG4 | CAREKINALGEIIWLPCLTYDQI(Kme)AFIAALNDDPCQSSEILSEAKELCS | NH2 |
| C370 | 306 | Biotin-PEG4 | CAREKIAALSEIIWLPCLTYAQI(Kme)AFIAKLNDDPCQSSEILSEAKELCS | NH2 |
| C371 | 307 | Biotin-PEG4 | CAREKIAALSEIIWLPCLTYAQI(Kme)AFIA(Kme)LNDDPCQSSEILSEAKELCS | NH2 |
| C372 | 308 | Biotin-PEG4 | CAREKIAALSEIIWLPCLTYAQI(Kme)AFIAQLNDDPCQSSEILSEAKELCS | NH2 |
| C373 | 309 | Biotin-PEG4 | CAREKIAALSEIIWLPCLTYAQI(Kme)AFIAALNDDPCQSAEILSEAKELCS | NH2 |
| C374 | 310 | Biotin-PEG4 | CAREKIAALSEIIWLPCLTYAQI(Kme)AFIAALNDDPCQSANILSEAKELCS | NH2 |
| C375 | 311 | Biotin-PEG4 | CAREKIAALSEIIWLPCLTYAQI(Kme)AFIAALNDDPCQSANILAEAKELCS | NH2 |

TABLE 2C-continued

Additional Exemplary B7-H3 Miniproteins[6]

| Compound ID NO[7] | SEQ ID NO[8] | N-Term | Sequence[9] | C-Term |
|---|---|---|---|---|
| C376 | 312 | Biotin-PEG4 | CAREKIAALSEIIWLPCLTYAQI(Kme)AFIAALNDDPCQSSNILAEAKELCS | NH2 |
| C377 | 313 | Biotin PEG4 | CA(Kme3)EKINALSEIIWLPCLTYAQI(Kme2)AFIAALNDDPCQSSEILSEAKELCS | NH2 |
| C378 | 314 | Biotin-PEG4 | CA(Kme3)EKIAALSEIIWLPCLTYAQI(Kme2)AFIAALNDDPCQSSEILSEAKELCG | NH2 |
| C379 | 315 | Biotin-PEG4 | CA(Kme3)EKIAALSEIIWLPCLTYAQI(Kme2)AFIAALNDDPCQSSEILSEAKELCA | NH2 |
| C380 | 316 | Biotin-PEG4 | CA(Kme3)EKIAALSEIIWLPCLTYAQI(Kme2)AFIAALNDDPCQSSEILSEAKELCQ | NH2 |
| C381 | 317 | Biotin-PEG4 | CA(Kme3)EKIAALSEIIWLPCLTYAQI(Kme2)AFIAALNDDPCQSSEILSEAKELCE | NH2 |
| C382 | 318 | Biotin-PEG4 | CAREKINALSEIIWLPCLTYDQI(Kme)AFIAALNDDPCQSSEILSEAKELCS | NH2 |
| C383 | 319 | Biotin-PEG4 | CAREKINALSEIIWLPCLTYAQI(Kme)AFIAALNDDPCQSSEILSEAKELCS | NH2 |
| C384 | 320 | Biotin-PEG4 | CA(Kme3)EKIAALSEIIWLPCLTYAQI(Kme2)AFIAALNDDPCQYAEILSEAKELCS | NH2 |
| C385 | 321 | Biotin-PEG4 | CAREKINALGEIIWLPCLTYAQI(Kme)AFIAALNDDPCQSSEILSEAKELCS | NH2 |
| C386 | 322 | Biotin-PEG4 | CAREKIAALGEIIWLPCLTYAQI(Kme)AFIAALNDDPCQSSEILSEAKELCS | NH2 |
| C387 | 323 | Biotin-PEG4 | CAREKINALGEIIWLPCLTYDQI(Kme)AFIAALNDDPCQSAEILSEAKELCS | NH2 |
| C388 | 324 | Biotin-PEG4 | CAREKINALGEIIWLPCLTYDQI(Kme)AFIAALNDDPCQSANILSEAKELCS | NH2 |
| C389 | 325 | Biotin-PEG4 | CAREKINALGEIIWLPCLTYDQI(Kme)AFIAALNDDPCQSANILAEAKELCS | NH2 |
| C390 | 326 | Biotin-PEG4 | CA(Kme3)EKIAALSEIIWLPCLTYDQI(Kme2)AFIAALNDDPCQSSEILSEAKELCS | NH2 |
| C391 | 327 | Biotin-PEG4 | CA(Kme3)EKIAALSEIIWLPCLTYNQI(Kme2)AFIAALNDDPCQSSEILSEAKELCS | NH2 |
| C392 | 328 | Biotin-PEG4 | CAREKINALGEIIWLPCLTYDQI(Kme)AFIAALNDDPCQSAEILSEA(Kme)ELCS | NH2 |
| C393 | 329 | Biotin-PEG4 | CAREKINALGEIIWLPCLTYDQI(Kme)AFIAALNDDPCQSANILSEA(Kme)ELCS | NH2 |
| C394 | 330 | Biotin-PEG4 | CAREKINALGEIIWLPCLTYDQI(Kme)AFIAALNDDPCQSANILAEA(Kme)ELCS | NH2 |
| C611 | 330 | DOTA-PEG4 | CAREKINALGEIIWLPCLTYDQI(Kme)AFIAALNDDPCQSANILAEA(Kme)ELCS | NH2 |
| C395 | 331 | Biotin-PEG4 | CA(Kme3)EKIAALSEIIWLPCLTYAQI(Kme)AFIAALNDDPCQSSEILSEAQELCS | NH2 |
| C396 | 332 | Biotin-PEG4 | CA(Kme3)EKIAVLSEIIWLPCLTYAQI(Kme2)AFIAALNDDPCQSSEILSEAKELCS | NH2 |
| C397 | 333 | Biotin-PEG4 | CA(Kme3)EKIAILSEIIWLPCLTYAQI(Kme2)AFIAALNDDPCQSSEILSEAKELCS | NH2 |
| C398 | 334 | Biotin-PEG4 | CA(Kme3)EKIQALSEIIWLPCLTYAQI(Kme2)AFIAALNDDPCQSSEILSEAKELCS | NH2 |
| C399 | 335 | Biotin-PEG4 | CAREKIAALSEIIWLPCLTYAQI(Kme)AFIA(Kme)LNDDPCQSAEILSEAKELCS | NH2 |

TABLE 2C-continued

| Additional Exemplary B7-H3 Miniproteins[6] | | | | |
|---|---|---|---|---|
| Compound ID NO[7] | SEQ ID NO[8] | N-Term | Sequence[9] | C-Term |
| C400 | 336 | Biotin-PEG4 | CAREKIAALSEIIWLPCLTYAQI(Kme)AFIA(Kme)LNDDPCQSANILSEAKELCS | NH2 |
| C401 | 337 | Biotin-PEG4 | CAREKINALGEIIWLPCLTYDQI(Kme)AFIA(Kme)LNDDPCQSSEILSEAKELCS | NH2 |
| C402 | 338 | Biotin-PEG4 | CA(Kme3)EKIAALSEIIWLPCLTYAQI(Kme2)AFIAALNDDPCQSSEILSEA(Kme)ELCS | NH2 |
| C403 | 339 | Biotin-PEG4 | CA(Kme3)EKISALSEIIWLPCLTYAQI(Kme2)AFIAALNDDPCQSSEILSEAKELCS | NH2 |
| C404 | 340 | Biotin-PEG4 | CA(Kme3)EKIYALSEIIWLPCLTYAQI(Kme2)AFIAALNDDPCQSSEILSEAKELCS | NH2 |
| C405 | 341 | Biotin-PEG4 | CA(Kme3)EKIAALSEIIWLPCLTYAQI(Kme2)AFIAALNDDPCQASEILSEAKELCS | NH2 |
| C406 | 342 | Biotin-PEG4 | CA(Kme3)EKIAALSEIIWLPCLTYAQI(Kme2)AFIAALNDDPCQQSEILSEAKELCS | NH2 |
| C407 | 343 | Biotin-PEG4 | CA(Kme3)EKIAALSEIIWLPCLTYAQI(Kme2)AFIAALNDDPCQESEILSEAKELCS | NH2 |
| C408 | 344 | Biotin PEG4 | CA(Kme3)EKIAALSEIIWLPCLTYAQI(Kme2)AFIAALNDDPCQSSKILSEAKELCS | NH2 |
| C409 | 345 | Biotin-PEG4 | CA(Kme3)EKIAALSEIIWLPCLTYAQI(Kme)AFIAALSDDPCQSSEILSEAKELCS | NH2 |
| C410 | 346 | Biotin-PEG4 | CA(Kme3)EKIAALSEIIWLPCLTYAQI(Kme)AFIAALQDDPCQSSEILSEAKELCS | NH2 |
| C411 | 347 | Biotin-PEG4 | CA(Kme3)EKIAALSEIIWLPCLTYAQI(Kme)AFIAALRDDPCQSSEILSEAKELCS | NH2 |
| C412 | 348 | Biotin-PEG4 | CA(Kme3)EKIAALSEIIWLPCLTYAQI(Kme)AFIAALKDDPCQSSEILSEAKELCS | NH2 |
| C413 | 349 | Biotin-PEG4 | CA(Kme3)EKIAALSEIIWLPCLTYAQI(Kme)AFIAALEDDPCQSSEILSEAKELCS | NH2 |
| C414 | 350 | Biotin-PEG4 | CA(Kme3)EKIAALSEIIWLPCLTYAQI(Kme)AFIAALADDPCQSSEILSEAKELCS | NH2 |
| C415 | 351 | Biotin-PEG4 | CA(Kme3)EKIAALSEIIWLPCLTYAQI(Kme)AFIAALIDDPCQSSEILSEAKELCS | NH2 |
| C416 | 352 | Biotin-PEG4 | CA(Kme3)EKIAALSEIIWLPCLTYAQI(Kme2)AFIAALNDDPCQSSEILSEAKELCL | NH2 |
| C417 | 353 | Biotin-PEG4 | CA(Kme3)EKIAALSEIIWLPCLTYAQI(Kme2)AFIAALNDDPCQSSAILSEAKELCS | NH2 |
| C418 | 354 | Biotin-PEG4 | CA(Kme3)EKIAALSEIIWLPCLTYAQI(Kme2)AFIAALNDDPCQSSLILSEAKELCS | NH2 |
| C419 | 355 | Biotin-PEG4 | CA(Kme3)EKIAALSEIIWLPCLTYAQI(Kme2)AFIAALNDDPCQSSYILSEAKELCS | NH2 |
| C420 | 356 | Biotin-PEG4 | CAREKINALGEIIWLPCLTYDQI(Kme)AFI(Kme)ALNDDPCQSANILAEA(Kme)ELCS | NH2 |
| C421 | 357 | Biotin-PEG4 | CARQKINALGEIIWLPCLTYDQI(Kme)AFIAALNDDPCQSANILAEA(Kme)ELCS | NH2 |
| C422 | 358 | Biotin-PEG4 | CAREKINALGEIIWLPCLTYDQI(Kme)AFIAALNADPCQSANILAEA(Kme)ELCS | NH2 |
| C423 | 359 | Biotin-PEG4 | CAREKINALGEIIWLPCLTYDQI(Kme)AFIAALNFDPCQSANILAEA(Kme)ELCS | NH2 |
| C424 | 360 | Biotin-PEG4 | CA(Kme3)EKIAALSEIIWLPCLTYAQI(Kme)SFIAALNDDPCQSSEILSEAKELCS | NH2 |

TABLE 2C-continued

| Additional Exemplary B7-H3 Miniproteins[6] | | | | |
|---|---|---|---|---|
| Compound ID NO[7] | SEQ ID NO[8] | N-Term | Sequence[9] | C-Term |
| C425 | 361 | Biotin-PEG4 | CA(Kme3)EKIAALSEIIWLPCLTYAQI(Kme)YFIAALNDDPCQSSEILSEAKELCS | NH2 |
| C426 | 362 | Biotin-PEG4 | CA(Kme3)EKIAALSEIIWLPCLTYAQI(Kme)QFIAALNDDPCQSSEILSEAKELCS | NH2 |
| C427 | 363 | Biotin-PEG4 | CA(Kme3)EKIAALSEIIWLPCLTYAQI(Kme)LFIAALNDDPCQSSEILSEAKELCS | NH2 |
| C428 | 364 | Biotin-PEG4 | CA(Kme3)EKIAALSEIIWLPCLTYAQI(Kme)KFIAALNDDPCQSSEILSEAKELCS | NH2 |
| C429 | 365 | Biotin-PEG4 | CA(Kme3)EKIAALSEIIWLPCLTYAQI(Kme)K(me)FIAALNDDPCQSSEILSEAKELCS | NH2 |
| C430 | 366 | Biotin-PEG4 | CAREKINALGEIIWLPCLTYDQI(Kme2)AFIAALNDDPCQSANILAEA(Kme)ELCS | NH2 |
| C431 | 367 | Biotin-PEG4 | CAREKINALGEIIWLPCLTYDQI(Kme2)AFIAALNDDPCQSAEILSEA(Kme)ELCS | NH2 |
| C432 | 368 | Biotin-PEG4 | CAREKIEALGEIIWLPCLTYDQI(Kme)AFIAALNDDPCQSANILAEA(Kme)ELCS | NH2 |
| C433 | 369 | Biotin-PEG4 | CAREKIKALGEIIWLPCLTYDQI(Kme)AFIAALNDDPCQSANILAEA(Kme)ELCS | NH2 |
| C434 | 370 | Biotin-PEG4 | CA(Kme3)EKIAALSEIIWLPCLTYAQI(Kme)AFIQALNDDPCQSSEILSEAKELCS | NH2 |
| C435 | 371 | Biotin-PEG4 | CA(Kme3)EKIAALSEIIWLPCLTYAQI(Kme)AFILALNDDPCQSSEILSEAKELCS | NH2 |
| C436 | 372 | Biotin-PEG4 | CA(Kme3)EKIAALSEIIWLPCLTYAQI(Kme)AFISALNDDPCQSSEILSEAKELCS | NH2 |
| C437 | 373 | Biotin-PEG4 | CA(Kme3)EKIAALSEIIWLPCLTYAQI(Kme)AFIKALNDDPCQSSEILSEAKELCS | NH2 |
| C438 | 374 | Biotin-PEG4 | CA(Kme3)EKIAALSEIIWLPCLTYAQI(Kme)AFI(Kme)ALNDDPCQSSEILSEAKELCS | NH2 |
| C439 | 375 | Biotin-PEG4 | CAREKINALGEIIWLPCLTYDQI(Kme)AFIAALNDDPCQSANILAEAQELCS | NH2 |
| C440 | 376 | Biotin-PEG4 | CAREKINALGEIIWLPCLTYDQI(Kme)AFIAALNDDPCQSAEILAEAQELCS | NH2 |
| C441 | 377 | Biotin-PEG4 | CAREKINALGEIIWLPCLTYDQI(Kme)AFIAALNDDPCQSAEILSEAQELCS | NH2 |
| C442 | 378 | Biotin-PEG4 | CARGKINALGEIIWLPCLTYDQI(Kme)AFIAALNDDPCQSANILAEA(Kme)ELCS | NH2 |
| C443 | 379 | Biotin-PEG4 | CARHKINALGEIIWLPCLTYDQI(Kme)AFIAALNDDPCQSANILAEA(Kme)ELCS | NH2 |
| C444 | 380 | Biotin-PEG4 | CAREKINALGEIIWLPCLTYDQI(Kme)AFIAALNDDPCQSANILAEARELCS | NH2 |
| C445 | 381 | Biotin-PEG4 | CAREKINALLEIIWLPCLTYDQI(Kme)AFIAALNDDPCQSANILAEA(Kme)ELCS | NH2 |
| C446 | 382 | Biotin-PEG4 | CAREKINALYEIIWLPCLTYDQI(Kme)AFIAALNDDPCQSANILAEA(Kme)ELCS | NH2 |
| C447 | 383 | Biotin-PEG4 | CA(Kme3)EKINALGEIIWLPCLTYDQI(Kme2)AFIAALNDDPCQSANILAEA(Kme)ELCS | NH2 |
| C448 | 384 | Biotin-PEG4 | CA(Kme3)EKINALGEIIWLPCLTYDQI(Kme2)AFIAALNDDPCQSAEILSEA(Kme)ELCS | NH2 |
| C449 | 385 | Biotin-PEG4 | CA(Kme3)EKIAALSEIIWLPCLTYAQI(Kme2)AFIAALNDDPCQSSEILSEAQELCS | NH2 |

TABLE 2C-continued

Additional Exemplary B7-H3 Miniproteins[6]

| Compound ID NO[7] | SEQ ID NO[8] | N-Term | Sequence[9] | C-Term |
|---|---|---|---|---|
| C450 | 386 | Biotin-PEG4 | CAREKINALGEIIWLPCLTYDQI(Kme)AFIAALNRDPCQSANILAEA(Kme)ELCS | NH2 |
| C451 | 387 | Biotin-PEG4 | CAREKINALGEIIWLPCLTYDQI(Kme)AFIAALNHDPCQSANILAEA(Kme)ELCS | NH2 |
| C452 | 388 | Biotin-PEG4 | CA(Kme3)EKIAALSEIIWLPCLTYAQI(Kme)AFIAQLNDDPCQSSEILSEAKELCS | NH2 |
| C453 | 389 | Biotin-PEG4 | CA(Kme3)EKIAALSEIIWLPCLTYAQI(Kme)AFIARLNDDPCQSSEILSEAKELCS | NH2 |
| C454 | 390 | Biotin-PEG4 | CA(Kme3)EKIAALSEIIWLPCLTYAQI(Kme)AFIAELNDDPCQSSEILSEAKELCS | NH2 |
| C455 | 391 | Biotin-PEG4 | CA(Kme3)EKIAALSEIIWLPCLTYAQI(Kme)AFIAKLNDDPCQSSEILSEAKELCS | NH2 |
| C456 | 392 | Biotin-PEG4 | CA(Kme3)EKIAALSEIIWLPCLTYAQI(Kme)AFIA(Kme)LNDDPCQSSEILSEAKELCS | NH2 |
| C457 | 393 | Biotin-PEG4 | CA(Kme3)EKIAALKEIIWLPCLTYAQI(Kme2)AFIAALNDDPCQSSEILSEAKELCS | NH2 |
| C458 | 394 | Biotin-PEG4 | CAREKINALGEIIWLPCLTYDQI(Kme)AFIA(Kme)LNDDPCQSSEILSEAQELCS | NH2 |
| C459 | 395 | Biotin-PEG4 | CA(Kme3)EKINALGEIIWLPCLTYDQI(Kme)AFIAALNDDPCQSANILAEA(Kme)ELCS | NH2 |
| C460 | 396 | Biotin-PEG4 | CA(Kme3)EKIAALSEIIWLPCLTYAQI(Kme)AFIAALNDDPCQSSEILSEAKELCS | NH2 |
| C461 | 397 | Biotin-PEG4 | CA(Kme3)EKIAALSEIIWLPCLTYAQI(Kme)AFIAALNSDPCQSSEILSEAKELCS | NH2 |
| C462 | 398 | Biotin-PEG4 | CA(Kme3)EKIAALSEIIWLPCLTYAQI(Kme)AFIAALNFDPCQSSEILSEAKELCS | NH2 |
| C463 | 399 | Biotin-PEG4 | CA(Kme3)EKIAALSEIIWLPCLTYAQI(Kme)AFIAALNADPCQSSEILSEAKELCS | NH2 |
| C464 | 400 | Biotin-PEG4 | CA(Kme3)EKIAALSEIIWLPCLTYAQI(Kme)AFIAALNKDPCQSSEILSEAKELCS | NH2 |
| C465 | 401 | Biotin-PEG4 | CA(Kme3)EKIAALSEIIWLPCLTYAQI(Kme)AFIAALN(Kme)DPCQSSEILSEAKELCS | NH2 |
| C466 | 402 | Biotin-PEG4 | CAREKINALGEIIWLPCLTYDQI(Kme)AFIAALNDDPCQSSEILSEA(Kme)ELCS | NH2 |
| C467 | 402 | DOTA-PEG4 | CAREKINALGEIIWLPCLTYDQI(Kme)AFIAALNDDPCQSSEILSEA(Kme)ELCS | NH2 |
| C468 | 402 | In:DOTA-PEG4 | CAREKINALGEIIWLPCLTYDQI(Kme)AFIAALNDDPCQSSEILSEA(Kme)ELCS | NH2 |
| C469 | 403 | Biotin-PEG4 | CA(Kme3)EKIAALSEIIWLPCLTYAQI(Kme)AFIAALNRDPCQSSEILSEAKELCS | NH2 |
| C470 | 404 | Biotin-PEG4 | CAREKINALGEIIWLPCLTYDQI(Kme)AFIA(Kme)LNDDPCQSAEILSEA(Kme)ELCS | NH2 |
| C471 | 405 | Biotin-PEG4 | CAREKINALGEIIWLPCLTYDQI(Kme)AFIA(Kme)LNDDPCQSANILSEA(Kme)ELCS | NH2 |
| C472 | 406 | Biotin-PEG4 | CAREKINALGEIIWLPCLTYDQI(Kme)AFIA(Kme)LNDDPCQSANILAEA(Kme)ELCS | NH2 |
| C473 | 407 | Biotin-PEG4 | CAREKINALGEIIWLPCLTYDQI(Kme)AFIA(Kme)LNDDPCQSAEILSEAQELCS | NH2 |
| C474 | 408 | Biotin-PEG4 | CAREKINALGEIIWLPCLTYDQI(Kme)AFIA(Kme)LNDDPCQSANILSEAQELCS | NH2 |

TABLE 2C-continued

Additional Exemplary B7-H3 Miniproteins[6]

| Compound ID NO[7] | SEQ ID NO[8] | N-Term | Sequence[9] | C-Term |
|---|---|---|---|---|
| C475 | 409 | Biotin-PEG4 | CAREKINALGEIIWLPCLTYDQI(Kme)AFIA(Kme)LNDDPCQSANILAEAQELCS | NH2 |
| C476 | 410 | Biotin-PEG4 | CASEKIAALSEIIWLPCLTYAQI(Kme2)AFIAALNDDPCQSSEILSEAKELCS | NH2 |
| C477 | 411 | Biotin-PEG4 | CAHEKIAALSEIIWLPCLTYAQI(Kme2)AFIAALNDDPCQSSEILSEAKELCS | NH2 |
| C478 | 412 | Biotin-PEG4 | CAYEKIAALSEIIWLPCLTYAQI(Kme2)AFIAALNDDPCQSSEILSEAKELCS | NH2 |
| C479 | 413 | Biotin-PEG4 | CANEKIAALSEIIWLPCLTYAQI(Kme2)AFIAALNDDPCQSSEILSEAKELCS | NH2 |
| C480 | 414 | Biotin-PEG4 | CA(Kme3)EKINALGEIIWLPCLTYDQI(Kme)AFIA(Kme)LNDDPCQSSEILSEAKELCS | NH2 |
| C481 | 415 | Biotin-PEG4 | CA(Kme3)EKINALGEIIWLPCLTYDQI(Kme)AFIA(Kme)LNDDPCQSSEILSEA(Kme)ELCS | NH2 |
| C482 | 416 | Biotin-PEG4 | CA(Kme3)EKINALGEIIWLPCLTYDQI(Kme)AFIA(Kme)LNDDPCQSSEILSEAQELCS | NH2 |
| C483 | 417 | Biotin-PEG4 | CA(Kme3)EKINALGEIIWLPCLTYDQI(Kme)AFIAALNDDPCQSSEILSEA(Kme)ELCS | NH2 |
| C484 | 418 | Biotin-PEG4 | CA(Kme3)EKINALGEIIWLPCLTYDQI(Kme)AFIAALNDDPCQSSEILSEAQELCS | NH2 |
| C485 | 419 | Biotin-PEG4 | CA(Kme3)EKIAALSEIIWLPCLTYAQI(Kme)AFIAALNDSPCQSSEILSEAKELCS | NH2 |
| C486 | 420 | Biotin-PEG4 | CA(Kme3)EKIAALSEIIWLPCLTYAQI(Kme)AFIAALNDYPCQSSEILSEAKELCS | NH2 |
| C487 | 421 | Biotin-PEG4 | CA(Kme3)EKIAALSEIIWLPCLTYAQI(Kme)AFIAALNDAPCQSSEILSEAKELCS | NH2 |
| C488 | 422 | Biotin-PEG4 | CA(Kme3)EKIAALSEIIWLPCLTYAQI(Kme)AFIAALNDQPCQSSEILSEAKELCS | NH2 |
| C489 | 423 | Biotin-PEG4 | CA(Kme3)EKIAALSEIIWLPCLTYAQI(Kme)AFIAALNDLPCQSSEILSEAKELCS | NH2 |
| C490 | 424 | Biotin-PEG4 | CA(Kme3)EKIAALSEIIWLPCLTYAQI(Kme)AFIAALNDRPCQSSEILSEAKELCS | NH2 |
| C491 | 425 | Biotin-PEG4 | CA(Rme2s)EKINALGEIIWLPCLTYDQI(Kme)AFIA(Kme)LNDDPCQSSEILSEA(Kme)ELCS | NH2 |
| C492 | 426 | Biotin-PEG4 | CAREKINALGEIIWLPCLTYDQI(Kme)AFIA(Kme)LNDDPCQSSEILSEA(Kme)ELCS | NH2 |
| C493 | 426 | DOTA-PEG4 | CAREKINALGEIIWLPCLTYDQI(Kme)AFIA(Kme)LNDDPCQSSEILSEA(Kme)ELCS | NH2 |
| C494 | 426 | In:DOTA-PEG4 | CAREKINALGEIIWLPCLTYDQI(Kme)AFIA(Kme)LNDDPCQSSEILSEA(Kme)ELCS | NH2 |
| C495 | 427 | Biotin-PEG4 | CA(Kme3)EKIAALSEIIWLPCLTYAQI(Kme)AFIAALNDDPCQSSEILSEAKEQCS | NH2 |
| C496 | 428 | Biotin-PEG4 | CA(Kme3)EKIAALSEIIWLPCLTYAQI(Kme)AFIAALNDDPCQSSEILSEAKEECS | NH2 |
| C497 | 429 | Biotin-PEG4 | CA(Kme3)EKIAALSEIIWLPCLTYAQI(Kme)AFIAALNDDPCQSSEILSEAKESCS | NH2 |
| C498 | 430 | Biotin-PEG4 | CA(Kme3)EKIAALSEIIWLPCLTYAQI(Kme)AFIAALNDDPCQSSEILSEAKEACS | NH2 |
| C499 | 431 | Biotin-PEG4 | CA(Kme3)EKIAALSEIIWLPCLTYAQI(Kme)AFIAALNDDPCQSSEILSEAKENCS | NH2 |

TABLE 2C-continued

Additional Exemplary B7-H3 Miniproteins[6]

| Compound ID NO[7] | SEQ ID NO[8] | N-Term | Sequence[9] | C-Term |
|---|---|---|---|---|
| C500 | 432 | Biotin-PEG4 | CA(Kme3)EKIAALSEIIWLPCLTYAQI(Kme)AFIAALNDDPCQSSEILSEAKEFCS | NH2 |
| C501 | 433 | Biotin-PEG4 | CAREKINALGEIIWLPCLTYDQI(Kme)AFIA(Kme)LNRDPCQSSEILSEA(Kme)ELCS | NH2 |
| C502 | 434 | Biotin-PEG4 | CAREKINALGEIIWLPCLTYDQI(Kme)AFIAALNADPCQSSEILSEA(Kme)ELCS | NH2 |
| C503 | 435 | Biotin-PEG4 | CA(Kme3)QKIAALSEIIWLPCLTYAQI(Kme)AFIAALNDDPCQSSEILSEAKELCS | NH2 |
| C504 | 436 | Biotin-PEG4 | CA(Kme3)AKIAALSEIIWLPCLTYAQI(Kme)AFIAALNDDPCQSSEILSEAKELCS | NH2 |
| C505 | 437 | Biotin-PEG4 | CAREKINALGEIIWLPCLTYDQI(Kme2)AFIAALNDDPCQSSEILSEA(Kme)ELCS | NH2 |
| C506 | 438 | Biotin-PEG4 | CAREKINALGEIIWLPCLTYDQI(Kme2)AFIAALNDDPCQSSEILSEAQELCS | NH2 |
| C507 | 439 | Biotin-PEG4 | CA(Kme3)EKINALGEIIWLPCLTYDQI(Kme2)AFIAALNDDPCQSSEILSEA(Kme)ELCS | NH2 |
| C508 | 440 | Biotin-PEG4 | CAREKINALGEIIWLPCLTYEQI(Kme)AFIAALNDDPCQSANILAEA(Kme)ELCS | NH2 |
| C509 | 441 | Biotin-PEG4 | CAREKINALGEIIWLPCLTYQQI(Kme)AFIAALNDDPCQSANILAEA(Kme)ELCS | NH2 |
| C510 | 442 | Biotin-PEG4 | CAREKINALGEIIWLPCLTYLQI(Kme)AFIAALNDDPCQSANILAEA(Kme)ELCS | NH2 |
| C511 | 443 | Biotin-PEG4 | CAREKINALGEIIWLPCLTYYQI(Kme)AFIAALNDDPCQSANILAEA(Kme)ELCS | NH2 |
| C512 | 444 | Biotin-PEG4 | CAREKINALGEIIWLPCLTYKQI(Kme)AFIAALNDDPCQSANILAEA(Kme)ELCS | NH2 |
| C513 | 445 | Biotin-PEG4 | CA(Kme3)EKIAALSEIIWLPCLTYAQI(Kme)YFI(Kme)ALNDDPCQSSEILSEA(Kme)ELCS | NH2 |
| C514 | 446 | Biotin-PEG4 | CA(Rme2a)EKINALGEIIWLPCLTYDQI(Kme)AFIA(Kme)LNDDPCQSSEILSEA(Kme)ELCS | NH2 |
| C515 | 447 | Biotin-PEG4 | CAREKINALGEIIWLPCLTYDQI(Kme)AFIA(Kme)LNADPCQSSEILSEA(Kme)ELCS | NH2 |
| C516 | 448 | Biotin-PEG4 | CAREKINALGEIIWLPCLTYDQI(Kme)AFIAALNRDPCQSSEILSEA(Kme)ELCS | NH2 |
| C517 | 449 | Biotin-PEG4 | CAREKINALGEIIWLPCLTYDQI(Kme)AFIARLNDDPCQSSEILSEA(Kme)ELCS | NH2 |
| C518 | 450 | Biotin-PEG4 | CAREKINALGEIIWLPCLTYDQI(Kme)AFIA(Kme)LNDDPCQSSEILSEA(Kme3)ELCS | NH2 |
| C519 | 451 | Biotin-PEG4 | CAREKINALGEIIWLPCLTYDQI(Kme)AFIAALNDDPCQSSEILSEA(Kme3)ELCS | NH2 |
| C520 | 452 | Biotin-PEG4 | CA(Kme3)EKIAALSEIIWLPCLKYAQI(Kme)AFIAALNDDPCQSSEILSEA(Kme)ELCS | NH2 |
| C521 | 453 | Biotin-PEG4 | CA(Kme3)EKIAALSEIIWLPCL(Kme)YAQI(Kme)AFIAALNDDPCQSSEILSEA(Kme)ELCS | NH2 |
| C522 | 454 | Biotin-PEG4 | CA(Kme3)EKIAALSSIIWLPCLTYAQI(Kme)AFIAALNDDPCQSSEILSEA(Kme)ELCS | NH2 |
| C523 | 455 | Biotin-PEG4 | CA(Kme3)EKIAALSQIIWLPCLTYAQI(Kme)AFIAALNDDPCQSSEILSEA(Kme)ELCS | NH2 |
| C524 | 456 | Biotin-PEG4 | CA(Kme3)EKIAALSVIIWLPCLTYAQI(Kme)AFIAALNDDPCQSSEILSEA(Kme)ELCS | NH2 |

TABLE 2C-continued

Additional Exemplary B7-H3 Miniproteins[6]

| Compound ID NO[7] | SEQ ID NO[8] | N-Term | Sequence[9] | C-Term |
|---|---|---|---|---|
| C525 | 457 | Biotin-PEG4 | CA(Kme3)EKIAALSEIIWLPCLTYAQI(Kme)YFIA(Kme)LNDDPCQSSEILSEA(Kme)ELCS | NH2 |
| C526 | 458 | Biotin-PEG4 | CA(Kme3)EKIAALSEIIWLPCLTYAQI(Kme)YFIAALN(Kme)DPCQSSEILSEA(Kme)ELCS | NH2 |
| C527 | 459 | Biotin-PEG4 | CA(Kme3)EKIAALSEIIWLPCLSYAQI(Kme)AFIAALNDDPCQSSEILSEA(Kme)ELCS | NH2 |
| C528 | 460 | Biotin-PEG4 | CA(Kme3)EKIAALSEIIWLPCLTYAQI(Kme)AFI(Kme)(Kme)LNDDPCQSSEILSEA(Kme)ELCS | NH2 |
| C529 | 461 | Biotin-PEG4 | CA(Kme3)EKIAALSEIIWLPCLTYAQI(Kme)AFI(Kme)ALN(Kme)DPCQSSEILSEA(Kme)ELCS | NH2 |
| C530 | 462 | Biotin-PEG4 | CA(Kme3)EKIAALSEIIWLPCLTYAQI(Kme)AFIARLN(Kme)DPCQSSEILSEA(Kme)ELCS | NH2 |
| C531 | 463 | Biotin-PEG4 | CA(Kme3)EKIAALSYIIWLPCLTYAQI(Kme)AFIAALNDDPCQSSEILSEA(Kme)ELCS | NH2 |
| C532 | 464 | Biotin-PEG4 | CA(Kme3)EKIAALSKIIWLPCLTYAQI(Kme)AFIAALNDDPCQSSEILSEA(Kme)ELCS | NH2 |
| C533 | 465 | Biotin-PEG4 | CA(Kme3)EKIAALSEIIWLPCLTYAQI(Kme2)AFIAALNDDPCQSSEILSEA(Kme3)ELCS | NH2 |
| C534 | 466 | Biotin-PEG4 | CA(Kme3)EKIAALSEIIWLPCLTYAQI(Kme2)AFI(Kme)ALNDDPCQSSEILSEA(Kme)ELCS | NH2 |
| C535 | 467 | Biotin-PEG4 | CA(Kme3)EKIAALSEIIWLPCLTYAQI(Kme2)AFI(Kme)RLNDDPCQSSEILSEA(Kme)ELCS | NH2 |
| C536 | 468 | Biotin-PEG4 | CA(Kme3)EKIAALSEIIWLPCLTYAQI(Kme2)AFI(Kme)(Kme)LNDDPCQSSEILSEA(Kme)ELCS | NH2 |
| C537 | 469 | Biotin-PEG4 | CA(Kme3)EKIAALSEIIWLPCLTYAQI(Kme2)AFI(Kme)(Cit)LNDDPCQSSEILSEA(Kme)ELCS | NH2 |
| C538 | 470 | Biotin-PEG4 | CA(Kme3)EKIAALSEIIWLPCLTYAQI(Kme2)AFI(Kme)ALN(Kme)DPCQSSEILSEA(Kme)ELCS | NH2 |
| C539 | 471 | Biotin-PEG4 | CA(Kme3)EKIAALSEIIWLPCLTYAQI(Kme2)AFIARLNDDPCQSSEILSEA(Kme)ELCS | NH2 |
| C540 | 472 | Biotin-PEG4 | CA(Kme3)EKIAALSEIIWLPCLTYAQI(Kme2)AFIA(Cit)LNDDPCQSSEILSEA(Kme)ELCS | NH2 |
| C541 | 473 | Biotin-PEG4 | CA(Kme3)EKIAALSEIIWLPCLTYAQI(Kme2)SFI(Kme)ALNDDPCQSSEILSEA(Kme)ELCS | NH2 |
| C542 | 474 | Biotin-PEG4 | CA(Kme3)EKIAALSEIIWLPCLTYAQI(Kme2)EFIAALNDDPCQSSEILSEA(Kme)ELCS | NH2 |
| C543 | 475 | Biotin-PEG4 | CA(Kme3)EKIAALSEIIWLPCLTYAQI(Kme2)EFI(Kme)ALNDDPCQSSEILSEA(Kme)ELCS | NH2 |
| C544 | 476 | Biotin-PEG4 | CA(Kme3)EKIAALSEIIWLPCLTYAQI(Kme2)AFI(Cit)ALNDDPCQSSEILSEA(Kme)ELCS | NH2 |
| C545 | 477 | Biotin-PEG4 | CA(Kme3)EKIAALSEIIWLPCLTYAQI(Kme2)(Cit)FIAALNDDPCQSSEILSEA(Kme)ELCS | NH2 |
| C546 | 478 | Biotin-PEG4 | CA(Kme3)EKIAALSEIIWLPCLTYAQI(Kme)YFIAALNDDPCQSSEILSEA(Kme)ELCS | NH2 |
| C547 | 479 | Biotin-PEG4 | CA(Kme3)HKIAALSEIIWLPCLTYAQI(Kme)AFIAALNDDPCQSSEILSEAKELCS | NH2 |
| C548 | 480 | Biotin-PEG4 | CA(Kme3)VKIAALSEIIWLPCLTYAQI(Kme)AFIAALNDDPCQSSEILSEAKELCS | NH2 |

TABLE 2C-continued

| Additional Exemplary B7-H3 Miniproteins[6] | | | | |
|---|---|---|---|---|
| Compound ID NO[7] | SEQ ID NO[8] | N-Term | Sequence[9] | C-Term |
| C549 | 481 | Biotin-PEG4 | CA(Kme3)YKIAALSEIIWLPCLTYAQI(Kme)AFIAALNDDPCQSSEILSEAKELCS | NH2 |
| C550 | 482 | Biotin-PEG4 | CA(Kme3)EKIAALSEIIWLPCLTYAQI(Kme)AFIAALNDDPCDSSEILSEA(Kme)ELCS | NH2 |
| C551 | 483 | Biotin-PEG4 | CA(Kme3)E(Kme)IAALSEIIWLPCLTYAQI(Kme2)AFIAALNDDPCQSSEILSEA(Kme)ELCS | NH2 |
| C552 | 484 | Biotin-PEG4 | CA(Kme3)IKIAALSEIIWLPCLTYAQI(Kme)AFIAALNDDPCQSSEILSEAKELCS | NH2 |
| C553 | 485 | Biotin-PEG4 | CA(Kme3)EKIAALSEIIWLPCLTYAQI(Kme)AFIAALNDDPCSSSEILSEA(Kme)ELCS | NH2 |
| C554 | 486 | Biotin-PEG4 | CA(Kme3)EKIAALSEIIWLPCLTYAQI(Kme)AFIAALNDDPCYSSEILSEA(Kme)ELCS | NH2 |
| C555 | 487 | Biotin-PEG4 | CA(Kme3)EKIAALSEIIWLPCLTYAQI(Kme)AFIAALNDDPCISSEILSEA(Kme)ELCS | NH2 |
| C556 | 488 | Biotin-PEG4 | CA(Kme3)EKIAALSEIIWLPCLTYAQI(Kme)AFIAALNDDPCRSSEILSEA(Kme)ELCS | NH2 |
| C557 | 489 | Biotin-PEG4 | CA(Kme3)EKINALGEIIWLPCLTYDQI(Kme)AFIARLNDDPCQSSEILSEA(Kme)ELCS | NH2 |
| C558 | 490 | Biotin-PEG4 | CA(Kme3)EKIAALSEIIWLPCLTYAQI(Kme)AFIAALNDDPCQSSEILSVA(Kme)ELCS | NH2 |
| C559 | 491 | Biotin-PEG4 | CA(Kme3)EKIAALSEIIWLPCLTYAQI(Kme)AFIAALNDDPCQSSEILSYA(Kme)ELCS | NH2 |
| C560 | 492 | Biotin-PEG4 | CA(Kme3)EKIAALSEIIWLPCLTYAQI(Kme)AFIAALNDDPCQSSEILSHA(Kme)ELCS | NH2 |
| C561 | 493 | Biotin-PEG4 | CA(Kme3)EKIAALSEIIWLPCLTYAQI(Kme)AFIAALNDDPCQSSEILSRA(Kme)ELCS | NH2 |
| C562 | 494 | Biotin-PEG4 | CA(Kme3)EKIAALSEIIWLPCLTYAQI(Kme)AFIAALNDDPCQSSEILSKA(Kme)ELCS | NH2 |
| C563 | 495 | Biotin-PEG4 | CA(Kme3)EKIAALSEIIWLPCLTYAQI(Kme)AFIAALNDDPCQSSEILS(Kme)A(Kme)ELCS | NH2 |
| C564 | 496 | Biotin-PEG4 | CA(Kme3)EKIAALSEIIWLPCLTYAQI(Kme)YFIARLNDDPCQSSEILSEA(Kme)ELCS | NH2 |
| C565 | 497 | Biotin-PEG4 | CA(Kme3)EKIAALSEIIWLPCLTYAQI(Kme)AFI(Kme)RLNDDPCQSSEILSEA(Kme)ELCS | NH2 |
| C566 | 498 | Biotin-PEG4 | CA(Kme3)EKIAALSEIIWLPCLTYAQI(Kme2)QFI(Kme)ALNDDPCQSSEILSEA(Kme)ELCS | NH2 |
| C567 | 499 | Biotin-PEG4 | CAREKINALGEIIWLPCLTYDQI(Kme)AFIA(Kme)LNDDPCQSSEILSEARELCS | NH2 |
| C568 | 500 | Biotin-PEG4 | CAREKINALGEIIWLPCLTYDQI(Kme)AFIA(Kme)LNDDPCQSSEILSEA(hArg)ELCS | NH2 |
| C569 | 501 | Biotin-PEG4 | CAREKINALGEIIWLPCLTYDQI(Kme)AFIA(Kme)LNDDPCQSSEILSEA(Cit)ELCS | NH2 |
| C570 | 502 | Biotin-PEG4 | CAREKINALGEIIWLPCLTYDQI(Kme2)AFIA(Kme)LNDDPCQSSEILSEAKELCS | NH2 |
| C571 | 503 | Biotin-PEG4 | CAREKINALGEIIWLPCLTYDQI(Kme2)AFIA(Kme)LNDDPCQSSEILSEA(Kme)ELCS | NH2 |
| C572 | 504 | Biotin-PEG4 | CAREKINALGEIIWLPCLTYDQI(Kme2)AFIA(Kme)LNDDPCQSSEILSEAQELCS | NH2 |
| C573 | 505 | Biotin-PEG4 | CA(Kme3)EKINALGEIIWLPCLTYDQI(Kme2)AFIA(Kme)LNDDPCQSSEILSEAKELCS | NH2 |

TABLE 2C-continued

Additional Exemplary B7-H3 Miniproteins[6]

| Compound ID NO[7] | SEQ ID NO[8] | N-Term | Sequence[9] | C-Term |
|---|---|---|---|---|
| C574 | 506 | Biotin-PEG4 | CA(Kme3)EKINALGEIIWLPCLTYDQI(Kme2)AFIA(Kme)LNDDPCQSSEILSEA(Kme)ELCS | NH2 |
| C575 | 507 | Biotin-PEG4 | CA(Kme3)EKINALGEIIWLPCLTYDQI(Kme2)AFIA(Kme)LNDDPCQSSEILSEAQELCS | NH2 |
| C576 | 508 | Biotin-PEG4 | CA(Kme3)EKINALGEIIWLPCLTYDQI(Kme2)AFIAALNDDPCQSSEILSEAQELCS | NH2 |
| C577 | 509 | Biotin-PEG4 | CA(Kme3)EKIAALSEIIWVPCLTYAQI(Kme)AFIAALNDDPCQSSEILSEA(Kme)ELCS | NH2 |
| C578 | 510 | Biotin-PEG4 | CA(Kme3)EKIAALSEIIWIPCLTYAQI(Kme)AFIAALNDDPCQSSEILSEA(Kme)ELCS | NH2 |
| C579 | 511 | Biotin-PEG4 | CA(Kme3)EKIAALSEIIWWPCLTYAQI(Kme)AFIAALNDDPCQSSEILSEA(Kme)ELCS | NH2 |
| C580 | 512 | Biotin-PEG4 | CA(Kme3)EKIAALSEIIWRPCLTYAQI(Kme)AFIAALNDDPCQSSEILSEA(Kme)ELCS | NH2 |
| C581 | 513 | Biotin-PEG4 | CAREKINALGEIIWLPCLTYDQI(Kme)AFIA(Kme)LNDDPCQSSEILSEA(Kme)QLCS | NH2 |
| C582 | 514 | Biotin-PEG4 | CAREKINALGEIIWLPCLTYDQI(Kme)AFIA(Kme)LNDDPCQSSEILSEA(Kme)SLCS | NH2 |
| C583 | 515 | Biotin-PEG4 | CAREKINALGEIIWLPCLTYDQI(Kme)AFIA(Kme)LNDDPCQSSEILSEA(Kme)ALCS | NH2 |
| C584 | 516 | Biotin-PEG4 | CA(Cit)EKIAALSEIIWLPCLTYAQI(Kme)AFIARLNDDPCQSAEILSEA(Kme)ELCS | NH2 |
| C585 | 517 | Biotin-PEG4 | CA(Rme2s)EKIAALSEIIWLPCLTYAQI(Kme)AFIARLNDDPCQSAEILSEA(Kme)ELCS | NH2 |
| C586 | 518 | Biotin-PEG4 | CA(Kme3)EKIAALSEIIWLPCLTYAQI(Kme2)AFI(Kme)ALNDDPCQSSEILSEA(Kme3)ELCS | NH2 |
| C587 | 519 | Biotin-PEG4 | CA(Kme3)EKIAALSEIIWLPCLTYAQI(Kme2)AFI(Kme)(Kme)LNDDPCQSSEILSEA(Kme3)ELCS | NH2 |
| C588 | 520 | Biotin-PEG4 | CA(Kme3)EKIAALSEIIWLPCLTYAQI(Kme2)AFIA(Kme)LNDDPCQSSEILSEA(Kme3)ELCS | NH2 |
| C589 | 521 | Biotin-PEG4 | CA(Kme3)EKIAALSEIIWLPCLTYAQI(Kme2)AFIAALN(Kme)DPCQSSEILSEA(Kme3)ELCS | NH2 |
| C590 | 522 | Biotin-PEG4 | CA(Kme3)EKIAALSEIIWLPCLTYAQI(Kme2)AFIA(Cit)LNDDPCQSSEILSEA(Kme3)ELCS | NH2 |
| C591 | 523 | Biotin-PEG4 | CA(Kme3)EKIAALSEIIWLPCLTYAQI(Kme2)AFIARLNDDPCQSSEILSEA(Kme3)ELCS | NH2 |
| C592 | 524 | Biotin-PEG4 | CAREKIAALSEIIWLPCLTYAQI(Kme)AFIAALNADPCQSAEILSEAKELCS | NH2 |
| C593 | 525 | Biotin-PEG4 | CA(Rme2s)EKIAALSEIIWLPCLTYAQI(Kme)AFIAALNADPCQSAEILSEAKELCS | NH2 |
| C594 | 526 | Biotin-PEG4 | CA(Kme3)EKIAALSEIIWLPCLTYAQI(Kme)AFIA(Cit)LN(Kme)DPCQSSEILSEA(Kme)ELCS | NH2 |
| C595 | 527 | Biotin-PEG4 | CA(Kme3)EKIAALSEIIWLPCLTYAQI(Kme)AFIARLN(Kme)DPCQSSEILSEA(Kme3)ELCS | NH2 |
| C596 | 528 | Biotin-PEG4 | CA(Kme3)EKIAALSEIIWLPCLNYAQI(Kme)AFI(Kme)ALNDDPCQSSEILSEA(Kme)ELCS | NH2 |
| C597 | 529 | Biotin-PEG4 | CA(Kme3)EKIAALSEIIWLPCL(Kme)YAQI(Kme)AFI(Kme)ALNDDPCQSSEILSEA(Kme)ELCS | NH2 |

TABLE 2C-continued

Additional Exemplary B7-H3 Miniproteins[6]

| Compound ID NO[7] | SEQ ID NO[8] | N-Term | Sequence[9] | C-Term |
|---|---|---|---|---|
| C598 | 530 | Biotin-PEG4 | CA(Kme3)EKIAALSEIIWLPCLTYAQI(Kme)AFI(Kme)ALNDDPCQSSEILSEA(Kme)EQCS | NH2 |
| C599 | 531 | Biotin-PEG4 | CA(Rme2s)EKIAALSEIIWLPCLTYAQI(Kme)AFIAALNDDPCQSAEILSEAKELCS | NH2 |
| C600 | 532 | Biotin-PEG4 | CA(Kme3)EKIAALSEIIWLPCLTYAQI(Kme2)AFIAALN(Cit)DPCQSSEILSEA(Kme3)ELCS | NH2 |
| C601 | 533 | Biotin-PEG4 | CAREKIAALSEIIWLPCLTYAQI(Kme)AFIAALNDDPCQSAEILSEARELCS | NH2 |
| C602 | 534 | Biotin-PEG4 | CAREK(Tle)AALSEIIWLPCLTYAQI(Kme)AFIAALNDDPCQSAEILSEARELCS | NH2 |
| C603 | 535 | Biotin-PEG4 | CAREKIAALSEIIWLPCLTYAQI(Kme)AFIAALNADPCQSAEILSEARELCS | NH2 |
| C604 | 536 | Biotin-PEG4 | CA(Kme3)HKIAALSEIIWLPCLTYAQI(Kme)AFIA(Kme)LN(Kme)DPCQSSEILSEAKELCS | NH2 |
| C605 | 537 | Biotin-PEG4 | CAREKIAALSEIIWLPCLTYDQI(Kme)AFIA(Kme)LNDDPCQSAEILSEARELCS | NH2 |
| C606 | 537 | DOTA-PEG4 | CAREKIAALSEIIWLPCLTYDQI(Kme)AFIA(Kme)LNDDPCQSAEILSEARELCS | NH2 |
| C607 | 537 | In:DOTA-PEG4 | CAREKIAALSEIIWLPCLTYDQI(Kme)AFIA(Kme)LNDDPCQSAEILSEARELCS | NH2 |
| C608 | 544 | Biotin-PEG4 | CA(Kme3)EKIAALS(E(CO-))IIWLPCLTYAQI(Kme)AFIAALNDDPCNSSEILSEA(K(NH-))ELCS | NH2 |

[6]Constraints (e.g., disulfide bonds) can be introduced between pairs of amino acids (e.g., cysteine residues).

[7]Each compound is identified via a compound # (e.g., "C1", "C2", C3", etc.) and refers to the combination of the N-terminal, Linker (if present), Sequence, and C-terminal components.

[8]Refers to sequences in the "Sequence" column.

9"Cit" refers to citrulline; "(Kme)" refers to monomethyllysine; "(Kme)2" refers to dimethyllysine; "(Kme3)" refers to trimethyllysine; "K(Ac)" refers to acetylated lysine; "N4-methyl-A" refers to $N^4$-methyl-L-asparagine; "Nva" refers to norvaline; "(Nle)" refers to (Nle); "OH-(Nle)" refers to hydroxy(Nle); "(k)" refers to D-lysine; "(MO2)" refers to methionine sulfone; "Abu" refers to alpha-aminobutyric acid; C(t-butyl) can also be written as Cys-(t-butyl) or tert-butylcysteine; "dD" refers to D-aspartic acid; "hR" refers to homo-arginine; "hyP" refers to hydroxyproline; "1Nal" refers to 1-naphthylamine; "sRme2" refers to symmetric dimethyl arginine; "Rme" and "Rme2" refer to mono and di-methylated arginine, respectively; "Kipr" refers to Nϵ-isopropyl-L-Lysine; "Dap" refers to diaminopimelic acid; "K(Ac)" refers to acetylated lysine; "RNO2" or "Arg(NO2)" refer to nitroarginine; "LCN" refers to Leu-13C6,15N; "NI" refers to hydroxynorleucine, "Nle" refers to Norleucine.

[10]Actinium-225.

Linkers

In some embodiments the present disclosure provides linkers for use in one or more conjugates. In some embodiments, a linker is attached to the N-terminus of a miniprotein provided herein. In some embodiments, a linker is attached to the C-terminus of a miniprotein provided herein. For example, in some embodiments, a linker is linked to a chelator. In some embodiments, a linker is linked to a chelator, which itself is coupled to a radionuclide. In some embodiments, a miniprotein is conjugated to a chelator and/or radionuclide. In some embodiments, a miniprotein is conjugated to a chelator, optionally, through a linker. In some embodiments, a composition as provided herein comprises one or more linkers. In some embodiments, a miniprotein is conjugated to a chelator and/or a cold-metal surrogate.

As described herein, in some embodiments, a miniprotein conjugate comprises a linker. In some embodiments, the linker functions to connect the chelator to miniprotein. In some embodiments, a linker is non-cleavable. In some embodiments, a linker is cleavable. In some embodiments, selection and placement of one or more linkers and chelators on a miniprotein aids to maintain desired potency and receptor engagement profile, enhance binder affinity and optimize physicochemical and pharmacokinetic properties of a miniprotein or conjugate thereof. Any suitable linker known in the art can be utilized. Exemplary linkers include, but are not limited to polyethylene glycol (PEG) linkers (e.g., PEG, PEG2, PEG (4-36), e.g., PEG4, PEG6, PEG8, PEG10, PEG12, etc.), an ester linker, an amide linker, a maleimide linker, a valine-citrulline linker, a hydrazone linker, a N-succinimidyl-4-(2-pyridyldithio)butyrate (SPDB) linker, a succinimidyl-4-(N-maleimidomethyl)cyclohexane-1-carboxylate (SMCC) linker, a vinylsulfone-based linker, a propanoic acid linker, a caproleic acid linker, a Lys(MPB)-PEG linker (e.g., Lys(MPB)-PEG4), a Lys (IPB)-PEG linker (e.g., Lys(IPB)-PEG4), an HE(1-3) linker (SEQ ID NO: 554), an (SE)1-3 linker (SEQ ID NO: 555), an (E)1-3 linker, an aminocaproic acid (Ahx) linker, or a linker including any combination thereof. One or more additional linkers may be contemplated as will be known to those of skill in the art and chosen given the context and components of a given composition. In some embodiments, the linker is a PEG linker. In some embodiments, the linker is a non-cleavable PEG linker. In some embodiments, the PEG linker is any of PEG (1-36). In some embodiments, the PEG linker is PEG (4-36). In some embodiments, a linker is a PEG4, PEG, PEG2, PEG6, PEG8, etc. In certain embodiments, the linker is a PEG4 linker.

In some embodiments, linkers are used to assess lead polypeptide sequences binding to a target, a target expressed on cells, and target selectivity and/or affinity. For instance, in some embodiments, confirmation of in vitro on-target binding and affinity for lead polypeptide sequences and lead polypeptide sequences-linker-fluorophore reagent can be assessed using Biacore. In some embodiments, other linkers such as a fast clear linker or a halogen linker are also contemplated.

In some embodiments, no linker is present. For example, in certain embodiments, a miniprotein is attached (e.g., covalently) directly to a chelator. In some embodiments, a miniprotein is directly radiolabeled (e.g., no chelator, no linker).

Chelators

In some embodiments, a composition (e.g., conjugate) as provided herein comprises a linker. In some embodiments, a composition comprises a linker and a chelator. In some embodiments, a composition comprises a linker, a chelator, and a radionuclide. In some embodiments, a composition comprises a miniprotein, optional linker, chelator, and/or radionuclide. In some embodiments, a chelator is covalently attached to a miniprotein. In some embodiments, a chelator binds to a radionuclide. In some embodiments, a chelator binds to a cold-metal surrogate. In some embodiments, a chelator refers to any molecule or moiety that "binds" to a metal ion, in solution (effectively collecting/binding up metal ions so that they may, e.g., no longer participate in one or more cellular activities or processes). In some embodiments a chelator chelates one or more components of a metabolic pathway in a cell (e.g., metal ions, e.g., copper, iron, zinc, etc.). In some such embodiments, a chelator disrupts a life-cycle of a cancer cell and may, in some embodiments, reduce its viability, function, and/or ability to grow or proliferate. In some embodiments, a chelator chelates one or more toxins that are produced as a result of targeted radiotherapy (e.g., to reduce toxicity of the therapy). In some embodiments, no chelator is present (e.g., a miniprotein is directly radiolabeled, e.g., a miniprotein is attached to a linker and radiolabeled, e.g., without a chelator).

In some embodiments, a chelator comprises or consists of, but is not limited to tetrazacyclododecane-1,4,7,10-tetraacetic acid (DOTA), diethylenetriamine pentaacetic acid (DTPA), ethylenediaminetetraacetic acid (EDTA), 1,4,7-triazacyclononane-N,N',N"-triacetic acid (NOTA), ethylenediaminetetraacetic acid (EDTA), diethylenetriaminepentaacetic acid (DTPA), ({4-[2-(bis-carboxymethyl-amino)-ethyl]-7-carboxymethyl-[1,4,7]triazonan-1-yl}acetic acid (NETA), Macropa, lead specific chelator (PSC) (e.g., a cyclen-based Pb specific chelator), N-succinimidyl 3-(tri-n-butylstannyl)benzoate (BuSTB), N-succinimidyl 3-trimethylstannylbenzoate (MeSTB), p-bromoacetamidobenzyl-tetraethylaminetetraacetic acid (TETA), porphyrins, polyamines, crown ethers, bis-thiosemicarbazones, or polyoximes. In some embodiments, the chelator is 1,4,7,10-tetraazacyclododecane-1,4,7,10-tetraacetic acid (DOTA). In some embodiments, the chelator is lead specific chelator (PSC). In some embodiments, the chelator is N-succinimidyl 3-(tri-n-butylstannyl)benzoate (BuSTB). In some embodiments, the chelator is N-succinimidyl 3-trimethylstannylbenzoate (MeSTB), In some embodiments, the chelator is In some embodiments, a chelator comprises or consists of, but is not limited to diethylenetriamine pentaacetic acid (DTPA), tetrazacyclododecane-1,4,7,10-tetraacetic acid (DOTA), ethylenediaminetetraacetic acid (EDTA), 1,4,7-triazacyclononane-N,N',N"-triacetic acid (NOTA), ethylenediaminetetraacetic acid (EDTA), diethylenetriaminepentaacetic acid (DTPA), 4,7-triazacyclononane-N,N',N"-triacetic acid (NOTA), ({4-[2-(bis-carboxymethyl-amino)-ethyl]-7-carboxymethyl-[1,4,7]triazonan-1-yl}acetic acid (NETA), Macropa, p-bromoacetamidobenzyl-tetraethylaminetetraacetic acid (TETA), PSC, N-succinimidyl 3-(tri-n-butylstannyl)benzoate (BuSTB), N-succinimidyl 3-trimethylstannylbenzoate (MeSTB), porphyrins, polyamines, crown ethers, bis-thiosemicarbazones, or polyoximes. In some embodiments, the chelator is 1,4,7,10-tetraazacyclododecane-1,4,7,10-tetraacetic acid (DOTA). In some embodiments, the chelator is Macropa.

In some embodiments, a chelator comprises or consists of, but is not limited to diethylenetriamine pentaacetic acid (DTPA), tetrazacyclododecane-1,4,7,10-tetraacetic acid (DOTA), ethylenediaminetetraacetic acid (EDTA), 1,4,7-triazacyclononane-N,N',N"-triacetic acid (NOTA), ethylenediaminetetraacetic acid (EDTA), diethylenetriaminepentaacetic acid (DTPA), 1,4,7-triazacyclononane-N,N',N"-triacetic acid (NOTA), ({4-[2-(bis-carboxymethyl-amino)-ethyl]-7-carboxymethyl-[1,4,7]triazonan-1-yl}acetic acid (NETA), Macropa, and p-bromoacetamidobenzyl-tetraethylaminetetraacetic acid (TETA), porphyrins, polyamines, crown ethers, bis-thiosemicarbazones, polyoximes. In some embodiments, the chelator is 1,4,7,10-tetraazacyclododecane-1,4,7,10-tetraacetic acid (DOTA). In some embodiments, the chelator is Macropa. In some embodiments, a chelator comprises or consists of:

i) NOPO

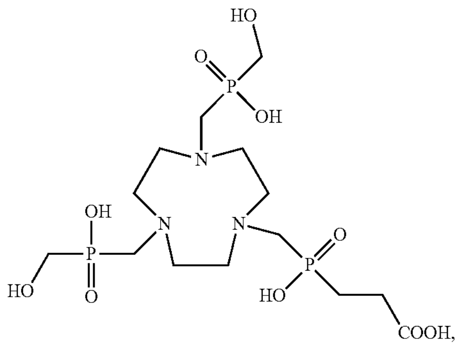

NOPO

-continued ii) CROWN

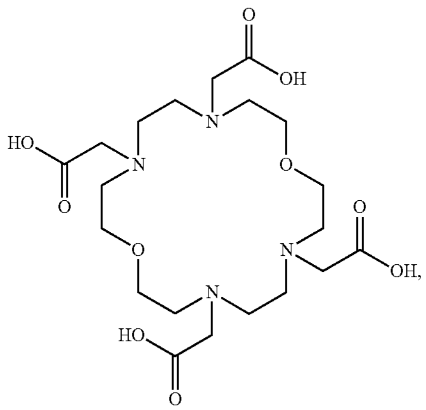

Crown iii) DOTA

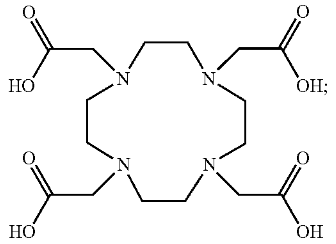

; or iv) Macropa

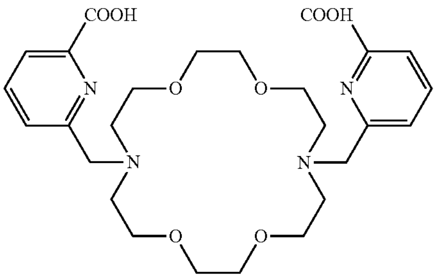

Macropa

.

In additional embodiments, the chelation conditions are optimized using methods known to those of skill in the art (see, e.g., J Nucl Med. 1998 December; 39(12):2105-10). In some embodiments, chelation efficiency is about >99%, >98%, >97%, >96%, >95%, >94%, >93%, >92%, >91%, >90%, >89%, >88%, >87%, >86%, >85%, >84%, >83%, >82%, >81%, or >80%.

In some embodiments, a chelator for use in a composition as described herein is chosen based on if and which radionuclide is present. As provided herein, in some embodiments, a chelator is DOTA, NOPO, Crown, PSC, N-succinimidyl 3-(tri-n-butylstannyl)benzoate (BuSTB), N-succinimidyl 3-trimethylstannylbenzoate (MeSTB), or Macropa. In some embodiments, DOTA is the chelator and the radionuclide is Ac-225, In-111, Ga-68, Pb-212, Lu-177, Cu-67, Cu-64, La-132, La-135, Ce-134, F-18, I-131, I-124, Pb-203, Th-232, Bi-123, or At-211. In some embodiments, Crown is the chelator and the radionuclide is Ac-225, In-111, Ga-68, Pb-212, Lu-177, Cu-67, Cu-64, La-132, La-135, Ce-134, F-18, I-131, I-124, Pb-203, Th-232, Bi-123, or At-211. In some embodiments, NOPO is the chelator, and the radionuclide is Ac-225, In-111, Ga-68, Pb-212, Lu-177, Cu-67, Cu-64, La-132, La-135, Ce-134, F-18, I-131, I-124, Pb-203, Th-232, Bi-123, or At-211. In some embodiments, Macropa is the chelator, and the radionuclide is Ac-225, In-111, Ga-68, Pb-212, Lu-177, Cu-67, Cu-64, La-132, La-135, Ce-134, F-18, I-131, I-124, Pb-203, Th-232, Bi-123, or At-211.

In some embodiments, a chelator for use in a composition as described herein is chosen based on if and which radionuclide is present. As provided herein, in some embodiments, a chelator is DOTA, NOPO, Crown, or Macropa. In some embodiments, DOTA is the chelator and the radionuclide is Ac-225, Lu-177, Ga-68, La-132, La-135, Cu-64, or In-111. In some embodiments, Crown is the chelator and the radionuclide is Ac-225, Lu-177, Ga-68, La-132, La-135, Cu-64, or In-111. In some embodiments, NOPO is the chelator, and the radionuclide is Ga-68, La-132, La-135, Cu-64, or In-111. In some embodiments, Macropa is the chelator, and the radionuclide is Ac-225, Lu-177, Ga-68, La-132, La-135, Cu-64, or In-111.

In some embodiments, a particular chelator or type of chelator may be chosen for certain applications. For instance, in some embodiments, NOPO is used in diagnostic or theranostic applications. In some embodiments, Crown is used for therapeutic applications. In some embodiments, DOTA is used for diagnostic, theranostic, and/or therapeutic applications. In some embodiments, Macropa is used for diagnostic, theranostic, and/or therapeutic applications.

It is recognized that screening chelators for certain characteristics is within the scope of this disclosure and methods for such screening are known to those of skill in the art. For example, in some embodiments, chelators are screened for their ability to bind radionuclides (e.g., Ga68, Ac225 and daughter(s) of Ac225 (e.g., Bi213)) and display serum stability.

In some embodiments, a miniprotein conjugate described herein comprises a chelator. Any suitable chelator known in the art can be utilized. In some embodiments the chelator is directly conjugated to the miniprotein. In some embodiments, the chelator is indirectly connected to the miniprotein through a linker. In some embodiments, the chelator is indirectly connected to the miniprotein through a linker (e.g., a linker described herein).

Radionuclides

In some embodiments the present disclosure provides one or more radionuclides for use in a composition (e.g., conjugate).

In some embodiments, the radionuclide is on the N-terminal side of the miniprotein and, optionally includes a linker and chelator, wherein the linker is attached to the N-terminus of the miniprotein and the chelator is attached to the linker (see, e.g., compounds as set forth in Table 2A and/or Table 2C). In some embodiments, the radionuclide is on the C-terminal side of the miniprotein, and, optionally includes a linker and chelator, wherein the linker is attached to the C-terminus of the miniprotein and the chelator is attached to the linker.

In some embodiments, miniprotein conjugates comprise a radionuclide bound to a chelator.

As will be understood to those of skill in the art, any suitable radionuclide known in the art may be used. In some embodiments, a radionuclide is selected for imaging of a tumor within a human having cancer. In some embodiments, a radionuclide is selected for its inability to kill cells in vivo. In some embodiments, the radionuclide is selected for its ability to kill cells in vivo.

In some embodiments, a composition of the present disclosure comprises one or more cytotoxic payloads including particle-emitting isotopes such as alpha-, beta-particles, and Auger electrons in radiotherapeutic applications. In some embodiments, a radionuclide of the present disclosure is an alpha emitter. As will be known to those of skill in the art, in some embodiments, an alpha emitter has a more localized area of impact such that when internalized into a cell it will act to, e.g., kill a cancer cell, but will spare surrounding tissue from extensive damage such as could occur with use of a beta or gamma emitter.

Studies have evaluated alpha nuclide therapy versus beta nuclide therapy with the stronger clinical results pointing to alpha nuclides. In some embodiments, a benefit of alpha therapy is that the short path length means patients do not have to physically distance themselves from family and health care providers making treatment more tolerable. Further, in some embodiments, alpha therapy exhibits better cell killing potency due to its ability to induce double stranded DNA breaks.

In some embodiments, a composition comprises a linker, chelator, and radionuclide. In some embodiments, a composition comprises a miniprotein, optional linker, chelator, and a radionuclide. Without being bound by any particular theory, the present disclosure contemplates that a wide variety of radionuclides can be used in the pharmaceutical composition or as a diagnostic. Exemplary radionuclides, include but are not limited to, Actinium-225, Astatine-211, Bismuth-212, Bismuth-213, Cesium-137, Chromium-51, Cobalt-60, Copper-64 Dysprosium-165, Erbium-169, Fermium-255, Fluor-18, Gallium-67, Gallium-68, Gold-198, Holmium-166, Indium-111, Iodine-123, Iodine-124, Iodine-125, Iodine-131, Iridium-192, Iron-59, Lead-212, Lutetium-177, Molybdenum-99, Palladium-103, Phosphorus-32, Potassium-42, Rhenium-186, Rhenium-188, Samarium-153, Technetium-99m, Radium-223, Ruthenium-106, Sodium-24, Strontium-89, Terbium-149, Thorium-227, Xenon-133, Ytterbium-169, Ytterbium-177, Yttrium-90, and Zirconium-89. Accordingly, in some embodiments, a radionuclide is selected from: iodine (131I or 125I), yttrium (90Y), lutetium (177Lu), actinium (225Ac), praseodymium, astatine (211At), rhenium (186Re), bismuth (212Bi or 213Bi), indium (111In), technetium (99Tc), phosphorus (32P), rhodium (188Rh), sulfur (35S), carbon (14C), tritium (3H), chromium (51Cr), chlorine (36C1), cobalt (57Co or 58Co), iron (59Fe), selenium (75Se), or gallium (67Ga) or (68Ga). In some embodiments, the present disclosure contemplates that certain radioisotopes may be useful in or as therapeutic agents including but not limited to yttrium (90Y), lutetium (177Lu), actinium (225Ac), praseodymium, astatine (211At), rhenium (186Re), bismuth (212 Bi or 213Bi), and rhodium (188Rh). In some embodiments, radioisotopes are useful as labels, e.g., for use in diagnostics. In some such embodiments, such radioisotopes may include but are not limited to iodine (131I or 125I), indium (111In), technetium (99Tc), phosphorus (32P), carbon (14C), lead (212Pb) or tritium (3H). See, e.g., U.S. Pat. No. 7,514,078. In certain embodiments, a radionuclide is selected from Ac-225, In-111, Ga-68, Pb-212, Lu-177, Cu-67, Cu-64, La-132, La-135, Ce-134, F-18, I-131, I-124, Pb-203, Th-232, Bi-123, and At-211.

In some embodiments, radionuclides are conjugated to different complexing agents and chelators. In some embodiments, chelators are identified and attached/bound to miniproteins through a linker or by acyclic, cyclic and macrocyclic chelates such as, for example, 1,4,7,10,13,16-hexaazacyclohexadecane-N,N',N",N"',N"",N""'-hexaacetic acid (HEHA), 1,4,7,10-tetraazacyclododecane-N,N',N",N"'-tetraacetic acid (DOTA), NOPO, Crown, etc. In some embodiments, certain chelators may be preferred for certain radionuclides such as, for example, Ac-225 with DOTA or Crown, Ga-68 with NOPO, etc. In some embodiments, preferred combinations of chelators and radionuclides comprise one or more of the following: DOTA and Ac-225, Lu-177, Ga-68, La-132, La-135, Cu-64 or In-111; Crown and Ac-225, Lu-177, Ga-68, La-132, La-135, Cu-64 or In-111; NOPO and Ga-68, La-132, La-135, Cu-64 or In-111; and/or Macropa and Ac-225, Lu-177, Ga-68, La132, La135, Cu-64, or In-111.

Preferably, in certain embodiments, a preferred radionuclide complex comprises Ac-225, Ga-68, or Cu-64. In some such embodiments, such a complex with desired stability is selected. That is, in some embodiments, a complex comprising an Ac-225, Ga-68, or Cu-64 is characterized as having better stability in vivo in comparison to other complexes. Without wishing to be bound by theory, the present disclosure contemplates that, in some embodiments, a radionuclide complex comprising a miniprotein forms with the miniprotein target (e.g., B7-H3 or a fragment thereof). In some such embodiments, such a complex is internalized in the target cell.

In some embodiments, a radionuclide complex forms with a chelator (e.g., DOTA, NOPO, Crown, Macropa, etc.) and is considerably more stable in vivo. In some embodiments, a miniprotein forms internalizing complexes with targets (e.g., B7-H3).

In some embodiments, a composition provided by the present disclosure comprises Actinium-225. In some embodiments, a composition provided by the present disclosure comprises gallium (Ga-68). In some embodiments, a composition provided by the present disclosure comprises copper (Cu-64). In some embodiments, a composition provided by the present disclosure comprises indium (In-111). In some embodiments, a composition provided by the present disclosure comprises lutetium (Lu-177). In some embodiments, a composition provided by the present disclosure comprises lead (Pb-212) For example, in some embodiments, radioimmunotherapy comprising Ac-225 may provide i) limited range in tissue of a few cell diameters; ii) high linear energy transfer leading to dense radiation damage along each alpha track; iii) a 10 day half-life; and/or iv) four net alpha particles emitted per decay (see, e.g., as described in Scheinberg, David A, and Michael R McDevitt. "Actinium-225 in targeted alpha-particle therapeutic applications." Current Radiopharmaceuticals (2011), 4(4): 306-20).

In some embodiments, targeting constructs (e.g., 225-Ac-drug constructs, e.g., 68-Ga-constructs) have potential for use in cancer. For example, in some such embodiments, such constructs may be used in the treatment of cancer, such as, for example 225-Ac-drug constructs. In some embodiments, such constructs may be used in imaging, such as for prognostics, diagnostics, and/or monitoring, such as Ga-68 or Cu-64-based constructs.

In some embodiments, Ac-225 is conjugated to a miniprotein as provided herein. In some embodiments, the actinium is conjugated onto a chelator and may include an optional linker to link it to a miniprotein, which miniprotein targets the conjugate to a cell expressing the target (e.g., B7-H3).

In some embodiments, Ga-68 is conjugated to a miniprotein as provided herein. In some embodiments, the gallium is conjugated onto a chelator and may include an optional linker to link it to a miniprotein, which miniprotein targets the conjugate to a cell expressing the target (e.g., B7-H3).

In some embodiments, Cu-64 is conjugated to a miniprotein as provided herein. In some embodiments, the copper is conjugated onto a chelator and may include an optional linker to link it to a miniprotein, which miniprotein targets the conjugate to a cell expressing the target (e.g., B7-H3).

In some embodiments, In-111 is conjugated to a miniprotein as provided herein. In some embodiments, the indium is conjugated onto a chelator and may include an optional linker to link it to a miniprotein, which miniprotein targets the conjugate to a cell expressing the target (e.g., B7-H3).

In some embodiments, Lu-177 is conjugated to a miniprotein as provided herein. In some embodiments, the lutetium is conjugated onto a chelator and may include an optional linker to link it to a miniprotein, which miniprotein targets the conjugate to a cell expressing the target (e.g., B7-H3).

In some embodiments, Pb-212 is conjugated to a miniprotein as provided herein. In some embodiments, the lead is conjugated onto a chelator and may include an optional linker to link it to a miniprotein, which miniprotein targets the conjugate to a cell expressing the target (e.g., B7-H3).

In some embodiments, Cu-67 is conjugated to a miniprotein as provided herein. In some embodiments, the copper is conjugated onto a chelator and may include an optional linker to link it to a miniprotein, which miniprotein targets the conjugate to a cell expressing the target (e.g., B7-H3).

In some embodiments, La-132 is conjugated to a miniprotein as provided herein. In some embodiments, the lanthanum is conjugated onto a chelator and may include an optional linker to link it to a miniprotein, which miniprotein targets the conjugate to a cell expressing the target (e.g., B7-H3).

In some embodiments, La-135 is conjugated to a miniprotein as provided herein. In some embodiments, the lanthanum is conjugated onto a chelator and may include an optional linker to link it to a miniprotein, which miniprotein targets the conjugate to a cell expressing the target (e.g., B7-H3).

In some embodiments, Ce-134 is conjugated to a miniprotein as provided herein. In some embodiments, the cerium is conjugated onto a chelator and may include an optional linker to link it to a miniprotein, which miniprotein targets the conjugate to a cell expressing the target (e.g., B7-H3).

In some embodiments, I-131 is conjugated to a miniprotein as provided herein. In some embodiments, the iodine is conjugated onto a chelator and may include an optional linker to link it to a miniprotein, which miniprotein targets the conjugate to a cell expressing the target (e.g., B7-H3).

In some embodiments, I-124 is conjugated to a miniprotein as provided herein. In some embodiments, the iodine is conjugated onto a chelator and may include an optional linker to link it to a miniprotein, which miniprotein targets the conjugate to a cell expressing the target (e.g., B7-H3).

In some embodiments, Pb-203 is conjugated to a miniprotein as provided herein. In some embodiments, the lead is conjugated onto a chelator and may include an optional linker to link it to a miniprotein, which miniprotein targets the conjugate to a cell expressing the target (e.g., B7-H3).

In some embodiments, Th-232 is conjugated to a miniprotein as provided herein. In some embodiments, the thorium is conjugated onto a chelator and may include an optional linker to link it to a miniprotein, which miniprotein targets the conjugate to a cell expressing the target (e.g., B7-H3).

In some embodiments, Bi-123 is conjugated to a miniprotein as provided herein. In some embodiments, the bismuth is conjugated onto a chelator and may include an optional linker to link it to a miniprotein, which miniprotein targets the conjugate to a cell expressing the target (e.g., B7-H3).

In some embodiments, alpha particles (e.g., of Actinium-225, etc.) are positively charged. In some such embodiments, the range of penetration in tissue varies between 5 and 10 cell diameters (40 to 100 m) depending on their energy (Radiobiologic principles in radionuclide therapy. Kassis A I, Adelstein S J J Nucl Med. 2005 January; 46 (Suppl 1):4S-12S). In some such embodiments, such penetration allows for localized irradiation of target cells with minimal toxicity on surrounding normal cells, and internalization by cancer cells with as few as 1-3 tracks across the cell nucleus resulting in cell death (Humm 1987; Macklis et al. 1988; Humm and Chin 1993; Couturier et al 2005) causing single- and double-stranded DNA breaks. See, e.g., Sofou S. Radionuclide carriers for targeting of cancer. Int J Nanomedicine. 2008; 3(2):181-199. doi:10.2147/ijn.s2736.

Radionuclides and Chelation

A radionuclide can be bound to a chelator through any method known in the art. In some embodiments, chelation methods may differ based on the radionuclide and chelator selected. For example, in some embodiments, chelation can be carried out in one step by incubating the miniprotein-chelator conjugate with the radionuclide for a predetermined period at a predetermined temperature to achieve a sufficient amount of chelation. In some embodiments, a miniprotein-chelator conjugate comprises a chelator or variant thereof as provided herein (e.g., DOTA, e.g., NOPO, e.g., Crown, e.g., Macropa, etc.). In some embodiments, miniprotein-chelator conjugates can be chelated to a radionuclide (e.g., Actinium-225, Gallium-68, Copper-64, Lutetium-177, Indium-111, Lead-212, etc.) by incubation with the radionuclide for about 1 hour at 70° C. In some embodiments, miniprotein-chelator conjugates can be chelated to a radionuclide (e.g., Actinium-225, Gallium-68, Copper-64, Lutetium-177, Indium-111, Lead-212, etc.) by incubation with the radionuclide for about 1 hour at 70° C.

In some embodiments, the chelation process yields a preparation in which at least 90%, 91%, 92%, 93%, 94%, 95%, 96%, 97%, 98%, or 99% of the miniprotein-chelator is bound to a radionuclide. In some embodiments, the chelation process yields a preparation in which more than 90%, 91%, 92%, 93%, 94%, 95%, 96%, 97%, 98%, or 99% of the miniprotein-chelator is bound to a radionuclide. Excess radionuclide can be removed from the preparation by purification methods known in the art.

Conjugates and Compounds

The disclosure provides conjugates and compounds that comprise a polypeptide as provided herein. Exemplary conjugates are provided, for example, in TABLE 2A and Table 2C. Such compounds as set forth in Tables 2A and 2C have exemplary N- and C-termini. As will be apparent to those of ordinary skill in the art, exemplary compounds as set forth in Tables 2A and 2C may have the same miniprotein (i.e., same SEQ ID NO:), but different N- and/or C-termini. Depending on context, a given miniprotein may be used in compounds of various formulas and arrangements as provided herein (e.g., M-L-C-R, wherein each of L, C, and R is independently optional). For example, in certain embodiments, an exemplary compound, such as comprising a DOTA chelator and PEG4 linker, such as C235 (SEQ ID NO: 204) that is described as used in an assay, such as set forth herein, will be understood to have been labeled with a radionuclide prior to use.

As provided herein, in certain embodiments, a compound can comprise a miniprotein having an amino acid sequence with 90% identity to any of SEQ ID NOs: 204 and 262-272, and further comprise one or more additional components according to a formula M-L-C-R, wherein L is a linker, C is a chelator, and R is a radionuclide. In some embodiments, the miniprotein has 90% identity to SEQ ID NO: 267. In some embodiments, the miniprotein has 90% identity to at least 40 41, 42, 43, 44, 45, 46, 47, or 48 amino acids of SEQ ID NO: 267. In some embodiment, the miniprotein has 100% identity to SEQ ID NO: 267. In some embodiments, the miniprotein has 100% identity to at least 40, 41, 42, 43, 44, 45, 46, 47, or 48 amino acids of SEQ ID NO: 267.

In some embodiments, L comprises or consists of a polyethylene glycol (PEG) linker of PEG4, PEG, PEG2, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, any linker set forth in TABLE 2A, or (Gly)n-(gGlu)n- (SEQ ID NO: 551) or (PEG)n, wherein n is from 1 to 36, (Gly)1-10 (SEQ ID NO: 552), or any fragment or combination via covalent bond thereof.

In some embodiments, C comprises or consists of DOTA, Crown, NOPO, Macropa, lead specific chelator (PSC), N-succinimidyl 3-(tri-n-butylstannyl)benzoate (BuSTB), or N-succinimidyl 3-trimethylstannylbenzoate (MeSTB). In some embodiments, R comprises or consists of Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211.

In some aspects, the disclosure provides a compound comprising a miniprotein 90% identical to at least 48 amino acids of the amino acid sequence of SEQ ID NO: 267, wherein the N and/or C-terminus comprise between one and thirty additional amino acids, and/or wherein the C-terminus comprises one fewer amino acids or up to 30 additional amino acids, provided that the entire miniprotein is no greater than about 100 amino acids in length.

In some embodiments, the disclosure provides a miniprotein conjugate comprising one or more components including a miniprotein and one or more of a linker, chelator, and/or radionuclide.

In some embodiments, a miniprotein conjugate comprises: (i) miniprotein (M) that specifically binds to B7-H3; (ii) a chelator (C) conjugated to (M) through an optional linker (L), wherein (C) comprises DOTA, and (L), when present, comprises PEG; and (ii) a radionuclide (R) chelated to (C), wherein (R) is Actinium-225.

In some embodiments, a miniprotein conjugate comprises: (i) miniprotein (M) that specifically binds to B7-H3; (ii) a chelator (C) conjugated to (M) through an optional linker (L), wherein (C) comprises DOTA, and (L), when present, comprises PEG; and (ii) a radionuclide (R) chelated to (C), wherein (R) is Copper-64.

In some embodiments, a miniprotein conjugate comprises: (i) miniprotein (M) that specifically binds to B7-H3; (ii) a chelator (C) conjugated to (M) through an optional linker (L), wherein (C) comprises DOTA, and (L), when present, comprises PEG; and (ii) a radionuclide (R) chelated to (C), wherein (R) is Indium-111.

In some embodiments, a miniprotein conjugate comprises: (i) miniprotein (M) that specifically binds to B7-H3; (ii) a chelator (C) conjugated to (M) through an optional linker (L), wherein (C) comprises DOTA, and (L), when present, comprises PEG; and (ii) a radionuclide (R) chelated to (C), wherein (R) is Lead-212.

In some embodiments, a miniprotein conjugate comprises: (i) miniprotein (M) that specifically binds to B7-H3; (ii) a chelator (C) conjugated to (M) through an optional linker (L), wherein (C) comprises DOTA, and (L), when present, comprises PEG; and (ii) a radionuclide (R) chelated to (C), wherein (R) is Lutetium-177.

In some embodiments, a miniprotein conjugate comprises: (i) miniprotein (M) that specifically binds to B7-H3; (ii) a chelator (C) conjugated to (M) through an optional linker (L), wherein (C) comprises DOTA, and (L), when present, comprises PEG; and (ii) a radionuclide (R) chelated to (C), wherein (R) is Gallium-68.

In some embodiments, the PEG linker is PEG (1-36). In certain embodiments, the PEG linker is PEG4, PEG, PEG2, PEG6, PEG8, PEG10, PEG12, PEG14, PEG16, PEG18, PEG20, PEG22, PEG24, PEG36, etc. In some embodiment, the PEG linker is PEG4.

In some embodiments, a conjugate of the disclosure comprises a polypeptide, M, which has an amino acid sequence comprising any one of the amino acid sequences set forth in any of SEQ ID NOs: 198-272. In certain embodiments, M has an amino acid sequence comprising any one of the amino acid sequences set forth in any of SEQ ID NOs: 204 and 262-272.

In some embodiments, the amino acid sequence has at least 90% identity to that of at least 48 amino acids of SEQ ID NO: 267, wherein the amino acids corresponding to each of X1, X17, X35, and X48 are C and the amino acids corresponding to each of X3, X24, and X29 are as follows: X3 is Kme3, R, or Rme; X24 is Kme, Kme2, or Kme3; and X29 is Kme, A, or R. In some embodiments, the amino acid corresponding to X49 is absent.

In some embodiments, M has an amino acid sequence comprising or consisting of SEQ ID NO: 267. In some embodiments, M has an amino acid sequence comprising or consisting of any of SEQ ID NOs: 204 and 262-272.

Decoys and Co-Administration

In some embodiments, a composition provided herein is co-administered with one or more additional proteins such as a decoy. As used herein the term "co-administration" refers to delivering a composition provided herein at substantially the same time (e.g., concomitant, e.g., sequential) as one or more additional proteins such as a decoy. Co-administration can also be used to refer to co-treatment (e.g., in vitro, e.g., in vivo, e.g., of a population of cells, e.g., of a test subject, e.g., of a patient, etc.) or co-incubation (e.g., in vitro by contacting a population of cells with two components (1) a composition provided herein and (2) one or more additional proteins, such as a decoy.

Decoys of the disclosure can be monomeric or multimeric. For example, in some embodiments, a decoy is a monomer. In some embodiments, a decoy is a multimer of one or more monomers of the same or different miniprotein. A multimer may have one or more monomers attached to one another by one or more linkers, such as peptide linkers, covalent bonds, non-covalent linkages, etc.

Without wishing to be limited by theory, the disclosure contemplates that, in some embodiments, co-administration of the composition with a decoy results in reduced or substantially no kidney uptake due to inhibition of proximal tubule cell surface entities (e.g., cell surface transporter(s)). See Xiong, C. et al. Mol. Pharmaceutics 2019, 16, 808-15; Melis, M. et al. Eur J Nucl Med Imaging, 2009, 36, 1968-76. In some embodiments, co-administration with decoy results in reduced or substantially no liver uptake. In some embodiments, uptake is blocked. In some embodiments, retention is blocked. In some embodiments, decoys can block uptake of a composition of the disclosure (e.g., a radiotherapeutic). Regardless of blocking off-target uptake, B7-H3 binding polypeptides (e.g., miniproteins and conjugates thereof) as disclosed herein are not displaced from target binding. That is, including as demonstrated herein, while off-target uptake can be blocked using decoys such as those disclosed herein, there is little to no measureable impact on binding of a B7-H3-targeted polypeptide in when used in combination (before, during, or after) with decoys.

As used herein, the term "scaffold" is used to describe miniproteins that share a general set of structural characteristics (e.g., certain constraints, secondary structures, tertiary structures, etc.). Any individual scaffold may include varying amounts of alpha helix, turn, and/or beta sheet, e.g., all alpha helix proteins ("a"), all beta sheet proteins ("b"), blended alpha helix/beta sheet proteins ("a/b"), blended alpha and beta proteins ("a+b"), and small proteins. Examples and features of certain scaffolds are provided herein.

Decoys of the disclosure may be based on a particular scaffold (e.g., type A, type B, etc.). In certain embodiments, one type of scaffold comprises a miniprotein with alpha helical secondary structures, comprising a truncated and constrained primary sequence containing at least one, two, or three constraints, and binding to B7-H3 strongly. In certain embodiments, the truncation and constraint is relative to length and arrangement of any polypeptide sequences as set forth in Table 2A.

A scaffold of a given decoy may be the same or different from a polypeptide of the disclosure (e.g., a miniprotein, e.g., a B7-H3-targeting miniprotein,) with which it can be combined (co-administered, such as in the same vial, or serially administered vials, etc.), in order to act as a decoy (e.g., block uptake into kidney and/or liver tissue). For example, a scaffold B polypeptide that binds to a target (e.g., B7-H3) can be used for co-administration with either a scaffold A or scaffold B decoy (e.g., concomitantly, sequentially, etc.). In some embodiments, a scaffold A decoy can be used for co-administration with a scaffold B polypeptide (e.g., concomitantly, sequentially, etc.), e.g., as set forth in Table 2A. In some embodiments, a scaffold A decoy can be used for co-administration with a polypeptide having a scaffold comprising alpha helical secondary structure, a truncated primary sequence relative to those set forth in Table 2A, and at least one (e.g., one, two, three, etc.) constraint. See, e.g., Table 2C. In some embodiments, a scaffold B decoy cannot decoy a scaffold A polypeptide that binds to a target (e.g., a non-B7-H3 target). In certain embodiments, a scaffold B decoy cannot decoy a polypeptide having a scaffold comprising alpha helical secondary structure, a truncated primary sequence relative to those set forth in Table 2A, and at least one (e.g., one, two, three, etc.) constraint. See, e.g., Table 2C.

The present disclosure contemplates that compositions (e.g., comprising a miniprotein) do not need to be combined with a decoy of the same scaffold in order for the decoy to block uptake and/or retention of the miniprotein (e.g., a cold-labelled miniprotein, e.g., a radionuclide-labeled miniprotein) into non-tumor tissue (e.g., kidney tissue, e.g., liver tissue)

Furthermore, the disclosure contemplates that decoys provided herein can decoy compositions (e.g., comprising polypeptides as provided herein) that have one or more modifications to an N-terminus and/or C-terminus, and/or, one or more positions on a polypeptide backbone (e.g., the polypeptide of the composition, e.g., the target-binding polypeptide). That is, a polypeptide that binds to a target (e.g., B7-H3) can be modified by one or more N- and/or C-terminal modifications and/or one or more polypeptide backbone modifications and, in addition, decoys such as disclosed herein, can still block uptake and/or retention into a non-tumor tissue when co-administered with one or more such polypeptides. Compositions that can be combined with decoys of the disclosure include, for example, polypeptides modified on N- and/or C-termini and/or their polypeptide backbones such as to include one or more modifications and/or payloads (e.g., radionuclide payloads, e.g., antimitotic payloads, etc.).

Without wishing to be limited by theory, the disclosure contemplates that, in some embodiments, co-administration of the composition with a decoy results in reduced or substantially no kidney uptake due to competitive inhibition of the proximal tubule cell receptors. In some embodiments, co-administration with a functional inhibitor results in reduced or substantially no kidney uptake. In some embodiments, uptake is blocked. In some embodiments, retention is reduced or otherwise mitigated. In some embodiments, decoys can block retention and/or uptake of a composition of the disclosure (e.g., a radiotherapeutic). Decoys of the disclosure may be based on a particular scaffold (e.g., a particular miniprotein scaffold, e.g., an affibody scaffold, such as in certain B7-H3-binding miniproteins provided herein, e.g., SEQ ID NOs: 4-96, 100-261 e.g., C4-C118, C121-C297, e.g., a type B scaffold). The scaffold of a given decoy may be the same or different from a polypeptide of the disclosure (e.g., a miniprotein, e.g., a B7-H3 binding miniprotein). Such a decoy can be combined (co-administered, such as in the same vial, or serially administered vials, etc.) with a composition comprising a B7-H3 binding miniprotein (e.g., as set forth in Tables 1B-1E, 2A, and 2C) that targets a B7-H3 expressing cell (e.g., a cancer cell), in order to act as a decoy (e.g., to block uptake and/or retention into a tissue, such as a kidney tissue). In some embodiments, a polypeptide that binds to B7-H3 can have the same or different scaffold as a decoy used for co-administration with the polypeptide. In certain embodiments, a miniprotein that binds to B7-H3 is linear (non-constrained, e.g., as in C1-C116, C121-C608 and C611) and in such embodiments, can have the same (e.g., C7 if the polypeptide is selected from C4-C6, C8-C117, or C121-C297) or a different (e.g., C118-C120) scaffold as a decoy can be used for co-administration with a decoy (e.g., concomitantly, sequentially, etc.). In some embodiments, the B7-H3-binding miniprotein is constrained (e.g., C121-C608 and C611) and the decoy can be of a different scaffold (e.g., scaffold B, e.g., C7, e.g., scaffold A, e.g., C118-C120). In some embodiments, a scaffold B decoy may have one or more differences in its amino acid sequence as compared to certain B7-H3-binding miniproteins such as those selected from SEQ ID NOs: 4-6, 8-94, and 100-197. The present disclosure contemplates that compositions (e.g., comprising a miniprotein) do not need to be combined with a decoy of the same scaffold in order for the decoy to block uptake and/or retention of the miniprotein (e.g., a cold-labeled miniprotein, e.g., a radionuclide-labeled miniprotein) into a kidney tissue.

Certain decoys are provided herein, such as C10 or C118-C120 (SEQ ID NOs: 7, or 97-99, respectively). Certain decoys of the disclosure may bind to a target protein (e.g., B7-H3) with an affinity of about $10^{-9}$ M, $10^{-8}$ M, $10^{-7}$ M, $10^{-6}$ M, $10^{-5}$ M, $10^{-4}$ M, $10^{-3}$ M, or greater (e.g., $10^{-2}$ M, etc.), may not bind to B7-H3, may not specifically bind to B7-H3, or may have binding that is not detectable using measures including those provided herein.

Without wishing to be bound by theory, the disclosure describes, in some embodiments, a decoy peptide (or decoy) that decoys a composition such as a radiotherapeutic, which means that presence of the decoy in a non-tumor tissue (e.g., kidney, e.g., liver) blocks uptake and/or retention of the radiotherapeutic into the non-tumor tissue (e.g., kidney, e.g., liver). For clarity, when a decoy peptide is referred to as "decoying," e.g., a composition, e.g., a compound, e.g., a miniprotein that binds to a target (e.g., B7-H3), the decoy is not acting on the composition (or compound or miniprotein), rather, it is acting on its own and, for example, even in the absence of a composition that it is decoying, if administered alone, would still be present in the non-tumor tissue (e.g., kidney, e.g., liver).

In certain embodiments, the decoy comprises or consists of a scaffold A decoy. In some embodiments, the scaffold A decoy comprises or consists of a compound selected from any of C118-C120 and/or has an amino acid sequence comprising or consisting of any of SEQ ID NOs: 97-99. In some embodiments, the scaffold B decoy comprises or consists of comprises or consists of compound C10 and/or has an amino acid sequence comprising or consisting of SEQ ID NO: 7.

In certain embodiments, the decoy comprises or consists of a miniprotein having an amino acid sequence comprising, consisting essentially of, or consisting of any of SEQ ID NO: 7 or SEQ ID NOs: 97-99. In some embodiments, the decoy comprises or consists any of compounds C10 or C118-C120, as set forth in Table 2D.

TABLE 2D

Exemplary Decoys

| Compound NO: | SEQ ID NO: | N-term | Amino Acid Sequence | C-term |
|---|---|---|---|---|
| C10 | 7 | Acetyl | AEAKYAKEKIAALSEII(3-(1-naphthyl)-L-alanine) LPNLTHGQIMAFIAALNDDPSQSSELLSEAKKLNDSQAPK | OH |
| C118 | 97 | Acetyl | CEYDEEFFTELERLKGGDICYYIKKKFDKVPRLCIKEIRDKLGC | NH2 |
| C119 | 98 | Acetyl | CEYKEEFFTELKRLYGGDICYYIKKKFKKVPDLCIEEILDKLGC | NH2 |
| C120 | 99 | Acetyl | CEYDEEFFTELERLKGGDICYYIKKKFDKVPDLCIKEIRDKLGC | NH2 |

The disclosure contemplates that the combination of reduction in non-tumor tissue (e.g., kidney, e.g., liver) retention and/or uptake at the same time as successful uptake and/or retention in tumor tissue may represent an improvement in a therapeutic index (TI), including while reducing non-tumor tissue uptake and/or retention. Therapeutic index, as used herein, refers to a ratio that compares blood concentration at which an agent (e.g., a compound as provided herein, e.g., a radionuclide conjugate as provided herein) becomes toxic versus the concentration at which the drug is effective. Typically, a quantitative measure of TI is LD50 (median lethal dose) over ED50 (median effective dose). When TI is quantified by LD50/ED50, improvement in TI is characterized by a decrease in LD50/ED50 due to a decrease in LD50, an increase in ED50, or a combination of both.

In some embodiments, the decoy has an amino acid sequence comprising any one of SEQ ID NO: 7 or SEQ ID NOs: 97-99. In some embodiments, the decoy is a compound selected from any of C10 or C118-C120. In some embodiments, the decoy is present at a concentration of about 2×, 5×, 10×, 20×, 30×, 40×, 50×, 60×, 70×, 80×, 90×, 100×, 250×, 500×, 750×, 1000×, 2500×, 5000×, 7500×, 10000×, or greater as compared to the concentration of M. Example 10 and Example 13 each provide data on levels of kidney retention measured in mice treated with radioactively-labeled peptides and imaged via SPECT/CT, as provided herein. In some embodiments, the decoy reduces or prevents uptake of M (e.g., of a composition of the disclosure) in the kidney, such as shown in, e.g., FIG. 8, FIG. 9, and FIG. 13A.

In certain embodiments, the decoy comprises or consists of a compound selected from any of C118-C120 and/or has an amino acid sequence selected from any of SEQ ID NOs: 97-99. In certain embodiments, the miniprotein comprises or consists of any compound or amino acid sequence selected from Table 2A or Table 2C.

In certain embodiments, the decoy comprises or consists of a scaffold A decoy. In some embodiments, the scaffold A decoy comprises or consists of a compound selected from any of C118-C120 and/or has an amino acid sequence selected from any of SEQ ID NOs: 97-99.

In some embodiments, the scaffold B decoy comprises or consists of a compound C10 and/or comprises or consists of an amino acid sequence of SEQ ID NO: 7.

In certain embodiments, the decoy comprises or consists of a scaffold A decoy and the miniprotein comprises or consists of a scaffold B target-binding miniprotein. In some embodiments, the scaffold A decoy is selected from any of C118-C120 and the scaffold B target-binding miniprotein comprises or consists of a B7-H3-targeting protein selected from Table 2A. In certain embodiments, the B7-H3-binding miniprotein is not a scaffold B miniprotein and is a constrained B7-H3-binding miniprotein (e.g., as set forth in Table 2C).

In certain embodiments, the decoy comprises or consists of a scaffold B decoy and the miniprotein comprises or consists of a scaffold B target-binding miniprotein. In some embodiments, the decoy comprises or consists of C10 and the scaffold B target-binding miniprotein comprises or consists of a B7-H3-targeting protein selected from Table 2A or Table 2C.

The present disclosure contemplates that, in some embodiments, the decoy reduces uptake of a composition comprising a miniprotein (M) (e.g., of a composition of the disclosure, e.g., of a cold-metal labeled compound of the disclosure, e.g., of a radionuclide composition of the disclosure) in a kidney by competitive inhibition (e.g., competitive inhibition by the decoy, of M, for uptake and/or retention into a tissue such as non-tumor tissue (e.g., kidney, liver, etc.)). In some embodiments, the decoy can be of a desirable length. In some such embodiments, the desirable length is about the same length as that of the M portion of a composition for which uptake by the kidney is being reduced or prevented. In some aspects, amino acid residues added to the N-terminal end or the C-terminal end of the decoys disclosed herein may prevent ubiquitination, improve stability, help maintain the three dimensional structure of the peptide, or a combination thereof. In some embodiments, a given decoy has similar features (e.g., length, secondary structure, charge, etc.) and/or is of the same scaffold (e.g., scaffold A, scaffold B, etc.) of a target-binding composition that it is being co-administered with, and, in some embodiments, a given decoy has different features than the target-binding composition. In such embodiments, regardless of the scaffold of the miniprotein of the composition or the decoy, the decoy is able to block or reduce uptake and/or retention of the composition comprising the miniprotein (e.g., labeled miniprotein, e.g., cold-labeled, e.g., radiolabeled, etc.) in kidney tissue.

In some aspects, the decoys disclosed herein can further comprise a peptide or polypeptide having one or more amino acid residues with a modified side chain. In some aspects, one or more amino acids of any of the decoys disclosed here can have a modified side chain. Examples of side chain modifications include but are not limited to modifications of amino acid groups, such as reductive alkylation; amidination with methylacetimidate; acylation with acetic anhydride; carbamolyation of amino groups with cynate; trinitrobenzylation of amino acid with 2,4,6-trinitrobenzene sulfonic acid (TNBS); alkylation of amino groups with succinic anhydride; and pyridoxylation with pridoxal-5-phosphate followed by reduction with NaBH4.

In some aspects, the decoys provided herein can be further modified, for example, to improve stability. In some such embodiments, any of the amino acid residues of the decoys described herein can be modified to improve stability. In some aspects, decoys can have at least one amino acid residue that has an acetyl group, a fluorenylmethoxy carbonyl group, a formyl group, a palmitoyl group, a myristyl group, a stearyl group, or polyethylene glycol. In some aspects, an acetyl protective group can be bound to the decoy peptide described herein.

In some aspects, the amino acid sequence of the decoy peptides described herein can include a peptide sequence that has substantial identity to any of the sequences of the decoy peptides disclosed herein. As used herein, the term "substantial identity" means that two amino acid sequences, when optimally aligned and then analyzed by an algorithm normally used in the art, such as BLAST, GAP, or BESTFIT, or by visual inspection, share at least about 60%, 70%, 80%, 85%, 90%, or 95% sequence identity. Methods of alignment for sequence comparison are known in the art.

In some aspects, the amino acid sequence of the decoy peptides described herein can include a peptide sequence that has some degree of identity or homology to any of sequences of the decoy peptides disclosed herein. The degree of identity can vary and be determined by methods known to one of ordinary skill in the art. The terms "homology" and "identity" each refer to sequence similarity between two polypeptide sequences. Homology and identity can each be determined by comparing a position in each sequence which can be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be referred to as homologous at that position. A percentage of homology or identity between sequences is a function of the number of matching or homologous positions shared by the sequences. The decoy peptides described herein can have at least or about 25%, 50%, 65%, 75%, 80%, 85%, 90%, 95%, 96%, 97%, 98%, or 99% identity or homology to the decoy peptide.

In some embodiments, a composition provided herein is co-administered—with one or more decoys. Furthermore, the disclosure contemplates that, in some embodiments, a conjugate as provided herein (e.g., a radionuclide conjugate) can be administered to a patient sequentially (e.g., a radionuclide conjugate, e.g., comprising the same or different B7-H3 binding miniprotein and a different radionuclide). That is, in certain embodiments, a subject may be administered a first radiotherapeutic (e.g., a first B7-H3 conjugate comprising a first radionuclide (e.g., 225-Ac)), which first radiotherapeutic may optionally be co-administered (e.g., concomitantly) with a decoy followed by administration with a second radiotherapeutic (e.g., a B7-H3 conjugate comprising a second radionuclide (e.g., 177-Lu)), which second radiotherapeutic may optionally be co-administered (e.g., concomitantly) with a decoy. The B7-H3 binding miniprotein may be the same or different in the first and second radiotherapeutics. Furthermore, such conjugates may be administered serially (e.g., one after another, in any order) and each may also be independently administered with a decoy, wherein the decoy administered with the first and second radiotherapeutics, if used, may be the same or different.

Dose Calculation

In some embodiments, a dose of a radiotherapeutic is calculated. In some such embodiments, calculation of an absorbed dose (D) is necessary to quantitatively correlate tumor response to a particular radiotherapeutic modality and to project on the potential effect of other radiotherapeutic modalities or administration strategies. That is, in some embodiments, the absorbed dose from a target site is defined as the energy (E) absorbed by a particular mass of tissue, normalized by the tissue mass (M): D=E/M (Sgouros 2005). The absorbed energy is defined as a function of three parameters: the number of disintegrations within the particular volume of interest (6), the energy emitted per disintegration (s), and the fraction of emitted energy that is absorbed by the particular volume of interest (the target mass) (f): E=δ×F×f. For the relatively long-range beta emitters, the dose evaluation at a target site includes not only the energy emitted by radionuclides localized within the target volume, but also the energy emitted by radionuclides accumulated in neighboring organs or areas whose emissions cross along their path the target volume of interest (Kolbert et al 2003). In other words, in some embodiments, the calculated total absorbed dose is the sum of the dose contributions from all regions containing radionuclides that act as secondary sources. In some embodiments, the adsorbed dose due to photon emissions is usually calculated separately and added to the dose due to alpha or beta particles. In some embodiments, where a composition comprises an alpha particle emitter, such cross organ absorbed doses may be of no significance due to their short recoil distances. In some embodiments, given appropriate context, at the micron-scale and at distances comparable to a few cells, microdosimetric evaluations are used to evaluate dose or 'hits' acquired by cancer cells within micrometastatic clusters (Palm et al. 2002).

In some embodiments, a polypeptide of the disclosure (e.g., a miniprotein, e.g., a miniprotein conjugate comprising a radionuclide) displays binding specificity to human B7-H3. In some embodiments, the miniprotein comprises a binding affinity characterized by a dissociation constant ranging from about 1 pM to about 500 nM, e.g., 500, 400, 300, 200, 100, 90, 80, 70, 60, 50, 40, 30 20, 10, 9, 8, 7, 6, 5, 4, 3, 2, or 1 nM, 100, 90, 80, 70, 60, 50, 40, 30, 20, 10, 9, 8, 7, 6, 5, 4, 3, 2, or 1 pM binding affinity to human B7-H3. Without wishing to be bound by theory, the present disclosure contemplates that, in some embodiments, a preferred dissociation constant of a miniprotein is about 10 nM or less, about 7.5 nM, about 5 nM or less, about 2.5 nM or less, about 1 nM or less (e.g., in the picomolar range). In some embodiments, a dissociation constant (e.g., KD, as measured using surface plasmon resonance), is between about 10 pM and 100 nM. In certain embodiments, the dissociation constant is between about 20 pM and 50 nM. In some embodiments, the dissociation constant is stronger than about 100 nM, 75 nM, 50 nM, 25 nM, 10 nM, 5 nM, 1 nM, 750 pM, 500 pM, 250 pM, 100 pM, 75 pM, 50 pM, 25 pM, 15 pM, 10 pM, 9 pM, 8 pM, 7 pM, 6 pM, 5 pM, 4 pM, 3 pM, 2 pM, or 1 pM.

In some embodiments, a polypeptide (e.g., a miniprotein, e.g., a miniprotein conjugate comprising a radionuclide) in accordance with the present disclosure binds to B7-H3 with a binding affinity of about 1 pM to 100 nM, about 10 pM to about 100 nM, about 10 pM to about 50 nM, etc. In some embodiments, a miniprotein in accordance with the present disclosure binds to B7-H3 with a binding affinity of about 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950 or 1000 nM. In some embodiments, a miniprotein in accordance with the present disclosure binds to B7-H3 with a binding affinity of about 1 pM to 100 pM, 10 pM to 1 nM, 100 pM to 10 nM, or 1 nM to 100 nM.

In some embodiments, compositions as provided herein are characterized for one or more of absorbed dose, dose rate, tumor penetration profile of radionuclides, intracellular localization profiles of radionuclides of shorter range, and tumor radiosensitivity (see, e.g., Sofou S. Radionuclide carriers for targeting of cancer. Int J Nanomedicine. 2008; 3(2):181-199).

As is known to those of skill in the art, due to toxicity of radionuclides, dose needs to be carefully controlled and considered. Accordingly, in some embodiments, compositions comprising radionuclides of the present disclosure address dose-limiting toxicity of compositions such that radionuclides do not accumulate significantly (e.g., in a toxicity-limiting manner) in vital organs.

In some embodiments, alpha particle-emitting isotopes engage in on-target cell killing while minimizing toxic effects (e.g., to surrounding tissue, e.g., as compared to, e.g., beta emitters, etc.).

In some embodiments, compositions provided herein (comprising a radionuclide) are administered in a single step such as, e.g., using a ligand, e.g., a miniprotein resulting in improved biodistributions (e.g., specific targeting), pK with partial and acceptable damage or no damage to normal tissues, enhanced penetration of the pharmaceutical composition into the tumor heterogeneous interstitial space.

In some embodiments, one or more radionuclides is conjugated to a miniprotein. Relatedly, in some embodiments, radiolabeling efficiency of a miniprotein is optimized to radiolabel a desired number of radionuclides. In some embodiments, a ratio of radionuclides conjugated to a miniprotein is 1:1, 2:1, 3:1, 4:1, 5:1, 6:1, 7:1, 8:1, 9:1, 10:1. In some embodiments, radionuclides conjugated to a miniprotein does not present toxicity. In some embodiments, a composition comprising a miniprotein and radionuclide does not accumulate in the liver, spleen, and the pancreas and is cleared rapidly when administered to a subject. For instance, in some embodiments, after administration to a subject, biodistribution and $t_{1/2}$ in the kidney is >10% of the injected dose (ID) in tumors at 24 hrs and tumors is >3% ID at 24 hrs.

In some embodiments, a dose calculation comprises or consists of a dose calculation for a compound comprising a radionuclide and/or a compound comprising a decoy. In some embodiments, a decoy dose calculation depends on a dose of a radionuclide (e.g., nCi). In some embodiments, a decoy, when administered (e.g., co-administered, e.g., before, concomitant with, after administration of a radionuclide) is dosed at an excess (a mass or molar excess) as compared to the radionuclide dose. For example, in some embodiments, a dose excess may be 1, 2, 3, 4, 5, 10, 25, 50, 100, 250, 500, 750, 1,000, 1,250, 1,500, 1,750, 2,000, 2,250, 2,500, 2,750, 3,000, 3,250, 3,500, 3,750, 4,000, 4,250, 4,500, 4,750, 5,000, 7,500, 10,000-fold excess, or greater. In some embodiments, the excess is a fold-excess based on molarity of the concentration of a compound and/or radionuclide. In some embodiments, the excess is a fold-excess based on mass of the concentration of a compound and/or radionuclide.

In some embodiments, a dose calculation may include more than one administration of a given compound (e.g., a radioactive compound, e.g., a radionuclide-labeled compound of the disclosure, etc.). For example, in some embodiments, dose is measured as absorbed dose to a location (e.g., a tissue, e.g., an organ, e.g., kidney). In some such embodiments, dose can be measured using methods know to those of skill in the art, such as in RBE5Gy/MBq, and dose limits, such as for a particular organ, are determined by guidelines, such as accepted clinical guidelines known to those of ordinary skill in the art. Without wishing to be bound by theory, the disclosure contemplates that co-administration (e.g., of a radionuclide compound of the disclosure and a decoy of the disclosure) can allow a greater number of administrations of the radionuclide-labeled compound as compared to the radionuclide compound alone (in the absence of a decoy). In some embodiments, a number of administrations increases while absorbed dose (e.g., to kidney, e.g., to liver) decreases. In some embodiments, co-administration of a decoy with a target-binding radionuclide of the disclosure reduces an absorbed dose to the kidney by 5, 10, 15, 20, 25, 30, 35, 40, 45, 50, 55, 60, 65% or more. In some embodiments, number of administrations achieved with co-administration increases by 5, 10, 15, 20, 25, 30, 35, 40, 45, 50, 55, 60, 65% or more. In some embodiments, absorbed dose to the kidney decreases while number of administrations increases. In some embodiments, administration of the decoy enables higher dosing with one or more radiotherapeutic treatments. as compared to dosing in the absence of a decoy with no change in toxicity grade of the therapeutic.

Non-Tumor Tissue Uptake and Retention

Among other things, the disclosure provides the insight that administration of a conjugate (e.g., a radiotherapeutic conjugate) of the disclosure in combination with a decoy can reduce uptake and/or retention of a radioactive compound in non-tumor tissue. Without being limited by theory, the disclosure contemplates that administration of a decoy along with a therapeutic molecule, such as a radiotherapeutic for use in targeting tumor cells (e.g., in a tumor) can be improved including by (1) decreasing off-target uptake, accumulation, retention excretion, and/or non-tumor tissue toxicity; and/or (2) improving uptake and/or retention in a tumor tissue comprising tumor cells. In some embodiments, a tumor is not in a kidney or a liver tissue. In some embodiments, non-tumor tissue uptake and/or retention is reduced in kidney tissue. In some embodiments, non-tumor tissue uptake and/or retention is reduced in liver tissue.

In some aspects, the disclosure provides methods and compositions to address undesirable effects of radionuclide therapy upon transit through the kidney and/or liver. Accordingly, disclosed herein are compositions (e.g., comprising target-binding miniproteins) characterized to exhibit reduced non-tumor tissue uptake and/or retention, or compositions characterized to bind to a target and used in combination with one or more additional proteins such as decoys provided to block uptake and/or retention of compositions into non-tumor tissues. In some embodiments, non-tumor tissues include one or more of liver and kidney.

The disclosure contemplates that, in some embodiments, kidney and/or liver retention and/or uptake or absorption of peptide-based radiopharmaceuticals may be attributed as a result of target expression in an organ such as kidney (e.g., PSMA), or protein conservation from ultrafiltration and reuptake into the proximal tubule cells, or expression of one or more receptors or co-receptors that uptakes proteins and/or molecules into the kidney for clearance through the body. Reuptake in the proximal tubule cells of kidney is thought to occur through protein or peptide cleavable by the kidney brush border peptidases and reuptake of short peptides, as well as receptor mediated reuptake. Without wishing to be bound by theory, in receptor mediated reuptake, a peptide-based radiopharmaceutical may bind to the megalin/cubulin receptor complex of the kidney, undergo receptor mediated endocytosis, and get degraded and retained in lysosomes, which can result in extended retention of radioactivity in the proximal tubules of the kidneys and dose-limiting toxicity of the radiopharmaceutical. Geenen et al., Nucl. Med. Biol, 2021, 102-103: 1-11.

Similarly, uptake and/or retention into the liver may occur through one or more liver-specific cellular uptake mechanisms which could cause uptake and/or extended retention and/or accumulation, and/or metabolisis of a compound (e.g., a radiolabeled compound) in the liver.

The disclosure provides decoys and uses thereof to block uptake and/or retention in non-tumor tissue (e.g., kidney tissue, e.g., liver tissue) by a target-binding miniprotein (e.g., a radiolabeled target-binding miniprotein such as a radiolabeled compound as provided in Table 2A, Table 2C, and/or otherwise herein).

Thus, among other things, provided herein, are improvements in methods of use or treatment of compositions comprising a target-binding miniprotein (e.g., to a target (e.g., B7-H3), e.g., a miniprotein or compound of Table 2A, e.g., a miniprotein or compound of Table 2C). Improvements can be achieved, for example, by co-administration of a decoy with a target-binding miniprotein (e.g., a radionuclide labeled miniprotein, e.g., a miniprotein or compound as provided in Table 2A, e.g., a miniprotein or compound of Table 2C, e.g., a miniprotein that binds to a target (e.g., B7-H3)). In some embodiments, an improvement comprises blocking absorption and/or uptake and/or retention of a compound into the kidney and/or liver by co-administration with a decoy. In some embodiments, the decoy is a scaffold A decoy. In some embodiments, the decoy is a scaffold B decoy. In some embodiments, the scaffold of the target-binding miniprotein or compound is the same or is different from the co-administered decoy. In certain embodiments, the target-binding (B7-H3-binding) miniprotein or compound is not a Scaffold A or Scaffold B miniprotein.

In some embodiments, the disclosure provides a method comprising means for blocking uptake into kidney tissue of a target-binding miniprotein or compound provided herein. In some such embodiments, the means for blocking comprises or consists of a decoy. In some embodiments, the decoy is selected from any of C10 and C118-C120 and/or has an amino acid sequence comprising, consisting essentially of, or consisting of any of SEQ ID NO: 7 or SEQ ID NOs: 97-99. In some embodiments, the decoy is a scaffold A peptide (e.g., C118-C120, e.g., SEQ ID NOs: 97-99). In some embodiments, the decoy is a scaffold B peptide (e.g., C10, e.g., SEQ ID NO: 7).

Nucleic Acids

Among other things, the present disclosure provides herein polynucleotides and methods of use thereof. In some embodiments, all or a portion of the polynucleotides encode a polypeptide (e.g., a miniprotein) that specifically binds to B7-H3. In some embodiments, the B7-H3 is murine or human B7-H3. In some embodiments, the nucleic acid sequence has a specific sequence. In some embodiments, a polynucleotide of the present disclosure is codon-optimized (i.e., the nucleic acid sequence is codon optimized).

In some embodiments, a polynucleotide of the present disclosure comprises or consists of a nucleic acid sequence encoding a polypeptide that is or comprises a miniprotein that specifically binds to B7-H3. or any portion, fragment, or variant thereof.

In some embodiments, a miniprotein is represented by a nucleic acid molecule encoding an amino acid that, when folded, comprises one or more disulfide bridges.

In some embodiments, for example, a nucleic acid molecule (e.g., a polynucleotide) may be non-identical to a reference sequence as provided herein, but still encode a binder as provided by the present disclosure. In some such embodiments, such as a provided polynucleotide (e.g., encoding a miniprotein or analog thereto) hybridizes under stringent conditions as disclosed herein.

In some embodiments, the present disclosure provides nucleic acid molecules comprising a fragment of any polynucleotide as provided herein. In some embodiments, a polynucleotide fragment comprises or consists of a portion of contiguous nucleic acid residues. For instance, in some embodiments, a polynucleotide fragment comprises or consists of 20, 25, 30, 35, 40, 45, 50, 55, 60, 65, 70, 75, 80, 85, 100 or more nucleic acid residues.

In some embodiments, fragments of the present disclosure display utility in a variety of systems and methods. For example, the fragments may be used as probes in various assays. For instance, in some embodiments, fragments may be used in hybridization techniques. Depending on the method, the target nucleic acid sequences may be either DNA or RNA. The target nucleic acid sequences may be fractionated (e.g., by gel electrophoresis) prior to the hybridization, or the hybridization may be performed on samples in situ. One of skill in the art will appreciate that nucleic acid probes of known sequence find utility in determining chromosomal structure (e.g., by Southern blotting) and in measuring gene expression (e.g., by Northern blotting). In such experiments, the sequence fragments are preferably detectably labeled, so that their specific hybridization to target sequences can be detected and optionally quantified. In some embodiments, fragments may be used as probes, e.g., such as when immobilized on a microarray. Methods for creating microarrays by deposition and fixation of nucleic acids onto support substrates are well known in the art. Reviewed in DNA Microarrays: A Practical Approach (Practical Approach Series), Schena (ed.), Oxford University Press (1999) (ISBN: 0199637768); Nature Genet. 21(1) (suppl):1-60 (1999); Microarray Biochip: Tools and Technology, Schena (ed.), Eaton Publishing Company/BioTechniques Books Division (2000) (ISBN: 1881299376), the disclosures of which are incorporated herein by reference in their entireties. Analysis of, for example, gene expression using microarrays comprising nucleic acid sequence fragments, such as the nucleic acid sequence fragments disclosed herein, is a well-established utility for sequence fragments in the field of cell and molecular biology. Other uses for sequence fragments immobilized on microarrays are described in Gerhold et al., Trends Biochem. Sci. 24:168-173 (1999) and Zweiger, Trends Biotechnol. 17:429-436 (1999); DNA Microarrays: A Practical Approach (Practical Approach Series), Schena (ed.), Oxford University Press (1999) (ISBN: 0199637768); Nature Genet. 21(1)(suppl):1-60 (1999); Microarray Biochip: Tools and Technology, Schena (ed.), Eaton Publishing Company/BioTechniques Books Division (2000) (ISBN: 1881299376).

One of skill in the art will appreciate that the nucleic acid fragments of the present disclosure may be used in a wide variety of techniques capture and/or detection techniques not specifically described herein.

In some embodiments, a polynucleotide of the present disclosure comprises or consists of a sequence that encodes a polypeptide of SEQ ID NOs: 4-6, 8-94, 100-537 and/or as set forth in Tables 1B, 1C, 1D, 1E, 2A and/or 2C or a portion or functional variant thereof. In some such embodiments, a polynucleotide encodes a polypeptide, such as those set forth in 4-6, 8-94, 100-537 and/or as set forth in Tables 1B, 1C, 1D, 1E, 2A and/or 2C or a portion or functional variant thereof, that binds to a target represented by SEQ ID NOs 1 or 2.

In some embodiments, a polynucleotide of the present disclosure comprises or consists of a nucleic acid sequence encoding a polypeptide that is or comprises a miniprotein that binds to B7-H3 or any portion, fragment, or variant thereof. In some embodiments, the polynucleotide encodes a polypeptide that comprises or consists of the amino acid sequence set forth in any one of SEQ ID NOs: 4-6, 8-94, 100-537 and/or as set forth in Tables 1B, 1C, 1D, 1E, 2A and/or 2C or a portion or functional variant thereof. In some embodiments, the polynucleotide encodes a polypeptide sequence having at least 70%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or more identity to the amino acid sequences provided in a polypeptide according to those set forth in TABLES 1B-1E and/or a polypeptide of a compound of Table 2A or 2C.

In some embodiments, the disclosure provides an isolated polynucleotide comprising one or more nucleic acid sequences encoding a polypeptide selected from any one of SEQ ID NOs: 4-6, 8-94, 100-537 and/or as set forth in Tables 1B, 1C, 1D, 1E, 2A and/or 2C; or a nucleic acid sequence encoding a polypeptide comprising at least 90%, 95%, 96%, 97%, 98%, 99% or greater identity to any one of SEQ ID NOs: 4-6, 8-94, 100-537 and/or as set forth in Tables 1B, 1C, 1D, 1E, 2A and/or 2C.

In some embodiments, a miniprotein comprises one or more disulfide bridges. In some embodiments, a miniprotein is represented by a nucleic acid sequence encoding a polypeptide that, when folded, comprises one or more disulfide bridges.

In some embodiments, the present disclosure provides nucleic acid molecules comprising or consisting of a sequence as set forth in SEQ ID NO: 1 or SEQ ID NO: 2, or variations (e.g., codon-optimized) thereof.

In some embodiments, for example, a nucleic acid molecule (i.e., a polynucleotide) may be non-identical to a reference sequence as provided herein, but still encode a miniprotein or close analog as provided by the present disclosure (e.g., a miniprotein in accordance with any one of SEQ ID NOs: 34-6, 8-94, 100-537 and/or as set forth in Tables 1B, 1C, 1D, 1E, 2A and/or 2C or a portion or functional variant thereof as provided for herein). In some such embodiments, such as provided polynucleotide (i.e., encoding a miniprotein or analog thereto) hybridizes under stringent conditions as disclosed herein.

In some embodiments, the present disclosure provides nucleic acid molecules comprising a fragment of any polynucleotide as provided herein. In some embodiments, a polynucleotide fragment comprises or consists of a portion of contiguous nucleic acid residues identical to that of a polynucleotide of any of SEQ ID NOs: 4-6, 8-94, 100-537 and/or as set forth in Tables 1B, 1C, 1D, 1E, 2A and/or 2C or a portion or functional variant thereof. For instance, in some embodiments, a polynucleotide fragment comprises or consists of 20, 25, 30, 35, 40, 45, 50, 55, 60, 65, 70, 75, 80, 85, 100 or more nucleic acid residues encoding some or all of a polypeptide or fragment thereof as set forth in any one of SEQ ID NOs: 34-6, 8-94, 100-537 and/or as set forth in Tables 1B, 1C, 1D, 1E, 2A and/or 2C or a portion or functional variant thereof.

Vectors

Also provided herein are vectors, including expression vectors, which comprise, among other things, nucleic acids comprising or consisting of sequences encoding miniproteins that specifically bind to B7-H3. In some embodiments, a vector is used to produce a polypeptide encoding a binder that binds to B7-H3. In some embodiments, the B7-H3 is murine or human B7-H3. In some embodiments, given appropriate contexts, a miniprotein is represented by an amino acid sequence with a corresponding nucleic acid sequence that has been codon optimized. In some such embodiments, one of skill in the art is capable of designing and optimizing polynucleotides that correspond to amino acids of miniproteins that bind to a target (e.g., B7-H3), for which exemplary amino acid sequences are set forth in Table 1A. In some embodiments, a vector comprises a nucleic acid sequence that comprises or consists of a sequence encoding B7-H3.

In some embodiments, the vector comprises a nucleic acid sequence encoding B7-H3 or a fragment or variant thereof, wherein the polynucleotide is codon-optimized (i.e., the nucleic acid sequence is codon optimized). In some embodiments, the vector comprises a nucleic acid sequence encoding up to 100 amino acids. In some embodiments, a vector of the present disclosure comprises or consists of a nucleic acid sequence that encodes an amino acid sequence of a miniprotein. In some embodiments, the vectors of the present disclosure further comprise a nucleic acid sequence as provided herein operably linked to one or more expression control sequences.

Also provided herein are vectors, including expression vectors, which comprise, among other things, nucleic acids comprising or consisting of those described herein. In some embodiments, a vector is used to produce a polypeptide encoding a miniprotein that binds to B7-H3. In some embodiments, the B7-H3 is murine or human B7-H3. In some embodiments, given appropriate contexts, a B7-H3 miniprotein (e.g., as provided in Table 2A and/or Table 2C) has a corresponding nucleic acid sequence that has been codon-optimized. In some such embodiments, one of skill in the art is capable of designing and optimizing polynucleotides that correspond to amino acids of particular B7-H3 miniproteins such as, for example, polynucleotides comprising nucleic acid sequences that correspond to amino acid sequences of Table 2A and/or Table 2C.

In some embodiments, a vector comprises a nucleic acid sequence encoding a miniprotein that binds to a protein comprising all or a portion of the amino acid sequence set forth in SEQ ID NO: 1. In some embodiments, a vector comprises a nucleic acid sequence encoding a miniprotein that binds to a protein comprising all or a portion of the amino acid sequence set forth in SEQ ID NO: 2.

In some embodiments, a vector comprises a nucleic acid sequence that comprises or consists of a sequence having 70%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or more identity to wild type B7-H3. In some embodiments, the vector comprises a nucleic acid sequence encoding B7-H3 or a fragment or variant thereof, wherein the polynucleotide is codon-optimized (i.e., the nucleic acid sequence is codon-optimized). In some embodiments, the vector comprises a nucleic acid sequence encoding up to 50, 55, 60, 65, 70, 75, 80, 85, 90, 95, or 100 amino acids of any one of SEQ ID NOs: 4-6, 8-94, 100-537 and/or as set forth in Tables 1B, 1C, 1D, 1E, 2A and/or 2C or a portion or functional variant thereof. In some embodiments, a vector of the present disclosure comprises or consists of a nucleic acid sequence, wherein the nucleic acid sequence encodes an amino acid sequence comprising those as set forth in in TABLES 1B, 1C, 1D, and/or 2A or a portion or functional variant thereof. In some embodiments, the nucleic acid sequence is a codon-optimized nucleic acid sequence. In some embodiments, the vectors of the present disclosure further comprise a nucleic acid sequence as provided herein operably linked to one or more expression control sequences.

Host Cell Transformants

In some embodiments, the present disclosure provides host cells transformed with polynucleotides, polypeptides, and/or vectors of the present disclosure, and any combinations as well as any descendants thereof. In some embodiments host cells comprise and carry nucleic acid sequences of the present disclosure on vectors. In some embodiments, a host cell is a cell line. In some embodiments, a host cell is a primary cell, such as an immune cell. In some embodiments, such a primary cell is derived from or made compatible with a subject. In some embodiments, a subject is a mammal. In some embodiments, a mammal is a human. In some embodiments, a human is at risk of having or has been diagnosed as having cancer. In some embodiments, the disclosure provides a host cell transformed with an isolated polypeptide or vector as provided herein.

In some such embodiments, such vectors may but need not be freely replicating vectors. In some embodiments, nucleic acid sequences or polynucleotides provided by the present disclosure have been integrated into a genome of a host cell.

In some embodiments, host cells of the present disclosure can be mutated by recombination with a disruption, deletion, or mutation of the isolated nucleic acid of the present disclosure so that the activity of one or more functional activities in the host cell is reduced or eliminated compared to a host cell lacking the mutation.

Without limitation, and as will be appreciated by those of skill in the art, a wide variety of host cells is contemplated in various embodiments in order to express binders of the present disclosure (via use of, e.g., nucleic acid sequences, amino acid sequences, and/or additional components as provided here).

Combination Compositions

The disclosure provides the insight that a combination of one or more components provided herein may confer one or more advantages, such as improvement in treatment, for a subject or group of subjects in need thereof. For example, a combination composition may comprise a radionuclide therapeutic as provided herein and a decoy peptide (decoy) as provided herein. Such compositions may each be provided in a different container, but administered "together" which can be concomitant or serial administration. Without wishing to be bound by theory, the disclosure contemplates that a combination composition provides one or more positive effects on a disease, disorder, or condition as disclosed herein that is at least as good or better, relative to either composition of the combination alone.

Combination compositions can include miniproteins (e.g., in a fusion, as a decoy) having the same or different scaffolds as one another. For example, a combination composition may comprise a compound or miniprotein as provided herein, such as a radionuclide conjugate comprising a miniprotein (M), and a decoy, where the miniprotein of the conjugate is a scaffold A miniprotein and the decoy is a scaffold A decoy. In certain embodiments, the miniprotein may be a scaffold B miniprotein such as an affibody and the decoy may be a scaffold A decoy. In some embodiments, the miniprotein may be a scaffold B miniprotein and the decoy can be a scaffold B decoy.

In one aspect, the disclosure provides a combination composition comprising: (i) a radionuclide therapeutic comprising a composition represented by the formula selected from one or more of M-L-C-R, M-L-C, M-C-R, M-L-R, M-C, M-L, and M-R, wherein M comprises a miniprotein (M), L comprises a linker (L), C comprises a chelator (C), and R comprises a radionuclide (R), wherein the M is of a particular scaffold; and (ii) a decoy comprising or consisting of an amino acid sequence selected from SEQ ID NO: 7 or SEQ ID NOs: 97-99. In some embodiments, the decoy does not comprise the same scaffold as the M. In some embodiments, the decoy comprises a scaffold A decoy. In some embodiments, the decoy comprises a scaffold B decoy. In certain embodiments, the miniprotein is or comprises a scaffold B miniprotein.

In another aspect, the disclosure provides a combination composition comprising a conjugate comprising miniprotein (M) or compound selected from any of Table 2A or Table 2C and a decoy. In some embodiments, the decoy is of a scaffold that is the same scaffold as a B7-H3 binding protein as provided herein (e.g., Table 2A, Table 2C, etc.). In some embodiments, the decoy is selected from any of compounds C10 or C118-C120, and/or has an amino acid sequence comprising, consisting essentially of, or consisting of any of SEQ ID NO: 7 or SEQ ID NOs: 97-99. In certain embodiments, the decoy is administered together or separately from a conjugate as provided herein (e.g., a radioactive conjugate, e.g., a radionuclide therapeutic as provided herein). In certain embodiments, the decoy is administered prior to or after the conjugate. In certain embodiments, administration of a therapeutic compound (e.g., comprising a miniprotein, e.g., a radionuclide therapeutic) is administered concomitant with the decoy. In certain embodiments, the sequential administering comprises administering the decoy followed by administering the composition comprising the miniprotein (M) (e.g., a radionuclide therapeutic as disclosed herein). In certain embodiments, the sequential administering comprises administering the composition comprising the miniprotein (e.g., a radionuclide therapeutic as disclosed herein) followed by administering the decoy.

Pharmaceutical Compositions

The present disclosure provides, among other things, pharmaceutical compositions comprise a polypeptide, polynucleotide, vector and/or host cell encoding a miniprotein (e.g., affibody, CDP, knottin, binder, engineered Kunitz domain, monobody, anticalin, designed ankyrin repeat domain (DARPin), avimer) as provided herein. It is to be understood that a pharmaceutical composition comprising a miniprotein (e.g., affibody, CDP, knottin, binder, engineered Kunitz domain, monobody, anticalin, designed ankyrin repeat domain (DARPin), avimer) is interpreted as a pharmaceutical composition comprising a miniprotein (e.g., affibody, CDP, knottin, binder, engineered Kunitz domain, monobody, anticalin, designed ankyrin repeat domain (DARPin), avimer) per se and/or one or more components encoding a miniprotein (e.g., affibody, CDP, knottin, binder, engineered Kunitz domain, monobody, anticalin, designed ankyrin repeat domain (DARPin), avimer) (e.g., a vector, e.g., a host cell). In some embodiments, a pharmaceutical composition comprises a linker and a chelator. In some embodiments, a pharmaceutical composition comprises a linker, chelator, and radionuclide. In some embodiments, a composition comprises a miniprotein, optional linker, and chelator. In some embodiments, a composition comprises a miniprotein, optional linker, chelator, and radionuclide. In some embodiments, a pharmaceutical composition provided by the present disclosure comprises a miniprotein (e.g., affibody, CDP, knottin, binder, engineered Kunitz domain, monobody, anticalin, designed ankyrin repeat domain (DARPin), avimer) that selectively binds to B7-H3. In some embodiments, the B7-H3 is human B7-H3.

In some embodiments, a pharmaceutical composition comprises a combination of miniprotein conjugate that is radiolabeled as provided herein and a miniprotein that is not conjugated.

In some embodiments, the present disclosure provides pharmaceutical compositions comprising a conjugate in accordance with the present disclosure and a pharmaceutically acceptable excipient.

In some embodiments, the composition is formulated for intravenous administration. In some embodiments, the composition is formulated for subcutaneous administration. In some embodiments, the composition is formulated for parenteral or oral administration.

In some embodiments, a pharmaceutical composition comprises a combination of a miniprotein conjugate that is conjugated to a radionuclide as provided herein and a miniprotein conjugate that is conjugated to a cold-metal surrogate as provided herein.

In some embodiments, a pharmaceutical composition comprises a combination of miniprotein conjugate that is radiolabeled with an alpha emitter radionuclide as provided herein and a miniprotein that is radiolabeled with a beta emitter radionuclide.

In various embodiments, compositions disclosed herein comprise a plurality of miniprotein conjugates, wherein each miniprotein conjugate is represented by a formula selected from one or more of (M)x-L-C-R, (M)x-L-C, (M)x-C-R, (M)x-L-R, (M)x-C, (M)x-L, and (M)x-R, wherein M comprises a miniprotein (M), L comprises a linker (L), C comprises a chelator (C), R comprises a radionuclide (R), and x is 1, 2, 3, or 4, wherein M comprises an amino acid sequence of any one of SEQ ID NOs: 4-6, 8-94, 100-537 and/or as set forth in Tables 1B, 1C, 1D, 1E, 2A and/or 2C. In various embodiments, the plurality of miniprotein conjugates comprise at least a first subset and a second subset. For example, a first subset of the plurality of miniprotein conjugates comprise radionuclides (R) comprising a hot radionuclide and a second subset of the plurality of miniprotein conjugates comprise radionuclides (R) comprising a cold-metal surrogate of a radionuclide.

In various embodiments, the first subset accounts for less than 10%, less than 20%, less than 30%, less than 40%, less than 50%, less than 60%, less than 70%, less than 80%, or less than 90% of miniprotein conjugates in the plurality of miniprotein conjugates. In various embodiments, the second subset accounts for less than 10%, less than 20%, less than 30%, less than 40%, less than 50%, less than 60%, less than 70%, less than 80%, or less than 90% of miniprotein conjugates in the plurality of miniprotein conjugates.

In various embodiments, the first subset of the plurality of miniprotein conjugates comprise radionuclides (R) comprises an alpha emitter and a second subset of the plurality of miniprotein conjugates comprise radionuclides (R) comprises a beta emitter. In various embodiments, the first subset accounts for less than 10%, less than 20%, less than 30%, less than 40%, less than 50%, less than 60%, less than 70%, less than 80%, or less than 90% of miniprotein conjugates in the plurality of miniprotein conjugates. In various embodiments, the second subset accounts for less than 10%, less than 20%, less than 30%, less than 40%, less than 50%, less than 60%, less than 70%, less than 80%, or less than 90% of miniprotein conjugates in the plurality of miniprotein conjugates.

In various embodiments, compositions disclosed herein comprise one or more isolated polypeptides comprising an amino acid sequence of any one of SEQ ID NOs: 4-6, 8-94, 100-537 and/or as set forth in Tables 1B, 1C, 1D, 1E, 2A and/or 2C. For example, such isolated polypeptides can be mixed in the composition with a plurality of miniprotein conjugates. In various embodiments, the miniprotein conjugates have an amino acid sequence selected from SEQ ID NOs: 4-6, 8-94, 100-537 and/or as set forth in Tables 1B, 1C, 1D, 1E, 2A and/or 2C and the isolated polypeptides have the same amino acid sequence selected from SEQ ID NOs: 34-6, 8-94, 100-537 and/or as set forth in Tables 1B, 1C, 1D, 1E, 2A and/or 2C. An example of an isolated polypeptide is a polypeptide that is not conjugated to a linker, a chelator, or a radionuclide. For example, an isolated polypeptide may, in various embodiments, consist of an amino acid sequence selected from SEQ ID NOs: 4-6, 8-94, 100-537 and/or as set forth in Tables 1B, 1C, 1D, 1E, 2A and/or 2C.

In certain embodiments, a pharmaceutical composition comprises a miniprotein (e.g., affibody, CDP, knottin, binder, engineered Kunitz domain, monobody, anticalin, designed ankyrin repeat domain (DARPin), avimer) comprising one or more cysteine-rich domains. In some embodiments, the pharmaceutical composition comprises a miniprotein (e.g., affibody, CDP, knottin, binder, engineered Kunitz domain, monobody, anticalin, designed ankyrin repeat domain (DARPin), avimer) having one or more disulfide bonds. In some embodiments, the pharmaceutical composition comprises a miniprotein (e.g., affibody, CDP, knottin, binder, engineered Kunitz domain, monobody, anticalin, designed ankyrin repeat domain (DARPin), avimer) represented or encoded by an amino acid sequence having <100 amino acids (AAs), <90AAs, <80AAs, <85AAs, <75AAs, <70AAs, <65AAs, <60AAs, <55AAs, <50AAs, <45AAs, <40AAs, <35AAs, <30AAs, <25AAs, <20AAs, <15AAs, or <10AAs.

In some embodiments, a pharmaceutical composition comprising a miniprotein (e.g., affibody, CDP, knottin, binder, engineered Kunitz domain, monobody, anticalin, designed ankyrin repeat domain (DARPin), avimer) as provided herein is characterized as having a molecule weight equal to or less than 12 kDa.

In some embodiments, a pharmaceutical composition comprising a miniprotein (e.g., affibody, CDP, knottin, binder, engineered Kunitz domain, monobody, anticalin, designed ankyrin repeat domain (DARPin), avimer) does not elicit an undesirable immune response or elicits a tolerable immune response. In some embodiments, a pharmaceutical composition of the present disclosure comprises a miniprotein (e.g., affibody, CDP, knottin, binder, engineered Kunitz domain, monobody, anticalin, designed ankyrin repeat domain (DARPin), avimer) having high tissue penetrating properties.

In some embodiments, a pharmaceutical composition comprising a miniprotein comprises acceptable half-life and/or stability. In some such embodiments, acceptable stability is between about 30 minutes to 48 hours in serum and 1-4 days or more in a tumor or tumor microenvironment. By way of non-limiting example, for instance, in some embodiments, a miniprotein of the present disclosure has stability of about 2.5 hours in serum. In some embodiments, stability of a miniprotein is about 30 minutes, 60 minutes, 1, 2, 3, 4, 5, 6, 7, 8, 9, 10, 11, 12, 13, 14, 15, 16, 1718, 19, 20, 21, 22, 23, 24, 30, 36, 40, or 48 hours in serum. In some embodiments, stability in a tumor or tumor microenvironment is 24, 36, 48, 60, 72, 84, 96 hours or more.

In some embodiments, the pharmaceutical composition is characterized as stable in vivo. In some embodiments, a pharmaceutical composition provided herein is not taken up in kidney or liver.

In some embodiments, a pharmaceutical composition provided herein is taken up and/or retained in a tissue, such as a non-tumor tissue, for example, kidney or liver. In some such embodiments, where a pharmaceutical composition is taken up and/or retained in a tissue, the uptake and/or retention is blocked by co-administration with a decoy as provided herein. In some embodiments, a pharmaceutical composition provided herein does not bind megalin and/or cubulin. In some embodiments, a pharmaceutical composition provided herein, when taken up in kidney or liver, clears kidney and/or liver faster than a pharmaceutical composition not comprising a polypeptide as provided herein. In some such embodiments, such clearance is improved by co-administration of a decoy. In some embodiments, biodistribution may be measured at a timepoint in accordance with the percent injected dose per gram of a tissue (% ID/g). For example, biodistribution in a tumor in a subject (e.g., a murine subject, e.g., a human subject) of a pharmaceutical composition can be measured in accordance with % ID/g of the tumor tissue. In some embodiments, biodistribution of a composition disclosed herein in a tumor in a subject (e.g., a murine subject, e.g., a human subject) is between about 1 and about 300% ID/g, between about 1.5 and about 200% ID/g, between about 2 and about 100% ID/g, between about 2.5 and about 50% ID/g, between about 3 and about 40% ID/g, between about 3.5 and about 30% ID/g, between about 4 and about 20% ID/g, between about 4.5 and about 10% ID/g, or between about 5 and about 8% ID/g. In some embodiments, biodistribution of a composition disclosed herein in a tumor in a subject (e.g., a murine subject, e.g., a human subject) is between about 10 and about 300% ID/g, between about 30 and about 250% ID/g, between about 50 and about 200% ID/g, between about 75 and about 180% ID/g, between about 85 and about 160% ID/g, between about 100 and about 150% ID/g, between about 110 and about 140% ID/g, between about 120 and about 130% ID/g, or between about 124 and about 126% ID/g. In some embodiments biodistribution in a tumor in a subject (e.g., a murine subject, e.g., a human subject) of a pharmaceutical composition as provided herein four and/or 24 h after administration is greater than 5% ID/g, 10% ID/g, 15% ID/g, 20% ID/g, 40% ID/g, 60% ID/g, 80% ID/g, 100% ID/g, 120% ID/g, 140% ID/g, 160% ID/g, 180% ID/g, or 200% ID/g.

In some embodiments, biodistribution in a tumor in a subject (e.g., a murine subject, e.g., a human subject) of a pharmaceutical composition as provided herein is measured at four hours after administration and is between about 1 and about 10 (% ID/g), between about 1 and about 9 (% ID/g), between about 1 and about 8 (% ID/g), between about 1 and about 7 (% ID/g), between about 1 and about 6 (% ID/g), between about 1 and about 5 (% ID/g), between about 1 and about 4 (% ID/g), between about 1 and about 3 (% ID/g), or between about 1 and about 2 (% ID/g). In some embodiments, concentration in a tumor is greater than concentration in a kidney of a subject to whom a pharmaceutical composition comprising a polypeptide provided herein is administered. In some such embodiments, concentration in a tumor is even greater than in a kidney when the pharmaceutical composition is co-administered with a decoy.

In some embodiments, a pharmaceutical composition as provided herein has a positive tumor/kidney (T/K) % ID/g ratio. In some embodiments, a pharmaceutical composition as provided herein achieves a T/K ratio greater than 0.5% ID/g, 1% ID/g, 1.5% ID/g, 2% ID/g, 2.5% ID/g, 3% ID/g, 3.5% ID/g, 4% ID/g, 4.5% ID/g, 5% ID/g, 5.5% ID/g, 6% ID/g, 6.5% ID/g, 7% ID/g, 7.5% ID/g, 8% ID/g, 8.5% ID/g, 9% ID/g, 9.5% ID/g, or 10% ID/g.

In some embodiments, a pharmaceutical composition as provided herein achieves a T/K ratio greater than 5% ID/g, 10% ID/g, 15% ID/g, 20% ID/g, 25% ID/g, 30% ID/g, 35% ID/g, 40% ID/g, 45% ID/g, 50% ID/g, 55% ID/g, 60% ID/g, 65% ID/g, 70% ID/g, 75% ID/g, 80% ID/g, 85% ID/g, 90% ID/g, 95% ID/g, or 100% ID/g.

In some embodiments, a pharmaceutical composition of the present disclosure exhibits solubility of >0.05 mg/mL, >0.1 mg/mL, >0.2 mg/mL, >0.3 mg/mL, >0.4 mg/mL, >0.5 mg/mL, >0.6 mg/mL, >0.7 mg/mL, >0.8 mg/mL, >0.9 mg/mL, >1 mg/mL, >2 mg/mL, >3 mg/mL, >4 mg/mL, >5 mg/mL, >6 mg/mL, >7 mg/mL, >8 mg/mL, >9 mg/mL, or >10 mg/mL.

In some embodiments, a pharmaceutical composition provided by the present disclosure exhibits stability of >80%, >81%, >82%, >83%, >84%, 85%, >86%, >87%, >88%, >89%, >90%, >91%, >92%, >93%, >94%, 95%, >96%, >97%, >98%, or >99%.

In some embodiments, a pharmaceutical composition of the present disclosure is characterized as comprising a certain purity, represented as a percentage of parent molecule still intact. In some embodiments, a pharmaceutical composition of the present disclosure comprises about 85% purity or greater at 5 days at room temperature. In some embodiments, a pharmaceutical composition of the present disclosure is characterized as having about 90% purity or greater at 40° C. for 4 hr. In some embodiments, a pharmaceutical composition of the present disclosure comprises cyclic or acyclic sequence.

In some embodiments, a pharmaceutical composition in accordance with the present disclosure comprises a miniprotein (e.g., affibody, CDP, knottin, binder, engineered Kunitz domain, monobody, anticalin, designed ankyrin repeat domain (DARPin), avimer) and one or more additional components. For example, in some embodiments, one or more additional components may be a linker and/or a conjugate such as a cytotoxic payload or detectable moiety for use in diagnosis and/or imaging. In some such embodiments, a pharmaceutical composition comprises a linker, chelator, and/or radionuclide as provided herein.

In some embodiments, pharmaceutical compositions modulating, binding, or inhibiting human B7-H3 (or any related activity thereto) are provided. In some embodiments, a pharmaceutical composition is or comprises a therapeutic. In some embodiments, a pharmaceutical composition is or comprises a detectable moiety (e.g., as used for imaging such as MRI, CT, PET, etc.).

In preferred embodiments, one or more characteristics of the pharmaceutical compositions are identified for optimized administration parameters including but not limited to dose, effective dose, dose rate, tumor penetration profile, intracellular localization profile, binding specificity, etc. (See Sofou S. Radionuclide carriers for targeting of cancer. Int J Nanomedicine. 2008; 3(2):181-199. doi:10.2147/ijn.s2736).

In some embodiments, a pharmaceutical composition of the present disclosure does not present toxicity or presents less toxicity than a composition comprising one or more different components such as a larger targeting peptide, or a different radionuclide (e.g., beta emitter, etc.).

In some embodiments, a pharmaceutical composition of the present disclosure does not accumulate in the liver, spleen, and the pancreas and is cleared rapidly. For instance, the biodistribution and $t_{1/2}$ in the kidney is >10% of injected dose (ID; initial dose injected) in tumors at 24 hrs and tumors is >3% ID at 24 hrs.

In some embodiments, a pharmaceutical composition of the present disclosure does not accumulate in the liver, spleen, and/or pancreas and is cleared rapidly. For instance, in some embodiments, after administration to a subject, biodistribution in the kidney is >10% of the injected dose/g (% ID/g) at 24 h and in tumors is >3% ID/g at 24 h. In some embodiments, after administration to a subject, $t_{1/2}$ is shorter than that of, e.g., a B7-H3 antibody, etc.

Theranostic Compositions

In some embodiments, theranostic compositions are provided. In some embodiments, the present disclosure provides a diagnostic or a screening to detect the presence or absence, and/or the level of B7-H3 in a subject or sample. In some embodiments, the subject is a mammal. In some embodiments, the subject is a rodent (e.g., mouse). In some embodiments, the subject is a non-human primate. In some embodiments, the subject is a human and the B7-H3 is human B7-H3. In some embodiments, presence of B7-H3 in a subject is related to a risk of developing a disease, disorder, or condition. In some embodiments, presence of a particular level of B7-H3 indicates an increased risk of developing or diagnosis of a disease, disorder, or condition. In some embodiments, a reduction in a level of B7-H3 (e.g., as compared to a prior measurement) is associated with treatment of a diagnosed disease.

In certain aspects, theranostic compositions are provided. In some embodiments, the present disclosure provides a diagnostic or a screening to detect the presence or absence, and/or the level of human B7-H3 in a subject or sample.

In certain aspects, the present disclosure provides methods for defining the structure activity relationship of a pharmaceutical composition comprising:

(i) a B7-H3-specific miniprotein;
(ii) an optional linker;
(iii) a chelator; and
(iv) a radioactive molecule, wherein the modified polypeptide sequence modulates human B7-H3 activity.

Methods of Screening and Development

In some embodiments, directed evolution and computational folding algorithms can be combined for de novo creation of miniproteins (e.g., affibodies, CDPs, knottins, binders). For example, in some embodiments, hundreds of miniprotein backbones with various secondary structure elements, orientations, and loop lengths can be matched with hotspot binding motifs on a protein target or antigen of interest (e.g., B7-H3). In some such embodiments, if the binding motifs of the miniprotein do not clash with the backbone of the target, the monomer and interaction energies are optimized with Rosetta combinatorial sequence optimization.

In some embodiments, oligonucleotide pools encoding design sequences selected through the computational approach can be synthesized, amplified, and co-transformed into yeast. The resulting yeast libraries displaying the design sequences can be incubated with fluorescently labeled target protein or antigen. Cells that display the designs that bind the target can be retrieved by fluorescence-activated cell sorting (FACS) and deep sequenced. Once miniproteins (e.g., affibodies, CDPs, knottins, binders) are identified either through affinity-maturation or original designs, they can be chemically synthesized or expressed, e.g., in *Escherichia coli*, and purified, and characterized in solution.

In some embodiments, libraries of stable miniproteins (e.g., affibodies, CDPs, knottins, binders) may be developed to allow for screening against specific chosen targets. Such a library designs a hydrophobic core to the miniprotein (e.g., affibody, CDP, knottin, binder, engineered Kunitz domain, monobody, anticalin, designed ankyrin repeat domain (DARPin), avimer) to enable folding in addition to cysteine crosslinking, improving the number of folded structures in a library.

In some embodiments, once miniprotein (e.g., affibodies, CDPs, knottins, binders) are identified or engineered, they may be produced via chemical synthesis or recombinant expression. In some embodiments, a miniprotein (e.g., affibody, CDP, knottin, binder, engineered Kunitz domain, monobody, anticalin, designed ankyrin repeat domain (DARPin), avimer) may be produced by solid phase peptide synthesis followed by in vitro folding. Standard 9-fluorenylmethyloxycarbonyl (Fmoc)-based solid phase peptide chemistry may be employed. In some such embodiments, the linear peptide may then be folded under conditions that promote oxidation of cysteine side chain thiols to form disulfide bonds, followed by purification, e.g., by reversed-phase high-performance liquid chromatography (RP-HPLC). An approach using recombinant DNA may also be employed to produce a miniprotein (e.g., affibody, CDP, knottin, binder, engineered Kunitz domain, monobody, anticalin, designed ankyrin repeat domain (DARPin), avimer) as provided herein.

Iterations between data-driven model improvement and experimental testing with miniproteins (e.g., affibodies, CDPs, knottins, binders) is likely to optimize the folding and binding abilities of miniproteins (e.g., affibodies, CDPs, knottins, binders), to develop pharmaceutically superior specific molecules.

Characterization, Analysis & Synthesis

In some embodiments, a miniprotein (e.g., affibody, CDP, knottin, binder, engineered Kunitz domain, monobody, anticalin, designed ankyrin repeat domain (DARPin), avimer) of the present disclosure is characterized. For example, in some embodiments, binding specificity, binding affinity, binding localization, etc. are performed using methods known to those of skill in the art. For instance, in some embodiments, binding localization is performed using one or more techniques such as immunohistochemistry/immunocytochemistry (e.g., using cell lines or tissue biopsy samples). In some embodiments, binding affinity is performed using surface plasmon resonance measurements. In some such embodiments, binding affinity (e.g., dissociation constant expressed as $K_D$) is measured in one or more assays (e.g., a yeast-based assay where the target is recombinantly expressed in yeast and exposed to a miniprotein (e.g., affibody, CDP, knottin, binder, engineered Kunitz domain, monobody, anticalin, designed ankyrin repeat domain (DARPin), avimer) provided by the present disclosure).

In some embodiments, synthesis and analysis techniques including, without limitation, HPLC, LCMS, CD, quantitative thin layer chromatography and others known to those of skill in the art are used to efficiently synthesize via solid phase peptide synthesis methods, characterize miniprotein (e.g., affibody, CDP, knottin, binder)s and fully optimized clinical pharmaceutical composition candidates.

Methods of Screening and Development of Miniproteins

Directed evolution and computational folding algorithms can be combined for de novo creation of miniproteins as provided herein. In some embodiments, hundreds of miniprotein backbones with various secondary structure elements, orientations, and loop lengths can be matched with hotspot binding motifs on a target of interest (e.g., B7-H3). In some such embodiments, if binding motifs of the miniprotein do not clash with the backbone of the target, the monomer and interaction energies are optimized with Rosetta combinatorial sequence optimization.

In some embodiments, oligo pools encoding the design sequences selected through the computational approach can be synthesized, amplified, and co-transformed into yeast. In some embodiments, resulting yeast libraries displaying the design sequences can be incubated with fluorescently labeled target. In some embodiments, cells that display the designs that bind the target can be retrieved by fluorescence-activated cell sorting (FACS) and deep sequenced. In some embodiments, once miniproteins are identified either through affinity-maturation or original designs, miniproteins can be chemically synthesized or expressed in *Escherichia coli*, purified, and characterized in solution.

In some embodiments, libraries of stable CDPs or knottin peptides may be developed to allow for screening against specific chosen targets. The library designs a hydrophobic core to the miniproteins to enable folding in addition to cystine crosslinking, improving the number of folded structures in a library.

In some embodiments, once miniproteins are identified or engineered, they may be produced via chemical synthesis or recombinant expression. In some embodiments, a miniprotein peptide may be produced by solid phase peptide synthesis followed by in vitro folding. Standard 9-fluorenylmethyloxycarbonyl (Fmoc)-based solid phase peptide chemistry may be employed. In some such embodiments, a linear peptide may then be folded under conditions that promote oxidation of cysteine side chain thiols to form disulfide bonds, followed by purification, e.g., by reversed-phase high-performance liquid chromatography (RP-HPLC). In some embodiments, an approach using recombinant DNA may also be employed to produce a desired miniprotein.

In some embodiments, iterations between data-driven model improvement and experimental testing with miniproteins is likely to optimize the folding and binding abilities of the miniproteins, in order to develop pharmaceutically superior specific molecules.

In some embodiments, the miniprotein or a portion thereof is engineered at the DNA level (e.g., degenerate codons can be introduced by oligonucleotide assembly using overlap extension PCR; or the genetic material can be amplified using flanking primers with sufficient overlap with the yeast display vector for homologous recombination).

Modifications to Miniproteins

In some embodiments, the disclosure further provides one or more modifying components. In some embodiments, a modifying component comprises or consists of an inducible or repressible promoter that is operably linked to the coding sequence of a miniprotein as provided herein. In some embodiments, expression profile of a miniprotein or its underlying amino acid sequence can be altered via the promoter. In some aspects, the expression profile of the miniprotein can be temporally altered or controlled by temporally altering or controlling promoter function. In some embodiments, a promoter may be spatially and/or environmentally controlled. In some embodiments, a modifying component comprises or consists of an enhancer. In some such embodiment, an enhancer is used to modify expression profile of a miniprotein (e.g., binder, affibody, etc.) but not necessarily operably linked to the coding sequence of the binder; rather, in some embodiments, an enhancer is located upstream or downstream of a coding sequence of a miniprotein (e.g., binder, affibody, etc.) of the present disclosure. In some embodiments, an enhancer may be temporally controlled. In some embodiments, an enhancer may be spatially and/or environmentally controlled.

In some embodiments, an expression profile of a miniprotein (e.g., binder, affibody, etc.) and/or a sequence encoding it (e.g., a nucleic acid sequence, e.g., an amino acid sequence such as, e.g., a gene or portion thereof) of the present disclosure can be altered via one or more modifications. In some such embodiments, the one or more modifications comprise one or more mutations in a sequence (e.g., nucleic acid sequence, e.g., amino acid sequence) provided by the present disclosure. In some aspects, a sequence of the present disclosure comprises a deletion relative to a parental sequence or portion thereof.

Modifications may also be made using changes to amino acid sequences and bonds. For example, chemical crosslinking can be used to improve binding ability or affinity of a miniprotein for a target. In some embodiments, changes such as amino acid residues (e.g., lysine, etc., e.g., non-natural amino acids, etc.) fusion proteins, or other chemical moieties can be used to generate miniproteins with enhanced binding and functional activity, e.g., as compared to those without modifications. In some embodiments, miniproteins can be characterized as having small disulfide-rich peptide scaffolds and can have difficulties folding. For example, in some embodiments, miniproteins can form various isomers (e.g., a miniprotein with three core disulfide bonds can, in some embodiments, form at least 15 different isomers). In some such embodiments, such a variety of isomers can impact yield. In some embodiments, miniproteins without cysteine residues (e.g., two or more cysteines, e.g., at least one disulfide bridge) may be modified to improve stability without need for additional chemical crosslinking by increased numbers of disulfide bonds.

A modification (e.g., to a polypeptide amino acid sequence) can refer to an amino acid sequence that comprises at least one substitution, alteration, inversion, addition, or deletion of an amino acid residue compared to a reference amino acid sequence. An alteration can include but is not limited to a change to or of one or more atoms of a side chain, such as, for example addition of a small alkyl group (e.g., a methyl-group) onto the nitrogen of the side chain (e.g., addition of a small alkyl group (e.g., methyl) onto lysine to generate monomethylated lysine). In some embodiments, a natural amino acid is modified such as set forth herein. In some embodiments, a modification includes addition of at least one small alkyl group attached to the nitrogen of an amino acid side chain, such as, for example, a lysine side chain. As used herein, a "small alkyl group" refers to an alkyl group with a short carbon chain, typically having one to four carbon atoms, such as methyl, ethyl, propyl, or butyl, and also including, for example, dimethyl, trimethyl, isopropyl, etc. In some embodiments, for example, one or more small alkyl groups can be added to the nitrogen of a lysine side chain to produce monomethyl, dimethyl, or trimethyllysine. In some embodiments, one, two, three, four or more small alkyl groups may be added to a given amino acid (e.g., through attachment to the nitrogen of the side chain). In some embodiments no more than five, four, three, two, or one small alkyl groups are added. In some embodiments, for example, binding affinity of miniproteins can be improved using an SAR approach. For instance, various amino acid residues within the miniprotein structures can be replaced with optimal substitutions, resulting in improved binding affinity. In some embodiments, these substitutions can include natural and/or non-natural amino acids, conjugated chemical moieties, and/or other small molecule attachments.

In some embodiments, chemical crosslinking can be used to provide proper structural conformation and stability. Proper structural conformation can be critical to retention of certain binding affinity (e.g., in an improved B7-H3 miniprotein, e.g., as compared to a miniprotein that has not been improved using an SAR or other approach). In some embodiments, miniproteins have small disulfide-rich peptide scaffolds and difficulties folding. In some such embodiments, using techniques and approaches known to those of ordinary skill in the art, optimized conditions for folding and purification via reverse-phase HPLC can be used to ensure final (e.g., optimized) compounds (comprising miniproteins as provided herein) have correct structure, conformation, and purity.

Binding Assays

In some embodiments, binding assays are used to determine binding affinities and/or binding/dissociation constants or a composition or one or more components thereof (e.g., of a miniprotein with or without one or more additional components as provided herein). For example, in some embodiments, an equilibrium dissociation constant (Kd) is determined using fluorescent labeling and detection methods. In some embodiments, a cell population (e.g., yeast cells) engineered to express a library of miniproteins (e.g., affibodies, CDPs, knottins, binders) (e.g., binders that bind to a target) is produced. In some embodiments, the cells express a target. Depending on whether a set of cells expresses targets or miniproteins (e.g., affibodies, CDPs, knottins, binders), in some embodiments, a cell library is incubated with a target (e.g., B7-H3) or with a miniprotein (e.g., affibody, CDP, knottin, binder, engineered Kunitz domain, monobody, anticalin, designed ankyrin repeat domain (DARPin), avimer) or set of miniproteins (e.g., affibodies, CDPs, knottins, binders) as provided herein. In some such embodiments, cells and miniproteins (e.g., affibodies, CDPs, knottins, binders) are assessed using flow cytometry and/or FACS analysis to determine binding affinity using methods known to those of skill in the art. (See, e.g., "Chapter Nine—Engineering CDPs as Novel Binding Agents." Methods in Enzymology, edited by K. Dane Wittrup and Gregory L. Verdine, vol. 503, Academic Press, 2012, pp. 223-51. ScienceDirect, doi:10.1016/B978-0-12-396962-0.00009-4.).

Affinity Maturation

In some embodiments, a miniprotein (e.g., affibody, CDP, knottin, binder, engineered Kunitz domain, monobody, anticalin, designed ankyrin repeat domain (DARPin), avimer) of the present disclosure comprises or consists of a sequence that exhibits certain desired affinity ranges for a target. In some embodiments, affinity maturation is performed on a sequence as provided by the present disclosure wherein the affinity matured sequence displays the same or better selectivity and/or affinity for B7-H3 as compared to the starting sequence or another sequence with "less" affinity as compared to the affinity matured sequence. In some embodiments, affinity maturation is performed using a B7-H3 antigen and a sequence that binds to the antigen is that of a miniprotein (e.g., affibody, CDP, knottin, binder, engineered Kunitz domain, monobody, anticalin, designed ankyrin repeat domain (DARPin), avimer) as provided herein.

In some embodiments, affinity maturation is performed on a sequence that selectively binds to B7-H3. In some embodiments, the B7-H3 is human B7-H3.

In preferred aspects of the present disclosure, the modified polypeptide sequence of the pharmaceutical composition comprises nM or sub-nM binding affinity to a target on a cell line expressing human B7-H3, binding potency on protein target or in a cell-based assay.

In certain embodiments, the modified polypeptide sequence comprises a binding affinity of 900, 800, 700, 600, 500, 400, 300. 200, 100, 90, 80, 70, 60, 50, 40, 30 20, 10, 9, 8, 7, 6, 5, 4, 3, 2, 1 nM binding affinity to the human B7-H3. In some embodiments, a polypeptide of the disclosure (e.g., a miniprotein, e.g., a miniprotein conjugate comprising a radionuclide) displays binding specificity to human B7-H3. In some embodiments, the miniprotein comprises a binding affinity characterized by a dissociation constant ranging from about 1 pM to about 500 nM, e.g., 500, 400, 300, 200, 100, 90, 80, 70, 60, 50, 40, 30 20, 10, 9, 8, 7, 6, 5, 4, 3, 2, or 1 nM, 100, 90, 80, 70, 60, 50, 40, 30, 20, 10, 9, 8, 7, 6, 5, 4, 3, 2, or 1 pM binding affinity to human B7-H3. In some embodiments, a dissociation constant (e.g., KD, as measured using surface plasmon resonance), is between about 10 pM and 100 nM. In certain embodiments, the dissociation constant is between about 20 pM and 50 nM. In some embodiments, the dissociation constant is stronger than about 100 nM, 75 nM, 50 nM, 25 nM, 10 nM, 5 nM, 1 nM, 750 pM, 500 pM, 250 pM, 100 pM, 75 pM, 50 pM, 25 pM, 15 pM, 10 pM, 9 pM, 8 pM, 7 pM, 6 pM, 5 pM, 4 pM, 3 pM, 2 pM, or 1 pM.

In some embodiments, a polypeptide (e.g., a miniprotein, e.g., a miniprotein conjugate comprising a radionuclide) in accordance with the present disclosure binds to B7-H3 with a binding affinity of about 1 pM to 100 nM, about 10 pM to about 100 nM, about 10 pM to about 50 nM, etc. In some embodiments, a miniprotein in accordance with the present disclosure binds to B7-H3 with a binding affinity of about 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950 or 1000 nM. In some embodiments, a miniprotein in accordance with the present disclosure binds to B7-H3 with a binding affinity of about 1 pM to 100 pM, 10 pM to 1 nM, 100 pM to 10 nM, or 1 nM to 100 nM.

In one embodiment, the modified polypeptide sequence comprises a binding affinity of 500 nM to human B7-H3.

In more preferred embodiments, the modified polypeptide sequence comprises a picomolar binding affinity.

In some embodiments, a B7-H3 binding polypeptide as provided herein binds to B7-H3 with an affinity no stronger than about 10 pM to no weaker than about 100 nM as measured by SPR.

In other preferred embodiments, the modified polypeptide sequence exhibits selectivity with which the sequence binds to only the B7-H3 protein target.

In some embodiments, affinity maturation is performed using magnetic-based assays. In some embodiments, affinity maturation is performed using flow cytometry/FACS-based assays in accordance with procedures known to those of skill in the art.

Methods of Miniprotein Manufacturing

In some embodiments, synthesis of a miniprotein comprises solid phase synthesis. In some embodiments, miniproteins are synthesized using standard solid phase peptide synthesis as is known to those of skill in the art. (See, e.g., Johannes Meienhofer, Hormonal Proteins and Peptides, Volume II, 1973, Pages 45-267). In some embodiments, SPS comprises synthesis using methods known to those of skill in the art including, for example, Fmoc or Boc amino protecting groups. In some embodiments, synthesis comprises protection from reaction with incoming N-protected amino acids. In some embodiments, synthesized polypeptides are analyzed to determine sequence, structure, and related properties using HPLC/LC-MS.

In some embodiments, a miniprotein is manufactured using recombinant production methods as are known to those of skill in the art including, for example, yeast-based approaches and chemical synthesis.

Methods of Conjugation

In some embodiments, conjugates of the present disclosure comprise a linker and a chelator. In some embodiments, the chelator has a bound radionuclide. In some embodiments, a linker and chelator, or a linker, chelator, and radionuclide are conjugated to a miniprotein. In some embodiments, a chelator and/or radionuclide are conjugated to a miniprotein. In some embodiments, a miniprotein is conjugated to a chelator either directly or through a linker (e.g., a linker described herein). Any known conjugation chemistry can be utilized to conjugate a miniprotein directly to a chelator or to conjugate a linker to the miniprotein and to the chelator.

In some embodiments, a miniprotein comprises a surface exposed functional group to allow for site specific conjugation. In some embodiments, a miniprotein comprises a surface exposed lysine or cysteine residue that can serve for site specific conjugation. In some embodiments, a miniprotein conjugate comprises one or more non-naturally occurring amino acids that can serve for site specific conjugation.

A person of ordinary skill in the art will recognize that numerous chemical conjugation strategies provide ready access to present technology, whereby exposed amino acid residues on a protein undergo well-known reactions with reactive moieties on a chelator.

A person of ordinary skill in the art will recognize that cysteine coupling reactions may be employed to conjugate chelators with thiol-reactive termini to protein surfaces through exposed thiol side chains on cysteine residues on the protein surface. (See generally Tsuchikama & An, supra, at 36-37; see also, e.g., Pierre Adumeau et al., Thiol-Reactive Bifunctional Chelators for the Creation of Site-Selectively Modified Radioimmuno conjugates with Improved Stability, 29 Bioconjugate Chem. 1364 (2018)). In some embodiments, because cysteine residues readily form disulfide linkages with nearby cysteine residues under physiological conditions, rather than existing as free thiols, some cysteine coupling strategies may rely upon selective reduction of disulfides to generate a higher number of reactive free thiols. Cysteine coupling techniques known in the art include, but are not limited to, cys alkylation reactions, cysteine rebridging reactions, and cys-aryl coupling using organometallic palladium reagents. (See, e.g., C. R. Behrens et al., Antibody-Drug Conjugates (ADCs) Derived from Interchain Cysteine Cross-Linking Demonstrates Improved Homogeneity and Other Pharmacological Properties Over Conventional Heterogeneous ADCs, 12 Mol. Pharm. 3986 (2015); Vinogradova et al., Organometallic Palladium Reagents for Cysteine Bioconjugation, 526 Nature 687 (2015); see also Tsuchikama, supra, at 37).

Protein conjugation strategies using non-natural amino acid side chains are also well known in the art. For example, in some embodiments, "click chemistries" provide access to conjugated proteins, by rapid and selective chemical transformations under a diverse range of reaction conditions. In some embodiments, click chemistries are known to yield peptide conjugates with limited by-product formation, despite the presence of unprotected functional groups, in aqueous conditions. For instance, in some embodiments, a click reaction in the formation of conjugated peptides is the copper(I)-catalyzed azide-alkyne 1,3-dipolar cycloaddition reaction (CuAAC). (See Liyuan Liang & Didier Astruc, The Copper(I)-CatalysedAlkyne-Azide Cycloaddition (CuAAC) "Click" Reaction and Its Applications: An Overview, 255 COORD. CHEM. Rev 2933 (2011); see also, e.g., Herman S. Gill & Jan Marik, Preparation of 18F-labeled Peptides using the Copper(I)-Catalyzed Azide-Alkyne 1,3-Dipolar Cycloaddition, 6 Nature Protocols 1718 (2011)). In some embodiments, a CuAAC click reaction may be carried out in the presence of ligands to enhance reaction rates. In some such embodiments, such ligands may include, for example, polydentate nitrogen donors, including amines (e.g., tris (triazolyl)methyl amines) and pyridines. (See Liang & Astruc, supra, at 2934 (collecting examples); P. L. Goias et al., 39 Macromolecules 6451 (2006)). In some embodiments, other widely-utilized click reactions include, but are not limited to, thiol-ene, oxime, Diels-Alder, Michael addition, and pyridyl sulfide reactions.

In some embodiments, copper-free (Cu-free) click methods are also known in the art for delivery of therapeutic and/or diagnostic agents, such as radionuclides (e.g., 18F), chemotherapeutic agents, dyes, contrast agents, fluorescent labels, chemiluminescent labels, or other labels, to protein surfaces. In some embodiments, Cu-free click methods may permit stable covalent linkage between target molecules and prosthetic groups. In some embodiments, Cu-free click chemistry may include reacting an antibody or antigen binding fragment, which has been modified with a non-natural amino acid side chain that includes an activating moiety such as a cyclooctyne (e.g., dibenzocyclooctyne (DBCO)), a nitrone or an azide group, with a prosthetic group that presents a corresponding or complementary reactive moiety, such as an azide, nitrone or cyclooctyne (e.g., DBCO). (See, e.g., David. J. Donnelly et al., Synthesis and Biologic Evaluation of a Novel 18F-Labeled Adnectin as a PET Radio ligand for Imaging PD-L1 Expression, 59 J. NUCL. MED. 529 (2018)). For instance, in some embodiments, where a targeting molecule comprises a cyclooctyne, the prosthetic group may include an azide, nitrone, or similar reactive moiety. In some embodiments, where a targeting molecule includes an azide or nitrone, the prosthetic group may present a complementary cyclooctyne, alkyne, or similar reactive moiety. In some embodiments, Cu-free click reactions may be carried out at room temperature, in aqueous solution, in the presence of phosphate-buffered saline (PBS). In some such embodiments, prosthetic group may be radiolabeled (e.g., with 18F) or may be conjugated to any alternative diagnostic and/or therapeutic agent (e.g., a chelator). (See id. at 531.)

In some embodiments, conjugation chemistries such as the Huisgen cyclo-addition ("click" reaction) are available for synthesis of chelates and peptides. In some embodiments, an efficient, high-yielding three-step synthesis of a versatile monofluoro-substituted cyclooctyne (MFCO) has been shown to facilitate a variety of bioconjugation processes (M. Martin et al., 2013). In some embodiments, MFCO can be utilized to prepare a DOTA derivative for copper-free click chemical addition at an internal azide-modified lysine residue of the CDP or knottin peptide.

In some embodiments, a miniprotein conjugate provided herein has a lysine at a specific position (e.g., in a cysteine knot, or cysteine-dense region) and can be replaced with an azide derivative for "click" chemistry with DOTA-MFCO.

In some embodiments, a DOTA-MFCO-CDP conjugate can be prepared by first coupling an amine-modified DOTA to MFCO, then conjugating the DOTA-MFCO to the azide on the desired lysine of the miniprotein.

In some embodiments, the chelator and miniprotein are joined together by a cycloaddition reaction in the presence of a transition metal catalyst. In some embodiments, a metal catalyst is based on Cu or Rh.

In some embodiments, utilizing solution phase conjugation, a chelator (DOTA) and a miniprotein are joined with 1-ethyl-3-[3-(dimethylamino)propyl](EDC) and N-hydroxysulfonosuccinimide (SNHS) in water (pH 5.5) for 40 min at room temperature using a 1:1:1 molar ratio of DOTA:EDC:SNHS. In some such embodiments, peptides are dissolved in sodium phosphate buffer and added to the above sulfosuccinimidyl ester of DOTA (DOTA-OSSu). In some such embodiments, a molar excess of DOTA-OSSu is used to drive the conjugation on the N-termini of the peptide (See, e.g., Kimura, Richard H et al. "Engineered knottin peptides: a new class of agents for imaging integrin expression in living subjects." Cancer research vol. 69, 6 (2009): 2435-42. doi:10.1158/0008-5472.CAN-08-2495).

In some embodiments, a new DOTA derivative, α-amino-DOTA is prepared with the objective of attaching DOTA to the C-terminus of a peptide, since in some scenarios, the peptide function might be compromised because of DOTA conjugation to the N-terminus or to lysine side chains.

In some embodiments, a miniprotein is generated by solid-phase peptide synthesis (SPPS). The tris-tert-butyl ester of DOTA, a bifunctional ligand (in the salt free, zwitterionic form), is readily soluble in most organic solvents and the tert-butyl ester protection is fully compatible with standard SPPS techniques. The most convenient way of conjugation comprises the addition of DOTA to the N-terminus of the protected peptide chain as the last amino acid in an automated peptide synthesizer followed by cleavage from the resin and removal of the acid-labile protecting groups. It can also be attached to Lys side chains. The preformed activated NHS ester of DOTA-tris(tert-butyl ester) has also been synthesized, and this reagent does not require a coupling agent to couple DOTA to free amino groups. The DOTA unit is linked to peptides through one of the acetate sidearms, and the conjugate has four amino, three carboxylates, and one amide group available for metal binding (See, e.g., De León-Rodríguez L M, Kovacs Z. The synthesis and chelation chemistry of DOTA-peptide conjugates. Bioconjug Chem. 2008 February; 19(2):391-402. doi: 10.1021/bc700328s. Epub 2007 Dec. 12. PMID: 18072717).

In some embodiments, a more general method involves the use of preformed DOTA-amino acid derivatives which allows the introduction of a DOTA unit into any desired position in the peptide sequence without the need of orthogonal protection. Protected DOTA-Lys and DOTA-Phe derivatives that are fully compatible with standard SPPS conditions (N—R-Fmoc protection, free carboxyl for the coupling, and acid-labile tert-butyl protection of the remaining acetate sidearms of the DOTA unit) have been synthesized. These DOTA-amino acids can be used in SPPS to build peptides that incorporate the DOTA moiety in any desired position (See, e.g., De León-Rodríguez L M, Kovacs Z. The synthesis and chelation chemistry of DOTA-peptide conjugates. Bioconjug Chem. 2008 February; 19(2):391-402. doi: 10.1021/bc700328s. Epub 2007 Dec. 12. PMID: 18072717).

General methods for coupling DOTA-type macrocycles to targeting groups through a linker (e.g., by activation of one of the carboxylates of the DOTA to form an active ester, which is then reacted with an amino group on the linker to form a stable amide bond), are known to those skilled in the art. (See e.g., Tweedle et al. U.S. Pat. No. 4,885,363).

A linker may be incorporated between the chelator and the targeting vector to influence the pharmacokinetic properties of the conjugate. Hydrocarbon, PEG, or polypeptide linkers can alter the pharmacokinetics and biodistribution by changing the overall charge and hydrophilicity of the radiopharmaceutical (See, e.g., De León-Rodríguez L M, Kovacs Z. The synthesis and chelation chemistry of DOTA-peptide conjugates. Bioconjug Chem. 2008 February; 19(2):391-402. doi: 10.1021/bc700328s. Epub 2007 Dec. 12. PMID: 18072717).

Miniprotein Conjugate Orientation

In some embodiments, a conjugate has the following orientation: linker-chelator, linker-chelator-radionuclide, linker-radionuclide, chelator-radionuclide. In some such embodiments a conjugate has the following orientation: miniprotein-linker-Radionuclide, miniprotein-Chelator, Chelator-miniprotein, miniprotein-linker-Chelator, Chelator-linker-miniprotein, miniprotein-Chelator-Radionuclide, Radionuclide-Chelator-miniprotein, miniprotein-linker-Chelator-Radionuclide, or Radionuclide-Chelator-linker-miniprotein.

In some embodiments, a conjugate provided by the present disclosure comprises a miniprotein. In some such embodiments, the miniprotein functions as a targeting moiety, e.g., specifically binding to a target, e.g., a protein expressed on the surface of a target tumor cell. Accordingly, in some embodiments, the miniprotein in the conjugates of the present disclosure may vary depending on the target of interest.

In another aspect, the disclosure provides a composition represented by a formula selected from one or more of (M)x-L-C-R, (M)x-L-C)x-C-R, (M)x-L-R, (M)x-C, (M)x-L, and (M)x-R, wherein M comprises a miniprotein (M), L comprises a linker (L), C comprises a chelator (C), R comprises a radionuclide (R), and x is 1, 2, 3, or 4, wherein M comprises an amino acid sequence of Formula I:

X1X2X3X4YX6X7EX9IX11ALX14EIIWLPNX22X23X24X25QIX28AFIAALNX36DPSQSSELLSEAX49X50LX52DSX55X56X57X58 (SEQ ID NO: 95), wherein X1 is A, N, or absent; X2 is A, E, or absent; X3 is A, Q, or absent; X4 is K, (KAc), L, or absent; X6 is A, D, E, I, L, N, Q, S, T, or Y; X7 is A, E, K, (KAc), (Kme3), L, Q, or S; X9 is K, (KAc), or (Kme)(Kme3); X11 is A, Q, S, T, or Y; X14 is E, Q, S, or Y; X22 is A, D, F, ((homo-leucine)), I, L, N, ((Nle)), T, or Y; X23 is T or V; X24 is H or Y; X25 is A or G; X28 is A, ((homo-leucine)), M, M(O2), ((Nle)), S, T, or V; X36 is A, (Cit), D, E, L, N, Q, S, or T; X49 is A, E, G, K, (KAc), L, Q, S, or Y; X50 is A, (Cit), D, E, G, (hSer), K, (KAc), L, Q, S, or Y; X52 is A, D, G, N, Q, T, or Y; X55 is D, E, L, Q, S, Y, or absent; X56 is A or absent; X57 is P or absent; and X58 is G, K, (KAc), or absent; wherein if X28 is A, ((homo-leucine)), M(O2), S, T, or V, then X24 is Y; or wherein if X28 is M, then X7 is A, E, (Kme3), L, Q, or S.

In some embodiments, if X4 is K or (KAc), then X24 is Y.

In certain embodiments, the amino acid sequence comprises Formula II:

X1X2X3X4YAX7EKIAALSEIIWLPNX22TX24X25QI X28AFIAALNX36DPSQSSELLSE AX49X50LNDSQAP (SEQ ID NO: 96), wherein X1 is A or absent; X2 is E or absent; X3 is A or absent; X4 is L or absent; X7 is K or Q; X22 is D or L; X24 is H or Y; X25 is A or G; X28 is ((homo-leucine)) or M; X36 is D or N; X49 is E or K; and X50 is E.

In certain embodiments, the amino acid sequence shares 90% (e.g., 91, 92, 93, 94, 95, 96, 97, 98, 99 or more percent) identity to any one of the SEQ ID NOs: 4-6 or SEQ ID NOs: 12-94.

In certain embodiments, the amino acid sequence shares 90% (e.g., 91, 92, 93, 94, 95, 96, 97, 98, 99 or more percent) identity to any one of SEQ ID NOs: 6, 21, or 30.

In certain embodiments, the amino acid sequence shares 100% identity to any one of the SEQ ID NOs: 4-6 or SEQ ID NOs: 12-94.

In certain embodiments, the composition comprises any one of C3, C4, C6-C14, or C19-C116.

In certain embodiments, the amino acid sequence shares 100% identity to any one of SEQ ID NOs: 6, 21, or 30.

In certain embodiments, the composition comprises any one of C6-C9, C28-C31, or C40-C42.

In certain embodiments, the amino acid sequence shares 90% (e.g., 91, 92, 93, 94, 95, 96, 97, 98, 99 or more percent) identity to SEQ ID NO: 6.

In certain embodiments, the amino acid sequence shares 100% identity to SEQ ID NO: 6.

In certain embodiments, the linker comprises or consists of a polyethylene glycol (PEG) linker of PEG2, PEG, PEG4, PEG6, PEG8, PEG12, PEG24, PEG36, lys(MPB)-PEG4, lys(IPB)-PEG4, an ester linker, an amide linker, a maleimide linker, a succinimidyl-4-(N-maleimidomethyl) cyclohexane-1-carboxylate (SMCC) linker, a propanoic acid linker, a caproleic acid linker, a Lys(MPB)-PEG linker (e.g., Lys(MPB)-PEG4), a Lys(IPB)-PEG linker (e.g., Lys(IPB)-PEG4), an HE(1-3) linker (SEQ ID NO: 554), an (SE)1-3 linker (SEQ ID NO: 555), an (E)1-3 linker, an aminocaproic acid (Ahx) linker, or (Gly)n-(γGlu)n- or (PEG)n, wherein n is from 1 to 36, (Gly)1-10, or any fragment or combination via covalent bond thereof.

In certain embodiments, the chelator comprises or consists of:

i) NOPO

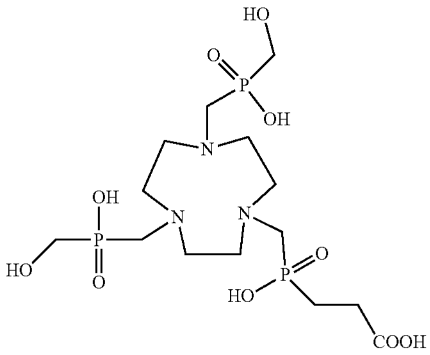

NOPO ii) Crown

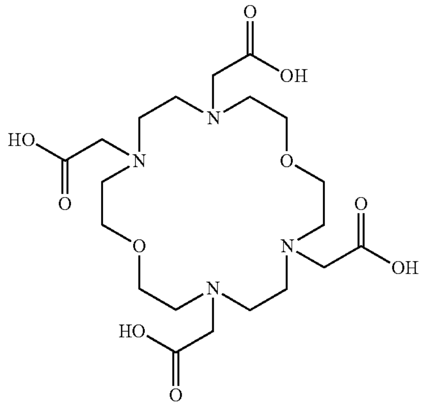

Crown iii) DOTA

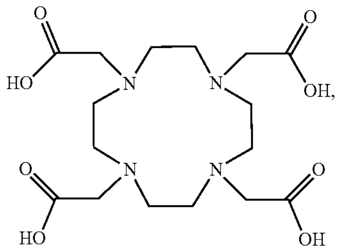

or iv) Macropa

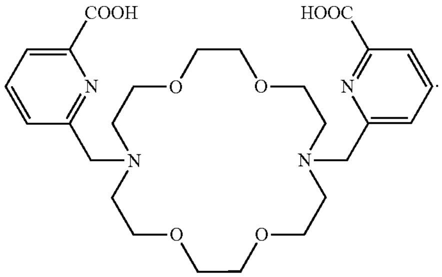

Macropa

In certain embodiments, the chelator comprises or consists of derivative of NOPO, Crown, Macropa, or tetrazacyclododecane-1,4,7,10-tetraacetic acid (DOTA).

In certain embodiments, the radionuclide comprises or consists of Ac-225, Ga-68, In-111, Pb-212, Lu-177, Cu-67, Cu-64, La-132, La-135, Ce-134, F-18, or At-211.

In certain embodiments, when present, the linker is attached to the N-terminal or C-terminal end of the mini-protein.

In certain embodiments, when present, the chelator is attached to either the miniprotein or the linker.

In certain embodiments, when present, the radionuclide is attached to the chelator.

In certain embodiments, the miniprotein comprises or consists of a linear polypeptide, a folded polypeptide (e.g., covalently linked polypeptide, non-covalently linked poly-peptide, or polypeptide include a di-sulfide linkage), cyste-ine-dense peptide, a knottin peptide, a binder, an affibody, an engineered Kunitz domain, a monobody, an anticalin, a designed ankyrin repeat domain (DARPin), or an avimer.

In certain embodiments, the miniprotein comprises at least one disulfide bridge.

In certain embodiments, the miniprotein selectively binds to B7-H3 or a portion thereof.

In certain embodiments, the miniprotein exhibits a binding affinity of 10 pM to 200 nM, 10 pM to 100 nM, or 10 nM to 100 nM to B7-H3, or a portion thereof, in vivo or in a cell-based assay.

In another aspect, the disclosure provides a composition represented by a formula selected from one or more of (M)x-L-C-R, (M)x-L-C)x-C-R, (M)x-L-R, (M)x-C, (M)x-L, and (M)x-R, wherein M comprises a miniprotein (M), L comprises a linker (L), C comprises a chelator (C), R comprises a radionuclide (R), and x is 1, 2, 3, or 4, wherein M comprises an amino acid sequence that shares 90% identity to any one of the SEQ ID NOs: 4-6, SEQ ID NOs: 12-94, or SEQ ID NOs: 100-537.

In some embodiments, the amino acid sequence shares 90% (e.g., 91, 92, 93, 94, 95, 96, 97, 98, 99 or more percent) identity to any one of SEQ ID NOs: 6, 21, 30, 130-131, 183, 199, 204, 241 or 267.

In some embodiments, the amino acid sequence shares 100% identity to any one of the SEQ ID NOs: 4-6, SEQ ID NOs: 12-94, or SEQ ID NOs: 100-537.

In some embodiments, the composition comprises any one of C3, C4, C6-C14, C19-C116, or C121-C608 and C611.

In some embodiments, the amino acid sequence shares 100% identity to any one of SEQ ID NOs: 6, 21, 30, 130-131, 183, 199, 204, 241 or 267.

In some embodiments, the composition comprises any one of C6-C9, C28-C31, C40-C42, C152-C153, C211, C228, C234, C275 C309, C325, or C332.

In some embodiments, the amino acid sequence shares 90% identity to any one of SEQ ID NOs: 6, 130-131, 183, 199, 204, 241 or 267.

In some embodiments, the amino acid sequence shares 100% identity to any one of SEQ ID NOs: 6, 130-131, 183, 199, 204, 241 or 267.

In some embodiments, the composition comprises any one of C6-C9, C152-C153, C211, C228, C234, C275 C309, C325, or C332.

In some embodiments, the amino acid sequence shares 90% (e.g., 91, 92, 93, 94, 95, 96, 97, 98, 99 or more percent) identity to any one of SEQ ID NOs: 4-6, 12-94 or 100-197.

In some embodiments, the amino acid sequence shares 90% (e.g., 91, 92, 93, 94, 95, 96, 97, 98, 99 or more percent) identity to any one of SEQ ID NOs: 6, 21, 30, 130-131, or 183.

In some embodiments, the amino acid sequence shares 100% identity to any one of SEQ ID NOs: 4-6, 12-94 or 100-197.

In some embodiments, the composition comprises any one of C6-C14, C19-C116, or C121-C226.

In some embodiments, the amino acid sequence shares 100% identity to any one of SEQ ID NOs: 6, 21, 30, 130-131, or 183.

In some embodiments, the composition comprises any one of C6-C9, C152-C153, or C211.

In some embodiments, M further comprises one or more disulfide bridges.

In some embodiments, the amino acid sequence shares 90% identity to any one of SEQ ID NOs: 198-272.

In some embodiments, the amino acid sequence shares 90% (e.g., 91, 92, 93, 94, 95, 96, 97, 98, 99 or more percent) identity to any one of SEQ ID NOs: 199, 204, 241 or 267.

In some embodiments, the amino acid sequence shares 100% identity to any one of SEQ ID NOs: 198-272.

In some embodiments, the composition comprises any one of C227-C319.

In some embodiments, the amino acid sequence shares 100% identity to any one of SEQ ID NOs: 199, 204, 241 or 267.

In some embodiments, the composition comprises any one of C228, C234, C275 or C309.

In some embodiments, the linker comprises or consists of a polyethylene glycol (PEG) linker of PEG4, PEG, PEG2, PEG6, PEG8, PEG12, PEG24, PEG36, lys(MPB)-PEG4, lys(IPB)-PEG4, an ester linker, an amide linker, a maleimide linker, a succinimidyl-4-(N-maleimidomethyl) cyclo-hexane-1-carboxylate (SMCC) linker, a propanoic acid linker, a caproleic acid linker, a Lys(MPB)-PEG linker (e.g., Lys(MPB)-PEG4), a Lys(IPB)-PEG linker (e.g., Lys(IPB)-PEG4), an HE(1-3) linker (SEQ ID NO: 554), an (SE)1-3 linker (SEQ ID NO: 555), an (E)1-3 linker, an aminocaproic acid (Ahx) linker, or (Gly)n-(γGlu)n- or (PEG)n, wherein n is from 1 to 36, $(Gly)_{1-10}$, or any fragment or combination via covalent bond thereof.

In some embodiments, the chelator comprises or consists of:

i) NOPO

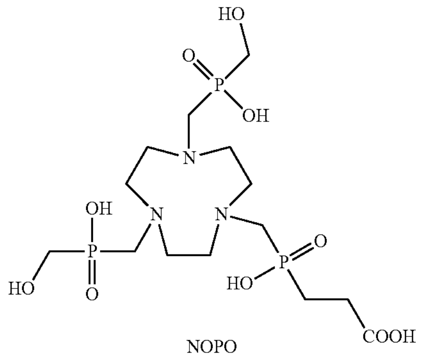

NOPO

-continued ii) Crown

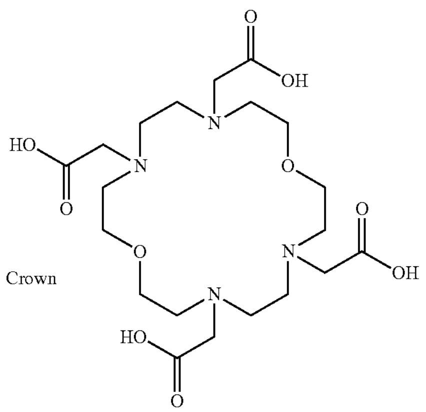

Crown iii) DOTA

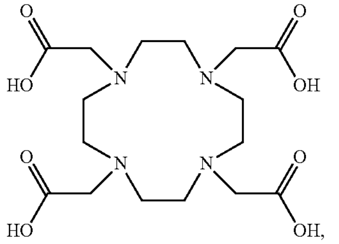

or iv) Macropa

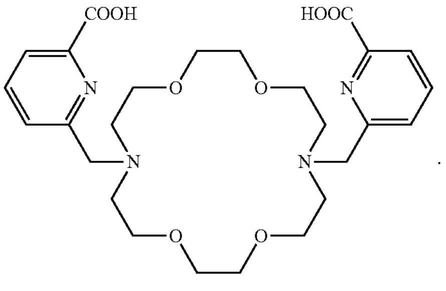

Macropa

In some embodiments, the chelator, when present, comprises or consists of derivative of NOPO, Crown, Macropa, or tetrazacyclododecane-1,4,7,10-tetraacetic acid (DOTA).

In some embodiments, the radionuclide, when present, comprises or consists of Ac-225, Ga-68, In-111, Pb-212, Lu-177, Cu-67, Cu-64, La-132, La-135, Ce-134, F-18, or At-211.

In some embodiments, the linker, when present, is attached to the N-terminal or C-terminal end of the miniprotein.

In some embodiments, the chelator, when present, is attached to either the miniprotein or the linker.

In some embodiments, the radionuclide, when present, is attached to the chelator.

In some embodiments, the miniprotein comprises or consists of a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer.

In some embodiments, the miniprotein comprises at least one disulfide bridge.

In some embodiments, the miniprotein selectively binds to B7-H3 or a portion thereof.

In some embodiments, the miniprotein exhibits a binding affinity of 10 pM to 200 nM, 10 pM to 100 nM, or 10 nM to 100 nM to B7-H3, or a portion thereof, in vivo or in a cell-based assay.

Exemplary Miniprotein Conjugates

The following provides exemplary embodiments of miniprotein conjugates as provided herein. In some such embodiments, such miniproteins specifically bind to B7-H3 expressed on the surface of a cancer cell (e.g., a solid tumor cell). In some embodiments, a conjugate comprises a linker, a chelator, and/or a radionuclide.

In some embodiments, a conjugate comprises a miniprotein, optional linker, chelator, and radionuclide. In some embodiments, a miniprotein comprises or consists of a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer In some embodiments, a chelator comprises or consists of DOTA, Crown, NOPO, PSC, N-succinimidyl 3-(tri-n-butylstannyl)benzoate (BuSTB), N-succinimidyl 3-trimethylstannylbenzoate (MeSTB), or Macropa. In some embodiments, a radionuclide comprises or consists of an alpha emitter. In some embodiments, a radionuclide comprises or consists of a beta emitter. In some embodiments, a radionuclide comprises or consists of Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211.

In some embodiments, the linker, chelator, and/or radionuclide are connected to the N-terminus of the miniprotein. In some embodiments, the linker, chelator, and/or radionuclide are connected to the C-terminus of the miniprotein. In some embodiments, when present, a linker is attached to the N- and/or C-terminus of the polypeptide, and the chelator, when present, can be attached to the linker, or directly to the polypeptide.

In some embodiments, a conjugate comprises a miniprotein, optional linker, chelator, and radionuclide. In some embodiments, a miniprotein comprises or consists of an affibody, a binder, a CDP, or a knottin. In some embodiments, a chelator comprises or consists of DOTA, Crown, NOPO, or Macropa. In some embodiments, a radionuclide comprises or consists of an alpha emitter. In some embodiments, a radionuclide comprises or consists of a beta emitter. In some embodiments, a radionuclide comprises or consists of Ac-225, Lu-177, Cu-64, Ga-68, La-132, La-135, or In-111.

In some embodiments, a conjugate comprises or consists of a miniprotein that specifically binds to B7-H3, an optional PEG linker, a DOTA chelator, and Ac-225.

In some embodiments, a conjugate comprises or consists of a miniprotein that specifically binds to B7-H3, an optional PEG linker, a DOTA chelator, and Ac-225.

In some embodiments, a conjugate comprises or consists of a miniprotein that specifically binds to B7-H3, an optional PEG linker, a DOTA chelator, and Lu-177.

In some embodiments, a conjugate comprises or consists of a miniprotein that specifically binds to B7-H3, an optional PEG linker, a DOTA chelator, and Ga-68.

In some embodiments, a conjugate comprises or consists of a miniprotein that specifically binds to B7-H3, an optional PEG linker, a DOTA chelator, and La-132.

In some embodiments, a conjugate comprises or consists of a miniprotein that specifically binds to B7-H3, an optional PEG linker, a DOTA chelator, and La-135.

In some embodiments, a conjugate comprises or consists of a miniprotein that specifically binds to B7-H3, an optional PEG linker, a DOTA chelator, and Cu-64.

In some embodiments, a conjugate comprises or consists of a miniprotein that specifically binds to B7-H3, an optional PEG linker, a DOTA chelator, and In-111.

In some embodiments, a conjugate comprises or consists of a miniprotein that specifically binds to B7-H3, an optional PEG linker, a Crown chelator, and Ac-225.

In some embodiments, a conjugate comprises or consists of a miniprotein that specifically binds to B7-H3, an optional PEG linker, a Crown chelator, and Lu-177.

In some embodiments, a conjugate comprises or consists of a miniprotein that specifically binds to B7-H3, an optional PEG linker, a Crown chelator, and Ga-68.

In some embodiments, a conjugate comprises or consists of a miniprotein that specifically binds to B7-H3, an optional PEG linker, a Crown chelator, and La-132.

In some embodiments, a conjugate comprises or consists of a miniprotein that specifically binds to B7-H3, an optional PEG linker, a Crown chelator, and La-135.

In some embodiments, a conjugate comprises or consists of a miniprotein that specifically binds to B7-H3, an optional PEG linker, a Crown chelator, and Cu-64.

In some embodiments, a conjugate comprises or consists of a miniprotein that specifically binds to B7-H3, an optional PEG linker, a Crown chelator, and In-111.

In some embodiments, a conjugate comprises or consists of a miniprotein that specifically binds to B7-H3, an optional PEG linker, a NOPO chelator, and Ga-68.

In some embodiments, a conjugate comprises or consists of a miniprotein that specifically binds to B7-H3, an optional PEG linker, a NOPO chelator, and La-132.

In some embodiments, a conjugate comprises or consists of a miniprotein that specifically binds to B7-H3, an optional PEG linker, a NOPO chelator, and La-135.

In some embodiments, a conjugate comprises or consists of a miniprotein that specifically binds to B7-H3, an optional PEG linker, a NOPO chelator, and Cu-64.

In some embodiments, a conjugate comprises or consists of a miniprotein that specifically binds to B7-H3, an optional PEG linker, a NOPO chelator, and In-111.

In some embodiments, a conjugate comprises or consists of a miniprotein that specifically binds to B7-H3, an optional PEG linker, a Macropa chelator, and Ac-225.

In some embodiments, a conjugate comprises or consists of a miniprotein that specifically binds to B7-H3, an optional PEG linker, a Macropa chelator, and Lu-177.

In some embodiments, a conjugate comprises or consists of a miniprotein that specifically binds to B7-H3, an optional PEG linker, a Macropa chelator, and Ga-68.

In some embodiments, a conjugate comprises or consists of a miniprotein that specifically binds to B7-H3, an optional PEG linker, a Macropa chelator, and La-132.

In some embodiments, a conjugate comprises or consists of a miniprotein that specifically binds to B7-H3, an optional PEG linker, a Macropa chelator, and La-135.

In some embodiments, a conjugate comprises or consists of a miniprotein that specifically binds to B7-H3, an optional PEG linker, a Macropa chelator, and Cu-64.

In some embodiments, a conjugate comprises or consists of a miniprotein that specifically binds to B7-H3, an optional PEG linker, a Macropa chelator, and In-111.

In some embodiments, an exemplary imaging/diagnostic miniprotein conjugate described herein comprises a miniprotein that specifically binds to B7-H3 or a fragment or portion thereof (e.g., expressed on the surface of a solid tumor cell), a PEG linker, a DOTA chelator, and Gallium-68.

In some embodiments, an exemplary imaging/diagnostic miniprotein conjugate described herein comprises a miniprotein that specifically binds to B7-H3 or a fragment or portion thereof (e.g., expressed on the surface of a solid tumor cell), a PEG linker, a DOTA chelator, and Copper-64.

In some embodiments, an exemplary imaging/diagnostic miniprotein conjugate described herein comprises a miniprotein that specifically binds to B7-H3 or a fragment or portion thereof (e.g., expressed on the surface of a solid tumor cell), a PEG linker, a DOTA chelator, and Indium-111.

In some embodiments, an exemplary imaging/diagnostic miniprotein conjugate described herein comprises a miniprotein that specifically binds to B7-H3 or a fragment or portion thereof (e.g., expressed on the surface of a solid tumor cell), a PEG linker, a DOTA chelator, and Lutetium-177.

In some embodiments, exemplary imaging/diagnostic CDP conjugate described herein comprises a miniprotein that specifically binds to B7-H3 or a fragment or portion thereof (e.g., expressed on the surface of a solid tumor cell), a PEG linker, a DOTA chelator, and Lead-212.

In some embodiments, a conjugate comprises or consists of a miniprotein that specifically binds to B7-H3, an optional PEG linker, a DOTA chelator, and Cu-64.

In some embodiments, a conjugate comprises or consists of a miniprotein that specifically binds to B7-H3, an optional PEG linker, a DOTA chelator, and In-111.

In some embodiments, a conjugate comprises or consists of a miniprotein that specifically binds to B7-H3, an optional PEG linker, a DOTA chelator, and Ga-68.

In some embodiments, a conjugate comprises or consists of a miniprotein that specifically binds to B7-H3, an optional PEG linker, a DOTA chelator, and Lu-177.

In some embodiments, a conjugate comprises or consists of a miniprotein that specifically binds to B7-H3, an optional PEG linker, a DOTA chelator, and La-132.

In some embodiments, a conjugate comprises or consists of a miniprotein that specifically binds to B7-H3, an optional PEG linker, a DOTA chelator, and La-135.

In some embodiments, a conjugate comprises or consists of a miniprotein that specifically binds to B7-H3, an optional PEG linker, a DOTA chelator and Cu-67.

In some embodiments, a conjugate comprises or consists of a miniprotein that specifically binds to B7-H3, an optional PEG linker, a DOTA chelator, and Ce-134.

In some embodiments, a conjugate comprises or consists of a miniprotein that specifically binds to B7-H3, an optional PEG linker, a DOTA chelator, and I-131.

In some embodiments, a conjugate comprises or consists of a miniprotein that specifically binds to B7-H3, an optional PEG linker, a DOTA chelator, and I-124.

In some embodiments, a conjugate comprises or consists of a miniprotein that specifically binds to B7-H3, an optional PEG linker, a DOTA chelator, and Pb-203.

In some embodiments, a conjugate comprises or consists of a miniprotein that specifically binds to B7-H3, an optional PEG linker, a DOTA chelator, and Pb-212.

In some embodiments, a conjugate comprises or consists of a miniprotein that specifically binds to B7-H3, an optional PEG linker, a DOTA chelator, and Th-232

In some embodiments, a conjugate comprises or consists of a miniprotein that specifically binds to B7-H3, an optional PEG linker, a DOTA chelator, and Bi-123.

In some embodiments, a conjugate comprises or consists of a miniprotein that specifically binds to B7-H3, an optional PEG linker, a DOTA chelator, and Sm-153.

In some embodiments, a conjugate comprises or consists of a miniprotein that specifically binds to B7-H3, an optional PEG linker, a DOTA chelator, and Ra-225.

In some embodiments, a conjugate comprises or consists of a miniprotein that specifically binds to B7-H3, an optional PEG linker, a DOTA chelator, and Tb-165.

In some embodiments, a conjugate comprises or consists of a miniprotein that specifically binds to B7-H3, an optional PEG linker, a Crown chelator, and Ac-225.

In some embodiments, a conjugate comprises or consists of a miniprotein that specifically binds to B7-H3, an optional PEG linker, a Crown chelator, and Cu-64.

In some embodiments, a conjugate comprises or consists of a miniprotein that specifically binds to B7-H3, an optional PEG linker, a Crown chelator, and Lu-177.

In some embodiments, a conjugate comprises or consists of a miniprotein that specifically binds to B7-H3, an optional PEG linker, a Crown chelator, and In-111.

In some embodiments, a conjugate comprises or consists of a miniprotein that specifically binds to B7-H3, an optional PEG linker, a Crown chelator, and Ga-68.

In some embodiments, a conjugate comprises or consists of a miniprotein that specifically binds to B7-H3, an optional PEG linker, a Crown chelator, and La-132.

In some embodiments, a conjugate comprises or consists of a miniprotein that specifically binds to B7-H3, an optional PEG linker, a Crown chelator, and La-135.

In some embodiments, a conjugate comprises or consists of a miniprotein that specifically binds to B7-H3, an optional PEG linker, a Crown chelator, and Cu-67.

In some embodiments, a conjugate comprises or consists of a miniprotein that specifically binds to B7-H3, an optional PEG linker, a Crown chelator, and Ce-134.

In some embodiments, a conjugate comprises or consists of a miniprotein that specifically binds to B7-H3, an optional PEG linker, a Crown chelator, and I-131.

In some embodiments, a conjugate comprises or consists of a miniprotein that specifically binds to B7-H3, an optional PEG linker, a Crown chelator, and I-124.

In some embodiments, a conjugate comprises or consists of a miniprotein that specifically binds to B7-H3, an optional PEG linker, a Crown chelator, and Pb-203.

In some embodiments, a conjugate comprises or consists of a miniprotein that specifically binds to B7-H3, an optional PEG linker, a Crown chelator, and Pb-212.

In some embodiments, a conjugate comprises or consists of a miniprotein that specifically binds to B7-H3, an optional PEG linker, a Crown chelator, and Th-232

In some embodiments, a conjugate comprises or consists of a miniprotein that specifically binds to B7-H3, an optional PEG linker, a Crown chelator, and Bi-123.

In some embodiments, a conjugate comprises or consists of a miniprotein that specifically binds to B7-H3, an optional PEG linker, a Crown chelator, and Sm-153.

In some embodiments, a conjugate comprises or consists of a miniprotein that specifically binds to B7-H3, an optional PEG linker, a Crown chelator, and Ra-225.

In some embodiments, a conjugate comprises or consists of a miniprotein that specifically binds to B7-H3, an optional PEG linker, a Crown chelator, and Tb-165.

In some embodiments, a conjugate comprises or consists of a miniprotein that specifically binds to B7-H3, an optional PEG linker, a NOPO chelator, and Ac-225.

In some embodiments, a conjugate comprises or consists of a miniprotein that specifically binds to B7-H3, an optional PEG linker, a NOPO chelator, and In-111.

In some embodiments, a conjugate comprises or consists of a miniprotein that specifically binds to B7-H3, an optional PEG linker, a NOPO chelator, and Ga-68.

In some embodiments, a conjugate comprises or consists of a miniprotein that specifically binds to B7-H3, an optional PEG linker, a NOPO chelator, and La-132.

In some embodiments, a conjugate comprises or consists of a miniprotein that specifically binds to B7-H3, an optional PEG linker, a NOPO chelator, and La-135.

In some embodiments, a conjugate comprises or consists of a miniprotein that specifically binds to B7-H3, an optional PEG linker, a NOPO chelator, and Cu-64.

In some embodiments, a conjugate comprises or consists of a miniprotein that specifically binds to B7-H3, an optional PEG linker, a NOPO chelator, and Cu-67.

In some embodiments, a conjugate comprises or consists of a miniprotein that specifically binds to B7-H3, an optional PEG linker, a NOPO chelator, and Ce-134.

In some embodiments, a conjugate comprises or consists of a miniprotein that specifically binds to B7-H3, an optional PEG linker, a NOPO chelator, and I-131.

In some embodiments, a conjugate comprises or consists of a miniprotein that specifically binds to B7-H3, an optional PEG linker, a NOPO chelator, and I-124.

In some embodiments, a conjugate comprises or consists of a miniprotein that specifically binds to B7-H3, an optional PEG linker, a NOPO chelator, and Pb-203.

In some embodiments, a conjugate comprises or consists of a miniprotein that specifically binds to B7-H3, an optional PEG linker, a NOPO chelator, and Pb-212.

In some embodiments, a conjugate comprises or consists of a miniprotein that specifically binds to B7-H3, an optional PEG linker, a NOPO chelator, and Th-232

In some embodiments, a conjugate comprises or consists of a miniprotein that specifically binds to B7-H3, an optional PEG linker, a NOPO chelator, and Bi-123.

In some embodiments, a conjugate comprises or consists of a miniprotein that specifically binds to B7-H3, an optional PEG linker, a NOPO chelator, and Sm-153.

In some embodiments, a conjugate comprises or consists of a miniprotein that specifically binds to B7-H3, an optional PEG linker, a NOPO chelator, and Ra-225.

In some embodiments, a conjugate comprises or consists of a miniprotein that specifically binds to B7-H3, an optional PEG linker, a NOPO chelator, and Tb-165.

In some embodiments, a conjugate comprises or consists of a miniprotein that specifically binds to B7-H3, an optional PEG linker, a Macropa chelator, and Ac-225.

In some embodiments, a conjugate comprises or consists of a miniprotein that specifically binds to B7-H3, an optional PEG linker, a Macropa chelator, and Cu-64.

In some embodiments, a conjugate comprises or consists of a miniprotein that specifically binds to B7-H3, an optional PEG linker, a Macropa chelator, and Lu-177.

In some embodiments, a conjugate comprises or consists of a miniprotein that specifically binds to B7-H3, an optional PEG linker, a Macropa chelator, and In-111.

In some embodiments, a conjugate comprises or consists of a miniprotein that specifically binds to B7-H3, an optional PEG linker, a Macropa chelator, and Ga-68.

In some embodiments, a conjugate comprises or consists of a miniprotein that specifically binds to B7-H3, an optional PEG linker, a Macropa chelator, and La-132.

In some embodiments, a conjugate comprises or consists of a miniprotein that specifically binds to B7-H3, an optional PEG linker, a Macropa chelator, and La-135.

In some embodiments, a conjugate comprises or consists of a miniprotein that specifically binds to B7-H3, an optional PEG linker, a Macropa chelator, and Cu-67.

In some embodiments, a conjugate comprises or consists of a miniprotein that specifically binds to B7-H3, an optional PEG linker, a Macropa chelator, and Ce-134.

In some embodiments, a conjugate comprises or consists of a miniprotein that specifically binds to B7-H3, an optional PEG linker, a Macropa chelator, and I-131.

In some embodiments, a conjugate comprises or consists of a miniprotein that specifically binds to B7-H3, an optional PEG linker, a Macropa chelator, and I-124.

In some embodiments, a conjugate comprises or consists of a miniprotein that specifically binds to B7-H3, an optional PEG linker, a Macropa chelator, and Pb-203.

In some embodiments, a conjugate comprises or consists of a miniprotein that specifically binds to B7-H3, an optional PEG linker, a Macropa chelator, and Pb-212.

In some embodiments, a conjugate comprises or consists of a miniprotein that specifically binds to B7-H3, an optional PEG linker, a Macropa chelator, and Th-232

In some embodiments, a conjugate comprises or consists of a miniprotein that specifically binds to B7-H3, an optional PEG linker, a Macropa chelator, and Bi-123.

In some embodiments, a conjugate comprises or consists of a miniprotein that specifically binds to B7-H3, an optional PEG linker, a Macropa chelator, and Sm-153.

In some embodiments, a conjugate comprises or consists of a miniprotein that specifically binds to B7-H3, an optional PEG linker, a Macropa chelator, and Ra-225.

In some embodiments, a conjugate comprises or consists of a miniprotein that specifically binds to B7-H3, an optional PEG linker, a DOTA chelator, and Tb-165.

In certain embodiments, a conjugate comprises or consists of a miniprotein that specifically binds to B7-H3, an optional PEG linker, a lead-specific chelator, and a radionuclide that is not lead (e.g., Ac-225, In-111, Lu-177, etc.).

In some embodiments, a conjugate comprises or consists of a miniprotein that specifically binds to B7-H3, an optional PEG linker, a lead-specific chelator, and Pb-203.

In some embodiments, a conjugate comprises or consists of a miniprotein that specifically binds to B7-H3, an optional PEG linker, a lead-specific chelator, and Pb-212.

In some embodiments, a conjugate comprises or consists of a miniprotein that specifically binds to B7-H3, an optional PEG linker, a N-succinimidyl 3-(tri-n-butylstannyl)benzoate (BuSTB) chelator, and Ac-225.

In some embodiments, a conjugate comprises or consists of a miniprotein that specifically binds to B7-H3, an optional PEG linker, a N-succinimidyl 3-(tri-n-butylstannyl)benzoate (BuSTB) chelator, and In-111.

In some embodiments, a conjugate comprises or consists of a miniprotein that specifically binds to B7-H3, an optional PEG linker, a N-succinimidyl 3-(tri-n-butylstannyl)benzoate (BuSTB) chelator, and Lu-177.

In some embodiments, a conjugate comprises or consists of a miniprotein that specifically binds to B7-H3, an optional PEG linker, a N-succinimidyl 3-(tri-n-butylstannyl)benzoate (BuSTB) chelator, and Ga-68.

In some embodiments, a conjugate comprises or consists of a miniprotein that specifically binds to B7-H3, an optional PEG linker, a N-succinimidyl 3-(tri-n-butylstannyl)benzoate (BuSTB) chelator, and La-132.

In some embodiments, a conjugate comprises or consists of a miniprotein that specifically binds to B7-H3, an optional PEG linker, a N-succinimidyl 3-(tri-n-butylstannyl)benzoate (BuSTB) chelator, and La-135.

In some embodiments, a conjugate comprises or consists of a miniprotein that specifically binds to B7-H3, an optional PEG linker, a N-succinimidyl 3-(tri-n-butylstannyl)benzoate (BuSTB) chelator, and Cu-64.

In some embodiments, a conjugate comprises or consists of a miniprotein that specifically binds to B7-H3, an optional PEG linker, a N-succinimidyl 3-(tri-n-butylstannyl)benzoate (BuSTB) chelator, and Cu-67.

In some embodiments, a conjugate comprises or consists of a miniprotein that specifically binds to B7-H3, an optional PEG linker, a N-succinimidyl 3-(tri-n-butylstannyl)benzoate (BuSTB) chelator, and Ce-134.

In some embodiments, a conjugate comprises or consists of a miniprotein that specifically binds to B7-H3, an optional PEG linker, a N-succinimidyl 3-(tri-n-butylstannyl)benzoate (BuSTB) chelator, and I-131.

In some embodiments, a conjugate comprises or consists of a miniprotein that specifically binds to B7-H3, an optional PEG linker, a N-succinimidyl 3-(tri-n-butylstannyl)benzoate (BuSTB) chelator, and I-124.

In some embodiments, a conjugate comprises or consists of a miniprotein that specifically binds to B7-H3, an optional PEG linker, a N-succinimidyl 3-(tri-n-butylstannyl)benzoate (BuSTB) chelator, and Pb-203.

In some embodiments, a conjugate comprises or consists of a miniprotein that specifically binds to B7-H3, an optional PEG linker, a N-succinimidyl 3-(tri-n-butylstannyl)benzoate (BuSTB) chelator, and Pb-212.

In some embodiments, a conjugate comprises or consists of a miniprotein that specifically binds to B7-H3, an optional PEG linker, a N-succinimidyl 3-(tri-n-butylstannyl)benzoate (BuSTB) chelator, and Th-232

In some embodiments, a conjugate comprises or consists of a miniprotein that specifically binds to B7-H3, an optional PEG linker, a N-succinimidyl 3-(tri-n-butylstannyl)benzoate (BuSTB) chelator, and Bi-123.

In some embodiments, a conjugate comprises or consists of a miniprotein that specifically binds to B7-H3, an optional PEG linker, a N-succinimidyl 3-trimethylstannylbenzoate (MeSTB) chelator, and Ac-225.

In some embodiments, a conjugate comprises or consists of a miniprotein that specifically binds to B7-H3, an optional PEG linker, a N-succinimidyl 3-trimethylstannylbenzoate (MeSTB) chelator, and In-111.

In some embodiments, a conjugate comprises or consists of a miniprotein that specifically binds to B7-H3, an optional PEG linker, a N-succinimidyl 3-trimethylstannylbenzoate (MeSTB) chelator, and Lu-177.

In some embodiments, a conjugate comprises or consists of a miniprotein that specifically binds to B7-H3, an optional PEG linker, a N N-succinimidyl 3-trimethylstannylbenzoate (MeSTB) chelator, and Ga-68.

In some embodiments, a conjugate comprises or consists of a miniprotein that specifically binds to B7-H3, an optional PEG linker, a N-succinimidyl 3-trimethylstannylbenzoate (MeSTB) chelator, and La-132.

In some embodiments, a conjugate comprises or consists of a miniprotein that specifically binds to B7-H3, an optional PEG linker, a N N-succinimidyl 3-trimethylstannylbenzoate (MeSTB) chelator, and La-135.

In some embodiments, a conjugate comprises or consists of a miniprotein that specifically binds to B7-H3, an optional PEG linker, N-succinimidyl 3-trimethylstannylbenzoate (MeSTB) chelator, and Cu-64.

In some embodiments, a conjugate comprises or consists of a miniprotein that specifically binds to B7-H3, an optional PEG linker, a N N-succinimidyl 3-trimethylstannylbenzoate (MeSTB) chelator, and Cu-67.

In some embodiments, a conjugate comprises or consists of a miniprotein that specifically binds to B7-H3, an optional PEG linker, a N-succinimidyl 3-trimethylstannylbenzoate (MeSTB) chelator, and Ce-134.

In some embodiments, a conjugate comprises or consists of a miniprotein that specifically binds to B7-H3, an optional PEG linker, a N-succinimidyl 3-trimethylstannylbenzoate (MeSTB) chelator, and I-131.

In some embodiments, a conjugate comprises or consists of a miniprotein that specifically binds to B7-H3, an optional PEG linker, a N-succinimidyl 3-trimethylstannylbenzoate (MeSTB) chelator, and I-124.

In some embodiments, a conjugate comprises or consists of a miniprotein that specifically binds to B7-H3, an optional PEG linker, a N-succinimidyl 3-trimethylstannylbenzoate (MeSTB) chelator, and Pb-203.

In some embodiments, a conjugate comprises or consists of a miniprotein that specifically binds to B7-H3, an optional PEG linker, a N-succinimidyl 3-trimethylstannylbenzoate (MeSTB) chelator, and Pb-212.

In some embodiments, a conjugate comprises or consists of a miniprotein that specifically binds to B7-H3, an optional PEG linker, a N-succinimidyl 3-trimethylstannylbenzoate (MeSTB) chelator, and Th-232

In some embodiments, a conjugate comprises or consists of a miniprotein that specifically binds to B7-H3, an optional PEG linker, a N-succinimidyl 3-trimethylstannylbenzoate (MeSTB) chelator, and Bi-123.

In some embodiments, a conjugate comprises or consists of a miniprotein that specifically binds to B7-H3, an optional PEG linker, a N-succinimidyl 3-trimethylstannylbenzoate (MeSTB) chelator, and Sm-153.

In some embodiments, a conjugate comprises or consists of a miniprotein that specifically binds to B7-H3, an optional PEG linker, a N-succinimidyl 3-trimethylstannylbenzoate (MeSTB) chelator, and Ra-225.

In some embodiments, a conjugate comprises or consists of a miniprotein that specifically binds to B7-H3, an optional PEG linker, a N-succinimidyl 3-trimethylstannylbenzoate (MeSTB) chelator, and Tb-165.

In some embodiments, one or more different linkers and different chelators for different radionuclides and their respective chelators are operably linked to the same miniprotein.

In some embodiments, a pharmaceutical composition comprising the radionuclide is employed in imaging scans to detect or diagnosis one or more diseases. Further embodiments include use as companion diagnostics.

In some embodiments, one or more different linkers and different chelators for Ga-68 (e.g., NOPO) and Ac-225 (e.g., Crown or DOTA) for both are operably linked to the same miniprotein.

In some embodiments, a conjugate comprises or consists of a miniprotein having an amino acid sequence comprising any one of SEQ ID NOs: 4-6, 8-94, and 100-537, or as set forth in Tables 1B-1D, 2A, 2C, or any of SEQ ID NOs: 538-543 and Table 1E. In some embodiments, a conjugate comprises or consists of a compound disclosed herein selected from any one of C3, C4, C6-C14, C19-C116, or C121-C608 and C611. In some embodiments, a conjugate comprises or consists of a compound disclosed herein selected from any one of C6-C9, C28-C31, C40-C42, C152-C153, C211, C228, C234, C275 or C309. In some embodiments, a conjugate comprises or consists of a compound C6. In some embodiments, a conjugate comprises or consists of a compound C7. In some embodiments, a conjugate comprises or consists of a compound C8. In some embodiments, a conjugate comprises or consists of a compound C9. In some embodiments, a conjugate comprises or consists of a compound C28. In some embodiments, a conjugate comprises or consists of a compound C29. In some embodiments, a conjugate comprises or consists of a compound C30. In some embodiments, a conjugate comprises or consists of a compound C31. In some embodiments, a conjugate comprises or consists of a compound C40. In some embodiments, a conjugate comprises or consists of a compound C41. In some embodiments, a conjugate comprises or consists of a compound C42. In some embodiments, a conjugate comprises or consists of a compound C152. In some embodiments, a conjugate comprises or consists of a compound C153. In some embodiments, a conjugate comprises or consists of a compound C211. In some embodiments, a conjugate comprises or consists of a compound C228. In some embodiments, a conjugate comprises or consists of a compound C234. In some embodiments, a conjugate comprises or consists of a compound C275. In some embodiments, a conjugate comprises or consists of a compound C309. In some embodiments, a conjugate comprises or consists of a compound C325. In some embodiments, a conjugate comprises or consists of a compound C332.

Methods of Use

In some embodiments, the present disclosure provides methods of treating or preventing disease or disorder in a subject, the method comprising administering to the subject the pharmaceutical composition in an amount effective that modulates, binds, or inhibits human B7-H3 to treat or prevent disease or disorder in the subject. In preferred embodiments, the disease or disorder associated with B7-H3 is treated (e.g., prevented, progression is slowed, symptoms are relieved, tumor size reduced to improve overall survival, etc.).

In some embodiments, a cell expresses B7-H3. In some embodiments, the B7-H3 cell is a cancer cell and is part of a heterogenous population of cells (e.g., that do not express B7-H3). Without wishing to be bound by theory, the disclosure contemplates that compositions provided herein treat cancers with heterogenous cancer cell populations. For example, in some such embodiments, cancer cells apposed to B7-H3-expressing cells that do not themselves express B7-H3 are also treated (e.g., killed) by internalization of the pharmaceutical composition into the B7-H3-expressing cells. For example, internalization of a radionuclide into a neighboring cell, e.g., in a tumor, can kill cancer cells that do not themselves internalize the composition. Without wishing to be limited by theory, the disclosure also contemplates that, in some embodiments, treatment with a composition as provided herein can induce a secondary immune response whereby immune cells of a subject are recruited and/or arrive at the site of the cancer cells, even if such cancer cells do not, have not ever and/or do not any longer express B7-H3. In some such embodiments, the immune system of the subject can further result in death or damage to cancer cells.

In some embodiments, subjects, e.g., patients or patient inclusion criteria include, without limitation, B7-H3 positive candidates shown via imaging (e.g., DOTA PET/CT), candidates with progressive disease, advanced or metastatic disease, candidates who are not candidates for surgery, refractory or relapsed candidates.

In some embodiments, possible certain side effects including nausea, suppression of blood cell counts are managed through one or more medications. In some embodiments, side effects may include renal toxicity, myelodysplastic syndrome, however, it is contemplated that the pharmaceutical compositions are manageable, and treatment is generally well-tolerated. The disclosure also contemplates that such off-target effects may be managed with one or more medications and/or additional treatments, including, but not limited to administration of a decoy as provided herein. In some embodiments, one or more additional agents or processes may be added such as, e.g., one or more medications, such as for suppression of blood cell counts or treatment of nausea, etc.

Depending on context, compositions (e.g., polypeptides, pharmaceutical composition, compounds, etc.) can be used in any method provided herein. For example, in some embodiments, a method comprises treatment of cancer. In certain embodiments, a method comprises use for treatment, imaging, diagnosis or prognosis (e.g., in a subject in need or suspected of being in need thereof). In certain embodiments, a composition can be used to modify uptake and/or retention in a non-cancerous cell and/or tissue (e.g., reduce or block uptake and/or retention in kidney tissue, as compared to, e.g., cancer cells, e.g., tumor tissue).

In certain embodiments, a method of use comprises use of a composition, compound, or pharmaceutical composition provided herein (e.g., that binds to B7-H3) which composition a polypeptide having an amino acid sequence, wherein the amino acid sequence comprises: at least four cysteines, which form two disulfide bonds; an arginine, modified arginine, or modified lysine at a position corresponding to amino acid 3, a lysine at a position corresponding to amino acid 5, an isoleucine at a position corresponding to amino acid 6, a tryptophan at a position corresponding to amino acid 14, at least one modified lysine residue at a position corresponding to amino acid 24, and an alanine, arginine, or modified lysine at a position corresponding to 29, where each position is linear, from N-to-C-terminus relative to SEQ ID NO: 267, wherein the modification comprises at least one small alkyl group attached to the nitrogen of the lysine side chain or to the Guanidino group of the arginine side chain, optionally comprising a methyl, dimethyl, or trimethyl; at least 48 amino acids in length; and has a binding affinity for B7-H3 stronger than 100 nM in a cell-based assay. In certain embodiments, the polypeptide has an amino acid sequence comprising any one of SEQ ID NOs: 204 and 262-272. In certain embodiments, the polypeptide is part of a compound selected from any one of C234-235 and C309-C332.

In one aspect, the disclosure provides a method of use (e.g., a method of treating cancer, e.g., a method of reducing kidney uptake and/or retention, e.g., after administration, e.g., to as subject in need thereof), comprising a composition comprising a polypeptide of at least 48 amino acids in length and having an amino sequence according to Formula VI (SEQ ID NO: 541), comprising at least four cysteines and two disulfide bonds, wherein X24 is (Kme) or (Kme2); X29 is (Kme) or A or R; X32 is D or (Kme) or (Cit); and X45 is (Kme) or K.

In another aspect, the composition comprises a polypeptide having an amino acid sequence according to Formula III (SEQ ID NO: 538) as follows:

CAX3EKIAALSEIIWLPCLX19YAQIX24AFIX28X29LNX32DPCX36SX38X3 5ELCS, wherein X3 is (Kme3) or R or (Rme); X19 is T or N; X24 is (Kme2) or (Kme); X28 is A or (Kme); X29 is A or (Kme) or R; X32 is D or (Kme) or (Cit); X36 is Q or N; X38 is S or A; X39 is E or N; and X45 is K or (Kme). In certain embodiments, the polypeptide (e.g., a B7-H3-binding miniprotein) has an amino acid sequence comprising an amino acid sequence of any one of SEQ ID NOs: 204, 238, 239, 241, 247, 262-273, 292, 295, 297, 298, 307, 309, 310, 314-317, 335, 336, 338, 352, 374, 389, 392, 396, 401, 460-462, 466-468, 470, 471, 497, and 528. In certain embodiments, the polypeptide has an amino acid sequence comprising any one of SEQ ID NOs: 204 and 262-272. In some embodiments, the polypeptide is part of a compound selected from any one of C234-235 and C309-C332.

In another aspect, the method comprises use of composition comprising a polypeptide having an amino acid sequence according to Formula IV (SEQ ID NO: 539) as follows:

```
CAX3EKIAALSEIIWLPCLX19YAQIX24AFIAX29LNX32DPC
QSSEILSEAX45ELCS,
```

wherein X3 is (Kme3) or R or (Rme); X19 is T or N; X24 is (Kme2) or (Kme); X29 is A or (Kme); X32 is D or (Kme); and X45 is K or (Kme). In certain embodiments, the polypeptide (e.g., a B7-H3-binding miniprotein) has an amino acid sequence comprising an amino acid sequence of any one of SEQ ID NOs: 204, 241, 262, 265, 267, 268, 292, 307, 314-317, 338, 352, 392, 396, and 401. In certain embodiments, the polypeptide has an amino acid sequence comprising any one of SEQ ID NOs: 204, 262, 265, 267, and 268. In certain embodiments, a compound selected from any one of C234, C235, C298, C299, C304, C305, C308, C309, C310, C311, C320, C323, C325, C326 and C332.

In another aspect, the disclosure provides a method of use of a composition comprising a polypeptide having an amino acid sequence according to Formula V (SEQ ID NO: 540) as follows:

```
CAX3EKIAALSEIIWLPCLTYAQIX24AFIX28X29LNX32DPC
QSSEILSEAX45ELCS,
```

wherein X3 is (Kme3) or (Rme) or R; X24 is (Kme2) or (Kme); X28 is A or (Kme); X29 is A or (Kme) or R; X32 is D or (Kme) or (Cit); and X45 is (Kme) or K. In certain embodiments, the polypeptide (e.g., a B7-H3-binding miniprotein) has an amino acid sequence comprising an amino acid sequence of any one of SEQ ID NOs: 204, 241, 262, 265-267, 270, 272, 292, 307, 314-317, 338, 352, 374, 389, 392, 396, 401, 460-462, 466, 467, 468, 470, 471, and 497. In certain embodiments, the polypeptide has an amino acid sequence comprising any one of SEQ ID NOs: 265, 266, 267, 270, and 272. In certain embodiments, the polypeptide is part of a compound selected from any one of C304-C309, C314, C315, C318, C319, C323, C324, C325, C328, C330, and C332.

In another aspect, the disclosure provides a method of use of a composition comprising a polypeptide having an amino acid sequence according to Formula VI (SEQ ID NO: 541) as follows:

```
CA(Kme3)EKIAALSEIIWLPCLTYAQIX24AFIAX29LNX32D

PCQSSEILSEAX45ELCS,
```

wherein X24 is (Kme) or (Kme2); X29 is (Kme) or A or R; X32 is D or (Kme) or (Cit); and X45 is K or (Kme). In certain embodiments, the polypeptide (e.g., a B7-H3-binding miniprotein) has an amino acid sequence comprising an amino acid sequence of any one of SEQ ID NOs: 204, 262, 265, 267, 270, 272, 314-317, 338, 352, 389, 392, 396, 401, 462, 471. In some embodiments, the polypeptide has an amino acid sequence comprising any one of SEQ ID NOs: 204, 262, 265, 266, 267, 270, and 272. In some embodiments, the polypeptide is part of a compound selected from any one of C234, C235, C298, C299, C304-C309, C314, C315, C318-C320, C323, C324, C325, C328, C330, and C332.

In one aspect, the disclosure provides a polypeptide (e.g., a B7-H3-binding miniprotein) with an amino acid sequence comprising an amino acid sequence according to Formula VII (SEQ ID NO: 542) as follows:

CAX3EKIX7ALX10EIIWLPX17LTYX21QIX24AFIX28X29LNX32DPCQSX38X39X40LX42EAX45ELCS, wherein X3 is (Kme3) or R or K; X7 is A or N; X10 is S or G; X17 is C or N; X21 is A or D; X24 is (Kme3) or (Kme2) or (Kme); X28 is A or (Kme); X29 is A or (Kme) or R; X32 is D or (Kme); X38 is S or A; X39 is E or N; X40 is I or L; X42 is S or A; and X45 is K or (Kme) or (Kme3) or Q. In certain embodiments, the polypeptide (e.g., a B7-H3-binding miniprotein) has an amino acid sequence comprising an amino acid sequence of any one of SEQ ID NOs: 204, 206, 217, 219, 221, 238, 239, 241, 247, 250, 262-267, 273, 278-280, 287, 288, 292, 295, 297-302, 304, 305, 307, 309-319, 321-326, 328-331, 335-338, 352, 356, 366, 367, 374-377, 383-385, 389, 392, 394-396, 401, 402, 404-409, 414-418, 426, 437-439, 449-451, 460-462, 465-468, 470, 471, 489, 497, 502-508, 518-521, 523, and 527.

In one aspect, the disclosure provides a polypeptide (e.g., a B7-H3-binding miniprotein) with an amino acid sequence comprising an amino acid sequence according to Formula VIII (SEQ ID NO: 543) as follows:

CAX3EKIX7ALX10EIIWLPCLTYX21QIX24AFIX28X29LNX32DPCQSX38X39X40LX4 2EAX45ELCS, wherein X3 is (Kme3) or R; X7 is A or N; X10 is S or G; X21 is A or D; X24 is (Kme3) or (Kme2) or (Kme); X28 is A or (Kme); X29 is A or (Kme) or R; X32 is D or (Kme); X38 is S or A; X39 is E or N; X40 is I or L; X42 is S or A; and X45 is K or (Kme) or (Kme3) or Q. In certain embodiments, the polypeptide (e.g., a B7-H3-binding miniprotein) has an amino acid sequence comprising an amino acid sequence of any one of SEQ ID NOs: 204, 206, 238, 239, 241, 247, 250, 262-267, 273, 278-280, 287, 288, 292, 295, 297-302, 304, 305, 307, 309-319, 321-326, 328, 329, 330, 331, 335-338, 352, 356, 366, 367, 374, 375-377, 383-385, 389, 392, 394-396, 401, 402, 404-409, 414-418, 426, 437-439, 449-451, 460-462, 465-468, 470, 471, 489, 497, 502-508, 518-521, 523, and 527.

In one aspect, the disclosure provides a polypeptide (e.g., a B7-H3-binding miniprotein) with an amino acid sequence comprising an amino acid sequence according to Formula IX (SEQ ID NO: 546) as follows:

CAX3EKIX7ALX10EIIWLPX17LTYX21QIX24X25FIX28X29LNX32DPCQSX38X39X40LX42EAX45X46LX48S, wherein X3 is (Kme3) or K or Q or R; X7 is A or N; X10 is S or G; X17 is C or N; X21 is A or D; X24 is (Kme2) or (Kme) or (homo-leucine); X25 is A or E; X28 is A or (Kme); X29 is A or (Kme) or R; X32 is D or (Kme) or (Cit) or A; X38 is S or A; X39 is E or N; X40 is I or L; X42 is S or A; X45 is K or (Kme) or (Kme3) or Q or R; X46 is E or A; and X48 is C or N. In certain embodiments, the polypeptide (e.g., a B7-H3-binding miniprotein) has an amino acid sequence comprising an amino acid sequence of any one of SEQ ID NOs: 203-205, 209-213, 216-220, 225, 226, 230-233, 235, 238, 239, 241, 242, 247, 248, 250, 262-267, 270, 272, 273, 278-280, 287, 288, 292, 294-302, 304, 305, 307, 309-319, 321-326, 328, 329, 330, 331, 335-338, 352, 356, 358, 366, 367, 374-377, 380, 383-385, 389, 392, 394-396, 399, 401, 402, 404-409, 414-418, 426, 434, 437-439, 447, 449, 450, 451, 460-462, 465-468, 470, 471, 474, 475, 489, 497, 499, 502-508, 515, 518-521, 523, 524, 527, 532, 533, 535, and 537.

In one aspect, the disclosure provides a polypeptide (e.g., a B7-H3-binding miniprotein) with an amino acid sequence comprising an amino acid sequence according to Formula X (SEQ ID NO: 547) as follows:

CAX3EKIX7ALX10EIIWLPX17LTYX21QIX24AFIX28X29LNX32DPCQSX38X39X40LX42EAX45ELX48S, wherein X3 is (Kme3) or K or R; X7 is A or N; X10 is S or G; X17 is C or N; X21 is A or D; X24 is (Kme2) or (Kme) or (homo-leucine); X28 is A or (Kme); X29 is A or (Kme) or R; X32 is D or (Kme); X38 is S or A; X39 is E or N; X40 is I or L; X42 is S or A; X45 is K or (Kme) or (Kme3) or Q; and X48 is C or N. In certain embodiments, the polypeptide (e.g., a B7-H3-binding miniprotein) has an amino acid sequence comprising an amino acid sequence of any one of SEQ ID NOs: 204, 209-213, 217-220, 225, 226, 238, 239, 241, 242, 247, 250, 262-267, 273, 278-280, 287, 288, 292, 295, 297-302, 304, 305, 307, 309-319, 321-326, 328, 329, 330, 331, 335-338, 352, 356, 366, 367, 374-377, 383-385, 389, 392, 394-396, 401, 402, 404-409, 414-418, 426, 437-439, 449-451, 460-462, 465-468, 470, 471, 489, 497, 502-508, 518-521, 523, and 527.

In one aspect, the disclosure provides a polypeptide (e.g., a B7-H3-binding miniprotein) with an amino acid sequence comprising an amino acid sequence according to Formula XI (SEQ ID NO: 548) as follows:

CAX3EKIX7ALX10EIIWLPCLTYX21QIX24AFIX28X29LNDDPCQSX38X39X40LX42E AX45ELX48S, wherein X3 is (Kme3) or K or R; X7 is A or N; X10 is S or G; X21 is A or D; X24 is (Kme2) or (Kme); X28 is A or (Kme); X29 is A or (Kme) or R; X38 is S or A; X39 is E or N; X40 is I or L; X42 is S or A; X45 is K or (Kme) or Q; and X48 is C or N. In certain embodiments, the polypeptide (e.g., a B7-H3-binding miniprotein) has an amino acid sequence comprising an amino acid sequence of any one of SEQ ID NOs: 204, 217-220, 238, 239, 241, 242, 247, 250, 262-266, 273, 278, 279, 280, 287, 288, 292, 295, 297-302, 304, 305, 307, 309-319, 321-326, 328, 329, 330, 331, 335-338, 352, 356, 366, 367, 374-377, 383-385, 389, 392, 394-396, 402, 404-409, 414-418, 426, 437-439, 449, 460, 466-468, 471, 489, 497, and 502-508.

In one aspect, the disclosure provides a polypeptide (e.g., a B7-H3-binding miniprotein) with an amino acid sequence comprising an amino acid sequence according to Formula XII (SEQ ID NO: 549) as follows:

CAX3EKIX7ALX10EIIWLPCLTYX21QIX24AFIX28 X29LNDDPCQSX38X39X40LX42E AX45ELX48S, wherein X3 is (Kme3) or K or R; X7 is A or N; X10 is S or G; X21 is A or D; X24 is (Kme2) or (Kme); X28 is A or (Kme); X29 is A or (Kme); X38 is S or A; X39 is E or N; X40 is I or L; X42 is S or A; X45 is K or (Kme); and X48 is C or N. In certain embodiments, the polypeptide (e.g., a B7-H3-binding miniprotein) has an amino acid sequence comprising an amino acid sequence of any one of SEQ ID NOs: 204, 217-220, 238, 239, 241, 242, 247, 262-266, 273, 278, 279, 280, 287, 292, 295, 297-302, 304, 305, 307, 309-319, 321-326, 328-330, 335-338, 352, 356, 366, 367, 374, 383, 384, 392, 395, 396, 402, 404-406, 414, 415, 417, 426, 437, 439, 460, 466, 468, 502, 503, 505, and 506.

In one aspect, the disclosure provides a polypeptide (e.g., a B7-H3-binding miniprotein) with an amino acid sequence comprising an amino acid sequence according to Formula XIII (SEQ ID NO: 550) as follows:

CAX3EKIX7ALX10EIIWLPCLTYX21QIX24AFIAX2 9LNDDPCQSX38EILSEAX45ELC S, wherein X3 is (Kme3) or R; X7 is A or N; X10 is S or G; X21 is A or D; X24 is (Kme2) or (Kme); X29 is A or (Kme); X38 is S or A; and X45 is K or (Kme). In certain embodiments, the polypeptide (e.g., a B7-H3-binding miniprotein) has an amino acid sequence comprising an amino acid sequence of any one of SEQ ID NOs: 204, 238, 241, 262, 263, 265, 292, 295, 297, 302, 304, 305, 307, 309, 313-319, 321-323, 326, 328, 335, 337, 338, 352, 367, 384, 392, 396, 402, 404, 414, 415, 417, 426, 437, 439, 502, 503, 505, and 506.

In another aspect, the disclosure provides a method of use of a composition, comprising a B7-H3 binding polypeptide having an amino acid sequence comprising at least 48 amino acids, wherein the amino acids include (i) a cysteine at each of four positions corresponding to 1, 17, 35, and 48 of SEQ ID NO: 267 and wherein X3 is (Kme3) or R or (Rme); X19 is T or N; X24 is (Kme2) or (Kme); X28 is A or (Kme); X29 is A or (Kme) or R; X32 is D or (Kme) or (Cit); X36 is Q or N; X38 is S or A; X39 is E or N; X45 is K or (Kme), and X49 is S or absent.

In one aspect, the disclosure provides a method of use of a composition, comprising a B7-H3 binding polypeptide having an amino acid sequence, wherein the amino acid sequence comprises: at least four cysteines, which form two disulfide bonds; at least one modified lysine residue at a position corresponding to X24 of SEQ ID NO: 267, wherein the modification comprises at least one small alkyl group attached to the nitrogen of the lysine side chain, optionally comprising a methyl, dimethyl, or trimethyl; at least 48 amino acids in length; and has a binding affinity for B7-H3 stronger than 100 nM in a cell-based assay.

Treatment, Imaging, and Diagnostic/Prognostic Methods of Use

In some embodiments, the present disclosure provides methods of treating cancer in a human subject by administering a miniprotein conjugate described herein. As provided herein, a B7-H3 positive cancer is a cancer having cancer cells expressing B7-H3, but does not explicitly require assaying a tumor prior to treatment to determine if the tumor expresses B7-H3. In some embodiments, the cancer expresses the target (e.g., B7-H3) specifically bound by the miniprotein of the conjugate. In some embodiments, the target protein is expressed on the surface of malignant cells with limited expression on cells of normal tissues, and/or expressed at much higher density on malignant versus normal cells. In some embodiments, a method of treating includes a method of targeting and/or contacting a population of cancer cells. In some embodiments, a malignant cell is part of a population of cells, wherein the population is heterogenous and only a portion expresses a target (e.g., B7-H3). Without wishing to be bound by theory, the disclosure contemplates that, in some such embodiments, a heterogenous population of cancer cells including cells that express the target and cells that do not express the target can be treated by a composition provided herein. For example, if a B7-H3-expressing cell internalizes a composition provided herein, cells apposed to but not expressing B7-H3 can also be treated (e.g., killed) by uptake of the composition into the B7-H3 cell, thereby treating a heterogenous tumor by targeting the target (e.g., B7-H3).

In some embodiments, the cancer is a solid tumor. In some embodiments, the cancer is characterized by presence of one or more tumor cells. In some embodiments, the cancer is characterized by one or more cancer cells (e.g., but not necessarily a cancer cell in a tumor such as a solid tumor). In some embodiments, the cancer is metastatic. In some embodiments, the cancer is recurrent. In some embodiments, the cancer is remitting. In some embodiments, the cancer is selected from the group consisting of bladder, breast, pancreas, ovary, stomach, gastrointestinal tract, liver, lung, prostate, skin, colon, rectum, colon and rectum, skin.

In some embodiment, miniprotein conjugates provided herein can be used for imaging and treating a wide variety of cancers, including, but not limited to, breast cancer, ovarian cancer, melanoma, pancreatic cancer, peripheral neuroma, glioblastoma, adrenocortical carcinoma, AIDS-related lymphoma, anal cancer, bladder cancer, meningioma, glioma, astrocytoma, cervical cancer, chronic myeloproliferative disorders, colon cancer, endometrial cancer, ependymoma, esophageal cancer, Ewing's sarcoma, extracranial germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma, Kaposi sarcoma, laryngeal cancer, leukemia, lip cancer, oral cavity cancer, liver cancer, male breast cancer, malignant mesothelioma, medulloblastoma, Merkel cell carcinoma, metastatic squamous neck cell carcinoma, multiple myeloma and other plasma cell neoplasms, mycosis fungoides and the Sezary syndrome, myelodysplastic syndromes, nasopharyngeal cancer, neuroblastoma, non-small cell lung cancer, small cell lung cancer, head and neck cancer, skin cancer, oropharyngeal cancer, bone cancers, including osteosarcoma and malignant fibrous histiocytoma of bone, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilms tumor and other childhood kidney tumors.

As will be known to those of skill in the art, determination of the appropriate dose and regimen of a composition provided by the present disclosure can be made by the clinician, e.g., using parameters or factors known or suspected in the art to affect treatment or predicted to affect treatment. In some embodiments, actual dosage levels of the active ingredients in compositions provided by the present disclosure may be varied so as to obtain an amount of the active ingredient which is effective to achieve the desired therapeutic response for a particular patient, composition, and mode of administration, without being toxic to the patient. In some embodiments, the selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors known in the medical arts.

In some embodiments, the present disclosure provides methods of imaging, diagnosing and/or monitoring (including determining prognosis) of presence of a target in a subject. In some embodiments, a conjugate (e.g., a miniprotein conjugate comprising, e.g., a chelator and/or radionuclide) of the present disclosure is useful for PET, SPECT, or MRI imaging.

In some embodiments, conjugates (e.g., miniprotein conjugates comprising a chelator and/or radionuclide) of the present disclosure can be used in image-guided surgery. For example, in some embodiments, tissue of interest suspected of containing cancerous cells or a tumor can be contacted with a B7-H3-targeted miniprotein (e.g., affibody, CDP, knottin, binder), such that the B7-H3-targeted miniprotein (e.g., affibody, CDP, knottin, binder, engineered Kunitz domain, monobody, anticalin, designed ankyrin repeat domain (DARPin), avimer) or component(s) thereof (chelator, radionuclide) accumulates in metastatic cancerous cells. Imaging of tissues labeled with the B7-H3 miniprotein conjugate wherein the conjugate comprises more additional detectable components (e.g., chelator, e.g., radionuclide, e.g., other detectable imaging moiety) can be used, for example, for detection of metastatic cells, tumor margin delineation, evaluation of the completeness of resection, and evaluation of the efficacy of treatment.

In some embodiments, the present disclosure provides methods of imaging a cancer in a subject. In some embodiments, miniprotein conjugates of the present disclosure are useful for PET, SPECT, or MRI imaging. In some embodiments, a detectably effective amount of a miniprotein conjugate is administered to a subject; that is, an amount that is sufficient to yield an acceptable image using the imaging equipment that is available for clinical use. In some embodiments, a detectably effective amount of a miniprotein conjugate may be administered in more than one injection if needed. In some such embodiments, a detectably effective amount of miniprotein conjugate needed for an individual may vary according to factors such as the degree of uptake of miniprotein conjugates into cancerous tissue, the age, sex, and weight of the individual, and the particular medical imaging method used. Optimization of such factors is within the level of skill in the art.

In some embodiments, imaging with miniprotein conjugates can be used in assessing efficacy of therapeutic drugs in treating cancer. For example, images can be acquired after treatment with an anti-cancer therapy to determine if the individual is responding to treatment. In some embodiments, in a subject with cancer, imaging with miniprotein conjugate can be used to evaluate whether a tumor is shrinking or growing. Further, the extent of cancerous disease (how far and where the cancer has spread) can be determined to aid in determining prognosis and evaluating optimal strategies for treatment (e.g., surgery, radiation, or chemotherapy).

In some embodiments, miniprotein conjugates can be used in image-guided surgery. Tissue of interest suspected of containing cancerous cells or a tumor can be contacted with a miniprotein conjugate, such that the miniproteins or components thereof (e.g., chelator, e.g., radionuclide) accumulate in metastatic cancerous cells. In some embodiments, imaging of tissues labeled with miniprotein conjugate in this way can be used, for example, for detection of metastatic cells, tumor margin delineation, evaluation of the completeness of resection, and evaluation of the efficacy of treatment.

In another aspect, the disclosure provides a method of treating an individual, a group of individuals, or a population of individuals that are diagnosed with a cancer, the method comprising administering to the individual a means for blocking uptake of a radiotherapeutic to non-tumor tissue, and a radionuclide therapeutic comprising a composition represented by the formula selected from one or more of M-L-C-R, M-L-C, M-C-R, M-L-R, M-C, M-L, and M-R, wherein M comprises a miniprotein (M), L comprises a linker (L), C comprises a chelator (C), and R comprises a radionuclide (R), wherein the M is of a particular scaffold. In some embodiments, the non-tumor tissue is a kidney tissue or a liver tissue. In some embodiments, the means for binding to kidney tissue reduces or prevents uptake of the radiotherapeutic into the kidney. In some embodiments, the radiotherapeutic is targeted to a tumor. In some embodiments, the radiotherapeutic targeted to the tumor is at a greater concentration than in the absence of the means for binding to non-tumor tissue.

In another aspect, the disclosure provides a method of improving a cancer treatment in an individual or group or population of individuals experiencing one or more off-target effects, the method comprising administering: (a) a decoy; and (b) a radionuclide therapeutic, wherein the one or more off-target effects is prevented or reduced as compared to administering the radiotherapeutic in the absence of the decoy. In some embodiments, the radionuclide therapeutic comprises a miniprotein that targets a protein (e.g., B7-H3). In some embodiments, the radionuclide therapeutic comprises a miniprotein that targets B7-H3. In some embodiments, the radionuclide therapeutic comprises a compound selected from Table 2A. In some embodiments, the radionuclide therapeutic comprises a compound selected from Table 2C.

In some embodiments, methods and compositions of the present disclosure include multistep or pre-targeting approaches. For instance, in some embodiments, a radionuclide can be decoupled to a provided composition and may be subsequently administered after an initial step of administering a miniprotein or an antibody (e.g., a first ligand binding moiety). In such embodiments, the first ligand binding moiety is not conjugated to a radionuclide and has the desired affinity and specificity for the tumor cells. The first ligand binding moiety is then targeted by a second moiety carrying the radionuclide. For instance, the first ligand binding moiety may comprise an antibody to the target protein (e.g., B7-H3) and the second moiety may be the pharmaceutical composition comprising the miniprotein, linker, chelator, and the radionuclide, wherein the miniprotein may exhibit a desired avidity to the first ligand binding moiety.

In some embodiments, the present disclosure provides methods of use (e.g., treatment, manufacture, etc.) of miniproteins (e.g., affibodies, CDPs, knottins, binders, engineered Kunitz domains, monobodies, anticalins, designed ankyrin repeat domains (DARPins), avimers) as provided herein.

In some embodiments, anti-target protein (e.g., B7-H3) compositions and pharmaceutical compositions are produced, e.g., using miniproteins (e.g., affibodies, CDPs, knottins, binders, engineered Kunitz domains, monobodies, anticalins, designed ankyrin repeat domains (DARPins), avimers), as provided herein.

In some embodiments, miniproteins of the target (e.g., B7-H3) proteins (e.g., affibodies, CDPs, knottins, binders, engineered Kunitz domains, monobodies, anticalins, designed ankyrin repeat domains (DARPins), avimers) provided by the present disclosure are formatted to generate peptides, antibodies, antibody and antibody fragments, ADCs, BiTEs, CAR-Ts, and TRuCs, Fe-domain components, portions, or modifications, bispecific antibodies etc. In some such embodiments, such compositions and pharmaceutical compositions are used in treatment of a disease, disorder, or condition wherein expression of the target proteins (e.g., B7-H3) is suspected or detected. In some such embodiments, the disease, disorder, or condition is related to overexpression and/or aberrant expression the target proteins (e.g., B7-H3). In some embodiments, the disease, disorder and/or condition is cancer. Accordingly, the present disclosure provides various anti-target (e.g., B7-H3) protein compositions and pharmaceutical compositions for the treatment of disease related to the target proteins (e.g., B7-H3).

Among other things, the present disclosure provides methods of treating a subject in need thereof by administering a composition as provided herein. In some such embodiments, a composition is or comprises a miniprotein (e.g., affibody, CDP, knottin, binder, affibody, engineered Kunitz domain, monobody, anticalin, designed ankyrin repeat domain (DARPin), avimer). In some embodiments, the composition is a miniprotein conjugate comprising a miniprotein and one or more of a chelator and radionuclide, as well as, optionally, a linker (e.g., linking the chelator to the miniprotein).

In some embodiments, a subject treated herein is at risk of having or has been diagnosed as having a cancer. In some embodiments, the subject is a mammal. In some embodiments, the mammal is a human. In some embodiments, the human is a fetus, infant, child, adolescent, adult, or elderly adult. In some embodiments, a human subject having a cancer is treated by administering a miniprotein (e.g., affibody, CDP, knottin, binder, affibody, engineered Kunitz domain, monobody, anticalin, designed ankyrin repeat domain (DARPin), avimer) as described herein.

In some embodiments, the cancer expresses a target protein (e.g., B7-H3) specifically bound by a miniprotein (e.g., affibody, CDP, knottin, binder, affibody, engineered Kunitz domain, monobody, anticalin, designed ankyrin repeat domain (DARPin), avimer) of the present disclosure. In some embodiments, the target protein (e.g., B7-H3) or portion thereof is expressed on the surface of a cancer cell of the subject. In some such embodiments, the target protein (e.g., B7-H3) is expressed on the cancer cell and has lower or non-detectable expression on cells of normal tissues, and/or is expressed at much higher density on cancer cells versus normal cells.

In some embodiments, the cancer is a solid tumor. In some embodiments, the cancer is metastatic. In some embodiments, the cancer is recurrent. In some embodiments, the cancer is remitting. In some embodiments, the cancer is selected from bladder, breast, pancreas, ovary, stomach, gastrointestinal tract, liver, lung, prostate, skin, colon, rectum, colon, and rectum, and/or skin.

In some embodiments, miniproteins (e.g., affibodies, CDPs, knottins, binders, engineered Kunitz domains, monobodies, anticalins, designed ankyrin repeat domains (DARPins), avimers) provided herein can be used in conjunction with one or more additional components. For example, in some embodiments, a miniprotein (e.g., affibody, CDP, knottin, binder, engineered Kunitz domain, monobody, anticalin, designed ankyrin repeat domain (DARPin), avimer) may be combined with one or more other components for use in imaging, diagnosis, prognosis/monitoring and/or treating a disease, disorder or condition. In some embodiments, the disease is cancer. In some embodiments, a miniprotein (e.g., affibody, CDP, knottin, binder, engineered Kunitz domain, monobody, anticalin, designed ankyrin repeat domain (DARPin), avimer) of the present disclosure may be used in a wide variety of cancers, including, but not limited to, breast cancer, ovarian cancer, melanoma, pancreatic cancer, peripheral neuroma, glioblastoma, adrenocortical carcinoma, AIDS-related lymphoma, anal cancer, bladder cancer, meningioma, glioma, astrocytoma, cervical cancer, chronic myeloproliferative disorders, colon cancer, endometrial cancer, ependymoma, esophageal cancer, Ewing's sarcoma, extracranial germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma, Kaposi sarcoma, laryngeal cancer, leukemia, lip cancer, oral cavity cancer, liver cancer, male breast cancer, malignant mesothelioma, medulloblastoma, Merkel cell carcinoma, metastatic squamous neck cell carcinoma, multiple myeloma and other plasma cell neoplasms, mycosis fungoides and the Sezary syndrome, myelodysplastic syndromes, nasopharyngeal cancer, neuroblastoma, non-small cell lung cancer, small cell lung cancer, head and neck cancer, skin cancer, oropharyngeal cancer, bone cancers, including osteosarcoma and malignant fibrous histiocytoma of bone, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilms tumor and other childhood kidney tumors.

In some embodiments, treatment (e.g., including with a miniprotein (e.g., affibody, CDP, knottin, binder, engineered Kunitz domain, monobody, anticalin, designed ankyrin repeat domain (DARPin), avimer) of the present disclosure), diagnosis, prognosis/monitoring, or imaging is in a subject who does not exhibit signs or symptoms of a disease, disorder, and/or condition. In some embodiments, treatment is in a subject who exhibits one or more signs or symptoms of a disease, disorder, or condition even if, for example, such signs or symptoms are not objectively observable without further testing such as laboratory diagnostics. In some embodiments, a subject is susceptible to having or at risk of developing a disease, disorder, or condition (e.g., cancer), based on one or more factors (e.g., level of the target protein (e.g., B7-H3) that are related to increased risk of developing of the disease, disorder, or condition. In some embodiments, a subject has been diagnosed as having a disease, disorder, or condition (e.g., cancer).

In some embodiments, present disclosure provides methods of treating or preventing disease or disorder in a subject, the method comprising administering to the subject a pharmaceutical composition comprising a miniprotein (e.g., affibody, CDP, knottin, binder, engineered Kunitz domain, monobody, anticalin, designed ankyrin repeat domain (DARPin), avimer) of the present disclosure in an amount effective that modulates, binds or inhibits human isoform of the target protein (e.g., B7-H3) to treat or prevent disease or disorder in the subject. In some embodiments, the disease or disorder is cancer. In some embodiments, the cancer is treated (e.g., resolved, prevented, progression is slowed, symptoms are relieved, tumor size reduced to improve overall survival, etc.).

In another aspect, the disclosure provides a method of treating an individual with a cancer, the method comprising administering to the individual a means for blocking uptake of a radiotherapeutic to non-tumor tissue, and a radionuclide therapeutic comprising a composition represented by the formula selected from one or more of M-L-C-R, M-L-C, M-C-R, M-L-R, M-C, M-L, and M-R, wherein M comprises a miniprotein (M), L comprises a linker (L), C comprises a chelator (C), and R comprises a radionuclide (R), wherein the M is of a particular scaffold. In some embodiments, the non-tumor tissue is a kidney tissue. In some embodiments, the means for binding to kidney tissue reduces or prevents uptake of the radiotherapeutic into the kidney. In some embodiments, the radiotherapeutic is targeted to a tumor. In some embodiments, the radiotherapeutic targeted to the tumor is at a greater concentration than in the absence of the means for binding to non-tumor tissue.

In another aspect, the disclosure provides a method of improving a cancer treatment in an individual experiencing one or more off-target effects, the method comprising administering: (a) a decoy; and (b) a radionuclide therapeutic, wherein the one or more off-target effects is prevented or reduced as compared to administering the radiotherapeutic in the absence of the decoy. In some embodiments, the radionuclide therapeutic comprises a miniprotein that targets B7-H3. In some embodiments, the radionuclide therapeutic comprises a compound selected from Table 2A. In some embodiments, the radionuclide therapeutic comprises a compound selected from Table 2C.

In some embodiments, methods and compositions of the present disclosure include multistep or pre-targeting approaches. For instance, in some embodiments, a radionuclide can be decoupled to a provided composition and may be subsequently administered after an initial step of administering a miniprotein or an antibody (e.g., a first ligand binding moiety). In such embodiments, the first ligand binding moiety is not conjugated to a radionuclide and has the desired affinity and specificity for the tumor cells. The first ligand binding moiety is then targeted by a second moiety carrying the radionuclide. For instance, the first ligand binding moiety may comprise an antibody to the B7-H3 and the second moiety may be the pharmaceutical composition comprising the miniprotein, linker, chelator, and the radionuclide, wherein the miniprotein may exhibit a desired avidity to the first ligand binding moiety.

In some embodiments, the present disclosure provides methods of use (e.g., treatment, manufacture, etc.) of miniproteins (e.g., a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer) as provided herein.

In some embodiments, anti-B7-H3 compositions and pharmaceutical compositions are produced, e.g., using miniproteins, as provided herein.

In some embodiments, B7-H3 miniproteins provided by the present disclosure are formatted to generate peptides. In some such embodiments, such compositions and pharmaceutical compositions are used in treatment of a disease, disorder, or condition wherein B7-H3 expression is suspected or detected. In some such embodiments, the disease, disorder, or condition is related to overexpression and/or aberrant expression of B7-H3. In some embodiments, the disease, disorder and/or condition is cancer. Accordingly, the present disclosure provides various anti-B7-H3 compositions and pharmaceutical compositions for the treatment of disease related to B7-H3.

Among other things, the present disclosure provides methods of treating a subject in need thereof by administering a composition as provided herein. In some such embodiments, a composition is or comprises a miniprotein. In some embodiments, the composition is a miniprotein conjugate comprising a miniprotein and one or more of a chelator and radionuclide, as well as, optionally, a linker (e.g., linking the chelator to the miniprotein).

In some embodiments, a subject treated herein is at risk of having or has been diagnosed as having a cancer. In some embodiments, the subject is a mammal. In some embodiments, the mammal is a human. In some embodiments, the human is a fetus, infant, child, adolescent, adult, or elderly adult. In some embodiments, a human subject having a cancer is treated by administering a miniprotein as described herein.

In some embodiments, the cancer expresses a target protein (e.g., B7-H3) specifically bound by a miniprotein of the present disclosure. In some embodiments, the B7-H3 or portion thereof is expressed on the surface of a cancer cell of the subject. In some such embodiments, the B7-H3 is expressed on the cancer cell and has lower or non-detectable expression on cells of normal tissues, and/or is expressed at much higher density on cancer cells versus normal cells.

In some embodiments, the cancer is a solid tumor. In some embodiments, the cancer is metastatic. In some embodiments, the cancer is recurrent. In some embodiments, the cancer is remitting. In some embodiments, the cancer is selected from the group consisting of bladder, breast, pancreas, ovary, stomach, gastrointestinal tract, liver, lung, prostate, skin, colon, rectum, colon and rectum, skin.

In some embodiments, the one or more off-target effects includes uptake, accumulation, and/or retention of a radiotherapeutic in a non-tumor tissue. In some embodiments, off-target effects can also include, but are not limited to, symptoms such as nausea, fatigue, muscle wasting, one or more indicators of toxicity, such as set forth in regulatory agency guidance for toxicity, such as, e.g., at the United States FDA website, fda.gov/media/73679/download.

In some embodiments, the disclosure provides a method for treatment comprising administering a pharmaceutical composition as provided herein in the absence of administering targeted conditioning or pre-conditioning regimens where conditioning is necessary prior to administration of therapies, e.g., adoptive cell therapies and gene therapies to ablate certain cells.

In some embodiments, miniproteins provided herein can be used in conjunction with one or more additional components. For example, in some embodiments, a miniprotein (e.g., that targets B7-H3, e.g., that binds to cells expressing B7-H3, etc.) may be combined with one or more other components for use in imaging, diagnosis, prognosis/monitoring and/or treating a disease, disorder, or condition. In some embodiments, a miniprotein or composition of the present disclosure may be administered in combination with one or more treatment or components for use in monoclonal antibody therapy, immunotherapy, chemotherapy, radiotherapy, gene therapy, or RNA therapy.

In some embodiments, a miniprotein or composition of the present disclosure is administered in combination with an immunotherapy treatment. In some embodiments, a miniprotein or composition of the present disclosure is administered in combination with an immune checkpoint inhibitors. Exemplary immune checkpoint inhibitors include agents that inhibit one or more of (i) cytotoxic T lymphocyte-associated antigen 4 (CTLA4), (ii) programmed cell death protein 1 (PDT), (iii) PDL1, (iv) LAG3, (v) B7-H3, (vi) B7H4, and (vii) TIM3.

In some embodiments, the miniprotein or composition is administered in combination with monoclonal antibody agents that target non-checkpoint targets (e.g., herceptin) and non-cytotoxic agents (e.g., tyrosine-kinase inhibitors).

In some embodiments, the miniprotein or composition is administered in combination with other anti-cancer agents, including, for example: (i) an inhibitor selected from an ALK Inhibitor, an ATR Inhibitor, an A2A Antagonist, a Base Excision Repair Inhibitor, a Bcr-Abl Tyrosine Kinase Inhibitor, a Bruton's Tyrosine Kinase Inhibitor, a CDC7 Inhibitor, a CHK1 Inhibitor, a Cyclin-Dependent Kinase Inhibitor, a DNA-PK inhibitor, an inhibitor of both DNA-PK and mTOR, a DNMT1 Inhibitor, a DNMT1 Inhibitor plus 2-chloro-deoxyadenosine, an HD AC Inhibitor, a Hedgehog Signaling Pathway Inhibitor, an IDO Inhibitor, a JAK Inhibitor, a mTOR Inhibitor, a MEK Inhibitor, a MELK Inhibitor, a MTH1 Inhibitor, a PARP Inhibitor, a Phosphoinositide 3-Kinase Inhibitor, an Inhibitor of both PARP1 and DHODH, a Proteasome Inhibitor, a Topoisomerase-II Inhibitor, a Tyrosine Kinase Inhibitor, a VEGFR Inhibitor, and a WEEI Inhibitor; (ii) an agonist of OX40, CD137, CD40, GITR, CD27, HVEM, TNFRSF25, or ICOS; and (iii) a cytokine selected from IL-12, IL-15, GM-CSF, and G-CSF.

In some embodiments, the miniprotein or composition is administered in combination with a radiotherapy treatment. Examples of radiotherapy treatment include external beam radiation therapy and internal radiation therapy.

In some embodiments, the disease is cancer. In some embodiments, a miniprotein of the present disclosure may be used in a wide variety of cancers, including, but not limited to, breast cancer, ovarian cancer, melanoma, pancreatic cancer, peripheral neuroma, glioblastoma, adrenocortical carcinoma, AIDS-related lymphoma, anal cancer, bladder cancer, meningioma, glioma, astrocytoma, cervical cancer, chronic myeloproliferative disorders, colon cancer, endometrial cancer, ependymoma, esophageal cancer, Ewing's sarcoma, extracranial germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma, Kaposi sarcoma, laryngeal cancer, leukemia, lip cancer, oral cavity cancer, liver cancer, male breast cancer, malignant mesothelioma, medulloblastoma, Merkel cell carcinoma, metastatic squamous neck cell carcinoma, multiple myeloma and other plasma cell neoplasms, mycosis fungoides and Sezary syndrome, myelodysplastic syndromes, nasopharyngeal cancer, neuroblastoma, non-small cell lung cancer, small cell lung cancer, head and neck cancer, skin cancer, oropharyngeal cancer, bone cancers, including osteosarcoma and malignant fibrous histiocytoma of bone, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilms tumor and other childhood kidney tumors.

In some embodiments, the miniprotein or composition is administered in combination with a second therapeutic agent, including, for example, a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, proteasome inhibitors, inhibitors of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder, a DHFR inhibitor, a topoisomerase inhibitor, an auristatin (e.g., monomethyl auristatin E), and/or an immunotoxin.

In some embodiments, the miniprotein or composition is administered in combination with a second therapeutic agent that is a DNA damage response (DDR) inhibitor. A DDR inhibitor may be an inhibitor of Serine-protein kinase ATM (ATM), Serine/threonine-protein kinase ATR (ATR), Serine/threonine-protein kinase Chk1 (CHK1/2), DNA-dependent protein kinase catalytic subunit (DNA-PK), Poly [ADP-ribose]polymerase (PARP), Membrane-associated tyrosine- and threonine-specific CDC2-inhibitory kinase (PKMYT1), RNA-directed DNA polymerase (POL0), and/or DNA repair protein RAD51 homolog 1 (RAD51).

In some embodiments, treatment (e.g., including with a miniprotein (e.g., a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer) of the present disclosure), diagnosis, prognosis/monitoring, or imaging is in a subject who does not exhibit signs or symptoms of a disease, disorder, and/or condition. In some embodiments, treatment is in a subject who exhibits one or more signs or symptoms of a disease, disorder, or condition even if, for example, such signs or symptoms are not objectively observable without further testing such as laboratory diagnostics. In some embodiments, a subject is susceptible to having or at risk of developing a disease, disorder, or condition (e.g., cancer), based on one or more factors (e.g., level of B7-H3, etc.) that are related to increased risk of developing of the disease, disorder, or condition. In some embodiments, a subject has been diagnosed as having a disease, disorder, or condition (e.g., cancer).

In some aspects, the disclosure provides a method of treating an individual with cancer comprising administering a polypeptide as provided herein or a composition as provided herein comprising a miniprotein (M) and a radionuclide (R); and (b) a decoy, the improvement comprising reducing one or more off-target effects or toxicity measures after administration of the composition and the decoy molecule as compared to administration of the composition in the absence of the decoy. In some embodiments, the polypeptide or the composition binds to B7-H3.

In some aspects, the disclosure provides a method of treating an individual with a cancer by administering: (a) (i) a polypeptide as provided herein or (ii) a composition as provided herein, wherein, in either case, the polypeptide or the composition comprises a radionuclide (R); and (b) a decoy molecule, the improvement comprising achieving a reduction in concentration of R in a non-tumor tissue in the presence of the decoy as compared to the concentration of R in the non-tumor tissue in the absence of the decoy. In some embodiments, the non-tumor tissue is a liver tissue or a kidney tissue. In some embodiments, wherein the one or more off-target effects or toxicity measures is measured as a reduction in one or more toxicity grades of each of the one or more off-target effects or toxicity measures. In some embodiments, wherein the reduction in concentration of R in the kidney tissue is measured by urine output of R. In some embodiments, wherein the percent of administered radiation recovered in the presence of the decoy is increased as compared to radiation recovered in absence of the decoy. In some embodiments, wherein the reduction in concentration of R in the kidney tissue is determined by maintenance of eGFR over at least the period that the subject is receiving treatment. In some embodiments, wherein the administration of the composition can be repeated at least twice as many times in the presence of the decoy as in the absence of the decoy before a dose limiting toxicity is reached.

In another aspect, the disclosure provides a method of treating an individual with a cancer, the method comprising administering to the individual a means for blocking uptake of a radiotherapeutic to a non-tumor tissue, and a radionuclide therapeutic comprising a polypeptide as provided herein or a composition as provided herein, wherein the polypeptide or the composition comprise a radionuclide (R). In some embodiments, the non-tumor tissue is a kidney tissue or a liver tissue. In some embodiments, the means for binding to kidney tissue reduces or prevents uptake of the radiotherapeutic into the kidney. In some embodiments, the radiotherapeutic is targeted to a tumor. In some embodiments, the radiotherapeutic targeted to the tumor is at a greater concentration than in the absence of the means for binding to kidney tissue.

In another aspect, the disclosure provides a method of improving a cancer treatment in an individual experiencing one or more off-target effects, the method comprising administering a decoy molecule; and a radionuclide therapeutic comprising a radionuclide (R) and a polypeptide as provided herein, wherein the one or more off-target effects is prevented or reduced as compared to administering the radiotherapeutic in the absence of the decoy molecule. In some embodiments, the radionuclide therapeutic comprises a miniprotein that targets B7-H3. In some embodiments, the radionuclide therapeutic comprises a miniprotein selected from any of SEQ ID NOs 4-6, SEQ ID NOs: 8-94, or SEQ ID NOs: 100-537 or Compound ID Nos C1-C9, C11-C117, or C121-C608 and C611. In some embodiments, the radionuclide therapeutic comprises a compound selected from Table 2A or Table 2C.

Methods of Modifying Uptake and/or Retention in Non-Tumor Tissue

Decoys of the disclosure can be used to avoid any such off-target effects or impact that would decrease effective dosage and/or increase potential toxicity due to uptake and/or retention such as of a radionuclide in a non-tumor tissue. As will be understood, given context, in some embodiments, non-tumor tissue is tissue that is not a tumor and/or does not include a population of cancers cells. For example, in some embodiments, kidney and/or liver tissue is biopsy tissue, e.g., from a subject, e.g., a healthy subject, e.g., a subject in need of treatment. In some embodiments, kidney and/or liver tissue includes a population of cells, such as dissociated cells. In some such embodiments, cells may be biopsy cells, cells from an animal model, cells from a cell line (e.g., OK-PTC cells, etc.), engineered cells, etc. In some embodiments, a kidney and/or liver tissue is in vivo, ex vivo, or in vitro. As provided herein, methods and compositions treat a disease, disorder, or condition, such as a cancer, in in a subject or group of subjects or population by mitigating or preventing off-target effects including, but not limited to uptake and/or retention in a non-tumor tissue such as liver and/or kidney, while also maintaining or improving efficacy of the radiotherapeutic for treatment of the tumor by co-administration of a decoy with a therapeutic of the disclosure.

In some embodiments, the disclosure provides improved methods of reducing off-target effects of a composition as provided herein. In some such embodiments, reduction of off-target effects can be associated with a reduction in toxicity. In some embodiments, the toxicity level can be assessed by using the toxicity scale as described in, for example, "Common Terminology Criteria for Adverse Events v3.0 (CTCAE)." Toxicity scales can be graded on a scale of 1-4 as follows: Mild (Grade 1); Moderate (Grade 2); Severe (Grade 3); Potentially Life Threatening (Grade 4). Measures that can be evaluated using a toxicity scale such as described herein include, but are not limited to, pain (at a particular site, throughout the body), fever, heart rate (e.g., tachycardia, bradycardia), hypertension, respiration rate, nausea/vomiting, diarrhea, headache, fatigue, myalgia, systemic illness or clinical adverse event, laboratory abnormalities (such as in, e.g., a complete blood count including hemoglobin, white blood cells, red blood cells, precursor blood cells, platelets, fibrinogen, PTT, etc., one or more electrolyte values, liver enzyme values and/or kidney protein values, e.g., sodium, potassium, glucose, blood urea nitrogen, creatinine, calcium, magnesium, phosphorus, CPK, albumin, total protein, alkaline phosphatase, ALT, AST, bilirubin, cholesterol, pancreatic enzymes such as amylase and lipase, etc., urine measurements (e.g., protein, glucose, blood, specific gravity, etc.). Those of ordinary skill in the art will be knowledgeable about applying toxicity scales and grades to any particular symptom using clinically relevant and acceptable standards, including, such as defined in a clinical trial protocol or treatment brochure.

In some embodiments, a toxicity grade of a therapeutic (e.g., a radiotherapeutic as provided herein, a commercially available radiotherapeutic, etc.) will be reduced by one or more grade points on one or more measures in the presence of a decoy as compared to the absence of a decoy. The disclosure contemplates that one or more decoys as provided herein may be administered in conjunction with one or more radiotherapeutics including those provided herein. In some embodiments, a decoy can be provided as a standalone therapy for use in subjects being treated with one or more radiotherapeutic treatments (e.g., not limited to those provided herein). In some embodiments, administration of the decoy enables higher dosing with one or more radiotherapeutic treatments. as compared to dosing in the absence of a decoy with no change in toxicity grade of the therapeutic.

In some embodiments, the disclosure provides methods of reducing one or more off-target effects of a composition as provided herein. In some such embodiments, reduction of one or more off-target effects includes reduced uptake and/or retention of a composition (e.g., a radiolabeled composition) as provided herein in non-tumor tissue (e.g., kidney, liver, etc.) in % ID/g of tissue. In some embodiments, the reduced uptake and/or retention in non-tumor tissue (e.g., kidney) can be determined by measuring recovered radiation (e.g., from urine).

Recovered radiation can be determined using standard methods known to those of skill in the art, including, for example, collecting urine at one or more time points after administration of a radiolabeled compound and determining the amount of radiation in the sample as compared to the amount of radiation administered. In some embodiments, if more radiation is recovered in urine in connection with administration of a decoy, less radiation is being retained in a kidney. In some embodiments, a decoy results in an increase in output of radiation by a kidney. In some embodiments, administration of a decoy results in more radiation being taken up by a tumor and less being taken up and/or retained in a non-tumor tissue (e.g., kidney, e.g., liver). In some embodiments, the present disclosure comprises a method for treatment, comprising administering a pharmaceutical composition as provided herein in the absence of administering targeted conditioning or pre-conditioning regimens where conditioning is necessary prior to administration of therapies, e.g., adoptive cell therapies and gene therapies to ablate certain cells.

In some embodiments, methods and compositions of the present disclosure include multistep or pre-targeting approaches. For instance, in some embodiments, a radionuclide can be decoupled to a provided composition and may be subsequently administered after an initial step of administering a miniprotein or an antibody (e.g., a first ligand binding moiety). In such embodiments, the first ligand binding moiety is not conjugated to a radionuclide and has the desired affinity and specificity for the tumor cells. The first ligand binding moiety is then targeted by a second moiety carrying the radionuclide. For instance, the first ligand binding moiety may comprise an antibody to the B7-H3 and the second moiety may be the pharmaceutical composition comprising the miniprotein, linker, chelator, and the radionuclide, wherein the miniprotein may exhibit a desired avidity to the first ligand binding moiety.

In some embodiments, the present disclosure provides methods of use (e.g., treatment, manufacture, etc.) of miniproteins (e.g., affibodies, CDPs, knottins, binders) as provided herein.

In some embodiments, anti-B7-H3 compositions and pharmaceutical compositions are produced, e.g., using miniproteins (e.g., affibodies, CDPs, knottins, binders), as provided herein.

In some embodiments, B7-H3 miniproteins (e.g., affibodies, CDPs, knottins, binders) provided by the present disclosure are formatted to generate peptides, antibodies, antibody and antibody fragments, ADCs, BiTEs, CAR-Ts, and TRuCs, Fc-domain components, portions, or modifications, bispecific antibodies etc. In some such embodiments, such compositions and pharmaceutical compositions are used in treatment of a disease, disorder, or condition wherein B7-H3 expression is suspected or detected. In some such embodiments, the disease, disorder, or condition is related to overexpression and/or aberrant expression of B7-H3. In some embodiments, the disease, disorder and/or condition is cancer. Accordingly, the present disclosure provides various anti-B7-H3 compositions and pharmaceutical compositions for the treatment of disease related to B7-H3.

Among other things, the present disclosure provides methods of treating a subject in need thereof by administering a composition as provided herein. In some such embodiments, a composition is or comprises a miniprotein (e.g., affibody, CDP, knottin, binder). In some embodiments, the composition is a miniprotein conjugate comprising a miniprotein and one or more of a chelator and radionuclide, as well as, optionally, a linker (e.g., linking the chelator to the miniprotein).

In some embodiments, a subject treated herein is at risk of having or has been diagnosed as having a cancer. In some embodiments, the subject is a mammal. In some embodiments, the mammal is a human. In some embodiments, the human is a fetus, infant, child, adolescent, adult, or elderly adult. In some embodiments, a human subject having a cancer is treated by administering a miniprotein (e.g., affibody, CDP, knottin, binder, engineered Kunitz domain, monobody, anticalin, designed ankyrin repeat domain (DARPin), avimer) as described herein.

In some embodiments, the cancer expresses a target protein (e.g., B7-H3) specifically bound by a miniprotein (e.g., affibody, CDP, knottin, binder, engineered Kunitz domain, monobody, anticalin, designed ankyrin repeat domain (DARPin), avimer) of the present disclosure. In some embodiments, the B7-H3 or portion thereof is expressed on the surface of a cancer cell of the subject. In some such embodiments, the B7-H3 is expressed on the cancer cell and has lower or non-detectable expression on cells of normal tissues, and/or is expressed at much higher density on cancer cells versus normal cells.

In some embodiments, the cancer is a solid tumor. In some embodiments, the cancer is metastatic. In some embodiments, the cancer is recurrent. In some embodiments, the cancer is remitting. In some embodiments, the cancer is selected from the group consisting of bladder, breast, pancreas, ovary, stomach, gastrointestinal tract, liver, lung, prostate, skin, colon, rectum, colon and rectum, skin.

In some embodiments, miniproteins (e.g., affibodies, CDPs, knottins, binders) provided herein can be used in conjunction with one or more additional components. For example, in some embodiments, a miniprotein (e.g., affibody, CDP, knottin, binder, engineered Kunitz domain, monobody, anticalin, designed ankyrin repeat domain (DARPin), avimer) may be combined with one or more other components for use in imaging, diagnosis, prognosis/monitoring and/or treating a disease, disorder or condition. In some embodiments, the disease is cancer. In some embodiments, a miniprotein (e.g., affibody, CDP, knottin, binder, engineered Kunitz domain, monobody, anticalin, designed ankyrin repeat domain (DARPin), avimer) of the present disclosure may be used in a wide variety of cancers, including, but not limited to, breast cancer, ovarian cancer, melanoma, pancreatic cancer, peripheral neuroma, glioblastoma, adrenocortical carcinoma, AIDS-related lymphoma, anal cancer, bladder cancer, meningioma, glioma, astrocytoma, cervical cancer, chronic myeloproliferative disorders, colon cancer, endometrial cancer, ependymoma, esophageal cancer, Ewing's sarcoma, extracranial germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma, Kaposi sarcoma, laryngeal cancer, leukemia, lip cancer, oral cavity cancer, liver cancer, male breast cancer, malignant mesothelioma, medulloblastoma, Merkel cell carcinoma, metastatic squamous neck cell carcinoma, multiple myeloma and other plasma cell neoplasms, mycosis fungoides and the Sezary syndrome, myelodysplastic syndromes, nasopharyngeal cancer, neuroblastoma, non-small cell lung cancer, small cell lung cancer, head and neck cancer, skin cancer, oropharyngeal cancer, bone cancers, including osteosarcoma and malignant fibrous histiocytoma of bone, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilms tumor and other childhood kidney tumors.

In some embodiments, treatment (e.g., including with a miniprotein (e.g., affibody, CDP, knottin, binder, engineered Kunitz domain, monobody, anticalin, designed ankyrin repeat domain (DARPin), avimer) of the present disclosure), diagnosis, prognosis/monitoring, or imaging is in a subject who does not exhibit signs or symptoms of a disease, disorder, and/or condition. In some embodiments, treatment is in a subject who exhibits one or more signs or symptoms of a disease, disorder, or condition even if, for example, such signs or symptoms are not objectively observable without further testing such as laboratory diagnostics. In some embodiments, a subject is susceptible to having or at risk of developing a disease, disorder, or condition (e.g., cancer), based on one or more factors (e.g., level of B7-H3, etc.) that are related to increased risk of developing of the disease, disorder, or condition. In some embodiments, a subject has been diagnosed as having a disease, disorder, or condition (e.g., cancer).

In some embodiments, present disclosure provides methods of treating or preventing disease or disorder in a subject, the method comprising administering to the subject a pharmaceutical composition comprising a miniprotein (e.g., affibody, CDP, knottin, binder, engineered Kunitz domain, monobody, anticalin, designed ankyrin repeat domain (DARPin), avimer) of the present disclosure in an amount effective that modulates, binds or inhibits human B7-H3 to treat or prevent disease or disorder in the subject. In some embodiments, the disease or disorder is cancer. In some embodiments, the cancer is treated (e.g., resolved, prevented, progression is slowed, symptoms are relieved, tumor size reduced to improve overall survival, etc.).

In another aspect, the disclosure provides a method of reducing uptake by a non-tumor tissue of a composition the improvement comprising administering a composition comprising a radionuclide therapeutic comprising at least a polypeptide as provided herein or a composition as provided herein, and a radionuclide (R); and a decoy molecule, such that in the presence of the decoy, the radionuclide is less concentrated in the non-tumor tissue than in the absence of the decoy. In some embodiments, the non-tumor tissue is a kidney tissue or a liver tissue. In some embodiments, the reduction in concentration of R in the kidney tissue is measured by urine output of R. In some embodiments, the urine output is expressed as a percent of administered radiation recovered in the presence of the decoy and is increased as compared to radiation recovered in absence of the decoy. In some embodiments, the reduction in concentration of R in the kidney tissue is determined by maintenance of eGFR over at least the period that the subject is receiving treatment. In some embodiments, the administration of the composition can be repeated more often (e.g., at least 2, 3, 4, 5, 6, 7, 8, 9, 10 times more, etc.) than the presence of the decoy as in the absence of the decoy before a dose limiting toxicity is reached. In some embodiments, administration of the polypeptide or the composition is administered concomitant with the decoy peptide. In some embodiments, administration of the polypeptide or the composition is administered sequentially with the decoy peptide. In some embodiments, the sequential administering comprises administering the decoy molecule followed by administering the polypeptide or the composition. In some embodiments, the sequential administering comprises administering the polypeptide or the composition followed by administering the decoy peptide. In some embodiments, the decoy is administered in a molar or mass excess relative to the miniprotein (M). In some embodiments, the excess is at least about 2, 10, 50, 100, 250, 500, 750, 1,000, 2,500, 5,000, 7,500, or 10,000× excess relative to the polypeptide or the composition. In some embodiments, the decoy peptide comprises or consists of an amino acid sequence selected from any of compounds C10 or C118-C120. In some embodiments, the miniprotein comprises or consists of an amino acid sequence selected from any of compounds selected from Table 2A. In some embodiments, the decoy peptide comprises or consists of an amino acid sequence selected from any of compounds C118-C120. In some embodiments, the decoy peptide comprises or consists of an amino acid sequence of the compound C10. In some embodiments, the decoy peptide comprises or consists of an amino acid sequence selected from any of compounds C118-C120 and the miniprotein comprises or consists of an amino acid sequence selected any one of the compounds in Table 2A or Table 2C. In some embodiments, the decoy peptide comprises or consists of an amino acid sequence of compound C10 and the miniprotein comprises or consists of an amino acid sequence selected any one of the compounds in Table 2A or Table 2C.

In one aspect, the disclosure provides, in a method of improving binding affinity strength of a polypeptide to B7-H3, the improvement comprising modifying at least three amino acid residues of a polypeptide, which polypeptide has at least 48 amino acids in length and has cysteines at positions corresponding to 1, 17, 35, and 48 of SEQ ID NO: 267, wherein a position corresponding to X24 is (Kme) or (Kme2); X29 is A or (Kme); and X32 is D or (Kme) or (Cit), and wherein X49 is S or absent.

In some aspects, the disclosure provides a method of treating cancer. In one aspect, the disclosure provides a method of treating cancer, the method comprising administering to a subject in need thereof, a composition comprising a conjugate comprising a polypeptide with an amino acid sequence having at least 90% identity to at least 44 amino acids of an amino acid sequence as set forth in any one of SEQ ID NOs: 198-537 and a radionuclide. In some embodiments, the polypeptide has an amino acid sequence with 100% identity to any one of SEQ ID NOs: 198-537. In certain embodiments, the polypeptide has at least one, two, or three constraints (e.g., at least four cysteines and two disulfide bridges).

In some embodiments, the radionuclide is associated with the polypeptide with a linker and/or chelator according to a formula M-L-C-R, wherein M is the polypeptide, L is a linker, C is a chelator, and R is the radionuclide. In some embodiments, M has an amino acid sequence comprising or consisting of any one of SEQ ID NOs: 204 and 262-272. In some embodiments, M has an amino acid sequence comprising or consisting of SEQ ID NO: 267.

In some embodiments, L comprises or consists of a polyethylene glycol (PEG) linker of PEG4, PEG, PEG2, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, any linker set forth in Table 2A, or (Gly)n-(gGlu)n- (SEQ ID NO: 551) or (PEG)n, wherein n is from 1 to 36, (Gly)1-10 (SEQ ID NO: 552), or any fragment or combination via covalent bond thereof. In some embodiments, C comprises or consists of DOTA, Crown, NOPO, Macropa, lead specific chelator (PSC), N-succinimidyl 3-(tri-n-butylstannyl)benzoate (BuSTB), or N-succinimidyl 3-trimethylstannylbenzoate (MeSTB)

In some embodiments, R is Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211. In some embodiments, R is a therapeutic agent and/or an imaging agent. In some embodiments, R is Cu-64, Ga-68, Lu-177, In-111, Cu-67, La-132, or F-18. In one aspect, the disclosure provides in a method of improving binding affinity strength of a polypeptide to B7-H3, the improvement comprising modifying at least three amino acid residues of a polypeptide, which polypeptide has at least 40, 41, 42, 43, 44, 45, 46, 47, 48, or 49 amino acids in length and has cysteines at positions corresponding to 1, 17, 35, and 48 of SEQ ID NO: 267, wherein a position corresponding to X24 is (Kme) or (Kme2); X29 is A or (Kme); and X32 is D or (Kme) or (Cit), and wherein X49 is S or absent.

In one aspect, the disclosure provides a method of treating cancer, the method comprising administering to a subject in need thereof, a composition comprising a conjugate comprising a polypeptide having at least 90% identity to at least 44 amino acids of an amino acid sequence as set forth in any one of SEQ ID NOs: 198-537 and a radionuclide.

In some embodiments, the radionuclide is associated with the polypeptide with a linker and/or chelator according to a formula M-L-C-R, wherein M is the polypeptide, L is a linker, C is a chelator, and R is the radionuclide. In certain embodiments, the polypeptide has an amino acid sequence comprising or consisting of any of SEQ ID NOs: 204, or 262-272. In some embodiments, L comprises or consists of a polyethylene glycol (PEG) linker of PEG4, PEG, PEG2, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, any linker set forth in Table 2A, or (Gly)n-(gGlu)n- (SEQ ID NO: 551) or (PEG)n, wherein n is from 1 to 36, (Gly)1-10 (SEQ ID NO: 552), or any fragment or combination via covalent bond thereof. In some embodiments, C comprises or consists of DOTA, Crown, NOPO, Macropa, lead specific chelator (PSC), N-succinimidyl 3-(tri-n-butylstannyl)benzoate (BuSTB), or N-succinimidyl 3-trimethylstannylbenzoate (MeSTB). In some embodiments, R is Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211. Depending on context, R can be a therapeutic agent and/or an imaging agent. In certain embodiments, R is Cu-64, Ga-68, Lu-177, In-111, Cu-67, La-132, or F-18.

In one aspect, the disclosure provides a method of reducing kidney cell uptake of a composition comprising administering to a subject a B7-H3 binding protein having an amino acid sequence comprising at least one modified lysine residue at a position corresponding to X24 of SEQ ID NO: 267, wherein the modification comprises at least one small alkyl group attached to the nitrogen of the lysine side chain, optionally comprising a methyl, dimethyl, or trimethyl group, and the reduction is as compared to administration to the subject or a control subject an otherwise identical composition but not comprising the modified lysine residue at the position corresponding to X24. In some embodiments, the B7-H3 binding protein has an amino acid sequence in accordance with any of Tables 1D, 1E, and 2C. In some embodiments, the B7-H3 binding protein has an amino acid sequence with at least 90% identity to at least 44 amino acids to any sequence as set forth in Tables 1D, 1E, and 2C.

In another aspect, the disclosure provides, in a method of treating cancer, the improvement comprising administering a composition comprising a B7-H3 binding protein having an amino acid sequence comprising at least one modified lysine residue at a position corresponding to X24 of SEQ ID NO: 267, wherein the modification comprises at least one small alkyl group attached to the nitrogen of the lysine side chain, optionally comprising a methyl, dimethyl, or trimethyl group, and the reduction is as compared to administration to the subject or a control subject an otherwise identical composition but not comprising the modified lysine residue at the position corresponding to X24. In some embodiments, the B7-H3 binding protein has an amino acid sequence in accordance with any of Tables 1D, 1E, and 2C. In some embodiments, the B7-H3 binding protein has an amino acid sequence with at least 90% identity to at least 44 amino acids to any sequence as set forth in Tables 1D, 1E, and 2C.

In one aspect, the disclosure provides a method of treating a subject with refractory or recurrent cancer comprising administering a composition, compound, or pharmaceutical composition in accordance with the present disclosure, thereby treating the cancer. In some embodiments, the composition (e.g., composition, compound, pharmaceutical composition, etc.) comprises a polypeptide that has an amino acid sequence in accordance with any of Tables 1D, 1E, and 2C. In some embodiments, the composition comprises a polypeptide that has an amino acid sequence with at least 90% identity to at least 44 amino acids to any sequence as set forth in Tables 1D, 1E, and 2C.

In one aspect, the disclosure provides a method of improving biodistribution of a pharmaceutical composition for a B7-H3 positive population of cancer cells in a subject having a B7-H3-positive cancer, comprising contacting the population with a polypeptide that has a modified lysine at a position corresponding to X24 of SEQ ID NO: 267, wherein the lysine is modified by adding at least one small alkyl group to a lysine side chain and wherein the biodistribution is improved as compared to contacting the population without the modified lysine at a position corresponding to X24 of SEQ ID NO: 267.

In one aspect, the disclosure provides a method of improving biodistribution of a pharmaceutical composition for a B7-H3 positive population of cancer cells in a subject having a B7-H3-positive cancer, comprising contacting the population with a polypeptide that has a modified lysine at a position corresponding to X24 of SEQ ID NO: 241, wherein the lysine is modified by adding at least one small alkyl group to a lysine side chain and wherein the biodistribution is improved as compared to contacting the population without the modified lysine at a position corresponding to X24 of SEQ ID NO: 241.

In some embodiments, the polypeptide has an amino acid sequence in accordance with any of Tables 1D, 1E, and 2C.

In some embodiments, the polypeptide has an amino acid sequence with at least 90% identity to at least 44 amino acids to any sequence as set forth in Tables 1D, 1E, and 2C.

In another aspect, the disclosure provides a method of diagnosing presence of a B7-H3 positive population of cancer cells comprising: contacting a population of cells with a composition, compound, or pharmaceutical composition in accordance with the present disclosure; detecting the presence of the composition, compound, or pharmaceutical composition of step (a) by measuring a signal; and comparing the detection in step (b) to a control signal; and diagnosing cancer if the composition, compound, or pharmaceutical composition of step (a) is detected above the control. In certain embodiments, the contacting is performed by administering to a subject in need thereof. In some embodiments, the administering is intravenous or subcutaneous. In some embodiments, the contacting is outside of the subject, optionally in vitro with a biopsy sample.

In another aspect, the disclosure provides a method of treating a cancer in a subject using an immunotherapy, the method comprising administering to the subject a composition comprising a composition, compound, or pharmaceutical composition in accordance with the present disclosure, wherein the treatment treats the cancer.

In one aspect, the disclosure provides use of a composition, compound, or pharmaceutical composition in accordance with the present disclosure to treat cancer in a subject, wherein the treatment treats the cancer.

In one aspect, the disclosure provides a method of treating a subject in need thereof comprising administering to the subject in need thereof a composition, compound, or pharmaceutical composition in accordance with the present disclosure. In some embodiments, the subject is diagnosed as having cancer. In certain embodiments, a cancer cell from the subject expresses B7-H3, or a portion thereof. In some embodiments, the expression of B7-H3 is higher in the cancer cell than in a non-cancer cell, which expression can be measured by protein and/or nucleic acid levels. In some embodiments, the non-cancer cell is obtained from the subject. In some embodiments, the composition, compound, or pharmaceutical composition is not taken up and/or retained in the kidney as compared to a compound that does not comprise a composition, compound, or pharmaceutical composition in accordance with the present disclosure, thereby treating the cancer. In some embodiments, the composition, compound, or pharmaceutical composition is internalized in a cell expressing human B7-H3.

In certain embodiments, the cancer is selected from breast cancer, ovarian cancer, melanoma, pancreatic cancer, peripheral neuroma, glioblastoma, adrenocortical carcinoma, AIDS-related lymphoma, anal cancer, urothelial cancer, bladder cancer, meningioma, glioma, astrocytoma, cervical cancer, chronic myeloproliferative disorders, colon cancer, endometrial cancer, ependymoma, esophageal cancer, Ewing's sarcoma, extracranial germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma, Kaposi sarcoma, laryngeal cancer, leukemia, lip cancer, oral cavity cancer, liver cancer, male breast cancer, malignant mesothelioma, medulloblastoma, Merkel cell carcinoma, metastatic squamous neck cell carcinoma, multiple myeloma and other plasma cell neoplasms, mycosis fungoides and Sezary syndrome, myelodysplastic syndromes, nasopharyngeal cancer, neuroblastoma, non-small cell lung cancer, small cell lung cancer, head and neck cancer, skin cancer, oropharyngeal cancer, bone cancers, including osteosarcoma and malignant fibrous histiocytoma of bone, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilms tumor and other childhood kidney tumors.

In some embodiments, the composition, compound, or pharmaceutical composition is administered intravenously or subcutaneously.

In one aspect, the disclosure provides a method of targeting cancer cells expressing B7-H3, the method comprising: (i) determining or having determined a level of expression of B7-H3 in a population of cancer cells; and (ii) administering to a subject in need thereof a composition comprising a composition, compound, or pharmaceutical composition in accordance with the present disclosure, wherein the polypeptide of the composition, compound, or pharmaceutical composition is designed to specifically bind to human B7-H3, wherein the composition, compound, or pharmaceutical composition is attached to the surface and/or internalized into one or more B7-H3 expressing cancer cells. In some embodiments, the subject is treated after the administering as compared to prior to the administering.

In one aspect, the disclosure provides a method of targeting cancer cells expressing B7-H3, the method comprising: (i) administering to a subject in need thereof a composition comprising a composition, compound, or pharmaceutical composition in accordance with the present disclosure, wherein the polypeptide of the composition, compound, or pharmaceutical composition is designed to specifically bind to human B7-H3; and (ii) wherein the subject has cancer cells that express B7-H3, wherein the composition, compound, or pharmaceutical composition is attached to the surface and/or internalized into one or more B7-H3 expressing cancer cells. In certain embodiments, the method further comprises determining or having determined that the cancer cells express B7-H3. In some embodiments, the subject is treated after the administering as compared to prior to the administering.

In another aspect, the disclosure provides, in a method of targeting a population of cancer cells expressing B7-H3, the improvement comprising contacting the population with a composition, compound, or pharmaceutical composition in accordance with the present disclosure, wherein a position corresponding to X24 (relative to SEQ ID NO: 241) comprises a lysine with at least one additional small alkyl group attached to the nitrogen in the side chain, wherein the composition is taken up less by kidney cells than in a composition comprising a polypeptide that does not have a small alkyl group attached to a nitrogen on the side chain of a lysine at X24, wherein, optionally, the small alkyl group is part of a monomethyl, dimethyl, or trimethyl group. In another aspect, the disclosure provides, in a method of targeting a population of cancer cells expressing B7-H3, the improvement comprising contacting the population with a composition, compound, or pharmaceutical composition in accordance with the present disclosure, wherein a position corresponding to X24 (relative to SEQ ID NO: 267) comprises a lysine with at least one additional small alkyl group attached to the nitrogen in the side chain, wherein the composition is taken up less by kidney cells than in a composition comprising a polypeptide that does not have a small alkyl group attached to a nitrogen on the side chain of a lysine at X24, wherein, optionally, the small alkyl group is part of a monomethyl, dimethyl, or trimethyl group. In some embodiments, the composition (e.g., composition, compound, pharmaceutical composition, etc.) comprises a polypeptide that has an amino acid sequence in accordance with any of Tables 1D, 1E, and 2C. In some embodiments, the composition comprises a polypeptide that has an amino acid sequence with at least 90% identity to at least 44 amino acids to any sequence as set forth in Tables 1D, 1E, and 2C.

In one aspect, the disclosure provides a method of reducing kidney cell uptake of a composition comprising administering to a subject a B7-H3 binding protein having an amino acid sequence comprising at least one modified lysine residue at a position corresponding to X24 of SEQ ID NO: 267, wherein the modification comprises at least small alkyl group attached to the nitrogen of the lysine side chain, optionally comprising a monomethyl, dimethyl, or trimethyl group, and the reduction is as compared to administration to the subject or a control subject an otherwise identical composition but not comprising the modified lysine residue at the position corresponding to X24. In some embodiments, the B7-H3 binding protein has an amino acid sequence in accordance with any of Tables 1D, 1E, and 2C. In some embodiments, the B7-H3 binding protein has an amino acid sequence with at least 90% identity to at least 44 amino acids to any sequence as set forth in Tables 1D, 1E, and 2C.

In one aspect, the disclosure provides, in a method of treating cancer, the improvement comprising administering a composition comprising a B7-H3 binding protein having an amino acid sequence comprising at least one modified lysine residue at a position corresponding to X24 of SEQ ID NO: 267, wherein the modification comprises at least one carbon attached to the nitrogen of the lysine side chain, optionally comprising a monomethyl, dimethyl, or trimethyl group as compared to a composition not comprising a modified lysine residue at a position corresponding to X24. In some embodiments, the B7-H3 binding protein has an amino acid sequence in accordance with any of Tables 1D, 1E, and 2C. In some embodiments, the B7-H3 binding protein has an amino acid sequence with at least 90% identity to at least 44 amino acids to any sequence as set forth in Tables 1D, 1E, and 2C.

In one aspect, the disclosure provides a method of treating a subject with refractory or recurrent cancer comprising administering a composition, compound, conjugate, or pharmaceutical composition as provided herein.

In one aspect, the disclosure provides a method of improving biodistribution of a pharmaceutical composition for a B7-H3 positive population of cancer cells in a subject having a B7-H3-positive cancer, comprising contacting the population with a polypeptide that has a modified lysine at a position corresponding to X24 of SEQ ID NO: 267, wherein the lysine is modified by adding at least one small alkyl group to a lysine side chain and wherein the biodistribution is improved as compared to contacting the population without the modified lysine at a position corresponding to X24 of SEQ ID NO: 267. In some embodiments, the polypeptide has an amino acid sequence in accordance with any of Tables 1D, 1E, and 2C. In some embodiments, the polypeptide has an amino acid sequence with at least 90% identity to at least 44 amino acids to any sequence as set forth in Tables 1D, 1E, and 2C.

In one aspect, the disclosure provides a method of diagnosing presence of a B7-H3 positive population of cancer cells comprising: contacting a population of cells with a composition, compound, conjugate, or pharmaceutical composition thereof; detecting the presence of the composition, compound, or pharmaceutical composition of step (a) by measuring a signal; and comparing the detection in step (b) to a control signal; and diagnosing cancer if the composition, compound, or pharmaceutical composition of step (a) is detected above the control signal.

In some embodiments, the contacting is performed by administering to a subject in need thereof.

In some embodiments, the administering is intravenous or subcutaneous. In some embodiments, the contacting is outside of the subject, optionally in vitro with a biopsy sample.

In one aspect, the disclosure provides a method of treating a cancer in a subject using an immunotherapy, the method comprising administering to the subject a composition comprising a composition, compound, pharmaceutical composition or conjugate as provided herein.

Use of a composition, compound, pharmaceutical composition, or conjugate as provided herein to treat cancer in a subject.

In one aspect, the disclosure provides a method of treating a subject in need thereof comprising administering to the subject in need thereof a composition, compound, pharmaceutical composition, or conjugate as provided herein.

In some embodiments, the subject is diagnosed as having cancer. In some embodiments, a cancer cell from the subject expresses B7-H3, or a portion thereof.

In some embodiments, the expression of B7-H3 is higher in the cancer cell than in a non-cancer cell, which expression can be measured by protein and/or nucleic acid levels.

In some embodiments, the composition, compound, pharmaceutical composition, or conjugate as provided herein is not taken up and/or retained in the kidney as compared to a compound that does not comprise the composition, compound, pharmaceutical composition, or conjugate as provided herein.

In some embodiments, the composition, compound, or pharmaceutical composition is internalized in a cell expressing human B7-H3.

In some embodiments, the cancer is selected from breast cancer, ovarian cancer, melanoma, pancreatic cancer, peripheral neuroma, glioblastoma, adrenocortical carcinoma, AIDS-related lymphoma, anal cancer, urothelial cancer, bladder cancer, meningioma, glioma, astrocytoma, cervical cancer, chronic myeloproliferative disorders, colon cancer, endometrial cancer, ependymoma, esophageal cancer, Ewing's sarcoma, extracranial germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma, Kaposi sarcoma, laryngeal cancer, leukemia, lip cancer, oral cavity cancer, liver cancer, male breast cancer, malignant mesothelioma, medulloblastoma, Merkel cell carcinoma, metastatic squamous neck cell carcinoma, multiple myeloma and other plasma cell neoplasms, mycosis fungoides and Sezary syndrome, myelodysplastic syndromes, nasopharyngeal cancer, neuroblastoma, non-small cell lung cancer, small cell lung cancer, head and neck cancer, skin cancer, oropharyngeal cancer, bone cancers, including osteosarcoma and malignant fibrous histiocytoma of bone, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilms tumor and other childhood kidney tumors.

In some embodiments, the composition, compound, conjugate, or pharmaceutical composition is administered intravenously or subcutaneously.

In one aspect, the disclosure provides a method of targeting cancer cells expressing B7-H3, the method comprising: (i) determining or having determined a level of expression of B7-H3 in a population of cancer cells; and (ii) administering to a subject in need thereof a composition comprising a composition according to the composition, compound, pharmaceutical composition, or conjugate as provided herein, wherein the polypeptide of the composition, compound, or pharmaceutical composition is designed to specifically bind to human B7-H3, wherein the composition, compound, or pharmaceutical composition is attached to the surface and/or internalized into one or more B7-H3 expressing cancer cells.

In some embodiments, the subject is treated after the administering as compared to prior to the administering.

In one aspect, the disclosure provides, in a method of targeting a population of cancer cells expressing B7-H3, the improvement comprising contacting the population with the composition according to a composition, compound, pharmaceutical composition, or conjugate as provided herein, wherein a position corresponding to X24 of SEQ ID NO: 267 comprises a lysine with at least one additional small alkyl group attached to the nitrogen in the side chain, wherein the composition is taken up less by kidney cells than in a composition comprising a polypeptide that does not have a small alkyl group attached to a nitrogen on the side chain of a lysine at a position corresponding to X24, wherein, optionally, the small alkyl group is part of a monomethyl, dimethyl, a trimethyl group. In some embodiments, the composition (e.g., composition, compound, pharmaceutical composition, etc.) comprises a polypeptide that has an amino acid sequence in accordance with any of Tables 1D, 1E, and 2C. In some embodiments, the composition comprises a polypeptide that has an amino acid sequence with at least 90% identity to at least 44 amino acids to any sequence as set forth in Tables 1D, 1E, and 2C.

In one aspect, the disclosure provides a method of evaluating locations of one or more populations of cancerous cells in a subject, the method comprising administering to the subject a composition, compound, pharmaceutical composition, or conjugate as provided herein and detecting to determine location of the composition in the subject.

In one aspect, the disclosure provides, in a method of decreasing kidney uptake of a composition administered to detect and/or treat one or more populations of cancer cells, the improvement comprising administering to a subject in need thereof the composition according to a composition, compound, pharmaceutical composition, or conjugate as provided herein, wherein a position corresponding to X24 of SEQ ID NO: 241 comprises a lysine with at least one additional small alkyl group attached to the nitrogen in the side chain, wherein the composition is taken up less by kidney cells than in a composition comprising a polypeptide that does not have a small alkyl group attached to a nitrogen on the side chain of a lysine at a position corresponding to X24 of SEQ ID NO: 241, wherein, optionally, the small alkyl group is part of a monomethyl, dimethyl, or trimethyl group. In one aspect, the disclosure provides, in a method of decreasing kidney uptake of a composition administered to detect and/or treat one or more populations of cancer cells, the improvement comprising administering to a subject in need thereof the composition according to a composition, compound, pharmaceutical composition, or conjugate as provided herein, wherein a position corresponding to X24 of SEQ ID NO: 267 comprises a lysine with at least one additional small alkyl group attached to the nitrogen in the side chain, wherein the composition is taken up less by kidney cells than in a composition comprising a polypeptide that does not have a small alkyl group attached to a nitrogen on the side chain of a lysine at a position corresponding to X24 of SEQ ID NO: 267, wherein, optionally, the small alkyl group is part of a monomethyl, dimethyl, or trimethyl group. In some embodiments, the composition (e.g., composition, compound, pharmaceutical composition, etc.) comprises a polypeptide that has an amino acid sequence in accordance with any of Tables 1D, 1E, and 2C. In some embodiments, the composition comprises a polypeptide that has an amino acid sequence with at least 90% identity to at least 44 amino acids to any sequence as set forth in Tables 1D, 1E, and 2C.

In some embodiments, the detecting comprises an imaging procedure allows for selecting subjects, monitoring subjects, and/or treating subjects with a therapeutic comprising a miniprotein designed to bind to B7-H3 expressed on one or more cancer cells in the one or more populations of cancer cells.

In some embodiments, the therapeutic comprises a composition, compound, pharmaceutical composition, or conjugate as provided herein.

In one aspect, the disclosure provides, in a method of a method of improving delivery of a radionuclide to a population of cancer cells in a subject, the method comprising administering a composition, compound, pharmaceutical composition, or conjugate as provided herein, wherein the amino acid sequences of the polypeptide comprise amino acids corresponding to a position corresponding to X24 of SEQ ID NO: 241, and wherein X24 comprises a lysine with at least one additional small alkyl group attached to the nitrogen in the side chain, wherein uptake by kidney cells is less than with a polypeptide having an amino acid sequence that does not comprise an additional small alkyl group attached to a nitrogen on the side chain of a lysine at a position corresponding to X24 of SEQ ID NO: 241. In one aspect, the disclosure provides, in a method of a method of improving delivery of a radionuclide to a population of cancer cells in a subject, the method comprising administering a composition, compound, pharmaceutical composition, or conjugate as provided herein, wherein the amino acid sequences of the polypeptide comprise amino acids corresponding to a position corresponding to X24 of SEQ ID NO: 267, and wherein X24 comprises a lysine with at least one additional small alkyl group attached to the nitrogen in the side chain, wherein uptake by kidney cells is less than with a polypeptide having an amino acid sequence that does not comprise an additional small alkyl group attached to a nitrogen on the side chain of a lysine at a position corresponding to X24 of SEQ ID NO: 267. In some embodiments, the composition (e.g., composition, compound, pharmaceutical composition, etc.) comprises a polypeptide that has an amino acid sequence in accordance with any of Tables 1D, 1E, and 2C. In some embodiments, the composition comprises a polypeptide that has an amino acid sequence with at least 90% identity to at least 44 amino acids to any sequence as set forth in Tables 1D, 1E, and 2C.

In some embodiments, the small alkyl group comprises a monomethyl, dimethyl, or trimethyl group.

In one aspect, the disclosure provides, in a method of treating an individual with cancer, the improvement comprising reducing one or more off-target effects or toxicity measures by administering a composition, compound, pharmaceutical composition, or conjugate as provided herein, wherein the amino acid sequences of the polypeptide comprise amino acids corresponding to a position corresponding to X24 of SEQ ID NO: 241, and wherein X24 comprises lysine with at least one additional small alkyl group attached to the nitrogen in the side chain, wherein uptake by kidney cells is less than with a polypeptide having an amino acid sequence that does not comprise an additional small alkyl group attached to a nitrogen on the side chain of a lysine at a position corresponding to X24 of SEQ ID NO: 241. In one aspect, the disclosure provides, in a method of treating an individual with cancer, the improvement comprising reducing one or more off-target effects or toxicity measures by administering a composition, compound, pharmaceutical composition, or conjugate as provided herein, wherein the amino acid sequences of the polypeptide comprise amino acids corresponding to a position corresponding to X24 of SEQ ID NO: 267, and wherein X24 comprises lysine with at least one additional small alkyl group attached to the nitrogen in the side chain, wherein uptake by kidney cells is less than with a polypeptide having an amino acid sequence that does not comprise an additional small alkyl group attached to a nitrogen on the side chain of a lysine at a position corresponding to X24 of SEQ ID NO: 267. In some embodiments, the composition (e.g., composition, compound, pharmaceutical composition, etc.) comprises a polypeptide that has an amino acid sequence in accordance with any of Tables 1D, 1E, and 2C. In some embodiments, the composition comprises a polypeptide that has an amino acid sequence with at least 90% identity to at least 44 amino acids to any sequence as set forth in Tables 1D, 1E, and 2C.

In one aspect, the disclosure provides, in a method of treating an individual with cancer, the improvement comprising achieving a reduction in concentration of R in a kidney tissue in the presence of a composition, compound, pharmaceutical composition, or conjugate as provided herein, wherein the amino acid sequences of the polypeptide comprise amino acids corresponding to a position corresponding to X24 of SEQ ID NO: 241, and wherein X24 comprises lysine with at least one additional small alkyl group attached to the nitrogen in the side chain, wherein uptake by kidney cells is less than with a polypeptide having an amino acid sequence that does not comprise a small alkyl group attached to a nitrogen on the side chain of a lysine at a position corresponding to X24 as compared to the concentration of R in the kidney tissue in the absence the composition, compound, pharmaceutical composition or conjugate.

In one aspect, the disclosure provides, in a method of treating an individual with cancer, the improvement comprising achieving a reduction in concentration of R in a kidney tissue in the presence of a composition, compound, pharmaceutical composition, or conjugate as provided herein, wherein the amino acid sequences of the polypeptide comprise amino acids corresponding to a position corresponding to X24 of SEQ ID NO: 267, and wherein X24 comprises lysine with at least one additional small alkyl group attached to the nitrogen in the side chain, wherein uptake by kidney cells is less than with a polypeptide having an amino acid sequence that does not comprise a small alkyl group attached to a nitrogen on the side chain of a lysine at a position corresponding to X24 as compared to the concentration of R in the kidney tissue in the absence the composition, compound, pharmaceutical composition or conjugate. In some embodiments, the composition (e.g., composition, compound, pharmaceutical composition, etc.) comprises a polypeptide that has an amino acid sequence in accordance with any of Tables 1D, 1E, and 2C. In some embodiments, the composition comprises a polypeptide that has an amino acid sequence with at least 90% identity to at least 44 amino acids to any sequence as set forth in Tables 1D, 1E, and 2C.

In some embodiments, the reduction in concentration of R in the kidney tissue is measured by urine output of R as measured by percent of administered radiation recovered or by detection as measured by a cell-based in vitro assay, or an in vivo detection assay.

In some embodiments, the administration of the composition, compound, pharmaceutical composition, or conjugate as provided herein can be repeated at least 2, 3, 4, 5, 6, 7, 8, 9, or 10 times or more in the presence of the composition having 90% identity to at least 44 amino acids of SEQ ID NO: 241 including a modified lysine at positions corresponding to X24 of SEQ ID NO: 241 than in the presence of a Q, V, L, or K at positions corresponding to X24. In some embodiments, the composition (e.g., composition, compound, pharmaceutical composition, etc.) comprises a polypeptide that has an amino acid sequence in accordance with any of Tables 1D, 1E, and 2C. In some embodiments, the administration of the composition can be repeated at least 2, 3, 4, 5, 6, 7, 8, 9, or 10 times or more in the presence of the composition having 90% identity to at least 44 amino acids of SEQ ID NO: 267 including a modified lysine at positions corresponding to X24 of SEQ ID NO: 267 than in the presence of a Q, V, L, or K at positions corresponding to X24. In some embodiments, the composition (e.g., composition, compound, pharmaceutical composition, etc.) comprises a polypeptide that has an amino acid sequence in accordance with any of Tables 1D, 1E, and 2C. In some embodiments, the composition comprises a polypeptide that has an amino acid sequence with at least 90% identity to at least 44 amino acids to any sequence as set forth in Tables 1D, 1E, and 2C.

In one aspect, the disclosure provides, in a method of reducing uptake by a kidney tissue of a composition the improvement comprising administering a composition comprising (a) a radionuclide therapeutic comprising at least a polypeptide and a radionuclide (R); wherein the polypeptide has at least 90% identity to at least 44 amino acids of SEQ ID NO: 267 and/or has a modified lysine at a position corresponding to X24 of SEQ ID NO: 267, such that in the presence of the modified lysine, the radionuclide is less concentrated in the kidney tissue than in the absence of the polypeptide. In some embodiments, the composition (e.g., composition, compound, pharmaceutical composition, etc.) comprises a polypeptide that has an amino acid sequence in accordance with any of Tables 1D, 1E, and 2C. In some embodiments, the composition comprises a polypeptide that has an amino acid sequence with at least 90% identity to at least 44 amino acids to any sequence as set forth in Tables 1D, 1E, and 2C.

In one aspect, the disclosure provides a method comprising administering to a subject in need thereof a compound that binds to B7-H3 and at least one modified lysine at a position corresponding to X24 of SEQ ID NO: 267, wherein administration of the compound having a miniprotein with the at least one modified lysine reduces one or more off target effects, toxicity grades, and/or uptake and/or retention in a kidney tissue as compared to a compound having an unmodified lysine, or a Q, V, or L at a position corresponding to X24. In some embodiments, the compound comprises a polypeptide that has an amino acid sequence in accordance with any of Tables 1D, 1E, and 2C. In some embodiments, the compound comprises a polypeptide that has an amino acid sequence with at least 90% identity to at least 44 amino acids to any sequence as set forth in Tables 1D, 1E, and 2C.

In one aspect, the disclosure provides a method of treating an individual having or suspected of having a B7-H3-positive cancer, the method comprising administering to the individual: a means for blocking uptake of a radiotherapeutic to kidney tissue, and a linker, chelator, and a radionuclide.

In some embodiments, the means for binding to kidney tissue binds to B7-H3 and includes a modified lysine at a position corresponding to X24, respectively, of SEQ ID NO: 267 and/or has at least 90% identity to at least 44 amino acids of SEQ ID NO: 267 and a modified lysine at positions corresponding X24 of SEQ ID NO: 267. In some embodiments, the means (e.g., composition, compound, pharmaceutical composition, etc.) comprises a polypeptide that has an amino acid sequence in accordance with any of Tables 1D, 1E, and 2C. In some embodiments, the means comprises a polypeptide that has an amino acid sequence with at least 90% identity to at least 44 amino acids to any sequence as set forth in Tables 1D, 1E, and 2C.

In some embodiments, the means blocks uptake and/or retention of the radiotherapeutic into the kidney as compared to a means that does not include a modified lysine at a position corresponding to X24 of SEQ ID NO: 267 and/or has at least 90% identity to at least 44 amino acids of SEQ ID NO: 267 and/or has a modified lysine at positions corresponding to X24 of SEQ ID NO: 267. In some embodiments, the means comprises a polypeptide that has an amino acid sequence in accordance with any of Tables 1D, 1E, and 2C. In some embodiments, the means comprises a polypeptide that has an amino acid sequence with at least 90% identity to at least 44 amino acids to any sequence as set forth in Tables 1D, 1E, and 2C.

In some embodiments, the means is a radiotherapeutic. In some embodiments, the radiotherapeutic is targeted to a tumor or a population of cancer cells. In some embodiments, the radiotherapeutic targeted to the tumor or the population of cancer cells is at a greater concentration than in the absence of the means for binding to kidney tissue. In some embodiments, the radionuclide therapeutic comprises a polypeptide that targets B7-H3.

In some embodiments, the radionuclide therapeutic comprises or consists of a compound selected from C227-C608 and C611.

In some embodiments, the radionuclide of the radiotherapeutic is selected from Ac-225, Cu-64, Ga-68, In-111, Lu-177, or Pb-212.

Formulation and Administration

In various aspects formulations of the pharmaceutical compositions of the present disclosure include parenteral e.g., subcutaneous, intravenous, intraarterial, intramuscular, intradermal, intraperitoneal, interperitoneal, and intrathecal administration. See for instance, Remington: The Science and Practice of Pharmacy, Lippincott Williams & Wilkins; 22nd ed. (2013) described in more detail.

In some embodiments, a pharmaceutical composition comprising a miniprotein (e.g., affibody, CDP, knottin, binder, engineered Kunitz domain, monobody, anticalin, designed ankyrin repeat domain (DARPin), avimer) of the present disclosure is administered to a subject in need thereof. In some embodiments, the subject has or is at risk of having cancer. By way of non-limiting example, in some embodiments, the cancer is selected from breast cancer, ovarian cancer, melanoma, pancreatic cancer, peripheral neuroma, glioblastoma, adrenocortical carcinoma, AIDS-related lymphoma, anal cancer, bladder cancer, meningioma, glioma, astrocytoma, cervical cancer, chronic myeloproliferative disorders, colon cancer, endometrial cancer, ependymoma, esophageal cancer, Ewing's sarcoma, extracranial germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma, Kaposi sarcoma, laryngeal cancer, leukemia, lip cancer, oral cavity cancer, liver cancer, male breast cancer, malignant mesothelioma, medulloblastoma, Merkel cell carcinoma, metastatic squamous neck cell carcinoma, multiple myeloma and other plasma cell neoplasms, mycosis fungoides and Sezary syndrome, myelodysplastic syndromes, nasopharyngeal cancer, neuroblastoma, non-small cell lung cancer, small cell lung cancer, head and neck cancer, skin cancer, oropharyngeal cancer, bone cancers, including osteosarcoma and malignant fibrous histiocytoma of bone, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilms tumor and other childhood kidney tumors.

In some embodiments, determination of an appropriate dose and regimen of a miniprotein (e.g., affibody, CDP, knottin, binder, engineered Kunitz domain, monobody, anticalin, designed ankyrin repeat domain (DARPin), avimer) of the present disclosure can be made by the clinician, e.g., using parameters or factors known or suspected in the art to affect treatment or predicted to affect treatment. Actual dosage levels of the active ingredients (e.g., miniproteins (e.g., affibodies, CDPs, knottins, binders)) as provided by compositions of the present disclosure may be varied so as to obtain an amount of the active ingredient which is effective to achieve the desired therapeutic response for a particular patient, composition, and mode of administration, without being toxic to the patient. In some embodiments, the selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors known in the medical arts.

In some embodiments, administration is by one or more routes including, but not limited to bronchial, buccal, enteral, interdermal, transdermal, intra-arterial, intradermal, intragastric, intramedullary, intramuscular, intranasal, intraperitoneal, intrathecal, intravenous, intraventricular, within a specific organ and/or tissue, mucosal, nasal, oral, rectal, subcutaneous, sublingual, topical, tracheal (including by intratracheal instillation), transdermal, vaginal and vitreal.

In some embodiments, administration may comprise or consist of continuous dosing (e.g., intravenous administration) for a period of time.

In some embodiments, administration may comprise or consist of intermittent dosing.

In some embodiments, administration may comprise or consist of dosing separated by a selected period of time and with one or more doses, based on clinical response and/or activity following one or more doses.

In some embodiments, administration of the decoy enables higher dosing with one or more radiotherapeutic treatments, as compared to dosing in the absence of a decoy with no change in toxicity grade of the therapeutic.

In some embodiments, administration is to a subject is suffering from a relevant disease, disorder, or condition. In some embodiments, administration is to a subject susceptible to or at risk of developing a disease, disorder, or condition. In some such embodiments, a subject displays one or more symptoms or characteristics of a disease, disorder, or condition. In some embodiments, a subject does not display any symptom or characteristic of a disease, disorder, or condition. In some such embodiments, a subject is someone with one or more features characteristic of susceptibility to or at risk of developing a disease, disorder, or condition. In some embodiments, a subject has received a diagnosis of a disease, disorder, or condition.

In some embodiments, the present disclosure provides a method for modulating biological activity of B7-H3 in a subject. In some such embodiments, the method comprises administering a pharmaceutical composition provided by the disclosure to the subject in an amount effective to modulate the biological activity of B7-H3 in the subject.

In some embodiments, the present disclosure provides a method for treating or preventing cancer in a subject. In some embodiments, the method comprises administering to the subject a pharmaceutical composition provided by the present disclosure, wherein the miniprotein (e.g., affibody, CDP, knottin, binder, engineered Kunitz domain, monobody, anticalin, designed ankyrin repeat domain (DARPin), avimer) of the pharmaceutical composition selectively binds to B7-H3 in an amount effective to treat or prevent the cancer in the subject.

In some embodiments, the present disclosure provides methods and compositions that bind target (e.g., B7-H3) and are capable of activating or inhibiting immune cell response. In some embodiments, compositions are administered for the treatment of non-small-cell lung cancer (NSCLC), cutaneous squamous cell carcinoma, pancreatic cancer, primary hepatocellular carcinoma, colorectal carcinoma, clear cell renal carcinoma, breast cancer and prostate cancer. (Yang, S et al., Int J of Bio Sci 2020 Mar. 25 (16): 11; 1767-1773).

In some embodiments, the present disclosure provides a method for detecting the presence or extent of a cancer in a subject. In some such embodiments, the method comprises measuring a level of B7-H3 in a sample comprising one or more cells from the subject; wherein detection of the level of B7-H3 in the subject relative to the levels of the B7-H3 in one or more control subjects is indicative of the presence or extent of the cancer.

In some embodiments, a composition provided by the present disclosure is used to downregulate an inhibitory immune response in a subject. For example, in some embodiments, a miniprotein (e.g., affibody, CDP, knottin, binder, engineered Kunitz domain, monobody, anticalin, designed ankyrin repeat domain (DARPin), avimer) of the present disclosure specifically binds such that it may be used to deliver a cytotoxic payload and promote cellular cytotoxicity of T cells for specific B7-H3-expressing (e.g., tumor) cells. (See Goodman A, Patel S P, Kurzrock R Nat Rev Clin Oncol. 2017 April; 14(4):203-220.) In some such embodiments, the miniprotein (e.g., affibody, CDP, knottin, binder, engineered Kunitz domain, monobody, anticalin, designed ankyrin repeat domain (DARPin), avimer) modulates IFN-γ IL-2, IL-10, and IL-13 production during T-cell activation.

Kits

In one aspect, provided herein are kits comprising a pharmaceutical composition described herein for therapeutic, imaging, or diagnostic uses. In some embodiments, kits typically include a label indicating the intended use of the contents of the kit and instructions for use. The term label includes any writing, or recorded material supplied on or with the kit, or which otherwise accompanies the kit. Accordingly, this disclosure provides a kit for treating a subject afflicted with a cancer, the kit comprising: (a) a dosage of pharmaceutical composition described herein and (b) instructions for using the in methods of therapy methods disclosed herein. In certain embodiments for treating human patients, the kit comprises a pharmaceutical composition described herein comprising a miniprotein conjugate described herein.

In some embodiments, a kit comprises a cold miniprotein conjugate as provided herein (i.e., a miniprotein conjugate that contains a cold-metal surrogate of a radionuclide), and instructions for chelation of the miniprotein conjugate to the cold-metal surrogate of a radionuclide. In some embodiments, a cold-metal surrogate is a natural isotope of an element that is not radioactive. In some embodiments, an element may have more than one natural isotope that is not radioactive. In some embodiments, the kit comprises a hot miniprotein conjugate as provided herein (i.e., a miniprotein conjugate described herein comprising the radionuclide), with instructions for administration to a subject. In some embodiments, a kit comprises a combination of cold miniprotein conjugates (i.e., a miniprotein conjugate described herein comprising a cold-metal conjugate), and hot miniprotein conjugates as provided herein (i.e., a miniprotein conjugate described herein comprising the radionuclide), with instructions for administration to a subject. In some embodiments, a kit comprises a combination of a miniprotein conjugate that is conjugated to a radionuclide as provided herein and a miniprotein conjugate that is conjugated to a cold-metal surrogate as provided herein. In some embodiments, the cold miniprotein conjugates assists in diluting the hot miniprotein conjugate. In some embodiments, a cold miniprotein conjugate is combined with a hot miniprotein conjugate so a smaller radioactive dose can be administered to a patient. In some embodiments, the kit comprises less than 5% hot miniprotein conjugates and greater than 95% cold miniprotein conjugates, less than 10% hot miniprotein conjugates and greater than 90% cold miniprotein conjugates, less than 20% hot miniprotein conjugates and greater than 80% cold miniprotein conjugates, less than 30% hot miniprotein conjugates and greater than 70% cold miniprotein conjugates, less than 40% hot miniprotein conjugates and greater than 60% cold miniprotein conjugates, less than 50% hot miniprotein conjugates and greater than 50% cold miniprotein conjugates, less than 60% hot miniprotein conjugates and greater than 40% cold miniprotein conjugates, less than 70% hot miniprotein conjugates and greater than 30% cold miniprotein conjugates, less than 80% hot miniprotein conjugates and greater than 20% cold miniprotein conjugates, or less than 90% hot miniprotein conjugates and greater than 10% cold miniprotein conjugates. In some embodiments, the percentage of hot miniprotein conjugates refers to the specific activity of the radiolabeled product.

In some embodiments, a kit comprises a combination of miniprotein conjugate that is radiolabeled as provided herein and a miniprotein that is not conjugated. In some embodiments, a kit comprises a combination of miniprotein conjugate that is radiolabeled with an alpha emitter radionuclide as provided herein and a miniprotein that is radiolabeled with a beta emitter radionuclide. In some embodiments, the kit comprises less than 5% beta emitter miniprotein conjugates and greater than 95% alpha miniprotein conjugates, less than 10% beta emitter miniprotein conjugates and greater than 90% alpha emitter miniprotein conjugates, less than 20% beta emitter miniprotein conjugates and greater than 80% alpha emitter miniprotein conjugates, less than 30% beta emitter miniprotein conjugates and greater than 70% alpha emitter miniprotein conjugates, less than 40% beta emitter miniprotein conjugates and greater than 60% alpha emitter miniprotein conjugates, less than 50% beta emitter miniprotein conjugates and greater than 50% alpha emitter miniprotein conjugates, less than 60% beta emitter miniprotein conjugates and greater than 40% alpha emitter miniprotein conjugates, less than 70% beta emitter miniprotein conjugates and greater than 30% alpha emitter miniprotein conjugates, less than 80% beta emitter miniprotein conjugates and greater than 20% alpha emitter miniprotein conjugates, or less than 90% beta emitter miniprotein conjugates and greater than 10% alpha emitter miniprotein conjugates.

In some embodiments, a kit comprises a cold miniprotein conjugate as provided herein (i.e., a miniprotein conjugate that does not contain a radionuclide), and instructions for chelation of the miniprotein conjugate to the radionuclide. In some embodiments, the kit comprises a hot miniprotein conjugate as provided herein (i.e., a miniprotein conjugate described herein comprising the radionuclide), with instructions for administration to a subject.

In certain embodiments, a kit provided herein has a date of certification equal to or greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 days. In some embodiments, a kit provided herein has a date of certification equal to or greater than 1, 2, 3, 4, 5, 6, 7, 8, 9, 10, 11, 12, 13, 14, 15, 16, 17, 18, 19, or 20 days. In some embodiments, a kit provided herein has a date of certification equal to or greater than 1, 2, 3, 4, 5, 6, 7, 8, 9, or 10 days. For example, the date of certification can refer to a regulatory certification that establishes the time range in which the kit remains efficacious and/or safe. In some embodiments, the pharmaceutical composition comprised in the kit maintains stability and/or efficacy for equal to or greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 days such that the pharmaceutical composition can be administered to a patient. In some embodiments, the pharmaceutical composition comprised in the kit maintains stability and/or efficacy for equal to or greater than 1, 2, 3, 4, 5, 6, 7, 8, 9, 10, 11, 12, 13, 14, 15, 16, 17, 18, 19, or 20 days such that the pharmaceutical composition can be administered to a patient. In some embodiments, the pharmaceutical composition comprised in the kit maintains stability and/or efficacy for equal to or greater than 1, 2, 3, 4, 5, 6, 7, 8, 9, or 10 days such that the pharmaceutical composition can be administered to a patient.

In some embodiments, the present disclosure provides kits comprising a miniprotein (e.g., affibody, CDP, knottin, binder, engineered Kunitz domain, monobody, anticalin, designed ankyrin repeat domain (DARPin), avimer) as provided herein. In some embodiments, the kit comprises compositions for detecting the B7-H3 miniprotein (e.g., affibody, CDP, knottin, binder, engineered Kunitz domain, monobody, anticalin, designed ankyrin repeat domain (DARPin), avimer) (e.g., conjugation to one or more detectable moieties).

In some embodiments, a kit comprises a label indicating the intended use of the contents of the kit and instructions for use. The term label includes any writing, or recorded material supplied on or with the kit, or which otherwise accompanies the kit.

In some embodiments, the present disclosure provides a kit for treating, monitoring, or diagnosing a subject having or suspected of having cells overexpressing B7-H3, the kit comprising: (a) a unit of a pharmaceutical composition described herein and (b) instructions for using the in methods of administration disclosed herein. In certain embodiments for treating human patients, the kit comprises a pharmaceutical composition described herein comprising miniprotein (e.g., affibody, CDP, knottin, binder, engineered Kunitz domain, monobody, anticalin, designed ankyrin repeat domain (DARPin), avimer) as provided herein.

In some embodiments, the present disclosure provides a kit for treating, monitoring, or diagnosing a subject or a group or population of subjects having or suspected of having cells overexpressing a target protein (e.g., B7-H3), the kit comprising: (a) a unit of a pharmaceutical composition described herein and (b) instructions for using the in methods of administration disclosed herein. In certain embodiments for treating human patients, the kit comprises a pharmaceutical composition described herein comprising a miniprotein (e.g., affibody, CDP, knottin, binder, engineered Kunitz domain, monobody, anticalin, designed ankyrin repeat domain (DARPin), avimer) as provided herein. In one aspect, the disclosure provides a kit comprising a composition represented by the formula selected from one or more of M-L-C-R, M-L-C, M-C-R, M-L-R, M-C, M-L, and M-R, wherein M comprises a miniprotein (M), L comprises a linear, branched, or enzymatically cleavable linker (L), C comprises a chelator (C), and R comprises a radionuclide (R); a decoy, wherein the decoy blocks or reduces uptake of the composition into the kidney. In some embodiments, the decoy can have a higher affinity for kidney tissue than for tumor tissue. In certain embodiments, when R is present, it can be supplied separately from any of M, C, L, or the decoy. In some embodiments, when R is present, it can be added just prior to use. In some embodiments, binding affinities can be measured in vitro or in vivo, including such as by methods provided herein. In some embodiments, a decoy can be supplied in a molar or mass excess as compared to a composition comprising a miniprotein provided herein. For example, a decoy may be supplied in a molar or mass excess.

The molar or mass excess may be enough to be administered in an excess of about 1, 2, 5, 10, 100, 250, 500, 750, 1,000, 1,250, 1,500, 1,750, 2,000, 2,500, 3,000, 3,500, 4,000, 4,500, 5,000, 5,500, 6,000, 6,500, 7,000, 7,500, 8,000, 8,500, 9,000, 9,500, 10,000, or more times greater than the amount of miniprotein of a conjugate (e.g., a compound, a radiotherapeutic, etc. as provided herein). In some embodiments, a molar or mass excess is no greater than 10,000-fold greater than the amount of miniprotein of a conjugate.

In some aspects, the disclose provides a kit comprising a polypeptide as described herein or composition as described herein; and a decoy, wherein the decoy blocks uptake of the composition into a non-tumor tissue (e.g., a kidney tissue, a liver tissue, etc.). In some embodiments, the decoy and the composition are administered to a subject in need thereof. In some embodiments, after the administration, the decoy appears in a higher concentration in the non-tumor tissue than in the tumor tissue as measured by % ID/g. In some embodiments, the polypeptide or the composition comprises a radionuclide (R). In some embodiments, when R is present, it is supplied separately from any of M, C, L, or the decoy. In some embodiments, the decoy is selected from a scaffold A decoy or a scaffold B decoy. In some embodiments, the binding affinity is measured in vitro or in vivo. In some embodiments, the decoy molecule is supplied in a molar excess as compared to the composition, which molar excess may optionally be selected from a 10, 100, 1000, or more molar excess. In some embodiments, the R, if present, is added just prior to use.

In some embodiments, the disclosure provides a kit comprising a polypeptide and instructions for use, wherein the polypeptide has an amino acid sequence as set forth in a polypeptide of any one of a composition, compound, pharmaceutical composition or conjugate as provided herein.

In some embodiments, the kit further comprises one or more of a linker, chelator, and radionuclide.

In some embodiments, the linker comprises or consists of a polyethylene glycol (PEG) linker of PEG4, PEG, PEG2, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, or (Gly)n-(gGlu)n- (SEQ ID NO: 551) or (PEG)n, wherein n is from 1 to 36, (Gly)1-10 (SEQ ID NO: 552), or any fragment or combination via covalent bond thereof. In some embodiments, the chelator comprises or consists of DOTA, NOPO, Crown, Macropa, lead specific chelator (PSC), N-succinimidyl 3-(tri-n-butylstannyl)benzoate (BuSTB), or N-succinimidyl 3-trimethylstannylbenzoate (MeSTB).

In some embodiments, prior to use of the kit, the compound is labeled with a radionuclide, wherein the radionuclide is chelated to the chelator to produce a composition with a formula M-L-C-R. In some embodiments, the radionuclide is selected from Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211. In some embodiments, the radionuclide is Ac-225, Cu-64, Ga-68, In-111, Lu-177, or Pb-212.

In some embodiments, the polypeptide of the kit has an amino acid comprising any of those set forth in any one of SEQ ID NOs: 4-6, 8-94, 100-537, or as set forth in any of Tables 1B-1E, 2A, and 2C. In certain embodiments, the polypeptide further comprises a linker, wherein the linker is PEG4, and a chelator, wherein the chelator is DOTA. In some embodiments, when present, the linker is attached to the N-terminus amino acid of the polypeptide. In some embodiments, the C-terminal amino acid of the polypeptide is not cysteine. In some embodiments, when present, the chelator is attached to either the polypeptide or the linker. In some embodiments, when present, the radionuclide is attached to the chelator. In some embodiments, when present, the radionuclide is attached to the N-terminus amino acid of the polypeptide.

Certain Exemplary Embodiments

In some embodiments, the present disclosure provides compositions comprising a miniprotein (M), an optional linker (L), and one or both of a chelator (C) and a radionuclide (R), represented a formula selected from (M)x-L-C-R, (M)x-L-C, (M)x-C-R, (M)x-L-R, (M)x-C, (M)x-L, and (M)x-R. In some embodiments, the miniprotein comprises or consists of a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer. In some embodiments, the binder comprises or consists of a linear polypeptide and/or a non-disulfide sequence. In some embodiments, M is characterized in that it comprises 100 amino acids.

In some embodiments, the present disclosure provides compositions comprising a miniprotein (M), an optional linker (L), and one or both of a chelator (C) and a radionuclide (R), represented a formula selected from M-L-C-R, M-L-C, M-L-R, M-C-R, M-C, and/or M-R. In some embodiments, the miniprotein comprises or consists of a cysteine-dense peptide, a knottin peptide, or a binder. In some embodiments, the binder comprises or consists of a linear polypeptide and/or a non-disulfide sequence. In some embodiments, the miniprotein is characterized in that it comprises (i) no more than 100 amino acids and/or 12 kDa; (ii) at least one secondary structure elements; (iii) a sequestered hydrophobic core; and/or displays cooperative folding. In some embodiments, the miniprotein comprises no more than about 100 amino acids or less, 90 amino acids, 85 amino acids, 80 amino acids, 75 amino acids, 70 amino acids, 65 amino acids, 60 amino acids, 55 amino acids, 50 amino acids, 45 amino acids, 40 amino acids, 35 amino acids, 30 amino acids, 25 amino acids, 20 amino acids, 15 amino acids, or 10 amino acids. In some embodiments, the miniprotein comprises at least one disulfide bridge.

In some embodiments, the present disclosure provides compositions represented by the formula L-C, wherein L comprises or consists of a linker, C comprises or consists of a chelator, and wherein the linker is designed to be conjugated to a polypeptide.

In some embodiments, the present disclosure provides compositions represented by the formula L-C-R, wherein L comprises or consists of a linker, C comprises or consists of a chelator, and R comprises or consists of a radionuclide, and wherein the composition is capable of being conjugated to a miniprotein. In some embodiments, L comprises or consists of a polyethylene glycol (PEG) linker of, e.g., PEG4, PEG, PEG2, PEG6, PEG8, PEG12, PEG24, PEG36, etc., lys (MPB)-PEG4, lys(IPB)-PEG4, an ester linker, an amide linker, a maleimide linker, a, a succinimidyl-4-(N-maleimidomethyl) cyclohexane-1-carboxylate (SMCC) linker, a propanoic acid linker, a caproleic acid linker, a Lys(MPB)-PEG linker (e.g., Lys(MPB)-PEG4), a Lys(IPB)-PEG linker (e.g., Lys(IPB)-PEG4), an HE(1-3) linker (SEQ ID NO: 554), an (SE)1-3 linker, an (E)1-3 linker, an aminocaproic acid (Ahx) linker, or (Gly)n-(γGlu)n- (SEQ ID NO: 551) or (PEG)n, wherein n is from 1 to 36, $(Gly)_{1-10}$, (SEQ ID NO: 552) or any fragment or combination via covalent bond thereof. In some embodiments, C comprises or consists of NOPO, Crown, Macropa or tetrazacyclododecane-1,4,7,10-tetraacetic acid (DOTA) as set forth as follows:

i) NOPO

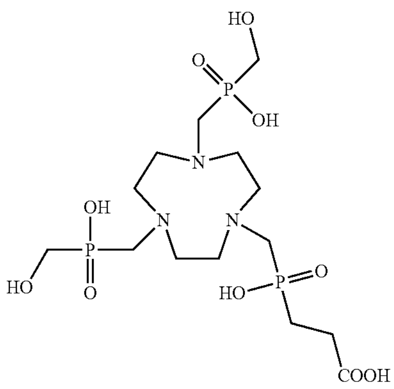

NOPO ii) Crown

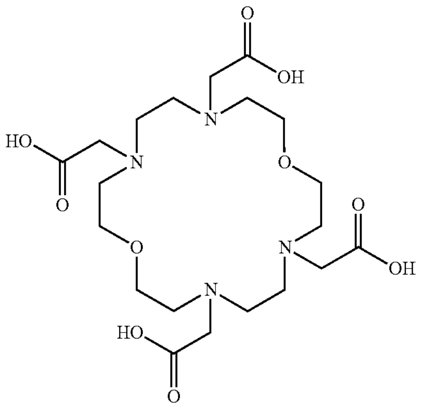

Crown iii) DOTA

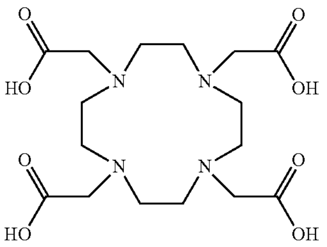

or iv) Macropa

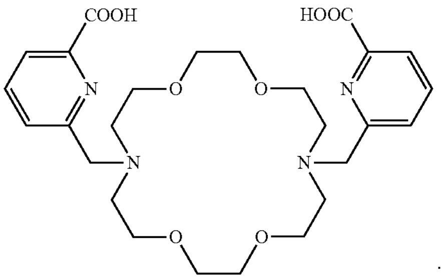

Macropa

In some embodiments, C comprises or consists of NOPO, Crown, Macropa, or tetrazacyclododecane-1,4,7,10-tetraacetic acid (DOTA) or a derivative thereof.

In some embodiments, the present disclosure provides isolated constructs, pharmaceutically acceptable salts thereof, or neutral molecules comprising a miniprotein, optional linker, and at least one of a chelator or radionuclide. In some embodiments, R comprises or consists of Ac-225, Ga-68, In-111, Pb-212, Lu-177, Cu-67, Cu-65, La-132, or La-135. In some embodiments, the composition comprises at least one additional component. In some embodiments, the composition can penetrate tumor tissue. In some embodiments, the miniprotein specifically binds to a target. In some embodiments, the composition displays m or nm binding affinity to the target in an in vitro assay (e.g., in an in vitro assay, e.g., in a cell isolated from a tumor e.g., in vivo, e.g., to a tumor). In some embodiments, the composition displays m or nM binding affinity to the target, e.g., in an in vitro assay. In some embodiments, the composition binds to the target with an affinity of 1 pM to 100 nM e.g., as measured by an in vitro binding assay. In some embodiments, the composition binds to the target with an affinity of 100 pM to 10 nM as measured by an in vitro binding assay. In some embodiments, the miniprotein binding to the target modulates biological function. In some embodiments, the miniprotein binding to the target does not elicit an immune response. In some embodiments, the immune response includes a systemic immune response or a local immune response. In some embodiments, the target is located in, on, or near a cell. In some embodiments, the target is a protein expressed on the surface of the cell. In some embodiments, the cell is a tumor cell. In some embodiments, the tumor cell is a solid tumor cell. In some embodiments, the cell is a human cell. In some embodiments, the target is B7-H3. In some embodiments, the miniprotein selectively binds to B7-H3 or a portion thereof.

In some embodiments, the present disclosure provides pharmaceutical compositions comprising a miniprotein, (M) an optional linker (L) and one or both of a chelator (C) and a nuclide. In some embodiments, when L is present, L comprises or consists of a polyethylene glycol (PEG) linker, an ester linker, an amide linker, a maleimide linker, a valine-citrulline linker, a hydrazone linker, a N-succinimidyl-4-(2-pyridyldithio)butyrate (SPDB) linker, a succinimidyl-4-(N-maleimidomethyl)cyclohexane-1-carboxylate (SMCC) linker, a vinylsulfone-based linker, a propanoic acid linker, a caproleic acid linker, a Lys(MPB)-PEG linker (e.g., Lys(MPB)-PEG4), a Lys(IPB)-PEG linker (e.g., Lys (IPB)-PEG4), an HE(1-3) linker (SEQ ID NO: 554), an (SE)1-3 linker (SEQ ID NO: 555), an (E)1-3 linker, an aminocaproic acid (Ahx) linker, or any fragment or combination thereof. In some embodiments, when C is present, C comprises or consists of NOPO, Crown, Macropa, or tetrazacyclododecane-1,4,7,10-tetraacetic acid (DOTA) as set forth as follows:

i) NOPO

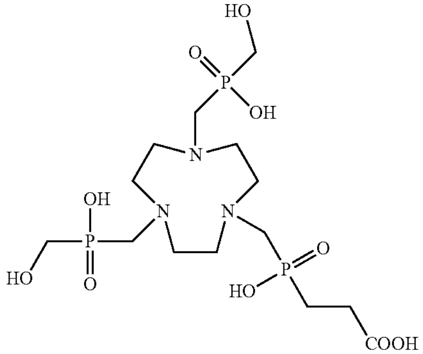

NOPO

-continued ii) Crown

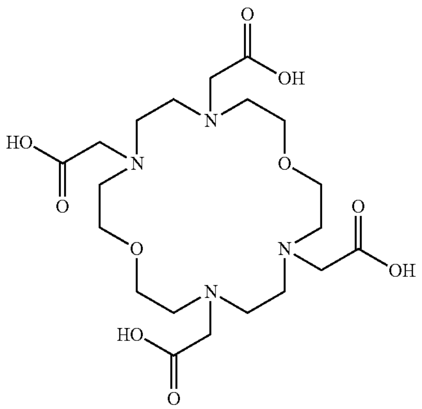

Crown iii) DOTA

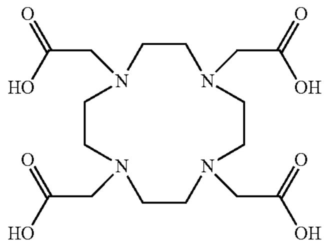

or iv) Macropa

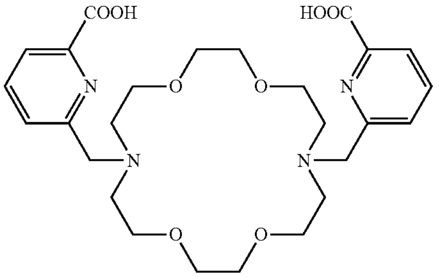

Macropa

In some embodiments, the chelator covalently attaches to the miniprotein. In some embodiments, the chelation efficiency is >90%. In some embodiments, when R is present, the radionuclide is an alpha-emitter. In some embodiments, the radionuclide is Ac-225, Pb-212, Lu-177, or Ga-68. In some embodiments, the miniprotein specifically binds to a target. In some embodiments, the target is B7-H3. In some embodiments, the B7-H3 is expressed on a cell. In some embodiments, the cell is a human cell. In some embodiments, the human cell is a tumor cell. In some embodiments, the tumor cell is a solid tumor cell. In some embodiments, the miniprotein comprises or consists of a cysteine-dense peptide, a knottin peptide, or a binder. In some embodiments, the miniprotein comprises one or more disulfide bonds. In some embodiments, the miniprotein is characterized in that it has nm or sub-nm binding affinity on the target in vivo or in a cell-based assay. In some embodiments, the miniprotein a binding affinity of 100 pM to 10 nM to B7-H3 on a cell line expressing human B7-H3. In some embodiments, the miniprotein has an amino acid sequence no more than about 100 amino acids or less, 90 amino acids, 85 amino acids, 80 amino acids, 75 amino acids, 70 amino acids, 65 amino acids, 60 amino acids, 55 amino acids, 50 amino acids, 45 amino acids, 40 amino acids, 35 amino acids, 30 amino acids, 25 amino acids, 20 amino acids, 15 amino acids, or 10 amino acids. In some embodiments, the miniprotein does not elicit an immune response or wherein the immune response elicited is tolerable. In some embodiments, the pharmaceutical composition comprises high tumor tissue penetration. In some embodiments, the pharmaceutical composition is not taken up and/or retained in the kidney or liver. In some embodiments, the pharmaceutical composition is internalized in a cell expressing human B7-H3. In some embodiments, the B7-H3 cell is a cancer cell and is part of a heterogenous population of cells. Without wishing to be bound by theory, the disclosure contemplates that compositions provided herein treat cancers with heterogenous cancer cell populations. For example, in some such embodiments, cancer cells apposed to B7-H3-expressing cells that do not themselves express B7-H3 are also treated (e.g., killed) by internalization of the pharmaceutical composition into the B7-H3-expressing cells. For example, internalization of a radionuclide into a neighboring cell, e.g., in a tumor, can kill cancer cells that do not themselves internalize the composition.

In some embodiments, the present disclosure provides methods of treating a subject in need thereof comprising administering a composition comprising a miniprotein (M), an optional linker (L), and one or both of a chelator (C) and a radionuclide (R). In some embodiments, when L is present, L comprises or consists of a polyethylene glycol (PEG) linker, an ester linker, an amide linker, a maleimide linker, a valine-citrulline linker, a hydrazone linker, a N-succinimidyl-4-(2-pyridyldithio)butyrate (SPDB) linker, a succinimidyl-4-(N-maleimidomethyl)cyclohexane-1-carboxylate (SMCC) linker, a vinylsulfone-based linker, a propanoic acid linker, a caproleic acid linker, a Lys(MPB)-PEG linker (e.g., Lys(MPB)-PEG4), a Lys(IPB)-PEG linker (e.g., Lys (IPB)-PEG4), an HE(1-3) linker (SEQ ID NO: 554), an (SE)1-3 linker (SEQ ID NO: 555), an (E)1-3 linker, an aminocaproic acid (Ahx) linker, or any fragment or combination thereof. In some embodiments, when C is present, C comprises or consists of NOPO, Crown, Macropa or tetrazacyclododecane-1,4,7,10-tetraacetic acid (DOTA) as set forth as follows:

i) NOPO

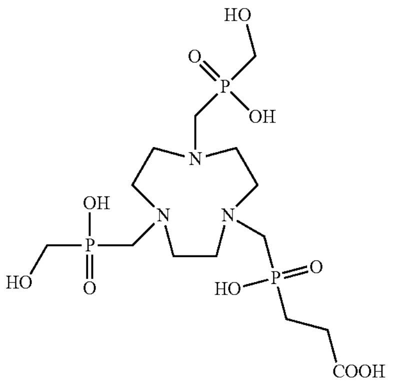

NOPO

-continued ii) Crown

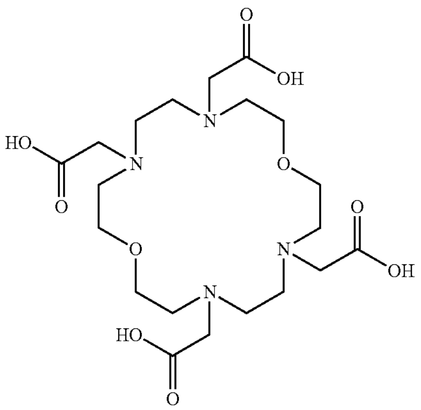

Crown iii) DOTA

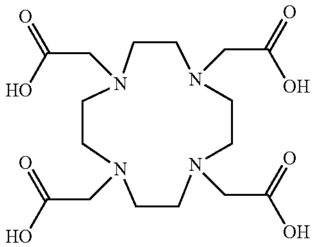

or iv) Macropa

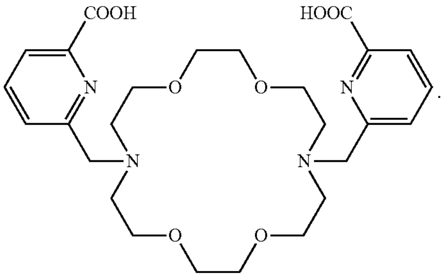

.

Macropa

In some embodiments, when R is present, R comprises or consists of Ac-225, I-111, Pb-212, Lu-177, Ga-68. In some embodiments, M comprises or consists of a cysteine-dense peptide, a knottin peptide, or a binder. In some embodiments, M is characterized in that it comprises (i) no more than 100 amino acids and/or 12 kDa; (ii) at least two secondary structure elements; (iii) a sequestered hydrophobic core; and/or displays cooperative folding. In some embodiments, a composition comprising M, optional L, and one or both of C and R, for use in a method of the present disclosure, comprises at least one additional component. In some embodiments, the composition can penetrate tumor tissue. In some embodiments, the miniprotein comprises no more than about 100 amino acids or less, 90 amino acids, 85 amino acids, 80 amino acids, 75 amino acids, 70 amino acids, 65 amino acids, 60 amino acids, 55 amino acids, 50 amino acids, 45 amino acids, 40 amino acids, 35 amino acids, 30 amino acids, 25 amino acids, 20 amino acids, 15 amino acids, or 10 amino acids. In some embodiment, the miniprotein comprises at least one disulfide bridge. In some embodiments, the miniprotein specifically binds to a target. In some embodiments, the composition displays mm or nm binding affinity to the target in an in vitro assay. In some embodiments, the composition binds to the target with an affinity of 100 pM to 10 nM as measured by an in vitro binding assay. In some embodiments, the composition is characterized in that it has high tissue penetrating properties relative to a composition comprising a full-size protein that binds to the same target. In some embodiments, the miniprotein binding to the target modulates biological function. In some embodiments, administration of the composition does not elicit an immune response. In some embodiments, the immune response includes a systemic immune response or a local immune response. In some embodiments, the target is located in, on, or near a cell. In some embodiments, the target is a protein expressed on the surface of the cell. In some embodiments, the cell is a tumor cell. In some embodiments, the tumor cell is a solid tumor cell. In some embodiments, the cell is a human cell. In some embodiments, the target is B7-H3. In some embodiments, the subject has or is at risk of having cancer. In some embodiments, the cancer is selected from breast cancer, ovarian cancer, melanoma, pancreatic cancer, peripheral neuroma, glioblastoma, adrenocortical carcinoma, AIDS-related lymphoma, anal cancer, bladder cancer, meningioma, glioma, astrocytoma, cervical cancer, chronic myeloproliferative disorders, colon cancer, endometrial cancer, ependymoma, esophageal cancer, Ewing's sarcoma, extracranial germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma, Kaposi sarcoma, laryngeal cancer, leukemia, lip cancer, oral cavity cancer, liver cancer, male breast cancer, malignant mesothelioma, medulloblastoma, Merkel cell carcinoma, metastatic squamous neck cell carcinoma, multiple myeloma and other plasma cell neoplasms, mycosis fungoides and Sezary syndrome, myelodysplastic syndromes, nasopharyngeal cancer, neuroblastoma, non-small cell lung cancer, small cell lung cancer, head and neck cancer, skin cancer, oropharyngeal cancer, bone cancers, including osteosarcoma and malignant fibrous histiocytoma of bone, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilms tumor and other childhood kidney tumors. In some embodiments, after administration of the composition, the cancer is treated. In some embodiments, the composition is administered intravenously or subcutaneously.

In some embodiments, the present disclosure provides methods of characterizing miniprotein conjugates comprising contacting a population of cells expressing B7-H3 with a miniprotein conjugate and measuring one or more of: (i) binding affinity; (ii) internalization; (iii) binding specificity; (iv) immune response as characterize by secretion or expression of one or more cytokines.

In some embodiments, the present disclosure provides methods of detecting cancer comprising administering to a subject a composition comprising a B7-H3-specific miniprotein, further comprising a detectable moiety, and detecting the presence and/or quantity of the composition in the subject, wherein detection of the miniprotein is associated with risk of developing or having cancer. In some embodiments, the miniprotein of the composition is designed for conjugation to one or more additional components. In some embodiments, the composition penetrates tumor tissue. In some embodiments, the miniprotein of the composition comprises less than 12 kDa. In some embodiments, the miniprotein of the composition comprises no more than about 100 amino acids or less, 90 amino acids, 85 amino acids, 80 amino acids, 75 amino acids, 70 amino acids, 65 amino acids, 60 amino acids, 55 amino acids, 50 amino acids, 45 amino acids, 40 amino acids, 35 amino acids, 30 amino acids, 25 amino acids, 20 amino acids, 15 amino acids, or 10 amino acids. In some embodiments, the miniprotein of the composition comprises at least one disulfide bond. In some embodiments, the miniprotein that does not comprise multiple cysteine residues such as, for example, a miniprotein comprising a single cysteine residue. In some such embodiments, the miniprotein may form a dimer, such as with another miniprotein (e.g., self-dimerization). In some embodiments, two miniproteins are linked together to form a dimer. In other embodiments, two miniproteins are each linked to a linker to form a dimer. In other embodiments, two different miniproteins are each linked to a linker to form a dimer.

In some embodiments, the method identifies a subject as having a cancer. In some embodiments, the cancer is selected from breast cancer, ovarian cancer, melanoma, pancreatic cancer, peripheral neuroma, glioblastoma, adrenocortical carcinoma, AIDS-related lymphoma, anal cancer, bladder cancer, meningioma, glioma, astrocytoma, cervical cancer, chronic myeloproliferative disorders, colon cancer, endometrial cancer, ependymoma, esophageal cancer, Ewing's sarcoma, extracranial germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma, Kaposi sarcoma, laryngeal cancer, leukemia, lip cancer, oral cavity cancer, liver cancer, male breast cancer, malignant mesothelioma, medulloblastoma, Merkel cell carcinoma, metastatic squamous neck cell carcinoma, multiple myeloma and other plasma cell neoplasms, mycosis fungoides and Sezary syndrome, myelodysplastic syndromes, nasopharyngeal cancer, neuroblastoma, non-small cell lung cancer, small cell lung cancer, head and neck cancer, skin cancer, oropharyngeal cancer, bone cancers, including osteosarcoma and malignant fibrous histiocytoma of bone, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilms tumor and other childhood kidney tumors. In some embodiments, a cancer cell from the subject expresses B7-H3, or a portion thereof. In some embodiments, the expression of the target is higher in the cancer cell than in a non-cancer cell.

In some embodiments, the present disclosure provides methods of targeting a population of cancer cells expressing B7-H3, the method comprising: (i) determining a level of expression of a target in a population of cancer cells; (ii) administering to a subject in need thereof a composition according to the present disclosure or a pharmaceutical composition according to the present disclosure, wherein the composition specifically binds B7-H3; and (iii) wherein the composition targets the B7-H3-expressing cells and is internalized into the B7-H3 expressing cells; (iv) wherein the patient is treated after the administering as compared to prior to the administering and (v) wherein the treatment does not damage cells not expressing B7-H3.

A miniprotein conjugate comprising: (i) miniprotein (M) that specifically binds to B7-H3; (ii) a chelator (C) conjugated to (M) through an optional linker (L), wherein (C) comprises DOTA, and (L), when present, comprises PEG; and (ii) a radionuclide (R) chelated to (C), wherein (R) is Actinium-225.

A miniprotein conjugate comprising: (i) miniprotein (M) that specifically binds to B7-H3; (ii) a chelator (C) conjugated to (M) through an optional linker (L), wherein (C) comprises DOTA, and (L), when present, comprises PEG; and (ii) a radionuclide (R) chelated to (C), wherein (R) is Lead-212.

A miniprotein conjugate comprising: (i) miniprotein (M) that specifically binds to B7-H3; (ii) a chelator (C) conjugated to (M) through an optional linker (L), wherein (C) comprises DOTA, and (L), when present, comprises PEG; and (ii) a radionuclide (R) chelated to (C), wherein (R) is Lutetium-177.

A miniprotein conjugate comprising: (i) miniprotein (M) that specifically binds to B7-H3; (ii) a chelator (C) conjugated to (M) through an optional linker (L), wherein (C) comprises DOTA, and (L), when present, comprises PEG; and (ii) a radionuclide (R) chelated to (C), wherein (R) is Gallium-68.

In some embodiments, no linker is present. For example, in certain embodiments, a miniprotein is attached directly to a chelator. In certain embodiments, a miniprotein is directly radiolabeled (e.g., M-R, wherein M is a miniprotein and R is a radionuclide).

In certain embodiments, a linker is a PEG linker. In some embodiments, the PEG linker is PEG (1-36), for example, PEG4, PEG, PEG2, PEG6, PEG8, PEG10, PEG12, PEG24, etc. In certain embodiments, a linker can include (HE)1-3, (SE)1-3, (E)1-3, and Ahx.

In some embodiments, a composition provided herein preferentially damages (e.g., to a greater extent, e.g., kills) cells expressing B7-H3 as compared to cells not expressing B7-H3. In some embodiments, a composition provided herein does not damage cells not expressing B7-H3. In some embodiments, administration comprises further administering a decoy. In some embodiments, damage to cells not expressing B7-H3 is reduced after administration of the polypeptide or the composition in presence of a decoy as compared to the administration in the absence of a decoy.

In some embodiments, the present disclosure provides pharmaceutical compositions comprising a conjugate in accordance with the present disclosure and a pharmaceutically acceptable excipient. In some embodiments, the composition if formulated for parenteral or oral administration.

In some embodiments, the present disclosure provides methods of imaging a cell or population of cells in a subject having or suspected of having cancer comprising administering a pharmaceutical composition in accordance with the present disclosure and detecting a presence of the pharmaceutical composition in the subject.

In some embodiments, the present disclosure provides methods of treating cancer in a subject in need thereof comprising administering a pharmaceutical composition in accordance with the present disclosure to the subject, wherein the subject is treated and non-cancer cells of the subject are not killed. In one aspect, the disclosure provides a kit comprising a composition represented by the formula selected from one or more of M-L-C-R, M-L-C, M-C-R, M-L-R, M-C, M-L, and M-R, wherein M comprises a miniprotein (M), L comprises a linker (L), C comprises a chelator (C), and R comprises a radionuclide (R); a decoy peptide, wherein the decoy peptide blocks or reduces uptake of the composition into the kidney. In some embodiments, the decoy peptide can have a higher affinity for kidney tissue than for tumor tissue. In certain embodiments, when R is present, it can be supplied separately from any of M, C, L, or the decoy. In some embodiments, when R is present, it can be added just prior to use. In some embodiments, binding affinities can be measured in vitro or in vivo, including such as by methods provided herein. In some embodiments, a decoy peptide can be supplied in a molar excess as compared to a composition comprising a miniprotein provided herein.

In another aspect, the disclosure provides a kit comprising a composition represented by the formula selected from one or more of M-L-C-R, M-L-C, M-C-R, M-L-R, M-C, M-L, and M-R, wherein M comprises a miniprotein (M), L comprises linker (L), C comprises a chelator (C), and R comprises a radionuclide (R); a decoy, wherein the decoy blocks uptake of the composition into a kidney tissue. In some embodiments, the decoy and the composition are administered to a subject in need thereof. In some embodiments, after the administration, the decoy appears in a higher concentration in the kidney tissue than in the tumor tissue as measured by % ID/g.

In some embodiments, when R is present, it is supplied separately from any of M, C, L, or the decoy. In some embodiments, the decoy is selected from C10, C118-C120/ or a miniprotein having an amino acid sequence comprising or consisting of an amino acid sequence of any of SEQ ID NOs: 7 and 97-99. In some embodiments, the decoy is supplied in a molar excess as compared to the composition, which molar excess may optionally be selected from a 10, 100, 1000, or more molar excess. In some embodiments, the R, if present, is added just prior to use.

The present disclosure is further illustrated by the following examples which should not be construed as further limiting. The contents of all references cited throughout this application are expressly incorporated herein by reference.

Additional Exemplary Embodiments

In certain embodiments, the disclosure provides a polypeptide, comprising: an amino acid sequence, wherein the amino acid sequence comprises Formula I:

X1X2X3X4YX6X7EX9IX11ALX14EIIWLPNX22X23 X24X25QIX28AFIAALNX36DPSQ SSELLSEAX49X50LX52DSX55X56X57X58 (SEQ ID NO: 95), wherein X1 is A, N, or absent; X2 is A, E, or absent; X3 is A, Q, or absent; X4 is K, K(Ac), L, or absent; X6 is A, D, E, I, L, N, Q, S, T, or Y; X7 is A, E, K, K(Ac), K(Me)3+, L, Q, or S; X9 is K, K(Ac), or K(Me)3+; X11 is A, Q, S, T, or Y; X14 is E, Q, S, or Y; X22 is A, D, F, (homo-leucine), I, L, N, (norleucine), T, or Y; X23 is T or V; X24 is H or Y; X25 is A or G; X28 is A, (homo-leucine), M, M(O2), (norleucine), S, T, or V; X36 is A, (Cit), D, E, L, N, Q, S, or T; X49 is A, E, G, K, K(Ac), L, Q, S, or Y; X50 is A, (Cit), D, E, G, (hSer), K, K(Ac), L, Q, S, or Y; X52 is A, D, G, N, Q, T, or Y; X55 is D, E, L, Q, S, Y, or absent; X56 is A or absent; X57 is P or absent; and X58 is G, K, K(Ac), or absent; wherein if X28 is A, (homo-leucine), (M 02), S, T, or V, then X24 is Y; or wherein if X28 is M, then X7 is A, E, K(Me)3+, L, Q, or S. In some embodiments, if X4 is K or K(Ac), then X24 is Y.

In some embodiments, the amino acid sequence comprises Formula IIX1X2X3X4YAX7EKIAALSEIIWLPNX22TX24X25QI X28AFIAALNX36DPSQSSELLS EAX49X50LNDSQAP (SEQ ID NO: 96), wherein X1 is A or absent; X2 is E or absent; X3 is A or absent; X4 is L or absent; X7 is K or Q; X22 is D or L; X24 is H or Y; X25 is A or G; X28 is (homo-leucine) or M; X36 is D or N; X49 is E or K; and X50 is E.

In some embodiments, the amino acid sequence shares at least 90% (e.g., 91, 92, 93, 94, 95, 96, 97, 98, 99 or more percent) identity to any one of the SEQ ID NOs: 4-6 or SEQ ID NOs: 12-94. In some embodiments, the amino acid sequence shares 90% (e.g., 91, 92, 93, 94, 95, 96, 97, 98, 99 or more percent) identity to any one of SEQ ID NOs: 6, 21, or 30. In some embodiments, the amino acid sequence shares 100% identity to any one of the SEQ ID NOs: 4-6 or SEQ ID NOs: 12-94. In some embodiments, the amino acid sequence shares 100% identity to any one of SEQ ID NOs: 6, 21, or 30. In some embodiments, the amino acid sequence shares 90% (e.g., 91, 92, 93, 94, 95, 96, 97, 98, 99 or more percent) identity to SEQ ID NO: 6. In some embodiments, the amino acid sequence shares 100% identity to SEQ ID NO: 6.

In one aspect, the disclosure provides a polypeptide that has an amino acid sequence comprising or consisting of any of SEQ ID NOs: 4-272.

In one aspect, the disclosure provides a polypeptide that has an amino acid sequence comprising or consisting of any of SEQ ID NOs: 4-6, 8-94 or 100-272.

In one aspect, the disclosure provides a polypeptide that has an amino acid sequence comprising or consisting of any of SEQ ID NOs: 4-6, 8-94 or 100-197.

In one aspect, the disclosure provides a polypeptide that has an amino acid sequence comprising or consisting of any of SEQ ID NOs: 198-272.

In some embodiments the miniprotein comprises at least one constraint. In some embodiments, the at least one constraint is a disulfide bridge. In some embodiments, the disulfide bridge is between any two cysteine residues corresponding to SEQ ID NO: 267 of Cys1, Cys17, Cys35, and Cys48.

In some embodiments, the at least one constraint comprises two disulfide bridges. In some embodiments, the two disulfide bridges are selected from pairs of cysteine residues corresponding to SEQ ID NO: 267 as follows: (i) Cys1-Cys35 and Cys17-Cys48; (ii) Cys1-Cys17 and Cys35-Cys48; and (iii) Cys1-Cys48 and Cys17-Cys35.

In certain embodiments, a polypeptide as provided herein further comprises one or more of a linker, chelator, and radionuclide.

In some embodiments, the linker, when present, comprises or consists of a polyethylene glycol (PEG) linker of PEG2, PEG, PEG4, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a caproleic acid linker, an aminocaproic acid (Ahx) linker, or (Gly)n-(γGlu)n- (SEQ ID NO: 551) or (PEG)n, wherein n is from 1 to 36, $(Gly)_{1-10}$, (SEQ ID NO: 552) or any fragment or combination via covalent bond thereof.

In some embodiments, the chelator, when present, comprises or consists of:

i) NOPO

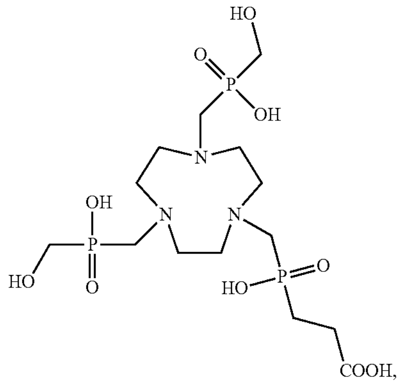

NOPO ii) Crown

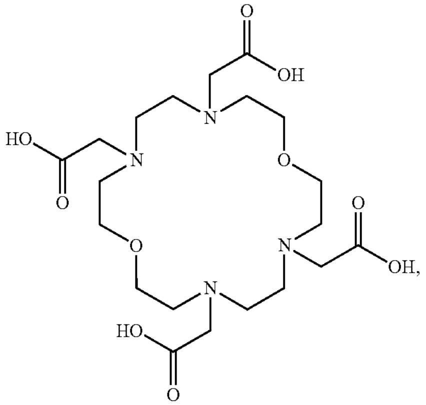

Crown iii) DOTA

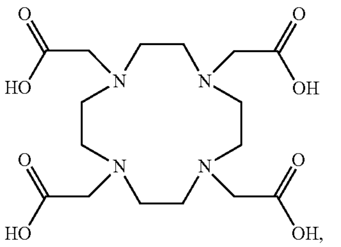

or iv) Macropa

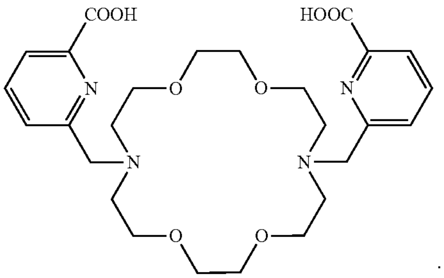

Macropa

In some embodiments, the chelator comprises or consists of derivative of NOPO, Crown, Macropa, or tetrazacyclododecane-1,4,7,10-tetraacetic acid (DOTA).

In some embodiments, the radionuclide, when present, comprises or consists of Ac-225, Ga-68, In-111, Pb-212, Lu-177, Cu-67, Cu-64, La-132, La-135, Ce-134, F-18, or At-211.

In some embodiments, the linker, when present, is attached to the N-terminal or C-terminal end of the polypeptide. In some embodiments, when present, the chelator is attached to either the polypeptide or the linker. In some embodiments, the radionuclide, when present, is attached to the chelator.

In some embodiments, the polypeptide comprises or consists of a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer. In some embodiments, the polypeptide comprises at least one disulfide bridge.

In some embodiments, a polypeptide provided herein selectively binds to B7-H3 or a portion thereof. In some embodiments, the polypeptide exhibits a binding affinity of 10 pM to 200 nM, 10 pM to 100 nM, or 10 nM to 100 nM to B7-H3, or a portion thereof, in vivo or in a cell-based assay.

In one aspect, the disclosure provides a pharmaceutical composition comprising a polypeptide as provided herein and a pharmaceutically acceptable excipient.

In one aspect, the disclosure provides an isolated polynucleotide comprising one or more nucleic acid sequences encoding a polypeptide as provided herein.

In one aspect, the disclosure provides a vector comprising an isolated polynucleotide comprising one or more nucleic acid sequences encoding a polypeptide as provided herein.

In one aspect, the disclosure provides a host cell transformed with an isolated polynucleotide comprising one or more nucleic acid sequences encoding a polypeptide as provided herein or a vector comprising an isolated polynucleotide comprising one or more nucleic acid sequences encoding a polypeptide as provided herein.

In one aspect, the disclosure provides a composition represented by a formula selected from one or more of (M)x-L-C-R, (M)x-L-C)x-C-R, (M)x-L-R, (M)x-C, (M)x-L, and (M)x-R, wherein M comprises a miniprotein (M), L comprises a linker (L), C comprises a chelator (C), R comprises a radionuclide (R), and x is 1, 2, 3, or 4, wherein M comprises an amino acid sequence of Formula I:

X1X2X3X4YX6X7EX9IX11ALX14EIIWLPNX22X23 X24X25QIX28AFIAALNX36DPSQ SSELLSEAX49X50LX52DSX55X56X57X58 (SEQ ID NO: 95), wherein X1 is A, N, or absent; X2 is A, E, or absent; X3 is A, Q, or absent; X4 is K, K(Ac), L, or absent; X6 is A, D, E, I, L, N, Q, S, T, or Y; X7 is A, E, K, K(Ac), K(Me)3+, L, Q, or S; X9 is K, K(Ac), or K(Me)3+; X11 is A, Q, S, T, or Y; X14 is E, Q, S, or Y; X22 is A, D, F, (homo-leucine), I, L, N, (norleucine), T, or Y; X23 is T or V; X24 is H or Y; X25 is A or G; X28 is A, (homo-leucine), M, M(O2), (norleucine), S, T, or V; X36 is A, (Cit), D, E, L, N, Q, S, or T; X49 is A, E, G, K, K(Ac), L, Q, S, or Y; X50 is A, (Cit), D, E, G, (hSer), K, K(Ac), L, Q, S, or Y; X52 is A, D, G, N, Q, T, or Y; X55 is D, E, L, Q, S, Y, or absent; X56 is A or absent; X57 is P or absent; and X58 is G, K, K(Ac), or absent; wherein if X28 is A, (homo-leucine), M(O2), S, T, or V, then X24 is Y; or wherein if X28 is M, then X7 is A, E, K(Me)3+, L, Q, or S.

In some embodiments, if X4 is K or K(Ac), then X24 is Y.

In some embodiments, the amino acid sequence comprises Formula II:

X1X2X3X4YAX7EKIAALSEIIWLPNX22TX24X25QIX28AFIAALNX36DPSQSSELLSEAX49X50LNDSQAP (SEQ ID NO: 96), wherein X1 is A or absent; X2 is E or absent; X3 is A or absent; X4 is L or absent; X7 is K or Q; X22 is D or L; X24 is H or Y; X25 is A or G; X28 is (homo-Leucine) or M; X36 is D or N; X49 is E or K; and X50 is E.

In some embodiments, the amino acid sequence shares 90% (e.g., 91, 92, 93, 94, 95, 96, 97, 98, 99 or more percent) identity to any one of the SEQ ID NOs: 4-6 or SEQ ID NOs: 12-94.

In some embodiments, the amino acid sequence shares 90% (e.g., 91, 92, 93, 94, 95, 96, 97, 98, 99 or more percent) identity to any one of SEQ ID NOs: 6, 21, or 30.

In some embodiments, the amino acid sequence shares 100% identity to any one of the SEQ ID NOs: 4-6 or SEQ ID NOs: 12-94.

In some embodiments, the composition comprises any one of C3, C4, C6-C14, or C19-C116.

In some embodiments, the amino acid sequence shares 100% identity to any one of SEQ ID NOs: 6, 21, or 30.

In some embodiments, the composition comprises any one of C6-C9, C28-C31, or C40-C42.

In some embodiments, the amino acid sequence shares 90% (e.g., 91, 92, 93, 94, 95, 96, 97, 98, 99 or more percent) identity to SEQ ID NO: 6.

In some embodiments, the amino acid sequence shares 100% identity to SEQ ID NO: 6.

In some embodiments, the linker comprises or consists of a polyethylene glycol (PEG) linker of PEG4, PEG, PEG2, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a caproleic acid linker, an aminocaproic acid (Ahx) linker, or (Gly)n-(γGlu)n- (SEQ ID NO: 551) or (PEG)n, wherein n is from 1 to 36, $(Gly)_{1-10}$, (SEQ ID NO: 552) or any fragment or combination via covalent bond thereof.

In some embodiments, the chelator comprises or consists of:

i) NOPO

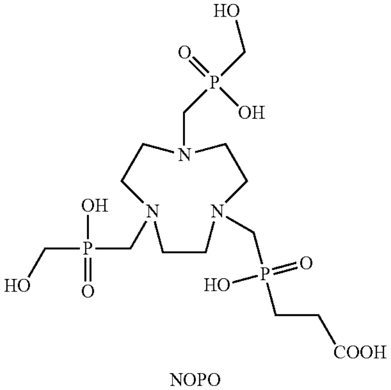

NOPO

-continued ii) Crown

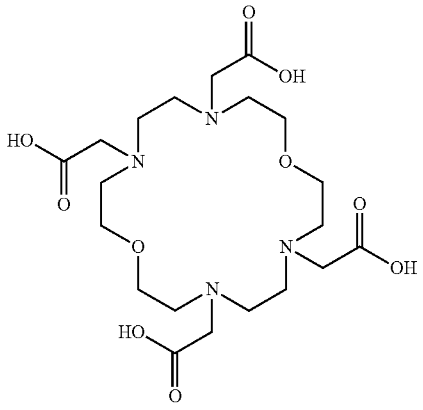

Crown iii) DOTA

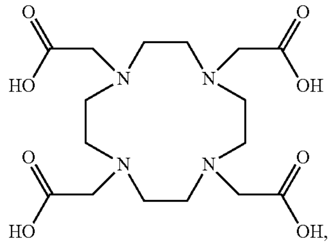

or iv) Macropa

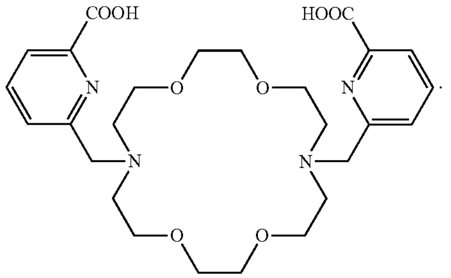

Macropa

In some embodiments, the chelator comprises or consists of a derivative of NOPO, Crown, Macropa, or tetrazacyclododecane-1,4,7,10-tetraacetic acid (DOTA).

In some embodiments, the radionuclide comprises or consists of Ac-225, Ga-68, In-111, Pb-212, Lu-177, Cu-67, Cu-64, La-132, La-135, Ce-134, F-18, or At-211.

In some embodiments, the linker, when present, is attached to the N-terminal or C-terminal end of the miniprotein.

In some embodiments, the chelator, when present, is attached to either the miniprotein or the linker.

In some embodiments, the radionuclide, when present, the radionuclide is attached to the chelator.

In some embodiments, the miniprotein comprises or consists of a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer.

In some embodiments, the miniprotein comprises at least one disulfide bridge.

In some embodiments, the miniprotein selectively binds to B7-H3 or a portion thereof. In some embodiments, the miniprotein exhibits a binding affinity of 10 pM to 200 nM, 10 pM to 100 nM, or 10 nM to 100 nM to B7-H3, or a portion thereof, in vivo or in a cell-based assay.

In one aspect, the disclosure provides a composition represented by a formula selected from one or more of (M)x-L-C-R, (M)x-L-C)x-C-R, (M)x-L-R, (M)x-C, (M)x-L, and (M)x-R, wherein M comprises a miniprotein (M), L comprises a linker (L), C comprises a chelator (C), R comprises a radionuclide (R), and x is 1, 2, 3, or 4, wherein M comprises an amino acid sequence that shares 90% (e.g., 91, 92, 93, 94, 95, 96, 97, 98, 99 or more percent) identity to any one of the SEQ ID NOs: 4-6, SEQ ID NOs: 12-94, or SEQ ID NOs: 100-272.

In some embodiments, the amino acid sequence shares 90% (e.g., 91, 92, 93, 94, 95, 96, 97, 98, 99 or more percent) identity to any one of SEQ ID NOs: 6, 21, 30, 130-131, 183, 199, 204, 241 or 267. In some embodiments, the amino acid sequence shares 100% identity to any one of the SEQ ID NOs: 4-6, SEQ ID NOs: 12-94, or SEQ ID NOs: 100-272.

In some embodiments, the composition comprises any one of C3, C4, C6-C14, C19-C116, or C121-C332.

In some embodiments, the amino acid sequence shares 100% identity to any one of SEQ ID NOs: 6, 21, 30, 130-131, 183, 199, 204, 241 or 267.

In some embodiments, the composition comprises any one of C6-C9, C28-C31, C40-C42, C152-C153, C211, C228, C234, C275 or C309.

In some embodiments, the amino acid sequence shares 90% (e.g., 91, 92, 93, 94, 95, 96, 97, 98, 99 or more percent) identity to any one of SEQ ID NOs: 6, 130-131, 183, 199, 204, 241 or 267.

In some embodiments, the amino acid sequence shares 100% identity to any one of SEQ ID NOs: 6, 130-131, 183, 199, 204, 241 or 267.

In some embodiments, the composition comprises any one of C6-C9, C152-C153, C211, C228, C234, C275 or C309.

In one aspect, the disclosure provides a composition represented by a formula selected from one or more of (M)x-L-C-R, (M)x-L-C)x-C-R, (M)x-L-R, (M)x-C, (M)x-L, and (M)x-R, wherein M comprises a miniprotein (M), L comprises a linker (L), C comprises a chelator (C), R comprises a radionuclide (R), and x is 1, 2, 3, or 4, wherein M comprises an amino acid sequence that shares 90% (e.g., 91%, 92%, 93%, 94%, 95, 96, 97, 98, 99 or more percent) identity to any one of the SEQ ID NOs: 4-6, SEQ ID NOs: 12-94, or SEQ ID NOs: 100-197.

In some embodiments, the amino acid sequence shares 90% (e.g., 91%, 92%, 93%, 94%, 95, 96, 97, 98, 99 or more percent) identity to any one of SEQ ID NOs: 6, 21, 30, 130-131, or 183.

In some embodiments, the amino acid sequence shares 100% identity to any one of SEQ ID NOs: 4-6, 12-94 or 100-197.

In some embodiments, the composition comprises any one of C6-C14, C19-C116, or C121-C226.

In some embodiments, the amino acid sequence shares 100% identity to any one of SEQ ID NOs: 6, 21, 30, 130-131, or 183.

In some embodiments, the composition comprises any one of C6-C9, C152-C153, or C211.

In some embodiments, M further comprises one or more disulfide bridges.

In one aspect, the disclosure provides a composition represented by a formula selected from one or more of (M)x-L-C-R, (M)x-L-C)x-C-R, (M)x-L-R, (M)x-C, (M)x-L, and (M)x-R, wherein M comprises a miniprotein (M), L comprises a linker (L), C comprises a chelator (C), R comprises a radionuclide (R), and x is 1, 2, 3, or 4, wherein M comprises an amino acid sequence that shares 90% (e.g., 91%, 92%, 93%, 94%, 95, 96, 97, 98, 99 or more percent) identity to any one of the SEQ ID NOs: 198-272.

In some embodiments, the amino acid sequence shares 90% (e.g., 91%, 92%, 93%, 94%, 95, 96, 97, 98, 99 or more percent) identity to any one of SEQ ID NOs: 199, 204, 241 or 267.

In some embodiments, the amino acid sequence shares 100% identity to any one of SEQ ID NOs: 198-272.

In some embodiments, the composition comprises any one of C227-C332.

In some embodiments, the amino acid sequence shares 100% identity to any one of SEQ ID NOs: 199, 204, 241 or 267.

In some embodiments, the composition comprises any one of C228, C234, C275 or C309.

In some embodiments, the linker comprises or consists of a polyethylene glycol (PEG) linker of PEG4, PEG, PEG2, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a caproleic acid linker, an aminocaproic acid (Ahx) linker, or (Gly)n-(γGlu) n- (SEQ ID NO: 551) or (PEG)n, wherein n is from 1 to 36, $(Gly)_{1-10}$, (SEQ ID NO: 552) or any fragment or combination via covalent bond thereof.

In some embodiments, the chelator comprises or consists of:

i) NOPO

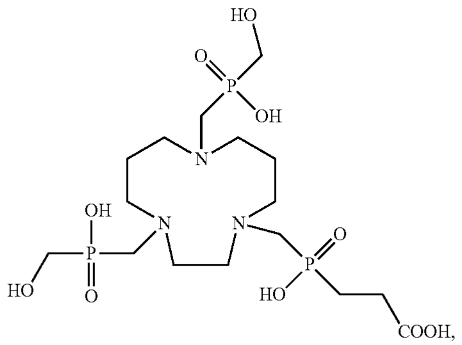

NOPO ii) Crown

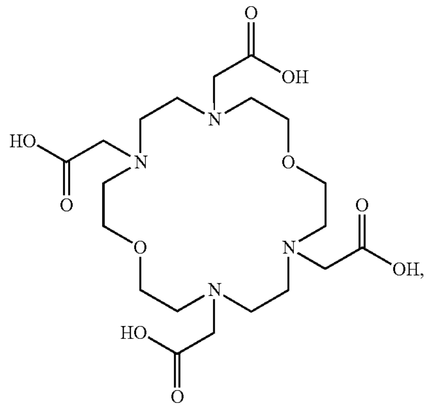

Crown

-continued iii) DOTA

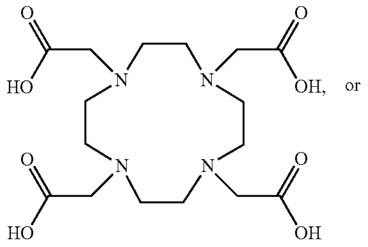

DOTA iv) Macropa

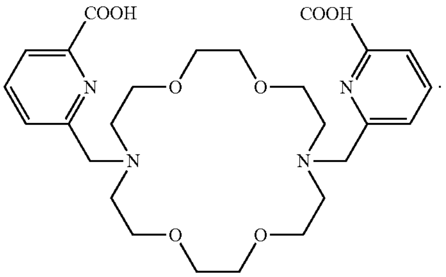

Macropa

In some embodiments, the chelator, when present, comprises or consists of derivative of NOPO, Crown, Macropa, or tetrazacyclododecane-1,4,7,10-tetraacetic acid (DOTA).

In some embodiments, the radionuclide, when present, comprises or consists of Ac-225, Ga-68, In-111, Pb-212, Lu-177, Cu-67, Cu-64, La-132, La-135, Ce-134, F-18, or At-211.

In some embodiments, the linker, when present, is attached to the N-terminal or C-terminal end of the miniprotein.

In some embodiments, the chelator, when present, is attached to either the miniprotein or the linker.

In some embodiments, the radionuclide, when present, is attached to the chelator.

In some embodiments, the miniprotein comprises or consists of a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer.

In some embodiments, the miniprotein comprises at least one constraint.

In some embodiments, the at least one constraint comprises a disulfide bridge.

In some embodiments, the at least one constraint comprises two disulfide bridges.

In some embodiments, the miniprotein selectively binds to B7-H3 or a portion thereof. In some embodiments, the miniprotein exhibits a binding affinity of 10 pM to 200 nM, 10 pM to 100 nM, or 10 nM to 100 nM to B7-H3, or a portion thereof, in vivo or in a cell-based assay.

In one aspect, the disclosure provides a pharmaceutical composition comprising a composition as provided herein and a pharmaceutically acceptable excipient.

In one aspect, the disclosure provides a use of a composition as provided herein, to treat cancer in a subject.

In one aspect, the disclosure provides a method of treating a subject in need thereof comprising administering to the subject in need thereof a polypeptide as provided herein or a composition as provided herein.

In some embodiments, the method further comprises administering a scaffold A decoy or a scaffold B decoy.

In some embodiments, the scaffold A decoy is selected from any of C118-C119.

In some embodiments, the decoy has an amino acid sequence comprising an amino acid sequence of any of SEQ ID NOs: 97-99.

In some embodiments, the scaffold B decoy selected is C10.

In some embodiments, the decoy has an amino acid sequence comprising an amino acid sequence of SEQ ID NO: 7.

In some embodiments, the administration of the decoy reduces one or more off-target effects and/or reduces uptake and/or retention of the polypeptide or composition in one or more non-tumor tissues (e.g., kidney, e.g., liver). In some embodiments, the administration of the polypeptide or the composition to a subject in need thereof does not elicit an immune response or wherein the immune response elicited is tolerable to the subject. In some embodiments, the tolerable immune response includes a systemic immune response or a local immune response. In some embodiments, the subject is diagnosed as having cancer. In some embodiments, a cancer cell from the subject expresses B7-H3, or a portion thereof. In some embodiments, the expression of B7-H3 is higher in the cancer cell than in a non-cancer cell. In some embodiments, the composition is not taken up and/or retained in the kidney and/or liver. In some embodiments, the polypeptide or composition is taken up and/or retained in the liver or kidney, but administration of the decoy reduces uptake of the polypeptide or composition in the liver and/or kidney as compared to administration without the decoy. In some embodiments, the polypeptide or the composition is internalized in a cell expressing human B7-H3. In some embodiments, the cancer is selected from breast cancer, ovarian cancer, melanoma, pancreatic cancer, peripheral neuroma, glioblastoma, adrenocortical carcinoma, AIDS-related lymphoma, anal cancer, bladder cancer, meningioma, glioma, astrocytoma, cervical cancer, chronic myeloproliferative disorders, colon cancer, endometrial cancer, ependymoma, esophageal cancer, Ewing's sarcoma, extracranial germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma, Kaposi sarcoma, laryngeal cancer, leukemia, lip cancer, oral cavity cancer, liver cancer, male breast cancer, malignant mesothelioma, medulloblastoma, Merkel cell carcinoma, metastatic squamous neck cell carcinoma, multiple myeloma and other plasma cell neoplasms, mycosis fungoides and Sezary syndrome, myelodysplastic syndromes, nasopharyngeal cancer, neuroblastoma, non-small cell lung cancer, small cell lung cancer, head and neck cancer, skin cancer, oropharyngeal cancer, bone cancers, including osteosarcoma and malignant fibrous histiocytoma of bone, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilms tumor and other childhood kidney tumors.

In some embodiments, the polypeptide or the composition is administered intravenously or subcutaneously. In some embodiments, the administration of the decoy is before, concomitant with, or after the administration of the polypeptide or composition.

In some embodiments, the administration of the polypeptide or the composition results in treatment of the cancer.

In some embodiments, the cancer is treated and one or more off-target effects and/or toxicity grade is reduced in the presence of the decoy as compared to treatment without administration of the decoy.

In some embodiments, a method of the disclosure comprising administering a polypeptide further comprises administering a second polypeptide. In some embodiments, the second polypeptide is not a decoy. In some embodiments, the second polypeptide comprises an amino acid sequence of any one of SEQ ID NOs: 4-6, SEQ ID NOs: 12-94, or 100-272. In some embodiments, the second polypeptide is conjugated to a cold-metal surrogate or a radionuclide. In some embodiments, the second polypeptide is conjugated to an alpha emitter. In some embodiments, the second polypeptide is conjugated to a beta emitter.

In some embodiments, a method of the disclosure comprising administering a polypeptide further comprises administering a second therapeutic agent selected from a treatment or component for use in monoclonal antibody therapy, a DNA damage response (DDR) inhibitor, immunotherapy, chemotherapy, radiotherapy, gene therapy, or RNA therapy. In some embodiments, the second therapeutic agent comprises an immunotherapy or radiotherapy treatment. In some embodiments, the DDR inhibitor is selected from an inhibitor of Serine-protein kinase ATM (ATM), Serine/threonine-protein kinase ATR (ATR), Serine/threonine-protein kinase Chk1 (CHK1/2), DNA-dependent protein kinase catalytic subunit (DNA-PK), Poly [ADP-ribose] polymerase (PARP), Membrane-associated tyrosine- and threonine-specific CDC2-inhibitory kinase (PKMYT1), RNA-directed DNA polymerase (POL0), and DNA repair protein RAD51 homolog 1 (RAD51).

In some embodiments, the polypeptide or the composition achieves a tumor/kidney (T/K) ratio greater than 0.5% ID/g, 1% ID/g, 1.5% ID/g, 2% ID/g, 2.5% ID/g, 3% ID/g, 3.5% ID/g, 4% ID/g, 4.5% ID/g, 5% ID/g, 5.5% ID/g, 6% ID/g, 6.5% ID/g, 7% ID/g, 7.5% ID/g, 8% ID/g, 8.5% ID/g, 9% ID/g, 9.5% ID/g, or 10% ID/g.

In one aspect, the disclosure provides a method of targeting a population of cancer cells expressing B7-H3, the method comprising: (i) determining a level of expression of a target in a population of cancer cells; (ii) administering a polypeptide as provided herein or a composition as provided herein, wherein the polypeptide or the miniprotein of the composition specifically binds B7-H3; and (iii) wherein the polypeptide or the miniprotein of the composition targets the B7-H3-expressing cells and is internalized into the B7-H3 expressing cells. In some embodiments, the method comprises administering the polypeptide or the composition comprises administering the polypeptide or the composition to a patient in need thereof, wherein the administering results in treatment of the patient as compared to prior to the administering. In some embodiments, the method further comprises administering a scaffold A decoy or scaffold B decoy. In some embodiments, the treatment does not damage cells not expressing or lowly expressing B7-H3. In some embodiments, damage to cells not expressing B7-H3 is reduced after administration of the polypeptide or the composition in presence of a decoy as compared to the administration in absence of a decoy.

In one aspect, the disclosure provides a kit comprising: a composition represented by the formula selected from one or more of M-L-C-R, M-L-C, M-C-R, M-L-R, M-C, M-L, and M-R, wherein M comprises a miniprotein (M), L comprises a linker (L), C comprises a chelator (C), and R comprises a radionuclide (R); and a decoy, wherein the decoy blocks uptake of the composition into a non-tumor tissue (e.g., a kidney tissue).

In some embodiments, the kit comprises (a) (i) a polypeptide as provided herein or (ii) a composition as provided herein; and (b) a decoy, wherein the decoy blocks uptake of the composition into a non-tumor tissue (e.g., a kidney tissue, a liver tissue, etc.).

In some embodiments, the polypeptide or the composition comprises a radionuclide (R). In some embodiments, when R is present, it is supplied separately from any other components (e.g., M, C, L) of the polypeptide or composition or the decoy. In some embodiments, the R, if present, is added just prior to use. In some embodiments, the decoy and the composition are administered to a subject in need thereof. In some embodiments, the decoy appears in a higher concentration in the non-tumor tissue than in the tumor tissue as measured by % ID/g. In some embodiments, the decoy is selected from a scaffold A decoy or a scaffold B decoy. In some embodiments, the decoy is selected from any one of C10 or C118-C119 and/or has an amino acid sequence comprising SEQ ID NO: 7 or SEQ ID NOs: 97-99. In some embodiments, the miniprotein has an amino acid sequence comprising any of SEQ ID NOs: 4-6, SEQ ID NOs: 12-94, or 100-272. In some embodiments, the decoy molecule is supplied in a molar excess as compared to the composition, which molar excess may optionally be selected from a 10, 100, 1000, or more molar excess.

In some embodiments, the disclosure provides, in a method of treating an individual with cancer comprising administering (a) (i) a polypeptide provided herein or (ii) a composition as provided herein comprising a miniprotein (M) and a radionuclide (R); and (b) a decoy, the improvement comprising reducing one or more off-target effects or toxicity measures after administration of the composition and the decoy molecule as compared to administration of the composition in the absence of the decoy. In some embodiments, the polypeptide or the composition binds to B7-H3.

In some embodiments, the disclosure provides, in a method of treating an individual with a cancer by administering: (a) (i) a polypeptide as provided herein or (ii) a composition as provided herein, wherein, in either case, the polypeptide or the composition comprises a radionuclide (R); and (b) a decoy molecule, the improvement comprising achieving a reduction in concentration of R in a non-tumor tissue in the presence of the decoy as compared to the concentration of R in the non-tumor tissue in the absence of the decoy.

In some embodiments, the miniprotein has an amino acid sequence comprising a sequence selected from any of SEQ ID NOs: 4-6, SEQ ID NOs: 12-94, or 100-272. In some embodiments, the decoy is a scaffold A decoy or a scaffold B decoy. In some embodiments, the decoy has an amino acid sequence comprising the amino acid sequence of any of SEQ ID NO: 7 or SEQ ID NOs: 97-99. In some embodiments, the non-tumor tissue is a liver tissue or a kidney tissue. In some embodiments, the one or more off-target effects or toxicity measures is measured as a reduction in one or more toxicity grades of each of the one or more off target effects or toxicity measures. In some embodiments, the reduction in concentration of R in the kidney tissue is measured by urine output of R as measured by percent of administered radiation recovered. In some embodiments, the percent of administered radiation recovered in the presence of the decoy is increased as compared to radiation recovered in absence of the decoy. In some embodiments, the reduction in concentration of R in the kidney tissue is determined by maintenance of eGFR over at least the period that the subject is receiving treatment. In some embodiments, the administration of the composition can be repeated at least twice as many times in the presence of the decoy as in the absence of the decoy before a dose limiting toxicity is reached.

In some embodiments, the disclosure provides, in a method of reducing uptake by a non-tumor tissue of a composition the improvement comprising administering a composition comprising (a) a radionuclide therapeutic comprising at least a (i) polypeptide as provided herein or (ii) composition as provided herein and (iii) a radionuclide (R); and (b) a decoy molecule, such that in the presence of the decoy, the radionuclide is less concentrated in the non-tumor tissue than in the absence of the decoy.

In some embodiments, the non-tumor tissue is a kidney tissue or a liver tissue. In some embodiments, the reduction in concentration of R in the kidney tissue is measured by urine output of R. In some embodiments, the urine output is expressed as a percent of administered radiation recovered in the presence of the decoy and is increased as compared to radiation recovered in absence of the decoy. In some embodiments, the reduction in concentration of R in the kidney tissue is determined by maintenance of eGFR over at least the period that the subject is receiving treatment. In some embodiments, the administration of the composition can be repeated at least twice as much in the presence of the decoy as in the absence of the decoy before a dose limiting toxicity is reached. In some embodiments, the administration of the polypeptide or the composition is administered concomitant with the decoy peptide. In some embodiments, administration of the polypeptide or the composition is administered sequentially with the decoy peptide. In some embodiments, the sequential administering comprises administering the decoy molecule followed by administering the polypeptide or the composition. In some embodiments, the sequential administering comprises administering the polypeptide or the composition followed by administering the decoy peptide. In some embodiments, the decoy is administered in a molar or mass excess relative to the miniprotein (M). In some embodiments, the excess is at least about 2, 10, 50, 100, 250, 500, 750, 1,000, 2,500, 5,000, 7,500, or 10,000× molar or mass excess relative to the polypeptide or the composition. In some embodiments, the decoy is a scaffold A decoy or a scaffold B decoy.

In some embodiments, the decoy comprises or consists of an amino acid sequence comprising that of any of SEQ ID NO: 7 or SEQ ID NOs: 97-99.

In some embodiments, the decoy is selected from any of compounds C10 or C118-C120.

In some embodiments, the miniprotein comprises or consists of an amino acid sequence selected from any of compounds selected from Table 2A or Table 2C.

In some embodiments, the decoy peptide comprises or consists of an amino acid sequence selected from any of compounds C118-C120.

In some embodiments, the decoy peptide comprises or consists of an amino acid sequence of the compound C10.

In some embodiments, the decoy peptide comprises or consists of an amino acid sequence selected from any of compounds C118-C120 and the miniprotein comprises or consists of an amino acid sequence selected any one of the compounds in Table 2A or Table 2C.

In some embodiments, the decoy peptide comprises or consists of an amino acid sequence of compound C10 and the miniprotein comprises or consists of an amino acid sequence selected any one of the compounds in Table 2A or Table 2C.

In one aspect, the disclosure provides a combination composition comprising: (i) a radionuclide therapeutic comprising a radionuclide (R) and a polypeptide as provided herein or a composition as provided herein; and (ii) a decoy molecule selected from SEQ ID NO. 7 and/or SEQ ID NOs: 97-99. In some embodiments, the decoy and the polypeptide or composition have the same scaffold. In some embodiments, the decoy and the polypeptide or composition have different scaffolds. In some embodiments, the decoy comprises a scaffold B decoy. In some embodiments, the decoy comprises a scaffold A decoy. In some embodiments, the polypeptide or composition comprises a scaffold B polypeptide or composition.

In one aspect, the disclosure provides a method of treating an individual with a cancer, the method comprising administering to the individual: a means for blocking uptake of a radiotherapeutic to a non-tumor tissue, and a radionuclide therapeutic comprising a polypeptide as provided herein or a composition as provided herein, wherein the polypeptide or the composition comprise a radionuclide (R). In some embodiments, the non-tumor tissue is a kidney tissue or a liver tissue. In some embodiments, the means for binding to kidney tissue reduces or prevents uptake and/or retention of the radiotherapeutic into the kidney. In some embodiments, the radiotherapeutic is targeted to a tumor or a population of tumor cells. In some embodiments, the radiotherapeutic targeted to the tumor or the population of tumor cells is at a greater concentration than in the absence of the means for binding to kidney tissue.

In one aspect, the disclosure provides a combination composition comprising a polypeptide that binds to B7-H3 and a decoy.

In some embodiments, the polypeptide is selected from any one of the compounds in Table 2A or Table 2C. In some embodiments, the decoy molecule is selected from C10 and C118-C120 and/or has an amino acid sequence comprising, consisting essentially of, or consisting of any of SEQ ID NO: 7 or SEQ ID NOs: 97-99. In some embodiments, the decoy molecule is administered together or separately from the polypeptide that binds to B7-H3. In some embodiments, the decoy molecule is administered sequentially with (prior to or after) the polypeptide that binds to B7-H3. In some embodiments, administration of the polypeptide that binds to B7-H3 is administered concomitant with the decoy. In some embodiments, the sequential administering comprises administering the decoy followed by administering the composition comprising the polypeptide that binds to B7-H3. In some embodiments, the sequential administering comprises administering the composition comprising a miniprotein followed by administering the decoy.

In one aspect, the disclosure provides a method of improving a cancer treatment in an individual experiencing one or more off-target effects, the method comprising administering: (a) a decoy molecule; and (b) a radionuclide therapeutic comprising a radionuclide (R) and a polypeptide as provided herein or a composition as provided herein, wherein the one or more off-target effects is prevented or reduced as compared to administering the radiotherapeutic in the absence of the decoy molecule. In some embodiments, the radionuclide therapeutic comprises a miniprotein that targets B7-H3. In some embodiments, the radionuclide therapeutic comprises a miniprotein selected from any of SEQ ID NOs 4-6, SEQ ID NOs: 12-94, or 100-272, or Compound ID Nos C1-C9, C11-C117, or C121-C332. In some embodiments, the radionuclide therapeutic comprises a compound selected from Table 2A or Table 2C. In some embodiments, the decoy is selected from C10 or C118-C120 and/or has an amino acid sequence comprising, consisting essentially of, or consisting of any of SEQ ID NO: 7 or SEQ ID NOs: 97-99.

In one aspect, the disclosure provides a method of improving stability of a miniprotein, the method comprising introducing at least one disulfide bridge between at least two cysteines selected from positions corresponding to Cys1, Cys17, Cys35, and Cys48 with reference to linear positions from N-to-C of SEQ ID NO: 267, of any sequence set forth in TABLE 2C, wherein the miniprotein is more thermally stable than as compared to the same miniprotein without the at least one disulfide bridge. In some embodiments, the at least one disulfide bridge is between any two cysteines corresponding to Cys1, Cys17, Cys35, and Cys48. In some embodiments, the miniprotein comprises two disulfide bridges. In some embodiments, the two disulfide bridges are between any two pairs of cysteines corresponding to Cys1, Cys17, Cys35, and Cys48. In some embodiments, the miniprotein has an amino acid sequence comprising any one of SEQ ID NOs: 204, 241, or 267.

The present disclosure is further illustrated by the following examples which should not be construed as further limiting. The contents of all references cited throughout this application are expressly incorporated herein by reference.

EXAMPLES

Example 1: Engineering Miniproteins for Improved B7-H3 Binding

This Example describes exemplary engineering of miniproteins that bind to B7-H3 to achieve, among other things, improved binding affinity to B7-H3 or a portion or fragment thereof as compared to proteins that are not engineered as provided herein.

To improve the binding affinity of the engineered miniproteins to B7-H3, a structure-activity relationship (SAR) approach was used, wherein, various amino acid residues within the engineered structure were replaced with optimal substitutions, resulting in improved binding affinity. These substitutions included natural and non-natural amino acids, conjugated chemical moieties, and other small molecule attachments. Namely, beginning with a base sequence (e.g., AEAKYAKEKIAALSEIIWLPNLTHGQIMAFIAAL-NDDPSQ SSELLSEAKKLNDSQAPK (SEQ ID NO: 3)), substitutions were carefully introduced. For example, SAR was performed on position 24 (with reference to length from N-to-C terminus of SEQ ID NO: 3) of the miniprotein sequence to remove the positive residue. Standard affinity maturation techniques were also used to engineer improvements in B7-H3 binding affinity. Exemplary miniprotein sequences are shown in Table 2A (e.g., SEQ ID NOs: 4-197).

Example 2: Peptide Binding Assay to Target Protein Via Surface Plasma Resonance (SPR)

This Example evaluates binding of exemplary B7-H3-miniproteins to B7-H3 using surface plasmon resonance (SPR). Peptide binding affinity to the target protein was measured by SPR using a Biacore T200 instrument.

Surface plasmon resonance (SPR) analyses were performed using Biacore T200 (GE Healthcare). His-tagged B7-H3 protein (ThermoFisher, catalog #B7-H3_NP_001019907), ("ligand") was immobilized to a Series S NTA chip (Cytiva #28994951). Running buffer was 0.05% Surfactant P20 in HEPES buffered saline (HBS—P), pH 7.4 (Cytiva). Immobilization was performed at 25° C. The ligand was reconstituted by manufacturer at 0.51 mg/mL and diluted to 10 μg/mL in running buffer. Pulsatile injections were made to target a specific immobilization level. Test peptides ("analyte") were injected to the prepared ligand surface and blank reference surface in increasing concentrations to cover 0.1-10× the expected $K_D$ range at 25° C. Increase in signal (RU) is proportional to an increase in binding events between the analyte and ligand surface. Then injection was then stopped, and dissociation was measured. The resulting sensorgram is reference surface and blank injection subtracted prior to curve fitting. Measured association ($k_a$, $1/Ms^{-1}$) and dissociation ($k_d$, $s^{-1}$) were fit to a 1:1 binding model to calculate an equilibrium dissociation constant, $K_D$ (M) for each analyte as shown in FIGS. 1A, 1B, 2A, 2B, 3A, 3B, and 4. Equilibrium binding constants (KD) for exemplar miniprotein scaffolds to B7-H3 are shown in Table 3. KD was calculated using a 1:1 binding model at 25° C. Notably, compounds C2 (with corresponding SEQ ID NO: 4) and C6 (with corresponding SEQ ID NO: 6) demonstrated improved equilibrium binding in comparison to compound C1 with the base sequence (e.g., SEQ ID NO: 3).

TABLE 3

| Equilibrium Binding Constants | | | |
|---|---|---|---|
| FIG(s)/Compound ID NO | KD | $Chi^2$ | $k_d$ |
| 1A & 1B; Compound ID NO: C1 | 14.76 nM | 0.0303 | 0.03051 $s^{-1}$ |
| 2A & 2B; Compound ID NO: C2 | 6.178 nM | 0.0616 | 0.01205 $s^{-1}$ |
| 3A & 3B; Compound ID NO: C2 | 5.512 nM | 0.0325 | 0.01426 $s^{-1}$ |
| 4; Compound ID NO: C6 | 1.522 nM | 0.00309 | 0.01821 $s^{-1}$ |

Example 3: Binding Affinity and Thermal Stability Assays of Exemplary B7-H3 Miniproteins This Example shows results of binding affinity and thermal stability evaluations of exemplary B7-H3 miniprotein conjugates.

Figure 5A:
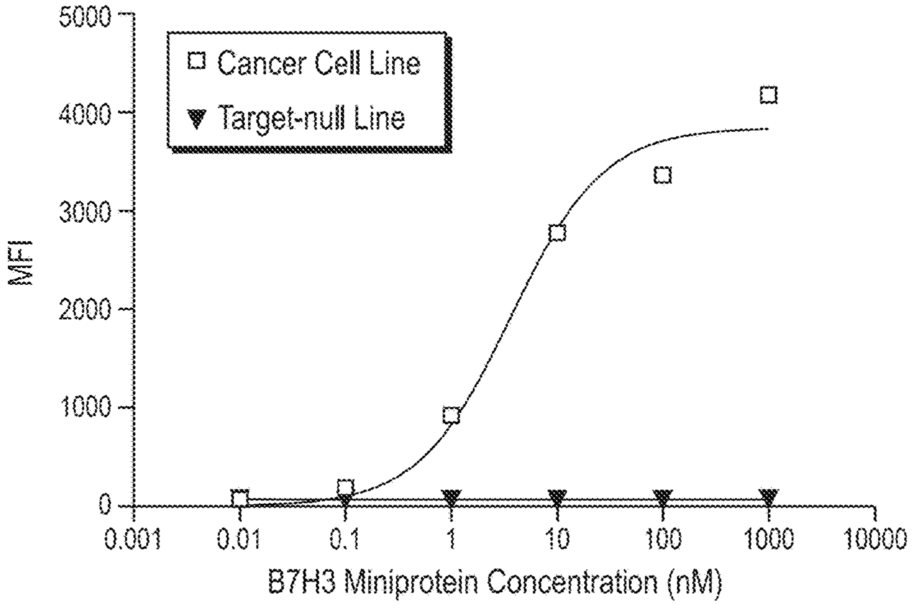
FIGS. 5A and 5B show the relative binding of an exemplary miniprotein to B7-H3 expressing cancer cells (Cancer Cell Line) in comparison to control (Target-null Line) as measured by flow cytometry.

A cell-binding assay was utilized to measure binding of B7-H3 miniproteins to B7-H3 expressed on the surface of mammalian cells or to a B7-H3 null cell line as a control. Binding intensity was measured using fluorescence (mean fluorescence intensity; MFI) at different concentrations of miniprotein (0.01 nM, 0.1 nM, 1 nM, 10 nM, 100 nM, and 1000 nM). Labeled miniproteins were incubated with cancer cells that expressed B7-H3 on their surfaces or cells that do not express B7-H3 (target null cells). After incubation, cells were analyzed with a flow cytometer determining the MFI at each miniprotein concentration using data analysis software. As shown in FIG. 5A, MFI increased with increasing concentration of B7-H3 miniprotein on cancer cells expressing B7-H3, whereas MFI remained at baseline/flat in cells not expressing B7-H3.

SPR was performed as described in Example 2 or as follows using Biacore T200 (GE Healthcare). Target protein ("ligand") was immobilized to a CM5 Series S sensor chip (Cytiva) using amine-coupling chemistry. Running buffer was 0.05% Surfactant P20 in HEPES buffered saline (HBS—P), pH 7.4 (Cytiva). Immobilization was performed at 25° C. Carboxyl groups in each flow cell were activated using a 1:1 mixture of 0.4 M 1-ethyl-3-(3-dimethylamino-propyl)-carbodiimide in water (EDC) and 0.1 M N-hydroxysuccinimide in water (NHS) for 7 minutes. The ligand was prepared in 10 mM Sodium acetate pH 5 (Cytiva). Pulsatile injections were made to target a specific immobilization level. Any remaining amine-reactive esters on the chip surface were blocked with a 7-minute injection of 1 M ethanolamine, pH 8.5. Three 10-second pulses of 50 mM Sodium hydroxide were then made to remove any unbound ligand. To determine $K_D$ constants, compounds were injected to the prepared ligand surface and blank reference surface in increasing concentrations to cover 0.1-10× the expected $K_D$ range at 25° C. Increase in signal (RU) is proportional to an increase in binding events between the analyte and ligand surface. The injection was then stopped, and dissociation was measured. The resulting sensorgram has reference surface and blank injection subtracted prior to curve fitting. Measured association ($k_a$, 1/Ms-1) and dissociation ($k_d$, $s^{-1}$) were fit to a 1:1 binding model to calculate an equilibrium dissociation constant, $K_d$ (M) for each analyte. Equilibrium binding constants ($K_D$) and binding inhibition constants (Ki) estimated from DELFIA® binding assays for exemplary compounds C1, C2, and C6 (each as set forth in Tables 2A and 2B). Estimated $K_D$ constants for exemplary compounds C1 and C2 are recorded in Table 4B.

Figure 5B:
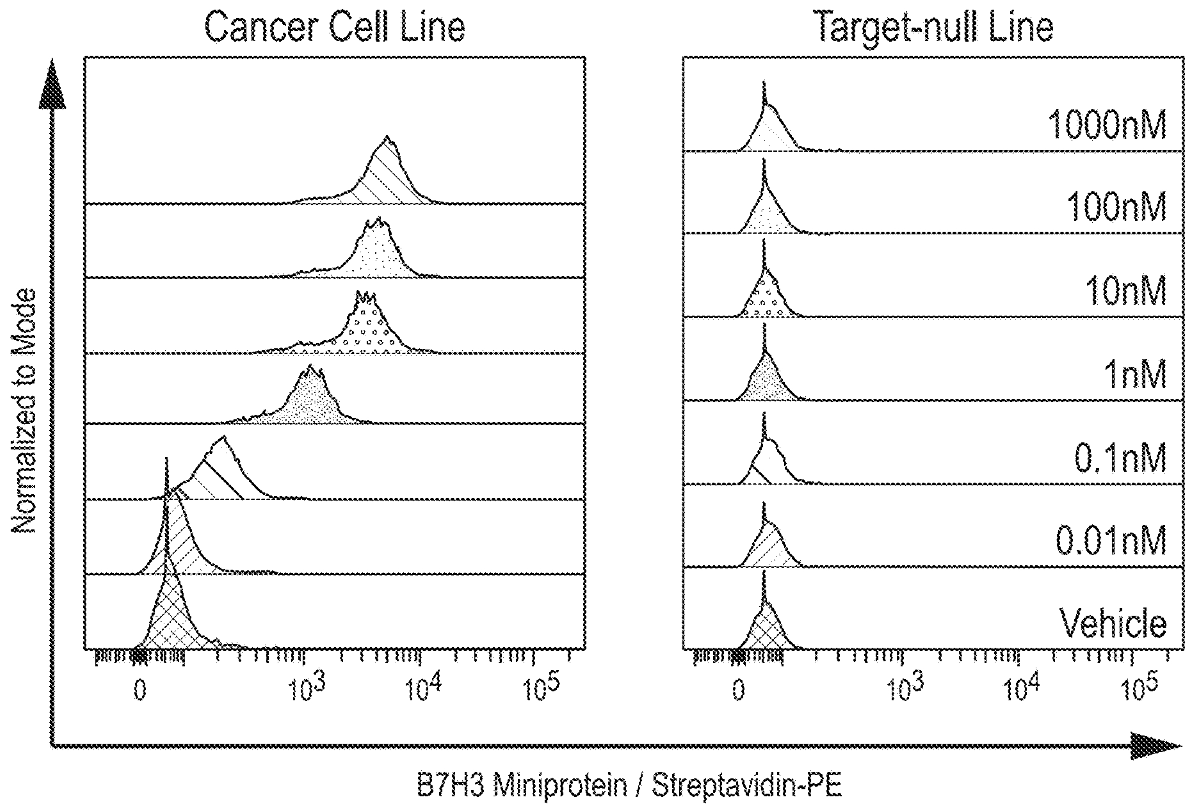

The affinities of miniproteins to the B7-H3 expressed on the surface of mammalian cells were measured using flow cytometry at increasing concentrations of miniprotein (0.01 nM, 0.1 nM, 1 nM, 10 nM, 100 nM, and 1000 nM) as compared to a vehicle control. As shown in FIG. 5B, miniprotein concentrations between 0.1 nM to about 1000 nM were tested on B7-H3 expressing cancer cells (left panel) and a B7-H3 null line (right panel). B7-H3 binding on cancer cells (expressing B7-H3) increased as concentration of B7-H3 miniprotein increased (left panel). No binding was observed in B7-H3 null cells at any concentration tested (right panel).

Solubility and thermal stability of exemplary B7-H3 compounds was also analyzed. Thermal stability of compounds was analyzed at a concentration of 1 mg/mL at 75° C. in 0.9% saline solution. A heating plate was set to 75° C. and the sample was heated for a period of one hour. The vial was shaken prior to collecting 10 mL aliquots at 5, 10, 15, 30, 60, and 120 minute time intervals. The % parent remaining was analyzed by HPLC using the following system and method: Analytical Agilent 1100 HPLC system using a 4.6×250 mm, 300 Angstrom, BEH300, 5 mm, Xbridge C18 column at 1.0 vmL/min. The solvent system consisted of A=Water+0.1% TFA, B=Acetonitrile+0.1% TFA. The gradient consisted of 5% to 70% B over 15 minutes, then the column was washed and equilibrated to initial conditions. Solubility of exemplary compounds C1, C2, and C6, and thermal stability of exemplary compounds C1 and C2 are recorded in Table 4.

As shown in Table 4, compound C2 demonstrated improved thermal stability and binding affinity in comparison to compound C1 with the base sequence (e.g., SEQ ID NO: 3).

TABLE 4

Exemplary Solubility and Stability Analyses

| Compound ID NO | Solubility (mg/mL) | Solvent | Thermal Stability (min) | SPR/Biacore $K_D$ (nM) to B7-H3 |
|---|---|---|---|---|
| C1 | >45 | Saline | 5 (90° C.) | 14.8 |
| C2 | 108 | Saline | 120 (60° C.) | 5.8 |
| C6 | 1 | Saline | N/A | 1.52 |

Example 4: Internalization Assay of Fluorescently-Labeled Conjugate

Figure 6:
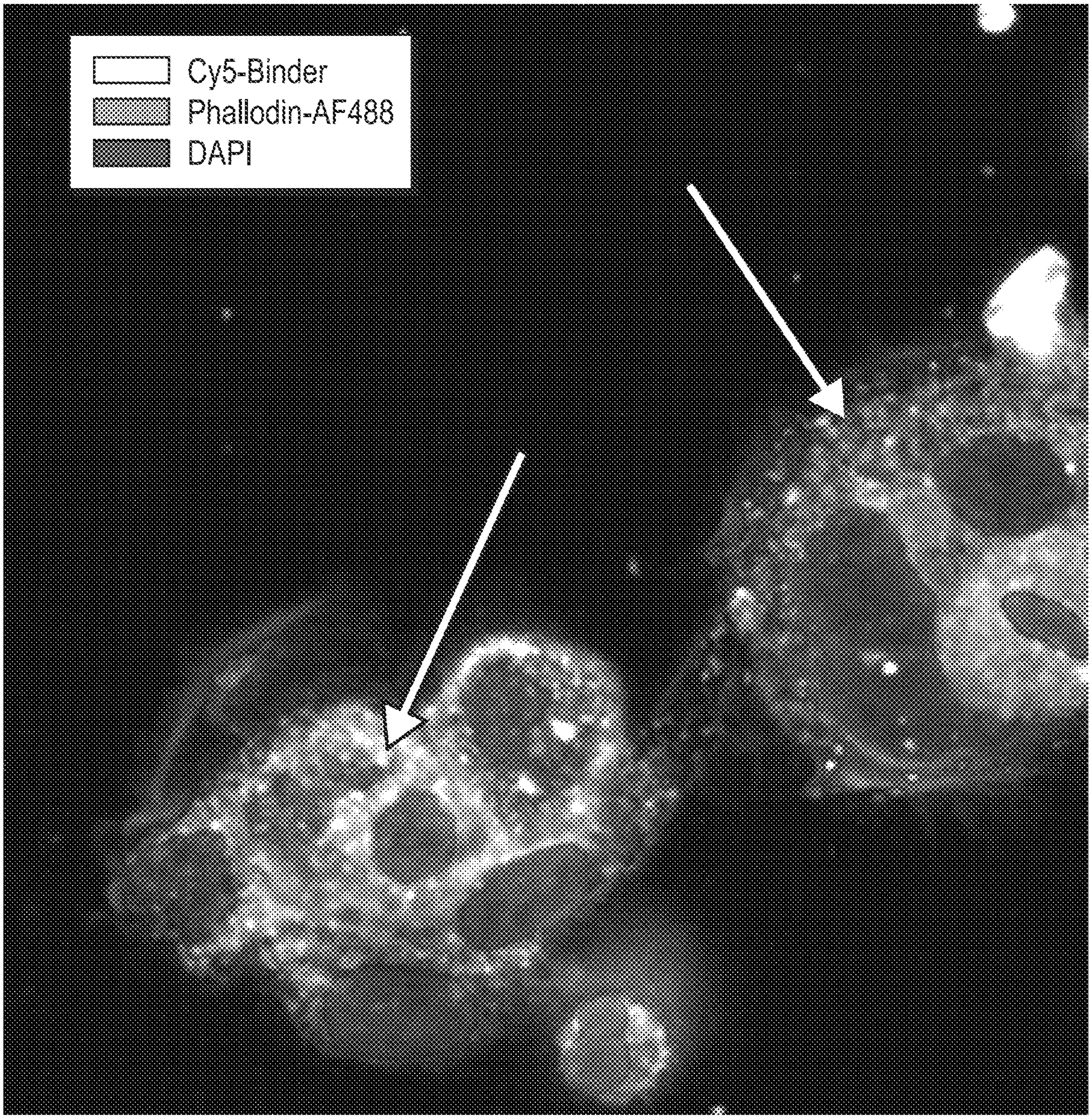
FIG. 6 shows internal localization of Cy5-labeled B7-H3-specific miniprotein in B7-H3-expressing cancer cells. Cell nuclei are labeled with DAPI stain and arrows indicate localization of the Cy5-labeled B7-H3 miniprotein.
Figure 7:
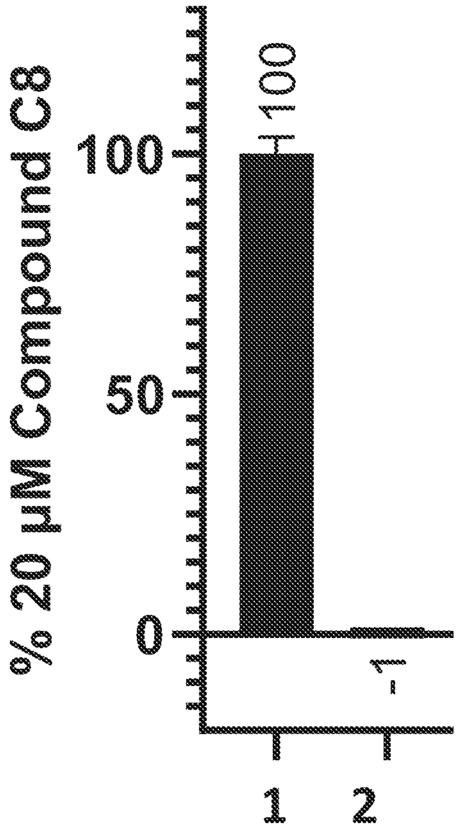
FIG. 7 depicts quantitative uptake in the Opossum kidney proximal tubule cell (OK-PTC) uptake assay. Co-treatment (bar 2, right side) with an exemplary decoy peptide (Compound ID NO: C10) at 20× molar excess reduces the uptake of biotinylated test agent (Compound ID NO: C8) as compared to biotinylated test agent, alone (C8, left side).

This Example describes an internalization assay of an exemplary B7-H3-conjugate. To investigate whether B7-H3 miniprotein conjugates are internalized, the targeting miniprotein moiety of the conjugate was coupled to a visualizable fluorescent dye (Cy5). B7-H3-expressing cells were incubated with the Cy5 labelled-B7-H3 conjugate (C610; SEQ ID NO: 545). Cells were fixed and permeabilized with methanol, followed by staining with a phalloidin cell marker and DAPI. The Cy5-labeled B7-H3 miniprotein was internalized (FIG. 6).

Example 5: Evaluating B7-H3 Miniprotein Conjugate Uptake in Opossum Kidney (OK) Cells in Presence or Absence of Decoys This Example evaluates uptake of exemplary fluorescently-labeled biotin conjugated test agents (e.g., B7-H3-miniprotein conjugates, e.g., comprising a detectable label, e.g., biotin, e.g., a fluorophore) in an exemplary renal cell line. Opossum kidney (OK) proximal tubule cells were: (i) plated in the upper chamber of 24-well transwell plates containing 600 mcL of growth media in the lower chamber and were incubated overnight at 37° C. in 5% CO2 or (ii) plated in 96-well flat bottom plates. The following day, the media was changed, and cells were incubated an additional 24 hours with moderate (e.g., 100-200 RPM) orbital shaking. Next, cells were washed and treated in duplicates with either fluorophore conjugated test agents or biotinylated test agents pre-complexed with streptavidin-AF647 (C4, C8, and C117) for 1-20 hours at 37° C. and 5% CO2 with continuous orbital shaking alone or in the presence of an exemplary scaffold B (C8) or scaffold A (C118-120) decoy. Following incubation, the cells were washed three times with 1×PBS and either (i) lysed with RIPA buffer containing protease and phosphatase inhibitor cocktail and Pierce universal nuclease for 30 minutes and (a) analyzed on a plate reader (streptavidin-AF complexes in transwell plates) or (b) directly analyzed on a plate reader (streptavidin-AF647 complexes in a 96-well flat bottom plates) or (ii) fixed with 4% paraformaldehyde and imaged (fluorophore conjugates in transwell plates). Uptake was measured on 100 mcL of lysates using a plate-based fluorimeter. Quantitative uptake of miniprotein conjugates with or without decoys is shown in FIGS. 7, 10A, 10B, 11, 12A, and 12B.

Example 6: Evaluating In Vitro Metabolic Stability of Test Articles

This Example describes in vitro metabolic stability of exemplary B7-H3 miniprotein conjugates.

Miniprotein test articles (TAs) were spiked into biological matrices at initial concentration between 1-2 μM. Tested matrices were varied by species (mouse, rat, human) and type (plasma, serum, and kidney brush border membrane preparations tested each from 0.625-100 μg/mL protein content). Tested conditions were incubated with TAs at 37° C. for 4 hours. At collection points of 0, 15, 30, 60, 120, 240 minutes, 50 μL of each condition were quenched by organic solvent (methanol or acetonitrile) or the addition of 4% phosphoric acid solution. Fractions of each quenched time-point were subsequently assayed for parent TA concentration by high resolution LC-MS. Percent-parent-remaining-time plots were constructed from the ratio of each given time collection to the time-zero parent TA. In the case of cleavable linkers, cleaved products were also identified by high resolution LC-MS and in some cases, doubling time of cleavage products was calculated. In vitro stability and pharmacokinetic results using exemplary compounds are shown in Table 5. Pharmacokinetic assessments are described in Example 18.

TABLE 5

Exemplary In Vitro Stability and Pharmacokinetics Analyses

| TA/Compound ID NO | In vitro Stability (mouse) - KBBM | In vitro Stability (mouse) - Plasma | PK - CL (ml/min/kg) | PK - t½ (min) | PK - Vss_BW (mL/kg) |
|---|---|---|---|---|---|
| C1A | >12 (rat) | >12 (rat) | | | |
| C2 | >12 (rat) | >12 (rat) | | | |
| C4 | | | 10.7 (1.9) | | |
| C6 | >12 | >12 | | | |
| C7 | | | 1.2 (0.1) | 64 (6) | |
| C10 | >12 | >12 | | 50.2 | |
| C15 | | >12 | | | |
| C16 | | NR (solubility) | | | |
| C17 | | >12 | | | |
| C18 | | >12 | | | |
| C28 | >12 | >12 | | | |
| C30 | | | 3.6 (0.29) | 39.6 (1.7) | 165 (7.4) |
| C41 | >12 | >12 | | | |
| C43 | 7.7 | >12 | | | |
| C44 | >12 | >12 | | | |
| C46 | >12 | 9.4 | | | |
| C49 | >12 | >12 | | | |
| C51 | >12 | 10.3 | | | |
| C55 | >12 | 7.1 | | | |

Example 7: $^{111}$In Labeling of Miniproteins for Biodistribution

This Example describes radiolabeling of exemplary B7-H3 miniprotein conjugates for biodistribution analyses.

In-111 labeling of exemplary miniproteins (e.g., as provided herein, e.g., C15-C18, C30, C41, C46, C320-C330, etc.) was performed in MES buffer or sodium acetate Buffer. For MES buffer, In-111 was neutralized with 0.5 M MES buffer pH 5.5. This mixture was added to miniproteins prepared at 2 mg/mL in water with an equivalent amount of 0.5 M MES buffer pH 5.5, in a 1.5 mL Eppendorf vial and heated at 75° C. for 30 minutes. After the reaction, an HPLC sample was taken and an equivalent amount of 10 mM DTPA in 0.1 M ammonium acetate pH 5 was added and incubated for at least 15 minutes. The sample was then used for HPLC analysis. For sodium acetate buffer, In-111 was neutralized with 0.1 M sodium acetate buffer pH 5. This mixture was added to miniprotein prepared at 5 mg/mL in sodium acetate buffer, with various amounts of 0.1 M sodium acetate buffer pH 5, in a 1.5 mL Eppendorf vial and heated at 75° C. for 30 minutes. After the reaction, an HPLC sample was taken and an equivalent amount of 10 mM DTPA in 0.1 M ammonium acetate pH 5 was added and incubated for at least 15 minutes. The sample was then used for HPLC analysis.

Purification of $^{111}$In-labeled miniproteins was done on two of the crude reaction mixtures mixed with 10 mM DTPA in 0.1 M ammonium acetate pH 5 and incubated for 15 minutes. A 3 kDa 0.5 mL amicon filter was used for purification and the filter was spun at 15,000 RCF for 9 minutes. Saline was used as a formulation buffer. Purified conjugates were used in analyses, including biodistribution analyses as described in Example 8.

Example 8: In Vivo Biodistribution Analysis of Exemplary 111-In-Labeled Miniprotein Conjugates and Image Analysis Methods This Example describes methods for biodistribution experiments using exemplary In-111-labeled B7-H3 miniprotein conjugates alone and in combination with an exemplary decoy.

Animals: Female athymic nude mice (6-8 weeks of age) were purchased from Charles River Laboratories and house according to IACUC guidelines with ad libitum feeding.

Animal grouping and treatment: Animals were monitored for body weight bi-weekly and at the time of experimentation, grouped into groups of n=3. Animals were administered test-agents (TAs) that were prepared as described above. Animals received 350 μCi of activity (111-In) at approximately 3-5 μg of total peptide per mouse (or a dose of ~37 MBq/nmol).

Animal imaging: Animals were sedated using isoflurane gas and imaged in a 3 bed hotel using a NanoScan SPECT/CT scanner (Mediso). Animals were imaged at 4 and 24 h post-dosing via SPECT scan followed CT scans.

Humane endpoints: All animals were euthanized following the final imaging time point and carcasses were discarded according to IACUC protocols.

Images of biodistribution experiments were processed as follows: Images were generated as SPECT/CT pair with the SPECT reported in units of activity. Namely, the values assigned to the voxels (volume elements) comprising the SPECT images were in units of μCi. SPECT images were co-registered to the CT scan for anatomical reference, resampled to 0.2 $mm^3$ voxels, masked to remove the CT background, and cropped to a uniform size prior to analysis.

Estimating tissue uptake: Regions of interest (ROIs) were defined using VivoQuant software. The kidneys and bladder were segmented as fixed volume phantoms and registered using the CT for anatomical reference. Two fixed volume spheres were used to create the liver ROI. Spheres were placed at appropriate anatomical locations based on CT and SPECT signal. Group and individual master spreadsheets were generated which included the volume, activity, and concentration (Activity/Volume) at each time point for each ROI generated. Additionally, plots of activity were generated using Matplotlib based python tools to highlight trends in the data. Outputs of each region were plotted and reported in percent injected dose per gram (% ID/g) and regions which were fully segmented were additionally presented in percent injected dose (% ID). Plots of body weights and tumor volumes measured manually in the lab were also created in the same manner.

Uptake unit definitions: Results were presented in units of percent injected dose (% ID) and percent injected dose per gram (% ID/g). The definition of these units can be found in the equations below: The % ID for each analyzed region from the in vivo imaging data can be defined as stated in Equation 1:

$$\%ID = \frac{\text{Uptake}}{\text{Injected Dose}} * 100$$

where, Uptake=Radioactivity (μCi) in a particular ROI, decay-corrected to the time of injection, and Injected dose=Radioactivity (μCi) injected into the subject.

The % ID/g for each analyzed region from the in vivo imaging data can be defined as stated in Equation 2:

$$\frac{ID}{\text{g}} = \frac{\frac{\text{Uptake}}{\text{Injected Dose}} * 100}{ROI \text{ weight}}$$

where, Uptake=Radioactivity (μCi) in a particular ROI, decay-corrected to the time of injection. Injected dose=Radioactivity (μCi) injected into the subject. Weight=For in vivo, this is the volume of the particular ROI in mL.

Image generation: After the preprocessing described in A, individual maximum intensity projections (MIPs) were created with VivoQuant software for each subject at each time point and scaled in percent injected dose per gram (% ID/g). The CT for each image was windowed from −500 to 4500 Hounsfield Units (HU). The SPECT was windowed at various ranges to highlight different regions of uptake. Images were then stitched together using Image Magick based python tools to create montages of subjects over time and time points over groups.

Figure 8:
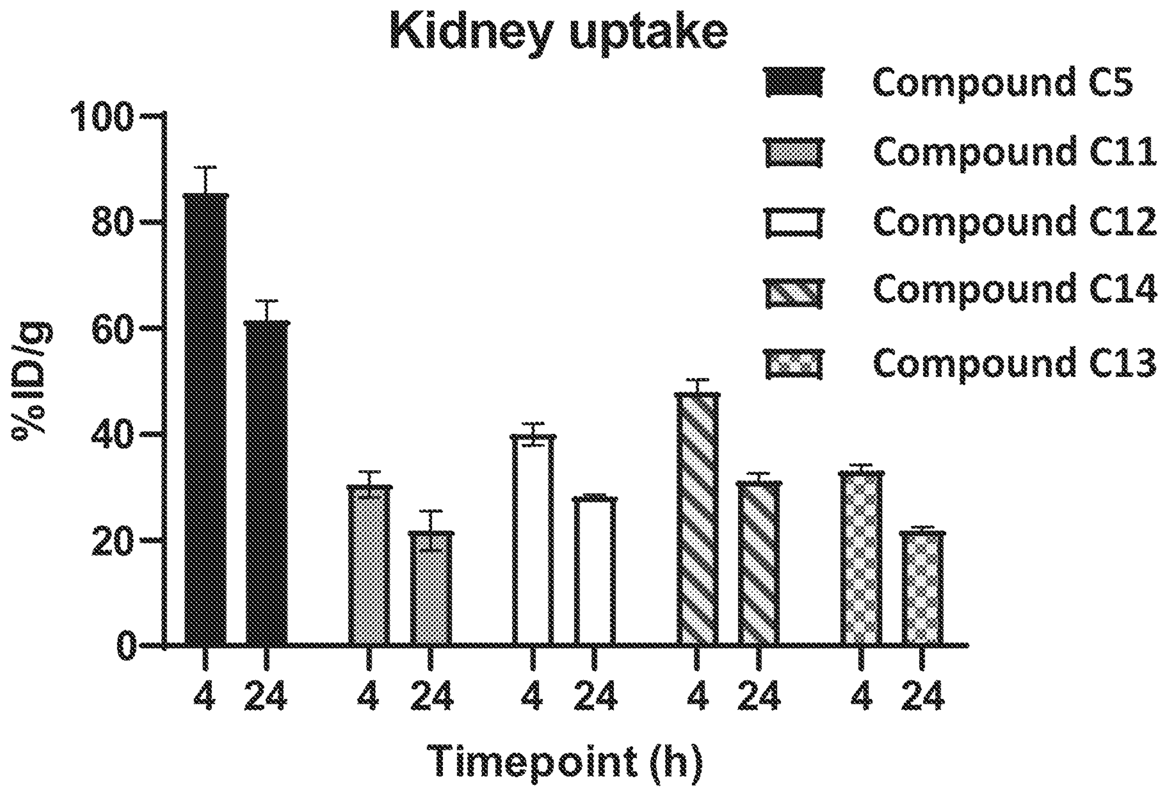
FIG. 8 depicts analysis generated from SPECT/CT scans to quantify the injected dose per gram (% ID/g) of kidney tissue in mice. Exemplary B7-H3 charge variant conjugates (Compound ID NOs: C5, C11-C14) demonstrate reduced levels of kidney retention in mouse biodistribution.
Figure 9:
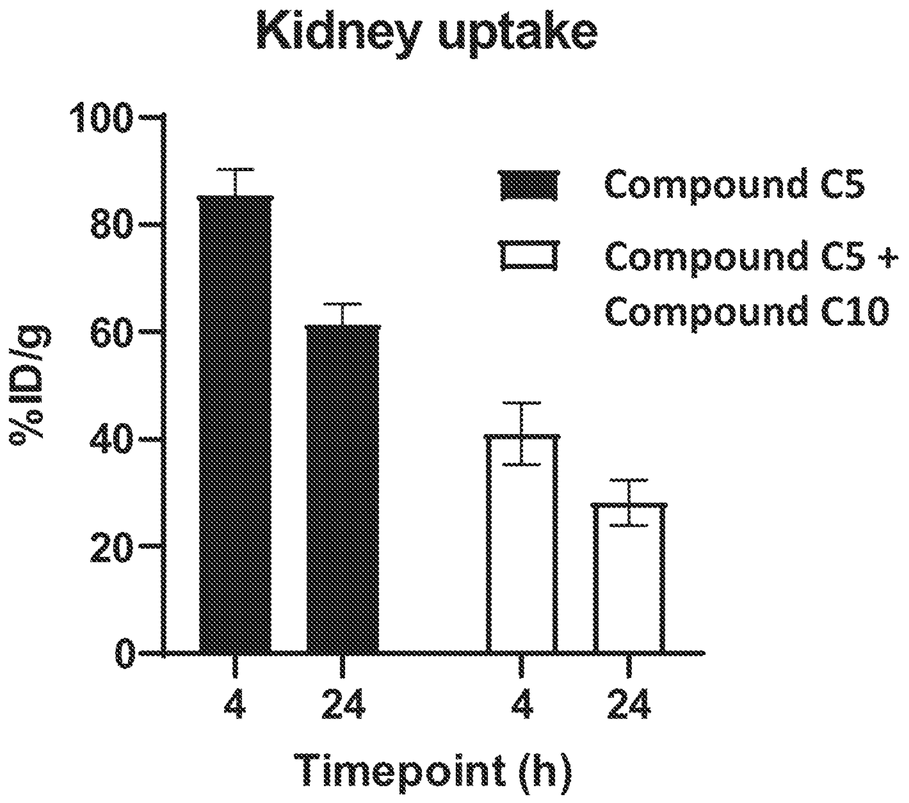
FIG. 9 depicts analysis generated from SPECT/CT scans to quantify the injected dose per gram (% ID/g) of kidney tissue in mice. Co-administration of an exemplary decoy peptide (Compound ID NO: C10) reduces kidney uptake of an exemplary B7-H3 targeting affibody conjugate (Compound ID NO: C5).

ROIs for quantitative analysis were generated from CT scans in order to quantify the injected dose per gram (% ID/g) of kidney tissue in mice as indicated of the different miniprotein scaffolds are shown in FIGS. 8 and 9. All ROIs were generated based on data at both 4 and 24 hours post-administration.

Regions of Interest (ROIs) were determined in mice treated with exemplary B7-H3 miniprotein conjugates. B7-H3 charge variant conjugates (Compound ID NOs: C5, C11-C14) were analyzed at both 4 and 24 hours post-administration. Reduced levels of kidney retention in mouse biodistribution were observed (FIG. 8).

In mice co-administered an exemplary decoy peptide (Compound ID NO: C10) of the same scaffold (Scaffold B) in combination with an exemplary B7-H3 conjugate (Compound ID NO: C5), as compared to those administered an exemplary B7-H3 conjugate (Compound ID NO: C5) alone, kidney uptake was reduced at both 4 and 24 hours post-administration (FIG. 9).

Example 9: In Vitro Reduction of Exemplary Scaffold B Miniprotein Compounds by an Exemplary Scaffold a Decoy in OK-PTC Cells This Example describes reduction of uptake of exemplary scaffold B, B7-H3 miniprotein conjugates (C4 and C8) when combined with an exemplary scaffold A decoy (C120) as compared to no decoy. Uptake of compounds was evaluated in opossum kidney proximal tubule cells (as described in Example 5). Here, cells were treated with a compound alone or were co-incubated with a compound and a decoy that were added together or at substantially the same time) and measured after incubation in presence or absence of a 20-fold molar excess of exemplary scaffold A decoy, C120.

Figures 10A, 10B:
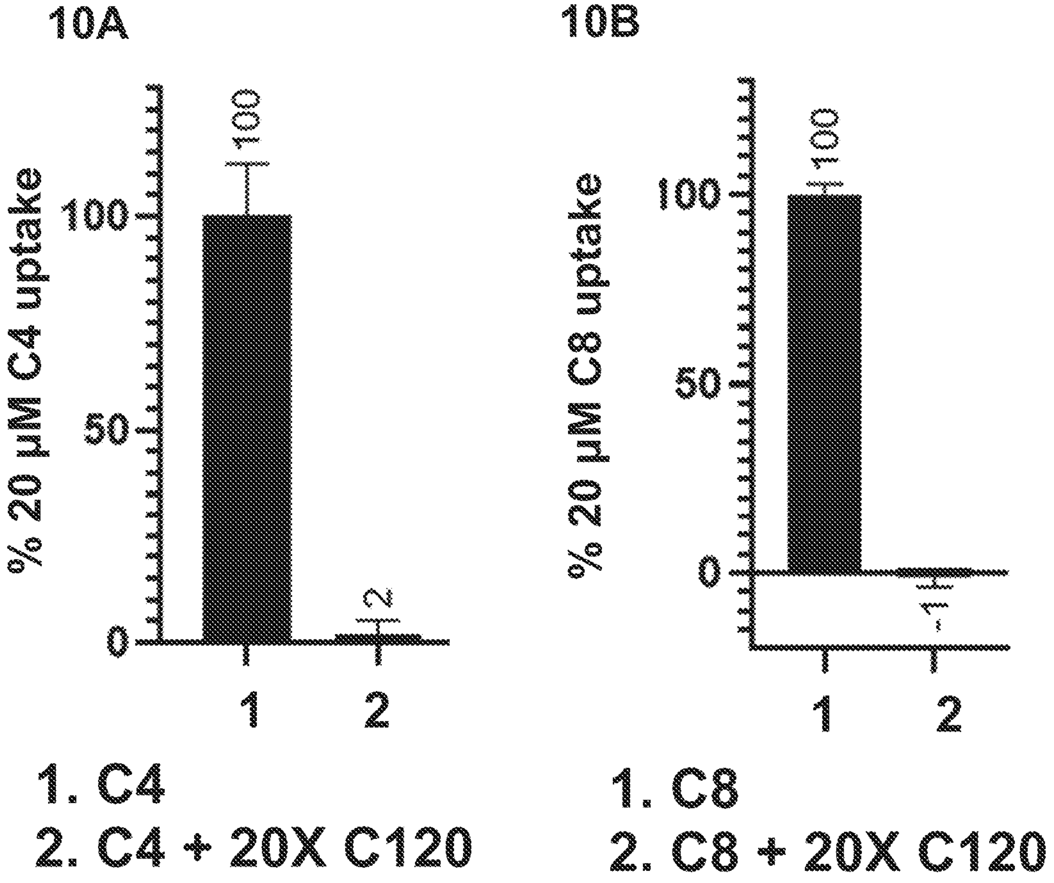
FIGS. 10A and 10B are graphs depicting data showing reduction in cellular uptake of exemplary target-binding scaffold B miniprotein conjugates when combined with an exemplary scaffold A decoy in vitro.

Graphs depicting results from assays measuring uptake of two exemplary scaffold B7-H3-targeting affibody compounds, C4 and C8, in OK-PTC cells in the presence and absence of exemplary decoy C120 (a scaffold A decoy) are shown in FIGS. 10A and 10B. The B7-H3-targeting compounds were used at a concentration of 20 μM and the decoy used at a 20-fold molar excess. FIG. 10A shows percent uptake (on the y-axis) of an exemplary B7-H3-targeting scaffold B miniprotein (C4) alone (20 μM; column 1, x-axis) or in combination (column 2, x-axis) with a 20-fold molar excess of an exemplary scaffold A decoy (C120). FIG. 10B shows percent uptake (on the y-axis) of 20 μM of an exemplary B7-H3-targeting scaffold B miniprotein (C8) alone (20 μM; column 1, x-axis) or in combination (column 2; x-axis) with a 20-fold molar excess of an exemplary scaffold A decoy (C120). As shown in both FIG. 10A and FIG. 10B, uptake of scaffold B, B7-H3-targeting compounds is reduced by co-incubation of OK-PTC cells with an exemplary scaffold A decoy. These results show that a scaffold A decoy can effectively decoy scaffold B miniproteins.

Example 10: In Vitro Reduction of an Exemplary Scaffold B Miniprotein Compound by Exemplary Scaffold a Decoys in OK-PTC Cells This Example describes reduction of uptake of an exemplary scaffold B, B7-H3-targeting binding protein (C8) when combined with one of three exemplary scaffold A decoys (C118, C119, or C120) as compared to no decoy. Uptake of compounds was evaluated in opossum kidney proximal tubule cells (as described in Example 5). Here, cells were treated with a compound alone or were co-incubated with a compound and a decoy that were added together or at substantially the same time) and measured after incubation in presence or absence of a 20-fold molar excess of exemplary scaffold A decoys, C118, C119, and C120.

Figure 11:
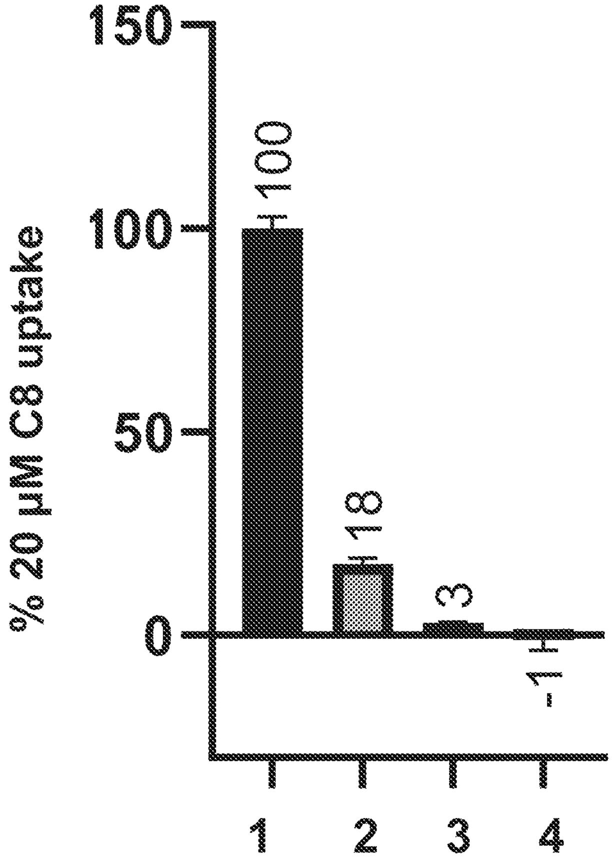
FIG. 11 is a graph depicting data showing reduction in cellular uptake of an exemplary B7-H3-binding scaffold B miniprotein conjugate when combined with one of three exemplary scaffold A decoys in vitro. The bar graph shows percent uptake (on the y-axis) of an exemplary B7-H3-targeting scaffold B miniprotein conjugate (C8) alone/without a decoy (20 μM; column 1, on the x-axis) or in combination with a 20-fold molar excess of one of three exemplary scaffold A decoys (C118, column 2; C119, column 3; and C120, column 4 on the x-axis). Error bars represent standard error of the mean (SEM).

Graphs depicting results from assays measuring uptake of an exemplary scaffold B7-H3-targeting affibody compound, C8, in OK-PTC cells in the presence and absence of each of three exemplary scaffold A decoys C118, C119, and C120 are shown in FIG. 11. The B7-H3-targeting compound was used at a concentration of 20 μM and the decoys were each used at a 20-fold molar excess.

Uptake of C8 was reduced by co-treatment with a 20-fold molar excess of each of decoys C118, C119, and C120. FIG. 11 shows reduction in cellular uptake of an exemplary target-binding scaffold B miniprotein compound when combined with one of three exemplary scaffold A decoys in vitro, with percent uptake (on the y-axis) of an exemplary B7-H3-targeting scaffold B miniprotein (C8) alone (20 μM; column 1, on the x-axis) or in combination with a 20-fold molar excess of one of three exemplary scaffold A decoys (C118, column 2; C119, column 3; and C120, column 4 on the x-axis). These results show that scaffold A decoys can reduce uptake of scaffold B miniproteins.

Example 11: In Vitro Reduction of Exemplary Scaffold B Miniprotein Compounds by an Exemplary Scaffold B Decoy in OK-PTC Cells at Different Concentrations of Miniprotein Compounds and Decoys This example describes reduction of uptake of exemplary scaffold B, B7-H3 biotinylated (C8) or fluorophore (C117) miniprotein conjugates when combined with an exemplary scaffold B decoy (C10) as compared to no decoy. Uptake of compounds was evaluated in opossum kidney proximal tubule cells (assay as described in Example 5). Here, cells were treated with a compound alone or were co-incubated with a compound and a decoy that were added together or at substantially the same time) and measured after incubation in presence or absence of a 20-fold (C8) or 100-fold (C117) molar excess of exemplary scaffold B decoy, C10.

Figures 12A, 12B:
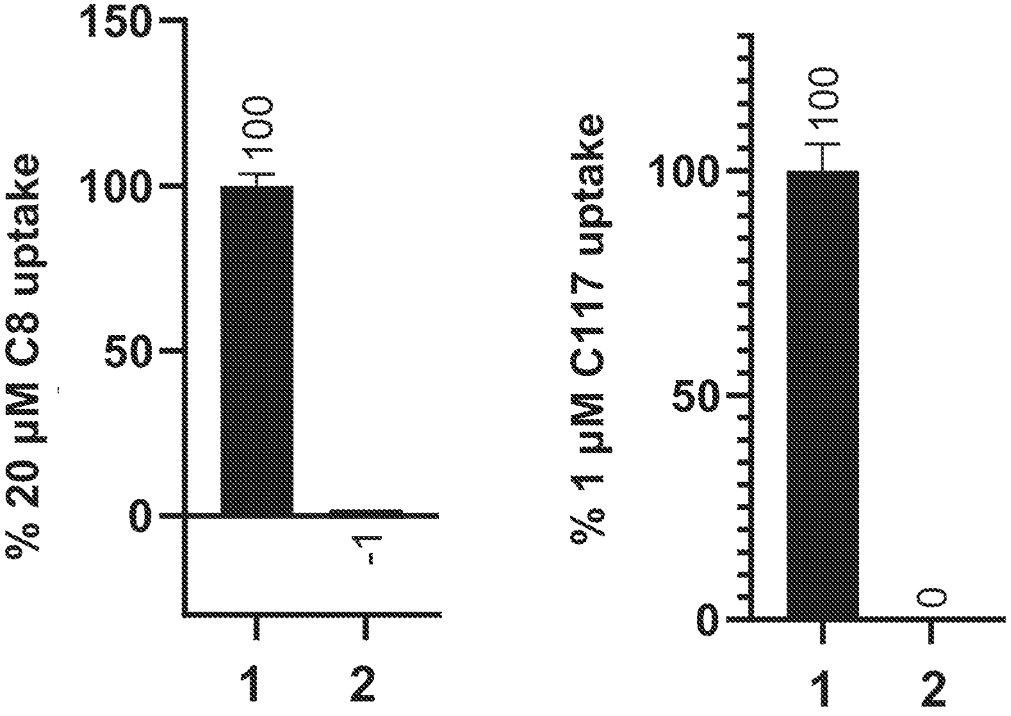
FIGS. 12A and 12B are graphs depicting data showing reduction in cellular uptake of exemplary scaffold B target-binding miniprotein compounds when combined with an exemplary scaffold B decoy in vitro.

Graphs depicting results from assays measuring uptake of two exemplary scaffold B7-H3-targeting affibody compounds, C8 and C117, in OK-PTC cells in the presence and absence of exemplary decoy C10 (a scaffold B decoy) are shown in FIGS. 12A and 12B. The B7-H3-targeting compounds were used at a concentration of 20 μM for C8 and 1 μM C117 with decoy used at a 20-fold or 100-fold molar excess, respectively.

Uptake of each of 20 μM C8 and 1 μM C117 was reduced by co-treatment with a 20-fold or 100-fold molar excess, respectively, of decoy C10.

FIGS. 12A and 12B show reduction in cellular uptake of exemplary scaffold B target-binding miniprotein compounds when combined with an exemplary scaffold B decoy in vitro. FIG. 12A shows percent uptake (on the y-axis) of an exemplary B7-H3-targeting scaffold B miniprotein (C8) alone (20 μM; column 1, x-axis) or in combination (column 2, x-axis) with a 20-fold molar excess of an exemplary scaffold B decoy (C10). FIG. 12B shows percent uptake (on the y-axis) of an exemplary B7-H3-targeting scaffold B miniprotein (C117) alone (1 μM; column 1, x-axis) or in combination (column 2, x-axis) with a 100-fold molar excess of an exemplary scaffold B decoy (C10). These results show that scaffold B decoys can decoy scaffold B miniproteins at different concentrations of miniprotein and fold excess of decoy.

Example 12: In Vivo Reduction in Uptake and Retention in Kidney and Liver of a Scaffold B Miniprotein Compound in Presence of a Scaffold B Decoy This Example shows reduction in kidney and liver uptake and retention (in % ID/g) of an exemplary scaffold B miniprotein (C5) compound in presence or absence of an exemplary scaffold B decoy (C10). Biodistribution in kidney and liver tissues was determined in a non-tumor bearing mouse model with methods similar to those described in Examples 8 and 9.

Figure 13A:
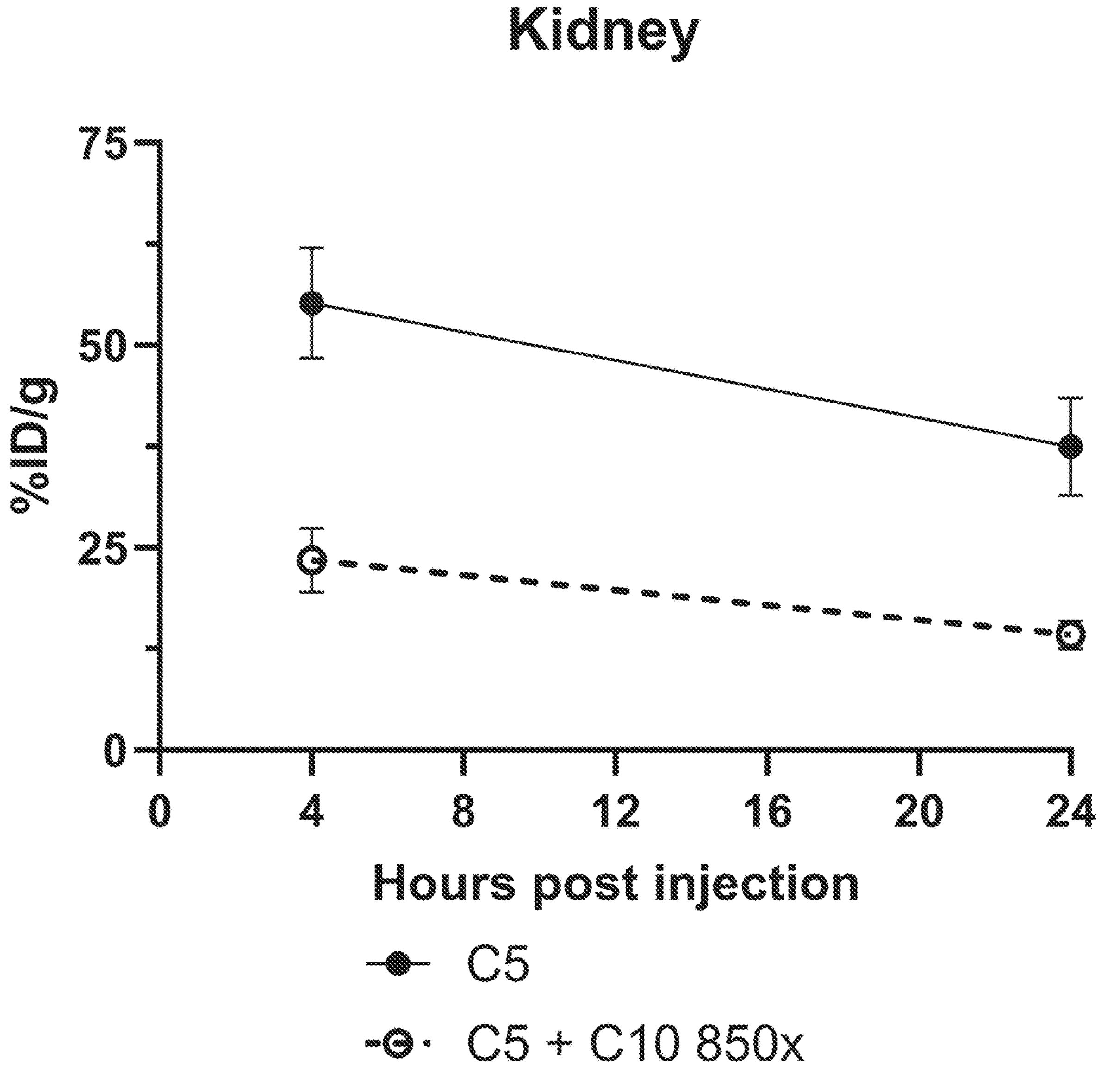
FIGS. 13A and 13B are graphs depicting results from analysis of SPECT/CT scans to quantify in vivo kidney (FIG. 13A) or liver (FIG. 13B) uptake and retention of a scaffold or scaffold plus decoy in mice, shown as percent injected dose per gram (% ID/g; y-axis) after injection of an $^{111}$In-labeled exemplary B7-H3-targeting scaffold B miniprotein conjugate ($^{111}$In-C5) alone/without a decoy (C5; solid line with solid circles in FIG. 13A and in FIG. 13B) or co-administered with 850-fold molar excess of an exemplary scaffold B decoy (C10; dotted line with open circles in FIG. 13A and FIG. 13B) from 4-24 hours post-injection (x-axis). Error bars represent standard deviation (SD).
Figure 13B:
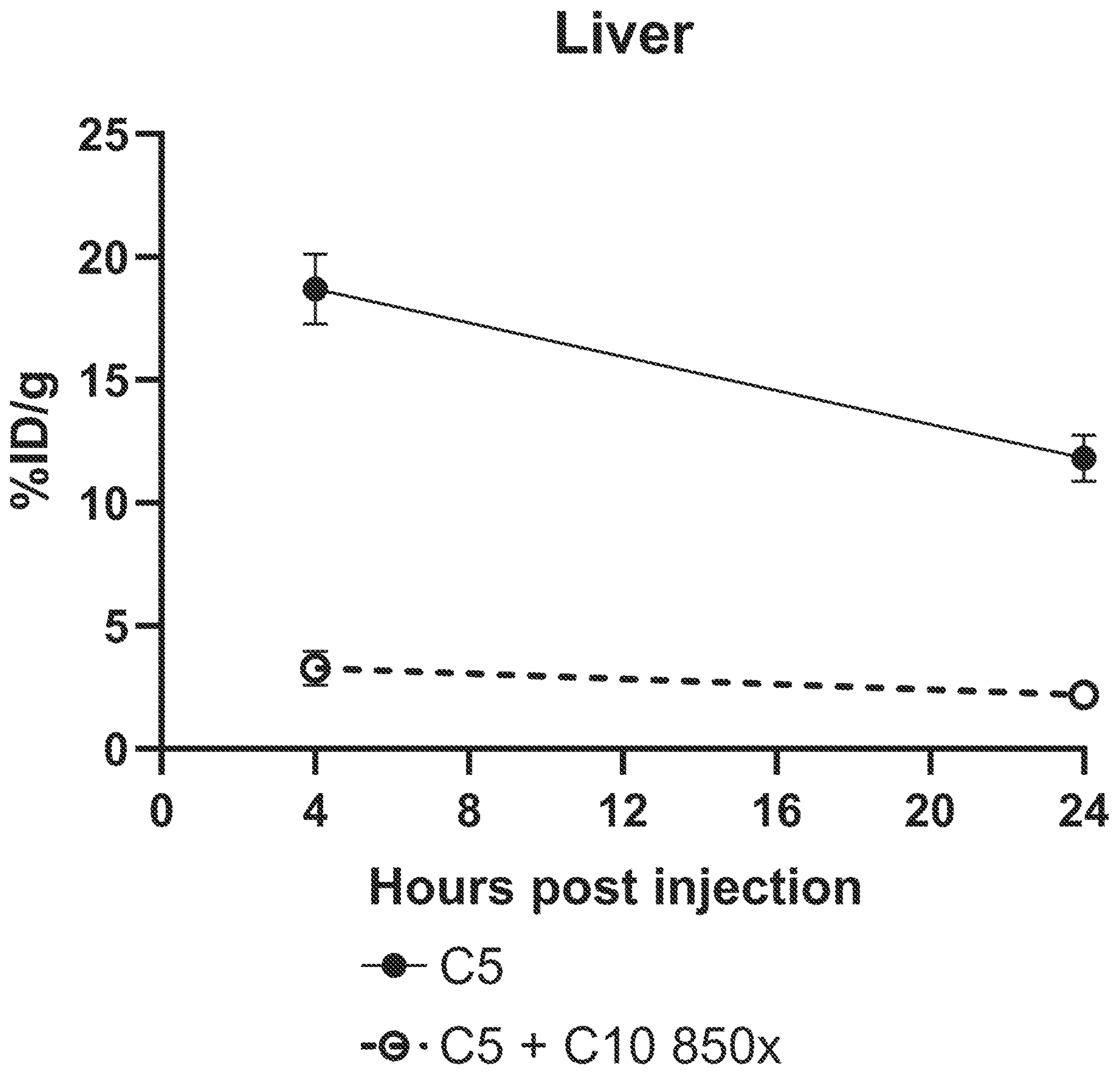

Mice were administered: (1) 1.1 μg of an $^{111}$In-labeled exemplary scaffold B compound, C5 ($^{111}$In-C5), or (2) 1.3 μg of $^{111}$In-C5 and 850-fold molar excess of an exemplary scaffold B decoy, C10. Kidney uptake and retention (in % ID/g) were reduced at both 4 and 24 hours post-injection in mice co-administered C10 and $^{111}$In-C5 as compared to those receiving $^{111}$In-C5 alone (FIG. 13A and Table 6A). Similarly, liver uptake and retention (in % ID/g) were reduced at both 4 hours and 24 hours post-injection in mice co-administered C10 and $^{111}$In-C5 as compared to those receiving $^{111}$In-C5 alone (FIG. 13B and Table 6B). Scaffold B decoys can reduce uptake and retention of scaffold B miniproteins in both liver and kidney tissues.

FIG. 13A shows results from analysis generated from SPECT/CT scans to quantify the injected dose per gram (% ID/g, y-axis) of kidney tissue in mice and demonstrates reduction in uptake and retention in kidney tissue after injection of an $^{111}$In-labeled exemplary B7-H3-targeting scaffold B miniprotein ($^{111}$In-C5) alone (solid line with solid circles) or co-administered with 850× of an exemplary scaffold B decoy (C10; dotted line with open circles) from 4-24 hours post-injection (x-axis). These results show that scaffold B decoys can reduce uptake and retention of scaffold B miniprotein compounds in kidney tissue.

TABLE 6A

Exemplary In Vivo Kidney Biodistribution Analysis Of An Exemplary Scaffold B Compound Co-Administered With An Exemplary Scaffold B Decoy

| Compound ID NO/Scaffold | Decoy/ Scaffold (fold excess) | 4 h (% ID/g) Average | 4 h (% ID/g) StDev | 24 h (% ID/g) Average | 24 h (% ID/g) StDev |
|---|---|---|---|---|---|
| $^{111}$In-labeled C5/B | — | 55.2 | 6.8 | 37.5 | 6.0 |
| $^{111}$In-labeled C5/B | C10/B (850) | 23.4 | 3.9 | 14.2 | 1.8 |

FIG. 13B shows results from analysis generated from SPECT/CT scans to quantify the injected dose per gram (% ID/g, y-axis) of liver tissue in mice and demonstrates reduction in uptake and retention in liver tissue after injection of an $^{111}$In-labeled exemplary B7-H3-targeting scaffold B miniprotein ($^{111}$In-C5) alone (solid line with solid circles) or co-administered with 850× of an exemplary scaffold B decoy (C10; dotted line with open circles) from 4-24 hours post-injection (x-axis). These results show that scaffold B decoys can reduce uptake and retention of scaffold B miniprotein compounds in liver tissue.

TABLE 6B

Exemplary In Vivo Liver Biodistribution Analysis Of An Exemplary Scaffold B Compound Co-Administered With An Exemplary Scaffold B Decoy

| Compound ID NO/Scaffold | Decoy/ Scaffold (fold excess) | 4 h (% ID/g) Average | 4 h (% ID/g) StDev | 24 h (% ID/g) Average | 24 h (% ID/g) StDev |
|---|---|---|---|---|---|
| $^{111}$In-labeled C5/B | — | 18.70 | 1.42 | 11.82 | 0.94 |
| $^{111}$In-labeled C5/B | C10/B (850) | 3.29 | 0.70 | 2.21 | 0.40 |

Example 13: Further Engineering and Modification of Affinity Matured Miniproteins This Example shows further engineering of certain exemplary B7-H3-binding miniproteins to improve affinity and stability.

To begin, certain engineered B7-H3 miniproteins developed in Example 1 were further modified. Starting with a miniprotein having an amino acid sequence of SEQ ID NO: 3, certain amino acids were truncated (removed). Specifically, miniproteins were engineered to truncate certain residues at the N- and C-terminus (e.g., amino acids corresponding to positions 1-6 beginning at the N-terminus and positions 54-58 at the C-terminus with reference to N-to-C terminal positions along the length of SEQ ID NO: 3) were made. In addition, cysteines were placed at positions corresponding to Cys1, Cys17, Cys35, and Cys48 and disulfide bonds were introduced between pairs of cysteines. The modified sequences are set forth in SEQ ID NOs: 198-272 (see Table 2C) and the miniproteins having these sequences are included in compounds C227-C332.

Further, a molecule with a combination of three constraints, two disulfide bridges and one lactam bridge, was engineered and synthesized as set forth in SEQ ID NO:544 and made as the conjugate set forth in C608.

Thermal stability was assessed for several exemplary miniprotein conjugates and reported as Tm (e.g., see Table 7A).

Figure 14:
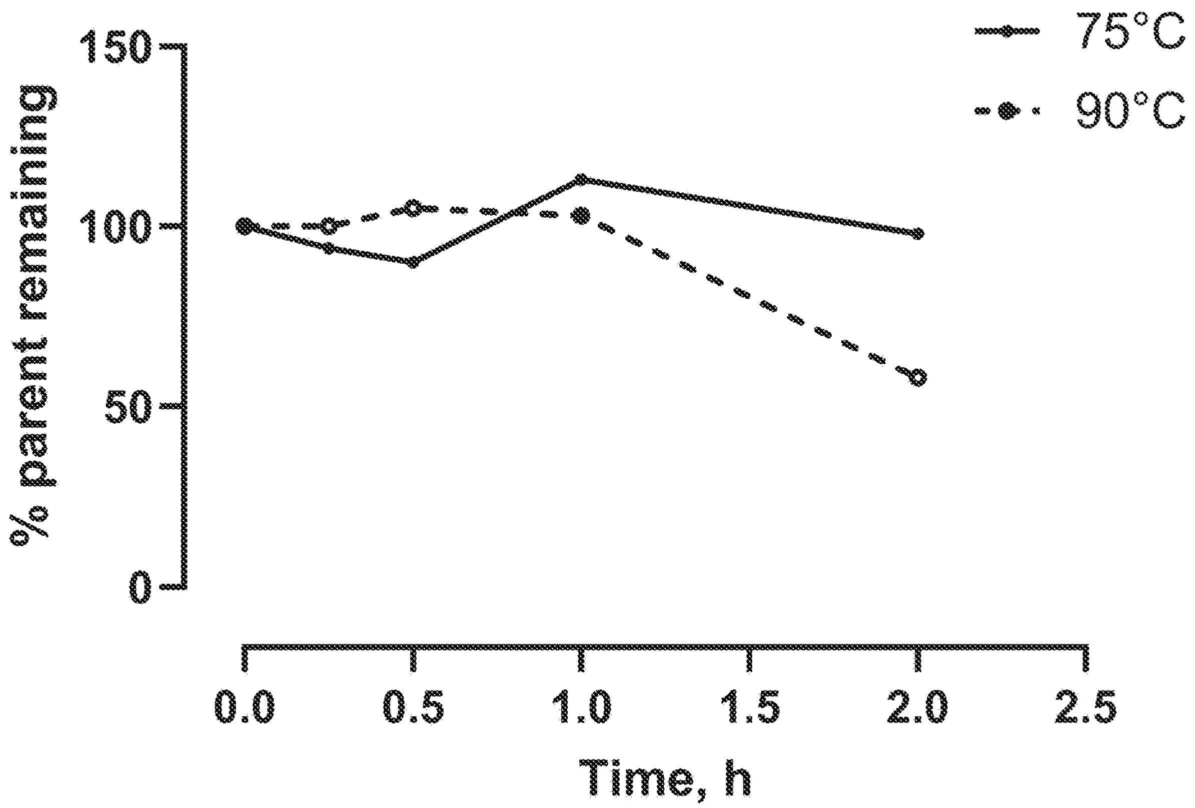
FIG. 14 is a graph showing thermal stability of an exemplary compound comprising a conjugate with an exemplary constrained B7-H3 binding miniprotein. Percent of C309 (miniprotein of SEQ ID NO: 267) remaining (x-axis) was measured over time (y-axis, hours (h)) at 75° C. (solid line) and 90° C. (dotted line).

The thermal stability of exemplary compounds, C211, C234, C275, C294, and C309, was each analyzed at a concentration of 1 mg/mL at 75° C. in 0.1 μM ammonium acetate (pH 5.5). A heating plate was set to 75° C. and each sample was heated for a period of 0, 15, 30, 60, or 120 mins. The vial was shaken prior to collecting 10 μL aliquots at 5, 10, 15, 30, and 60 minute time intervals. The % parent remaining was analyzed by UPLC-MS (i.e., measured as loss of intact precursor by calculating area under the chromatographic peak) using the following system and method: Agilent 1290 UPLC system using a Waters 2.1×50 mm, CORTECS C18+, 1.6 μm, C18 column at 0.55 mL/min. The solvent system consisted of A=Water+0.1% FA, B=Acetonitrile+0.1% FA. The gradient consisted of 5% to 90% "B" over 1.75 minutes, then the column was washed and equilibrated to initial conditions. Loss of intact precursor was measured using a SCIEX Triple TOF mass spectrometer to calculate the area under the chromatographic peak. As shown in FIG. 14, C309 (SEQ ID NO: 267) was determined to remain stable for over 60 min at 75° C. Specifically, C309 had greater than 85% purity at 75° C. for at least one hour. As shown in FIG. 14 percent of C309 (miniprotein of SEQ ID NO: 267) remaining (x-axis) was measured as a function of time (y-axis, hours (h)) at 75° C. (solid line) and 90° C. (dotted line).

As compared to unconstrained sequences (e.g., as in Table 2A and shown for C211 in Table 7A), those with disulfide bonds (e.g., as in Table 2C and shown for C234, C275, C294, and C309 in Table 7A) were more thermally stable (see Table 7A), and exemplary compounds with two disulfide bridges (C234, C275, and C309) were stable at higher temperatures than an exemplary compound with one disulfide bridge (C294).

TABLE 7A

Thermal Stability of Exemplary B7-H3 Miniprotein Conjugates

| Compound NO: | SEQ ID NO: | Disulfides | Tm (° C.) |
|---|---|---|---|
| C211 | 183 | 0 | ~≥45 |
| C294 | 259 | 1 | ~≥60 |
| C234 | 204 | 2 | ~≥75 |
| C275 | 241 | 2 | ~≥75 |
| C309 | 267 | 2 | ~≥75 |

Example 14: Binding Characteristics of Exemplary Constrained B7-H3 Miniproteins This Example demonstrates certain binding characteristics of eleven exemplary constrained B7-H3 miniprotein conjugates, with two (C234/C298 (SEQ ID NO: 204/262)) or three (C608; SEQ ID NO: 544) constraints, as well as binding affinity and inhibition constants for various truncated, constrained B7-H3 miniprotein conjugates (see Table 7B).

Equilibrium binding affinity ($K_D$) was determined using SPR (as in Example 2) or a live cell binding assay (DELFIA) on MCF7 cells that express B7-H3. Binding inhibition constant ($K_i$) of miniprotein ligands was also determined using MCF7 cells expressing a B7-H3. Cells were dispensed into a 384-well plate and incubated at 37° C. in 5% $CO_2$ overnight. The next day cells were gently washed once in assay buffer prior to addition of europium chelated ligand.

To determine $K_D$, the exemplary conjugates, labeled with europium, and in the presence or absence of 100-fold excess unconjugated ligand, were incubated with cells over 12 different concentrations ranging from 100 times below to 100 times above expected $K_D$ values.

To determine $K_i$, a single concentration ($K_D$ equivalent concentration) of europium-chelate miniprotein was added to each well followed immediately by the addition of unconjugated competing ligand at up to 12 different concentrations ranging from 100 times below to 100 times above expected $K_i$ values. The plate was incubated for 1.5 h at room temperature to reach equilibrium. Cells were then washed to remove unbound ligand and treated according to manufacturer instructions for a DELFIA® (dissociation-enhanced lanthanide fluorescent immunoassay, Revvity Health Sciences). In brief, 2 M HCl was added to each well and incubated for 2 h at 37° C. Following this step, 2 M NaOH and fluorescent inducer solution were added to each well and incubated for 30 minutes at room temperature. Plates were read on an Envision plate reader and a curve-fitting model was applied to estimate $K_D$ and $K_i$ values.

Figure 15:
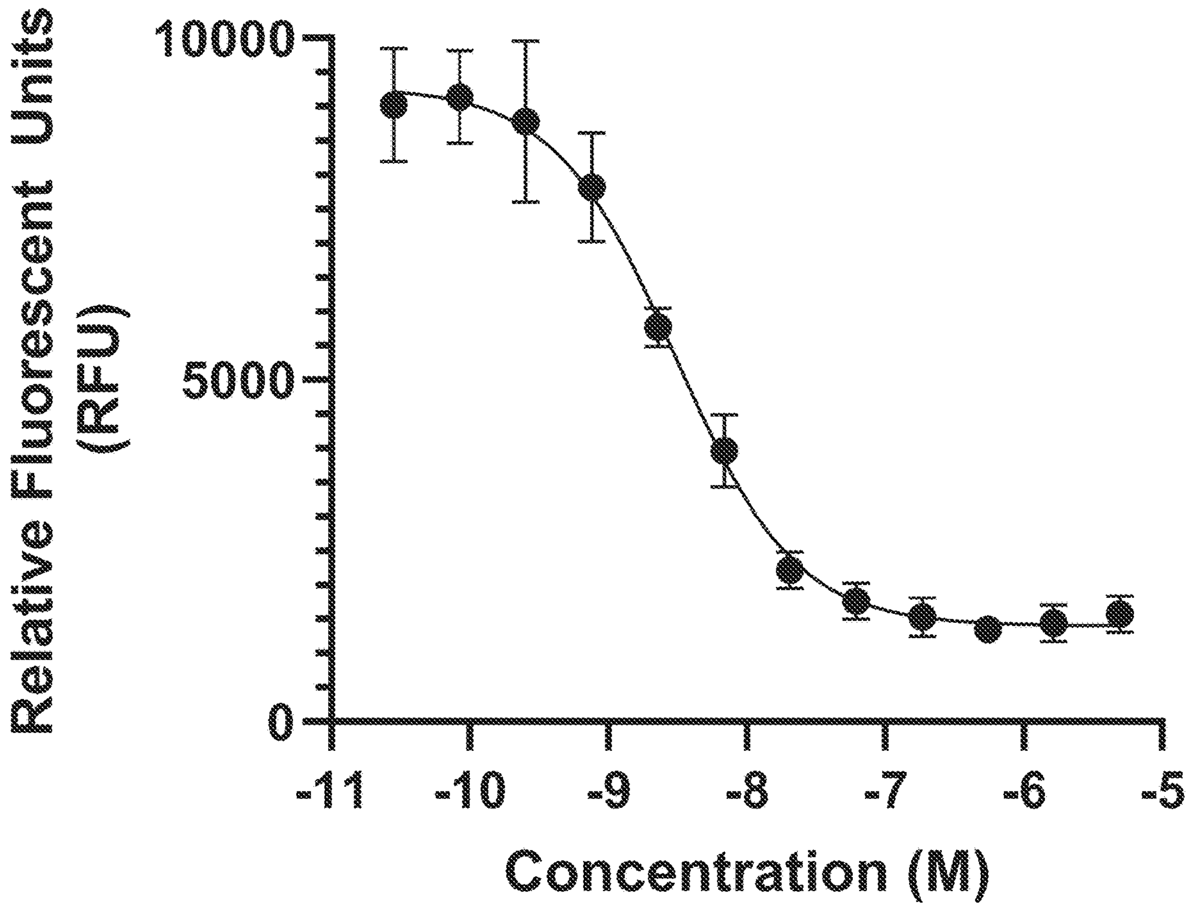
FIG. 15 is a graph showing on-cell binding as used to measure Ki for an exemplary constrained B7-H3 miniprotein conjugate (C234 with miniprotein of SEQ ID NO: 204).

FIG. 15 illustrates the on-cell binding for C234 (SEQ ID NO: 204, which is also C298 with SEQ ID NO: 262) in the competition assay where the Ki for this experiment was approximately 1.36 nM. Table 7B shows binding characteristics (KD by SPR and Ki) of C234, C300, C302, C304, C306, C308, C310, C312, C316, C318, and C609. These results show that constrained B7-H3-binding proteins bind to B7-H3 with strong affinity.

TABLE 7B

Binding Characteristics of Exemplary Truncated, Constrained B7-H3 Miniprotein Conjugates

| SEQ ID NO: of miniprotein | Compound | KD (nM), SPR | Ki ± SD (nM), DELFIA |
|---|---|---|---|
| 204 | C234 | 1.36 | 1.72 ± 0.99 |
| 263 | C300 | 0.506 | 1.91 ± 0.28 |
| 264 | C302 | 0.558 | 1.34 ± 0.073 |
| 265 | C304 | 1.43 | 2.24 ± 0.26 |
| 266 | C306 | 0.761 | 1.24 ± 0.27 |
| 267 | C308 | 0.482 | 0.872 ± 0.37 |
| 268 | C310 | 0.782 | 0.886 ± 0.16 |
| 269 | C312 | 0.485 | 1.01 ± 0.20 |
| 271 | C316 | 0.621 | 0.873 ± 0.41 |
| 272 | C318 | 1.24 | 1.24 ± 0.34 |
| 544 | C609 | not measured | 3.58 |

Example 15: Synthesis of B7-H3 Miniprotein-PEG4-Dota Conjugates

This Example describes synthesis of exemplary B7-H3 miniprotein-PEG4-DOTA conjugates as set forth in compounds C299, C301, C303, C305, C307, C309, C311, C313, C315, C317, and C319 (each as set forth in Table 2C), which can also be further labeled with radiolabels or cold-metal surrogates thereof.

Synthesis of Polypeptide and Conjugation of Chelator

Polypeptides were synthesized on a peptide synthesizer, such as a Chorus peptide synthesizer (Gyros Protein Technologies Inc., Tucson, AZ) by solid-phase methods using Fmoc strategy with N-[(dimethylamino)-1H-1,2,3-triazolo-[4,5-b]pyridin-1-ylmethylene]-N-methylmethanaminium hexafluorophosphate N-oxide (HATU) (0.4 M, 5-fold molar excess to amino acid) in N,N-dimethylformamide (DMF) as the activator, and N'N-diisopropylethylamine (DIEA), 0.8 M, was used as the base. A 20% piperidine/DMF solution was used for Fmoc deprotection. The resin was Fmoc-Lys (Boc)-Wang resin (AnaSpec) with loading of (0.30 mmol/g) or Rink Amide MBHA LL (Novabiochem) with loading of (0.30-0.40) mmol/g on a (20-40) μmol scale. Fmoc-protected amino acids were coupled sequentially, using 15- or 30-minute double-couple cycles, at ambient temperature. Upon completion of the synthesis, the n-terminal Fmoc-protecting group was removed using a 20% solution of Piperidine/DMF.

Metal-chelating motifs were covalently attached to polypeptide chains at the end of the linear SPPS. First, orthogonally protected linkers (e.g., amino-discrete polyethylene glycols, amino-hexanoic acids, and amino acids) were coupled to either the N-terminal amine or alternatively, the ε-amino side chain of a lysine. After an appropriate deprotection step (20% piperidine in dimethylformamide for Fmoc), metal chelators were coupled to the linker-polypeptide chain with conventional HATU activation in DMF containing 2% N,N-diisopropylethylamine (DIEA). Chelators such as tri-t-butyl-DOTA, bis-t-butyl-NOTA, tetra-t-butyl-DTPA, or CROWN were coupled to the linker also using HATU activation in DMF containing 2% N,N-diisopropylethylamine (DIEA). Finally, polypeptides were cleaved from solid support and acid-labile protecting groups were removed with a cocktail of TFA. Incorporation of the PEG4 linker was done using standard SPPS methods and Fmoc-(PEG4)-OH as the coupling partner to the free amine of the resin-bound peptide. Upon completion, the Fmoc-protecting group was removed, and the DOTA chelator was attached using standard SPPS methods mentioned above using (2-(4,7,10-Tris(2-(tert-butoxy)-2-oxoethyl)-1,4,7,10-tetraazacyclododecan-1-yl)acetic acid) as the coupling partner.

Final deprotection and cleavage of the peptide from the solid support was performed by treatment of the resin with 95% TFA, 2% thioanisole, 2% water and 1% triisopropylsilane for 2-3 h.

The cleaved peptide was precipitated using cold diethyl ether. The diethyl ether was decanted, and the solids were triturated with cold diethyl ether and pelleted by centrifugation to yield a white solid.

Disulfide bridge formation was accomplished via natural folding cyclization. The white solid was dissolved in 10-15 mL of (water:acetonitrile (1:1 with 0.1% TFA), and allowed to stir. The pH of the solution was adjusted to 7.5 using a 1 M solution of ammonium bicarbonate or ammonium hydroxide in water. Next, a 0.2 M solution of Disulfiram in acetonitrile was added to the solution and the mixture allowed to stir overnight at room temperature. A small sample was tested by HPLC/MS to confirm disulfide formation reaction completion. The pH of the reaction solution was adjusted to 4-5 using TFA, and filtered to give a clear, off-white solution. The solution was purified via a Gilson preparative HPLC system using the 30×250 Waters XBridge Protein BEH C4 OBD™ Prep 300 Å 5 μm column at 25° C. A gradient was used within the ranges of 10-50% acetonitrile/water with 0.1% TFA over 30-45 minutes at a flow rate of 30 mL/min, λ–215 nm. The appropriate fractions containing the desired product were combined and lyophilized to give a white solid, which was confirmed to be the desired product by HPLC/MS.

Formation of Metal Complex with Polypeptide

Peptides with covalently attached metal chelators were complexed with either their cold-metal surrogates (e.g., indium, lanthanum, gallium, copper, or europium) or radionuclides (e.g., 111-In or 225-Ac). Metalation reactions were carried out in aqueous buffers that were close to neutral pH. Peptides were dissolved in buffers comprised of 100 mM ammonium acetate, pH 5-6 with 2 molar equivalents of metal. Additional weakly coordinating formulants were also used to avoid oxidation of some metals. Metalation reactions were monitored by RP-HPLC under neutral mobile phases such as 100 mM triethylammonium acetate as a modifier. Ultra-violet signals were used to identify analytes and their shifting retention times were indicative of metalated peptides. Elevated temperatures of 60-70° C. were used, as appropriate, for efficient complexation. After the completion of the metal complexation, excess metal was separated from metalated peptide by semi-prep HPLC under neutral conditions. Mass spectroscopy was used to confirm the metalated peptide species. Radioactive species were characterized for radiochemical yield and purity with either radio-HPLC or radio-TLC.

Example 16: Radiolabeling of B7-H3-PEG4-DOTA with $In^{111}$ or $Ac^{225}$

This Example describes radiolabeling of exemplary B7-H3 miniprotein-PEG4-DOTA conjugates with In-111 or Ac-225.

Compounds C235, C299, C301, C303, C305, C307, C309, C311, C313, C315, C317, or C319 (each as set forth in Table 2C) were each labeled with In-111 (to generate compounds C320, C321, C322, C323, C324, C325, C326, C327, C328, C329, and C330, as set forth in Table 2C). In-111, in the form of [111In] indium chloride, was prepared from reconstitution of dried [111In] indium chloride residue in hydrochloric acid (40 mM), and added to a solution of DOTA containing miniprotein, prepared at 1 mg/mL in ultrapure water containing 0.2 M NH40Ac, 4 mg/mL Ascorbic Acid, and 0.1% Tween-20, pH 5.3-5.6, in a 1.5 mL Eppendorf vial and heated at 75° C. for 30 minutes. In-111 radiolabeled products were purified using a PD-Minitrap G25 column and eluted with Saline containing 0.1% Tween-20, 0.05 mg/mL DTPA, 2 mg/mL sodium ascorbate, and 4 mg/mL sodium acetate, pH 6-7. The radiochemical purity was determined as ratio of main product peak to other peaks. The radiochemical yield was determined as the ratio of final activity of the product over the starting activity used for the reaction adjusted for the radioactive decay.

Compounds C301 and C319 (as set forth in Table 2C) were each labeled with Ac-225 (to generate compounds C331 and C332, respectively, as set forth in Table 2C). Ac-225, in the form of [225Ac]actinium chloride, was prepared from reconstitution of dried [225Ac]actinium nitrate residue in nitric acid (50 mM), and added to a solution of DOTA containing miniprotein, prepared at 1 mg/mL in HEPES buffer, pH adjusted to pH 6.2-6.5 using ultrapure ammonium hydroxide, in a 1.5 mL Eppendorf vial and heated at 75° C. for 30 minutes. Ac-225 radiolabeled products were purified using a PD-10 column and eluted with saline containing 0.1% Tween-20, 0.05 mg/mL DTPA, 2 mg/mL sodium ascorbate, and 4 mg/mL sodium acetate, pH 6-7. The radiochemical purity was determined as ratio of main product peak to other peaks. The radiochemical yield was determined as the ratio of final activity of the product over the starting activity used for the reaction adjusted for the radioactive decay.

Example 17: Evaluating In Vitro Metabolic Stability of B7-H3 Miniprotein Conjugates This Example evaluates in vitro metabolic stability of exemplary constrained B7-H3 miniprotein conjugates.

Exemplary miniprotein conjugates were spiked into biological matrices at initial concentration between 1-2 μM. Tested matrices were varied by species (mouse, rat, human) and type (plasma, serum, and kidney brush border membrane preparations tested each from 0.625-100 μg/mL protein content). Tested conditions were incubated with TAs at 37° C. for 4 hours. At collection points of 0, 15, 30, 60, 120, 240 minutes, 50 μL of each condition were quenched by organic solvent (methanol or acetonitrile) or the addition of 4% phosphoric acid solution. Fractions of each quenched timepoint were subsequently assayed for parent TA concentration by high resolution LC-MS. Percent-parent-remaining-time plots were constructed from the ratio of each given time collection to the time-zero parent TA. Percent-parent-remaining in mouse serum and plasma for exemplary miniproteins are recorded in Table 8.

TABLE 8

In Vitro Stability of Exemplary B7-H3 Miniprotein Conjugates

| TA/Compound ID NO: | In vitro Stability (mouse) - KBBM | In vitro Stability (mouse) - Plasma |
|---|---|---|
| C192 | >12 | >12 |
| C235/C299 | >12 | >12 |
| C301 | >12 | >12 |
| C303 | >12 | >12 |
| C305 | >12 | >12 |
| C306 | >12 | >12 |
| C307 | >12 | >12 |
| C309 | >12 | >12 |
| C311 | >12 | >12 |
| C313 | >12 | >12 |
| C317 | not tested | >12 |
| C319 | >12 | >12 |
| C333 | >12 | 11.5 |
| C349 | >12 | >12 |
| C354 | >12 | >12 |
| C467 | >12 | >12 |
| C493 | >12 | >12 |

Example 18: Plasma Pharmacokinetic Analysis in Sprague Dawley Rats

This Example describes plasma pharmacokinetic analysis of compounds provided herein using plasma analysis in Sprague Dawley rats.

To begin, double jugular vein-cannulated Sprague Dawley rats were dosed with bolus intravenous injections of miniproteins (0.03-0.3 mg/kg) and FITC-sinistrin. Nine blood collection timepoints were taken between approximately zero and four hours, processed to plasma with $K_2$ EDTA, and were frozen for subsequent bioanalysis. Plasma miniprotein concentrations were measured by LC-MS/MS. All unknown sample measurements were interpolated against known authentic standards spiked into normal rat plasma to calculate concentration. Finally, non-compartmental analysis was performed to estimate plasma pharmacokinetic parameters.

Exemplary plasma terminal half-lives, steady-state volumes of distribution, and plasma clearances are reported in Table 9.

TABLE 9

Pharmacokinetic Analyses of Exemplary B7-H3 Miniprotein Conjugates

| TA/Compound ID NO: | Rat PK - CL (ml/min/kg) | Rat PK - t1/2 (min) | Rat PK - Vss_BW (mL/kg) |
|---|---|---|---|
| C320 | 6.0 | 79.2 | 275 |
| C321 | 2.4 | 102 | 262 |
| C322 | 2.0 | 84.0 | 184 |
| C323 | 5.1 | 53.6 | 288 |
| C324 | 5.4 | 42.4 | 240 |
| C325 | 5.2 | 57.1 | 322 |
| C326 | 5.2 | 53.6 | 298 |
| C327 | 6.1 | 49.0 | 278 |
| C329 | 4.5 | 57.0 | 287 |
| C369 | 3.6 | 54.1 | 218 |
| C468 | 3.2 | 51 | 189 |
| C494 | 2.6 | 47.9 | 136 |

Example 19: Biodistribution Analysis Involving Constrained $^{111}$In-Labeled Miniprotein Conjugates (In Vivo and Ex Vivo)

This Example describes in vivo and ex vivo biodistribution experiments using exemplary In-111-labeled linear (C1B, C131, and C165) and constrained (C229, C235, C276, C301, and C333) B7-H3 miniprotein conjugates alone and in combination with an exemplary decoy.

Animals: Female athymic nude mice (6-8 weeks of age) were purchased from Charles River Laboratories and house according to IACUC guidelines with ad libitum feeding. Tumor-bearing experiments used tumor xenograft models generated by inoculating mice subcutaneously with $3\times10^6$ NCI-H358 cells in 200 μL (50:50 PBS/Matrigel) in right flank. Tumors were monitored beginning 7 days after inoculation and measured by caliper to determine tumor volumes. Mice with tumor volumes between 150 $mm^3$ and 250 $mm^3$ were selected for study inclusion and randomized to treatment arms. An excess of 60% of required study mice were inoculated with tumor cells to ensure enough mice with appropriate tumor ranges were generated. Radiolabeling of miniprotein conjugates was performed similar to as described in Example 16.

Animal grouping and treatment: Animals were monitored for body weight bi-weekly and at the time of experimentation, grouped into groups of n=3. Animals were administered test-agents (TAs; B7-H3 miniprotein conjugates) that were prepared as described above. Animals received 0.185 MBq of activity (111-In) at approximately 2.3 MBq/nmol miniprotein.

Humane endpoints: All animals were euthanized following the final imaging time point and carcasses were discarded according to IACUC protocols.

Figure 16A:
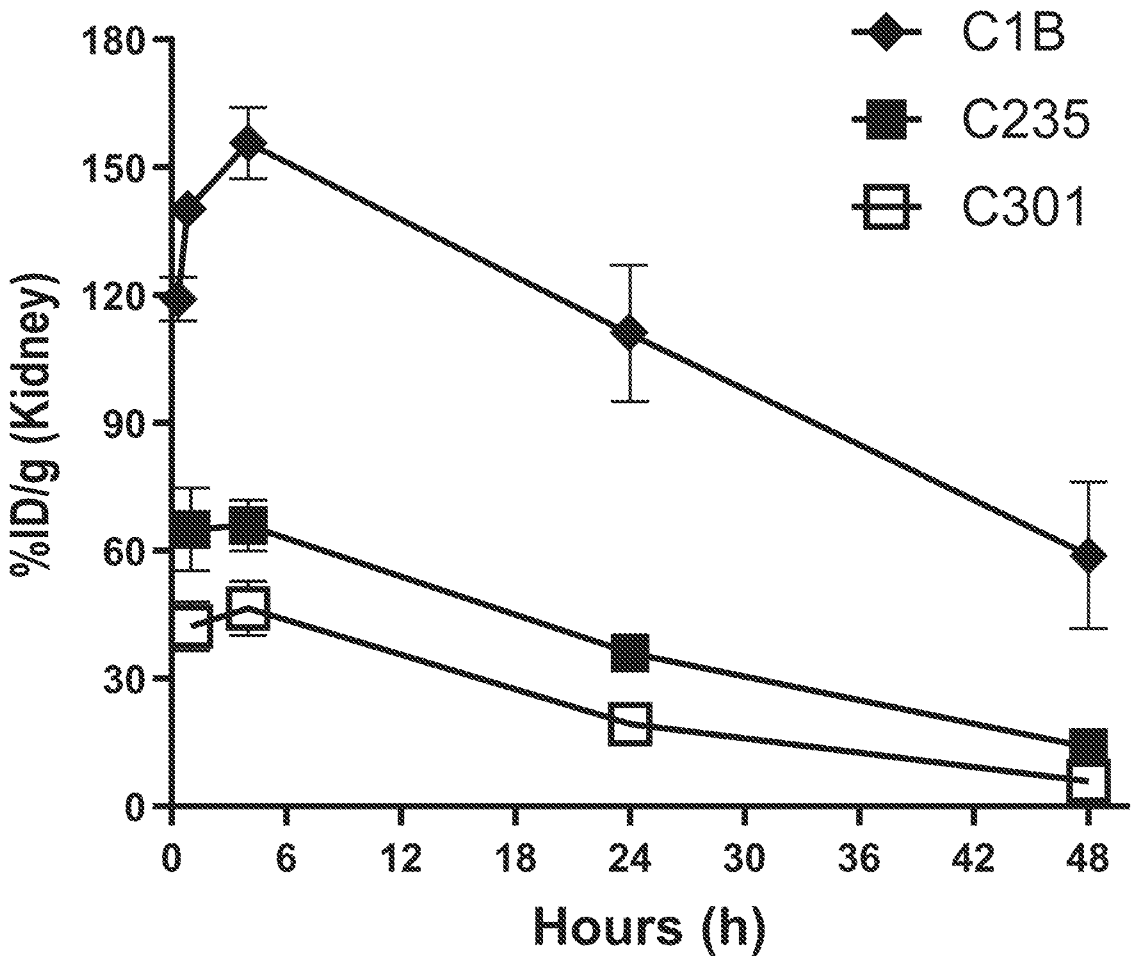
FIGS. 16A-16B are line graphs showing % ID/g of one of three miniprotein conjugates (C1B, C235, and C301) between 0-48 hours after administration.
Figure 16B:
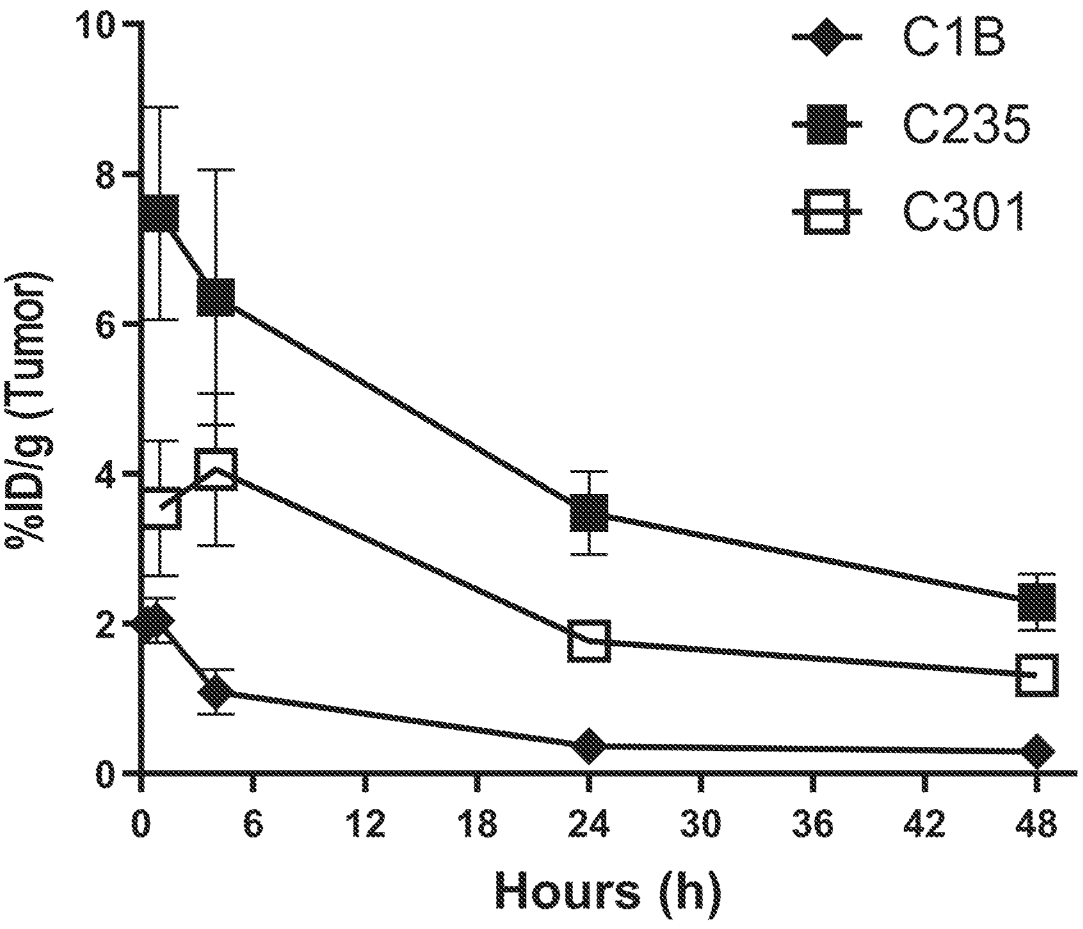

In vivo analysis of kidney and tumor uptake: Animal imaging and analysis was conducted similar to protocols and procedures set forth in Example 8. Time points analyzed were at approximately 1, 4, 24, and 48 hours. Compounds tested were C1B, C235, and C301, and C309, each labeled with 111-In. As shown in FIG. 16A, exemplary truncated and constrained B7-H3 miniprotein conjugates (C235 and C301) showed less than 75% ID/g at all times, decreasing to substantially less than 30% ID/g by 48 hours post administration. In contrast, an exemplary linear B7-H3 miniprotein conjugate (C1B) showed greater than 150% ID/g by 4 hours post administration, never decreased to below 60% ID/g by 48 hours. As shown in FIG. 16B, in tumor tissue, in addition to showing minimal kidney accumulation and/or retention, C235 and C301 also showed between about 4-8% ID/g in tumor tissue between 1 and 4 hours post administration, and remained between about 2-4% ID/g by 48 hours post-administration, whereas C1B had a maximal tumor tissue concentration of about 2% ID/g, dropping to almost nothing by 24 and 48 hours post administration.

Figure 17A:
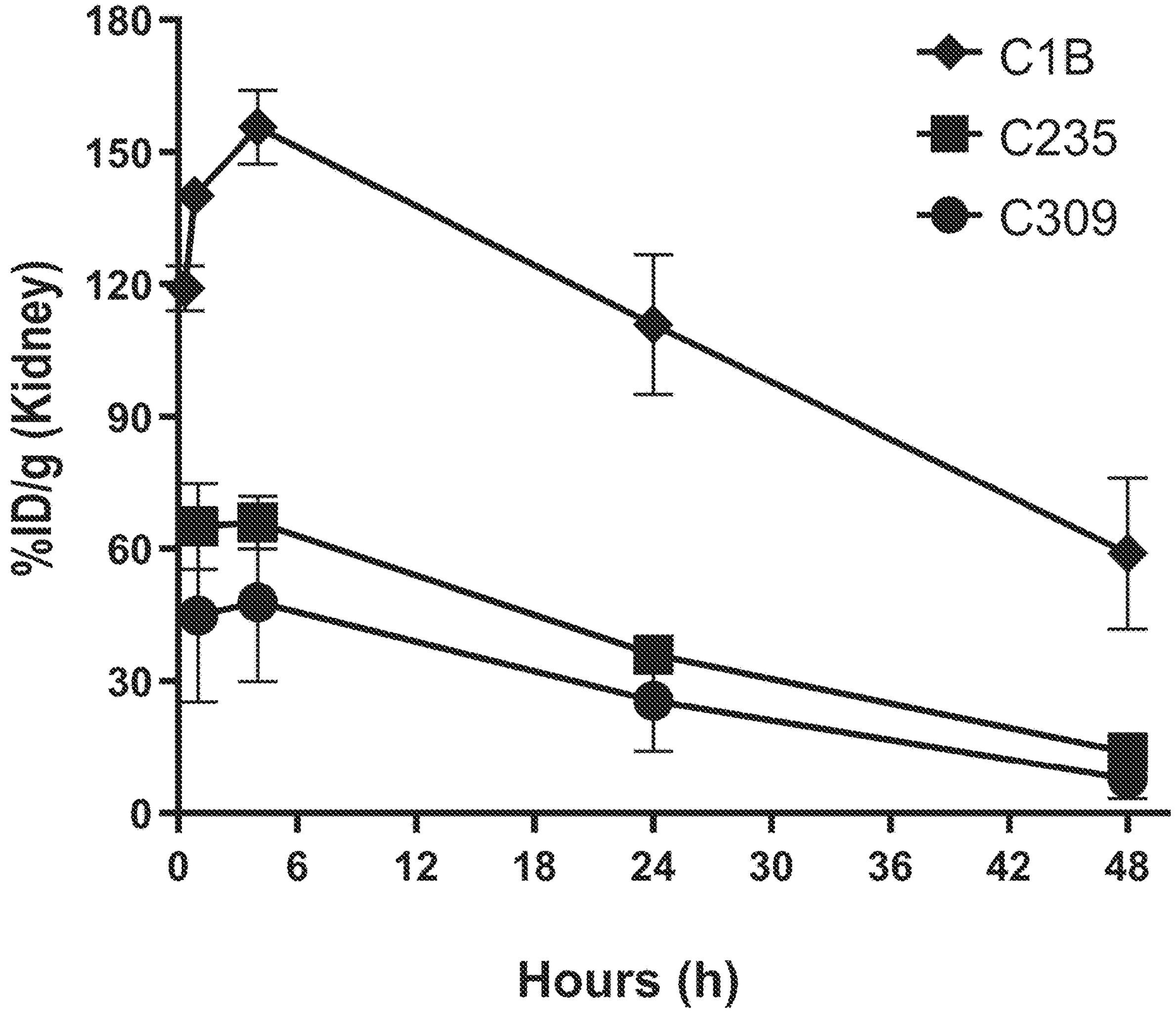
FIGS. 17A-17B are line graphs showing % ID/g of one of three miniprotein conjugates (C1B, C235, and C309) between 0-48 hours after administration.
Figure 17B:
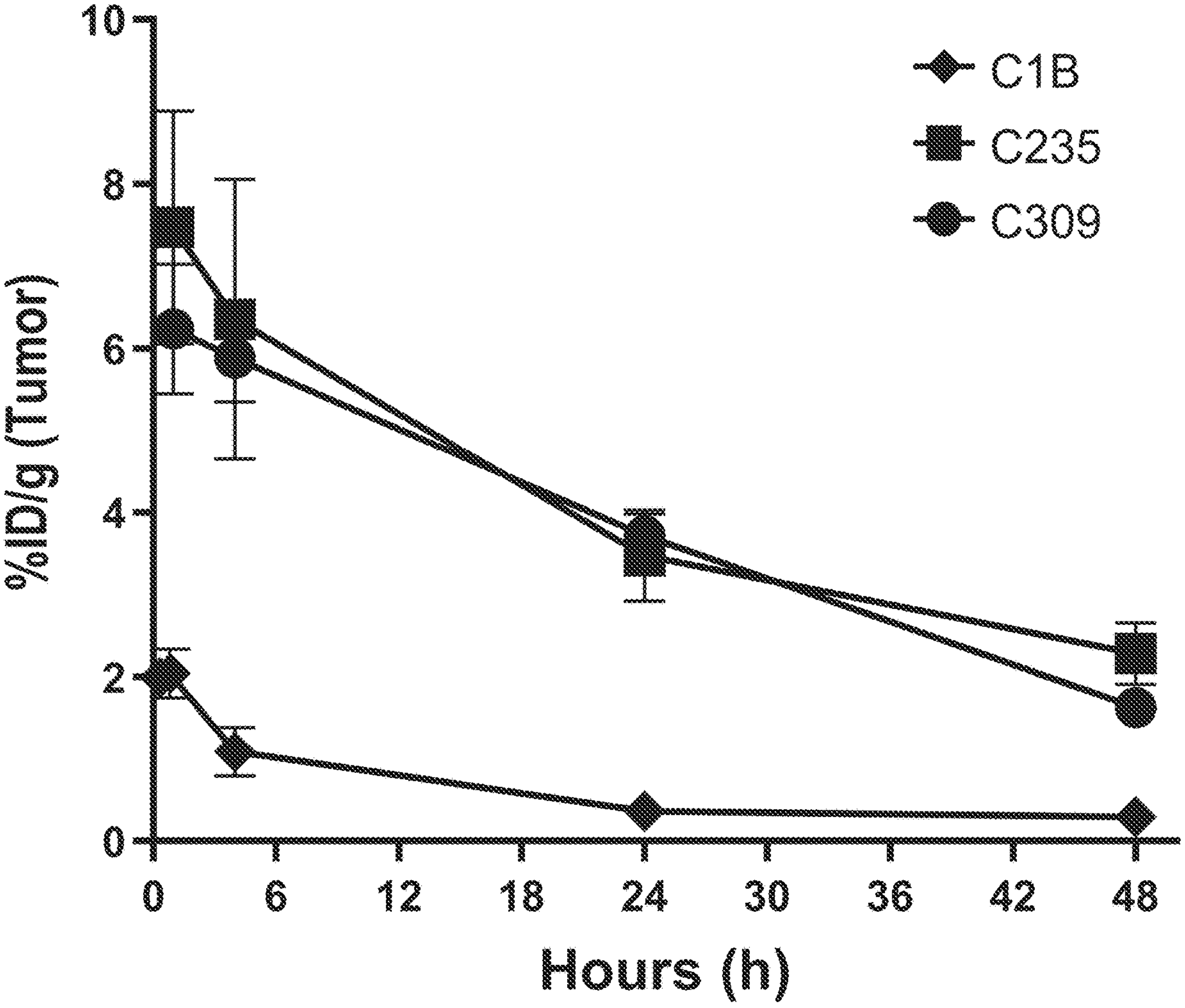

Similarly, as shown in FIG. 17A, exemplary truncated and constrained B7-H3 miniprotein conjugates (C235 and C309) showed less than 75% ID/g at all times, decreasing to substantially less than 30% ID/g by 48 hours post administration. In contrast, an exemplary linear B7-H3 miniprotein conjugate (C1B) showed greater than 150% ID/g by 4 hours post administration, never decreased to below 60% ID/g by 48 hours. As shown in FIG. 17B, in tumor tissue, in addition to showing minimal kidney accumulation and/or retention, C235 and C309 also showed between about 6-8% ID/g in tumor tissue between 1 and 4 hours post administration, and remained between about 4-5% ID/g by 24 hours and between about 2-3% ID/g by 48 hours post-administration, whereas C1B had a maximal tumor tissue concentration of about 2% ID/g, dropping to almost nothing by 24 and 48 hours post administration.

Overall, constrained B7-H3 miniprotein conjugates had substantially less uptake and/or retention in kidney tissue and substantially more uptake and retention in tumor tissue as compared to an exemplary linear B7-H3 miniprotein conjugate, supporting an improvement in tumor targeting and decrease in risk to uptake and retention in non-target tissue (e.g., kidney).

Figure 18A:
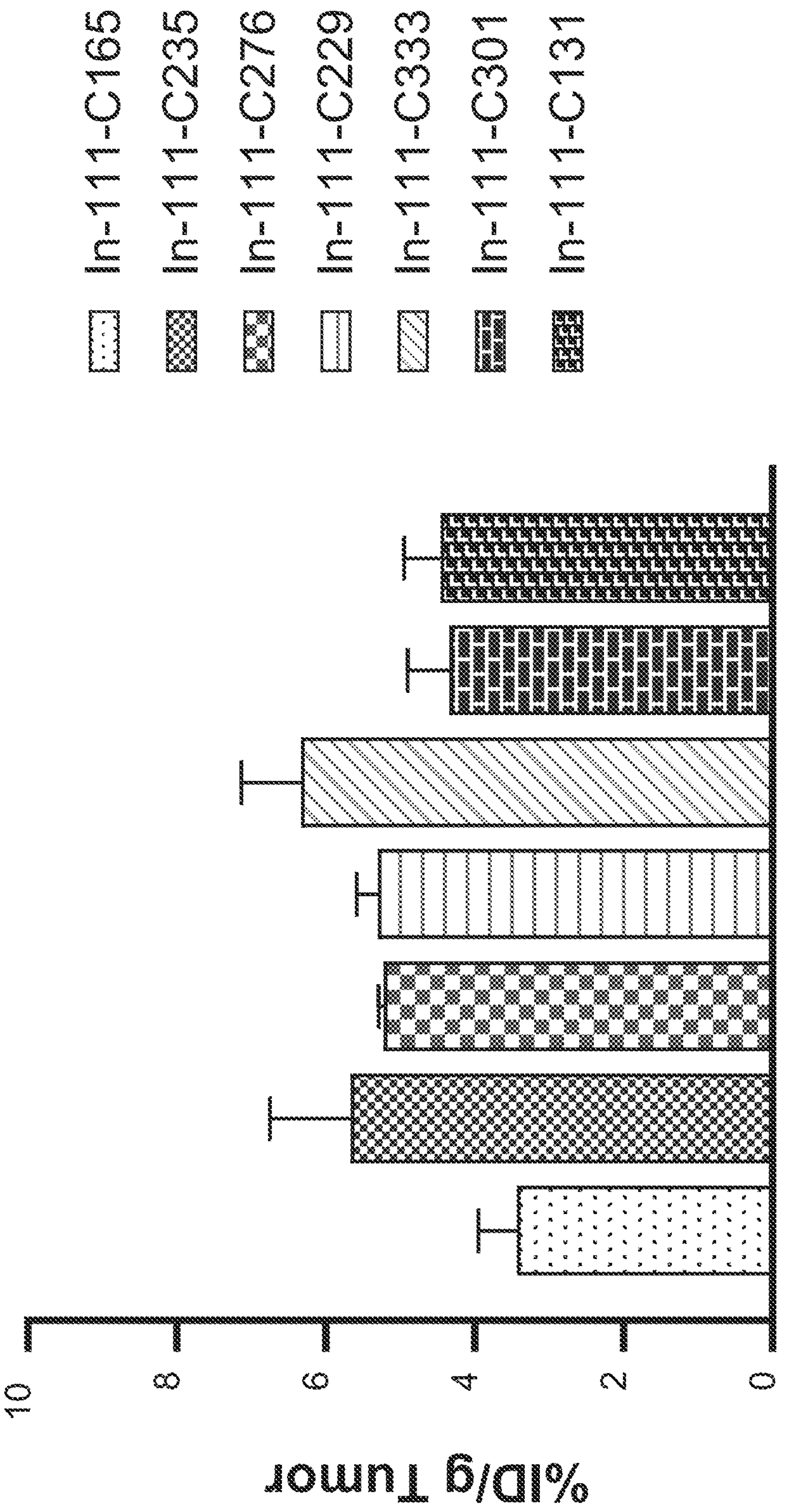
FIGS. 18A-18B are bar graphs showing % ID/g as measured 24 hours after administration of one of several exemplary 111-In labeled linear (C131 and C165) or constrained (C229, C235, C276, C301, and C333) B7-H3 miniprotein conjugates in tumor (FIG. 18A) and kidney (FIG. 18B), showing increased concentration in tumor and decreased concentration in kidney for exemplary constrained B7-H3 miniprotein conjugates as compared to exemplary linear B7-H3 miniprotein conjugates.
Figure 18B:
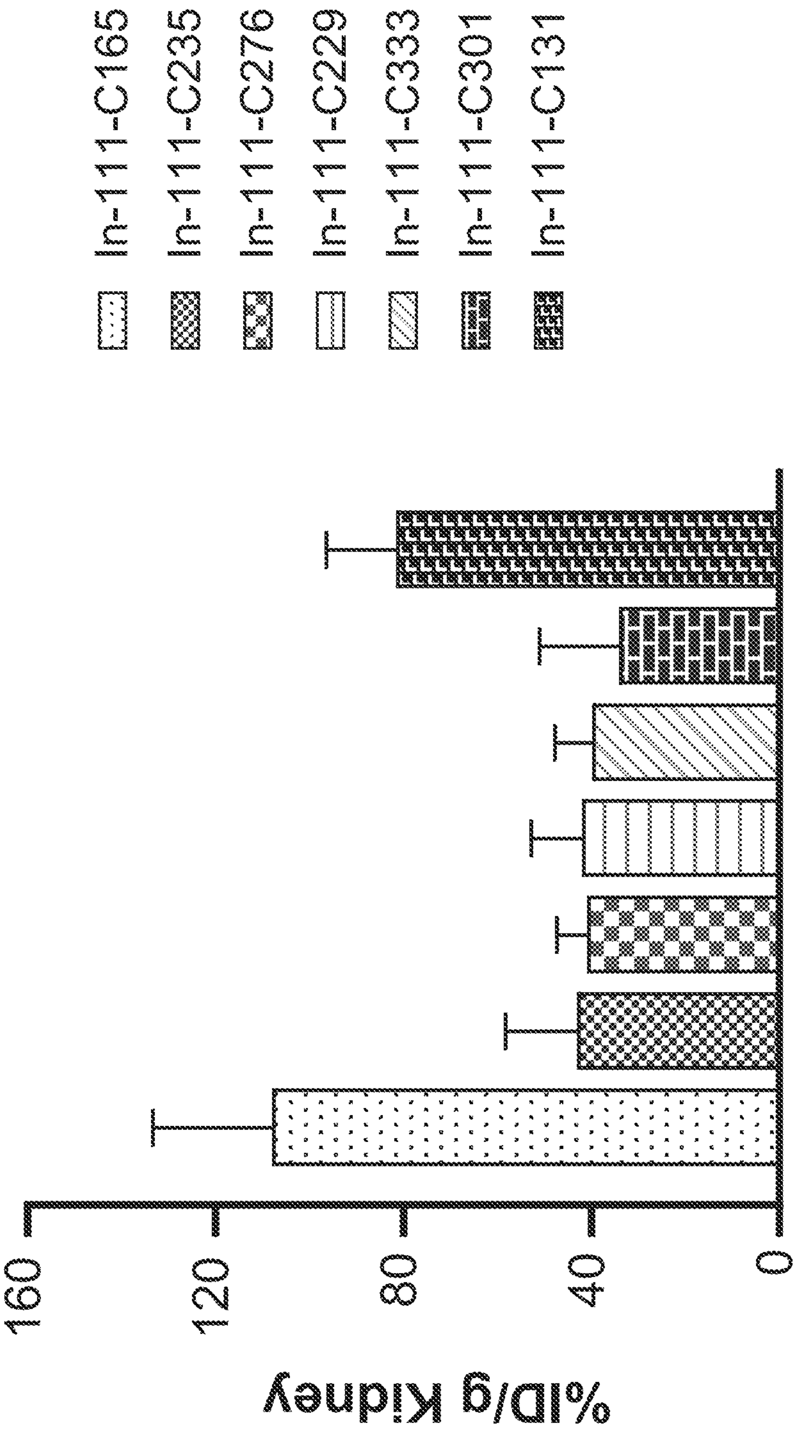

Tissue ex vivo analysis: 24 hours after treatment, animals were humanly euthanized (cervical dislocation) and necropsies performed. Tissues, organs, and blood were collected and transferred into pre-weighed polypropylene tubes. The tubes containing samples were re-weighed to determine sample weight and counted for 1 minute on Hidex automatic gamma counter. Percents of injected dose in each sample were calculated and normalized for sample weight. Tissues evaluated included kidneys, liver, muscle, spleen, and tumor. Amount of radiolabel detected was either negligible or absent in all tissues examined other than kidney and tumor (data not shown). As shown in measurements of % ID/g at 24 h, FIG. 18A (tumor) and FIG. 18B (kidney), C229, C235, C276, C301, and C333 (conjugates with constrained B7-H3 miniproteins) showed both increased concentration in tumor and decreased concentration in kidney relative to C131 and C165 (conjugates with linear B7-H3 miniproteins).

Example 20: In Vivo Evaluation of B7-H3 Miniprotein Conjugates in Mouse Xenografts This Example describes measuring the effect of exemplary radiolabeled B7-H3 miniprotein conjugates in treating xenografted tumors in mice.

Animals: Female athymic nude mice (6-8 weeks of age) were purchased from Charles River Laboratories and housed according to IACUC guidelines with ad libitum feeding. In vivo efficacy study experiments were performed in tumor bearing athymic nude mice. Tumor xenograft models were generated by inoculating mice subcutaneously with $3\times10^6$ NCI-H358 cells or $2.5\times10^6$ NCI-H1915 cells in 200 μL (50:50 PBS/Matrigel) in right flank. H358 cells express higher levels of B7-H3 as compared to H1915 cells, which express B7-H3, but not as highly as H358. Tumors were monitored beginning 7 days after inoculation and measured by caliper to determine tumor volumes. Mice with tumor volumes between 150 $mm^3$ and 250 $mm^3$ were selected for study inclusion and randomized to treatment arms. An excess of 60% of required study mice were inoculated with tumor cells to ensure enough mice with appropriate tumor ranges were generated.

Radiolabeling of miniprotein conjugates was performed similar to as described in Example 16.

Animal grouping and Treatment: One day prior to treatment, $^{225}Ac$-labeled test articles were prepared as described above at a specific activity of approximately 1 μCi/μg (equivalent to ~37 kBq), with activity measurements made at secular equilibrium on a dose calibrator. On the day of treatment, dose measurements for a sample injected dose were measured and confirmed on a gamma counter and corrected for decay. Indicated doses of vehicle or radiolabeled test article were prepared corresponding to the indicated administered dose levels per group. Doses were administered via tail vein injection while the mice were restrained and awake. Syringes with prepared doses were weighed pre and post injection and the weights were recorded.

Animal monitoring: Tumor volume, measured by calipers, and body weight measurements for enrolled mice were performed twice a week for an initial planned monitoring period of 8 weeks. More frequent gross observations of mice were performed as needed.

Humane endpoints: Mice remained on the study until they reached the end of the 8-week monitoring period or a number of pre-defined humane endpoints, including:

1. An increase in tumor size ≥1.5 g, tumor burden ≥10% of body weight, or the tumor becomes ulcerated or necrotic.
2. A decrease in body weight ≥20% from recorded weight at study inclusion.
3. Any signs of pain or distress (i.e., consistent hunched posture, rough coat, squinted eyes, slowed gait).
4. Tumors that compromise mobility or ability to eat or drink.

As described in the experiment summarized in Table 10, there were three study arms per each of H358 and H1915 tumor cell types, varying in treatment and dose as follows: Group 1 received a vehicle, or control, as treatment. Group 2 and Group 3 received C332 (also identified as $^{225}$Ac—C309 in Table 2C; miniprotein of SEQ ID DO: 267). All groups received a total of one dose. Group 3 received twice the level of the dose as Group 2.

TABLE 10

Study Arms (H358 and H1915 with C332)

| Group | Treatment | Dose (nCi/kBg) | Route | Schedule |
|---|---|---|---|---|
| 1 (n = 8) | Vehicle | n/a | IV | Single Dose |
| 2 (n = 8) | $^{225}$Ac-C309 | 500/18.5 | IV | Single Dose |
| 3 (n = 8) | $^{225}$Ac-C309 | 1,000/37 | IV | Single Dose |

Analysis was performed as described in Example 8. Tumor volume over the first 17 days (H1915) or 42 days (H358) was monitored and measured. As shown in FIG. 19A (H1915 cells, showing days on the x-axis and tumor volume on the y-axis) and FIG. 19C (H358 cells, with days on the x-axis and tumor volume on the y-axis), tumor volume in Group 1 (vehicle) increased more than the tumor volume in Group 2 (C332, which is also $^{225}$Ac—C309; 18.5 kBq/500 nCi) and Group 3 (C332, which is also $^{225}$Ac—C309; 37 kBq/1000 nCi). Additionally, body weight was generally maintained over time in all three groups across both cell lines over the observed time period (FIG. 19B shows body-weights corresponding to FIG. 19A and FIG. 19D shows bodyweights corresponding to FIG. 19C).

In another experiment, a similar treatment plan was followed, but using only H358 cells and C331 (which is also $^{225}$Ac—C301) to treat Group 2 and Group 3, as summarized in Table 11.

TABLE 11

Study Arms (H351 with C331)

| Group | Treatment | Dose (nCi/kBg) | Route | Schedule |
|---|---|---|---|---|
| 1 (n = 8) | Vehicle | n/a | IV | Single Dose |
| 2 (n = 8) | $^{225}$Ac-C301 | 500/18.5 | IV | Single Dose |
| 3 (n = 8) | $^{225}$Ac-C301 | 1,000/37 | IV | Single Dose |

Tumor volume over the first 42 days is shown in FIG. 20A. Over time, the tumor volume in Group 1 (vehicle) increased more than the tumor volume in Group 2 (C331, which is also $^{225}$Ac—C301; 18.5 kBq/500 nCi) and Group 3 (C331, which is also $^{225}$Ac—C301; 37 kBq/1000 nCi). Additionally, as shown in FIG. 20B, body weight was generally maintained over time in all three groups over the observed time period.

These studies demonstrate reduction in tumor growth in groups treated with B7-H3 miniprotein conjugates over time as compared to vehicles. In addition, they demonstrate tumor growth inhibition as a function of B7-H3 expression, with greater inhibition in tumors grown from cells that express higher levels of B7-H3.

Example 21: Binding Characteristics and Proximal Tubule Epithelial Cell Uptake Assay of B7-H3 Miniprotein Conjugates with Modified Amino Acids This Example demonstrates impact of addition of a non-natural/modified (e.g., methylated) amino acid at an amino acid position corresponding to X24 of SEQ ID NO: 241. Both inhibition constant and OK cell uptake of exemplary engineered B7-H3 miniproteins were measured and mini-proteins with either a lysine, glutamine, valine, or leucine at a position corresponding to X24 of SEQ ID NO: 241 were compared to those having a homo-leucine or a modified lysine (di or trimethyllysine). Inhibition constant (Ki) of each conjugate was measured using DELFIA as described herein. Percent uptake of exemplary B7-H3-targeting mini-proteins and compounds with and without modified amino acids at a position corresponding to X24 were compared using opossum kidney proximal tubule cells as described in, e.g., Example 5 and measured relative to a control, C4 (SEQ ID NO: 4). Percent uptake of the control miniprotein in the presence of exemplary B7-H3-targeting miniproteins is provided in Table 12. Percent uptake of C290 (SEQ ID NO: 255), C291 (SEQ ID NO: 256), and C286 (SEQ ID NO: 251), which each have unmodified amino acids (Q, V, and L, respectively), and C284 (SEQ ID NO: 249), which has an unmodified lysine (K) at amino acid position 24 (along the length of the miniprotein sequence, SEQ ID NO: 241) were each substantially higher in those miniproteins and compounds without a methylated lysine at the corresponding position than C275 (SEQ ID NO: 241).

Furthermore, an exemplary miniprotein conjugate comprising a homo-leucine at an amino acid position corresponding to X24 of SEQ ID NO: 241 or X28 of SEQ ID NO: 213 showed substantially increased kidney uptake relative to C4 (SEQ ID NO: 4) as compared to miniprotein conjugates having a methylated lysine at the same position. That is, when compared to C245 (SEQ ID NO: 213), a miniprotein having a homo-leucine at a position corresponding to X28 of SEQ ID NO: 213, miniproteins with a Kme2 (C253, SEQ ID NO: 222) or Kme3 (C255, SEQ ID NO: 222) showed substantially reduced uptake on an OK cell assay relative to uptake of C4.

Overall, miniproteins having a modified lysine (modified with at least one small alkyl group such as a dimethyl) had (i) strong binding to B7-H3 (as determine by Ki measured by DELFIA); and (ii) substantially reduced kidney uptake as compared to compounds without an unmodified lysine at a position corresponding to X24 of SEQ ID NO: 241 or X28 of SEQ ID NO: 213. These data demonstrate that modification of lysine residues (e.g., by addition of one or more small alkyl groups) at position 24 decreases uptake of B7-H3-targeting miniproteins by kidney cells as compared to B7-H3 targeting miniproteins without a modified lysine residue at a position corresponding to X24 of SEQ ID NO: 241.

TABLE 12

| Ki and Percent Uptake Data for Exemplary B7-H3-targeting Miniproteins | | | | |
|---|---|---|---|---|
| Compound No. | SEQ ID NO: of miniprotein | Amino Acid corresponding to X24 | Ki (nM), DELFIA | % Uptake of C4 |
| C290 | 255 | Q | 13.8 | 17 |
| C291 | 256 | V | 7.7 | 30 |
| C286 | 251 | L | 23.9 | 26 |
| C284 | 249 | K | 2.02 | 56.6 |
| C275 | 241 | Kme2 | 1.42 | 3 |
| C245 | 213 | Homo-leucine | 2.8 | 95 |
| C253 | 220 | Kme2 | 5.36 | 18 |
| C255 | 222 | Kme3 | 8.75 | 13 |

Example 22: In Vitro Reduction of Exemplary Truncated & Constrained Miniprotein Compounds by Exemplary Scaffold a Decoys in OK-PTC Cells This Example describes reduction of uptake of exemplary truncated and constrained B7-H3 miniprotein conjugates (C272, C308, C234, C394, C250, and C228) when combined with exemplary scaffold A decoys (C118, C119 and C120) as compared to no decoy. Uptake of compounds was evaluated in opossum kidney proximal tubule cells (as described in Example 5). Here, cells were treated with a compound in the presence or absence of a 20-fold molar excess of exemplary scaffold A decoys, C118, C119, and C120. Results depicting uptake of six exemplary B7-H3-targeting compounds, C272, C308, C234, C394, C250, and C228, in OK-PTC cells in the presence and absence of exemplary decoys C118, C119, and C120 (scaffold A decoys) are shown in Table 13. The B7-H3-targeting compounds were used at 20 μM and the decoys used at a 20-fold (with C272, C308, C234, C394, and C250) and 10-fold (with C228) molar excess. Table 13 shows percent uptake suppression of exemplary B7-H3-targeting miniproteins (C272, C308, C234, C394, C250, and C228) at 20 μM concentration with a 20-fold (with C272, C308, C234, C394, and C250) and 10-fold (with C228) molar excess of exemplary scaffold A decoys (C118, C119, and C120). These results show that scaffold A decoys can effectively decoy truncated and constrained B7-H3 targeting miniproteins.

TABLE 13

| Uptake Assay of Exemplary Truncated, Constrained B7-H3 Miniprotein Conjugates in Presence of Scaffold A Decoys | | | | |
|---|---|---|---|---|
| Compound ID | | % Uptake reduction in the presence of a decoy | | |
| Biotin | DOTA | C118 | C119 | C120 |
| C272 | C301 | 95.6 | 98.8 | 97.5 |
| C308 | C309 | 107.9 | 108.6 | 104.5 |
| C234 | C235 | 86.4 | 96.2 | 96.9 |
| C394 | C611 | 90.1 | 97.5 | Not tested |
| C250 | C251 | 90.2 | 97.4 | Not tested |
| C228 | C229 | 93.7 | 94.6 | Not tested |

Example 23: Evaluation of Off-Target Binding of Exemplary B7-H3-Targeting Miniproteins This Example describes the evaluation of off-target binding of eight exemplary B7-H3-binding miniproteins relative to other human proteins.

To evaluate potential off-target binding, eight biotin-labeled molecules were tested in a cell microarray platform (Charles River Lab, Retrogenix Assay) having >6,500 different human proteins spanning diverse functions and subcellular locations. All exemplary miniproteins evaluated (C298, C300, C302, C304, C306, C308, C310, and C312) were found to have low-background binding to untransfected HEK293 cells and were deemed suitable for this assay.

Initially, two pools of molecules were tested. Pool #1 consisted of C298, C300, C302, C304, and pool #2 consisted of C306, C308, C310, and C312 at 2 μg/mL for each molecule. To perform this assay, HEK293 cells were plated on a dish and localized spots of cells were transiently over-expressed with a cDNA encoding for one of the >6,500 targets. Included in this library were two isoforms of CD276 (B7-H3) and B7-H3 related proteins (B7-1, B7-2, B7-H1/PD-L1, and B7-H2). The molecule pools were incubated on the fixed, over-expressing cell microarrays (n=2 per protein), and binding was visualized using Alexa Fluor 647 streptavidin fluorescence. All transfection efficiencies exceeded minimum thresholds for the microarray expression targets. Preliminary interactions identified from pooled results were re-spotted in duplicates, and each of the eight compounds were tested individually (n=2) at 2 μg/mL and/or in dose response against these targets as described above to validate the interactions.

All positive control interactions were strong and passed quality control. Specific interactions observed (median SNR≥1) confirmed on-target B7-H3 binding in two different isoforms for each of the eight test molecules. These interactions with the primary target occurred after fixation and in live cells (absence of fixation). No significant additional interactions were confirmed for any test molecules outside of B7-H3, indicating high specificity for the primary target (data not shown).

INCORPORATION BY REFERENCE

All publications and patents cited throughout the text of this specification (including all patents, patent applications, scientific publications, manufacturer's specifications, instructions, etc.), whether supra or infra, are hereby incorporated by reference in their entirety for all purposes. To the extent the material incorporated by reference contradicts or is inconsistent with this specification, the specification will supersede any such material.

EQUIVALENTS

The disclosure may be embodied in other specific forms without departing from the spirit or essential characteristics thereof. The foregoing embodiments are therefore to be considered in all respects illustrative rather than limiting the disclosure described herein. Scope of the disclosure is thus indicated by the appended claims rather than by the foregoing description, and all changes that come within the meaning and range of equivalency of the claims are intended to be embraced therein.

SEQUENCE LISTING

```
Sequence total quantity: 555
SEQ ID NO: 1            moltype = AA  length = 534
FEATURE                 Location/Qualifiers
source                  1..534
                        mol_type = protein
                        organism = Homo sapiens
SEQUENCE: 1
MLRRRGSPGM GVHVGAALGA LWFCLTGALE VQVPEDPVVA LVGTDATLCC SFSPEPGFSL  60
AQLNLIWQLT DTKQLVHSFA EGQDQGSAYA NRTALFPDLL AQGNASLRLQ RVRVADEGSF  120
TCFVSIRDFG SAAVSLQVAA PYSKPSMTLE PNKDLRPGDT VTITCSSYQG YPEAEVFWQD  180
GQGVPLTGNV TTSQMANEQG LFDVHSILRV VLGANGTYSC LVRNPVLQQD AHSSVTITPQ  240
RSPTGAVEVQ VPEDPVVALV GTDATLRCSF SPEPGFSLAQ LNLIWQLTDT KQLVHSFTEG  300
RDQGSAYANR TALFPDLLAQ GNASLRLQRV RVADEGSFTC FVSIRDFGSA AVSLQVAAPY  360
SKPSMTLEPN KDLRPGDTVT ITCSSYRGYP EAEVFWQDGQ GVPLTGNVTT SQMANEQGLF  420
DVHSVLRVVL GANGTYSCLV RNPVLQQDAH GSVTITGQPM TFPPEALWVT VGLSVCLIAL  480
LVALAFVCWR KIKQSCEEEN AGAEDQDGEG EGSKTALQPL KHSDSKEDDG QEIA        534

SEQ ID NO: 2            moltype = AA  length = 316
FEATURE                 Location/Qualifiers
source                  1..316
                        mol_type = protein
                        organism = Mus musculus
SEQUENCE: 2
MLRGWGGPSV GVCVRTALGV LCLCLTGAVE VQVSEDPVVA LVDTDATLRC SFSPEPGFSL  60
AQLNLIWQLT DTKQLVHSFT EGRDQGSAYS NRTALFPDLL VQGNASLRLQ RVRVTDEGSY  120
TCFVSIQDFD SAAVSLQVAA PYSKPSMTLE PNKDLRPGNM VTITCSSYQG YPEAEVFWKD  180
GQGVPLTGNV TTSQMANERG LFDVHSVLRV VLGANGTYSC LVRNPVLQQD AHGSVTITGQ  240
PLTFPPEALW VTVGLSVCLV VLLVALAFVC WRKIKQSCEE ENAGAEDQDG DGEGSKTALR  300
PLKPSENKED DGQEIA                                                 316

SEQ ID NO: 3            moltype = AA  length = 58
FEATURE                 Location/Qualifiers
source                  1..58
                        mol_type = protein
                        organism = synthetic construct
SEQUENCE: 3
AEAKYAKEKI AALSEIIWLP NLTHGQIMAF IAALNDDPSQ SSELLSEAKK LNDSQAPK    58

SEQ ID NO: 4            moltype = AA  length = 58
FEATURE                 Location/Qualifiers
source                  1..58
                        mol_type = protein
                        organism = synthetic construct
SITE                    28
                        note = Norleucine
SEQUENCE: 4
AEAKYAKEKI AALSEIIWLP NLTHGQIXAF IAALNDDPSQ SSELLSEAKK LNDSQAPK    58

SEQ ID NO: 5            moltype = AA  length = 58
FEATURE                 Location/Qualifiers
source                  1..58
                        mol_type = protein
                        organism = synthetic construct
SEQUENCE: 5
AEAKYDKEKI AALSEIIWLP NLTHGQIMAF IAALNNDPSQ SSELLSEAKK LNDSQAPK    58

SEQ ID NO: 6            moltype = AA  length = 53
FEATURE                 Location/Qualifiers
source                  1..53
                        mol_type = protein
                        organism = synthetic construct
SITE                    24
                        note = homo-leucine
SEQUENCE: 6
YAKEKIAALS EIIWLPNLTY AQIXAFIAAL NDDPSQSSEL LSEAKELNDS QAP         53

SEQ ID NO: 7            moltype = AA  length = 58
FEATURE                 Location/Qualifiers
source                  1..58
                        mol_type = protein
                        organism = synthetic construct
SITE                    18
                        note = 3-(1-naphthyl)-L-alanine
SEQUENCE: 7
AEAKYAKEKI AALSEIIXLP NLTHGQIMAF IAALNDDPSQ SSELLSEAKK LNDSQAPK    58

SEQ ID NO: 8            moltype = AA  length = 53
FEATURE                 Location/Qualifiers
```

-continued

```
source                  1..53
                        mol_type = protein
                        organism = synthetic construct
SITE                    24
                        note = homo-leucine
SEQUENCE: 8
YAKEKIAALS EIIWLPNLTH GQIXAFIAAL NDDPSQSSEL LSEAKKLNDS QAP         53

SEQ ID NO: 9            moltype = AA  length = 58
FEATURE                 Location/Qualifiers
source                  1..58
                        mol_type = protein
                        organism = synthetic construct
SITE                    4
                        note = acetylated lysine
SITE                    7
                        note = acetylated lysine
SITE                    9
                        note = acetylated lysine
SITE                    28
                        note = homo-leucine
SITE                    49
                        note = acetylated lysine
SITE                    50
                        note = acetylated lysine
SITE                    58
                        note = acetylated lysine
SEQUENCE: 9
AEAXYAXEXI AALSEIIWLP NLTHGQIXAF IAALNDDPSQ SSELLSEAXX LNDSQAPX    58

SEQ ID NO: 10           moltype = AA  length = 58
FEATURE                 Location/Qualifiers
source                  1..58
                        mol_type = protein
                        organism = synthetic construct
SITE                    4
                        note = acetylated lysine
SITE                    28
                        note = homo-leucine
SITE                    58
                        note = acetylated lysine
SEQUENCE: 10
AEAXYAKEKI AALSEIIWLP NLTHGQIXAF IAALNDDPSQ SSELLSEAKK LNDSQAPX    58

SEQ ID NO: 11           moltype = AA  length = 58
FEATURE                 Location/Qualifiers
source                  1..58
                        mol_type = protein
                        organism = synthetic construct
SITE                    4
                        note = acetylated lysine
SITE                    7
                        note = acetylated lysine
SITE                    9
                        note = acetylated lysine
SITE                    28
                        note = homo-leucine
SITE                    58
                        note = acetylated lysine
SEQUENCE: 11
AEAXYAXEXI AALSEIIWLP NLTHGQIXAF IAALNDDPSQ SSELLSEAKK LNDSQAPX    58

SEQ ID NO: 12           moltype = AA  length = 59
FEATURE                 Location/Qualifiers
source                  1..59
                        mol_type = protein
                        organism = synthetic construct
SITE                    28
                        note = homo-leucine
SITE                    29
                        note = homo-leucine
SEQUENCE: 12
AEAKYAKEKI AALSEIIWLP NDTYAQIXXA FIAALNDDPS QSSELLSEAK KLNDSQAPK   59

SEQ ID NO: 13           moltype = AA  length = 58
FEATURE                 Location/Qualifiers
source                  1..58
                        mol_type = protein
                        organism = synthetic construct
```

```
SITE                    28
                        note = homo-leucine
SEQUENCE: 13
AEAKYAKEKI AALSEIIWLP NATYAQIXAF IAALNDDPSQ SSELLSEAKK LNDSQAPK    58

SEQ ID NO: 14           moltype = AA  length = 58
FEATURE                 Location/Qualifiers
source                  1..58
                        mol_type = protein
                        organism = synthetic construct
SITE                    28
                        note = homo-leucine
SEQUENCE: 14
AEAKYAKEKI AALSEIIWLP NFTYAQIXAF IAALNDDPSQ SSELLSEAKK LNDSQAPK    58

SEQ ID NO: 15           moltype = AA  length = 58
FEATURE                 Location/Qualifiers
source                  1..58
                        mol_type = protein
                        organism = synthetic construct
SITE                    28
                        note = homo-leucine
SEQUENCE: 15
AEAKYAKEKI AALSEIIWLP NNTYAQIXAF IAALNDDPSQ SSELLSEAKK LNDSQAPK    58

SEQ ID NO: 16           moltype = AA  length = 58
FEATURE                 Location/Qualifiers
source                  1..58
                        mol_type = protein
                        organism = synthetic construct
SITE                    28
                        note = homo-leucine
SEQUENCE: 16
AEAKYAKEKI AALSEIIWLP NYTYAQIXAF IAALNDDPSQ SSELLSEAKK LNDSQAPK    58

SEQ ID NO: 17           moltype = AA  length = 58
FEATURE                 Location/Qualifiers
source                  1..58
                        mol_type = protein
                        organism = synthetic construct
SITE                    28
                        note = homo-leucine
SEQUENCE: 17
AEAKYAKEKI AALSEIIWLP NITYAQIXAF IAALNDDPSQ SSELLSEAKK LNDSQAPK    58

SEQ ID NO: 18           moltype = AA  length = 58
FEATURE                 Location/Qualifiers
source                  1..58
                        mol_type = protein
                        organism = synthetic construct
SITE                    28
                        note = homo-leucine
SEQUENCE: 18
AEAKYAKEKI AALSEIIWLP NTTYAQIXAF IAALNDDPSQ SSELLSEAKK LNDSQAPK    58

SEQ ID NO: 19           moltype = AA  length = 58
FEATURE                 Location/Qualifiers
source                  1..58
                        mol_type = protein
                        organism = synthetic construct
SITE                    28
                        note = homo-leucine
SEQUENCE: 19
AEAKYAKEKI AALSEIIWLP NDVYAQIXAF IAALNDDPSQ SSELLSEAKK LNDSQAPK    58

SEQ ID NO: 20           moltype = AA  length = 54
FEATURE                 Location/Qualifiers
source                  1..54
                        mol_type = protein
                        organism = synthetic construct
SITE                    24
                        note = homo-leucine
SEQUENCE: 20
YAKEKIAALS EIIWLPNDTY AQIXAFIAAL NDDPSQSSEL LSEAKKLNDS QAPK        54

SEQ ID NO: 21           moltype = AA  length = 53
FEATURE                 Location/Qualifiers
source                  1..53
                        mol_type = protein
```

```
                        organism = synthetic construct
SITE                    24
                        note = homo-leucine
SEQUENCE: 21
YAKEKIAALS EIIWLPNDTY AQIXAFIAAL NDDPSQSSEL LSEAKKLNDS QAP         53

SEQ ID NO: 22           moltype = AA  length = 58
FEATURE                 Location/Qualifiers
source                  1..58
                        mol_type = protein
                        organism = synthetic construct
SITE                    22
                        note = Norleucine
SITE                    28
                        note = homo-leucine
SEQUENCE: 22
AEAKYAKEKI AALSEIIWLP NXTYAQIXAF IAALNDDPSQ SSELLSEAKK LNDSQAPK    58

SEQ ID NO: 23           moltype = AA  length = 58
FEATURE                 Location/Qualifiers
source                  1..58
                        mol_type = protein
                        organism = synthetic construct
SITE                    22
                        note = homo-leucine
SITE                    28
                        note = homo-leucine
SEQUENCE: 23
AEAKYAKEKI AALSEIIWLP NXTYAQIXAF IAALNDDPSQ SSELLSEAKK LNDSQAPK    58

SEQ ID NO: 24           moltype = AA  length = 53
FEATURE                 Location/Qualifiers
source                  1..53
                        mol_type = protein
                        organism = synthetic construct
SITE                    24
                        note = homo-leucine
SEQUENCE: 24
YAKEKIAALS EIIWLPNLTY AQIXAFIAAL NDDPSQSSEL LSEAKGLNDS QAP         53

SEQ ID NO: 25           moltype = AA  length = 53
FEATURE                 Location/Qualifiers
source                  1..53
                        mol_type = protein
                        organism = synthetic construct
SITE                    24
                        note = homo-leucine
SEQUENCE: 25
YAKEKIAALS EIIWLPNLTY AQIXAFIAAL NDDPSQSSEL LSEAKALNDS QAP         53

SEQ ID NO: 26           moltype = AA  length = 53
FEATURE                 Location/Qualifiers
source                  1..53
                        mol_type = protein
                        organism = synthetic construct
SITE                    24
                        note = homo-leucine
SEQUENCE: 26
YAKEKIAALS EIIWLPNLTY AQIXAFIAAL NDDPSQSSEL LSEAKQLNDS QAP         53

SEQ ID NO: 27           moltype = AA  length = 53
FEATURE                 Location/Qualifiers
source                  1..53
                        mol_type = protein
                        organism = synthetic construct
SITE                    24
                        note = homo-leucine
SEQUENCE: 27
YAKEKIAALS EIIWLPNLTY AQIXAFIAAL NDDPSQSSEL LSEAKLLNDS QAP         53

SEQ ID NO: 28           moltype = AA  length = 53
FEATURE                 Location/Qualifiers
source                  1..53
                        mol_type = protein
                        organism = synthetic construct
SITE                    24
                        note = homo-leucine
SEQUENCE: 28
YAKEKIAALS EIIWLPNLTY AQIXAFIAAL NDDPSQSSEL LSEAKSLNDS QAP         53
```

```
SEQ ID NO: 29          moltype = AA  length = 53
FEATURE                Location/Qualifiers
source                 1..53
                       mol_type = protein
                       organism = synthetic construct
SITE                   24
                       note = homo-leucine
SEQUENCE: 29
YAKEKIAALS EIIWLPNLTY AQIXAFIAAL NDDPSQSSEL LSEAKYLNDS QAP         53

SEQ ID NO: 30          moltype = AA  length = 58
FEATURE                Location/Qualifiers
source                 1..58
                       mol_type = protein
                       organism = synthetic construct
SEQUENCE: 30
AEALYAQEKI AALSEIIWLP NLTHGQIMAF IAALNNDPSQ SSELLSEAEQ LNDSQAPG    58

SEQ ID NO: 31          moltype = AA  length = 54
FEATURE                Location/Qualifiers
source                 1..54
                       mol_type = protein
                       organism = synthetic construct
SEQUENCE: 31
YALEKIAALS EIIWLPNLTH GQIMAFIAAL NDDPSQSSEL LSEAQALNDS QAPG        54

SEQ ID NO: 32          moltype = AA  length = 54
FEATURE                Location/Qualifiers
source                 1..54
                       mol_type = protein
                       organism = synthetic construct
SEQUENCE: 32
YAQEKIAALS EIIWLPNLTH GQIMAFIAAL NNDPSQSSEL LSEALALNDS QAPG        54

SEQ ID NO: 33          moltype = AA  length = 54
FEATURE                Location/Qualifiers
source                 1..54
                       mol_type = protein
                       organism = synthetic construct
SEQUENCE: 33
YAQEKIAALS EIIWLPNLTH GQIMAFIAAL NNDPSQSSEL LSEALALNDS QAPG        54

SEQ ID NO: 34          moltype = AA  length = 58
FEATURE                Location/Qualifiers
source                 1..58
                       mol_type = protein
                       organism = synthetic construct
SEQUENCE: 34
AEALYAEEKI AALSEIIWLP NLTHGQIMAF IAALNDDPSQ SSELLSEALQ LNDSQAPG    58

SEQ ID NO: 35          moltype = AA  length = 53
FEATURE                Location/Qualifiers
source                 1..53
                       mol_type = protein
                       organism = synthetic construct
SITE                   24
                       note = homo-leucine
SEQUENCE: 35
YAKEKIAALS EIIWLPNLTY AQIXAFIAAL NDDPSQSSEL LSEAGELNDS QAP         53

SEQ ID NO: 36          moltype = AA  length = 53
FEATURE                Location/Qualifiers
source                 1..53
                       mol_type = protein
                       organism = synthetic construct
SITE                   24
                       note = homo-leucine
SEQUENCE: 36
YAKEKIAALS EIIWLPNLTY AQIXAFIAAL NDDPSQSSEL LSEAAELNDS QAP         53

SEQ ID NO: 37          moltype = AA  length = 53
FEATURE                Location/Qualifiers
source                 1..53
                       mol_type = protein
                       organism = synthetic construct
SITE                   24
                       note = homo-leucine
SEQUENCE: 37
```

-continued

```
YAKEKIAALS EIIWLPNLTY AQIXAFIAAL NDDPSQSSEL LSEAQELNDS QAP          53

SEQ ID NO: 38           moltype = AA  length = 53
FEATURE                 Location/Qualifiers
source                  1..53
                        mol_type = protein
                        organism = synthetic construct
SITE                    24
                        note = homo-leucine
SEQUENCE: 38
YAKEKIAALS EIIWLPNLTY AQIXAFIAAL NDDPSQSSEL LSEAEELNDS QAP          53

SEQ ID NO: 39           moltype = AA  length = 53
FEATURE                 Location/Qualifiers
source                  1..53
                        mol_type = protein
                        organism = synthetic construct
SITE                    24
                        note = homo-leucine
SEQUENCE: 39
YAKEKIAALS EIIWLPNLTY AQIXAFIAAL NDDPSQSSEL LSEALELNDS QAP          53

SEQ ID NO: 40           moltype = AA  length = 53
FEATURE                 Location/Qualifiers
source                  1..53
                        mol_type = protein
                        organism = synthetic construct
SITE                    24
                        note = homo-leucine
SEQUENCE: 40
YAKEKIAALS EIIWLPNLTY AQIXAFIAAL NDDPSQSSEL LSEASELNDS QAP          53

SEQ ID NO: 41           moltype = AA  length = 53
FEATURE                 Location/Qualifiers
source                  1..53
                        mol_type = protein
                        organism = synthetic construct
SITE                    24
                        note = homo-leucine
SEQUENCE: 41
YAKEKIAALS EIIWLPNLTY AQIXAFIAAL NDDPSQSSEL LSEAYELNDS QAP          53

SEQ ID NO: 42           moltype = AA  length = 53
FEATURE                 Location/Qualifiers
source                  1..53
                        mol_type = protein
                        organism = synthetic construct
SITE                    24
                        note = homo-leucine
SEQUENCE: 42
YAKEKIAALS EIIWLPNLTY AQIXAFIAAL NDDPSQSSEL LSEAKDLNDS QAP          53

SEQ ID NO: 43           moltype = AA  length = 54
FEATURE                 Location/Qualifiers
source                  1..54
                        mol_type = protein
                        organism = synthetic construct
SEQUENCE: 43
YAQEKIAALS EIIWLPNLTH GQIMAFIAAL NDDPSQSSEL LSEALELNDS QAPG         54

SEQ ID NO: 44           moltype = AA  length = 53
FEATURE                 Location/Qualifiers
source                  1..53
                        mol_type = protein
                        organism = synthetic construct
SITE                    24
                        note = homo-leucine
SEQUENCE: 44
YAKEKIAALS EIIWLPNLTY AQIXAFIAAL NADPSQSSEL LSEAKELNDS QAP          53

SEQ ID NO: 45           moltype = AA  length = 53
FEATURE                 Location/Qualifiers
source                  1..53
                        mol_type = protein
                        organism = synthetic construct
SITE                    24
                        note = homo-leucine
SEQUENCE: 45
YAKEKIAALS EIIWLPNLTY AQIXAFIAAL NEDPSQSSEL LSEAKELNDS QAP          53
```

-continued

```
SEQ ID NO: 46          moltype = AA  length = 53
FEATURE                Location/Qualifiers
source                 1..53
                       mol_type = protein
                       organism = synthetic construct
SITE                   24
                       note = homo-leucine
SEQUENCE: 46
YAKEKIAALS EIIWLPNLTY AQIXAFIAAL NLDPSQSSEL LSEAKELNDS QAP         53

SEQ ID NO: 47          moltype = AA  length = 53
FEATURE                Location/Qualifiers
source                 1..53
                       mol_type = protein
                       organism = synthetic construct
SITE                   24
                       note = homo-leucine
SEQUENCE: 47
YAKEKIAALS EIIWLPNLTY AQIXAFIAAL NSDPSQSSEL LSEAKELNDS QAP         53

SEQ ID NO: 48          moltype = AA  length = 53
FEATURE                Location/Qualifiers
source                 1..53
                       mol_type = protein
                       organism = synthetic construct
SITE                   24
                       note = homo-leucine
SEQUENCE: 48
YAKEKIAALS EIIWLPNLTY AQIXAFIAAL NNDPSQSSEL LSEAKELNDS QAP         53

SEQ ID NO: 49          moltype = AA  length = 53
FEATURE                Location/Qualifiers
source                 1..53
                       mol_type = protein
                       organism = synthetic construct
SITE                   24
                       note = homo-leucine
SEQUENCE: 49
YAKEKIAALS EIIWLPNLTY AQIXAFIAAL NTDPSQSSEL LSEAKELNDS QAP         53

SEQ ID NO: 50          moltype = AA  length = 53
FEATURE                Location/Qualifiers
source                 1..53
                       mol_type = protein
                       organism = synthetic construct
SITE                   24
                       note = homo-leucine
SITE                   32
                       note = citrulline
SEQUENCE: 50
YAKEKIAALS EIIWLPNLTY AQIXAFIAAL NXDPSQSSEL LSEAKELNDS QAP         53

SEQ ID NO: 51          moltype = AA  length = 53
FEATURE                Location/Qualifiers
source                 1..53
                       mol_type = protein
                       organism = synthetic construct
SITE                   24
                       note = homo-leucine
SEQUENCE: 51
YAKEKIAALS EIIWLPNLTY AQIXAFIAAL NDDPSQSSEL LSEALDLNDS QAP         53

SEQ ID NO: 52          moltype = AA  length = 53
FEATURE                Location/Qualifiers
source                 1..53
                       mol_type = protein
                       organism = synthetic construct
SITE                   24
                       note = homo-leucine
SEQUENCE: 52
YAKEKIAALS EIIWLPNLTY AQIXAFIAAL NQDPSQSSEL LSEAKELNDS QAP         53

SEQ ID NO: 53          moltype = AA  length = 53
FEATURE                Location/Qualifiers
source                 1..53
                       mol_type = protein
                       organism = synthetic construct
SITE                   24
```

```
                        note = homo-leucine
SITE                    46
                        note = citrulline
SEQUENCE: 53
YAKEKIAALS EIIWLPNLTY AQIXAFIAAL NDDPSQSSEL LSEAKXLNDS QAP         53

SEQ ID NO: 54           moltype = AA  length = 53
FEATURE                 Location/Qualifiers
source                  1..53
                        mol_type = protein
                        organism = synthetic construct
SITE                    24
                        note = homo-leucine
SEQUENCE: 54
YDKEKIAALS EIIWLPNLTY AQIXAFIAAL NDDPSQSSEL LSEAKELNDS QAP         53

SEQ ID NO: 55           moltype = AA  length = 53
FEATURE                 Location/Qualifiers
source                  1..53
                        mol_type = protein
                        organism = synthetic construct
SITE                    24
                        note = homo-leucine
SEQUENCE: 55
YIKEKIAALS EIIWLPNLTY AQIXAFIAAL NDDPSQSSEL LSEAKELNDS QAP         53

SEQ ID NO: 56           moltype = AA  length = 53
FEATURE                 Location/Qualifiers
source                  1..53
                        mol_type = protein
                        organism = synthetic construct
SITE                    24
                        note = homo-leucine
SEQUENCE: 56
YYKEKIAALS EIIWLPNLTY AQIXAFIAAL NDDPSQSSEL LSEAKELNDS QAP         53

SEQ ID NO: 57           moltype = AA  length = 53
FEATURE                 Location/Qualifiers
source                  1..53
                        mol_type = protein
                        organism = synthetic construct
SITE                    24
                        note = homo-leucine
SEQUENCE: 57
YSKEKIAALS EIIWLPNLTY AQIXAFIAAL NDDPSQSSEL LSEAKELNDS QAP         53

SEQ ID NO: 58           moltype = AA  length = 53
FEATURE                 Location/Qualifiers
source                  1..53
                        mol_type = protein
                        organism = synthetic construct
SITE                    24
                        note = homo-leucine
SEQUENCE: 58
YTKEKIAALS EIIWLPNLTY AQIXAFIAAL NDDPSQSSEL LSEAKELNDS QAP         53

SEQ ID NO: 59           moltype = AA  length = 53
FEATURE                 Location/Qualifiers
source                  1..53
                        mol_type = protein
                        organism = synthetic construct
SITE                    24
                        note = homo-leucine
SEQUENCE: 59
YNKEKIAALS EIIWLPNLTY AQIXAFIAAL NDDPSQSSEL LSEAKELNDS QAP         53

SEQ ID NO: 60           moltype = AA  length = 53
FEATURE                 Location/Qualifiers
source                  1..53
                        mol_type = protein
                        organism = synthetic construct
SITE                    24
                        note = homo-leucine
SEQUENCE: 60
YEKEKIAALS EIIWLPNLTY AQIXAFIAAL NDDPSQSSEL LSEAKELNDS QAP         53

SEQ ID NO: 61           moltype = AA  length = 53
FEATURE                 Location/Qualifiers
source                  1..53
```

```
                        mol_type = protein
                        organism = synthetic construct
SITE                    24
                        note = homo-leucine
SEQUENCE: 61
YLKEKIAALS EIIWLPNLTY AQIXAFIAAL NDDPSQSSEL LSEAKELNDS QAP          53

SEQ ID NO: 62           moltype = AA  length = 53
FEATURE                 Location/Qualifiers
source                  1..53
                        mol_type = protein
                        organism = synthetic construct
SITE                    24
                        note = homo-leucine
SEQUENCE: 62
YQKEKIAALS EIIWLPNLTY AQIXAFIAAL NDDPSQSSEL LSEAKELNDS QAP          53

SEQ ID NO: 63           moltype = AA  length = 54
FEATURE                 Location/Qualifiers
source                  1..54
                        mol_type = protein
                        organism = synthetic construct
SEQUENCE: 63
YAEEKIAALS EIIWLPNLTH GQIMAFIAAL NDDPSQSSEL LSEALQLNDS QAPG         54

SEQ ID NO: 64           moltype = AA  length = 53
FEATURE                 Location/Qualifiers
source                  1..53
                        mol_type = protein
                        organism = synthetic construct
SITE                    24
                        note = homo-leucine
SEQUENCE: 64
YALEKIAALS EIIWLPNLTY AQIXAFIAAL NDDPSQSSEL LSEAKELNDS QAP          53

SEQ ID NO: 65           moltype = AA  length = 53
FEATURE                 Location/Qualifiers
source                  1..53
                        mol_type = protein
                        organism = synthetic construct
SITE                    24
                        note = homo-leucine
SEQUENCE: 65
YAAEKIAALS EIIWLPNLTY AQIXAFIAAL NDDPSQSSEL LSEAKELNDS QAP          53

SEQ ID NO: 66           moltype = AA  length = 53
FEATURE                 Location/Qualifiers
source                  1..53
                        mol_type = protein
                        organism = synthetic construct
SITE                    24
                        note = homo-leucine
SEQUENCE: 66
YASEKIAALS EIIWLPNLTY AQIXAFIAAL NDDPSQSSEL LSEAKELNDS QAP          53

SEQ ID NO: 67           moltype = AA  length = 53
FEATURE                 Location/Qualifiers
source                  1..53
                        mol_type = protein
                        organism = synthetic construct
SITE                    24
                        note = homo-leucine
SEQUENCE: 67
YAKEKIAALS EIIWLPNLTY AQIXAFIAAL NDDPSQSSEL LSEAKELNDS QAP          53

SEQ ID NO: 68           moltype = AA  length = 53
FEATURE                 Location/Qualifiers
source                  1..53
                        mol_type = protein
                        organism = synthetic construct
SITE                    24
                        note = homo-leucine
SITE                    46
                        note = homo-serine
SEQUENCE: 68
YAKEKIAALS EIIWLPNLTY AQIXAFIAAL NDDPSQSSEL LSEAKXLNDS QAP          53

SEQ ID NO: 69           moltype = AA  length = 58
FEATURE                 Location/Qualifiers
```

```
source                  1..58
                        mol_type = protein
                        organism = synthetic construct
SITE                    28
                        note = homo-leucine
SEQUENCE: 69
AEAKYAKEKI QALSEIIWLP NITYAQIXAF IAALNDDPSQ SSELLSEAKK LNDSQAPK    58

SEQ ID NO: 70           moltype = AA  length = 58
FEATURE                 Location/Qualifiers
source                  1..58
                        mol_type = protein
                        organism = synthetic construct
SITE                    28
                        note = homo-leucine
SEQUENCE: 70
AEAKYAKEKI YALSEIIWLP NITYAQIXAF IAALNDDPSQ SSELLSEAKK LNDSQAPK    58

SEQ ID NO: 71           moltype = AA  length = 58
FEATURE                 Location/Qualifiers
source                  1..58
                        mol_type = protein
                        organism = synthetic construct
SITE                    28
                        note = homo-leucine
SEQUENCE: 71
AEAKYAKEKI AALQEIIWLP NITYAQIXAF IAALNDDPSQ SSELLSEAKK LNDSQAPK    58

SEQ ID NO: 72           moltype = AA  length = 58
FEATURE                 Location/Qualifiers
source                  1..58
                        mol_type = protein
                        organism = synthetic construct
SITE                    28
                        note = homo-leucine
SEQUENCE: 72
AEAKYAKEKI AALYEIIWLP NITYAQIXAF IAALNDDPSQ SSELLSEAKK LNDSQAPK    58

SEQ ID NO: 73           moltype = AA  length = 58
FEATURE                 Location/Qualifiers
source                  1..58
                        mol_type = protein
                        organism = synthetic construct
SITE                    28
                        note = homo-leucine
SEQUENCE: 73
AEAKYAKEKI AALEEIIWLP NITYAQIXAF IAALNDDPSQ SSELLSEAKK LNDSQAPK    58

SEQ ID NO: 74           moltype = AA  length = 58
FEATURE                 Location/Qualifiers
source                  1..58
                        mol_type = protein
                        organism = synthetic construct
SITE                    28
                        note = homo-leucine
SEQUENCE: 74
AEAKYAKEKI SALSEIIWLP NITYAQIXAF IAALNDDPSQ SSELLSEAKK LNDSQAPK    58

SEQ ID NO: 75           moltype = AA  length = 58
FEATURE                 Location/Qualifiers
source                  1..58
                        mol_type = protein
                        organism = synthetic construct
SITE                    28
                        note = homo-leucine
SEQUENCE: 75
AEAKYAKEKI TALSEIIWLP NITYAQIXAF IAALNDDPSQ SSELLSEAKK LNDSQAPK    58

SEQ ID NO: 76           moltype = AA  length = 57
FEATURE                 Location/Qualifiers
source                  1..57
                        mol_type = protein
                        organism = synthetic construct
SITE                    28
                        note = homo-leucine
SEQUENCE: 76
NAQLYAKEKI AALSEIIWLP NLTYAQIXAF IAALNDDPSQ SSELLSEAKE LNDSQAP     57

SEQ ID NO: 77           moltype = AA  length = 53
```

-continued

```
FEATURE                Location/Qualifiers
source                 1..53
                       mol_type = protein
                       organism = synthetic construct
SITE                   5
                       note = trimethyllysine
SITE                   24
                       note = homo-leucine
SEQUENCE: 77
YAKEXIAALS EIIWLPNLTY AQIXAFIAAL NDDPSQSSEL LSEAKELNDS QAP         53

SEQ ID NO: 78          moltype = AA  length = 53
FEATURE                Location/Qualifiers
source                 1..53
                       mol_type = protein
                       organism = synthetic construct
SITE                   24
                       note = homo-leucine
SEQUENCE: 78
YAKEKIAALS EIIWLPNITY AQIXAFIAAL NDDPSQSSEL LSEAKGLADS QAP         53

SEQ ID NO: 79          moltype = AA  length = 53
FEATURE                Location/Qualifiers
source                 1..53
                       mol_type = protein
                       organism = synthetic construct
SITE                   24
                       note = homo-leucine
SEQUENCE: 79
YAKEKIAALS EIIWLPNITY AQIXAFIAAL NDDPSQSSEL LSEAKGLQDS QAP         53

SEQ ID NO: 80          moltype = AA  length = 53
FEATURE                Location/Qualifiers
source                 1..53
                       mol_type = protein
                       organism = synthetic construct
SITE                   24
                       note = homo-leucine
SEQUENCE: 80
YAKEKIAALS EIIWLPNITY AQIXAFIAAL NDDPSQSSEL LSEAKGLTDS QAP         53

SEQ ID NO: 81          moltype = AA  length = 53
FEATURE                Location/Qualifiers
source                 1..53
                       mol_type = protein
                       organism = synthetic construct
SITE                   24
                       note = homo-leucine
SEQUENCE: 81
YAKEKIAALS EIIWLPNITY AQIXAFIAAL NDDPSQSSEL LSEAKGLNDS SAP         53

SEQ ID NO: 82          moltype = AA  length = 53
FEATURE                Location/Qualifiers
source                 1..53
                       mol_type = protein
                       organism = synthetic construct
SITE                   24
                       note = homo-leucine
SEQUENCE: 82
YAKEKIAALS EIIWLPNITY AQIXAFIAAL NDDPSQSSEL LSEAKGLNDS DAP         53

SEQ ID NO: 83          moltype = AA  length = 53
FEATURE                Location/Qualifiers
source                 1..53
                       mol_type = protein
                       organism = synthetic construct
SITE                   24
                       note = homo-leucine
SEQUENCE: 83
YAKEKIAALS EIIWLPNITY AQIXAFIAAL NDDPSQSSEL LSEAKGLNDS YAP         53

SEQ ID NO: 84          moltype = AA  length = 53
FEATURE                Location/Qualifiers
source                 1..53
                       mol_type = protein
                       organism = synthetic construct
SITE                   24
                       note = methionine sulfone
SEQUENCE: 84
```

```
YAKEKIAALS EIIWLPNLTY AQIXAFIAAL NDDPSQSSEL LSEAKELNDS QAP         53

SEQ ID NO: 85           moltype = AA  length = 53
FEATURE                 Location/Qualifiers
source                  1..53
                        mol_type = protein
                        organism = synthetic construct
SEQUENCE: 85
YAKEKIAALS EIIWLPNLTY AQITAFIAAL NDDPSQSSEL LSEAKELNDS QAP         53

SEQ ID NO: 86           moltype = AA  length = 53
FEATURE                 Location/Qualifiers
source                  1..53
                        mol_type = protein
                        organism = synthetic construct
SEQUENCE: 86
YAKEKIAALS EIIWLPNLTY AQIVAFIAAL NDDPSQSSEL LSEAKELNDS QAP         53

SEQ ID NO: 87           moltype = AA  length = 53
FEATURE                 Location/Qualifiers
source                  1..53
                        mol_type = protein
                        organism = synthetic construct
SITE                    24
                        note = homo-leucine
SEQUENCE: 87
YAKEKIAALS EIIWLPNITY AQIXAFIAAL NDDPSQSSEL LSEAKGLNDS LAP         53

SEQ ID NO: 88           moltype = AA  length = 53
FEATURE                 Location/Qualifiers
source                  1..53
                        mol_type = protein
                        organism = synthetic construct
SITE                    3
                        note = trimethyllysine
SITE                    24
                        note = homo-leucine
SEQUENCE: 88
YAXEKIAALS EIIWLPNLTY AQIXAFIAAL NDDPSQSSEL LSEAKELNDS QAP         53

SEQ ID NO: 89           moltype = AA  length = 53
FEATURE                 Location/Qualifiers
source                  1..53
                        mol_type = protein
                        organism = synthetic construct
SITE                    24
                        note = homo-leucine
SEQUENCE: 89
YAKEKIAALS EIIWLPNITY AQIXAFIAAL NDDPSQSSEL LSEAKGLYDS QAP         53

SEQ ID NO: 90           moltype = AA  length = 53
FEATURE                 Location/Qualifiers
source                  1..53
                        mol_type = protein
                        organism = synthetic construct
SITE                    24
                        note = homo-leucine
SEQUENCE: 90
YAKEKIAALS EIIWLPNITY AQIXAFIAAL NDDPSQSSEL LSEAKGLGDS QAP         53

SEQ ID NO: 91           moltype = AA  length = 53
FEATURE                 Location/Qualifiers
source                  1..53
                        mol_type = protein
                        organism = synthetic construct
SITE                    24
                        note = homo-leucine
SEQUENCE: 91
YAKEKIAALS EIIWLPNITY AQIXAFIAAL NDDPSQSSEL LSEAKGLDDS QAP         53

SEQ ID NO: 92           moltype = AA  length = 53
FEATURE                 Location/Qualifiers
source                  1..53
                        mol_type = protein
                        organism = synthetic construct
SITE                    24
                        note = homo-leucine
SEQUENCE: 92
YAKEKIAALS EIIWLPNITY AQIXAFIAAL NDDPSQSSEL LSEAKGLNDS EAP         53
```

```
SEQ ID NO: 93          moltype = AA  length = 53
FEATURE                Location/Qualifiers
source                 1..53
                       mol_type = protein
                       organism = synthetic construct
SEQUENCE: 93
YAKEKIAALS EIIWLPNLTY AQIAAFIAAL NDDPSQSSEL LSEAKELNDS QAP         53

SEQ ID NO: 94          moltype = AA  length = 53
FEATURE                Location/Qualifiers
source                 1..53
                       mol_type = protein
                       organism = synthetic construct
SEQUENCE: 94
YAKEKIAALS EIIWLPNLTY AQISAFIAAL NDDPSQSSEL LSEAKELNDS QAP         53

SEQ ID NO: 95          moltype = AA  length = 58
FEATURE                Location/Qualifiers
source                 1..58
                       mol_type = protein
                       organism = synthetic construct
VARIANT                1
                       note = A or N or absent
VARIANT                2
                       note = A or E or absent
VARIANT                3
                       note = A or Q or absent
VARIANT                4
                       note = K or acetylated lysine or L or absent
VARIANT                6
                       note = A or D or E or I or L or N or Q or S or T or Y
VARIANT                7
                       note = A or E or K or acetylated lysine or monomethyllysine
                        or L or Q or S
VARIANT                9
                       note = K or acetylated lysine or monomethyllysine
VARIANT                11
                       note = A or Q or S or T or Y
VARIANT                14
                       note = E or Q or S or Y
VARIANT                22
                       note = A or D or F or homo-leucine or I or L or N or
                        Norleucine or T or Y
VARIANT                23
                       note = T or V
VARIANT                24
                       note = H or Y
VARIANT                25
                       note = A or G
VARIANT                28
                       note = A or homo-leucine or M or methionine sulfone or
                        Norleucine or S or T or V
VARIANT                36
                       note = A or citrulline or D or E or L or N or Q or S or T
VARIANT                49
                       note = A or E or G or K or acetylated lysine or L or Q or S
                        or Y
VARIANT                50
                       note = A or citrulline or D or E or G or homo-serine or K
                        or acetylated lysine or L or Q or S or Y
VARIANT                52
                       note = A or D or G or N or Q or T or Y
VARIANT                55
                       note = D or E or L or Q or S or Y or absent
VARIANT                56
                       note = May be deleted
VARIANT                57
                       note = May be deleted
VARIANT                58
                       note = G or K or acetylated lysine or absent
SEQUENCE: 95
XXXXYXXEXI XALXEIIWLP NXXXXQIXAF IAALNXDPSQ SSELLSEAXX LXDSXAPX    58

SEQ ID NO: 96          moltype = AA  length = 57
FEATURE                Location/Qualifiers
source                 1..57
                       mol_type = protein
                       organism = synthetic construct
```

```
VARIANT                1
                       note = May be deleted
VARIANT                2
                       note = May be deleted
VARIANT                3
                       note = May be deleted
VARIANT                4
                       note = May be deleted
VARIANT                7
                       note = K or Q
VARIANT                22
                       note = D or L
VARIANT                24
                       note = H or Y
VARIANT                25
                       note = A or G
VARIANT                28
                       note = homo-leucine or M
VARIANT                36
                       note = D or N
VARIANT                49
                       note = E or K
SEQUENCE: 96
AEALYAXEKI AALSEIIWLP NXTXXQIXAF IAALNXDPSQ SSELLSEAXE LNDSQAP     57

SEQ ID NO: 97          moltype = AA  length = 44
FEATURE                Location/Qualifiers
source                 1..44
                       mol_type = protein
                       organism = synthetic construct
SEQUENCE: 97
CEYDEEFFTE LERLKGGDIC YYIKKKFDKV PRLCIKEIRD KLGC                   44

SEQ ID NO: 98          moltype = AA  length = 44
FEATURE                Location/Qualifiers
source                 1..44
                       mol_type = protein
                       organism = synthetic construct
SEQUENCE: 98
CEYKEEFFTE LKRLYGGDIC YYIKKKFKKV PDLCIEEILD KLGC                   44

SEQ ID NO: 99          moltype = AA  length = 44
FEATURE                Location/Qualifiers
source                 1..44
                       mol_type = protein
                       organism = synthetic construct
SEQUENCE: 99
CEYDEEFFTE LERLKGGDIC YYIKKKFDKV PDLCIKEIRD KLGC                   44

SEQ ID NO: 100         moltype = AA  length = 53
FEATURE                Location/Qualifiers
source                 1..53
                       mol_type = protein
                       organism = synthetic construct
SITE                   24
                       note = homo-leucine
SEQUENCE: 100
AAKEKIAALS EIIWLPNLTY AQIXAFIAAL NDDPSQSSEL LSEAKELNDS QAP         53

SEQ ID NO: 101         moltype = AA  length = 53
FEATURE                Location/Qualifiers
source                 1..53
                       mol_type = protein
                       organism = synthetic construct
SITE                   24
                       note = homo-leucine
SEQUENCE: 101
EAKEKIAALS EIIWLPNLTY AQIXAFIAAL NDDPSQSSEL LSEAKELNDS QAP         53

SEQ ID NO: 102         moltype = AA  length = 53
FEATURE                Location/Qualifiers
source                 1..53
                       mol_type = protein
                       organism = synthetic construct
SITE                   24
                       note = homo-leucine
SEQUENCE: 102
LAKEKIAALS EIIWLPNLTY AQIXAFIAAL NDDPSQSSEL LSEAKELNDS QAP         53
```

-continued

```
SEQ ID NO: 103         moltype = AA  length = 53
FEATURE                Location/Qualifiers
source                 1..53
                       mol_type = protein
                       organism = synthetic construct
SITE                   24
                       note = homo-leucine
SEQUENCE: 103
QAKEKIAALS EIIWLPNLTY AQIXAFIAAL NDDPSQSSEL LSEAKELNDS QAP         53

SEQ ID NO: 104         moltype = AA  length = 53
FEATURE                Location/Qualifiers
source                 1..53
                       mol_type = protein
                       organism = synthetic construct
SITE                   24
                       note = homo-leucine
SEQUENCE: 104
SAKEKIAALS EIIWLPNLTY AQIXAFIAAL NDDPSQSSEL LSEAKELNDS QAP         53

SEQ ID NO: 105         moltype = AA  length = 53
FEATURE                Location/Qualifiers
source                 1..53
                       mol_type = protein
                       organism = synthetic construct
SITE                   24
                       note = homo-leucine
SEQUENCE: 105
TAKEKIAALS EIIWLPNLTY AQIXAFIAAL NDDPSQSSEL LSEAKELNDS QAP         53

SEQ ID NO: 106         moltype = AA  length = 53
FEATURE                Location/Qualifiers
source                 1..53
                       mol_type = protein
                       organism = synthetic construct
SITE                   24
                       note = dimethyllysine
SEQUENCE: 106
YAAEKIAALS EIIWLPNLTY AQIXAFIAAL NDDPSQSSEL LSEAKELNDS QAP         53

SEQ ID NO: 107         moltype = AA  length = 53
FEATURE                Location/Qualifiers
source                 1..53
                       mol_type = protein
                       organism = synthetic construct
SITE                   3
                       note = dimethyllysine
SITE                   24
                       note = dimethyllysine
SEQUENCE: 107
YAXEKIAALS EIIWLPNLTY AQIXAFIAAL NDDPSQSSEI LSEAKELNDS QAP         53

SEQ ID NO: 108         moltype = AA  length = 53
FEATURE                Location/Qualifiers
source                 1..53
                       mol_type = protein
                       organism = synthetic construct
SITE                   3
                       note = dimethyllysine
SITE                   24
                       note = dimethyllysine
SEQUENCE: 108
YAXEKIAALS EIIWLPNLTY AQIXEFIAAL NDDPSQSSEL LSEAKELNDS QAP         53

SEQ ID NO: 109         moltype = AA  length = 53
FEATURE                Location/Qualifiers
source                 1..53
                       mol_type = protein
                       organism = synthetic construct
SITE                   3
                       note = trimethyllysine
SITE                   24
                       note = dimethyllysine
SEQUENCE: 109
YAXEKIAALS EIIWLPNLTY AQIXAFIAAL NDDPSQSSEI LSEAKELNDS QAP         53

SEQ ID NO: 110         moltype = AA  length = 53
FEATURE                Location/Qualifiers
source                 1..53
```

```
                      mol_type = protein
                      organism = synthetic construct
SITE                  3
                      note = trimethyllysine
SITE                  24
                      note = dimethyllysine
SEQUENCE: 110
YAXEKIAALS EIIWLPNLTY AQIXEFIAAL NDDPSQSSEL LSEAKELNDS QAP         53

SEQ ID NO: 111        moltype = AA  length = 53
FEATURE               Location/Qualifiers
source                1..53
                      mol_type = protein
                      organism = synthetic construct
SITE                  3
                      note = trimethyllysine
SEQUENCE: 111
YAXEKIAALS EIIWLPNLTY AQIMAFIAAL NDDPSQSSEL LSEAKELNDS QAP         53

SEQ ID NO: 112        moltype = AA  length = 53
FEATURE               Location/Qualifiers
source                1..53
                      mol_type = protein
                      organism = synthetic construct
SITE                  3
                      note = trimethyllysine
SITE                  24
                      note = norvaline
SEQUENCE: 112
YAXEKIAALS EIIWLPNLTY AQIXAFIAAL NDDPSQSSEL LSEAKELNDS QAP         53

SEQ ID NO: 113        moltype = AA  length = 53
FEATURE               Location/Qualifiers
source                1..53
                      mol_type = protein
                      organism = synthetic construct
SITE                  3
                      note = trimethyllysine
SEQUENCE: 113
YAXEKIAALS EIIWLPNLTY AQIVAFIAAL NDDPSQSSEL LSEAKELNDS QAP         53

SEQ ID NO: 114        moltype = AA  length = 53
FEATURE               Location/Qualifiers
source                1..53
                      mol_type = protein
                      organism = synthetic construct
SITE                  24
                      note = dimethyllysine
SEQUENCE: 114
YAKAKIAALS EIIWLPNLTY AQIXAFIAAL NDDPSQSSEL LSEAKELNDS QAP         53

SEQ ID NO: 115        moltype = AA  length = 53
FEATURE               Location/Qualifiers
source                1..53
                      mol_type = protein
                      organism = synthetic construct
SITE                  24
                      note = homo-leucine
SEQUENCE: 115
YAKCKIAALS EIIWLPNLTY AQIXAFIAAL NDDPSQCSEL LSEAKELNDS QAP         53

SEQ ID NO: 116        moltype = AA  length = 53
FEATURE               Location/Qualifiers
source                1..53
                      mol_type = protein
                      organism = synthetic construct
SITE                  5
                      note = D-Lysine
SEQUENCE: 116
YAKEXIAALS EIIWLPNLTY AQIVAFIAAL NDDPSQSSEL LSEAKELNDS QAP         53

SEQ ID NO: 117        moltype = AA  length = 53
FEATURE               Location/Qualifiers
source                1..53
                      mol_type = protein
                      organism = synthetic construct
SITE                  24
                      note = homo-leucine
SEQUENCE: 117
```

-continued

```
YAKECIAALS EIIWLPNLTY AQIXAFIAAL NDDCSQSSEL LSEAKELNDS QAP         53

SEQ ID NO: 118          moltype = AA  length = 53
FEATURE                 Location/Qualifiers
source                  1..53
                        mol_type = protein
                        organism = synthetic construct
SITE                    24
                        note = homo-leucine
SEQUENCE: 118
YAKECIAALS EIIWLPNLTY AQIXAFIAAL NDDPSQCSEL LSEAKELNDS QAP         53

SEQ ID NO: 119          moltype = AA  length = 53
FEATURE                 Location/Qualifiers
source                  1..53
                        mol_type = protein
                        organism = synthetic construct
SEQUENCE: 119
YAKEEIAALS EIIWLPNLTY AQIVAFIAAL NDDPSQSSEL LSEAKELNDS QAP         53

SEQ ID NO: 120          moltype = AA  length = 53
FEATURE                 Location/Qualifiers
source                  1..53
                        mol_type = protein
                        organism = synthetic construct
SITE                    5
                        note = HO-norvaline
SEQUENCE: 120
YAKEXIAALS EIIWLPNLTY AQIVAFIAAL NDDPSQSSEL LSEAKELNDS QAP         53

SEQ ID NO: 121          moltype = AA  length = 53
FEATURE                 Location/Qualifiers
source                  1..53
                        mol_type = protein
                        organism = synthetic construct
SITE                    5
                        note = dimethyllysine
SITE                    24
                        note = homo-leucine
SEQUENCE: 121
YAKEXIAALS EIIWLPNLTY AQIXAFIAAL NDDPSQSSEL LSEAKELNDS QAP         53

SEQ ID NO: 122          moltype = AA  length = 53
FEATURE                 Location/Qualifiers
source                  1..53
                        mol_type = protein
                        organism = synthetic construct
SITE                    5
                        note = monomethyllysine
SITE                    24
                        note = homo-leucine
SEQUENCE: 122
YAKEXIAALS EIIWLPNLTY AQIXAFIAAL NDDPSQSSEL LSEAKELNDS QAP         53

SEQ ID NO: 123          moltype = AA  length = 53
FEATURE                 Location/Qualifiers
source                  1..53
                        mol_type = protein
                        organism = synthetic construct
SITE                    24
                        note = homo-leucine
SEQUENCE: 123
YAKEKIAALS ECIWLPNLTY AQIXACIAAL NDDPSQSSEL LSEAKELNDS QAP         53

SEQ ID NO: 124          moltype = AA  length = 53
FEATURE                 Location/Qualifiers
source                  1..53
                        mol_type = protein
                        organism = synthetic construct
SITE                    24
                        note = homo-leucine
SEQUENCE: 124
YAKEKIAALS ECIWLPNLTY AQIXAFIAAL NDDPSQSSEL LSECKELNDS QAP         53

SEQ ID NO: 125          moltype = AA  length = 53
FEATURE                 Location/Qualifiers
source                  1..53
                        mol_type = protein
                        organism = synthetic construct
```

```
SITE                    24
                        note = homo-leucine
SEQUENCE: 125
YAKEKIAALS EIIWCPNCTY AQIXAFIAAL NDDPSQSSEL LSEAKELNDS QAP         53

SEQ ID NO: 126          moltype = AA  length = 53
FEATURE                 Location/Qualifiers
source                  1..53
                        mol_type = protein
                        organism = synthetic construct
SITE                    24
                        note = homo-leucine
SEQUENCE: 126
YAKEKIAALS EIIWLPCLTY AQIXAFIAAL NDDPSQSSEL LSEAKELCDS QAP         53

SEQ ID NO: 127          moltype = AA  length = 53
FEATURE                 Location/Qualifiers
source                  1..53
                        mol_type = protein
                        organism = synthetic construct
SITE                    24
                        note = homo-leucine
SEQUENCE: 127
YAKEKIAALS EIIWLPNCTY AQCXAFIAAL NDDPSQSSEL LSEAKELNDS QAP         53

SEQ ID NO: 128          moltype = AA  length = 53
FEATURE                 Location/Qualifiers
source                  1..53
                        mol_type = protein
                        organism = synthetic construct
SITE                    24
                        note = homo-leucine
SEQUENCE: 128
YAKEKIAALS EIIWLPNLCY ACIXAFIAAL NDDPCQSSEL LSEAKELNDS QAP         53

SEQ ID NO: 129          moltype = AA  length = 53
FEATURE                 Location/Qualifiers
source                  1..53
                        mol_type = protein
                        organism = synthetic construct
SITE                    24
                        note = homo-leucine
SEQUENCE: 129
YAKEKIAALS EIIWLPNLCY CQIXAFIAAL NDDPSQSSEL LSEAKELNDS QAP         53

SEQ ID NO: 130          moltype = AA  length = 53
FEATURE                 Location/Qualifiers
source                  1..53
                        mol_type = protein
                        organism = synthetic construct
SITE                    24
                        note = dimethyllysine
SEQUENCE: 130
YAKEKIAALS EIIWLPNLTY AQIXAFIAAL NDDPSQSSEI LSEAKELNDS QAP         53

SEQ ID NO: 131          moltype = AA  length = 53
FEATURE                 Location/Qualifiers
source                  1..53
                        mol_type = protein
                        organism = synthetic construct
SITE                    24
                        note = dimethyllysine
SEQUENCE: 131
YAKEKIAALS EIIWLPNLTY AQIXEFIAAL NDDPSQSSEI LSEAKELNDS QAP         53

SEQ ID NO: 132          moltype = AA  length = 53
FEATURE                 Location/Qualifiers
source                  1..53
                        mol_type = protein
                        organism = synthetic construct
SITE                    24
                        note = homo-leucine
SEQUENCE: 132
YAKEKIAALS EIIWLPNLTY AQIXACIAAL NDDPSQSSEL LSECKELNDS QAP         53

SEQ ID NO: 133          moltype = AA  length = 53
FEATURE                 Location/Qualifiers
source                  1..53
                        mol_type = protein
```

-continued

```
                         organism = synthetic construct
SITE                     24
                         note = homo-leucine
SEQUENCE: 133
YAKEKIAALS EIIWLPNLTY AQIXAFIAAL NDCPSCSSEL LSEAKELNDS QAP         53

SEQ ID NO: 134           moltype = AA  length = 53
FEATURE                  Location/Qualifiers
source                   1..53
                         mol_type = protein
                         organism = synthetic construct
SITE                     24
                         note = alpha-aminobutyric acid
SEQUENCE: 134
YAKEKIAALS EIIWLPNLTY AQIXAFIAAL NDDPSQSSEL LSEAKELNDS QAP         53

SEQ ID NO: 135           moltype = AA  length = 53
FEATURE                  Location/Qualifiers
source                   1..53
                         mol_type = protein
                         organism = synthetic construct
SITE                     24
                         note = tert-butylcysteine
SEQUENCE: 135
YAKEKIAALS EIIWLPNLTY AQIXAFIAAL NDDPSQSSEL LSEAKELNDS QAP         53

SEQ ID NO: 136           moltype = AA  length = 53
FEATURE                  Location/Qualifiers
source                   1..53
                         mol_type = protein
                         organism = synthetic construct
SITE                     24
                         note = Ethionine
SEQUENCE: 136
YAKEKIAALS EIIWLPNLTY AQIXAFIAAL NDDPSQSSEL LSEAKELNDS QAP         53

SEQ ID NO: 137           moltype = AA  length = 53
FEATURE                  Location/Qualifiers
source                   1..53
                         mol_type = protein
                         organism = synthetic construct
SEQUENCE: 137
YAKEKIAALS EIIWLPNLTY AQIGAFIAAL NDDPSQSSEL LSEAKELNDS QAP         53

SEQ ID NO: 138           moltype = AA  length = 53
FEATURE                  Location/Qualifiers
source                   1..53
                         mol_type = protein
                         organism = synthetic construct
SITE                     24
                         note = dimethyllysine
SEQUENCE: 138
YAKEKIAALS EIIWLPNLTY AQIXAFAAAL NDDPSQSSEI LSEAKELNDS QAP         53

SEQ ID NO: 139           moltype = AA  length = 53
FEATURE                  Location/Qualifiers
source                   1..53
                         mol_type = protein
                         organism = synthetic construct
SITE                     24
                         note = dimethyllysine
SITE                     27
                         note = alpha-aminobutyric acid
SEQUENCE: 139
YAKEKIAALS EIIWLPNLTY AQIXAFXAAL NDDPSQSSEI LSEAKELNDS QAP         53

SEQ ID NO: 140           moltype = AA  length = 53
FEATURE                  Location/Qualifiers
source                   1..53
                         mol_type = protein
                         organism = synthetic construct
SITE                     24
                         note = dimethyllysine
SEQUENCE: 140
YAKEKIAALS EIIWLPNLTY AQIXAFFAAL NDDPSQSSEI LSEAKELNDS QAP         53

SEQ ID NO: 141           moltype = AA  length = 53
FEATURE                  Location/Qualifiers
source                   1..53
```

-continued

```
                        mol_type = protein
                        organism = synthetic construct
SITE                    24
                        note = dimethyllysine
SEQUENCE: 141
YAKEKIAALS EIIWLPNLTY AQIXAFIAAL NDDPSQSSEI LSEAKELNDS QAP          53

SEQ ID NO: 142          moltype = AA  length = 53
FEATURE                 Location/Qualifiers
source                  1..53
                        mol_type = protein
                        organism = synthetic construct
SITE                    24
                        note = dimethyllysine
SEQUENCE: 142
YAKEKIAALS EIIWLPNLTY AQIXAFIAAL NDDPSQSSEL LSEAKELNDS QAP          53

SEQ ID NO: 143          moltype = AA  length = 53
FEATURE                 Location/Qualifiers
source                  1..53
                        mol_type = protein
                        organism = synthetic construct
SITE                    24
                        note = dimethyllysine
SEQUENCE: 143
YAKEKIAALS EIIWLPNLTY AQIXAFIAAL NEDPSQSSEL LSEAKELNDS QAP          53

SEQ ID NO: 144          moltype = AA  length = 53
FEATURE                 Location/Qualifiers
source                  1..53
                        mol_type = protein
                        organism = synthetic construct
SITE                    24
                        note = dimethyllysine
SEQUENCE: 144
YAKEKIAALS EIIWLPNLTY AQIXAFIAAL NSDPSQSSEL LSEAKELNDS QAP          53

SEQ ID NO: 145          moltype = AA  length = 53
FEATURE                 Location/Qualifiers
source                  1..53
                        mol_type = protein
                        organism = synthetic construct
SITE                    24
                        note = dimethyllysine
SITE                    29
                        note = citrulline
SEQUENCE: 145
YAKEKIAALS EIIWLPNLTY AQIXAFIAXL NDDPSQSSEL LSEAKELNDS QAP          53

SEQ ID NO: 146          moltype = AA  length = 53
FEATURE                 Location/Qualifiers
source                  1..53
                        mol_type = protein
                        organism = synthetic construct
SITE                    24
                        note = dimethyllysine
SEQUENCE: 146
YAKEKIAALS EIIWLPNLTY AQIXAFIAEL NDDPSQSSEL LSEAKELNDS QAP          53

SEQ ID NO: 147          moltype = AA  length = 53
FEATURE                 Location/Qualifiers
source                  1..53
                        mol_type = protein
                        organism = synthetic construct
SITE                    24
                        note = dimethyllysine
SEQUENCE: 147
YAKEKIAALS EIIWLPNLTY AQIXAFIALL NDDPSQSSEL LSEAKELNDS QAP          53

SEQ ID NO: 148          moltype = AA  length = 53
FEATURE                 Location/Qualifiers
source                  1..53
                        mol_type = protein
                        organism = synthetic construct
SITE                    24
                        note = dimethyllysine
SEQUENCE: 148
YAKEKIAALS EIIWLPNLTY AQIXAFIAQL NDDPSQSSEL LSEAKELNDS QAP          53
```

-continued

```
SEQ ID NO: 149         moltype = AA  length = 53
FEATURE                Location/Qualifiers
source                 1..53
                       mol_type = protein
                       organism = synthetic construct
SITE                   24
                       note = dimethyllysine
SEQUENCE: 149
YAKEKIAALS EIIWLPNLTY AQIXAFIASL NDDPSQSSEL LSEAKELNDS QAP         53

SEQ ID NO: 150         moltype = AA  length = 53
FEATURE                Location/Qualifiers
source                 1..53
                       mol_type = protein
                       organism = synthetic construct
SITE                   24
                       note = dimethyllysine
SEQUENCE: 150
YAKEKIAALS EIIWLPNLTY AQIXAFIAYL NDDPSQSSEL LSEAKELNDS QAP         53

SEQ ID NO: 151         moltype = AA  length = 53
FEATURE                Location/Qualifiers
source                 1..53
                       mol_type = protein
                       organism = synthetic construct
SITE                   24
                       note = dimethyllysine
SITE                   28
                       note = citrulline
SEQUENCE: 151
YAKEKIAALS EIIWLPNLTY AQIXAFIXAL NDDPSQSSEI LSEAKELNDS QAP         53

SEQ ID NO: 152         moltype = AA  length = 53
FEATURE                Location/Qualifiers
source                 1..53
                       mol_type = protein
                       organism = synthetic construct
SITE                   24
                       note = dimethyllysine
SEQUENCE: 152
YAKEKIAALS EIIWLPNLTY AQIXAFIEAL NDDPSQSSEL LSEAKELNDS QAP         53

SEQ ID NO: 153         moltype = AA  length = 53
FEATURE                Location/Qualifiers
source                 1..53
                       mol_type = protein
                       organism = synthetic construct
SITE                   24
                       note = dimethyllysine
SEQUENCE: 153
YAKEKIAALS EIIWLPNLTY AQIXAFIHAL NDDPSQSSEL LSEAKELNDS QAP         53

SEQ ID NO: 154         moltype = AA  length = 53
FEATURE                Location/Qualifiers
source                 1..53
                       mol_type = protein
                       organism = synthetic construct
SITE                   24
                       note = dimethyllysine
SEQUENCE: 154
YAKEKIAALS EIIWLPNLTY AQIXAFIIAL NDDPSQSSEI LSEAKELNDS QAP         53

SEQ ID NO: 155         moltype = AA  length = 53
FEATURE                Location/Qualifiers
source                 1..53
                       mol_type = protein
                       organism = synthetic construct
SITE                   24
                       note = dimethyllysine
SEQUENCE: 155
YAKEKIAALS EIIWLPNLTY AQIXAFILAL NDDPSQSSEL LSEAKELNDS QAP         53

SEQ ID NO: 156         moltype = AA  length = 53
FEATURE                Location/Qualifiers
source                 1..53
                       mol_type = protein
                       organism = synthetic construct
SITE                   24
                       note = dimethyllysine
```

```
SEQUENCE: 156
YAKEKIAALS EIIWLPNLTY AQIXAFIQAL NDDPSQSSEL LSEAKELNDS QAP          53

SEQ ID NO: 157          moltype = AA  length = 53
FEATURE                 Location/Qualifiers
source                  1..53
                        mol_type = protein
                        organism = synthetic construct
SITE                    24
                        note = dimethyllysine
SEQUENCE: 157
YAKEKIAALS EIIWLPNLTY AQIXAFISAL NDDPSQSSEI LSEAKELNDS QAP          53

SEQ ID NO: 158          moltype = AA  length = 53
FEATURE                 Location/Qualifiers
source                  1..53
                        mol_type = protein
                        organism = synthetic construct
SITE                    24
                        note = dimethyllysine
SEQUENCE: 158
YAKEKIAALS EIIWLPNLTY AQIXAFITAL NDDPSQSSEI LSEAKELNDS QAP          53

SEQ ID NO: 159          moltype = AA  length = 53
FEATURE                 Location/Qualifiers
source                  1..53
                        mol_type = protein
                        organism = synthetic construct
SITE                    24
                        note = dimethyllysine
SEQUENCE: 159
YAKEKIAALS EIIWLPNLTY AQIXAFIYAL NDDPSQSSEL LSEAKELNDS QAP          53

SEQ ID NO: 160          moltype = AA  length = 53
FEATURE                 Location/Qualifiers
source                  1..53
                        mol_type = protein
                        organism = synthetic construct
SITE                    24
                        note = dimethyllysine
SEQUENCE: 160
YAKEKIAALS EIIWLPNLTY AQIXAFLAAL NDDPSQSSEI LSEAKELNDS QAP          53

SEQ ID NO: 161          moltype = AA  length = 53
FEATURE                 Location/Qualifiers
source                  1..53
                        mol_type = protein
                        organism = synthetic construct
SITE                    24
                        note = dimethyllysine
SITE                    27
                        note = Norleucine
SEQUENCE: 161
YAKEKIAALS EIIWLPNLTY AQIXAFXAAL NDDPSQSSEI LSEAKELNDS QAP          53

SEQ ID NO: 162          moltype = AA  length = 53
FEATURE                 Location/Qualifiers
source                  1..53
                        mol_type = protein
                        organism = synthetic construct
SITE                    24
                        note = dimethyllysine
SITE                    27
                        note = norvaline
SEQUENCE: 162
YAKEKIAALS EIIWLPNLTY AQIXAFXAAL NDDPSQSSEI LSEAKELNDS QAP          53

SEQ ID NO: 163          moltype = AA  length = 53
FEATURE                 Location/Qualifiers
source                  1..53
                        mol_type = protein
                        organism = synthetic construct
SITE                    24
                        note = dimethyllysine
SEQUENCE: 163
YAKEKIAALS EIIWLPNLTY AQIXAFVAAL NDDPSQSSEI LSEAKELNDS QAP          53

SEQ ID NO: 164          moltype = AA  length = 53
FEATURE                 Location/Qualifiers
```

```
source                  1..53
                        mol_type = protein
                        organism = synthetic construct
SITE                    24
                        note = dimethyllysine
SEQUENCE: 164
YAKEKIAALS EIIWLPNLTY AQIXDFIAAL NDDPSQSSEL LSEAKELNDS QAP         53

SEQ ID NO: 165          moltype = AA  length = 53
FEATURE                 Location/Qualifiers
source                  1..53
                        mol_type = protein
                        organism = synthetic construct
SITE                    24
                        note = dimethyllysine
SEQUENCE: 165
YAKEKIAALS EIIWLPNLTY AQIXEFIAAL NDDPSQSSEI LSEAKELNDS QAP         53

SEQ ID NO: 166          moltype = AA  length = 53
FEATURE                 Location/Qualifiers
source                  1..53
                        mol_type = protein
                        organism = synthetic construct
SITE                    24
                        note = dimethyllysine
SEQUENCE: 166
YAKEKIAALS EIIWLPNLTY AQIXEFIAAL NDDPSQSSEL LSEAKELNDS QAP         53

SEQ ID NO: 167          moltype = AA  length = 53
FEATURE                 Location/Qualifiers
source                  1..53
                        mol_type = protein
                        organism = synthetic construct
SITE                    24
                        note = monomethyllysine
SEQUENCE: 167
YAKEKIAALS EIIWLPNLTY AQIXAFIAAL NDDPSQSSEL LSEAKELNDS QAP         53

SEQ ID NO: 168          moltype = AA  length = 53
FEATURE                 Location/Qualifiers
source                  1..53
                        mol_type = protein
                        organism = synthetic construct
SITE                    24
                        note = methionine sulfone
SEQUENCE: 168
YAKEKIAALS EIIWLPNLTY AQIXAFIAAL NDDPSQSSEL LSEAKELNDS QAP         53

SEQ ID NO: 169          moltype = AA  length = 53
FEATURE                 Location/Qualifiers
source                  1..53
                        mol_type = protein
                        organism = synthetic construct
SEQUENCE: 169
YAKEKIAALS EIIWLPNLTY AQIMAFIAAL NDDPSQSSEI LSEAKELNDS QAP         53

SEQ ID NO: 170          moltype = AA  length = 53
FEATURE                 Location/Qualifiers
source                  1..53
                        mol_type = protein
                        organism = synthetic construct
SEQUENCE: 170
YAKEKIAALS EIIWLPNLTY AQIMAFIAAL NDDPSQSSEL LSEAKELNDS QAP         53

SEQ ID NO: 171          moltype = AA  length = 53
FEATURE                 Location/Qualifiers
source                  1..53
                        mol_type = protein
                        organism = synthetic construct
SITE                    24
                        note = Norleucine
SEQUENCE: 171
YAKEKIAALS EIIWLPNLTY AQIXAFIAAL NDDPSQSSEL LSEAKELNDS QAP         53

SEQ ID NO: 172          moltype = AA  length = 53
FEATURE                 Location/Qualifiers
source                  1..53
                        mol_type = protein
                        organism = synthetic construct
```

```
SITE                    24
                        note = norvaline
SEQUENCE: 172
YAKEKIAALS EIIWLPNLTY AQIXAFIAAL NDDPSQSSEI LSEAKELNDS QAP         53

SEQ ID NO: 173          moltype = AA  length = 53
FEATURE                 Location/Qualifiers
source                  1..53
                        mol_type = protein
                        organism = synthetic construct
SITE                    24
                        note = norvaline
SEQUENCE: 173
YAKEKIAALS EIIWLPNLTY AQIXAFIAAL NDDPSQSSEL LSEAKELNDS QAP         53

SEQ ID NO: 174          moltype = AA  length = 53
FEATURE                 Location/Qualifiers
source                  1..53
                        mol_type = protein
                        organism = synthetic construct
SEQUENCE: 174
YAKEKIAALS EIIWLPNLTY AQIVAFIAAL NDDPSQSSEI LSEAKELNDS QAP         53

SEQ ID NO: 175          moltype = AA  length = 53
FEATURE                 Location/Qualifiers
source                  1..53
                        mol_type = protein
                        organism = synthetic construct
SITE                    24
                        note = dimethyllysine
SEQUENCE: 175
YAKEKIAALS ELIWLPNLTY AQIXAFIAAL NDDPSQSSEL LSEAKELNDS QAP         53

SEQ ID NO: 176          moltype = AA  length = 53
FEATURE                 Location/Qualifiers
source                  1..53
                        mol_type = protein
                        organism = synthetic construct
SITE                    24
                        note = dimethyllysine
SEQUENCE: 176
YAKEKIEALS EIIWLPNLTY AQIXAFIAAL NDDPSQSSEL LSEAKELNDS QAP         53

SEQ ID NO: 177          moltype = AA  length = 53
FEATURE                 Location/Qualifiers
source                  1..53
                        mol_type = protein
                        organism = synthetic construct
SEQUENCE: 177
YAKELIAALS EIIWLPNLTY AQIVAFIAAL NDDPSQSSEL LSEAKELNDS QAP         53

SEQ ID NO: 178          moltype = AA  length = 53
FEATURE                 Location/Qualifiers
source                  1..53
                        mol_type = protein
                        organism = synthetic construct
SEQUENCE: 178
YAKEQIAALS EIIWLPNLTY AQIVAFIAAL NDDPSQSSEL LSEAKELNDS QAP         53

SEQ ID NO: 179          moltype = AA  length = 53
FEATURE                 Location/Qualifiers
source                  1..53
                        mol_type = protein
                        organism = synthetic construct
SEQUENCE: 179
YAKERIAALS EIIWLPNLTY AQIVAFIAAL NDDPSQSSEL LSEAKELNDS QAP         53

SEQ ID NO: 180          moltype = AA  length = 53
FEATURE                 Location/Qualifiers
source                  1..53
                        mol_type = protein
                        organism = synthetic construct
SEQUENCE: 180
YAKESIAALS EIIWLPNLTY AQIVAFIAAL NDDPSQSSEL LSEAKELNDS QAP         53

SEQ ID NO: 181          moltype = AA  length = 53
FEATURE                 Location/Qualifiers
source                  1..53
                        mol_type = protein
```

```
                         organism = synthetic construct
SEQUENCE: 181
YAKEYIAALS EIIWLPNLTY AQIVAFIAAL NDDPSQSSEL LSEAKELNDS QAP         53

SEQ ID NO: 182           moltype = AA  length = 53
FEATURE                  Location/Qualifiers
source                   1..53
                         mol_type = protein
                         organism = synthetic construct
SITE                     24
                         note = dimethyllysine
SEQUENCE: 182
YAQEKIAALS EIIWLPNLTY AQIXAFIAAL NDDPSQSSEL LSEAKELNDS QAP         53

SEQ ID NO: 183           moltype = AA  length = 53
FEATURE                  Location/Qualifiers
source                   1..53
                         mol_type = protein
                         organism = synthetic construct
SITE                     24
                         note = dimethyllysine
SEQUENCE: 183
YAREKIAALS EIIWLPNLTY AQIXAFIAAL NDDPSQSSEI LSEAKELNDS QAP         53

SEQ ID NO: 184           moltype = AA  length = 53
FEATURE                  Location/Qualifiers
source                   1..53
                         mol_type = protein
                         organism = synthetic construct
SITE                     24
                         note = dimethyllysine
SEQUENCE: 184
YAREKIAALS EIIWLPNLTY AQIXAFIAAL NDDPSQSSEA LSEAKELNDS QAP         53

SEQ ID NO: 185           moltype = AA  length = 53
FEATURE                  Location/Qualifiers
source                   1..53
                         mol_type = protein
                         organism = synthetic construct
SITE                     24
                         note = dimethyllysine
SEQUENCE: 185
YAREKIAALS EIIWLPNLTY AQIXAFIAAL NDDPSQSSEI LSEAKELNDS QAP         53

SEQ ID NO: 186           moltype = AA  length = 49
FEATURE                  Location/Qualifiers
source                   1..49
                         mol_type = protein
                         organism = synthetic construct
SITE                     24
                         note = dimethyllysine
SEQUENCE: 186
YAREKIAALS EIIWLPNLTY AQIXAFIAAL NDDPSQSSEI LSEAKELNS              49

SEQ ID NO: 187           moltype = AA  length = 53
FEATURE                  Location/Qualifiers
source                   1..53
                         mol_type = protein
                         organism = synthetic construct
SITE                     24
                         note = dimethyllysine
SITE                     40
                         note = Norleucine
SEQUENCE: 187
YAREKIAALS EIIWLPNLTY AQIXAFIAAL NDDPSQSSEX LSEAKELNDS QAP         53

SEQ ID NO: 188           moltype = AA  length = 53
FEATURE                  Location/Qualifiers
source                   1..53
                         mol_type = protein
                         organism = synthetic construct
SITE                     24
                         note = dimethyllysine
SEQUENCE: 188
YAREKIAALS EIIWLPNLTY AQIXAFIAAL NDDPSQSSEQ LSEAKELNDS QAP         53

SEQ ID NO: 189           moltype = AA  length = 53
FEATURE                  Location/Qualifiers
source                   1..53
```

```
                        mol_type = protein
                        organism = synthetic construct
SITE                    24
                        note = dimethyllysine
SEQUENCE: 189
YAREKIAALS EIIWLPNLTY AQIXAFIAAL NDDPSQSSES LSEAKELNDS QAP         53

SEQ ID NO: 190          moltype = AA  length = 53
FEATURE                 Location/Qualifiers
source                  1..53
                        mol_type = protein
                        organism = synthetic construct
SITE                    24
                        note = dimethyllysine
SEQUENCE: 190
YAREKIAALS EIIWLPNLTY AQIXAFIAAL NDDPSQSSEV LSEAKELNDS QAP         53

SEQ ID NO: 191          moltype = AA  length = 53
FEATURE                 Location/Qualifiers
source                  1..53
                        mol_type = protein
                        organism = synthetic construct
SITE                    24
                        note = dimethyllysine
SEQUENCE: 191
YAREKIAALS EIIWLPNLTY AQIXAFIAAL NDDPSQSSEY LSEAKELNDS QAP         53

SEQ ID NO: 192          moltype = AA  length = 53
FEATURE                 Location/Qualifiers
source                  1..53
                        mol_type = protein
                        organism = synthetic construct
SITE                    24
                        note = dimethyllysine
SEQUENCE: 192
YAREKIAALS EIIWLPNLTY AQIXEFIAAL NDDPSQSSEI LSEAKELNDS QAP         53

SEQ ID NO: 193          moltype = AA  length = 53
FEATURE                 Location/Qualifiers
source                  1..53
                        mol_type = protein
                        organism = synthetic construct
SITE                    24
                        note = dimethyllysine
SEQUENCE: 193
YAREKIAALS EIIWLPNLTY AQIXEFIAAL NDDPSQSSEL LSEAKELNDS QAP         53

SEQ ID NO: 194          moltype = AA  length = 53
FEATURE                 Location/Qualifiers
source                  1..53
                        mol_type = protein
                        organism = synthetic construct
SITE                    24
                        note = dimethyllysine
SEQUENCE: 194
YARNKIAALS EIIWLPNLTY AQIXAFIAAL NDDPSQSSEI LSEAKELNDS QAP         53

SEQ ID NO: 195          moltype = AA  length = 53
FEATURE                 Location/Qualifiers
source                  1..53
                        mol_type = protein
                        organism = synthetic construct
SITE                    24
                        note = dimethyllysine
SEQUENCE: 195
YARQKIAALS EIIWLPNLTY AQIXAFIAAL NDDPSQSSEI LSEAKELNDS QAP         53

SEQ ID NO: 196          moltype = AA  length = 53
FEATURE                 Location/Qualifiers
source                  1..53
                        mol_type = protein
                        organism = synthetic construct
SITE                    24
                        note = dimethyllysine
SEQUENCE: 196
YARSKIAALS EIIWLPNLTY AQIXAFIAAL NDDPSQSSEI LSEAKELNDS QAP         53

SEQ ID NO: 197          moltype = AA  length = 53
FEATURE                 Location/Qualifiers
```

```
source                 1..53
                       mol_type = protein
                       organism = synthetic construct
SITE                   24
                       note = dimethyllysine
SEQUENCE: 197
YASEKIAALS EIIWLPNLTY AQIXAFIAAL NDDPSQSSEL LSEAKELNDS QAP         53

SEQ ID NO: 198         moltype = AA  length = 49
FEATURE                Location/Qualifiers
source                 1..49
                       mol_type = protein
                       organism = synthetic construct
SITE                   24
                       note = dimethyllysine
SEQUENCE: 198
CAEEKIAALS EIIWLPCLTY AQIXAFIAAL NDDPCQSSEI LSEAKELCS              49

SEQ ID NO: 199         moltype = AA  length = 49
FEATURE                Location/Qualifiers
source                 1..49
                       mol_type = protein
                       organism = synthetic construct
SITE                   3
                       note = dimethyllysine
SITE                   24
                       note = dimethyllysine
SEQUENCE: 199
CAXEKIAALS EIIWLPCLTY AQIXAFIAAL NDDPCQSSEI LSEAKELCS              49

SEQ ID NO: 200         moltype = AA  length = 49
FEATURE                Location/Qualifiers
source                 1..49
                       mol_type = protein
                       organism = synthetic construct
SITE                   3
                       note = trimethyllysine
SITE                   24
                       note = dimethyllysine
SEQUENCE: 200
CAXEKIAADS EIIWLPCLTY AQIXAFIAAL NDDPCQSSEI LSEAKELCS              49

SEQ ID NO: 201         moltype = AA  length = 49
FEATURE                Location/Qualifiers
source                 1..49
                       mol_type = protein
                       organism = synthetic construct
SITE                   3
                       note = trimethyllysine
SITE                   24
                       note = dimethyllysine
SEQUENCE: 201
CAXEKIAALS EIIWLPCLTY AQIXAFIAAL NDDPCESSEI LSEAKALCS              49

SEQ ID NO: 202         moltype = AA  length = 49
FEATURE                Location/Qualifiers
source                 1..49
                       mol_type = protein
                       organism = synthetic construct
SITE                   3
                       note = trimethyllysine
SITE                   24
                       note = dimethyllysine
SEQUENCE: 202
CAXEKIAALS EIIWLPCLTY AQIXAFIAAL NDDPCESSEI LSEAKELCS              49

SEQ ID NO: 203         moltype = AA  length = 49
FEATURE                Location/Qualifiers
source                 1..49
                       mol_type = protein
                       organism = synthetic construct
SITE                   3
                       note = trimethyllysine
SITE                   24
                       note = dimethyllysine
SEQUENCE: 203
CAXEKIAALS EIIWLPCLTY AQIXAFIAAL NDDPCQSSEI LSEAKALCS              49

SEQ ID NO: 204         moltype = AA  length = 49
```

-continued

```
FEATURE                Location/Qualifiers
source                 1..49
                       mol_type = protein
                       organism = synthetic construct
SITE                   3
                       note = trimethyllysine
SITE                   24
                       note = dimethyllysine
SEQUENCE: 204
CAXEKIAALS EIIWLPCLTY AQIXAFIAAL NDDPCQSSEI LSEAKELCS              49

SEQ ID NO: 205         moltype = AA  length = 49
FEATURE                Location/Qualifiers
source                 1..49
                       mol_type = protein
                       organism = synthetic construct
SITE                   3
                       note = trimethyllysine
SITE                   24
                       note = dimethyllysine
SEQUENCE: 205
CAXEKIAALS EIIWLPCLTY AQIXEFIAAL NDDPCQSSEI LSEAKELCS              49

SEQ ID NO: 206         moltype = AA  length = 49
FEATURE                Location/Qualifiers
source                 1..49
                       mol_type = protein
                       organism = synthetic construct
SITE                   3
                       note = trimethyllysine
SITE                   24
                       note = trimethyllysine
SEQUENCE: 206
CAXEKIAALS EIIWLPCLTY AQIXAFIAAL NDDPCQSSEI LSEAKELCS              49

SEQ ID NO: 207         moltype = AA  length = 49
FEATURE                Location/Qualifiers
source                 1..49
                       mol_type = protein
                       organism = synthetic construct
SITE                   3
                       note = trimethyllysine
SITE                   24
                       note = dimethyllysine
SEQUENCE: 207
CAXEKSAALS EIIWLPCLTY AQIXAFIAAL NDDPCQSSEI LSEAKELCS              49

SEQ ID NO: 208         moltype = AA  length = 53
FEATURE                Location/Qualifiers
source                 1..53
                       mol_type = protein
                       organism = synthetic construct
SITE                   24
                       note = homo-leucine
SEQUENCE: 208
CAKEKIAALS CIIWLPNLTY AQIXAFIAAL NDDPCQSSEL CSEAKELNDS QAP         53

SEQ ID NO: 209         moltype = AA  length = 50
FEATURE                Location/Qualifiers
source                 1..50
                       mol_type = protein
                       organism = synthetic construct
SITE                   24
                       note = homo-leucine
SEQUENCE: 209
CAKEKIAALS EIIWLPCLTY AQIXAFIAAL NDDPCQSSEL LSEAKELCDS             50

SEQ ID NO: 210         moltype = AA  length = 53
FEATURE                Location/Qualifiers
source                 1..53
                       mol_type = protein
                       organism = synthetic construct
SITE                   24
                       note = homo-leucine
SEQUENCE: 210
CAKEKIAALS EIIWLPCLTY AQIXAFIAAL NDDPCQSSEL LSEAKELCDS QAP         53

SEQ ID NO: 211         moltype = AA  length = 49
FEATURE                Location/Qualifiers
```

```
source                  1..49
                        mol_type = protein
                        organism = synthetic construct
SITE                    24
                        note = homo-leucine
SEQUENCE: 211
CAKEKIAALS EIIWLPCLTY AQIXAFIAAL NDDPCQSSEL LSEAKELCS              49

SEQ ID NO: 212          moltype = AA  length = 53
FEATURE                 Location/Qualifiers
source                  1..53
                        mol_type = protein
                        organism = synthetic construct
SITE                    24
                        note = homo-leucine
SEQUENCE: 212
CAKEKIAALS EIIWLPCLTY AQIXAFIAAL NDDPCQSSEL LSEAKELNDS CAP         53

SEQ ID NO: 213          moltype = AA  length = 53
FEATURE                 Location/Qualifiers
source                  1..53
                        mol_type = protein
                        organism = synthetic construct
SITE                    24
                        note = homo-leucine
SEQUENCE: 213
CAKEKIAALS EIIWLPCLTY AQIXAFIAAL NDDPCQSSEL LSEAKELNDS QCP         53

SEQ ID NO: 214          moltype = AA  length = 49
FEATURE                 Location/Qualifiers
source                  1..49
                        mol_type = protein
                        organism = synthetic construct
SITE                    24
                        note = dimethyllysine
SEQUENCE: 214
CAKEKIAALS EIIWLPCLTY AQIXAFIAAL DDDPCQSSEI LSEAKELCS              49

SEQ ID NO: 215          moltype = AA  length = 49
FEATURE                 Location/Qualifiers
source                  1..49
                        mol_type = protein
                        organism = synthetic construct
SITE                    24
                        note = dimethyllysine
SEQUENCE: 215
CAKEKIAALS EIIWLPCLTY AQIXAFIAAL NDDPCESSEI LSEAKELCS              49

SEQ ID NO: 216          moltype = AA  length = 53
FEATURE                 Location/Qualifiers
source                  1..53
                        mol_type = protein
                        organism = synthetic construct
SITE                    24
                        note = dimethyllysine
SEQUENCE: 216
CAKEKIAALS EIIWLPCLTY AQIXAFIAAL NDDPCQSSEI LSEAKALNDS QCP         53

SEQ ID NO: 217          moltype = AA  length = 49
FEATURE                 Location/Qualifiers
source                  1..49
                        mol_type = protein
                        organism = synthetic construct
SITE                    24
                        note = dimethyllysine
SEQUENCE: 217
CAKEKIAALS EIIWLPCLTY AQIXAFIAAL NDDPCQSSEI LSEAKELCS              49

SEQ ID NO: 218          moltype = AA  length = 53
FEATURE                 Location/Qualifiers
source                  1..53
                        mol_type = protein
                        organism = synthetic construct
SITE                    24
                        note = dimethyllysine
SEQUENCE: 218
CAKEKIAALS EIIWLPCLTY AQIXAFIAAL NDDPCQSSEI LSEAKELNDS QCP         53

SEQ ID NO: 219          moltype = AA  length = 49
```

-continued

```
FEATURE                Location/Qualifiers
source                 1..49
                       mol_type = protein
                       organism = synthetic construct
SITE                   24
                       note = dimethyllysine
SEQUENCE: 219
CAKEKIAALS EIIWLPCLTY AQIXAFIAAL NDDPCQSSEL LSEAKELCS              49

SEQ ID NO: 220         moltype = AA  length = 53
FEATURE                Location/Qualifiers
source                 1..53
                       mol_type = protein
                       organism = synthetic construct
SITE                   24
                       note = dimethyllysine
SEQUENCE: 220
CAKEKIAALS EIIWLPCLTY AQIXAFIAAL NDDPCQSSEL LSEAKELNDS QCP         53

SEQ ID NO: 221         moltype = AA  length = 49
FEATURE                Location/Qualifiers
source                 1..49
                       mol_type = protein
                       organism = synthetic construct
SITE                   24
                       note = trimethyllysine
SEQUENCE: 221
CAKEKIAALS EIIWLPCLTY AQIXAFIAAL NDDPCQSSEI LSEAKELCS              49

SEQ ID NO: 222         moltype = AA  length = 53
FEATURE                Location/Qualifiers
source                 1..53
                       mol_type = protein
                       organism = synthetic construct
SITE                   24
                       note = trimethyllysine
SEQUENCE: 222
CAKEKIAALS EIIWLPCLTY AQIXAFIAAL NDDPCQSSEL LSEAKELNDS QCP         53

SEQ ID NO: 223         moltype = AA  length = 53
FEATURE                Location/Qualifiers
source                 1..53
                       mol_type = protein
                       organism = synthetic construct
SEQUENCE: 223
CAKEKIAALS EIIWLPCLTY AQIMAFIAAL NDDPCQSSEL LSEAKELNDS CAP         53

SEQ ID NO: 224         moltype = AA  length = 55
FEATURE                Location/Qualifiers
source                 1..55
                       mol_type = protein
                       organism = synthetic construct
SEQUENCE: 224
CAKEKIAALS EIIWLPCLTY AQINVAAFIA ALNDDPCQSS ELLSEAKELN DSCAP       55

SEQ ID NO: 225         moltype = AA  length = 53
FEATURE                Location/Qualifiers
source                 1..53
                       mol_type = protein
                       organism = synthetic construct
SITE                   24
                       note = homo-leucine
SEQUENCE: 225
CAKEKIAALS EIIWLPNLTY AQIXAFIAAL NDDPCQSSEL LSEAKELNDS QAP         53

SEQ ID NO: 226         moltype = AA  length = 53
FEATURE                Location/Qualifiers
source                 1..53
                       mol_type = protein
                       organism = synthetic construct
SITE                   24
                       note = dimethyllysine
SEQUENCE: 226
CAKEKIAALS EIIWLPNLTY AQIXAFIAAL NDDPCQSSEL LSEAKELNDS QAP         53

SEQ ID NO: 227         moltype = AA  length = 53
FEATURE                Location/Qualifiers
source                 1..53
                       mol_type = protein
```

```
                          organism = synthetic construct
SITE                      24
                          note = dimethyllysine
SEQUENCE: 227
CAKERIAALS EIIWLPCLTY AQIXAFIAAL NDDPCQSSEL LSEAKELCDS QAP         53

SEQ ID NO: 228            moltype = AA  length = 49
FEATURE                   Location/Qualifiers
source                    1..49
                          mol_type = protein
                          organism = synthetic construct
SITE                      3
                          note = OH-Norleucine
SITE                      24
                          note = dimethyllysine
SEQUENCE: 228
CAXEKIAALS EIIWLPCLTY AQIXAFIAAL NDDPCQSSEI LSEAKELCS              49

SEQ ID NO: 229            moltype = AA  length = 53
FEATURE                   Location/Qualifiers
source                    1..53
                          mol_type = protein
                          organism = synthetic construct
SITE                      24
                          note = dimethyllysine
SEQUENCE: 229
CAQEKIAALS EIIWLPCLTH AQIXAFIYAL NDDPCQSSEL LSEAKSLNDS QCP         53

SEQ ID NO: 230            moltype = AA  length = 49
FEATURE                   Location/Qualifiers
source                    1..49
                          mol_type = protein
                          organism = synthetic construct
SITE                      24
                          note = dimethyllysine
SEQUENCE: 230
CAQEKIAALS EIIWLPCLTY AQIXAFIAAL NDDPCQSSEI LSEAKALCS              49

SEQ ID NO: 231            moltype = AA  length = 53
FEATURE                   Location/Qualifiers
source                    1..53
                          mol_type = protein
                          organism = synthetic construct
SITE                      24
                          note = dimethyllysine
SEQUENCE: 231
CAQEKIAALS EIIWLPCLTY AQIXAFIAAL NDDPCQSSEI LSEAKALNDS QCP         53

SEQ ID NO: 232            moltype = AA  length = 49
FEATURE                   Location/Qualifiers
source                    1..49
                          mol_type = protein
                          organism = synthetic construct
SITE                      24
                          note = dimethyllysine
SEQUENCE: 232
CAQEKIAALS EIIWLPCLTY AQIXAFIAAL NDDPCQSSEI LSEAKELCS              49

SEQ ID NO: 233            moltype = AA  length = 53
FEATURE                   Location/Qualifiers
source                    1..53
                          mol_type = protein
                          organism = synthetic construct
SITE                      24
                          note = dimethyllysine
SEQUENCE: 233
CAQEKIAALS EIIWLPCLTY AQIXAFIAAL NDDPCQSSEI LSEAKELNDS QCP         53

SEQ ID NO: 234            moltype = AA  length = 53
FEATURE                   Location/Qualifiers
source                    1..53
                          mol_type = protein
                          organism = synthetic construct
SITE                      24
                          note = dimethyllysine
SEQUENCE: 234
CAQEKIAALS EIIWLPCLTY AQIXAFIYAL NDDPCQSSEL LSEAKSLNDS QCP         53

SEQ ID NO: 235            moltype = AA  length = 49
```

-continued

```
FEATURE                Location/Qualifiers
source                 1..49
                       mol_type = protein
                       organism = synthetic construct
SITE                   24
                       note = dimethyllysine
SEQUENCE: 235
CAQEKIAALS EIIWLPCLTY AQIXEFIAAL NDDPCQSSEI LSEAKELCS              49

SEQ ID NO: 236         moltype = AA  length = 49
FEATURE                Location/Qualifiers
source                 1..49
                       mol_type = protein
                       organism = synthetic construct
SITE                   24
                       note = citrulline
SEQUENCE: 236
CAREKIAALS EIIWLPCLTY AQIXAFIAAL NDDPCQSSEI LSEAKELCS              49

SEQ ID NO: 237         moltype = AA  length = 49
FEATURE                Location/Qualifiers
source                 1..49
                       mol_type = protein
                       organism = synthetic construct
SEQUENCE: 237
CAREKIAALS EIIWLPCLTY AQIIAFIAAL NDDPCQSSEI LSEAKELCS              49

SEQ ID NO: 238         moltype = AA  length = 49
FEATURE                Location/Qualifiers
source                 1..49
                       mol_type = protein
                       organism = synthetic construct
SITE                   24
                       note = dimethyllysine
SEQUENCE: 238
CAREKIAALS EIIWLPCLTY AQIXAFIAAL NDDPCQSAEI LSEAKELCS              49

SEQ ID NO: 239         moltype = AA  length = 49
FEATURE                Location/Qualifiers
source                 1..49
                       mol_type = protein
                       organism = synthetic construct
SITE                   24
                       note = dimethyllysine
SEQUENCE: 239
CAREKIAALS EIIWLPCLTY AQIXAFIAAL NDDPCQSANI LSEAKELCS              49

SEQ ID NO: 240         moltype = AA  length = 49
FEATURE                Location/Qualifiers
source                 1..49
                       mol_type = protein
                       organism = synthetic construct
SITE                   24
                       note = dimethyllysine
SITE                   45
                       note = citrulline
SITE                   46
                       note = citrulline
SEQUENCE: 240
CAREKIAALS EIIWLPCLTY AQIXAFIAAL NDDPCQSSEI LSEAXXLCS              49

SEQ ID NO: 241         moltype = AA  length = 49
FEATURE                Location/Qualifiers
source                 1..49
                       mol_type = protein
                       organism = synthetic construct
SITE                   24
                       note = dimethyllysine
SEQUENCE: 241
CAREKIAALS EIIWLPCLTY AQIXAFIAAL NDDPCQSSEI LSEAKELCS              49

SEQ ID NO: 242         moltype = AA  length = 53
FEATURE                Location/Qualifiers
source                 1..53
                       mol_type = protein
                       organism = synthetic construct
SITE                   24
                       note = dimethyllysine
SEQUENCE: 242
```

```
CAREKIAALS EIIWLPCLTY AQIXAFIAAL NDDPCQSSEI LSEAKELNDS QCP        53

SEQ ID NO: 243         moltype = AA  length = 49
FEATURE                Location/Qualifiers
source                 1..49
                       mol_type = protein
                       organism = synthetic construct
SITE                   24
                       note = dimethyllysine
SEQUENCE: 243
CAREKIAALS EIIWLPCLTY AQIXAFIAAL NDDPCQSSEI LSEAKLLCS             49

SEQ ID NO: 244         moltype = AA  length = 49
FEATURE                Location/Qualifiers
source                 1..49
                       mol_type = protein
                       organism = synthetic construct
SITE                   24
                       note = dimethyllysine
SEQUENCE: 244
CAREKIAALS EIIWLPCLTY AQIXAFIAAL NDDPCQSSEI LSEALDLCS             49

SEQ ID NO: 245         moltype = AA  length = 49
FEATURE                Location/Qualifiers
source                 1..49
                       mol_type = protein
                       organism = synthetic construct
SITE                   24
                       note = dimethyllysine
SEQUENCE: 245
CAREKIAALS EIIWLPCLTY AQIXAFIAAL NDDPCQSSEI LSEALELCS             49

SEQ ID NO: 246         moltype = AA  length = 49
FEATURE                Location/Qualifiers
source                 1..49
                       mol_type = protein
                       organism = synthetic construct
SITE                   24
                       note = dimethyllysine
SEQUENCE: 246
CAREKIAALS EIIWLPCLTY AQIXAFIAAL NDDPCQSSEI LSEAQDLCS             49

SEQ ID NO: 247         moltype = AA  length = 49
FEATURE                Location/Qualifiers
source                 1..49
                       mol_type = protein
                       organism = synthetic construct
SITE                   24
                       note = dimethyllysine
SEQUENCE: 247
CAREKIAALS EIIWLPCLTY AQIXAFIAAL NDDPCQSSNI LSEAKELCS             49

SEQ ID NO: 248         moltype = AA  length = 49
FEATURE                Location/Qualifiers
source                 1..49
                       mol_type = protein
                       organism = synthetic construct
SITE                   24
                       note = dimethyllysine
SEQUENCE: 248
CAREKIAALS EIIWLPCLTY AQIXEFIAAL NDDPCQSSEI LSEAKELCS             49

SEQ ID NO: 249         moltype = AA  length = 49
FEATURE                Location/Qualifiers
source                 1..49
                       mol_type = protein
                       organism = synthetic construct
SEQUENCE: 249
CAREKIAALS EIIWLPCLTY AQIKAFIAAL NDDPCQSSEI LSEAKELCS             49

SEQ ID NO: 250         moltype = AA  length = 49
FEATURE                Location/Qualifiers
source                 1..49
                       mol_type = protein
                       organism = synthetic construct
SITE                   24
                       note = dimethyllysine
SEQUENCE: 250
CAREKIAALS EIIWLPCLTY AQIXAFIAAL NDDPCQSSEI LSEAQELCS             49
```

```
SEQ ID NO: 251          moltype = AA  length = 49
FEATURE                 Location/Qualifiers
source                  1..49
                        mol_type = protein
                        organism = synthetic construct
SEQUENCE: 251
CAREKIAALS EIIWLPCLTY AQILAFIAAL NDDPCQSSEI LSEAKELCS              49

SEQ ID NO: 252          moltype = AA  length = 49
FEATURE                 Location/Qualifiers
source                  1..49
                        mol_type = protein
                        organism = synthetic construct
SEQUENCE: 252
CAREKIAALS EIIWLPCLTY AQIMAFIAAL NDDPCQSSEI LSEAKELCS              49

SEQ ID NO: 253          moltype = AA  length = 50
FEATURE                 Location/Qualifiers
source                  1..50
                        mol_type = protein
                        organism = synthetic construct
SITE                    25
                        note = 4-methyl-Asn
SEQUENCE: 253
CAREKIAALS EIIWLPCLTY AQINXAFIAA LNDDPCQSSE ILSEAKELCS             50

SEQ ID NO: 254          moltype = AA  length = 49
FEATURE                 Location/Qualifiers
source                  1..49
                        mol_type = protein
                        organism = synthetic construct
SEQUENCE: 254
CAREKIAALS EIIWLPCLTY AQINAFIAAL NDDPCQSSEI LSEAKELCS              49

SEQ ID NO: 255          moltype = AA  length = 49
FEATURE                 Location/Qualifiers
source                  1..49
                        mol_type = protein
                        organism = synthetic construct
SEQUENCE: 255
CAREKIAALS EIIWLPCLTY AQIQAFIAAL NDDPCQSSEI LSEAKELCS              49

SEQ ID NO: 256          moltype = AA  length = 49
FEATURE                 Location/Qualifiers
source                  1..49
                        mol_type = protein
                        organism = synthetic construct
SEQUENCE: 256
CAREKIAALS EIIWLPCLTY AQIVAFIAAL NDDPCQSSEI LSEAKELCS              49

SEQ ID NO: 257          moltype = AA  length = 54
FEATURE                 Location/Qualifiers
source                  1..54
                        mol_type = protein
                        organism = synthetic construct
SITE                    25
                        note = homo-leucine
SEQUENCE: 257
CYAKEKIAAL SEIIWLPCLT YAQIXAFIAA LNDDPCQSSE LLSEAKELND SQCP        54

SEQ ID NO: 258          moltype = AA  length = 53
FEATURE                 Location/Qualifiers
source                  1..53
                        mol_type = protein
                        organism = synthetic construct
SITE                    24
                        note = homo-leucine
SEQUENCE: 258
TAKEKIAALS CIIWLPNLTY AQIXAFIAAL NDDPSQSSEL CSEAKELNDS QAP         53

SEQ ID NO: 259          moltype = AA  length = 53
FEATURE                 Location/Qualifiers
source                  1..53
                        mol_type = protein
                        organism = synthetic construct
SITE                    24
                        note = homo-leucine
SEQUENCE: 259
```

```
YAKEKIAALS CIIWLPNLTY AQIXAFIAAL NDDPSQSSEL CSEAKELNDS QAP         53

SEQ ID NO: 260         moltype = AA  length = 53
FEATURE                Location/Qualifiers
source                 1..53
                       mol_type = protein
                       organism = synthetic construct
SITE                   24
                       note = dimethyllysine
SEQUENCE: 260
YAKEKIAALS CIIWLPNLTY AQIXAFIAAL NDDPSQSSEL CSEAKELNDS QAP         53

SEQ ID NO: 261         moltype = AA  length = 53
FEATURE                Location/Qualifiers
source                 1..53
                       mol_type = protein
                       organism = synthetic construct
SITE                   24
                       note = homo-leucine
SEQUENCE: 261
YAKERIAALS CIIWLPNLTY AQIXAFIAAL NDDPSQSSEL CSEAKELNDS QAP         53

SEQ ID NO: 262         moltype = AA  length = 49
FEATURE                Location/Qualifiers
source                 1..49
                       mol_type = protein
                       organism = synthetic construct
SITE                   3
                       note = trimethyllysine
SITE                   24
                       note = dimethyllysine
SEQUENCE: 262
CAXEKIAALS EIIWLPCLTY AQIXAFIAAL NDDPCQSSEI LSEAKELCS              49

SEQ ID NO: 263         moltype = AA  length = 49
FEATURE                Location/Qualifiers
source                 1..49
                       mol_type = protein
                       organism = synthetic construct
SITE                   24
                       note = dimethyllysine
SEQUENCE: 263
CAREKIAALS EIIWLPCLTY AQIXAFIAAL NDDPCQSAEI LSEAKELCS              49

SEQ ID NO: 264         moltype = AA  length = 49
FEATURE                Location/Qualifiers
source                 1..49
                       mol_type = protein
                       organism = synthetic construct
SITE                   24
                       note = monomethyllysine
SITE                   45
                       note = monomethyllysine
SEQUENCE: 264
CAREKIAALS EIIWLPCLTY AQIXAFIAAL NDDPCQSANI LSEAXELCS              49

SEQ ID NO: 265         moltype = AA  length = 49
FEATURE                Location/Qualifiers
source                 1..49
                       mol_type = protein
                       organism = synthetic construct
SITE                   3
                       note = trimethyllysine
SITE                   24
                       note = monomethyllysine
SITE                   45
                       note = monomethyllysine
SEQUENCE: 265
CAXEKIAALS EIIWLPCLTY AQIXAFIAAL NDDPCQSSEI LSEAXELCS              49

SEQ ID NO: 266         moltype = AA  length = 49
FEATURE                Location/Qualifiers
source                 1..49
                       mol_type = protein
                       organism = synthetic construct
SITE                   3
                       note = trimethyllysine
SITE                   24
                       note = monomethyllysine
```

```
SITE                  28
                      note = monomethyllysine
SITE                  45
                      note = monomethyllysine
SEQUENCE: 266
CAXEKIAALS EIIWLPCLTY AQIXAFIXAL NDDPCQSSEI LSEAXELCS              49

SEQ ID NO: 267        moltype = AA  length = 49
FEATURE               Location/Qualifiers
source                1..49
                      mol_type = protein
                      organism = synthetic construct
SITE                  3
                      note = trimethyllysine
SITE                  24
                      note = monomethyllysine
SITE                  29
                      note = monomethyllysine
SITE                  32
                      note = monomethyllysine
SITE                  45
                      note = monomethyllysine
SEQUENCE: 267
CAXEKIAALS EIIWLPCLTY AQIXAFIAXL NXDPCQSSEI LSEAXELCS              49

SEQ ID NO: 268        moltype = AA  length = 49
FEATURE               Location/Qualifiers
source                1..49
                      mol_type = protein
                      organism = synthetic construct
SITE                  3
                      note = trimethyllysine
SITE                  24
                      note = monomethyllysine
SITE                  45
                      note = monomethyllysine
SEQUENCE: 268
CAXEKIAALS EIIWLPCLNY AQIXAFIAAL NDDPCQSSEI LSEAXELCS              49

SEQ ID NO: 269        moltype = AA  length = 49
FEATURE               Location/Qualifiers
source                1..49
                      mol_type = protein
                      organism = synthetic construct
SITE                  3
                      note = trimethyllysine
SITE                  24
                      note = monomethyllysine
SITE                  45
                      note = monomethyllysine
SEQUENCE: 269
CAXEKIAALS EIIWLPCLTY AQIXAFIAAL NDDPCNSSEI LSEAXELCS              49

SEQ ID NO: 270        moltype = AA  length = 49
FEATURE               Location/Qualifiers
source                1..49
                      mol_type = protein
                      organism = synthetic construct
SITE                  3
                      note = trimethyllysine
SITE                  24
                      note = dimethyllysine
SITE                  32
                      note = citrulline
SITE                  45
                      note = monomethyllysine
SEQUENCE: 270
CAXEKIAALS EIIWLPCLTY AQIXAFIAAL NXDPCQSSEI LSEAXELCS              49

SEQ ID NO: 271        moltype = AA  length = 49
FEATURE               Location/Qualifiers
source                1..49
                      mol_type = protein
                      organism = synthetic construct
SITE                  3
                      note = Rme
SITE                  24
                      note = monomethyllysine
SITE                  45
```

```
                        note = monomethyllysine
SEQUENCE: 271
CAXEKIAALS EIIWLPCLTY AQIXAFIARL NDDPCQSAEI LSEAXELCS              49

SEQ ID NO: 272          moltype = AA  length = 49
FEATURE                 Location/Qualifiers
source                  1..49
                        mol_type = protein
                        organism = synthetic construct
SITE                    3
                        note = trimethyllysine
SITE                    24
                        note = dimethyllysine
SITE                    29
                        note = monomethyllysine
SITE                    32
                        note = citrulline
SITE                    45
                        note = monomethyllysine
SEQUENCE: 272
CAXEKIAALS EIIWLPCLTY AQIXAFIAXL NXDPCQSSEI LSEAXELCS              49

SEQ ID NO: 273          moltype = AA  length = 49
FEATURE                 Location/Qualifiers
source                  1..49
                        mol_type = protein
                        organism = synthetic construct
SITE                    24
                        note = dimethyllysine
SEQUENCE: 273
CAREKIAALS EIIWLPCLTY AQIXAFIAAL NDDPCQSANI LSEAKELCS              49

SEQ ID NO: 274          moltype = AA  length = 49
FEATURE                 Location/Qualifiers
source                  1..49
                        mol_type = protein
                        organism = synthetic construct
SITE                    24
                        note = trimethyllysine
SITE                    45
                        note = citrulline
SEQUENCE: 274
CAREKIAALS EIIWLPCLTY AQIXAFIAAL NDDPCQSSEI LSEAXELCS              49

SEQ ID NO: 275          moltype = AA  length = 49
FEATURE                 Location/Qualifiers
source                  1..49
                        mol_type = protein
                        organism = synthetic construct
SITE                    24
                        note = dimethyllysine
SITE                    46
                        note = citrulline
SEQUENCE: 275
CAREKIAALS EIIWLPCLTY AQIXAFIAAL NDDPCQSSEI LSEAKXLCS              49

SEQ ID NO: 276          moltype = AA  length = 49
FEATURE                 Location/Qualifiers
source                  1..49
                        mol_type = protein
                        organism = synthetic construct
SITE                    24
                        note = hArg
SEQUENCE: 276
CAREKIAALS EIIWLPCLTY AQIXAFIAAL NDDPCQSSEI LSEAKELCS              49

SEQ ID NO: 277          moltype = AA  length = 49
FEATURE                 Location/Qualifiers
source                  1..49
                        mol_type = protein
                        organism = synthetic construct
SITE                    24
                        note = Orn
SEQUENCE: 277
CAREKIAALS EIIWLPCLTY AQIXAFIAAL NDDPCQSSEI LSEAKELCS              49

SEQ ID NO: 278          moltype = AA  length = 49
FEATURE                 Location/Qualifiers
source                  1..49
```

-continued

```
                        mol_type = protein
                        organism = synthetic construct
SITE                    24
                        note = dimethyllysine
SEQUENCE: 278
CAREKIAALS EIIWLPCLTY AQIXAFIAAL NDDPCQSSEI LAEAKELCS              49

SEQ ID NO: 279          moltype = AA  length = 49
FEATURE                 Location/Qualifiers
source                  1..49
                        mol_type = protein
                        organism = synthetic construct
SITE                    24
                        note = dimethyllysine
SEQUENCE: 279
CAREKIAALS EIIWLPCLTY AQIXAFIAAL NDDPCQSSNI LAEAKELCS              49

SEQ ID NO: 280          moltype = AA  length = 49
FEATURE                 Location/Qualifiers
source                  1..49
                        mol_type = protein
                        organism = synthetic construct
SITE                    24
                        note = dimethyllysine
SEQUENCE: 280
CAREKIAALS EIIWLPCLTY AQIXAFIAAL NDDPCQSANI LAEAKELCS              49

SEQ ID NO: 281          moltype = AA  length = 49
FEATURE                 Location/Qualifiers
source                  1..49
                        mol_type = protein
                        organism = synthetic construct
SITE                    3
                        note = trimethyllysine
SITE                    24
                        note = dimethyllysine
SEQUENCE: 281
CAXEKIAANS EIIWLPCLTY AQIXAFIAAL NDDPCQSSEI LSEAKELCS              49

SEQ ID NO: 282          moltype = AA  length = 49
FEATURE                 Location/Qualifiers
source                  1..49
                        mol_type = protein
                        organism = synthetic construct
SITE                    3
                        note = trimethyllysine
SITE                    24
                        note = dimethyllysine
SEQUENCE: 282
CAXEKNAALS EIIWLPCLTY AQIXAFIAAL NDDPCQSSEI LSEAKELCS              49

SEQ ID NO: 283          moltype = AA  length = 49
FEATURE                 Location/Qualifiers
source                  1..49
                        mol_type = protein
                        organism = synthetic construct
SITE                    3
                        note = trimethyllysine
SITE                    24
                        note = dimethyllysine
SEQUENCE: 283
CAXEKQAALS EIIWLPCLTY AQIXAFIAAL NDDPCQSSEI LSEAKELCS              49

SEQ ID NO: 284          moltype = AA  length = 53
FEATURE                 Location/Qualifiers
source                  1..53
                        mol_type = protein
                        organism = synthetic construct
SITE                    24
                        note = trimethyllysine
SEQUENCE: 284
CAREKIAALS EIIWLPNLTY AQIXAFIAAL NDDPCQSSEI LSEAKELNDS QAP         53

SEQ ID NO: 285          moltype = AA  length = 49
FEATURE                 Location/Qualifiers
source                  1..49
                        mol_type = protein
                        organism = synthetic construct
SITE                    24
```

```
                        note = K(Ac)
SEQUENCE: 285
CAREKIAALS EIIWLPCLTY AQIXAFIAAL NDDPCQSSEI LSEAKELCS               49

SEQ ID NO: 286          moltype = AA  length = 49
FEATURE                 Location/Qualifiers
source                  1..49
                        mol_type = protein
                        organism = synthetic construct
SITE                    24
                        note = K(Ac)
SEQUENCE: 286
CAREKIAALS EIIWLPCLTY AQIXAFIAAL NDDPCQSAEI LSEAKELCS               49

SEQ ID NO: 287          moltype = AA  length = 49
FEATURE                 Location/Qualifiers
source                  1..49
                        mol_type = protein
                        organism = synthetic construct
SITE                    24
                        note = monomethyllysine
SEQUENCE: 287
CAREKIAALS EIIWLPCLTY AQIXAFIAAL NDDPCQSAEI LAEAKELCS               49

SEQ ID NO: 288          moltype = AA  length = 49
FEATURE                 Location/Qualifiers
source                  1..49
                        mol_type = protein
                        organism = synthetic construct
SITE                    24
                        note = monomethyllysine
SEQUENCE: 288
CAREKIAALS EIIWLPCLTY AQIXAFIAAL NDDPCQSAEI LSEAQELCS               49

SEQ ID NO: 289          moltype = AA  length = 49
FEATURE                 Location/Qualifiers
source                  1..49
                        mol_type = protein
                        organism = synthetic construct
SITE                    24
                        note = hGln
SEQUENCE: 289
CAREKIAALS EIIWLPCLTY AQIXAFIAAL NDDPCQSSEI LSEAKELCS               49

SEQ ID NO: 290          moltype = AA  length = 49
FEATURE                 Location/Qualifiers
source                  1..49
                        mol_type = protein
                        organism = synthetic construct
SITE                    5
                        note = hGln
SITE                    24
                        note = monomethyllysine
SEQUENCE: 290
CAREXIAALS EIIWLPCLTY AQIXAFIAAL NDDPCQSSEI LSEAKELCS               49

SEQ ID NO: 291          moltype = AA  length = 49
FEATURE                 Location/Qualifiers
source                  1..49
                        mol_type = protein
                        organism = synthetic construct
SITE                    24
                        note = monomethyllysine
SITE                    45
                        note = hGln
SEQUENCE: 291
CAREKIAALS EIIWLPCLTY AQIXAFIAAL NDDPCQSSEI LSEAXELCS               49

SEQ ID NO: 292          moltype = AA  length = 49
FEATURE                 Location/Qualifiers
source                  1..49
                        mol_type = protein
                        organism = synthetic construct
SITE                    24
                        note = monomethyllysine
SITE                    45
                        note = monomethyllysine
SEQUENCE: 292
CAREKIAALS EIIWLPCLTY AQIXAFIAAL NDDPCQSSEI LSEAXELCS               49
```

-continued

```
SEQ ID NO: 293          moltype = AA  length = 49
FEATURE                 Location/Qualifiers
source                  1..49
                        mol_type = protein
                        organism = synthetic construct
SITE                    24
                        note = monomethyllysine
SITE                    45
                        note = monomethyllysine
SITE                    46
                        note = monomethyllysine
SEQUENCE: 293
CAREKIAALS EIIWLPCLTY AQIXAFIAAL NDDPCQSAEI LSEAXXLCS              49

SEQ ID NO: 294          moltype = AA  length = 49
FEATURE                 Location/Qualifiers
source                  1..49
                        mol_type = protein
                        organism = synthetic construct
SITE                    24
                        note = monomethyllysine
SEQUENCE: 294
CAREKIAALS EIIWLPCLTY AQIXEFIAAL NDDPCQSAEI LSEAKELCS              49

SEQ ID NO: 295          moltype = AA  length = 49
FEATURE                 Location/Qualifiers
source                  1..49
                        mol_type = protein
                        organism = synthetic construct
SITE                    24
                        note = monomethyllysine
SITE                    45
                        note = monomethyllysine
SEQUENCE: 295
CAREKIAALS EIIWLPCLTY AQIXAFIAAL NDDPCQSAEI LSEAXELCS              49

SEQ ID NO: 296          moltype = AA  length = 49
FEATURE                 Location/Qualifiers
source                  1..49
                        mol_type = protein
                        organism = synthetic construct
SITE                    24
                        note = monomethyllysine
SEQUENCE: 296
CAREKIAALS EIIWLPCLTY AQIXEFIAAL NDDPCQSANI LAEAKELCS              49

SEQ ID NO: 297          moltype = AA  length = 49
FEATURE                 Location/Qualifiers
source                  1..49
                        mol_type = protein
                        organism = synthetic construct
SITE                    3
                        note = trimethyllysine
SITE                    24
                        note = dimethyllysine
SEQUENCE: 297
CAXEKIAALS EIIWLPCLTY AQIXAFIAAL NDDPCQSAEI LSEAKELCS              49

SEQ ID NO: 298          moltype = AA  length = 49
FEATURE                 Location/Qualifiers
source                  1..49
                        mol_type = protein
                        organism = synthetic construct
SITE                    3
                        note = trimethyllysine
SITE                    24
                        note = dimethyllysine
SEQUENCE: 298
CAXEKIAALS EIIWLPCLTY AQIXAFIAAL NDDPCQSANI LSEAKELCS              49

SEQ ID NO: 299          moltype = AA  length = 49
FEATURE                 Location/Qualifiers
source                  1..49
                        mol_type = protein
                        organism = synthetic construct
SITE                    3
                        note = trimethyllysine
SITE                    19
```

-continued

```
                        note = monomethyllysine
SITE                    24
                        note = monomethyllysine
SITE                    32
                        note = monomethyllysine
SITE                    45
                        note = monomethyllysine
SEQUENCE: 299
CAXEKIAALS EIIWLPCLXY AQIXAFIAAL NXDPCQSSEI LSEAXELCS             49

SEQ ID NO: 300          moltype = AA  length = 49
FEATURE                 Location/Qualifiers
source                  1..49
                        mol_type = protein
                        organism = synthetic construct
SITE                    3
                        note = trimethyllysine
SITE                    19
                        note = monomethyllysine
SITE                    24
                        note = monomethyllysine
SITE                    45
                        note = monomethyllysine
SEQUENCE: 300
CAXEKIAALS EIIWLPCLXY AQIXAFIAAL NDDPCQSSEI LSEAXELCS             49

SEQ ID NO: 301          moltype = AA  length = 49
FEATURE                 Location/Qualifiers
source                  1..49
                        mol_type = protein
                        organism = synthetic construct
SITE                    3
                        note = trimethyllysine
SITE                    19
                        note = monomethyllysine
SITE                    24
                        note = dimethyllysine
SITE                    45
                        note = monomethyllysine
SEQUENCE: 301
CAXEKIAALS EIIWLPCLXY AQIXAFIAAL NDDPCQSSEI LSEAXELCS             49

SEQ ID NO: 302          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 302
CAXEKIAALS EIIWLPCLKY AQIXAFIAAL NDDPCQSSEI LSEAXELCS             49

SEQ ID NO: 303          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    28
                        note = monomethyllysine
SITE                    29
                        note = monomethyllysine
SITE                    36
                        note = monomethyllysine
SITE                    45
                        note = monomethyllysine
SEQUENCE: 303
CAXEKIAALS EIIWLPCLNY AQIXAFIXXL NDDPCXSSEI LSEAXELCS             49

SEQ ID NO: 304          moltype = AA  length = 49
FEATURE                 Location/Qualifiers
source                  1..49
```

```
                        mol_type = protein
                        organism = synthetic construct
SITE                    3
                        note = trimethyllysine
SITE                    24
                        note = monomethyllysine
SITE                    28
                        note = monomethyllysine
SITE                    29
                        note = monomethyllysine
SITE                    45
                        note = monomethyllysine
SEQUENCE: 304
CAXEKIAALS EIIWLPCLNY AQIXAFIXXL NDDPCNSSEI LSEAXELCS               49

SEQ ID NO: 305          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    28
                        note = monomethyllysine
SITE                    29
                        note = monomethyllysine
SITE                    45
                        note = monomethyllysine
SEQUENCE: 305
CAXEKIAALS EIIWLPCLNY AQIXAFIXXL NDDPCNSSEI LSEAXEQCS               49

SEQ ID NO: 306          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    28
                        note = monomethyllysine
SITE                    29
                        note = monomethyllysine
SITE                    45
                        note = monomethyllysine
SEQUENCE: 306
CAXEKIAALS EIIWLPCLNY AQIXAFIXXL NDDPCQSSEI LSEAXELCS               49

SEQ ID NO: 307          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    28
                        note = monomethyllysine
SITE                    29
                        note = monomethyllysine
SITE                    45
                        note = monomethyllysine
SEQUENCE: 307
CAXEKIAALS EIIWLPCLNY AQIXAFIXXL NDDPCQSSEI LSEAXEQCS               49

SEQ ID NO: 308          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    28
```

```
                        note = monomethyllysine
SITE                    29
                        note = monomethyllysine
SEQUENCE: 308
CAXEKIAALS EIIWLPCLNY AQIXAFIXXL NDDPCQSSEI LSEAKELCS               49

SEQ ID NO: 309          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    28
                        note = monomethyllysine
SITE                    29
                        note = monomethyllysine
SEQUENCE: 309
CAXEKIAALS EIIWLPCLNY AQIXAFIXXL NDDPCQSSEI LSEARELCS               49

SEQ ID NO: 310          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    28
                        note = monomethyllysine
SITE                    29
                        note = monomethyllysine
SITE                    45
                        note = monomethyllysine
SEQUENCE: 310
CAXEKIAALS EIIWLPCLNY AQIXAFIXXL NDDPCRSSEI LSEAXELCS               49

SEQ ID NO: 311          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    28
                        note = monomethyllysine
SITE                    29
                        note = monomethyllysine
SITE                    45
                        note = monomethyllysine
SEQUENCE: 311
CAXEKIAALS EIIWLPCLNY AQIXAFIXXL NDDPCSSSEI LSEAXELCS               49

SEQ ID NO: 312          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    28
                        note = monomethyllysine
SITE                    29
                        note = monomethyllysine
SITE                    45
                        note = monomethyllysine
SEQUENCE: 312
CAXEKIAALS EIIWLPCLNY AQIXAFIXXL NDDPCYSSEI LSEAXELCS               49

SEQ ID NO: 313          moltype = AA  length = 49
FEATURE                 Location/Qualifiers
source                  1..49
```

```
                        mol_type = protein
                        organism = synthetic construct
SITE                    3
                        note = trimethyllysine
SITE                    24
                        note = monomethyllysine
SITE                    32
                        note = monomethyllysine
SITE                    45
                        note = monomethyllysine
SEQUENCE: 313
CAXEKIAALS EIIWLPCLNY AQIXAFIAAL NXDPCNSSEI LSEAXELCS              49

SEQ ID NO: 314          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    32
                        note = monomethyllysine
SITE                    45
                        note = monomethyllysine
SEQUENCE: 314
CAXEKIAALS EIIWLPCLNY AQIXAFIAAL NXDPCNSSEI LSEAXEQCS              49

SEQ ID NO: 315          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    32
                        note = monomethyllysine
SITE                    45
                        note = monomethyllysine
SEQUENCE: 315
CAXEKIAALS EIIWLPCLNY AQIXAFIAAL NXDPCQSSEI LSEAXELCS              49

SEQ ID NO: 316          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    32
                        note = monomethyllysine
SITE                    45
                        note = monomethyllysine
SEQUENCE: 316
CAXEKIAALS EIIWLPCLNY AQIXAFIAAL NXDPCQSSEI LSEAXEQCS              49

SEQ ID NO: 317          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 317
CAXEKIAALS EIIWLPCLNY AQIXAFIAAL NDDPCNSSEI LSEAXELCS              49

SEQ ID NO: 318          moltype = AA  length = 49
FEATURE                 Location/Qualifiers
source                  1..49
                        mol_type = protein
```

```
                        organism = synthetic construct
SITE                    3
                        note = trimethyllysine
SITE                    24
                        note = monomethyllysine
SITE                    45
                        note = monomethyllysine
SEQUENCE: 318
CAXEKIAALS EIIWLPCLNY AQIXAFIAAL NDDPCNSSEI LSEAXEQCS              49

SEQ ID NO: 319          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SEQUENCE: 319
CAXEKIAALS EIIWLPCLNY AQIXAFIAAL NDDPCNSSEI LSEAKEQCS              49

SEQ ID NO: 320          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 320
CAXEKIAALS EIIWLPCLNY AQIXAFIAAL NDDPCQSSEI LSEAXEQCS              49

SEQ ID NO: 321          moltype = AA  length = 49
FEATURE                 Location/Qualifiers
source                  1..49
                        mol_type = protein
                        organism = synthetic construct
SITE                    3
                        note = trimethyllysine
SITE                    24
                        note = dimethyllysine
SITE                    32
                        note = citrulline
SITE                    45
                        note = monomethyllysine
SEQUENCE: 321
CAXEKIAALS EIIWLPCLNY AQIXAFIAAL NXDPCQSSEI LSEAXELCS              49

SEQ ID NO: 322          moltype = AA  length = 49
FEATURE                 Location/Qualifiers
source                  1..49
                        mol_type = protein
                        organism = synthetic construct
SITE                    3
                        note = trimethyllysine
SITE                    24
                        note = dimethyllysine
SITE                    45
                        note = monomethyllysine
SEQUENCE: 322
CAXEKIAALS EIIWLPCLNY AQIXAFIAAL NDDPCNSSEI LSEAXELCS              49

SEQ ID NO: 323          moltype = AA  length = 49
FEATURE                 Location/Qualifiers
source                  1..49
                        mol_type = protein
                        organism = synthetic construct
SITE                    3
                        note = trimethyllysine
SITE                    24
                        note = dimethyllysine
SITE                    45
                        note = trimethyllysine
SEQUENCE: 323
CAXEKIAALS EIIWLPCLNY AQIXAFIAAL NDDPCNSSEI LSEAXELCS              49
```

-continued

```
SEQ ID NO: 324          moltype = AA  length = 49
FEATURE                 Location/Qualifiers
source                  1..49
                        mol_type = protein
                        organism = synthetic construct
SITE                    3
                        note = trimethyllysine
SITE                    24
                        note = dimethyllysine
SITE                    45
                        note = monomethyllysine
SEQUENCE: 324
CAXEKIAALS EIIWLPCLNY AQIXAFIAAL NDDPCQSSEI LSEAXELCS              49

SEQ ID NO: 325          moltype = AA  length = 49
FEATURE                 Location/Qualifiers
source                  1..49
                        mol_type = protein
                        organism = synthetic construct
SITE                    3
                        note = trimethyllysine
SITE                    24
                        note = dimethyllysine
SITE                    45
                        note = trimethyllysine
SEQUENCE: 325
CAXEKIAALS EIIWLPCLNY AQIXAFIAAL NDDPCQSSEI LSEAXELCS              49

SEQ ID NO: 326          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    32
                        note = monomethyllysine
SITE                    45
                        note = monomethyllysine
SEQUENCE: 326
CAXEKIAALS EIIWLPCLSY AQIXAFIAAL NXDPCNSSEI LSEAXELCS              49

SEQ ID NO: 327          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    32
                        note = monomethyllysine
SITE                    45
                        note = monomethyllysine
SEQUENCE: 327
CAXEKIAALS EIIWLPCLSY AQIXAFIAAL NXDPCNSSEI LSEAXEQCS              49

SEQ ID NO: 328          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    32
                        note = monomethyllysine
SITE                    45
                        note = monomethyllysine
SEQUENCE: 328
CAXEKIAALS EIIWLPCLSY AQIXAFIAAL NXDPCQSSEI LSEAXELCS              49

SEQ ID NO: 329          moltype = AA  length = 49
FEATURE                 Location/Qualifiers
```

-continued

```
source                1..49
                      mol_type = protein
                      organism = synthetic construct
SITE                  3
                      note = trimethyllysine
SITE                  24
                      note = monomethyllysine
SITE                  32
                      note = monomethyllysine
SITE                  45
                      note = monomethyllysine
SEQUENCE: 329
CAXEKIAALS EIIWLPCLSY AQIXAFIAAL NXDPCQSSEI LSEAXEQCS             49

SEQ ID NO: 330        moltype = AA  length = 49
FEATURE               Location/Qualifiers
source                1..49
                      mol_type = protein
                      organism = synthetic construct
SITE                  3
                      note = trimethyllysine
SITE                  24
                      note = monomethyllysine
SITE                  45
                      note = monomethyllysine
SEQUENCE: 330
CAXEKIAALS EIIWLPCLSY AQIXAFIAAL NDDPCQSSEI LSEAXELCS             49

SEQ ID NO: 331        moltype = AA  length = 49
FEATURE               Location/Qualifiers
source                1..49
                      mol_type = protein
                      organism = synthetic construct
SITE                  3
                      note = trimethyllysine
SITE                  20
                      note = 3-4-Cl-Phe
SITE                  24
                      note = dimethyllysine
SEQUENCE: 331
CAXEKIAALS EIIWLPCLTX AQIXAFIAAL NDDPCQSSEI LSEAKELCS             49

SEQ ID NO: 332        moltype = AA  length = 49
FEATURE               Location/Qualifiers
source                1..49
                      mol_type = protein
                      organism = synthetic construct
SITE                  3
                      note = trimethyllysine
SITE                  20
                      note = 4-CN-Phe
SITE                  24
                      note = dimethyllysine
SEQUENCE: 332
CAXEKIAALS EIIWLPCLTX AQIXAFIAAL NDDPCQSSEI LSEAKELCS             49

SEQ ID NO: 333        moltype = AA  length = 49
FEATURE               Location/Qualifiers
source                1..49
                      mol_type = protein
                      organism = synthetic construct
SITE                  3
                      note = trimethyllysine
SITE                  20
                      note = 4-I-Phe
SITE                  24
                      note = dimethyllysine
SEQUENCE: 333
CAXEKIAALS EIIWLPCLTX AQIXAFIAAL NDDPCQSSEI LSEAKELCS             49

SEQ ID NO: 334        moltype = AA  length = 49
FEATURE               Location/Qualifiers
source                1..49
                      mol_type = protein
                      organism = synthetic construct
SITE                  3
                      note = trimethyllysine
SITE                  20
                      note = 4-NH2-Phe
```

```
SITE                    24
                        note = dimethyllysine
SEQUENCE: 334
CAXEKIAALS EIIWLPCLTX AQIXAFIAAL NDDPCQSSEI LSEAKELCS              49

SEQ ID NO: 335          moltype = AA  length = 49
FEATURE                 Location/Qualifiers
source                  1..49
                        mol_type = protein
                        organism = synthetic construct
SITE                    3
                        note = trimethyllysine
SITE                    20
                        note = Allylglycine
SITE                    24
                        note = dimethyllysine
SITE                    45
                        note = monomethyllysine
SEQUENCE: 335
CAXEKIAALS EIIWLPCLTX AQIXAFIAAL NDDPCQSSEI LSEAXELCS              49

SEQ ID NO: 336          moltype = AA  length = 49
FEATURE                 Location/Qualifiers
source                  1..49
                        mol_type = protein
                        organism = synthetic construct
SITE                    3
                        note = trimethyllysine
SITE                    20
                        note = Allylglycine
SITE                    24
                        note = dimethyllysine
SITE                    45
                        note = trimethyllysine
SEQUENCE: 336
CAXEKIAALS EIIWLPCLTX AQIXAFIAAL NDDPCQSSEI LSEAXELCS              49

SEQ ID NO: 337          moltype = AA  length = 49
FEATURE                 Location/Qualifiers
source                  1..49
                        mol_type = protein
                        organism = synthetic construct
SITE                    3
                        note = trimethyllysine
SITE                    20
                        note = Allylglycine
SITE                    24
                        note = dimethyllysine
SEQUENCE: 337
CAXEKIAALS EIIWLPCLTX AQIXAFIAAL NDDPCQSSEI LSEAKELCS              49

SEQ ID NO: 338          moltype = AA  length = 49
FEATURE                 Location/Qualifiers
source                  1..49
                        mol_type = protein
                        organism = synthetic construct
SITE                    3
                        note = trimethyllysine
SITE                    20
                        note = hGln
SITE                    24
                        note = monomethyllysine
SEQUENCE: 338
CAXEKIAALS EIIWLPCLTX AQIXAFIAAL NDDPCNSSEI LSEAKELCS              49

SEQ ID NO: 339          moltype = AA  length = 49
FEATURE                 Location/Qualifiers
source                  1..49
                        mol_type = protein
                        organism = synthetic construct
SITE                    3
                        note = trimethyllysine
SITE                    24
                        note = dimethyllysine
SEQUENCE: 339
CAXEKIAALS EIIWLPCLTH AQIXAFIAAL NDDPCQSSEI LSEAKELCS              49

SEQ ID NO: 340          moltype = AA  length = 49
FEATURE                 Location/Qualifiers
```

-continued

```
source                  1..49
                        mol_type = protein
                        organism = synthetic construct
SITE                    3
                        note = trimethyllysine
SITE                    24
                        note = monomethyllysine
SEQUENCE: 340
CAXEKIAALS EIIWLPCLTQ AQIXAFIAAL NDDPCNSSEI LSEAKELCS              49

SEQ ID NO: 341          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SEQUENCE: 341
CAXEKIAALS EIIWLPCLTR AQIXAFIAAL NDDPCNSSEI LSEAKELCS              49

SEQ ID NO: 342          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    25
                        note = monomethyllysine
SEQUENCE: 342
CAXEKIAALS EIIWLPCLTY AQIXXFIAAL NDDPCQSSEI LSEAKELCS              49

SEQ ID NO: 343          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    28
                        note = monomethyllysine
SITE                    29
                        note = monomethyllysine
SITE                    32
                        note = monomethyllysine
SITE                    45
                        note = monomethyllysine
SEQUENCE: 343
CAXEKIAALS EIIWLPCLTY AQIXAFIXXL NXDPCQSSEI LSEAXELCS              49

SEQ ID NO: 344          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    28
                        note = monomethyllysine
SITE                    29
                        note = monomethyllysine
SITE                    45
                        note = monomethyllysine
SEQUENCE: 344
CAXEKIAALS EIIWLPCLTY AQIXAFIXXL NDDPCQSSEI LSEAXELCS              49

SEQ ID NO: 345          moltype = AA  length = 49
FEATURE                 Location/Qualifiers
source                  1..49
                        mol_type = protein
                        organism = synthetic construct
```

```
SITE                  3
                      note = trimethyllysine
SITE                  24
                      note = monomethyllysine
SITE                  28
                      note = monomethyllysine
SITE                  29
                      note = monomethyllysine
SITE                  45
                      note = monomethyllysine
SEQUENCE: 345
CAXEKIAALS EIIWLPCLTY AQIXAFIXXL NDDPCQSSEI LSEAXEQCS              49

SEQ ID NO: 346        moltype = AA  length = 49
FEATURE               Location/Qualifiers
source                1..49
                      mol_type = protein
                      organism = synthetic construct
SITE                  3
                      note = trimethyllysine
SITE                  24
                      note = monomethyllysine
SITE                  28
                      note = monomethyllysine
SITE                  29
                      note = monomethyllysine
SEQUENCE: 346
CAXEKIAALS EIIWLPCLTY AQIXAFIXXL NDDPCQSSEI LSEAKELCS              49

SEQ ID NO: 347        moltype = AA  length = 49
FEATURE               Location/Qualifiers
source                1..49
                      mol_type = protein
                      organism = synthetic construct
SITE                  3
                      note = trimethyllysine
SITE                  24
                      note = monomethyllysine
SITE                  29
                      note = monomethyllysine
SITE                  32
                      note = monomethyllysine
SITE                  45
                      note = trimethyllysine
SEQUENCE: 347
CAXEKIAALS EIIWLPCLTY AQIXAFIAXL NXDPCQSSEI LSEAXELCS              49

SEQ ID NO: 348        moltype = AA  length = 49
FEATURE               Location/Qualifiers
source                1..49
                      mol_type = protein
                      organism = synthetic construct
SITE                  3
                      note = trimethyllysine
SITE                  24
                      note = monomethyllysine
SEQUENCE: 348
CAXEKIAALS EIIWLPCLTY AQIXAFIAAL ADDPCQSSEI LSEAKELCS              49

SEQ ID NO: 349        moltype = AA  length = 49
FEATURE               Location/Qualifiers
source                1..49
                      mol_type = protein
                      organism = synthetic construct
SITE                  3
                      note = trimethyllysine
SITE                  24
                      note = monomethyllysine
SEQUENCE: 349
CAXEKIAALS EIIWLPCLTY AQIXAFIAAL EDDPCQSSEI LSEAKELCS              49

SEQ ID NO: 350        moltype = AA  length = 49
FEATURE               Location/Qualifiers
source                1..49
                      mol_type = protein
                      organism = synthetic construct
SITE                  3
                      note = trimethyllysine
SITE                  24
```

```
                         note = monomethyllysine
SEQUENCE: 350
CAXEKIAALS EIIWLPCLTY AQIXAFIAAL IDDPCQSSEI LSEAKELCS               49

SEQ ID NO: 351           moltype = AA  length = 49
FEATURE                  Location/Qualifiers
source                   1..49
                         mol_type = protein
                         organism = synthetic construct
SITE                     3
                         note = trimethyllysine
SITE                     24
                         note = monomethyllysine
SEQUENCE: 351
CAXEKIAALS EIIWLPCLTY AQIXAFIAAL KDDPCQSSEI LSEAKELCS               49

SEQ ID NO: 352           moltype = AA  length = 49
FEATURE                  Location/Qualifiers
source                   1..49
                         mol_type = protein
                         organism = synthetic construct
SITE                     3
                         note = trimethyllysine
SITE                     24
                         note = monomethyllysine
SITE                     32
                         note = citrulline
SITE                     45
                         note = monomethyllysine
SEQUENCE: 352
CAXEKIAALS EIIWLPCLTY AQIXAFIAAL NXDPCQSSEI LSEAXELCS               49

SEQ ID NO: 353           moltype = AA  length = 49
FEATURE                  Location/Qualifiers
source                   1..49
                         mol_type = protein
                         organism = synthetic construct
SITE                     3
                         note = trimethyllysine
SITE                     24
                         note = monomethyllysine
SITE                     32
                         note = monomethyllysine
SITE                     36
                         note = citrulline
SITE                     45
                         note = monomethyllysine
SEQUENCE: 353
CAXEKIAALS EIIWLPCLTY AQIXAFIAAL NXDPCXSSEI LSEAXELCS               49

SEQ ID NO: 354           moltype = AA  length = 49
FEATURE                  Location/Qualifiers
source                   1..49
                         mol_type = protein
                         organism = synthetic construct
SITE                     3
                         note = trimethyllysine
SITE                     24
                         note = monomethyllysine
SITE                     32
                         note = monomethyllysine
SITE                     45
                         note = monomethyllysine
SEQUENCE: 354
CAXEKIAALS EIIWLPCLTY AQIXAFIAAL NXDPCNSSEI LSEAXELCS               49

SEQ ID NO: 355           moltype = AA  length = 49
FEATURE                  Location/Qualifiers
source                   1..49
                         mol_type = protein
                         organism = synthetic construct
SITE                     3
                         note = trimethyllysine
SITE                     24
                         note = monomethyllysine
SITE                     32
                         note = monomethyllysine
SITE                     45
                         note = monomethyllysine
```

```
SEQUENCE: 355
CAXEKIAALS EIIWLPCLTY AQIXAFIAAL NXDPCNSSEI LSEAXEQCS              49

SEQ ID NO: 356          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    32
                        note = monomethyllysine
SITE                    43
                        note = monomethyllysine
SITE                    45
                        note = monomethyllysine
SEQUENCE: 356
CAXEKIAALS EIIWLPCLTY AQIXAFIAAL NXDPCQSSEI LSXAXELCS              49

SEQ ID NO: 357          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    32
                        note = monomethyllysine
SITE                    45
                        note = monomethyllysine
SITE                    46
                        note = citrulline
SEQUENCE: 357
CAXEKIAALS EIIWLPCLTY AQIXAFIAAL NXDPCQSSEI LSEAXXLCS              49

SEQ ID NO: 358          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    32
                        note = monomethyllysine
SITE                    45
                        note = monomethyllysine
SEQUENCE: 358
CAXEKIAALS EIIWLPCLTY AQIXAFIAAL NXDPCQSSEI LSEAXALCS              49

SEQ ID NO: 359          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    32
                        note = monomethyllysine
SITE                    45
                        note = monomethyllysine
SEQUENCE: 359
CAXEKIAALS EIIWLPCLTY AQIXAFIAAL NXDPCQSSEI LSEAXELCS              49

SEQ ID NO: 360          moltype = AA  length = 49
FEATURE                 Location/Qualifiers
source                  1..49
                        mol_type = protein
                        organism = synthetic construct
SITE                    3
                        note = trimethyllysine
SITE                    24
```

```
                         note = monomethyllysine
SITE                     32
                         note = monomethyllysine
SITE                     45
                         note = monomethyllysine
SEQUENCE: 360
CAXEKIAALS EIIWLPCLTY AQIXAFIAAL NXDPCQSSEI LSEAXEQCS               49

SEQ ID NO: 361           moltype = AA  length = 49
FEATURE                  Location/Qualifiers
source                   1..49
                         mol_type = protein
                         organism = synthetic construct
SITE                     3
                         note = trimethyllysine
SITE                     24
                         note = monomethyllysine
SITE                     32
                         note = monomethyllysine
SITE                     45
                         note = monomethyllysine
SEQUENCE: 361
CAXEKIAALS EIIWLPCLTY AQIXAFIAAL NXDPCQSSEI LSEAXLLCS               49

SEQ ID NO: 362           moltype = AA  length = 49
FEATURE                  Location/Qualifiers
source                   1..49
                         mol_type = protein
                         organism = synthetic construct
SITE                     3
                         note = trimethyllysine
SITE                     24
                         note = monomethyllysine
SITE                     32
                         note = monomethyllysine
SITE                     45
                         note = dimethyllysine
SEQUENCE: 362
CAXEKIAALS EIIWLPCLTY AQIXAFIAAL NXDPCQSSEI LSEAXELCS               49

SEQ ID NO: 363           moltype = AA  length = 49
FEATURE                  Location/Qualifiers
source                   1..49
                         mol_type = protein
                         organism = synthetic construct
SITE                     3
                         note = trimethyllysine
SITE                     24
                         note = monomethyllysine
SITE                     32
                         note = monomethyllysine
SITE                     46
                         note = citrulline
SEQUENCE: 363
CAXEKIAALS EIIWLPCLTY AQIXAFIAAL NXDPCQSSEI LSEAKXLCS               49

SEQ ID NO: 364           moltype = AA  length = 49
FEATURE                  Location/Qualifiers
source                   1..49
                         mol_type = protein
                         organism = synthetic construct
SITE                     3
                         note = trimethyllysine
SITE                     24
                         note = monomethyllysine
SITE                     32
                         note = monomethyllysine
SEQUENCE: 364
CAXEKIAALS EIIWLPCLTY AQIXAFIAAL NXDPCQSSEI LSEAKALCS               49

SEQ ID NO: 365           moltype = AA  length = 49
FEATURE                  Location/Qualifiers
source                   1..49
                         mol_type = protein
                         organism = synthetic construct
SITE                     3
                         note = trimethyllysine
SITE                     24
                         note = monomethyllysine
```

-continued

```
SITE                    32
                        note = monomethyllysine
SEQUENCE: 365
CAXEKIAALS EIIWLPCLTY AQIXAFIAAL NXDPCQSSEI LSEAKELCS              49

SEQ ID NO: 366          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    32
                        note = monomethyllysine
SEQUENCE: 366
CAXEKIAALS EIIWLPCLTY AQIXAFIAAL NXDPCQSSEI LSEAKLLCS              49

SEQ ID NO: 367          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    32
                        note = monomethyllysine
SEQUENCE: 367
CAXEKIAALS EIIWLPCLTY AQIXAFIAAL NXDPCQSSEI LSEARELCS              49

SEQ ID NO: 368          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    32
                        note = monomethyllysine
SITE                    45
                        note = monomethyllysine
SEQUENCE: 368
CAXEKIAALS EIIWLPCLTY AQIXAFIAAL NXDPCQSSEI LSQAXELCS              49

SEQ ID NO: 369          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    32
                        note = monomethyllysine
SITE                    45
                        note = monomethyllysine
SEQUENCE: 369
CAXEKIAALS EIIWLPCLTY AQIXAFIAAL NXDPCQSSEI LSVAXELCS              49

SEQ ID NO: 370          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    32
                        note = monomethyllysine
SITE                    45
                        note = monomethyllysine
SEQUENCE: 370
```

-continued

```
CAXEKIAALS EIIWLPCLTY AQIXAFIAAL NXDPCQSSEI LSYAXELCS              49

SEQ ID NO: 371          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    32
                        note = monomethyllysine
SITE                    45
                        note = monomethyllysine
SEQUENCE: 371
CAXEKIAALS EIIWLPCLTY AQIXAFIAAL NXDPCRSSEI LSEAXELCS              49

SEQ ID NO: 372          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    32
                        note = monomethyllysine
SITE                    45
                        note = monomethyllysine
SEQUENCE: 372
CAXEKIAALS EIIWLPCLTY AQIXAFIAAL NXDPCSSSEI LSEAXELCS              49

SEQ ID NO: 373          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    32
                        note = monomethyllysine
SITE                    45
                        note = monomethyllysine
SEQUENCE: 373
CAXEKIAALS EIIWLPCLTY AQIXAFIAAL NXDPCYSSEI LSEAXELCS              49

SEQ ID NO: 374          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SEQUENCE: 374
CAXEKIAALS EIIWLPCLTY AQIXAFIAAL NADPCQSSEI LSEAKELCS              49

SEQ ID NO: 375          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SEQUENCE: 375
CAXEKIAALS EIIWLPCLTY AQIXAFIAAL NDAPCQSSEI LSEAKELCS              49

SEQ ID NO: 376          moltype = AA  length = 49
FEATURE                 Location/Qualifiers
source                  1..49
                        mol_type = protein
                        organism = synthetic construct
```

```
SITE                  3
                      note = trimethyllysine
SITE                  24
                      note = monomethyllysine
SITE                  45
                      note = monomethyllysine
SEQUENCE: 376
CAXEKIAALS EIIWLPCLTY AQIXAFIAAL NDDPCDSSEI LSEAXELCS              49

SEQ ID NO: 377        moltype = AA  length = 49
FEATURE               Location/Qualifiers
source                1..49
                      mol_type = protein
                      organism = synthetic construct
SITE                  3
                      note = trimethyllysine
SITE                  24
                      note = monomethyllysine
SITE                  45
                      note = monomethyllysine
SEQUENCE: 377
CAXEKIAALS EIIWLPCLTY AQIXAFIAAL NDDPCISSEI LSEAXELCS              49

SEQ ID NO: 378        moltype = AA  length = 49
FEATURE               Location/Qualifiers
source                1..49
                      mol_type = protein
                      organism = synthetic construct
SITE                  3
                      note = trimethyllysine
SITE                  24
                      note = monomethyllysine
SITE                  45
                      note = monomethyllysine
SITE                  46
                      note = citrulline
SEQUENCE: 378
CAXEKIAALS EIIWLPCLTY AQIXAFIAAL NDDPCNSSEI LSEAXXLCS              49

SEQ ID NO: 379        moltype = AA  length = 49
FEATURE               Location/Qualifiers
source                1..49
                      mol_type = protein
                      organism = synthetic construct
SITE                  3
                      note = trimethyllysine
SITE                  24
                      note = monomethyllysine
SITE                  45
                      note = monomethyllysine
SEQUENCE: 379
CAXEKIAALS EIIWLPCLTY AQIXAFIAAL NDDPCNSSEI LSEAXALCS              49

SEQ ID NO: 380        moltype = AA  length = 49
FEATURE               Location/Qualifiers
source                1..49
                      mol_type = protein
                      organism = synthetic construct
SITE                  3
                      note = trimethyllysine
SITE                  24
                      note = monomethyllysine
SITE                  45
                      note = monomethyllysine
SEQUENCE: 380
CAXEKIAALS EIIWLPCLTY AQIXAFIAAL NDDPCNSSEI LSEAXEQCS              49

SEQ ID NO: 381        moltype = AA  length = 49
FEATURE               Location/Qualifiers
source                1..49
                      mol_type = protein
                      organism = synthetic construct
SITE                  3
                      note = trimethyllysine
SITE                  24
                      note = monomethyllysine
SITE                  45
                      note = monomethyllysine
SEQUENCE: 381
```

```
CAXEKIAALS EIIWLPCLTY AQIXAFIAAL NDDPCNSSEI LSEAXLLCS             49

SEQ ID NO: 382          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 382
CAXEKIAALS EIIWLPCLTY AQIXAFIAAL NDDPCNSSEI LSEAXQLCS             49

SEQ ID NO: 383          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 383
CAXEKIAALS EIIWLPCLTY AQIXAFIAAL NDDPCNSSEI LSEAXSLCS             49

SEQ ID NO: 384          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 384
CAXEKIAALS EIIWLPCLTY AQIXAFIAAL NDDPCNSSEI LSEAXYLCS             49

SEQ ID NO: 385          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    43
                        note = monomethyllysine
SITE                    45
                        note = monomethyllysine
SEQUENCE: 385
CAXEKIAALS EIIWLPCLTY AQIXAFIAAL NDDPCQSSEI LSXAXELCS             49

SEQ ID NO: 386          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SEQUENCE: 386
CAXEKIAALS EIIWLPCLTY AQIXAFIAAL NDDPCQSSEI LSEAKEACS             49

SEQ ID NO: 387          moltype = AA  length = 49
FEATURE                 Location/Qualifiers
source                  1..49
                        mol_type = protein
                        organism = synthetic construct
SITE                    3
                        note = trimethyllysine
```

```
SITE                   24
                       note = monomethyllysine
SEQUENCE: 387
CAXEKIAALS EIIWLPCLTY AQIXAFIAAL NDDPCQSSEI LSEAKEECS              49

SEQ ID NO: 388         moltype = AA  length = 49
FEATURE                Location/Qualifiers
source                 1..49
                       mol_type = protein
                       organism = synthetic construct
SITE                   3
                       note = trimethyllysine
SITE                   24
                       note = monomethyllysine
SEQUENCE: 388
CAXEKIAALS EIIWLPCLTY AQIXAFIAAL NDDPCQSSEI LSEAKEFCS              49

SEQ ID NO: 389         moltype = AA  length = 49
FEATURE                Location/Qualifiers
source                 1..49
                       mol_type = protein
                       organism = synthetic construct
SITE                   3
                       note = trimethyllysine
SITE                   24
                       note = monomethyllysine
SEQUENCE: 389
CAXEKIAALS EIIWLPCLTY AQIXAFIAAL NDDPCQSSEI LSEAKELCS              49

SEQ ID NO: 390         moltype = AA  length = 49
FEATURE                Location/Qualifiers
source                 1..49
                       mol_type = protein
                       organism = synthetic construct
SITE                   3
                       note = trimethyllysine
SITE                   24
                       note = monomethyllysine
SEQUENCE: 390
CAXEKIAALS EIIWLPCLTY AQIXAFIAAL NDDPCQSSEI LSEAKENCS              49

SEQ ID NO: 391         moltype = AA  length = 49
FEATURE                Location/Qualifiers
source                 1..49
                       mol_type = protein
                       organism = synthetic construct
SITE                   3
                       note = trimethyllysine
SITE                   24
                       note = monomethyllysine
SEQUENCE: 391
CAXEKIAALS EIIWLPCLTY AQIXAFIAAL NDDPCQSSEI LSEAKEQCS              49

SEQ ID NO: 392         moltype = AA  length = 49
FEATURE                Location/Qualifiers
source                 1..49
                       mol_type = protein
                       organism = synthetic construct
SITE                   3
                       note = trimethyllysine
SITE                   24
                       note = monomethyllysine
SEQUENCE: 392
CAXEKIAALS EIIWLPCLTY AQIXAFIAAL NDDPCQSSEI LSEAKESCS              49

SEQ ID NO: 393         moltype = AA  length = 49
FEATURE                Location/Qualifiers
source                 1..49
                       mol_type = protein
                       organism = synthetic construct
SITE                   3
                       note = trimethyllysine
SITE                   24
                       note = monomethyllysine
SEQUENCE: 393
CAXEKIAALS EIIWLPCLTY AQIXAFIAAL NDDPCQSSEI LSEAQELCS              49

SEQ ID NO: 394         moltype = AA  length = 49
FEATURE                Location/Qualifiers
```

```
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 394
CAXEKIAALS EIIWLPCLTY AQIXAFIAAL NDDPCQSSEI LSHAXELCS              49

SEQ ID NO: 395          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 395
CAXEKIAALS EIIWLPCLTY AQIXAFIAAL NDDPCQSSEI LSKAXELCS              49

SEQ ID NO: 396          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 396
CAXEKIAALS EIIWLPCLTY AQIXAFIAAL NDDPCQSSEI LSRAXELCS              49

SEQ ID NO: 397          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 397
CAXEKIAALS EIIWLPCLTY AQIXAFIAAL NDDPCQSSEI LSVAXELCS              49

SEQ ID NO: 398          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 398
CAXEKIAALS EIIWLPCLTY AQIXAFIAAL NDDPCQSSEI LSYAXELCS              49

SEQ ID NO: 399          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SEQUENCE: 399
CAXEKIAALS EIIWLPCLTY AQIXAFIAAL NADPCQSSEI LSEAKELCS              49
```

```
SEQ ID NO: 400         moltype = AA  length = 49
FEATURE                Location/Qualifiers
source                 1..49
                       mol_type = protein
                       organism = synthetic construct
SITE                   3
                       note = trimethyllysine
SITE                   24
                       note = monomethyllysine
SEQUENCE: 400
CAXEKIAALS EIIWLPCLTY AQIXAFIAAL NKDPCQSSEI LSEAKELCS              49

SEQ ID NO: 401         moltype = AA  length = 49
FEATURE                Location/Qualifiers
source                 1..49
                       mol_type = protein
                       organism = synthetic construct
SITE                   3
                       note = trimethyllysine
SITE                   24
                       note = monomethyllysine
SITE                   32
                       note = monomethyllysine
SEQUENCE: 401
CAXEKIAALS EIIWLPCLTY AQIXAFIAAL NXDPCQSSEI LSEAKELCS              49

SEQ ID NO: 402         moltype = AA  length = 49
FEATURE                Location/Qualifiers
source                 1..49
                       mol_type = protein
                       organism = synthetic construct
SITE                   24
                       note = monomethyllysine
SITE                   45
                       note = monomethyllysine
SEQUENCE: 402
CAREKINALG EIIWLPCLTY DQIXAFIAAL NDDPCQSSEI LSEAXELCS              49

SEQ ID NO: 403         moltype = AA  length = 49
FEATURE                Location/Qualifiers
source                 1..49
                       mol_type = protein
                       organism = synthetic construct
SITE                   3
                       note = trimethyllysine
SITE                   24
                       note = monomethyllysine
SEQUENCE: 403
CAXEKIAALS EIIWLPCLTY AQIXAFIAAL NRDPCQSSEI LSEAKELCS              49

SEQ ID NO: 404         moltype = AA  length = 49
FEATURE                Location/Qualifiers
source                 1..49
                       mol_type = protein
                       organism = synthetic construct
SITE                   24
                       note = monomethyllysine
SITE                   29
                       note = monomethyllysine
SITE                   45
                       note = monomethyllysine
SEQUENCE: 404
CAREKINALG EIIWLPCLTY DQIXAFIAXL NDDPCQSAEI LSEAXELCS              49

SEQ ID NO: 405         moltype = AA  length = 49
FEATURE                Location/Qualifiers
source                 1..49
                       mol_type = protein
                       organism = synthetic construct
SITE                   24
                       note = monomethyllysine
SITE                   29
                       note = monomethyllysine
SITE                   45
                       note = monomethyllysine
SEQUENCE: 405
CAREKINALG EIIWLPCLTY DQIXAFIAXL NDDPCQSANI LSEAXELCS              49
```

-continued

```
SEQ ID NO: 406          moltype = AA  length = 49
FEATURE                 Location/Qualifiers
source                  1..49
                        mol_type = protein
                        organism = synthetic construct
SITE                    24
                        note = monomethyllysine
SITE                    29
                        note = monomethyllysine
SITE                    45
                        note = monomethyllysine
SEQUENCE: 406
CAREKINALG EIIWLPCLTY DQIXAFIAXL NDDPCQSANI LAEAXELCS              49

SEQ ID NO: 407          moltype = AA  length = 49
FEATURE                 Location/Qualifiers
source                  1..49
                        mol_type = protein
                        organism = synthetic construct
SITE                    24
                        note = monomethyllysine
SITE                    29
                        note = monomethyllysine
SEQUENCE: 407
CAREKINALG EIIWLPCLTY DQIXAFIAXL NDDPCQSAEI LSEAQELCS              49

SEQ ID NO: 408          moltype = AA  length = 49
FEATURE                 Location/Qualifiers
source                  1..49
                        mol_type = protein
                        organism = synthetic construct
SITE                    3
                        note = monomethyllysine
SITE                    24
                        note = monomethyllysine
SEQUENCE: 408
CAREKINALG EIIWLPCLTY DQIXAFIAXL NDDPCQSANI LSEAQELCS              49

SEQ ID NO: 409          moltype = AA  length = 49
FEATURE                 Location/Qualifiers
source                  1..49
                        mol_type = protein
                        organism = synthetic construct
SITE                    24
                        note = monomethyllysine
SITE                    29
                        note = monomethyllysine
SEQUENCE: 409
CAREKINALG EIIWLPCLTY DQIXAFIAXL NDDPCQSANI LAEAQELCS              49

SEQ ID NO: 410          moltype = AA  length = 49
FEATURE                 Location/Qualifiers
source                  1..49
                        mol_type = protein
                        organism = synthetic construct
SITE                    24
                        note = dimethyllysine
SEQUENCE: 410
CASEKIAALS EIIWLPCLTY AQIXAFIAAL NDDPCQSSEI LSEAKELCS              49

SEQ ID NO: 411          moltype = AA  length = 49
FEATURE                 Location/Qualifiers
source                  1..49
                        mol_type = protein
                        organism = synthetic construct
SITE                    24
                        note = dimethyllysine
SEQUENCE: 411
CAHEKIAALS EIIWLPCLTY AQIXAFIAAL NDDPCQSSEI LSEAKELCS              49

SEQ ID NO: 412          moltype = AA  length = 49
FEATURE                 Location/Qualifiers
source                  1..49
                        mol_type = protein
                        organism = synthetic construct
SITE                    24
                        note = dimethyllysine
SEQUENCE: 412
CAYEKIAALS EIIWLPCLTY AQIXAFIAAL NDDPCQSSEI LSEAKELCS              49
```

```
SEQ ID NO: 413          moltype = AA  length = 49
FEATURE                 Location/Qualifiers
source                  1..49
                        mol_type = protein
                        organism = synthetic construct
SITE                    24
                        note = dimethyllysine
SEQUENCE: 413
CANEKIAALS EIIWLPCLTY AQIXAFIAAL NDDPCQSSEI LSEAKELCS              49

SEQ ID NO: 414          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    29
                        note = monomethyllysine
SEQUENCE: 414
CAXEKINALG EIIWLPCLTY DQIXAFIAXL NDDPCQSSEI LSEAKELCS              49

SEQ ID NO: 415          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    29
                        note = monomethyllysine
SITE                    45
                        note = monomethyllysine
SEQUENCE: 415
CAXEKINALG EIIWLPCLTY DQIXAFIAXL NDDPCQSSEI LSEAXELCS              49

SEQ ID NO: 416          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    29
                        note = monomethyllysine
SEQUENCE: 416
CAXEKINALG EIIWLPCLTY DQIXAFIAXL NDDPCQSSEI LSEAQELCS              49

SEQ ID NO: 417          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 417
CAXEKINALG EIIWLPCLTY DQIXAFIAAL NDDPCQSSEI LSEAXELCS              49

SEQ ID NO: 418          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SEQUENCE: 418
```

-continued

```
CAXEKINALG EIIWLPCLTY DQIXAFIAAL NDDPCQSSEI LSEAQELCS              49

SEQ ID NO: 419          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SEQUENCE: 419
CAXEKIAALS EIIWLPCLTY AQIXAFIAAL NDSPCQSSEI LSEAKELCS              49

SEQ ID NO: 420          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SEQUENCE: 420
CAXEKIAALS EIIWLPCLTY AQIXAFIAAL NDYPCQSSEI LSEAKELCS              49

SEQ ID NO: 421          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SEQUENCE: 421
CAXEKIAALS EIIWLPCLTY AQIXAFIAAL NDAPCQSSEI LSEAKELCS              49

SEQ ID NO: 422          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SEQUENCE: 422
CAXEKIAALS EIIWLPCLTY AQIXAFIAAL NDQPCQSSEI LSEAKELCS              49

SEQ ID NO: 423          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SEQUENCE: 423
CAXEKIAALS EIIWLPCLTY AQIXAFIAAL NDLPCQSSEI LSEAKELCS              49

SEQ ID NO: 424          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SEQUENCE: 424
CAXEKIAALS EIIWLPCLTY AQIXAFIAAL NDRPCQSSEI LSEAKELCS              49

SEQ ID NO: 425          moltype = AA  length = 49
FEATURE                 Location/Qualifiers
source                  1..49
                        mol_type = protein
                        organism = synthetic construct
```

```
SITE                  3
                      note = Rme2s
SITE                  24
                      note = monomethyllysine
SITE                  29
                      note = monomethyllysine
SITE                  45
                      note = monomethyllysine
SEQUENCE: 425
CAXEKINALG EIIWLPCLTY DQIXAFIAXL NDDPCQSSEI LSEAXELCS              49

SEQ ID NO: 426        moltype = AA  length = 49
FEATURE               Location/Qualifiers
source                1..49
                      mol_type = protein
                      organism = synthetic construct
SITE                  24
                      note = monomethyllysine
SITE                  29
                      note = monomethyllysine
SITE                  45
                      note = monomethyllysine
SEQUENCE: 426
CAREKINALG EIIWLPCLTY DQIXAFIAXL NDDPCQSSEI LSEAXELCS              49

SEQ ID NO: 427        moltype = AA  length = 49
FEATURE               Location/Qualifiers
source                1..49
                      mol_type = protein
                      organism = synthetic construct
SITE                  3
                      note = trimethyllysine
SITE                  24
                      note = monomethyllysine
SEQUENCE: 427
CAXEKIAALS EIIWLPCLTY AQIXAFIAAL NDDPCQSSEI LSEAKEQCS              49

SEQ ID NO: 428        moltype = AA  length = 49
FEATURE               Location/Qualifiers
source                1..49
                      mol_type = protein
                      organism = synthetic construct
SITE                  3
                      note = trimethyllysine
SITE                  24
                      note = monomethyllysine
SEQUENCE: 428
CAXEKIAALS EIIWLPCLTY AQIXAFIAAL NDDPCQSSEI LSEAKEECS              49

SEQ ID NO: 429        moltype = AA  length = 49
FEATURE               Location/Qualifiers
source                1..49
                      mol_type = protein
                      organism = synthetic construct
SITE                  3
                      note = trimethyllysine
SITE                  24
                      note = dimethyllysine
SEQUENCE: 429
CAXEKIAALS EIIWLPCLTY AQIXAFIAAL NDDPCQSSEI LSEAKESCS              49

SEQ ID NO: 430        moltype = AA  length = 49
FEATURE               Location/Qualifiers
source                1..49
                      mol_type = protein
                      organism = synthetic construct
SITE                  3
                      note = trimethyllysine
SITE                  24
                      note = dimethyllysine
SEQUENCE: 430
CAXEKIAALS EIIWLPCLTY AQIXAFIAAL NDDPCQSSEI LSEAKEACS              49

SEQ ID NO: 431        moltype = AA  length = 49
FEATURE               Location/Qualifiers
source                1..49
                      mol_type = protein
                      organism = synthetic construct
SITE                  3
```

```
                        note = trimethyllysine
SITE                    24
                        note = dimethyllysine
SEQUENCE: 431
CAXEKIAALS EIIWLPCLTY AQIXAFIAAL NDDPCQSSEI LSEAKENCS               49

SEQ ID NO: 432          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SEQUENCE: 432
CAXEKIAALS EIIWLPCLTY AQIXAFIAAL NDDPCQSSEI LSEAKEFCS               49

SEQ ID NO: 433          moltype = AA  length = 49
FEATURE                 Location/Qualifiers
source                  1..49
                        mol_type = protein
                        organism = synthetic construct
SITE                    24
                        note = monomethyllysine
SITE                    29
                        note = monomethyllysine
SITE                    45
                        note = monomethyllysine
SEQUENCE: 433
CAREKINALG EIIWLPCLTY DQIXAFIAXL NRDPCQSSEI LSEAXELCS               49

SEQ ID NO: 434          moltype = AA  length = 49
FEATURE                 Location/Qualifiers
source                  1..49
                        mol_type = protein
                        organism = synthetic construct
SITE                    24
                        note = monomethyllysine
SITE                    45
                        note = monomethyllysine
SEQUENCE: 434
CAREKINALG EIIWLPCLTY DQIXAFIAAL NADPCQSSEI LSEAXELCS               49

SEQ ID NO: 435          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SEQUENCE: 435
CAXQKIAALS EIIWLPCLTY AQIXAFIAAL NDDPCQSSEI LSEAKELCS               49

SEQ ID NO: 436          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SEQUENCE: 436
CAXAKIAALS EIIWLPCLTY AQIXAFIAAL NDDPCQSSEI LSEAKELCS               49

SEQ ID NO: 437          moltype = AA  length = 49
FEATURE                 Location/Qualifiers
source                  1..49
                        mol_type = protein
                        organism = synthetic construct
SITE                    24
                        note = dimethyllysine
SITE                    45
                        note = monomethyllysine
SEQUENCE: 437
CAREKINALG EIIWLPCLTY DQIXAFIAAL NDDPCQSSEI LSEAXELCS               49
```

```
SEQ ID NO: 438         moltype = AA  length = 49
FEATURE                Location/Qualifiers
source                 1..49
                       mol_type = protein
                       organism = synthetic construct
SITE                   24
                       note = dimethyllysine
SEQUENCE: 438
CAREKINALG EIIWLPCLTY DQIXAFIAAL NDDPCQSSEI LSEAQELCS              49

SEQ ID NO: 439         moltype = AA  length = 49
FEATURE                Location/Qualifiers
source                 1..49
                       mol_type = protein
                       organism = synthetic construct
SITE                   3
                       note = trimethyllysine
SITE                   24
                       note = dimethyllysine
SITE                   45
                       note = monomethyllysine
SEQUENCE: 439
CAXEKINALG EIIWLPCLTY DQIXAFIAAL NDDPCQSSEI LSEAXELCS              49

SEQ ID NO: 440         moltype = AA  length = 49
FEATURE                Location/Qualifiers
source                 1..49
                       mol_type = protein
                       organism = synthetic construct
SITE                   24
                       note = monomethyllysine
SITE                   45
                       note = monomethyllysine
SEQUENCE: 440
CAREKINALG EIIWLPCLTY EQIXAFIAAL NDDPCQSANI LAEAXELCS              49

SEQ ID NO: 441         moltype = AA  length = 49
FEATURE                Location/Qualifiers
source                 1..49
                       mol_type = protein
                       organism = synthetic construct
SITE                   24
                       note = monomethyllysine
SITE                   45
                       note = monomethyllysine
SEQUENCE: 441
CAREKINALG EIIWLPCLTY QQIXAFIAAL NDDPCQSANI LAEAXELCS              49

SEQ ID NO: 442         moltype = AA  length = 49
FEATURE                Location/Qualifiers
source                 1..49
                       mol_type = protein
                       organism = synthetic construct
SITE                   24
                       note = monomethyllysine
SITE                   45
                       note = monomethyllysine
SEQUENCE: 442
CAREKINALG EIIWLPCLTY LQIXAFIAAL NDDPCQSANI LAEAXELCS              49

SEQ ID NO: 443         moltype = AA  length = 49
FEATURE                Location/Qualifiers
source                 1..49
                       mol_type = protein
                       organism = synthetic construct
SITE                   24
                       note = monomethyllysine
SITE                   45
                       note = monomethyllysine
SEQUENCE: 443
CAREKINALG EIIWLPCLTY YQIXAFIAAL NDDPCQSANI LAEAXELCS              49

SEQ ID NO: 444         moltype = AA  length = 49
FEATURE                Location/Qualifiers
source                 1..49
                       mol_type = protein
                       organism = synthetic construct
SITE                   24
```

```
                         note = monomethyllysine
SITE                     45
                         note = monomethyllysine
SEQUENCE: 444
CAREKINALG EIIWLPCLTY KQIXAFIAAL NDDPCQSANI LAEAXELCS              49

SEQ ID NO: 445           moltype = AA  length = 49
FEATURE                  Location/Qualifiers
source                   1..49
                         mol_type = protein
                         organism = synthetic construct
SITE                     3
                         note = trimethyllysine
SITE                     24
                         note = monomethyllysine
SITE                     28
                         note = monomethyllysine
SITE                     45
                         note = monomethyllysine
SEQUENCE: 445
CAXEKIAALS EIIWLPCLTY AQIXYFIXAL NDDPCQSSEI LSEAXELCS              49

SEQ ID NO: 446           moltype = AA  length = 49
FEATURE                  Location/Qualifiers
source                   1..49
                         mol_type = protein
                         organism = synthetic construct
SITE                     3
                         note = Rme2a
SITE                     24
                         note = monomethyllysine
SITE                     29
                         note = monomethyllysine
SITE                     45
                         note = monomethyllysine
SEQUENCE: 446
CAXEKINALG EIIWLPCLTY DQIXAFIAXL NDDPCQSSEI LSEAXELCS              49

SEQ ID NO: 447           moltype = AA  length = 49
FEATURE                  Location/Qualifiers
source                   1..49
                         mol_type = protein
                         organism = synthetic construct
SITE                     24
                         note = monomethyllysine
SITE                     29
                         note = dimethyllysine
SITE                     45
                         note = monomethyllysine
SEQUENCE: 447
CAREKINALG EIIWLPCLTY DQIXAFIAXL NADPCQSSEI LSEAXELCS              49

SEQ ID NO: 448           moltype = AA  length = 49
FEATURE                  Location/Qualifiers
source                   1..49
                         mol_type = protein
                         organism = synthetic construct
SITE                     24
                         note = monomethyllysine
SITE                     45
                         note = monomethyllysine
SEQUENCE: 448
CAREKINALG EIIWLPCLTY DQIXAFIAAL NRDPCQSSEI LSEAXELCS              49

SEQ ID NO: 449           moltype = AA  length = 49
FEATURE                  Location/Qualifiers
source                   1..49
                         mol_type = protein
                         organism = synthetic construct
SITE                     24
                         note = monomethyllysine
SITE                     45
                         note = monomethyllysine
SEQUENCE: 449
CAREKINALG EIIWLPCLTY DQIXAFIARL NDDPCQSSEI LSEAXELCS              49

SEQ ID NO: 450           moltype = AA  length = 49
FEATURE                  Location/Qualifiers
source                   1..49
```

```
                         mol_type = protein
                         organism = synthetic construct
SITE                     24
                         note = monomethyllysine
SITE                     29
                         note = monomethyllysine
SITE                     45
                         note = trimethyllysine
SEQUENCE: 450
CAREKINALG EIIWLPCLTY DQIXAFIAXL NDDPCQSSEI LSEAXELCS               49

SEQ ID NO: 451           moltype = AA  length = 49
FEATURE                  Location/Qualifiers
source                   1..49
                         mol_type = protein
                         organism = synthetic construct
SITE                     24
                         note = monomethyllysine
SITE                     45
                         note = trimethyllysine
SEQUENCE: 451
CAREKINALG EIIWLPCLTY DQIXAFIAAL NDDPCQSSEI LSEAXELCS               49

SEQ ID NO: 452           moltype = AA  length = 49
FEATURE                  Location/Qualifiers
source                   1..49
                         mol_type = protein
                         organism = synthetic construct
SITE                     3
                         note = trimethyllysine
SITE                     24
                         note = monomethyllysine
SITE                     45
                         note = monomethyllysine
SEQUENCE: 452
CAXEKIAALS EIIWLPCLKY AQIXAFIAAL NDDPCQSSEI LSEAXELCS               49

SEQ ID NO: 453           moltype = AA  length = 49
FEATURE                  Location/Qualifiers
source                   1..49
                         mol_type = protein
                         organism = synthetic construct
SITE                     3
                         note = trimethyllysine
SITE                     24
                         note = monomethyllysine
SITE                     29
                         note = monomethyllysine
SITE                     45
                         note = monomethyllysine
SEQUENCE: 453
CAXEKIAALS EIIWLPCLXY AQIXAFIAAL NDDPCQSSEI LSEAXELCS               49

SEQ ID NO: 454           moltype = AA  length = 49
FEATURE                  Location/Qualifiers
source                   1..49
                         mol_type = protein
                         organism = synthetic construct
SITE                     3
                         note = trimethyllysine
SITE                     24
                         note = monomethyllysine
SITE                     45
                         note = monomethyllysine
SEQUENCE: 454
CAXEKIAALS SIIWLPCLTY AQIXAFIAAL NDDPCQSSEI LSEAXELCS               49

SEQ ID NO: 455           moltype = AA  length = 49
FEATURE                  Location/Qualifiers
source                   1..49
                         mol_type = protein
                         organism = synthetic construct
SITE                     3
                         note = trimethyllysine
SITE                     24
                         note = monomethyllysine
SITE                     45
                         note = monomethyllysine
SEQUENCE: 455
```

```
CAXEKIAALS QIIWLPCLTY AQIXAFIAAL NDDPCQSSEI LSEAXELCS              49

SEQ ID NO: 456          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 456
CAXEKIAALS VIIWLPCLTY AQIXAFIAAL NDDPCQSSEI LSEAXELCS              49

SEQ ID NO: 457          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    29
                        note = monomethyllysine
SITE                    45
                        note = monomethyllysine
SEQUENCE: 457
CAXEKIAALS EIIWLPCLTY AQIXYFIAXL NDDPCQSSEI LSEAXELCS              49

SEQ ID NO: 458          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    29
                        note = monomethyllysine
SITE                    45
                        note = monomethyllysine
SEQUENCE: 458
CAXEKIAALS EIIWLPCLTY AQIXYFIAAL NXDPCQSSEI LSEAXELCS              49

SEQ ID NO: 459          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 459
CAXEKIAALS EIIWLPCLSY AQIXAFIAAL NDDPCQSSEI LSEAXELCS              49

SEQ ID NO: 460          moltype = AA  length = 49
FEATURE                 Location/Qualifiers
source                  1..49
                        mol_type = protein
                        organism = synthetic construct
SITE                    3
                        note = trimethyllysine
SITE                    24
                        note = dimethyllysine
SITE                    28..29
                        note = monomethyllysine
SITE                    45
                        note = monomethyllysine
SEQUENCE: 460
CAXEKIAALS EIIWLPCLTY AQIXAFIXXL NDDPCQSSEI LSEAXELCS              49

SEQ ID NO: 461          moltype = AA  length = 49
```

```
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    28
                        note = monomethyllysine
SITE                    32
                        note = monomethyllysine
SITE                    45
                        note = dimethyllysine
SEQUENCE: 461
CAXEKIAALS EIIWLPCLTY AQIXAFIXAL NXDPCQSSEI LSEAXELCS                49

SEQ ID NO: 462          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    32
                        note = monomethyllysine
SITE                    45
                        note = monomethyllysine
SEQUENCE: 462
CAXEKIAALS EIIWLPCLTY AQIXAFIARL NXDPCQSSEI LSEAXELCS                49

SEQ ID NO: 463          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 463
CAXEKIAALS YIIWLPCLTY AQIXAFIAAL NDDPCQSSEI LSEAXELCS                49

SEQ ID NO: 464          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 464
CAXEKIAALS KIIWLPCLTY AQIXAFIAAL NDDPCQSSEI LSEAXELCS                49

SEQ ID NO: 465          moltype = AA  length = 49
FEATURE                 Location/Qualifiers
source                  1..49
                        mol_type = protein
                        organism = synthetic construct
SITE                    3
                        note = trimethyllysine
SITE                    24
                        note = dimethyllysine
SITE                    45
                        note = trimethyllysine
SEQUENCE: 465
CAXEKIAALS EIIWLPCLTY AQIXAFIAAL NDDPCQSSEI LSEAXELCS                49

SEQ ID NO: 466          moltype = AA  length = 49
FEATURE                 Location/Qualifiers
source                  1..49
                        mol_type = protein
```

```
                       organism = synthetic construct
SITE                   3
                       note = trimethyllysine
SITE                   24
                       note = dimethyllysine
SITE                   28
                       note = monomethyllysine
SITE                   24
                       note = monomethyllysine
SEQUENCE: 466
CAXEKIAALS EIIWLPCLTY AQIXAFIXAL NDDPCQSSEI LSEAXELCS              49

SEQ ID NO: 467         moltype = AA  length = 49
FEATURE                Location/Qualifiers
source                 1..49
                       mol_type = protein
                       organism = synthetic construct
SITE                   3
                       note = trimethyllysine
SITE                   24
                       note = dimethyllysine
SITE                   28
                       note = monomethyllysine
SITE                   45
                       note = monomethyllysine
SEQUENCE: 467
CAXEKIAALS EIIWLPCLTY AQIXAFIXRL NDDPCQSSEI LSEAXELCS              49

SEQ ID NO: 468         moltype = AA  length = 49
FEATURE                Location/Qualifiers
source                 1..49
                       mol_type = protein
                       organism = synthetic construct
SITE                   3
                       note = trimethyllysine
SITE                   24
                       note = dimethyllysine
SITE                   28..29
                       note = monomethyllysine
SITE                   45
                       note = monomethyllysine
SEQUENCE: 468
CAXEKIAALS EIIWLPCLTY AQIXAFIXXL NDDPCQSSEI LSEAXELCS              49

SEQ ID NO: 469         moltype = AA  length = 49
FEATURE                Location/Qualifiers
source                 1..49
                       mol_type = protein
                       organism = synthetic construct
SITE                   3
                       note = trimethyllysine
SITE                   24
                       note = dimethyllysine
SITE                   28
                       note = monomethyllysine
SITE                   29
                       note = citrulline
SITE                   45
                       note = monomethyllysine
SEQUENCE: 469
CAXEKIAALS EIIWLPCLTY AQIXAFIXXL NDDPCQSSEI LSEAXELCS              49

SEQ ID NO: 470         moltype = AA  length = 49
FEATURE                Location/Qualifiers
source                 1..49
                       mol_type = protein
                       organism = synthetic construct
SITE                   3
                       note = trimethyllysine
SITE                   24
                       note = dimethyllysine
SITE                   28
                       note = monomethyllysine
SITE                   32
                       note = monomethyllysine
SITE                   45
                       note = monomethyllysine
SEQUENCE: 470
CAXEKIAALS EIIWLPCLTY AQIXAFIXAL NXDPCQSSEI LSEAXELCS              49
```

```
SEQ ID NO: 471          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    24
                        note = monomethyllysine
SEQUENCE: 471
CAXEKIAALS EIIWLPCLTY AQIXAFIARL NDDPCQSSEI LSEAXELCS              49

SEQ ID NO: 472          moltype = AA  length = 49
FEATURE                 Location/Qualifiers
source                  1..49
                        mol_type = protein
                        organism = synthetic construct
SITE                    3
                        note = trimethyllysine
SITE                    24
                        note = dimethyllysine
SITE                    29
                        note = citrulline
SITE                    45
                        note = monomethyllysine
SEQUENCE: 472
CAXEKIAALS EIIWLPCLTY AQIXAFIAXL NDDPCQSSEI LSEAXELCS              49

SEQ ID NO: 473          moltype = AA  length = 49
FEATURE                 Location/Qualifiers
source                  1..49
                        mol_type = protein
                        organism = synthetic construct
SITE                    3
                        note = trimethyllysine
SITE                    24
                        note = dimethyllysine
SITE                    28
                        note = monomethyllysine
SITE                    45
                        note = monomethyllysine
SEQUENCE: 473
CAXEKIAALS EIIWLPCLTY AQIXSFIXAL NDDPCQSSEI LSEAXELCS              49

SEQ ID NO: 474          moltype = AA  length = 49
FEATURE                 Location/Qualifiers
source                  1..49
                        mol_type = protein
                        organism = synthetic construct
SITE                    3
                        note = trimethyllysine
SITE                    24
                        note = dimethyllysine
SITE                    45
                        note = monomethyllysine
SEQUENCE: 474
CAXEKIAALS EIIWLPCLTY AQIXEFIAAL NDDPCQSSEI LSEAXELCS              49

SEQ ID NO: 475          moltype = AA  length = 49
FEATURE                 Location/Qualifiers
source                  1..49
                        mol_type = protein
                        organism = synthetic construct
SITE                    3
                        note = trimethyllysine
SITE                    24
                        note = dimethyllysine
SITE                    28
                        note = monomethyllysine
SITE                    45
                        note = monomethyllysine
SEQUENCE: 475
CAXEKIAALS EIIWLPCLTY AQIXEFIXAL NDDPCQSSEI LSEAXELCS              49

SEQ ID NO: 476          moltype = AA  length = 49
FEATURE                 Location/Qualifiers
```

```
source                  1..49
                        mol_type = protein
                        organism = synthetic construct
SITE                    3
                        note = trimethyllysine
SITE                    24
                        note = dimethyllysine
SITE                    28
                        note = citrulline
SITE                    45
                        note = monomethyllysine
SEQUENCE: 476
CAXEKIAALS EIIWLPCLTY AQIXAFIXAL NDDPCQSSEI LSEAXELCS              49

SEQ ID NO: 477          moltype = AA  length = 49
FEATURE                 Location/Qualifiers
source                  1..49
                        mol_type = protein
                        organism = synthetic construct
SITE                    3
                        note = trimethyllysine
SITE                    24
                        note = dimethyllysine
SITE                    25
                        note = citrulline
SITE                    45
                        note = monomethyllysine
SEQUENCE: 477
CAXEKIAALS EIIWLPCLTY AQIXXFIAAL NDDPCQSSEI LSEAXELCS              49

SEQ ID NO: 478          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 478
CAXEKIAALS EIIWLPCLTY AQIXYFIAAL NDDPCQSSEI LSEAXELCS              49

SEQ ID NO: 479          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SEQUENCE: 479
CAXHKIAALS EIIWLPCLTY AQIXAFIAAL NDDPCQSSEI LSEAKELCS              49

SEQ ID NO: 480          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SEQUENCE: 480
CAXVKIAALS EIIWLPCLTY AQIXAFIAAL NDDPCQSSEI LSEAKELCS              49

SEQ ID NO: 481          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SEQUENCE: 481
CAXYKIAALS EIIWLPCLTY AQIXAFIAAL NDDPCQSSEI LSEAKELCS              49
```

```
SEQ ID NO: 482          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 482
CAXEKIAALS EIIWLPCLTY AQIXAFIAAL NDDPCDSSEI LSEAXELCS              49

SEQ ID NO: 483          moltype = AA  length = 49
FEATURE                 Location/Qualifiers
source                  1..49
                        mol_type = protein
                        organism = synthetic construct
SITE                    3
                        note = trimethyllysine
SITE                    5
                        note = monomethyllysine
SITE                    24
                        note = monomethyllysine
SITE                    45
                        note = monomethyllysine
SEQUENCE: 483
CAXEXIAALS EIIWLPCLTY AQIXAFIAAL NDDPCQSSEI LSEAXELCS              49

SEQ ID NO: 484          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SEQUENCE: 484
CAXIKIAALS EIIWLPCLTY AQIXAFIAAL NDDPCQSSEI LSEAKELCS              49

SEQ ID NO: 485          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 485
CAXEKIAALS EIIWLPCLTY AQIXAFIAAL NDDPCSSSEI LSEAXELCS              49

SEQ ID NO: 486          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 486
CAXEKIAALS EIIWLPCLTY AQIXAFIAAL NDDPCYSSEI LSEAXELCS              49

SEQ ID NO: 487          moltype = AA  length = 49
FEATURE                 Location/Qualifiers
source                  1..49
                        mol_type = protein
                        organism = synthetic construct
SITE                    3
                        note = trimethyllysine
SITE                    24
```

```
                        note = monomethyllysine
SITE                    45
                        note = monomethyllysine
SEQUENCE: 487
CAXEKIAALS EIIWLPCLTY AQIXAFIAAL NDDPCISSEI LSEAXELCS              49

SEQ ID NO: 488          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 488
CAXEKIAALS EIIWLPCLTY AQIXAFIAAL NDDPCRSSEI LSEAXELCS              49

SEQ ID NO: 489          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 489
CAXEKINALG EIIWLPCLTY DQIXAFIARL NDDPCQSSEI LSEAXELCS              49

SEQ ID NO: 490          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 490
CAXEKIAALS EIIWLPCLTY AQIXAFIAAL NDDPCQSSEI LSVAXELCS              49

SEQ ID NO: 491          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 491
CAXEKIAALS EIIWLPCLTY AQIXAFIAAL NDDPCQSSEI LSYAXELCS              49

SEQ ID NO: 492          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 492
CAXEKIAALS EIIWLPCLTY AQIXAFIAAL NDDPCQSSEI LSHAXELCS              49

SEQ ID NO: 493          moltype = AA  length = 49
FEATURE                 Location/Qualifiers
source                  1..49
```

```
                        mol_type = protein
                        organism = synthetic construct
SITE                    3
                        note = trimethyllysine
SITE                    24
                        note = monomethyllysine
SITE                    45
                        note = monomethyllysine
SEQUENCE: 493
CAXEKIAALS EIIWLPCLTY AQIXAFIAAL NDDPCQSSEI LSRAXELCS              49

SEQ ID NO: 494          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 494
CAXEKIAALS EIIWLPCLTY AQIXAFIAAL NDDPCQSSEI LSKAXELCS              49

SEQ ID NO: 495          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    43
                        note = monomethyllysine
SITE                    45
                        note = monomethyllysine
SEQUENCE: 495
CAXEKIAALS EIIWLPCLTY AQIXAFIAAL NDDPCQSSEI LSXAXELCS              49

SEQ ID NO: 496          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    45
                        note = monomethyllysine
SEQUENCE: 496
CAXEKIAALS EIIWLPCLTY AQIXYFIARL NDDPCQSSEI LSEAXELCS              49

SEQ ID NO: 497          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    28
                        note = monomethyllysine
SITE                    45
                        note = monomethyllysine
SEQUENCE: 497
CAXEKIAALS EIIWLPCLTY AQIXAFIXRL NDDPCQSSEI LSEAXELCS              49

SEQ ID NO: 498          moltype = AA  length = 49
FEATURE                 Location/Qualifiers
source                  1..49
                        mol_type = protein
                        organism = synthetic construct
SITE                    3
                        note = trimethyllysine
SITE                    24
```

```
                        note = dimethyllysine
SITE                    28
                        note = monomethyllysine
SITE                    45
                        note = monomethyllysine
SEQUENCE: 498
CAXEKIAALS EIIWLPCLTY AQIXQFIXAL NDDPCQSSEI LSEAXELCS              49

SEQ ID NO: 499          moltype = AA  length = 49
FEATURE                 Location/Qualifiers
source                  1..49
                        mol_type = protein
                        organism = synthetic construct
SITE                    24
                        note = monomethyllysine
SITE                    29
                        note = monomethyllysine
SEQUENCE: 499
CAREKINALG EIIWLPCLTY DQIXAFIAXL NDDPCQSSEI LSEARELCS              49

SEQ ID NO: 500          moltype = AA  length = 49
FEATURE                 Location/Qualifiers
source                  1..49
                        mol_type = protein
                        organism = synthetic construct
SITE                    24
                        note = monomethyllysine
SITE                    29
                        note = monomethyllysine
SITE                    45
                        note = hArg
SEQUENCE: 500
CAREKINALG EIIWLPCLTY DQIXAFIAXL NDDPCQSSEI LSEAXELCS              49

SEQ ID NO: 501          moltype = AA  length = 49
FEATURE                 Location/Qualifiers
source                  1..49
                        mol_type = protein
                        organism = synthetic construct
SITE                    24
                        note = monomethyllysine
SITE                    29
                        note = monomethyllysine
SITE                    45
                        note = citrulline
SEQUENCE: 501
CAREKINALG EIIWLPCLTY DQIXAFIAXL NDDPCQSSEI LSEAXELCS              49

SEQ ID NO: 502          moltype = AA  length = 49
FEATURE                 Location/Qualifiers
source                  1..49
                        mol_type = protein
                        organism = synthetic construct
SITE                    24
                        note = dimethyllysine
SITE                    29
                        note = monomethyllysine
SEQUENCE: 502
CAREKINALG EIIWLPCLTY DQIXAFIAXL NDDPCQSSEI LSEAKELCS              49

SEQ ID NO: 503          moltype = AA  length = 49
FEATURE                 Location/Qualifiers
source                  1..49
                        mol_type = protein
                        organism = synthetic construct
SITE                    24
                        note = dimethyllysine
SITE                    29
                        note = monomethyllysine
SITE                    45
                        note = monomethyllysine
SEQUENCE: 503
CAREKINALG EIIWLPCLTY DQIXAFIAXL NDDPCQSSEI LSEAXELCS              49

SEQ ID NO: 504          moltype = AA  length = 49
FEATURE                 Location/Qualifiers
source                  1..49
                        mol_type = protein
                        organism = synthetic construct
```

```
SITE                  24
                      note = dimethyllysine
SITE                  29
                      note = monomethyllysine
SEQUENCE: 504
CAREKINALG EIIWLPCLTY DQIXAFIAXL NDDPCQSSEI LSEAQELCS              49

SEQ ID NO: 505        moltype = AA  length = 49
FEATURE               Location/Qualifiers
source                1..49
                      mol_type = protein
                      organism = synthetic construct
SITE                  3
                      note = trimethyllysine
SITE                  24
                      note = dimethyllysine
SITE                  29
                      note = monomethyllysine
SEQUENCE: 505
CAXEKINALG EIIWLPCLTY DQIXAFIAXL NDDPCQSSEI LSEAKELCS              49

SEQ ID NO: 506        moltype = AA  length = 49
FEATURE               Location/Qualifiers
source                1..49
                      mol_type = protein
                      organism = synthetic construct
SITE                  3
                      note = trimethyllysine
SITE                  24
                      note = dimethyllysine
SITE                  29
                      note = monomethyllysine
SITE                  45
                      note = monomethyllysine
SEQUENCE: 506
CAXEKINALG EIIWLPCLTY DQIXAFIAXL NDDPCQSSEI LSEAXELCS              49

SEQ ID NO: 507        moltype = AA  length = 49
FEATURE               Location/Qualifiers
source                1..49
                      mol_type = protein
                      organism = synthetic construct
SITE                  3
                      note = trimethyllysine
SITE                  24
                      note = dimethyllysine
SITE                  29
                      note = monomethyllysine
SEQUENCE: 507
CAXEKINALG EIIWLPCLTY DQIXAFIAXL NDDPCQSSEI LSEAQELCS              49

SEQ ID NO: 508        moltype = AA  length = 49
FEATURE               Location/Qualifiers
source                1..49
                      mol_type = protein
                      organism = synthetic construct
SITE                  3
                      note = trimethyllysine
SITE                  24
                      note = dimethyllysine
SEQUENCE: 508
CAXEKINALG EIIWLPCLTY DQIXAFIAAL NDDPCQSSEI LSEAQELCS              49

SEQ ID NO: 509        moltype = AA  length = 49
FEATURE               Location/Qualifiers
source                1..49
                      mol_type = protein
                      organism = synthetic construct
SITE                  3
                      note = trimethyllysine
SITE                  24
                      note = monomethyllysine
SITE                  45
                      note = monomethyllysine
SEQUENCE: 509
CAXEKIAALS EIIWVPCLTY AQIXAFIAAL NDDPCQSSEI LSEAXELCS              49

SEQ ID NO: 510        moltype = AA  length = 49
FEATURE               Location/Qualifiers
```

-continued

```
source                 1..49
                       mol_type = protein
                       organism = synthetic construct
SITE                   3
                       note = trimethyllysine
SITE                   24
                       note = monomethyllysine
SITE                   45
                       note = monomethyllysine
SEQUENCE: 510
CAXEKIAALS EIIWIPCLTY AQIXAFIAAL NDDPCQSSEI LSEAXELCS              49

SEQ ID NO: 511         moltype = AA  length = 49
FEATURE                Location/Qualifiers
source                 1..49
                       mol_type = protein
                       organism = synthetic construct
SITE                   3
                       note = trimethyllysine
SITE                   24
                       note = monomethyllysine
SITE                   45
                       note = monomethyllysine
SEQUENCE: 511
CAXEKIAALS EIIWWPCLTY AQIXAFIAAL NDDPCQSSEI LSEAXELCS              49

SEQ ID NO: 512         moltype = AA  length = 49
FEATURE                Location/Qualifiers
source                 1..49
                       mol_type = protein
                       organism = synthetic construct
SITE                   3
                       note = trimethyllysine
SITE                   24
                       note = monomethyllysine
SITE                   45
                       note = monomethyllysine
SEQUENCE: 512
CAXEKIAALS EIIWRPCLTY AQIXAFIAAL NDDPCQSSEI LSEAXELCS              49

SEQ ID NO: 513         moltype = AA  length = 49
FEATURE                Location/Qualifiers
source                 1..49
                       mol_type = protein
                       organism = synthetic construct
SITE                   24
                       note = monomethyllysine
SITE                   29
                       note = monomethyllysine
SITE                   45
                       note = monomethyllysine
SEQUENCE: 513
CAREKINALG EIIWLPCLTY DQIXAFIAXL NDDPCQSSEI LSEAXQLCS              49

SEQ ID NO: 514         moltype = AA  length = 49
FEATURE                Location/Qualifiers
source                 1..49
                       mol_type = protein
                       organism = synthetic construct
SITE                   24
                       note = monomethyllysine
SITE                   29
                       note = monomethyllysine
SITE                   45
                       note = monomethyllysine
SEQUENCE: 514
CAREKINALG EIIWLPCLTY DQIXAFIAXL NDDPCQSSEI LSEAXSLCS              49

SEQ ID NO: 515         moltype = AA  length = 49
FEATURE                Location/Qualifiers
source                 1..49
                       mol_type = protein
                       organism = synthetic construct
SITE                   24
                       note = monomethyllysine
SITE                   29
                       note = monomethyllysine
SITE                   45
                       note = monomethyllysine
```

```
SEQUENCE: 515
CAREKINALG EIIWLPCLTY DQIXAFIAXL NDDPCQSSEI LSEAXALCS              49

SEQ ID NO: 516          moltype = AA  length = 49
FEATURE                 Location/Qualifiers
source                  1..49
                        mol_type = protein
                        organism = synthetic construct
SITE                    3
                        note = citrulline
SITE                    24
                        note = monomethyllysine
SITE                    45
                        note = monomethyllysine
SEQUENCE: 516
CAXEKIAALS EIIWLPCLTY AQIXAFIARL NDDPCQSAEI LSEAXELCS              49

SEQ ID NO: 517          moltype = AA  length = 49
FEATURE                 Location/Qualifiers
source                  1..49
                        mol_type = protein
                        organism = synthetic construct
SITE                    3
                        note = Rme2s
SITE                    24
                        note = monomethyllysine
SITE                    45
                        note = monomethyllysine
SEQUENCE: 517
CAXEKIAALS EIIWLPCLTY AQIXAFIARL NDDPCQSAEI LSEAXELCS              49

SEQ ID NO: 518          moltype = AA  length = 49
FEATURE                 Location/Qualifiers
source                  1..49
                        mol_type = protein
                        organism = synthetic construct
SITE                    3
                        note = trimethyllysine
SITE                    24
                        note = dimethyllysine
SITE                    28
                        note = monomethyllysine
SITE                    45
                        note = trimethyllysine
SEQUENCE: 518
CAXEKIAALS EIIWLPCLTY AQIXAFIXAL NDDPCQSSEI LSEAXELCS              49

SEQ ID NO: 519          moltype = AA  length = 49
FEATURE                 Location/Qualifiers
source                  1..49
                        mol_type = protein
                        organism = synthetic construct
SITE                    3
                        note = trimethyllysine
SITE                    24
                        note = dimethyllysine
SITE                    28..29
                        note = monomethyllysine
SITE                    45
                        note = trimethyllysine
SEQUENCE: 519
CAXEKIAALS EIIWLPCLTY AQIXAFIXXL NDDPCQSSEI LSEAXELCS              49

SEQ ID NO: 520          moltype = AA  length = 49
FEATURE                 Location/Qualifiers
source                  1..49
                        mol_type = protein
                        organism = synthetic construct
SITE                    3
                        note = trimethyllysine
SITE                    24
                        note = dimethyllysine
SITE                    29
                        note = monomethyllysine
SITE                    45
                        note = trimethyllysine
SEQUENCE: 520
CAXEKIAALS EIIWLPCLTY AQIXAFIAXL NDDPCQSSEI LSEAXELCS              49
```

-continued

```
SEQ ID NO: 521         moltype = AA  length = 49
FEATURE                Location/Qualifiers
source                 1..49
                       mol_type = protein
                       organism = synthetic construct
SITE                   3
                       note = trimethyllysine
SITE                   24
                       note = dimethyllysine
SITE                   32
                       note = monomethyllysine
SITE                   45
                       note = monomethyllysine
SEQUENCE: 521
CAXEKIAALS EIIWLPCLTY AQIXAFIAAL NXDPCQSSEI LSEAXELCS              49

SEQ ID NO: 522         moltype = AA  length = 49
FEATURE                Location/Qualifiers
source                 1..49
                       mol_type = protein
                       organism = synthetic construct
SITE                   3
                       note = trimethyllysine
SITE                   24
                       note = dimethyllysine
SITE                   29
                       note = citrulline
SITE                   45
                       note = trimethyllysine
SEQUENCE: 522
CAXEKIAALS EIIWLPCLTY AQIXAFIAXL NDDPCQSSEI LSEAXELCS              49

SEQ ID NO: 523         moltype = AA  length = 49
FEATURE                Location/Qualifiers
source                 1..49
                       mol_type = protein
                       organism = synthetic construct
SITE                   3
                       note = trimethyllysine
SITE                   24
                       note = dimethyllysine
SITE                   45
                       note = trimethyllysine
SEQUENCE: 523
CAXEKIAALS EIIWLPCLTY AQIXAFIARL NDDPCQSSEI LSEAXELCS              49

SEQ ID NO: 524         moltype = AA  length = 49
FEATURE                Location/Qualifiers
source                 1..49
                       mol_type = protein
                       organism = synthetic construct
SITE                   24
                       note = monomethyllysine
SEQUENCE: 524
CAREKIAALS EIIWLPCLTY AQIXAFIAAL NADPCQSAEI LSEAKELCS              49

SEQ ID NO: 525         moltype = AA  length = 49
FEATURE                Location/Qualifiers
source                 1..49
                       mol_type = protein
                       organism = synthetic construct
SITE                   3
                       note = Rme2s
SITE                   24
                       note = monomethyllysine
SEQUENCE: 525
CAXEKIAALS EIIWLPCLTY AQIXAFIAAL NADPCQSAEI LSEAKELCS              49

SEQ ID NO: 526         moltype = AA  length = 49
FEATURE                Location/Qualifiers
source                 1..49
                       mol_type = protein
                       organism = synthetic construct
SITE                   3
                       note = trimethyllysine
SITE                   24
                       note = monomethyllysine
SITE                   29
                       note = citrulline
```

-continued

```
SITE                    45
                        note = monomethyllysine
SEQUENCE: 526
CAXEKIAALS EIIWLPCLTY AQIXAFIAXL NXDPCQSSEI LSEAXELCS              49

SEQ ID NO: 527          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    32
                        note = monomethyllysine
SITE                    45
                        note = trimethyllysine
SEQUENCE: 527
CAXEKIAALS EIIWLPCLTY AQIXAFIARL NXDPCQSSEI LSEAXELCS              49

SEQ ID NO: 528          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    28
                        note = monomethyllysine
SITE                    45
                        note = monomethyllysine
SEQUENCE: 528
CAXEKIAALS EIIWLPCLNY AQIXAFIXAL NDDPCQSSEI LSEAXELCS              49

SEQ ID NO: 529          moltype = AA  length = 49
FEATURE                 Location/Qualifiers
source                  1..49
                        mol_type = protein
                        organism = synthetic construct
SITE                    3
                        note = trimethyllysine
SITE                    19
                        note = monomethyllysine
SITE                    24
                        note = monomethyllysine
SITE                    28
                        note = monomethyllysine
SITE                    45
                        note = monomethyllysine
SEQUENCE: 529
CAXEKIAALS EIIWLPCLXY AQIXAFIXAL NDDPCQSSEI LSEAXELCS              49

SEQ ID NO: 530          moltype = AA  length = 49
FEATURE                 Location/Qualifiers
source                  1..49
                        mol_type = protein
                        organism = synthetic construct
SITE                    3
                        note = trimethyllysine
SITE                    24
                        note = monomethyllysine
SITE                    28
                        note = monomethyllysine
SITE                    45
                        note = monomethyllysine
SEQUENCE: 530
CAXEKIAALS EIIWLPCLTY AQIXAFIXAL NDDPCQSSEI LSEAXEQCS              49

SEQ ID NO: 531          moltype = AA  length = 49
FEATURE                 Location/Qualifiers
source                  1..49
                        mol_type = protein
                        organism = synthetic construct
SITE                    3
                        note = Rme2s
SITE                    24
```

-continued

```
                       note = monomethyllysine
SEQUENCE: 531
CAXEKIAALS EIIWLPCLTY AQIXAFIAAL NDDPCQSAEI LSEAKELCS               49

SEQ ID NO: 532         moltype = AA  length = 49
FEATURE                Location/Qualifiers
source                 1..49
                       mol_type = protein
                       organism = synthetic construct
SITE                   3
                       note = trimethyllysine
SITE                   24
                       note = dimethyllysine
SITE                   32
                       note = citrulline
SITE                   45
                       note = trimethyllysine
SEQUENCE: 532
CAXEKIAALS EIIWLPCLTY AQIXAFIAAL NXDPCQSSEI LSEAXELCS               49

SEQ ID NO: 533         moltype = AA  length = 49
FEATURE                Location/Qualifiers
source                 1..49
                       mol_type = protein
                       organism = synthetic construct
SITE                   24
                       note = monomethyllysine
SEQUENCE: 533
CAREKIAALS EIIWLPCLTY AQIXAFIAAL NDDPCQSAEI LSEARELCS               49

SEQ ID NO: 534         moltype = AA  length = 49
FEATURE                Location/Qualifiers
source                 1..49
                       mol_type = protein
                       organism = synthetic construct
SITE                   6
                       note = Tle
SITE                   24
                       note = monomethyllysine
SEQUENCE: 534
CAREKXAALS EIIWLPCLTY AQIXAFIAAL NDDPCQSAEI LSEARELCS               49

SEQ ID NO: 535         moltype = AA  length = 49
FEATURE                Location/Qualifiers
source                 1..49
                       mol_type = protein
                       organism = synthetic construct
SITE                   24
                       note = monomethyllysine
SEQUENCE: 535
CAREKIAALS EIIWLPCLTY AQIXAFIAAL NADPCQSAEI LSEARELCS               49

SEQ ID NO: 536         moltype = AA  length = 49
FEATURE                Location/Qualifiers
source                 1..49
                       mol_type = protein
                       organism = synthetic construct
SITE                   3
                       note = trimethyllysine
SITE                   24
                       note = monomethyllysine
SITE                   29
                       note = monomethyllysine
SITE                   32
                       note = monomethyllysine
SEQUENCE: 536
CAXHKIAALS EIIWLPCLTY AQIXAFIAXL NXDPCQSSEI LSEAKELCS               49

SEQ ID NO: 537         moltype = AA  length = 49
FEATURE                Location/Qualifiers
source                 1..49
                       mol_type = protein
                       organism = synthetic construct
SITE                   24
                       note = monomethyllysine
SITE                   29
                       note = monomethyllysine
SEQUENCE: 537
CAREKIAALS EIIWLPCLTY DQIXAFIAXL NDDPCQSAEI LSEARELCS               49
```

```
SEQ ID NO: 538          moltype = AA  length = 49
FEATURE                 Location/Qualifiers
source                  1..49
                        mol_type = protein
                        organism = synthetic construct
VARIANT                 3
                        note = trimethyllysine or R or methylated arginine
VARIANT                 19
                        note = T or N
VARIANT                 24
                        note = dimethyllysine or monomethyllysine
VARIANT                 28
                        note = A or monomethyllysine
VARIANT                 29
                        note = A or monomethyllysine or R
VARIANT                 32
                        note = D or monomethyllysine or citrulline
VARIANT                 36
                        note = Q or N
VARIANT                 38
                        note = S or A
VARIANT                 39
                        note = E or N
VARIANT                 45
                        note = K or monomethyllysine
SEQUENCE: 538
CAXEKIAALS EIIWLPCLXY AQIXAFIXXL NXDPCXSXXI LSEAXELCS              49

SEQ ID NO: 539          moltype = AA  length = 49
FEATURE                 Location/Qualifiers
source                  1..49
                        mol_type = protein
                        organism = synthetic construct
VARIANT                 3
                        note = trimethyllysine or R or methylated arginine
VARIANT                 19
                        note = T or N
VARIANT                 24
                        note = dimethyllysine or monomethyllysine
VARIANT                 28
                        note = A or monomethyllysine
VARIANT                 29
                        note = A or monomethyllysine or R
VARIANT                 32
                        note = D or monomethyllysine
VARIANT                 45
                        note = K or monomethyllysine
SEQUENCE: 539
CAXEKIAALS EIIWLPCLXY AQIXAFIAXL NXDPCQSSEI LSEAXELCS              49

SEQ ID NO: 540          moltype = AA  length = 49
FEATURE                 Location/Qualifiers
source                  1..49
                        mol_type = protein
                        organism = synthetic construct
VARIANT                 3
                        note = trimethyllysine or methylated arginine or R
VARIANT                 24
                        note = dimethyllysine or monomethyllysine
VARIANT                 28
                        note = A or monomethyllysine
VARIANT                 29
                        note = A or monomethyllysine or R
VARIANT                 32
                        note = D or monomethyllysine or citrulline
VARIANT                 45
                        note = K or monomethyllysine
SEQUENCE: 540
CAXEKIAALS EIIWLPCLTY AQIXAFIXXL NXDPCQSSEI LSEAXELCS              49

SEQ ID NO: 541          moltype = AA  length = 49
FEATURE                 Location/Qualifiers
source                  1..49
                        mol_type = protein
                        organism = synthetic construct
VARIANT                 24
                        note = monomethyllysine or dimethyllysine
VARIANT                 29
```

-continued

```
                        note = A or monomethyllysine
VARIANT                 32
                        note = D or monomethyllysine or citrulline
SEQUENCE: 541
CAXEKIAALS EIIWLPCLTY AQIXAFIAXL NXDPCQSSEI LSEAXELCS              49

SEQ ID NO: 542          moltype = AA  length = 49
FEATURE                 Location/Qualifiers
source                  1..49
                        mol_type = protein
                        organism = synthetic construct
VARIANT                 3
                        note = trimethyllysine or R or K
VARIANT                 7
                        note = A or N
VARIANT                 10
                        note = S or G
VARIANT                 17
                        note = C or N
VARIANT                 21
                        note = A or D
VARIANT                 24
                        note = trimethyllysine or dimethyllysine or monomethyllysine
VARIANT                 28
                        note = A or monomethyllysine
VARIANT                 29
                        note = A or monomethyllysine or R
VARIANT                 32
                        note = D or monomethyllysine
VARIANT                 38
                        note = S or A
VARIANT                 39
                        note = E or N
VARIANT                 40
                        note = I or L
VARIANT                 42
                        note = S or A
VARIANT                 45
                        note = K or monomethyllysine or trimethyllysine or Q
SEQUENCE: 542
CAXEKIXALX EIIWLPXLTY XQIXAFIXXL NXDPCQSXXX LXEAXELCS              49

SEQ ID NO: 543          moltype = AA  length = 49
FEATURE                 Location/Qualifiers
source                  1..49
                        mol_type = protein
                        organism = synthetic construct
VARIANT                 3
                        note = trimethyllysine or R
VARIANT                 7
                        note = A or N
VARIANT                 10
                        note = S or G
VARIANT                 21
                        note = A or D
VARIANT                 24
                        note = trimethyllysine or dimethyllysine or monomethyllysine
VARIANT                 28
                        note = A or monomethyllysine
VARIANT                 29
                        note = A or monomethyllysine or R
VARIANT                 32
                        note = D or monomethyllysine
VARIANT                 38
                        note = S or A
VARIANT                 39
                        note = E or N
VARIANT                 40
                        note = I or L
VARIANT                 42
                        note = S or A
VARIANT                 45
                        note = K or monomethyllysine or trimethyllysine Q
SEQUENCE: 543
CAXEKIXALX EIIWLPCLTY XQIXAFIXXL NXDPCQSXXX LXEAXELCS              49

SEQ ID NO: 544          moltype = AA  length = 49
FEATURE                 Location/Qualifiers
source                  1..49
```

```
                         mol_type = protein
                         organism = synthetic construct
SITE                     3
                         note = trimethyllysine
SITE                     11
                         note = E(CO-)
SITE                     24
                         note = monomethyllysine
SITE                     45
                         note = Lysine(NH-)
SEQUENCE: 544
CAXEKIAALS XIIWLPCLTY AQIXAFIAAL NDDPCNSSEI LSEAXELCS               49

SEQ ID NO: 545           moltype = AA  length = 58
FEATURE                  Location/Qualifiers
source                   1..58
                         mol_type = protein
                         organism = synthetic construct
SITE                     28
                         note = homo-leucine
SEQUENCE: 545
AEAKYAKEKI AALSEIIWLP NLTHGQIXAF IAALNDDPSQ SSELLSEAKK LNDSQAPK    58

SEQ ID NO: 546           moltype = AA  length = 49
FEATURE                  Location/Qualifiers
source                   1..49
                         mol_type = protein
                         organism = synthetic construct
SITE                     24
                         note = monomethyllysine
SEQUENCE: 546
CAXEKIXALX EIIWLPXLTY XQIXXFIXXL NXDPCQSXXX LXEAXXLXS               49

SEQ ID NO: 547           moltype = AA  length = 49
FEATURE                  Location/Qualifiers
source                   1..49
                         mol_type = protein
                         organism = synthetic construct
SITE                     24
                         note = monomethyllysine
SEQUENCE: 547
CAXEKIXALX EIIWLPXLTY XQIXAFIXXL NXDPCQSXXX LXEAXELXS               49

SEQ ID NO: 548           moltype = AA  length = 49
FEATURE                  Location/Qualifiers
source                   1..49
                         mol_type = protein
                         organism = synthetic construct
SITE                     24
                         note = monomethyllysine
SITE                     45
                         note = monomethyllysine
SEQUENCE: 548
CAXEKIXALX EIIWLPCLTY XQIXAFIXXL NDDPCQSXXX LXEAXELXS               49

SEQ ID NO: 549           moltype = AA  length = 49
FEATURE                  Location/Qualifiers
source                   1..49
                         mol_type = protein
                         organism = synthetic construct
SITE                     24
                         note = monomethyllysine
SEQUENCE: 549
CAXEKIXALX EIIWLPCLTY XQIXAFIXXL NDDPCQSXXX LXEAXELXS               49

SEQ ID NO: 550           moltype = AA  length = 49
FEATURE                  Location/Qualifiers
source                   1..49
                         mol_type = protein
                         organism = synthetic construct
SITE                     24
                         note = monomethyllysine
SEQUENCE: 550
CAXEKIXALX EIIWLPCLTY XQIXAFIAXL NDDPCQSXEI LSEAXELCS               49

SEQ ID NO: 551           moltype = AA  length = 72
FEATURE                  Location/Qualifiers
source                   1..72
                         mol_type = protein
```

-continued

```
                          organism = synthetic construct
VARIANT                   2..36
                          note = Residue may be deleted
SITE                      37..72
                          note = gamma-glutamine
VARIANT                   38..72
                          note = Residue may be deleted
SEQUENCE: 551
GGGGGGGGGG GGGGGGGGGG GGGGGGGGGG GGGGGGEEEE EEEEEEEEEE EEEEEEEEEE  60
EEEEEEEEEE EE                                                      72

SEQ ID NO: 552            moltype = AA  length = 10
FEATURE                   Location/Qualifiers
source                    1..10
                          mol_type = protein
                          organism = synthetic construct
VARIANT                   2..10
                          note = Residue may be deleted
SEQUENCE: 552
GGGGGGGGGG                                                         10

SEQ ID NO: 553            moltype = AA  length = 81
FEATURE                   Location/Qualifiers
source                    1..81
                          mol_type = protein
                          organism = synthetic construct
VARIANT                   2..16
                          note = Any amino acid or deleted
VARIANT                   18..32
                          note = Any amino acid or deleted
VARIANT                   34..48
                          note = Any amino acid or deleted
VARIANT                   50..64
                          note = Any amino acid or deleted
VARIANT                   66..80
                          note = Any amino acid or deleted
SEQUENCE: 553
CXXXXXXXXX XXXXXXCXXX XXXXXXXXXX XXCXXXXXXX XXXXXXXXCX XXXXXXXXXX  60
XXXXCXXXXX XXXXXXXXXX C                                            81

SEQ ID NO: 554            moltype = AA  length = 6
FEATURE                   Location/Qualifiers
source                    1..6
                          mol_type = protein
                          organism = synthetic construct
VARIANT                   3..6
                          note = Residue may be deleted
SEQUENCE: 554
HEHEHE                                                             6

SEQ ID NO: 555            moltype = AA  length = 6
FEATURE                   Location/Qualifiers
source                    1..6
                          mol_type = protein
                          organism = synthetic construct
VARIANT                   3..6
                          note = Residue may be deleted
SEQUENCE: 555
SESESE                                                             6
```

What is claimed is:

1. A composition comprising a polypeptide having an amino acid sequence comprising SEQ ID NO: 267.

2. The composition of claim 1, wherein the polypeptide is a miniprotein (M) that further comprises a chelator (C) conjugated to the N-terminus of (M) through a linker (L).

3. The composition of claim 2, further comprising a radionuclide (R) chelated to (C).

4. The composition of claim 2, wherein (L) is selected from the group consisting of a polyethylene glycol (PEG) linker of PEG4, PEG, PEG2, PEG6, PEG8, PEG12, PEG24, PEG36, or lys (MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, or (Gly) n-(gGlu) n, wherein n is from 0 to 10, (Gly) 1-10, and any combination via covalent bond thereof.

5. The composition of claim 2, wherein (C) is selected from the group consisting of DOTA, Crown, NOPO, Macropa, lead specific chelator (PSC), N-succinimidyl 3-(tri-n-butylstannyl)benzoate (BuSTB), and N-succinimidyl 3-trimethylstannylbenzoate (MeSTB).

6. The composition of claim 3, wherein R is selected from the group consisting of Ac-225, Cu-64, Ga-68, Lu-177, Pb-212, In-111, Cu-67, La-132, La-135, Ce-134, F-18, I-131, I-124, Pb-203, Bi-123, Sm-153, Ra-225, and At-211.

7. The composition of claim 2, wherein L is PEG4.

8. The composition of claim 2, wherein C is DOTA.

9. The composition of claim 3, wherein R is Ac-225 or Cu-64.

10. The composition of claim 6, wherein L is PEG4, C is DOTA, and R is Ac-225.

11. The composition of claim 6, wherein L is PEG4, C is DOTA, and R is Cu-64.

12. A composition comprising a polypeptide having an amino acid sequence comprising SEQ ID NO: 267, wherein the polypeptide is a miniprotein (M) that further comprises a radionuclide (R) chelated to a chelator (C), which chelator is conjugated to the N-terminus of (M) through a linker (L), wherein R is Ac-225, C is DOTA, and L is PEG4.

13. A composition comprising a polypeptide having an amino acid sequence comprising SEQ ID NO: 267, wherein the polypeptide is a miniprotein (M) that further comprises a radionuclide (R) chelated to a chelator (C), which chelator is conjugated to the N-terminus of (M) through a linker (L), wherein R is Cu-64, C is DOTA, and L is PEG4.

14. A method of treating cancer, the method comprising administering the composition of claim 6 to a subject in need thereof.

15. The method of claim 14, wherein the administering is intravenous or subcutaneous.

16. The method of claim 14, wherein the cancer is selected from prostate cancer, non-small cell lung cancer, small cell lung cancer, breast cancer, ovarian cancer, melanoma, pancreatic cancer, peripheral neuroma, glioblastoma, adrenocortical carcinoma, AIDS-related lymphoma, anal cancer, urothelial cancer, bladder cancer, meningioma, glioma, astrocytoma, cervical cancer, chronic myeloproliferative disorders, colon cancer, endometrial cancer, ependymoma, esophageal cancer, Ewing's sarcoma, extracranial germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma, Kaposi sarcoma, laryngeal cancer, leukemia, lip cancer, oral cavity cancer, liver cancer, male breast cancer, malignant mesothelioma, medulloblastoma, Merkel cell carcinoma, metastatic squamous neck cell carcinoma, multiple myeloma, plasma cell neoplasms, mycosis fungoides Sezary syndrome, myelodysplastic syndromes, nasopharyngeal cancer, neuroblastoma, head and neck cancer, skin cancer, oropharyngeal cancer, bone cancers, osteosarcoma, malignant fibrous histiocytoma of bone, paranasal sinus cancer, parathyroid cancer, penile cancer, pheochromocytoma, pituitary tumors, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilms tumor.

17. The method of claim 16, wherein the cancer is metastatic.

18. A method of treating cancer, the method comprising administering to a subject in need thereof a composition comprising a polypeptide having an amino acid sequence comprising SEQ ID NO: 267 and further comprising a chelator (C) conjugated to the N-terminus of (M) through a linker (L), and a radionuclide (R) chelated to (C), wherein (L) is selected from the group consisting of a polyethylene glycol (PEG) linker of PEG4, PEG, PEG2, PEG6, PEG8, PEG12, PEG24, PEG36, or lys (MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, or (Gly) n-(gGlu) n-, wherein n is from 0 to 10, (Gly) 1-10, and any combination via covalent bond thereof, (C) is selected from the group consisting of DOTA, Crown, NOPO, Macropa, lead specific chelator (PSC), N-succinimidyl 3-(tri-n-butylstannyl)benzoate (BuSTB), and N-succinimidyl 3-trimethylstannylbenzoate (MeSTB), and (R) is selected from the group consisting of Ac-225, Cu-64, Ga-68, Lu-177, Pb-212, In-111, Cu-67, La-132, La-135, Ce-134, F-18, I-131, 1-124, Pb-203, Bi-123, Sm-153, Ra-225, and At-211.

19. The method of claim 18, wherein (R) is selected from the group consisting of Ac-225, Lu-177, Pb-212, Cu-67, and I-131.

20. The method of claim 18, wherein (R) is selected from the group consisting of Cu-64, Ga-68, In-111, Pb-203, I-123, I-124, La-132, Ac-225, Lu-177, and F-18.

21. The method of claim 20, wherein the composition is a first composition and imaging is performed on the subject after the administration of the first composition.

22. The method of claim 21, wherein the subject is further administered a second composition after administration of the first composition, wherein the second composition comprises a polypeptide having an amino acid sequence comprising SEQ ID NO: 267 and further comprising a chelator (C) conjugated to the N-terminus of (M) through a linker (L), and a radionuclide (R) chelated to (C), wherein (L) is selected from the group consisting of a polyethylene glycol (PEG) linker of PEG4, PEG, PEG2, PEG6, PEG8, PEG12, PEG24, PEG36, or lys (MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, or (Gly) n-(gGlu) n-, wherein n is from 0 to 10, (Gly) 1-10, and any combination via covalent bond thereof, (C) is selected from the group consisting of DOTA, Crown, NOPO, Macropa, lead specific chelator (PSC), N-succinimidyl 3-(tri-n-butylstannyl)benzoate (BuSTB), and N-succinimidyl 3-trimethylstannylbenzoate (MeSTB), and R is selected from the group consisting of Ac-225, Lu-177, Pb-212, Cu-67, and I-131.

23. The method of claim 21, wherein the first composition comprises an (L) of PEG4, a (C) of DOTA, and an (R) of Cu-64.

24. The method of claim 22, wherein the second composition comprises an (L) of PEG4, a (C) of DOTA, and an (R) of Ac-225.

* * * * *